United States Patent
Selness et al.

(10) Patent No.: US 9,056,110 B2
(45) Date of Patent: Jun. 16, 2015

(54) SUBSTITUTED PYRIMIDINONE-PHENYL-PYRIMIDINYL COMPOUNDS

(71) Applicant: Confluence Life Sciences, Inc., St. Louis, MO (US)

(72) Inventors: Shaun R. Selness, Chesterfield, MO (US); Balekudru Devadas, Chesterfield, MO (US); Susan L. Hockerman, Kirkwood, MO (US); Joseph B. Monahan, St. Louis, MO (US)

(73) Assignee: CONFLUENCE LIFE SCIENCES, INC., St. Louis, MO (US)

( * ) Notice: Subject to any disclaimer, the term of this patent is extended or adjusted under 35 U.S.C. 154(b) by 246 days.

(21) Appl. No.: 13/707,326

(22) Filed: Dec. 6, 2012

(65) Prior Publication Data

US 2013/0143906 A1 Jun. 6, 2013

Related U.S. Application Data

(60) Provisional application No. 61/567,509, filed on Dec. 6, 2011.

(51) Int. Cl.

| | | |
|---|---|---|
| A61K 31/513 | (2006.01) | |
| A61K 45/06 | (2006.01) | |
| C07D 401/14 | (2006.01) | |
| C07D 413/14 | (2006.01) | |
| C07D 409/14 | (2006.01) | |
| C07D 417/14 | (2006.01) | |
| C07D 403/14 | (2006.01) | |
| C07D 239/52 | (2006.01) | |

(52) U.S. Cl.
CPC ............ *A61K 31/513* (2013.01); *C07D 239/52* (2013.01); *C07D 413/14* (2013.01); *C07D 417/14* (2013.01); *C07D 401/14* (2013.01); *A61K 45/06* (2013.01); *C07D 403/14* (2013.01); *C07D 409/14* (2013.01)

(58) Field of Classification Search
None
See application file for complete search history.

(56) References Cited

U.S. PATENT DOCUMENTS

| 7,067,540 B2 | 6/2006 | Devadas et al. ............... 514/348 |
|---|---|---|
| 2007/0167621 A1 | 7/2007 | Durley ............................ 544/60 |

FOREIGN PATENT DOCUMENTS

| WO | WO 00/17175 | 3/2000 | .......... C07D 277/48 |
|---|---|---|---|
| WO | WO 00/71535 | 11/2000 | .......... C07D 401/06 |
| WO | WO 02/42292 | 5/2002 | .......... C07D 401/06 |
| WO | WO 2004/087677 | 10/2004 | .......... C07D 239/00 |
| WO | WO 2005/018557 | 3/2005 | |
| WO | WO 2007/081901 | 7/2007 | .......... A61K 31/513 |
| WO | WO 2008/062905 | 5/2008 | |
| WO | WO 2008/153942 | 12/2008 | ............. A01N 43/54 |

OTHER PUBLICATIONS

Barnes, P.J. (1998) "Chronic obstructive pulmonary disease: New opportunities for drug development." *Trends Pharmacol. Sci.*, 19:415-23.
Burnette, et. al. (2009) "SD0006: A potent, selective and orally available inhibitor of p38 kinase." *Pharmacology*, 84:42-60.
Davidson, et. al. (2004) "Discovery and characterization of a substrate selective p38alpha inhibitor." *Biochemistry*, 43:11658-71.
DiMauro, et. al. (2006) "Discovery of aminoquinazolines as potent, orally bioavailable inhibitors of lck: Synthesis, SAR, and in vivo anti-inflammatory activity." *J. Med. Chem.*, 49:5671-5686.
Lopez and Murray, C.J.L. (1996) "A.D. Evidence based health policy-lessons from the global burden of disease study." *Science*, 274:740-743.

*Primary Examiner* — Savitha Rao
*Assistant Examiner* — Gregg Polansky
(74) *Attorney, Agent, or Firm* — Harness, Dickey & Pierce, P.L.C.

(57) ABSTRACT

The present disclosure provides pyrimidinone-phenyl-pyrimidinyl compounds useful in the treatment of p38 kinase mediated diseases, such as lymphoma and inflammatory disease, having the structure of Formula (I):

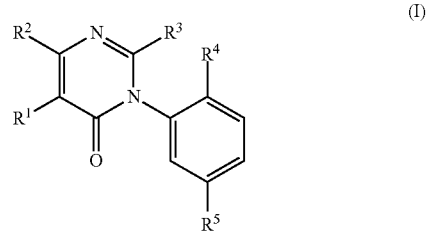

wherein $R^1$, $R^2$, $R^3$, $R^4$ and $R^5$ are as defined in the detailed description; pharmaceutical compositions comprising at least one of the compounds; and methods for treating p38 kinase mediated diseases using the compound.

47 Claims, No Drawings

SUBSTITUTED PYRIMIDINONE-PHENYL-PYRIMIDINYL COMPOUNDS

CROSS-REFERENCE TO RELATED APPLICATIONS

This application claims the benefit of U.S. Provisional Application No. 61/567,509, filed on 6 Dec. 2011, the entire disclosure of which is incorporated herein by reference.

FIELD

The present disclosure generally relates to a compound having enzyme inhibitory activity, pharmaceutical compositions comprising the compound, and methods useful for treating diseases. More specifically, the present disclosure relates to a class of pyrimidinone-phenyl-pyrimidinyl compounds, pharmaceutical compositions comprising the compound, and methods useful for treating p38 kinase mediated diseases.

BACKGROUND

Mitogen-activated protein kinases (MAPK) are a conserved family of enzymes that relay and propagate external stimuli, using phosphorylation cascades to generate a coordinated cellular response to the environment. The MAPK are proline-directed serine/threonine-specific protein kinases that regulate cellular activities, such as gene expression, mitosis, differentiation, and cell survival/apoptosis. To date, 4 distinct classes of mammalian MAPK have been identified: the extracellular signaling kinases (ERK1 and 2), the c-jun N-terminal kinase-1 (JNK1-3), the p38 MAPK (p38α, β, γ, and δ), and ERK5. The MAPK are activated by the dual phosphorylation of Thr and Tyr residues within a TXY activation motif by coordinated dual-specificity MAPKK, where X is Glu, Pro, and Gly in ERK, JNK, and p38 MAPK, respectively. MAPK are 60-70% identical to each other, yet differ in their activation loop sequences and sizes. The activation loop is adjacent to the enzyme-active site, and its phosphorylation allows the enzyme to reposition active-site residues into the optimal orientation for substrate binding and catalysis. Downstream substrates of MAPK include mitogen-activated protein-kinase-activated protein (MAPKAP) kinases and transcription factors, the phosphorylation of which, either directly or indirectly, regulates gene expression at several points, including transcription, nuclear export, and mRNA stability and translation. The cellular consequences of MAPK activation include inflammation, apoptosis, differentiation, and proliferation.

Distinct genes encode 4 p38 MAPK in humans: p38α, β, γ, and δ. Significant amino acid sequence homology is observed among the 4 isoforms, with 60%-75% overall sequence identity and >90% identity within the kinase domains. Tissue-selective expression is observed, with p38γ found predominantly in skeletal muscle, p38δ in the testes, pancreas, and small intestine. In contrast, p38α and β are more ubiquitously expressed.

An understanding of the broad biologic and pathophysiological roles of p38 MAPK family members has grown significantly over the past decade, as has the complexity of the signaling network leading to their activation. Scientific exploration of this pathway from biological, cellular, and in vivo perspectives was largely enabled by the availability of well-behaved, selective, small-molecule inhibitors of p38 MAPK that target the α and, to a lesser extent, β isoforms. p38α MAPK is the major isoform involved in the immune and inflammatory response. As such, its function is critical for the production and activity of multiple pro-inflammatory cytokines, including TNFα, IL-1, IL-6, and IL-8, in cells such as macrophages, monocytes, synovial cells, and endothelial cells. p38 MAPK is also responsible for the induction of key inflammatory enzymes such as COX2 and iNOS, the major sources of eicosanoids and nitric oxide at sites of inflammation, respectively. Additionally, the p38 MAPK pathway regulates the expression of matrix metalloproteinases (MMP), including MMP2, MMP9, and MMP13.

The use of selective and potent inhibitors has facilitated the discovery of several families of p38 MAPK substrates, including transcription factors, MAPKAP kinases, and other enzymes. p38 MAPK can directly phosphorylate several transcription factors, such as myocyte-specific enhancer binding factor 2C (MEF2C), CHOP, peroxisome proliferator-activated receptor (PPAR) α, PPAR γ co-activator 1 and p53. These transcription factors are involved in cellular functions such as apoptosis, gluconeogenesis, and synthesis of enzymes involved in fatty acid oxidation. p38 MAPK is also involved in the direct or indirect phosphorylation of enzyme substrates, such as cytosolic phospholipase A2, and the Cdc25 phosphatases, which are involved in the activation of cyclin-dependent protein kinase activity and cell-cycle regulation. Therefore in addition to its role in the inflammatory response, p38 MAPK has other functions associated with normal and abnormal cell growth and survival as well as cellular function and homeostasis.

The MAPKAP kinases—MK2, MK-3, and PRAK—are selectively phosphorylated by p38 MAPK, while the phosphorylation of MSK1/2, MNK1/2, and RSKb is catalyzed by both p38 MAPK and ERK. Activation of RSKb is thought to play a role in cell survival, although the identification of substrates has been difficult, due to the lack of specific inhibitors. MNK is involved in the phosphorylation of eukaryotic initiation factor-4E, which binds to the 'cap' structure of mRNA and enhances protein translation. MNK phosphorylates the mRNA binding protein hnRNP-A0, a protein that regulates mRNA stability of transcripts encoding inflammatory proteins. MSK1/2 is involved in the phosphorylation of the transcription factors CREB and ATF-1, which regulate AP-1 binding proteins. In addition, MSK1/2 can phosphorylate Histone H3, which is involved in chromatin remodeling. While evidence suggests that MSK and MNK play a role in the mediation of pro-inflammatory cytokines, in vivo data with selective inhibitors and/or knockout mice are lacking.

MK-2, MK-3, and PRAK, once phosphorylated and activated by p38 MAPK, share similar substrate specificities. All of these kinases can phosphorylate the small heat-shock protein Hsp27. Studies have shown that the PRAK- and MK3-deficient mice do not display any resistance to endotoxic shock or a decrease in lipopolysaccharide-(LPS)-induced cytokine production. In contrast, MK-2-deficient mice show a resistance to endotoxic shock and an impaired inflammatory response, as well as a significantly decreased production of cytokines such as TNFα, IFNγ and IL-6. Thus, the p38/MK2 axis specifically is necessary and sufficient for mediating pro-inflammatory responses.

Recently, Davidson (Davidson, et al. (2004) Discovery and characterization of a substrate selective p38alpha inhibitor, *Biochemistry* 43:11658-71) described a novel approach for increasing selectivity of a p38 MAPK inhibitors. In these studies, a high throughput screen was carried out using an assay that measured the p38-dependent phosphorylation and activation of MK2. The p38:MK2 complex is very stable with a Kd of 6 nM. The binding affinity of p38 for MK2 is driven by the C-terminal domain of MK2 containing several positively charged amino acid residues. Crystallographic studies of the p38:MK2 complex demonstrated that the C-terminal region of MK2 wraps around p38α and binds to the negatively charged ED binding site. The tight binding of p38 to MK2 may give rise to conformational changes providing additional binding pockets for inhibitors that would specifically be dependent upon the p38:MK2 interaction.

Taking advantage of the p38:MK2 interaction and using MK2 as the p38 substrate, a novel inhibitor of p38α was discovered exhibiting interesting properties (Davidson, et al. (2004), op. cit.). This inhibitor demonstrated substrate selectivity by preventing the p38α dependent phosphorylation of MK2 (Ki app 300 nM) while sparing the p38α dependent phosphorylation of ATF2 (Ki app >20 uM). This novel inhibitor is functionally unique compared with traditional p38 ATP competitive inhibitors that block the p38-dependent phosphorylation of all p38 substrates. This study demonstrates the concept that selective p38/MK2 axis blockade is achievable with small molecule inhibitors. In comparison to traditional p38 MAPK inhibitors these p38/MK2 inhibitors should retain or enhance potency and exhibit improved safety features in animal models of disease or in human clinical settings.

The p38/MK2 role in the regulation of inflammatory cytokines (TNFα, IL-1β, IL-6) and enzymes responsible for inflammation (COX-2, iNOS, and MMPs) makes it an attractive drug target.

Rheumatoid arthritis (RA) is a systemic, autoimmune, chronic inflammatory disease characterized by joint synovial inflammation leading to cartilage and bone destruction Current treatment for RA includes oral disease modifying anti-rheumatic drugs (DMARDs) (methotrexate, leflunomide, sulfasalazine), and parenterally administered biologic agents specifically directed against IL-1 (Ankinra®) or TNFα (Enbrel®, Remicade®, and Humira®), two key proinflammatory cytokines implicated in RA pathogenesis. The superior efficacy of these latter agents is somewhat offset by potential shortcomings, including requirement for parenteral administration, difficult dose titration, poor reversibility due to prolonged plasma half-lives, induction of host neutralizing antibody responses and high cost of treatment. Based on a p38 inhibitor's potential to inhibit a broad range of pro-inflammatory mediators purported to play a central role in RA pathogenesis (including TNFα, IL-1β, and IL-6) it is expected that a p38 inhibitor will have clinical efficacy equivalent or superior to biologics restricted to single cytokine modulation (e.g., TNFα). An orally administered DMARD with improved efficacy offers multiple advantages to both the patient and physician with respect to convenience and compliance of administration, lack of injection site/allergic reactions, superior dose titratability, and favorable cost of goods. A safe and effective p38 inhibitor thus potentially fulfills an evident unmet medical need and promises high potential to generate significant value for patients and physicians that deal with RA.

Airway tissue hypersensitivity, which includes chronic obstructive pulmonary disease (COPD), bronchitis, emphysema and asthma, is a common lung disease leading to a progressive decline in lung function and impairment of gas transfer. By far the most common cause of the disease is cigarette smoking, although both environmental and genetic factors have also been implicated in its aetiology. The prevalence of COPD in the developed world is between 4% and 8% of the population and incidence and prevalence rates are set to increase in the developing world in line with increasing tobacco exposure. COPD is associated with high morbidity and mortality, and both the direct and indirect socioeconomic costs of COPD are high. COPD was ranked as $12^{th}$ in the global impact of disease scale in 1990, but is predicted to rise to $5^{th}$ by the year 2020 (Lopez, A. D. and Murray, C. J. L., Evidence based health policy-lessons from the global burden of disease study. Science 1996; 274:740-743). Therapeutic options in COPD and other diseases of airway tissue hypersensitivity are limited. Despite the availability of short-acting and long-acting bronchodilators ($\beta_2$ agonist and anti-cholinergic classes) which provide a degree of symptomatic relief, unlike in asthma, no therapeutic class has consistently been shown to display anti-inflammatory properties across the spectrum of disease severity and there is a clear unmet need for novel therapies with demonstrable anti-inflammatory activity (Barnes P. J., Chronic obstructive pulmonary disease: New opportunities for drug development. Trends Pharmacol Sci 1998; 19:415-23).

Chronic inflammation of the airways is thought to underlie the pathogenesis of diseases of airway tissue hypersensitivity, such as COPD. Signaling through the stress activated protein kinase p38α is required for the expression of a range of inflammatory mediators such as TNFα, IL-1α, IL-6 and IL-8, which have been associated with the chronic lung inflammation characteristic of COPD. p38α is expressed on a range of inflammatory cells associated with COPD, and expression and activation are increased in the lungs of COPD patients compared to smoking and non-smoking controls. In addition, differentiation from steroids has been shown in vitro oxidative stress induced cytokine release assay, designed to model some aspects of the inflammation associated with COPD. Inhibition of protein kinase p38α is therefore an attractive target for treating diseases of airway tissue hypersensitivity, such as COPD.

Several classical p38 MAPK inhibitors have progressed to testing in clinical trials. Some of these candidates have failed, for safety or other reasons, but several have reported clinical data in diseases such as rheumatoid arthritis, pain, Crohn's disease, acute coronary syndrome, multiple myeloma and chronic obstructive pulmonary disease. In addition to these diseases several IL-1β mediated diseases could be impacted by a p38 inhibitor based upon the key role for the p38 MAPK pathway in the biosynthesis and activity of this cytokine. These diseases include the family of cryopyrin associated periodic disorders (CAPS), chronic gout, diabetes, Still's disease, Familial Mediterranean Fever among others.

In addition to human inflammatory pathways, p38 MAPK has been linked to canine B cell growth and survival. The role of p38 MAPK in B cell growth suggests that inhibition of this enzyme may be therapeutically beneficial for the treatment of canine B cell lymphoma. Canine lymphoma is one of the most common malignancies diagnosed in companion animals representing 10-25% of canine neoplasms and >80% of the hematopoietic tumors. An orally available, selective B cell growth inhibitor would meet a significant unmet medical need.

Compounds useful for treating diseases and conditions caused or exacerbated by unregulated p38 MAP Kinase and/or TNF activity are described in WO 2000/017175 published 30 Mar. 2000. The compounds described therein include a class of substituted urea compounds.

Compounds useful for treating diseases and conditions caused or exacerbated by unregulated p38 MAP Kinase and/or TNF activity are described in WO 2000/071535 published 30 Nov. 2000. The compounds described therein include a class of indole-type compounds.

Compounds useful for treating diseases and conditions caused or exacerbated by unregulated p38 MAP Kinase and/or TNF activity are described in WO 2002/042292 published 30 May 2002. The compounds described therein include a class of coupled indole-type derivatives.

Pyrimidinone derivatives (as inhibitors of protein kinases and useful in treating disorders related to abnormal protein kinase activities such as inflammatory diseases and certain types of cancer), are described in WO 2007/081901 published 19 Jul. 2008. The compounds described therein include di-fluorophenyl-methoxy-pyrimidinone-phenyl compounds wherein the phenyl fragment is substituted with a cyclopropanyl or a morpholinyl radical through an amidoalkylamido bridge.

Pyrimidinone derivatives (as inhibitors of protein kinases and useful in treating disorders related to abnormal protein kinase activities such as inflammatory diseases and certain types of cancer) are described in WO 2008/153942 published 18 Dec. 2008. The compounds described therein include di-fluorophenyl-methoxy-pyrimidinone-phenyl compounds where the phenyl radical is substituted with cyclopentyl or a cyclohexyl radical through an amido bridge.

Compounds useful for treating diseases and conditions caused or exacerbated by unregulated p38 MAP Kinase and/or TNF activity are described in U.S. Pat. No. 7,067,540 published 27 Jun. 2007. The compounds described therein include di-fluorophenyl-methoxy-pyridinone-phenyl compounds wherein the phenyl radical is substituted with a $C_5$-heteroaryl radical (e.g., pyrazolyl or imidazolyl).

Compounds useful for prophylaxis or treatment of circulatory diseases, metabolic diseases and/or central nervous system diseases are described in WO 2008/062905 published 29 May 2008. The compounds described therein include alkyl-pyrimidinone-phenyl compounds wherein the phenyl fragment is substituted with a cyclopropyl radical, e.g., 6-butyl-3-(3-cyclopropylphenyl)-2-methyl-5-{[2'-(5-oxo-4,5-dihydro-1,2,4-oxadizol-3-yl)biphenyl-4-yl]methyl}pyrimidin-4(3H)-one.

Various potential inhibitors or modulators of p38 kinase and the p38 kinase pathway are described in WO 2005/018557 published 3 Mar. 2005. The compounds described therein include di-fluorophenyl-methoxy-pyridinone-pyridyl compounds wherein the pyridyl fragment is substituted with various radicals including: alkyl, alkenyl, hydroxyalkyl, halo, cyano, amino, carboxy, carbamoyl, methoxycarbonyl and hydroxyalkenylimino radicals.

Compounds useful for treating diseases and conditions caused or exacerbated by unregulated p38 MAP Kinase and/or TNF activity are described in US 2007/0167621 published 19 Jul. 2007. The compounds described therein include di-fluorophenyl-methoxy-pyrimidinone-phenyl compounds wherein the phenyl fragment is substituted with methyl amido radical.

Compounds useful for treating diseases and conditions caused or exacerbated by unregulated p38 MAP Kinase and/or TNF activity are described in WO 2004/087677 published 14 Oct. 2004. The compounds described therein include di-fluorophenyl-methoxy-pyrimidinone-phenyl compounds wherein the phenyl fragment is substituted with piperazinyl or a morpholinyl radical through a carbonyl bridge.

SUMMARY

In one embodiment, there is provided a compound of Formula (I):

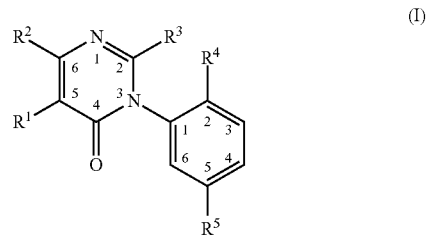

or a pharmaceutically acceptable salt thereof, wherein $R^1$, $R^2$, $R^3$, $R^4$ and $R^5$ are as defined hereinafter.

In another embodiment, there is provided a pharmaceutical composition comprising a compound of Formula (I) or a pharmaceutically acceptable salt thereof, and a pharmaceutically-acceptable carrier. In various embodiments, the pharmaceutical composition further comprises one or more additional pharmaceutically active compounds.

In yet another embodiment, there is provided a method for treating a condition comprising administering to a subject a therapeutically effective amount of a compound of Formula (I), wherein the condition to be treated includes, but is not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, and lymphoma. In various embodiments, the method comprises administering a combination of a compound of Formula (I) and at least one additional pharmaceutically active compound.

In yet another embodiment, there are provided intermediates useful in making a compound of Formula (I) or a pharmaceutically acceptable salt thereof.

DETAILED DESCRIPTION

The following description is merely exemplary in nature and is not intended to limit the present disclosure, application, or uses.

The present disclosure provides a compound having the structure of Formula (I):

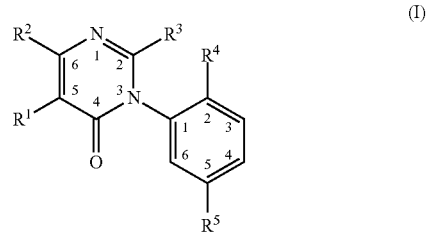

and a pharmaceutically acceptable salt thereof, wherein: $R^1$ is selected from the group consisting of —H, alkyl and halo; $R^2$ is selected from the group consisting of alkyl and alkoxy, wherein the alkyl or alkoxy is optionally substituted with one or more substituents independently selected from the group consisting of cycloalkyl, aryl and heterocyclyl; wherein the cycloalkyl, aryl or heterocyclyl is substituted with one or more substituents independently selected from the group consisting of alkyl, alkoxy, alkyl-O-alkyl, hydroxyl, hydroxyalkyl, amido, carboxy, acyl, carbamido, cyano, aminoalkyl, thiolalkyl, halo and haloalkyl; or $R^2$ is hydroxyl; $R^3$ and $R^4$ are independently selected from the group consisting of —H, alkyl and halo; and $R^5$ is selected from the group consisting of carbonyl, cycloalkyl, aryl and heterocyclyl; wherein the carbonyl is substituted with

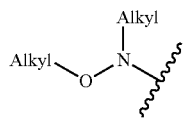

or alkynyl; and the cycloalkyl, aryl or heterocyclyl is substituted with one or more substituents independently selected from the group consisting of alkyl, alkoxy, alkyl-O-alkyl, hydroxyl, hydroxyalkyl, amido, carboxy, acyl, carbamido, cyano, aminoalkyl, thiolalkyl, halo and haloalkyl.

In one embodiment, $R^1$ is selected from the group consisting of —H, $C_{1-5}$alkyl, bromo, chloro and fluoro; $R^2$ is $C_{1-5}$alkoxy optionally substituted with one or more substituents independently selected from the group consisting of $C_{1-6}$cycloalkyl, aryl and heterocyclyl; wherein the $C_{1-6}$cycloalkyl, aryl or heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl; $R^3$ is selected from the group consisting of —H and $C_{1-5}$alkyl; $R^4$ is selected from the group consisting of —H, $C_{1-5}$alkyl, chloro, bromo and fluoro; and $R^5$ is heterocyclyl substituted with one or more substituents selected from the group consisting of $C_{1-5}$alkyl, $C_{1-5}$alkoxy, $C_{1-5}$alkyl-O—$C_{1-5}$alkyl, hydroxyl, hydroxy$C_{1-5}$alkyl, amido, carboxy, acyl, carbamido, cyano, amino$C_{1-5}$alkyl, thiol$C_{1-5}$alkyl, halo and halo$C_{1-5}$alkyl.

In another embodiment, $R^1$ is selected from the group consisting of methyl, ethyl, bromo and chloro; $R^2$ is $C_{1-3}$alkoxy optionally substituted with one or more substituents selected from the group consisting of five- or six-membered cycloalkyl, phenyl and five- or six-membered heterocyclyl; wherein the five- or six-membered cycloalkyl, phenyl or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl; $R^3$ is selected from the group consisting of —H and $C_{1-3}$alkyl; $R^4$ is selected from the group consisting of —H, methyl and chloro; and $R^5$ is five- or six-membered heteroaryl substituted with one or more substituents independently selected from the group consisting of $C_{1-5}$alkyl, $C_{1-5}$alkoxy, $C_{1-5}$alkyl-O—$C_{1-5}$alkyl, hydroxyl, hydroxy$C_{1-5}$alkyl, amido, carboxy, acyl, carbamido, cyano, amino$C_{1-5}$alkyl, thiol$C_{1-5}$alkyl, halo and halo$C_{1-5}$alkyl.

In yet another embodiment, $R^1$ is selected from the group consisting of methyl, ethyl, bromo and chloro; $R^2$ is methoxy optionally substituted with five- or six-membered cycloalkyl, phenyl, or five- or six-membered heterocyclyl; wherein the five- or six-membered cycloalkyl, phenyl, or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl; $R^3$ is selected from the group consisting of —H and $C_{1-3}$alkyl; $R^4$ is selected from the group consisting of —H, methyl and chloro; and $R^5$ is six-membered heteroaryl substituted with one or more substituents selected from the group consisting of $C_{1-5}$alkyl, $C_{1-5}$alkoxy, $C_{1-5}$alkyl-O—$C_{1-5}$alkyl, hydroxyl, hydroxy$C_{1-5}$alkyl, amido, carboxy, acyl, carbamido, cyano, amino$C_{1-5}$alkyl, thiol$C_{1-5}$alkyl, halo and halo$C_{1-5}$alkyl.

In yet another embodiment, $R^1$ is selected from the group consisting of methyl, ethyl, chloro and bromo; $R^2$ is methoxy optionally substituted with phenyl, or five- or six-membered heterocyclyl; wherein the phenyl, or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl; $R^3$ is selected from the group consisting of —H and $C_{1-3}$alkyl; $R^4$ is selected from the group consisting of —H, methyl and chloro; and $R^5$ is selected from the group consisting of pyridinyl, pyrazinyl, pyridazinyl and pyrimidinyl; wherein the pyridinyl, pyrazinyl, pyridazinyl or pyrimidinyl is substituted with one or more substituents independently selected from the group consisting of $C_{1-5}$alkyl, $C_{1-5}$alkoxy, $C_{1-5}$alkyl-O—$C_{1-5}$alkyl, hydroxyl, hydroxyalkyl, amido, carboxy, acyl, carbamido, cyano, amino$C_{1-5}$alkyl, thiol$C_{1-5}$alkyl, halo and halo$C_{1-5}$alkyl.

DEFINITIONS

The terms "substituent", "radical", "group", "moiety" and "fragment" may be used interchangeably.

The symbol "H" denotes a single hydrogen atom and may be used interchangeably with the symbol "—H". "H" may be attached, for example, to an oxygen atom to form a "hydroxy" radical (i.e., —OH), or two "H" atoms may be attached to a carbon atom to form a "methylene" (—$CH_2$—) radical.

The terms "hydroxyl" and "hydroxy" may be used interchangeably.

If a substituent is described as being "optionally substituted," the substituent may be either (1) not substituted or (2) substituted on a substitutable position. If a substitutable position is not substituted, the default substituent is H.

Singular forms "a" and "an" may include plural reference unless the context clearly dictates otherwise.

The number of carbon atoms in a substituent can be indicated by the prefix "$C_{A-B}$" where A is the minimum and B is the maximum number of carbon atoms in the substituent.

The term "halo" refers to fluoro (—F), chloro (—Cl), bromo (—Br) or iodo (—I).

The term "alkyl" denotes a linear or branched acyclic alkyl radical containing from 1 to about 15 carbon atoms. In some embodiments, alkyl is a $C_{1-10}$alkyl, $C_{1-6}$alkyl or $C_{1-3}$alkyl radical. Examples of alkyl include, but are not limited to, methyl, ethyl, propyl, isopropyl, butyl, isobutyl, tert-butyl, sec-butyl, pentan-3-yl (i.e.,

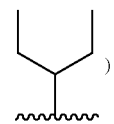

)

and the like.

The term "alkynyl" refers to an unsaturated, acyclic hydrocarbon radical with at least one triple bond. Such alkynyl radicals contain from 2 to about 15 carbon atoms. Non-limiting examples of alkynyl include ethynyl, propynyl and propargyl.

The term "hydroxyalkyl" embraces alkyl substituted with one or more hydroxyl radicals. Hydroxyalkyl embraces, for example, monohydroxyalkyl, dihydroxyalkyl and trihydroxyalkyl. More specific examples of hydroxyalkyl include hydroxymethyl, hydroxyethyl and hydroxypropyl (e.g., 2-hydroxypropan-2-yl).

The term "haloalkyl" embraces alkyl substituted with one or more halo radicals. Examples of haloalkyl include monohaloalkyl, dihaloalkyl and trihaloalkyl. A monohaloalkyl radical, for example, may have either a bromo, chloro or a fluoro atom. A dihalo radical, for example, may have two of the same halo radicals or a combination of different halo radicals. A trihaloalkyl radical may have three of the same halo radicals or a combination of different halo radicals. Non-limiting examples of haloalkyl include fluoromethyl, difluoromethyl, trifluoromethyl (or $CF_3$), difluoroethyl, trifluoroethyl, difluoropropyl, tetrafluoroethyl, pentafluoroethyl, heptafluoropropyl, chloromethyl, dichloromethyl, trichloromethyl, dichloroethyl, trichloroethyl, dichloropropyl, tetrachloroethyl, pentachloroethyl, heptachloropropyl, dichlorofluoromethyl, difluorochloromethyl, bromomethyl, dibromomethyl, tribromomethyl, iodomethyl, diiodomethyl and triiodomethyl.

The term "alkoxy" is RO— where R is alkyl. Non-limiting examples of alkoxy radicals include methoxy, ethoxy, propoxy and tert-butyloxy. The terms "alkyloxy", "alkoxy" and "alkyl-O—" may be used interchangeably.

The term "alkoxyalkyl" is ROR—, where R is alkyl. Examples of alkoxyalkyl radicals include methoxymethyl, methoxyethyl, methoxypropyl, ethoxyethyl and 2-methoxypropan-2-yl. The terms "alkoxyalkyl" and "alkyl-O-alkyl" may be used interchangeably.

The term "cyano" refers to a carbon radical having three of four covalent bonds shared by a single nitrogen atom (e.g.,

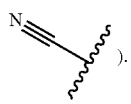).

The term "carbonyl" denotes a carbon radical having two of four covalent bonds shared with a single oxygen atom (e.g.,

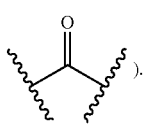 [SMILES: *C(*)=O]).

Carbonyl may be substituted with $R^{53}$ (e.g.,

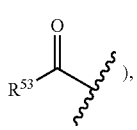), where $R^{53}$ is

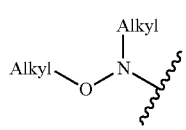

or alkynyl. More specific examples of carbonyl substituted with $R^{53}$ include

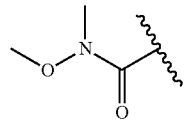 [SMILES: *C(=O)N(C)OC]

and

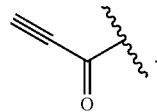 [SMILES: *C(=O)C#C].

The term "thiocarbonyl" denotes a carbon radical having two of four covalent bonds shared with a single sulfur atom.

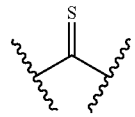 [SMILES: *C(*)=S]

The term "carbamido" denotes aminocarbonyl attached to a parent molecular scaffold through amino (e.g.,

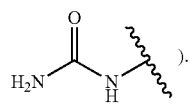).

The term "acyl", is

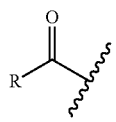

where R may be, for example, H, alkyl, aryl or heteroaryl. More specific examples of acyl include formyl, acetyl and benzoyl.

The term "carboxy" embraces a hydroxy radical attached to one of two unshared bonds in a carbonyl radical (e.g.

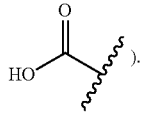).

The term "acylamino" embraces acyl attached to a parent molecular scaffold through amino (e.g.

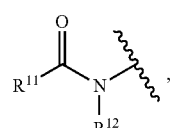, where $R^{11}$ and $R^{12}$ may be (independently), for example, H, alkyl, aryl or heteroaryl). A more specific example of acylamino is acetylamino.

The term "amido" embraces amino attached to a parent molecular scaffold through carbonyl (e.g.,

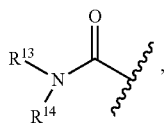

where $R^{13}$ and $R^{14}$ may be (independently), for example, H, alkyl, aryl or heteroaryl). The terms "amido", "carboxamido" and "aminocarbonyl" may be used interchangeably.

The term "monoalkylamino" embraces a single alkyl attached to a parent molecular scaffold through amino (e.g., alkyl-NH-scaffold). A specific non-limiting example of monoalkylamino is N-methylamino.

The term "dialkylamino" embraces two alkyl radicals attached to a parent molecular scaffold through a single amino group (e.g.,

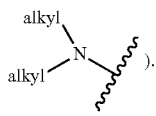

A specific non-limiting example of dialkylamino is N,N-dimethylamino.

The term "aminoalkyl" embraces an amino radical attached to a parent molecular scaffold through an alkyl radical (e.g., $NH_2$-alkyl-scaffold).

The term "aralkoxy" embraces arylalkyl attached to a parent molecular scaffold through an oxygen atom. The terms "arylalkoxy" and "aralkoxy" may be used interchangeably.

The term "aryloxy" is RO—, where R is aryl.

The term "thiol" is HS—.

The term "alkylthio" denotes alkyl attached to a parent molecular scaffold through a sulfur atom.

The term "thiolalkyl" embraces thiol attached to a parent molecular scaffold through alkyl.

The term "arylthio" embraces aryl attached to a parent molecular scaffold through a sulfur atom.

The term sulfamyl embraces amino attached to a molecular scaffold through sulfonyl (e.g., $NH_2SO_2$—). The terms "sulfamyl" and "aminosulfonyl" may be used interchangeably.

The term "cyclic ring" embraces any aromatic or non-aromatic cyclized carbon radical (e.g., aryl and cycloalkyl, respectively) which may contain one or more ring heteroatoms (e.g., heterocyclyl and heteroaryl).

The term "cycloalkyl" embraces any monocyclic, bicyclic or tricyclic cyclized carbon radical of 3 to about 15 carbon atoms that is fully or partially saturated. Cycloalkyl may be fused, for example, to an aryl, cycloalkyl or a heterocyclyl radical.

Cycloalkyl may be substituted with, for example, alkyl, alkoxy, alkoxyalkyl, hydroxyl, hydroxyalkyl, amido, carboxy, acyl, carbamido, cyano, aminoalkyl, thiolalkyl, halo and haloalkyl radicals.

The term "aryl" refers to any monocyclic, bicyclic or tricyclic cyclized carbon radical, wherein at least one ring is aromatic. An aromatic radical may be fused to a non-aromatic cycloalkyl or heterocyclyl radical. Examples of aryl include phenyl and naphthyl.

Aryl may be substituted with, for example, one or more alkyl, alkoxy, alkoxyalkyl,

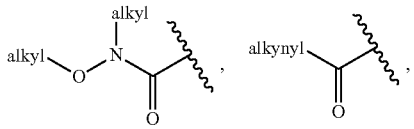

hydroxyl, hydroxyalkyl, amido, carboxy, acyl, carbamido, cyano, aminoalkyl, thiolalkyl, halo and haloalkyl radicals. More specific examples of substituted aryl include:

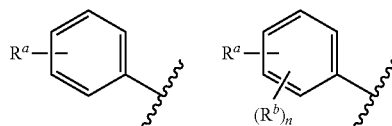

n = 0, 1, 2, 3 or 4

$R^a$ may be, for example, alkyl (e.g., methyl, tert-butyl or isopropyl), alkoxy (e.g., methoxy),

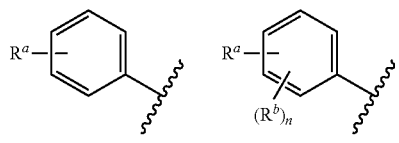

hydroxyl, hydroxyalkyl (e.g., 2-hydroxypropan-2-yl), halo (e.g., F) or trihaloalkyl (e.g., $CF_3$).

$R^b$ may be, for example, alkyl (e.g., methyl, tert-butyl or isopropyl), alkoxy (e.g., methoxy),

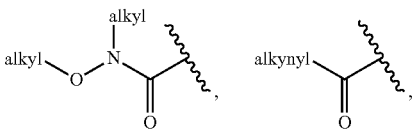

hydroxyl, hydroxyalkyl (e.g., 2-hydroxypropan-2-yl), halo (e.g., F) or trihaloalkyl (e.g., $CF_3$).

Even more specific examples of substituted aryl include:

| Structure | Name |
|---|---|
| 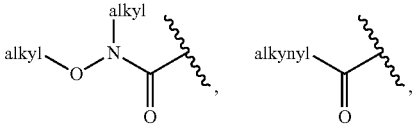 | 3-methylphenyl |
| 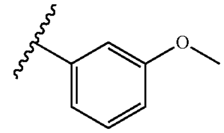 [SMILES: *c1cccc(OC)c1] | 3-methoxyphenyl |

| Structure | Name |
|---|---|
| 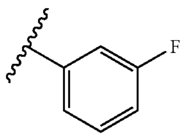 [SMILES: *c1cccc(F)c1] | 3-fluorophenyl |
| 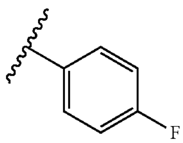 [SMILES: *c1ccc(F)cc1] | 4-fluorophenyl |
| 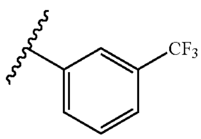 [SMILES: *c1cccc(C(F)(F)F)c1] | 3-trifluoromethylphenyl |
| 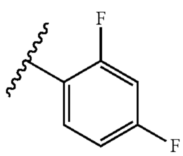 [SMILES: *c1ccc(F)cc1F] | 2,4-difluorophenyl |
| 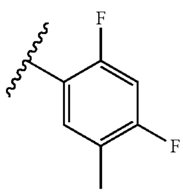 [SMILES: *c1cc(C)c(F)cc1F] | 2,4-difluoro-5-methylphenyl |
| 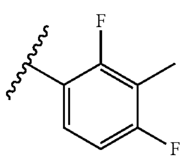 [SMILES: *c1ccc(F)c(C)c1F] | 2,4-difluoro-3-methylphenyl |

The term "aralkyl" embraces aryl attached to a parent molecular scaffold through alkyl and may be used interchangeably with the term "arylalkyl." Examples of aralkyl include benzyl, diphenylmethyl, triphenylmethyl, phenylethyl and diphenylethyl. The terms "benzyl" and "phenylmethyl" may be used interchangeably.

The term "heterocyclyl" refers to any monocyclic, bicyclic or tricyclic ring system having from 5 to about 15 ring members selected from carbon, nitrogen, sulfur and oxygen, wherein at least one ring member is a heteroatom. Heterocyclyl embraces a fully saturated, partially saturated and fully unsaturated radical (e.g., heteroaryl). Heterocyclyl may be fused to another heterocyclyl, aryl or cycloalkyl radical.

Heterocyclyl embraces combinations of different heteroatoms within the same cyclized ring system. When nitrogen is a ring member, heterocyclyl may be attached to the parent molecular scaffold through a ring nitrogen as long as aromaticity is preserved. Non-limiting examples of fully saturated five and six-membered heterocyclyl include: pyrrolidinyl, imidazolidinyl, piperidinyl, piperazinyl, tetrahydrofuranyl, morpholinyl and thiazolidinyl.

Examples of partially saturated heterocyclyl include dihydrothiophenyl

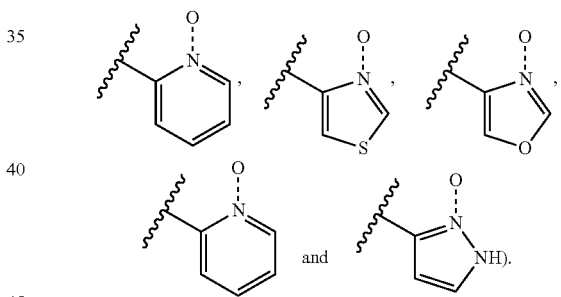

dihydropyranyl, dihydrofuranyl and dihydrothiazolyl.

Heterocyclyl may be substituted with, for example, one or more alkyl, alkoxy, alkoxyalkyl, hydroxyl, hydroxyalkyl, amido, carboxy, acyl, carbamido, cyano, aminoalkyl, thiolalkyl, halo and haloalkyl radicals. Non-limiting of substituted heterocyclyl include 5- or 6-membered heterocyclyl substituted with one or more alkyl, alkoxy, alkoxyalkyl, hydroxyl, hydroxyalkyl, amido, carboxy, acyl, carbamido, cyano, aminoalkyl, thiolalkyl, halo and haloalkyl radicals. Substituted and un-substituted 5- and 6-membered heterocyclyl may be fused to an additional heterocyclyl, aryl or cycloalkyl radical.

The term "heteroaryl" refers to an aromatic heterocyclyl radical. Heteroaryl may be fused to another heterocyclyl, aryl or cycloalkyl radical. Heteroaryl embraces combinations of different heteroatoms within the same cyclized radical. When nitrogen is a ring member, heteroaryl may be attached to a parent molecular scaffold through the ring nitrogen as long as aromaticity is preserved. In preferred embodiments, heteroaryl is a 5- or 6-membered ring system. The term "heteroaryl" embraces N-oxide derivatives of nitrogen-containing heteroaryl (e.g., and

).

Non-limiting examples of heteroaryl include:

| Structure | Name |
|---|---|
| 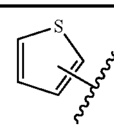 | thienyl |
| 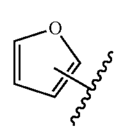 | furyl |
| 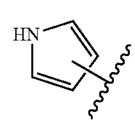 | pyrrolyl |

| Structure | Name |
|---|---|
| (imidazole) | imidazolyl |
| (pyrazole) | pyrazolyl |
| (isothiazole) | isothiazolyl |
| (oxadiazole) | oxadiazolyl |
| (oxatriazole) | oxatriazolyl |
| (thiazole) | thiazolyl |
| (isoxazole) | isoxazolyl |
| (oxazole) | oxazolyl |
| (furazan) | furazanyl |
| (triazole) | triazolyl |
| (pyridine) | pyridyl |
| (pyrazine) | pyrazinyl |
| (pyrimidine) | pyrimidinyl |
| (pyridazine) | pyridazinyl |
| (triazine) | triazinyl |

Heteroaryl may be substituted with, for example, one or more alkyl, alkoxy, alkoxyalkyl, hydroxyl, hydroxyalkyl, amido, carboxy, acyl, carbamido, cyano, aminoalkyl, thioalkyl, halo and haloalkyl radicals. When nitrogen is a ring member, heteroaryl may be substituted at a ring nitrogen as long as aromaticity is preserved. More specific examples of substituted heteroaryl include:

-continued

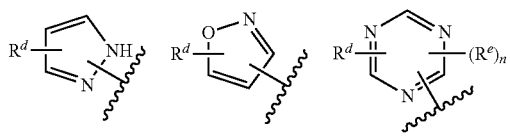

$R^d$ may be, for example, alkyl (e.g., methyl, tert-butyl or isopropyl), alkoxy (e.g., methoxy), hydroxyl, hydroxyalkyl (e.g., 2-hydroxypropan-2-yl), halo (e.g., F) or trihaloalkyl (e.g., $CF_3$);

$R^e$ may be, for example, H, alkyl (e.g., methyl, tert-butyl or iso-propyl), alkoxy (e.g., methoxy), hydroxyl, hydroxyalkyl (e.g., 2-hydroxypropan-2-yl), halo (e.g., F) or trihaloalkyl (e.g., $CF_3$);

where n = 0, 1, 2 or 3.

More specific examples of substituted heteroaryl include:

| Structure | Name |
|---|---|
|  | 6-methylpyridin-2-yl |
|  | 6-fluoropyridin-2-yl |
|  | 6-(trifluoromethyl)pyridin-2-yl |
|  | 3,5-difluoropyridin-2-yl |
|  | 6-methoxypyridin-2-yl |
|  | 2-(tert-butyl)-5-methylpyrimidin-4-yl |
|  | 2-(2-hydroxypropan-2-yl)-5-methylpyrimidin-4-yl |
| 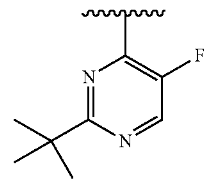 [SMILES: *c1nc(C(C)(C)C)ncc1F] | 5-fluoro-2-(tert-butyl)pyrimidin-4-yl |
| 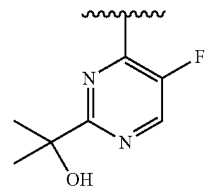 [SMILES: *c1nc(C(C)(C)O)ncc1F] | 5-fluoro-2-(2-hydroxypropan-2-yl)pyrimidin-4-yl |
| 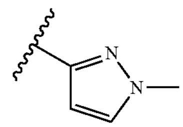 [SMILES: *c1ccn(C)n1] | 1-methyl-1H-pyrazol-3-yl |
| 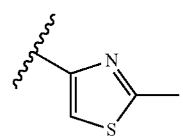 [SMILES: *c1csc(C)n1] | 2-methylthiazol-4-yl |
| 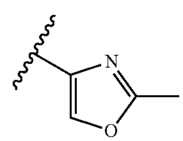 [SMILES: *c1coc(C)n1] | 2-methyloxazol-4-yl |
| 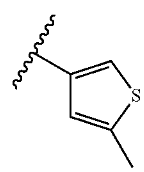 [SMILES: *c1csc(C)c1] | 5-methylthiophen-3-yl |
| 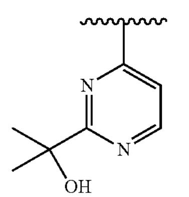 [SMILES: *c1ccnc(C(C)(C)O)n1] | 2-(2-hydroxypropan-2-yl)pyrimidin-4-yl |
| 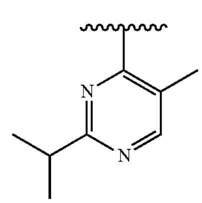 [SMILES: *c1nc(C(C)C)ncc1C] | 2-(iso-propyl)-5-methylpyrimidin-4-yl |
| 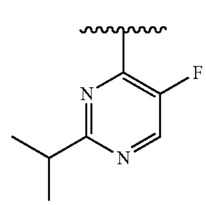 [SMILES: *c1nc(C(C)C)ncc1F] | 5-fluoro-2-(iso-propyl)pyrimidin-4-yl |

| Structure | Name |
| --- | --- |
| (structure) | 2-(iso-propyl)pyrimidin-4-yl |
| (structure) | 2-(tert-butyl)pyrimidin-4-yl |

The term "pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals (e.g., canines) and in humans.

The term "pharmaceutically-acceptable salt" refers to a salt which may enhance desired pharmacological activity or may enhance stability of a compound. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, hydriodic acid, sulfuric acid, nitric acid and phosphoric acid. Examples of acid addition salts formed with organic acids include acetic acid, propionic acid, hexanoic acid, heptanoic acid, cyclopentanepropionic acid, glycolic acid, pyruvic acid, lactic acid, citric acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, glucoheptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxynaphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases (e.g., cytosine, thymine, uracil and guanine).

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

The term "combination therapy" (or co-therapy), in defining use of the compounds of the present invention in combination with other pharmaceutically active compounds, as described herein, is intended to embrace administration of each agent in a sequential or simultaneous manner in a regimen that will provide beneficial effects arising from the co-action of the drug combination. Such co-administration of these agents may be oral ingestion of a single capsule having a fixed ratio of these active agents or ingestion of multiple, separate capsules for each agent. "Combination therapy" will also include simultaneous or sequential administration by intravenous, intramuscular or other parenteral routes into the body, including direct absorption through mucous membrane tissues, as found in the sinus passages. Sequential administration also includes drug combinations where the individual elements may be administered at different times and/or by different routes but which co-act in combination to provide a beneficial effect. It is expected that combination therapy of the compounds of the present invention and other pharmaceutically active compounds, as described herein, will result in co-action of the compounds, to provide a pharmacokinetic interaction, or a pharmacodynamic interaction, or both, where the compounds are administered either simultaneously or sequentially, to permit such co-action.

A compound of the present invention can exist in tautomeric, geometric or stereoisomeric (including atropisomers) forms. An ester, metabolite, oxime, prodrug, onium, hydrate, solvate and N-oxide of a compound of Formula (I) are also embraced by the invention. The present invention contemplates all such compounds, including cis- and trans-geometric isomers, R- and S-enantiomers, diastereomers, d-isomers, l-isomers, atropisomers, mixtures of isomers and racemates thereof, as falling within the scope of the invention.

The term "solvate" denotes a molecular or ionic complex of molecules or ions of solvent with those of a compound of the present invention. The term "solvate" embraces the term "hydrate".

The term "hydrate" denotes a compound of the present complexed with water.

List of abbreviations:
ACN acetonitrile
Boc tert-butyloxycarbonyl
DCI dicyclohexylcarbodiimide
DCM dichloromethane or methylenechloride
DIPEA diisopropylethylamine
DMAP 4-dimethylaminopyridine or N,N-dimethylaminopyridine
DME 1,2-dimethoxyethane
DMF N,N-dimethylformamide
DMSO dimethylsulfoxide
eq. equivalents
EtOAC ethyl acetate
EtOH ethanol
Fmoc fluorenylmethyloxycarbonyl chloride
HPLC high performance liquid chromatography hrs hours
$K_2CO_3$ potassium carbonate
LC/MS liquid chromatography mass spectrometry
LC/MS/MS liquid chromatography tandem mass spectrometry
MeOH methanol
$MgSO_4$ magnesium sulfate
min. minute(s)
mL milliliter
mmol millimole
$Na_2S_2O_3$ sodium thiosulfate
$Na_2SO_4$ sodium sulfate
NaH sodium hydride
$NaHCO_3$ sodium bicarbonate
NaI sodium iodide
$NaIO_4$ sodium periodate
$NaOCH_3$ sodium methoxide
NBS N-bromosuccinimide
NCS N-chlorosuccinimide
NMR nuclear magnetic resonance
psi pounds per square inch
$RuCl_3$ ruthenium trichloride hydrate
TEA triethylamine
TFA trifluoroacetic acid
THF tetrahydrofuran
TLC thin layer chromatography
TSA p-toluenesulfonic acid.

In another embodiment, there is provided a compound having the structure of Formula (II):

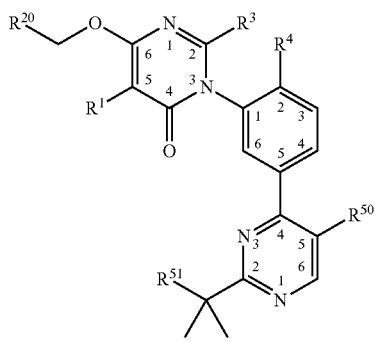

and a pharmaceutically acceptable salt or solvate thereof, wherein: $R^1$ is selected from the group consisting of methyl, ethyl, chloro and bromo; $R^3$ is selected from the group consisting of —H and methyl; $R^4$ is selected from the group consisting of —H, methyl and chloro; $R^{20}$ is phenyl substituted with one or more substituents selected from the group consisting of $C_{1-3}$alkyl, $C_{1-3}$alkoxy, amido, carboxy, formyl, carbamido, cyano, halo and halo$C_{1-3}$alkyl; or $R^{20}$ is five- or six-membered heteroaryl substituted with one or more substituents selected from the group consisting of $C_{1-3}$ alkyl, $C_{1-3}$alkoxy, $C_{1-5}$alkyl-O—$C_{1-5}$alkyl, amido, carboxy, formyl, carbamido, cyano, halo and halo$C_{1-3}$alkyl; $R^{50}$ is selected from the group consisting of —H, $C_{1-3}$alkyl and halo; and $R^{51}$ is selected from the group consisting of —H, $C_{1-3}$alkyl, hydroxyl, amino and thiol.

In another embodiment of Formula (II), $R^1$ is selected from the group consisting of methyl, chloro and bromo; $R^3$ is methyl; $R^4$ is selected from the group consisting —H, methyl and chloro; $R^{20}$ is phenyl substituted with one or more substituents selected from the group consisting of methyl, methoxy, amido, carboxy, formyl, carbamido, cyano and fluoro; or $R^{20}$ is selected from the group consisting thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl and triazinyl, wherein the thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl or triazinyl is substituted with one or more substituents selected from the group consisting of methyl, methoxy, amido, carboxy, formyl, carbamido, cyano, fluoro and trifluoromethyl; $R^{50}$ is selected from the group consisting —H, methyl and fluoro; and $R^{51}$ is selected from the group consisting of —H, methyl and hydroxyl.

In another embodiment of Formula (II), $R^1$ is selected from the group consisting of methyl, chloro and bromo; $R^3$ is methyl; $R^4$ is selected from the group consisting —H, methyl and chloro; $R^{20}$ is phenyl substituted with one or more substituents selected from the group consisting of methyl, methoxy, amido, carboxy, formyl carbamido, cyano and fluoro; or $R^{20}$ is selected from the group consisting thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl and triazinyl, wherein the thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl or triazinyl is substituted with one or more substituents selected from the group consisting of methyl, methoxy, amido, carboxy, formyl, carbamido, cyano, fluoro and trifluoromethyl; $R^{50}$ is methyl; and $R^{51}$ is selected from the group consisting of methyl and hydroxyl.

In yet another embodiment of Formula (II), $R^1$ is selected from the group consisting of chloro and bromo; $R^3$ is methyl; $R^4$ is methyl; $R^{20}$ is phenyl substituted with one or more substituents selected from the group consisting of methyl, methoxy and fluoro; or $R^{20}$ is selected from the group consisting pyridinyl, oxazolyl and thiazolyl, wherein the pyridinyl, oxazolyl or thiazolyl is substituted with one or more substituents selected from the group consisting of methyl, methoxy, fluoro and trifluoromethyl; $R^{50}$ is methyl; and $R^{51}$ is selected from the group consisting of methyl and hydroxyl.

In yet another embodiment of Formula (II), $R^1$ is selected from the group consisting of chloro and bromo; $R^3$ is methyl; $R^4$ is methyl; $R^{20}$ is selected from the group consisting of methoxyphenyl, methylphenyl, fluorophenyl, difluorophenyl and methyldifluorophenyl; or $R^{20}$ is selected from the group consisting methylpyridinyl, fluoropyridinyl, difluoropyridinyl, trifluoromethylpyridinyl, methyloxazolyl and methylthiazolyl; $R^{50}$ is methyl; and $R^{51}$ is selected from the group consisting of methyl and hydroxyl.

In yet another embodiment of Formula (II), $R^1$ is selected from the group consisting of chloro and bromo; $R^3$ is methyl; $R^4$ is methyl; $R^{20}$ is selected from the group consisting of 3-methoxyphenyl; 3-methylphenyl; 2,4-difluorophenyl; 4-fluorophenyl; 2,4-difluoro-3-methylphenyl; 2,4-difluoro-5-methylphenyl; 6-fluoropyridin-2-yl; 6-methylpyridin-2-yl; 6-(trifluoromethyl) pyridin-2-yl; 3,5-difluoropyridin-2-yl; 2-methyloxazol-4-yl and 2-methylthiazol-4-yl; $R^{50}$ is methyl; and $R^{51}$ is selected from the group consisting of methyl and hydroxyl.

Non-limiting examples of Formula (II) compounds include the following compounds and pharmaceutically acceptable salts or solvates thereof:

| Compound | Structure | Name |
|---|---|---|
| 1 | 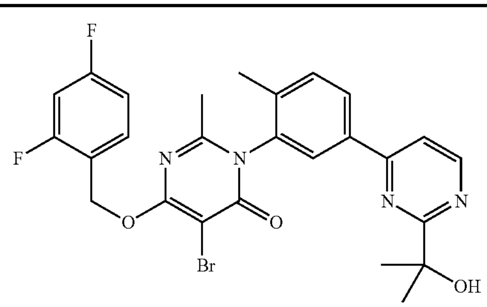 | 5-bromo-6-((2,4-difluorobenzyl)oxy)-3-(5-(2-(2-hydroxypropan-2-yl)pyrimidin-4-yl)-2-methylphenyl)-2-methylpyrimidin-4(3H)-one |

-continued

| Compound | Structure | Name |
|---|---|---|
| 2 | 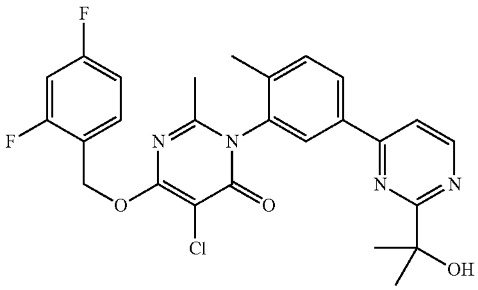 [SMILES: Cc1ccc(-c2ccnc(C(C)(C)O)n2)cc1-n1c(C)nc(OCc2ccc(F)cc2F)c(Br)c1=O] | 5-chloro-6-((2,4-difluorobenzyl)oxy)-3-(5-(2-(2-hydroxypropan-2-yl)pyrimidin-4-yl)-2-methylphenyl)-2-methylpyrimidin-4(3H)-one |
| 3 | 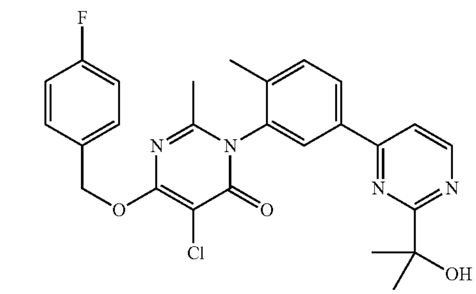 [SMILES: Cc1ccc(-c2ccnc(C(C)(C)O)n2)cc1-n1c(C)nc(OCc2ccc(F)cc2)c(Cl)c1=O] | 5-chloro-6-((4-fluorobenzyl)oxy)-3-(5-(2-(2-hydroxypropan-2-yl)pyrimidin-4-yl)-2-methylphenyl)-2-methylpyrimidin-4(3H)-one |
| 4 | 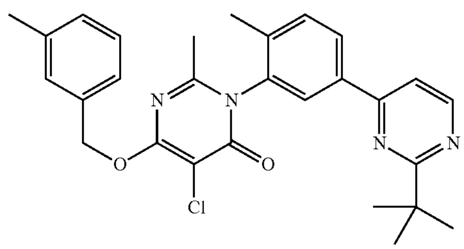 [SMILES: Cc1cccc(COc2nc(C)n(-c3cc(-c4ccnc(C(C)(C)C)n4)ccc3C)c(=O)c2Cl)c1] | 3-(5-(2-(tert-butyl)pyrimidin-4-yl)-2-methylphenyl)-5-chloro-2-methyl-6-((3-methylbenzyl)oxy)pyrimidin-4(3H)-one |
| 5 | 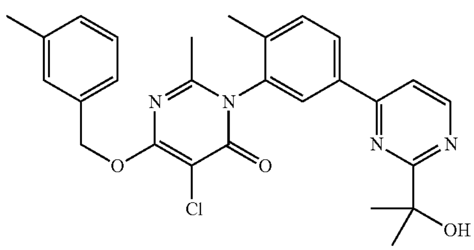 | 5-chloro-3-(5-(2-(2-hydroxypropan-2-yl)pyrimidin-4-yl)-2-methylphenyl)-2-methyl-6-((3-methylbenzyl)oxy)pyrimidin-4(3H)-one |
| 6 | 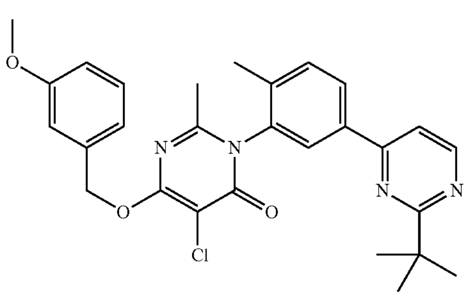 [SMILES: COc1cccc(COc2nc(C)n(-c3cc(-c4ccnc(C(C)(C)C)n4)ccc3C)c(=O)c2Cl)c1] | 3-(5-(2-(tert-butyl)pyrimidin-4-yl)-2-methylphenyl)-5-chloro-6-((3-methoxybenzyl)oxy)-2-methylpyrimidin-4(3H)-one |

-continued

| Compound | Structure | Name |
|---|---|---|
| 7 | 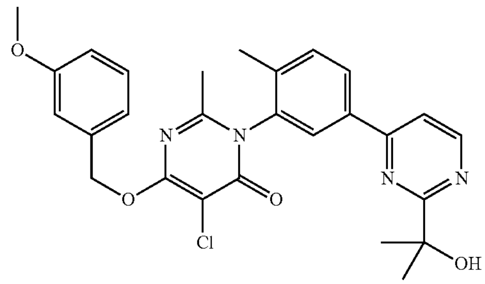 [SMILES: COc1cccc(COc2nc(C)n(-c3cc(-c4ccnc(C(C)(C)O)n4)ccc3C)c(=O)c2Cl)c1] | 5-chloro-3-(5-(2-(2-hydroxypropan-2-yl)pyrimidin-4-yl)-2-methylphenyl)-6-((3-methoxybenzyl)oxy)-2-methylpyrimidin-4(3H)-one |
| 8 | 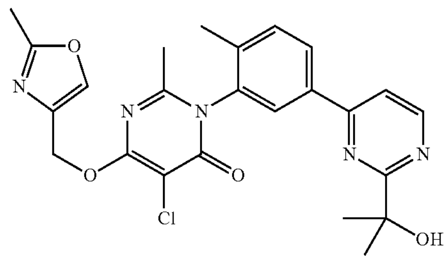 [SMILES: Cc1nc(COc2nc(C)n(-c3cc(-c4ccnc(C(C)(C)O)n4)ccc3C)c(=O)c2Cl)co1] | 5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one |
| 9 | 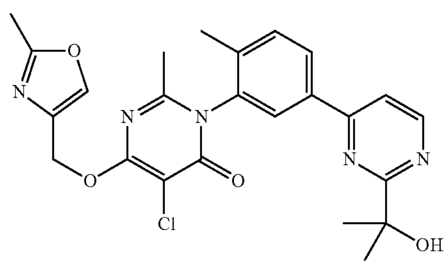 | (−)-5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one |
| 10 | 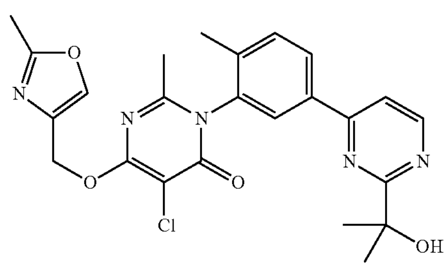 [SMILES: Cc1nc(COc2nc(C)n(-c3cc(-c4ccnc(C(C)(C)O)n4)ccc3C)c(=O)c2Cl)co1] | (+)-5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one |
| 11 | 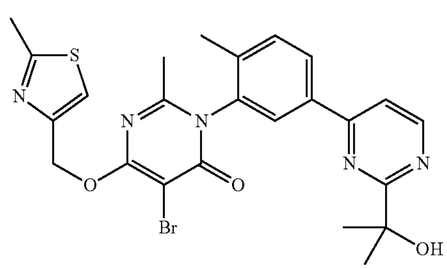 [SMILES: Cc1nc(COc2nc(C)n(-c3cc(-c4ccnc(C(C)(C)O)n4)ccc3C)c(=O)c2Cl)cs1] | 5-bromo-3-(5-(2-(2-hydroxypropan-2-yl)pyrimidin-4-yl)-2-methylphenyl)-2-methyl-6-((2-methylthiazol-4-yl)methoxy)pyrimidin-4(3H)-one |
| 12 | 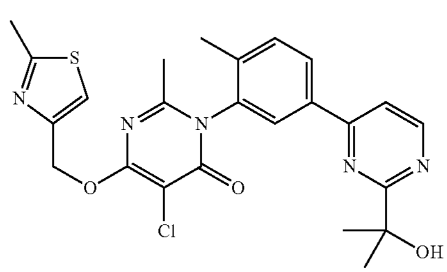 | 5-chloro-3-(5-(2-(2-hydroxypropan-2-yl)pyrimidin-4-yl)-2-methylphenyl)-2-methyl-6-((2-methylthiazol-4-yl)methoxy)pyrimidin-4(3H)-one |

| Compound | Structure | Name |
|---|---|---|
| 13 | 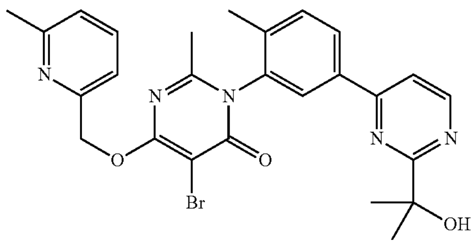 | 5-bromo-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one |
| 14 | 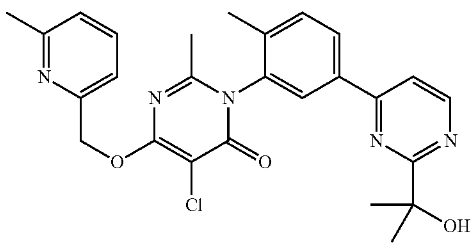 [SMILES: Cc1cccc(COc2nc(C)n(-c3cc(-c4ccnc(C(C)(C)O)n4)ccc3C)c(=O)c2Cl)n1] | 5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one |
| 15 | 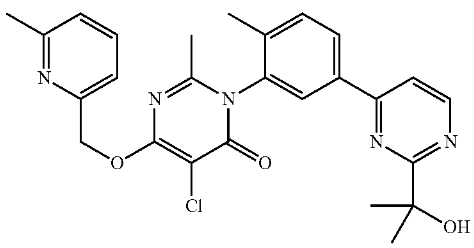 [SMILES: Cc1cccc(COc2nc(C)n(-c3cc(-c4ccnc(C(C)(C)O)n4)ccc3C)c(=O)c2Cl)n1] | (−)-5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one |
| 16 | 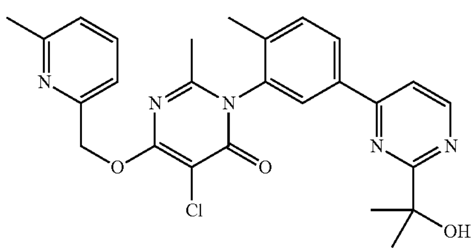 | (+)-5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one |
| 17 | 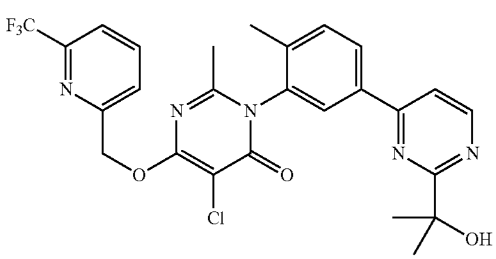 [SMILES: Cc1ccc(-c2ccnc(C(C)(C)O)n2)cc1-n1c(C)nc(OCc2cccc(C(F)(F)F)n2)c(Cl)c1=O] | 5-chloro-3-(5-(2-(2-hydroxypropan-2-yl)pyrimidin-4-yl)-2-methylphenyl)-2-methyl-6-((6-(trifluoromethyl)pyridin-2-yl)methoxy)pyrimidin-4(3H)-one |
| 18 | 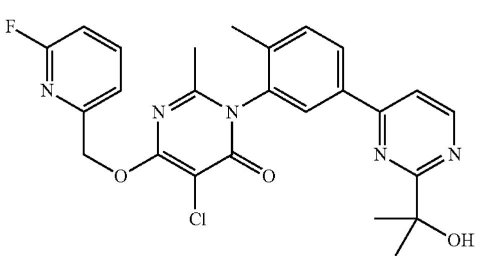 [SMILES: Cc1ccc(-c2ccnc(C(C)(C)O)n2)cc1-n1c(C)nc(OCc2cccc(F)n2)c(Cl)c1=O] | 5-chloro-6-((6-fluoropyridin-2-yl)methoxy)-3-(5-(2-(2-hydroxypropan-2-yl)pyrimidin-4-yl)-2-methylphenyl)-2-methylpyrimidin-4(3H)-one |

| Compound | Structure | Name |
| --- | --- | --- |
| 19 | 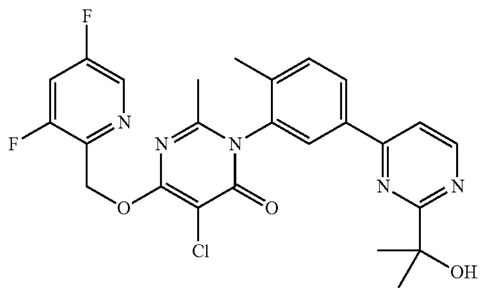 [SMILES: Cc1ccc(-c2ccnc(C(C)(C)O)n2)cc1-n1c(C)nc(OCc2ncc(F)cc2F)c(Cl)c1=O] | 5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one |
| 20 | 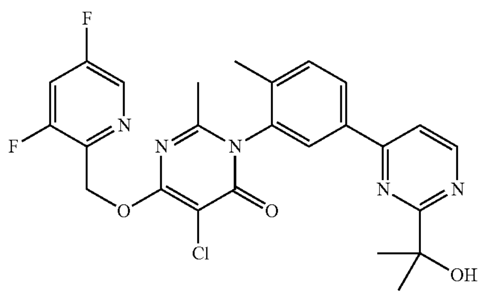 [SMILES: Cc1ccc(-c2ccnc(C(C)(C)O)n2)cc1-n1c(C)nc(OCc2ncc(F)cc2F)c(Cl)c1=O] | (+)-5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one |
| 21 | 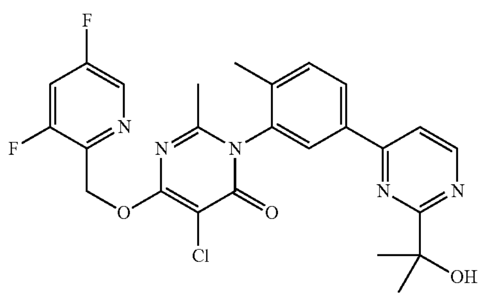 [SMILES: Cc1ccc(-c2ccnc(C(C)(C)O)n2)cc1-n1c(C)nc(OCc2ncc(F)cc2F)c(Cl)c1=O] | (−)-5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one |
| 22 | 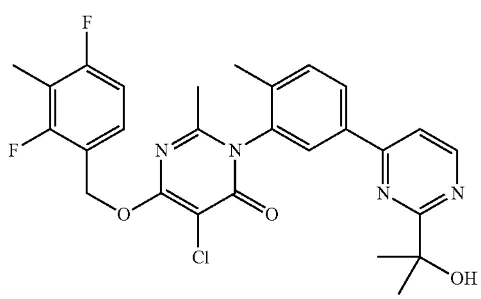 [SMILES: Cc1ccc(-c2ccnc(C(C)(C)O)n2)cc1-n1c(C)nc(OCc2ccc(F)c(C)c2F)c(Cl)c1=O] | 5-chloro-6-((2,4-difluoro-3-methylbenzyl)oxy)-3-(5-(2-(2-hydroxypropan-2-yl)pyrimidin-4-yl)-2-methylphenyl)-2-methylpyrimidin-4(3H)-one |
| 23 | 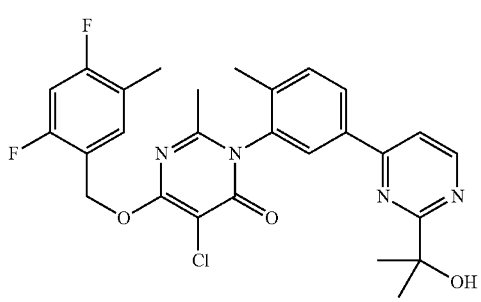 [SMILES: Cc1cc(COc2nc(C)n(-c3cc(-c4ccnc(C(C)(C)O)n4)ccc3C)c(=O)c2Cl)c(F)cc1F] | 5-chloro-6-((2,4-difluoro-5-methylbenzyl)oxy)-3-(5-(2-(2-hydroxypropan-2-yl)pyrimidin-4-yl)-2-methylphenyl)-2-methylpyrimidin-4(3H)-one |

-continued

| Compound | Structure | Name |
|---|---|---|
| 24 | 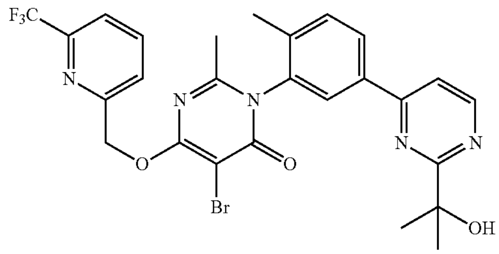 [SMILES: Cc1ccc(-c2ccnc(C(C)(C)O)n2)cc1-n1c(C)nc(OCc2cccc(C(F)(F)F)n2)c(Br)c1=O] | 5-bromo-3-(5-(2-(2-hydroxypropan-2-yl)pyrimidin-4-yl)-2-methylphenyl)-2-methyl-6-((6-(trifluoromethyl)pyridin-2-yl)methoxy)pyrimidin-4(3H)-one |
| 25 | 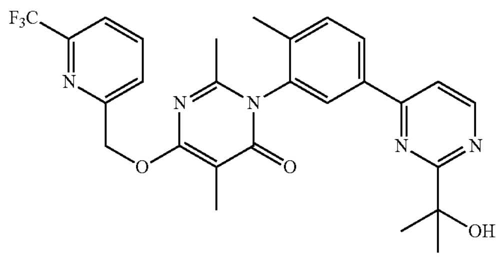 | 3-(5-(2-(2-hydroxypropan-2-yl)pyrimidin-4-yl)-2-methylphenyl)-2,5-dimethyl-6-((6-(trifluoromethyl)pyridin-2-yl)methoxy)pyrimidin-4(3H)-one |
| 26 | 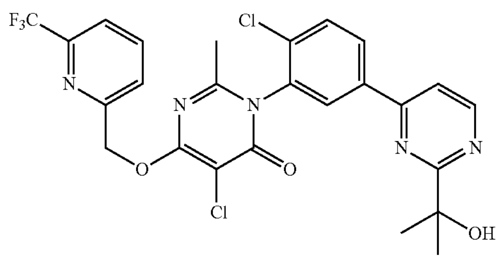 [SMILES: Cc1nc(OCc2cccc(C(F)(F)F)n2)c(Cl)c(=O)n1-c1cc(-c2ccnc(C(C)(C)O)n2)ccc1Cl] | 5-chloro-3-(2-chloro-5-(2-(2-hydroxypropan-2-yl)pyrimidin-4-yl)phenyl)-2-methyl-6-((6-(trifluoromethyl)pyridin-2-yl)methoxy)pyrimidin-4(3H)-one |
| 27 | 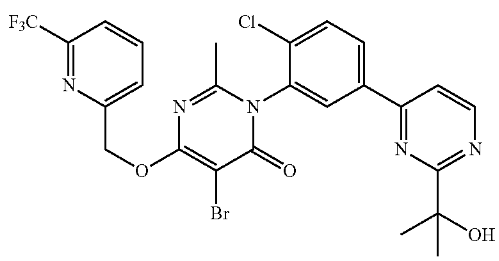 [SMILES: Cc1nc(OCc2cccc(C(F)(F)F)n2)c(Br)c(=O)n1-c1cc(-c2ccnc(C(C)(C)O)n2)ccc1Cl] | 5-bromo-3-(2-chloro-5-(2-(2-hydroxypropan-2-yl)pyrimidin-4-yl)phenyl)-2-methyl-6-((6-(trifluoromethyl)pyridin-2-yl)methoxy)pyrimidin-4(3H)-one |
| 28 | 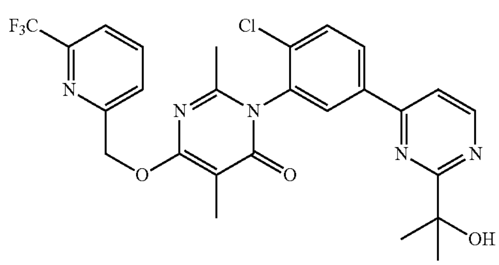 [SMILES: Cc1c(OCc2cccc(C(F)(F)F)n2)nc(C)n(-c2cc(-c3ccnc(C(C)(C)O)n3)ccc2Cl)c1=O] | 3-(2-chloro-5-(2-(2-hydroxypropan-2-yl)pyrimidin-4-yl)phenyl)-2,5-dimethyl-6-((6-(trifluoromethyl)pyridin-2-yl)methoxy)pyrimidin-4(3H)-one |
| 29 | 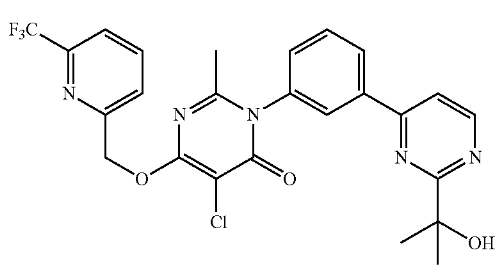 [SMILES: Cc1nc(OCc2cccc(C(F)(F)F)n2)c(Cl)c(=O)n1-c1cccc(-c2ccnc(C(C)(C)O)n2)c1] | 5-chloro-3-(3-(2-(2-hydroxypropan-2-yl)pyrimidin-4-yl)phenyl)-2-methyl-6-((6-(trifluoromethyl)pyridin-2-yl)methoxy)pyrimidin-4(3H)-one |

-continued

| Compound | Structure | Name |
|---|---|---|
| 30 | 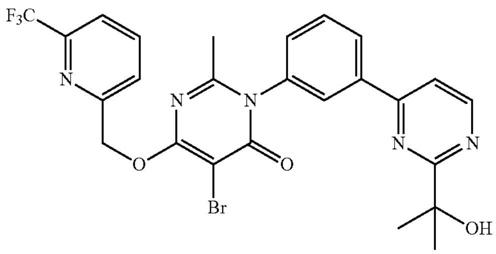 [SMILES: Cc1nc(OCc2cccc(C(F)(F)F)n2)c(Br)c(=O)n1-c1cccc(-c2ccnc(C(C)(C)O)n2)c1] | 5-bromo-3-(3-(2-(2-hydroxypropan-2-yl)pyrimidin-4-yl)phenyl)-2-methyl-6-((6-(trifluoromethyl)pyridin-2-yl)methoxy)pyrimidin-4(3H)-one |
| 31 | 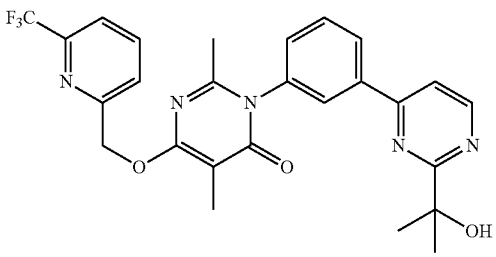 | 3-(3-(2-(2-hydroxypropan-2-yl)pyrimidin-4-yl)phenyl)-2,5-dimethyl-6-((6-(trifluoromethyl)pyridin-2-yl)methoxy)pyrimidin-4(3H)-one |
| 32 | 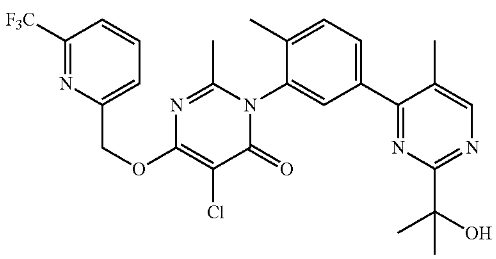 | 5-chloro-3-(5-(2-(2-hydroxypropan-2-yl)-5-methylpyrimidin-4-yl)-2-methylphenyl)-2-methyl-6-((6-(trifluoromethyl)pyridin-2-yl)methoxy)pyrimidin-4(3H)-one |
| 33 | 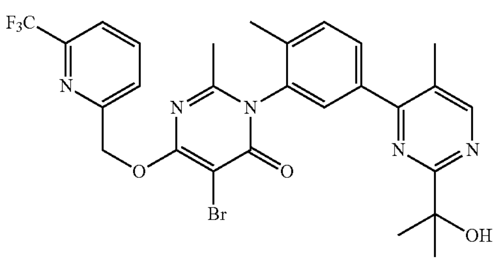 | 5-bromo-3-(5-(2-(2-hydroxypropan-2-yl)-5-methylpyrimidin-4-yl)-2-methylphenyl)-2-methyl-6-((6-(trifluoromethyl)pyridin-2-yl)methoxy)pyrimidin-4(3H)-one |
| 34 | 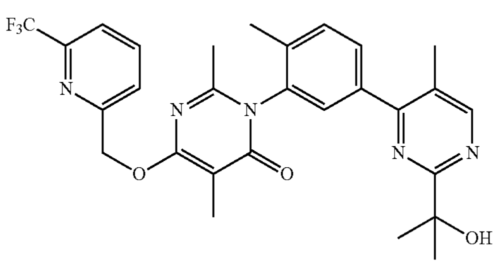 | 3-(5-(2-(2-hydroxypropan-2-yl)-5-methylpyrimidin-4-yl)-2-methylphenyl)-2,5-dimethyl-6-((6-(trifluoromethyl)pyridin-2-yl)methoxy)pyrimidin-4(3H)-one |
| 35 | 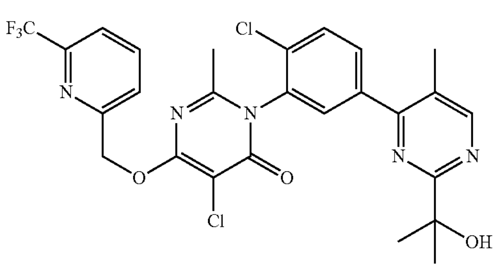 [SMILES: Cc1cnc(C(C)(C)O)nc1-c1ccc(Cl)c(-n2c(C)nc(OCc3cccc(C(F)(F)F)n3)c(Cl)c2=O)c1] | 5-chloro-3-(2-chloro-5-(2-(2-hydroxypropan-2-yl)-5-methylpyrimidin-4-yl)phenyl)-2-methyl-6-((6-(trifluoromethyl)pyridin-2-yl)methoxy)pyrimidin-4(3H)-one |

-continued

| Compound | Structure | Name |
|---|---|---|
| 36 | 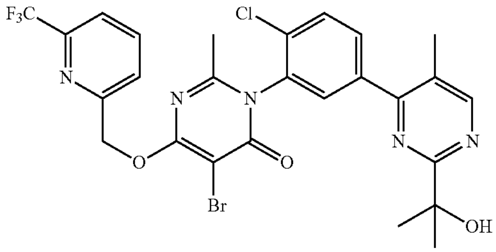 [SMILES: Cc1cnc(C(C)(C)O)nc1-c1ccc(Cl)c(-n2c(C)nc(OCc3cccc(C(F)(F)F)n3)c(Br)c2=O)c1] | 5-bromo-3-(2-chloro-5-(2-(2-hydroxypropan-2-yl)-5-methylpyrimidin-4-yl)phenyl)-2-methyl-6-((6-(trifluoromethyl)pyridin-2-yl)methoxy)pyrimidin-4(3H)-one |
| 37 | 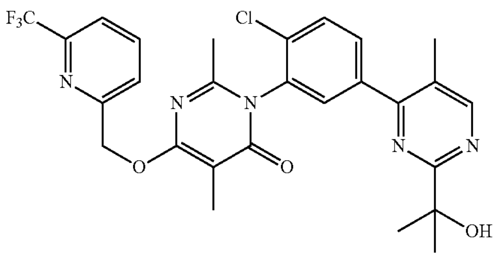 [SMILES: Cc1cnc(C(C)(C)O)nc1-c1ccc(Cl)c(-n2c(C)nc(OCc3cccc(C(F)(F)F)n3)c(C)c2=O)c1] | 3-(2-chloro-5-(2-(2-hydroxypropan-2-yl)-5-methylpyrimidin-4-yl)phenyl)-2,5-dimethyl-6-((6-(trifluoromethyl)pyridin-2-yl)methoxy)pyrimidin-4(3H)-one |
| 38 | 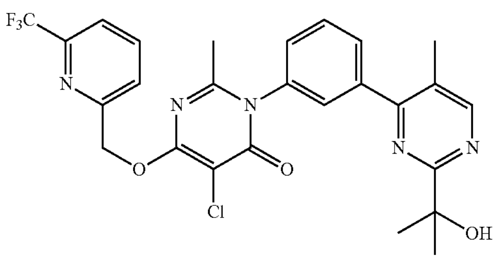 [SMILES: Cc1cnc(C(C)(C)O)nc1-c1cccc(-n2c(C)nc(OCc3cccc(C(F)(F)F)n3)c(Cl)c2=O)c1] | 5-chloro-3-(3-(2-(2-hydroxypropan-2-yl)-5-methylpyrimidin-4-yl)phenyl)-2-methyl-6-((6-(trifluoromethyl)pyridin-2-yl)methoxy)pyrimidin-4(3H)-one |
| 39 | 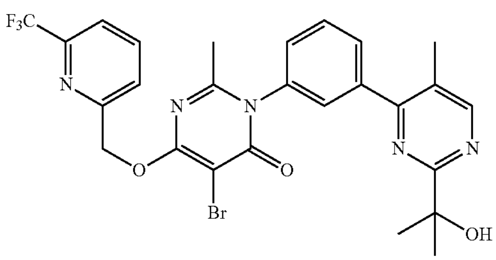 [SMILES: Cc1cnc(C(C)(C)O)nc1-c1cccc(-n2c(C)nc(OCc3cccc(C(F)(F)F)n3)c(Br)c2=O)c1] | 5-bromo-3-(3-(2-(2-hydroxypropan-2-yl)-5-methylpyrimidin-4-yl)phenyl)-2-methyl-6-((6-(trifluoromethyl)pyridin-2-yl)methoxy)pyrimidin-4(3H)-one |
| 40 | 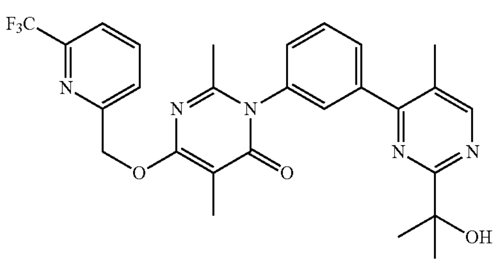 [SMILES: Cc1cnc(C(C)(C)O)nc1-c1cccc(-n2c(C)nc(OCc3cccc(C(F)(F)F)n3)c(C)c2=O)c1] | 3-(3-(2-(2-hydroxypropan-2-yl)-5-methylpyrimidin-4-yl)phenyl)-2,5-dimethyl-6-((6-(trifluoromethyl)pyridin-2-yl)methoxy)pyrimidin-4(3H)-one |
| 41 | 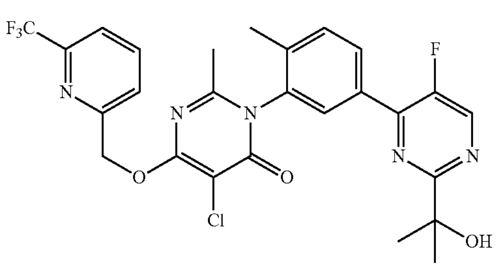 | 5-chloro-3-(5-(5-fluoro-2-(2-hydroxypropan-2-yl)pyrimidin-4-yl)-2-methylphenyl)-2-methyl-6-((6-(trifluoromethyl)pyridin-2-yl)methoxy)pyrimidin-4(3H)-one |

-continued

| Compound | Structure | Name |
|---|---|---|
| 42 | 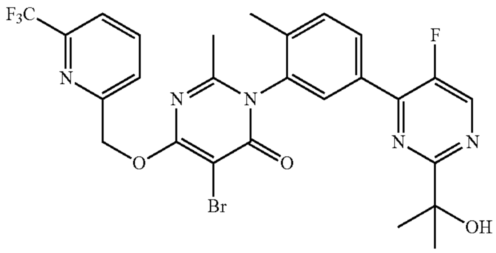 [SMILES: Cc1ccc(-c2nc(C(C)(C)O)ncc2F)cc1-n1c(C)nc(OCc2cccc(C(F)(F)F)n2)c(Br)c1=O] | 5-bromo-3-(5-(5-fluoro-2-(2-hydroxypropan-2-yl)pyrimidin-4-yl)-2-methylphenyl)-2-methyl-6-((6-(trifluoromethyl)pyridin-2-yl)methoxy)pyrimidin-4(3H)-one |
| 43 | 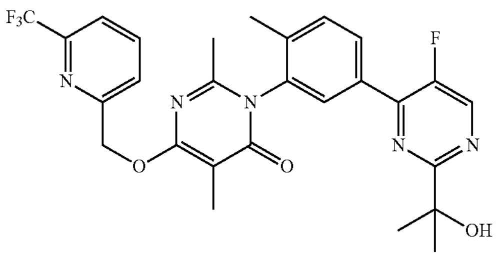 | 3-(5-(5-fluoro-2-(2-hydroxypropan-2-yl)pyrimidin-4-yl)-2-methylphenyl)-2,5-dimethyl-6-((6-(trifluoromethyl)pyridin-2-yl)methoxy)pyrimidin-4(3H)-one |
| 44 | 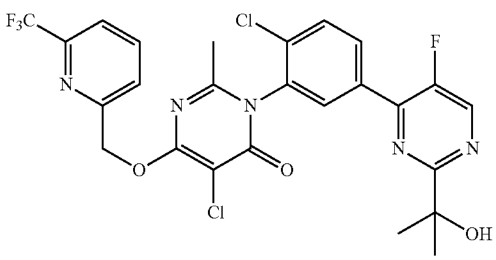 | 5-chloro-3-(2-chloro-5-(5-fluoro-2-(2-hydroxypropan-2-yl)pyrimidin-4-yl)phenyl)-2-methyl-6-((6-(trifluoromethyl)pyridin-2-yl)methoxy)pyrimidin-4(3H)-one |
| 45 | 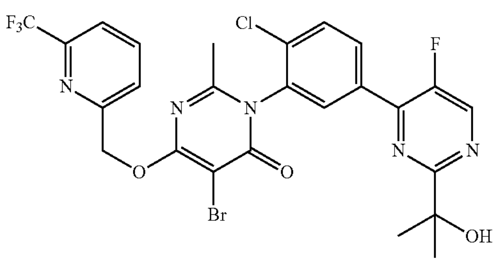 | 5-bromo-3-(2-chloro-5-(5-fluoro-2-(2-hydroxypropan-2-yl)pyrimidin-4-yl)phenyl)-2-methyl-6-((6-(trifluoromethyl)pyridin-2-yl)methoxy)pyrimidin-4(3H)-one |
| 46 | 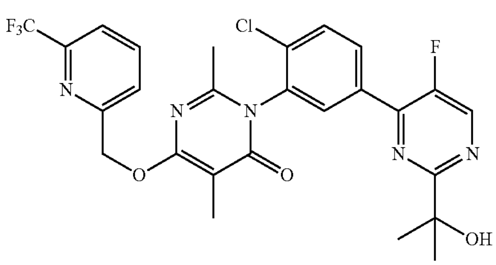 [SMILES: Cc1c(OCc2cccc(C(F)(F)F)n2)nc(C)n(-c2cc(-c3nc(C(C)(C)O)ncc3F)ccc2Cl)c1=O] | 3-(2-chloro-5-(5-fluoro-2-(2-hydroxypropan-2-yl)pyrimidin-4-yl)phenyl)-2,5-dimethyl-6-((6-(trifluoromethyl)pyridin-2-yl)methoxy)pyrimidin-4(3H)-one |
| 47 | 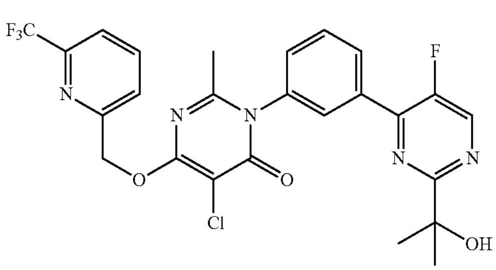 | 5-chloro-3-(3-(5-fluoro-2-(2-hydroxypropan-2-yl)pyrimidin-4-yl)phenyl)-2-methyl-6-((6-(trifluoromethyl)pyridin-2-yl)methoxy)pyrimidin-4(3H)-one |

-continued

| Compound | Structure | Name |
|---|---|---|
| 48 | 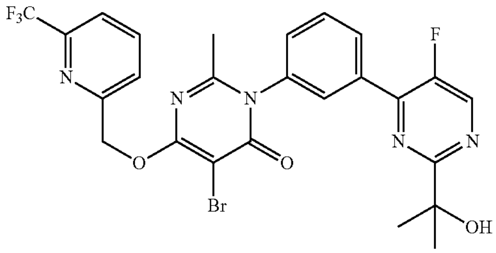 [SMILES: Cc1nc(OCc2cccc(C(F)(F)F)n2)c(Cl)c(=O)n1-c1cccc(-c2nc(C(C)(C)O)ncc2F)c1] | 5-bromo-3-(3-(5-fluoro-2-(2-hydroxypropan-2-yl)pyrimidin-4-yl)phenyl)-2-methyl-6-((6-(trifluoromethyl)pyridin-2-yl)methoxy)pyrimidin-4(3H)-one |
| 49 | 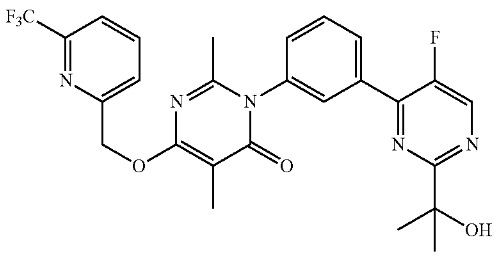 [SMILES: Cc1c(OCc2cccc(C(F)(F)F)n2)nc(C)n(-c2cccc(-c3nc(C(C)(C)O)ncc3F)c2)c1=O] | 3-(3-(5-fluoro-2-(2-hydroxypropan-2-yl)pyrimidin-4-yl)phenyl)-2,5-dimethyl-6-((6-(trifluoromethyl)pyridin-2-yl)methoxy)pyrimidin-4(3H)-one |
| 50 | 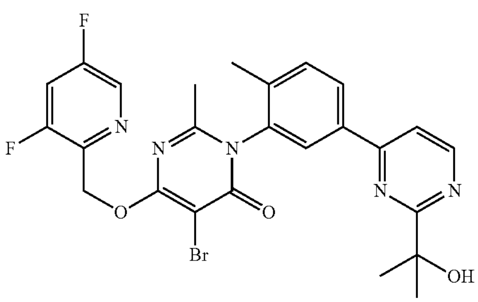 [SMILES: Cc1ccc(-c2ccnc(C(C)(C)O)n2)cc1-n1c(C)nc(OCc2ncc(F)cc2F)c(Br)c1=O] | 5-bromo-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one |
| 51 | 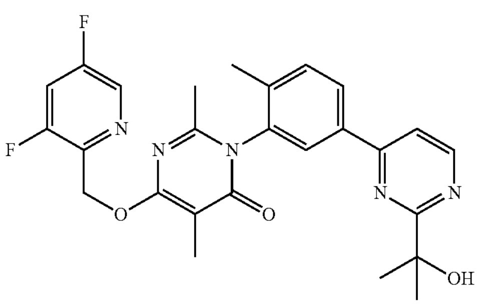 | 6-((3,5-difluoropyridin-2-yl)methoxy)-3-(5-(2-(2-hydroxypropan-2-yl)pyrimidin-4-yl)-2-methylphenyl)-2,5-dimethylpyrimidin-4(3H)-one |
| 52 | 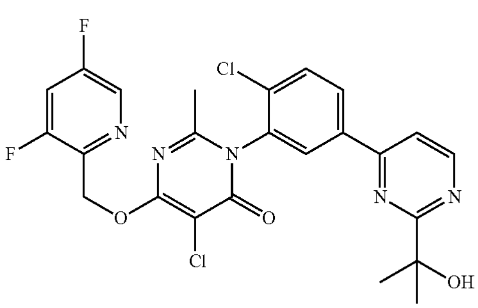 [SMILES: Cc1nc(OCc2ncc(F)cc2F)c(Cl)c(=O)n1-c1cc(-c2ccnc(C(C)(C)O)n2)ccc1Cl] | 5-chloro-3-(2-chloro-5-(2-(2-hydroxypropan-2-yl)pyrimidin-4-yl)phenyl)-6-((3,5-difluoropyridin-2-yl)methoxy)-2-methylpyrimidin-4(3H)-one |

| Compound | Structure | Name |
| --- | --- | --- |
| 53 | 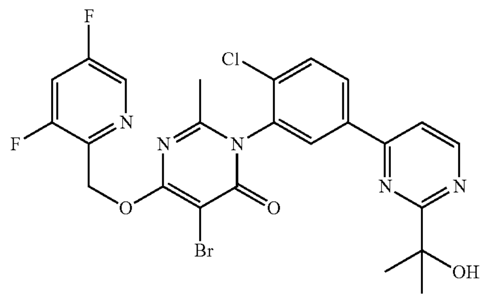 [SMILES: Cc1nc(OCc2ncc(F)cc2F)c(Br)c(=O)n1-c1cc(-c2ccnc(C(C)(C)O)n2)ccc1Cl] | 5-bromo-3-(2-chloro-5-(2-(2-hydroxypropan-2-yl)pyrimidin-4-yl)phenyl)-6-((3,5-difluoropyridin-2-yl)methoxy)-2-methylpyrimidin-4(3H)-one |
| 54 | 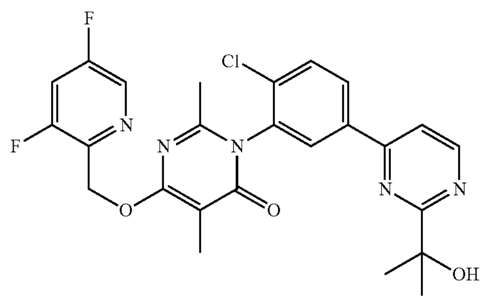 [SMILES: Cc1c(OCc2ncc(F)cc2F)nc(C)n(-c2cc(-c3ccnc(C(C)(C)O)n3)ccc2Cl)c1=O] | 3-(2-chloro-5-(2-(2-hydroxypropan-2-yl)pyrimidin-4-yl)phenyl)-6-((3,5-difluoropyridin-2-yl)methoxy)-2,5-dimethylpyrimidin-4(3H)-one |
| 55 | 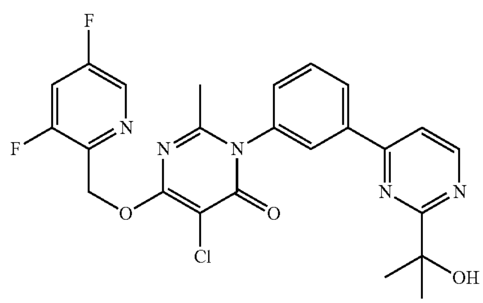 | 5-chloro-6-((3,5-difluoropyridin-2-yl)methoxy)-3-(3-(2-(2-hydroxypropan-2-yl)pyrimidin-4-yl)phenyl)-2-methylpyrimidin-4(3H)-one |
| 56 | 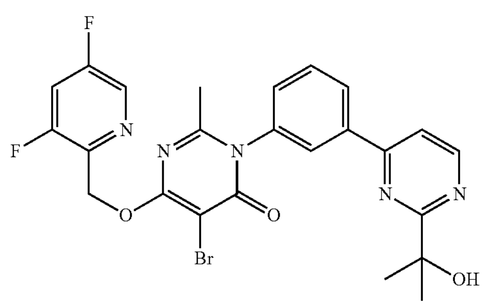 [SMILES: Cc1nc(OCc2ncc(F)cc2F)c(Br)c(=O)n1-c1cccc(-c2ccnc(C(C)(C)O)n2)c1] | 5-bromo-6-((3,5-difluoropyridin-2-yl)methoxy)-3-(3-(2-(2-hydroxypropan-2-yl)pyrimidin-4-yl)phenyl)-2-methylpyrimidin-4(3H)-one |
| 57 | 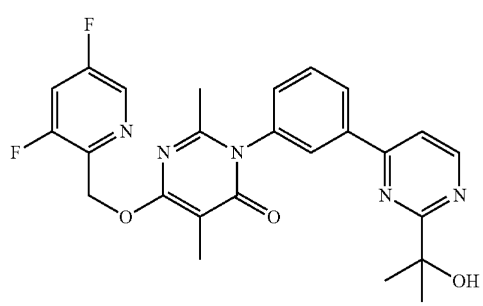 [SMILES: Cc1c(OCc2ncc(F)cc2F)nc(C)n(-c2cccc(-c3ccnc(C(C)(C)O)n3)c2)c1=O] | 6-((3,5-difluoropyridin-2-yl)methoxy)-3-(3-(2-(2-hydroxypropan-2-yl)pyrimidin-4-yl)phenyl)-2,5-dimethylpyrimidin-4(3H)-one |

-continued

| Compound | Structure | Name |
|---|---|---|
| 58 | 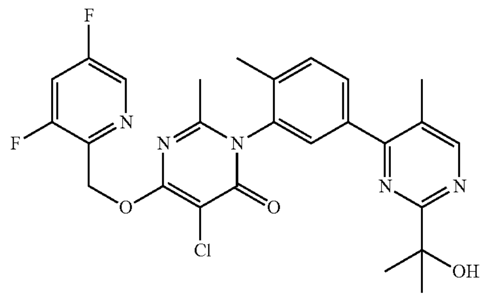 | 5-chloro-6-((3,5-difluoropyridin-2-yl)methoxy)-3-(5-(2-(2-hydroxypropan-2-yl)-5-methylpyrimidin-4-yl)-2-methylphenyl)-2-methylpyrimidin-4(3H)-one |
| 59 | 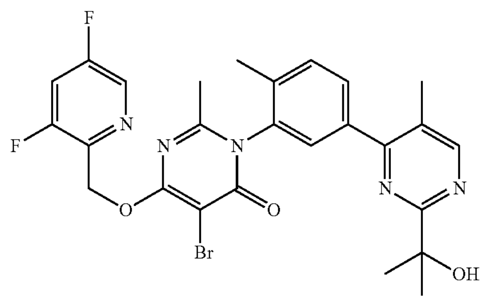 [SMILES: Cc1ccc(-c2nc(C(C)(C)O)ncc2C)cc1-n1c(C)nc(OCc2ncc(F)cc2F)c(Cl)c1=O] | 5-bromo-6-((3,5-difluoropyridin-2-yl)methoxy)-3-(5-(2-(2-hydroxypropan-2-yl)-5-methylpyrimidin-4-yl)-2-methylphenyl)-2-methylpyrimidin-4(3H)-one |
| 60 | 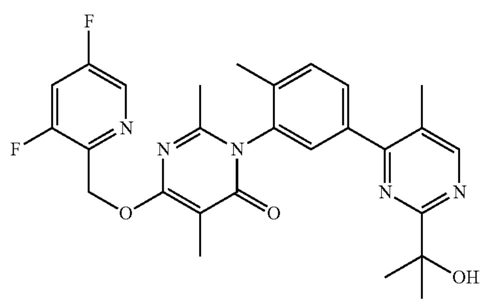 [SMILES: Cc1ccc(-c2nc(C(C)(C)O)ncc2C)cc1-n1c(C)nc(OCc2ncc(F)cc2F)c(C)c1=O] | 6-((3,5-difluoropyridin-2-yl)methoxy)-3-(5-(2-(2-hydroxypropan-2-yl)-5-methylpyrimidin-4-yl)-2-methylphenyl)-2,5-dimethylpyrimidin-4(3H)-one |
| 61 | 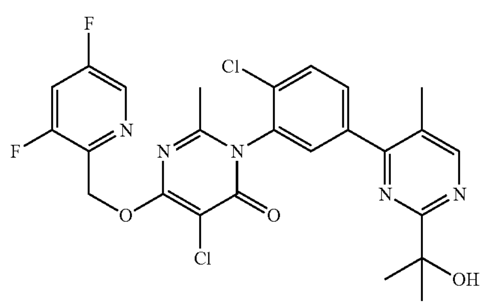 [SMILES: Cc1cnc(C(C)(C)O)nc1-c1ccc(Cl)c(-n2c(C)nc(OCc3ncc(F)cc3F)c(Cl)c2=O)c1] | 5-chloro-3-(2-chloro-5-(2-(2-hydroxypropan-2-yl)-5-methylpyrimidin-4-yl)phenyl)-6-((3,5-difluoropyridin-2-yl)methoxy)-2-methylpyrimidin-4(3H)-one |
| 62 | 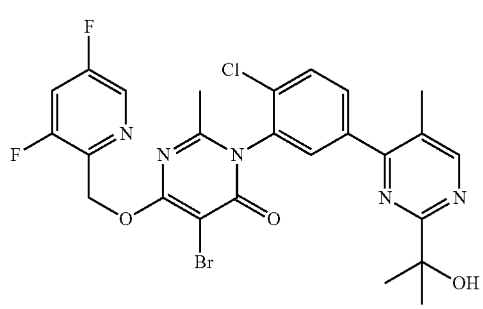 [SMILES: Cc1cnc(C(C)(C)O)nc1-c1ccc(Cl)c(-n2c(C)nc(OCc3ncc(F)cc3F)c(Br)c2=O)c1] | 5-bromo-3-(2-chloro-5-(2-(2-hydroxypropan-2-yl)-5-methylpyrimidin-4-yl)phenyl)-6-((3,5-difluoropyridin-2-yl)methoxy)-2-methylpyrimidin-4(3H)-one |

-continued

| Compound | Structure | Name |
|---|---|---|
| 63 | 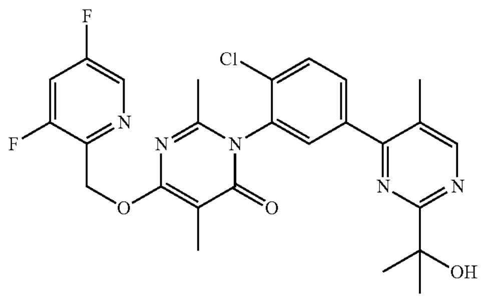 | 3-(2-chloro-5-(2-(2-hydroxypropan-2-yl)-5-methylpyrimidin-4-yl)phenyl)-6-((3,5-difluoropyridin-2-yl)methoxy)-2,5-dimethylpyrimidin-4(3H)-one |
| 64 | 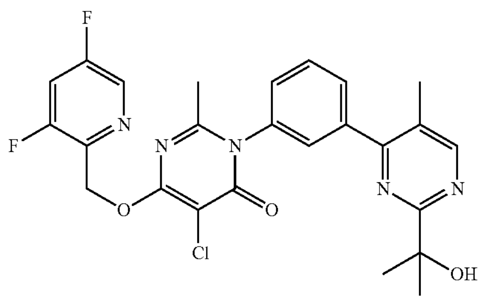 [SMILES: Cc1cnc(C(C)(C)O)nc1-c1cccc(-n2c(C)nc(OCc3ncc(F)cc3F)c(Cl)c2=O)c1] | 5-chloro-6-((3,5-difluoropyridin-2-yl)methoxy)-3-(3-(2-(2-hydroxypropan-2-yl)-5-methylpyrimidin-4-yl)phenyl)-2-methylpyrimidin-4(3H)-one |
| 65 | 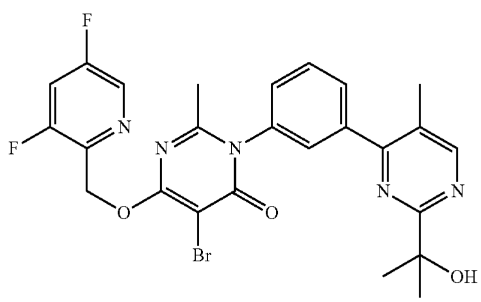 | 5-bromo-6-((3,5-difluoropyridin-2-yl)methoxy)-3-(3-(2-(2-hydroxypropan-2-yl)-5-methylpyrimidin-4-yl)phenyl)-2-methylpyrimidin-4(3H)-one |
| 66 | 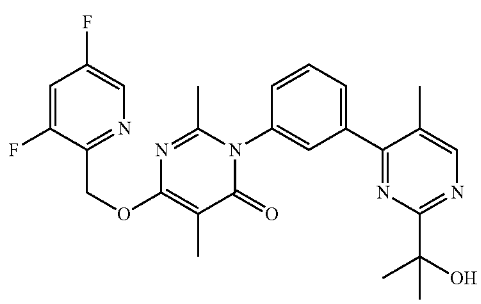 [SMILES: Cc1cnc(C(C)(C)O)nc1-c1cccc(-n2c(C)nc(OCc3ncc(F)cc3F)c(C)c2=O)c1] | 6-((3,5-difluoropyridin-2-yl)methoxy)-3-(3-(2-(2-hydroxypropan-2-yl)-5-methylpyrimidin-4-yl)phenyl)-2,5-dimethylpyrimidin-4(3H)-one |
| 67 | 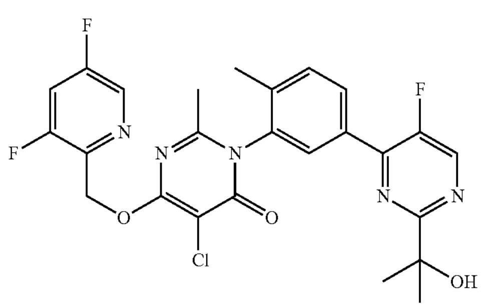 [SMILES: Cc1ccc(-c2nc(C(C)(C)O)ncc2F)cc1-n1c(C)nc(OCc2ncc(F)cc2F)c(Cl)c1=O] | 5-chloro-6-((3,5-difluoropyridin-2-yl)methoxy)-3-(5-(5-fluoro-2-(2-hydroxypropan-2-yl)pyrimidin-4-yl)-2-methylphenyl)-2-methylpyrimidin-4(3H)-one |

| Compound | Structure | Name |
|---|---|---|
| 68 | 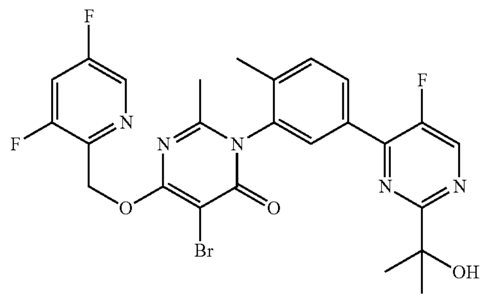 [SMILES: Cc1ccc(-c2nc(C(C)(C)O)ncc2F)cc1-n1c(C)nc(OCc2ncc(F)cc2F)c(Br)c1=O] | 5-bromo-6-((3,5-difluoropyridin-2-yl)methoxy)-3-(5-(5-fluoro-2-(2-hydroxypropan-2-yl)pyrimidin-4-yl)-2-methylphenyl)-2-methylpyrimidin-4(3H)-one |
| 69 | 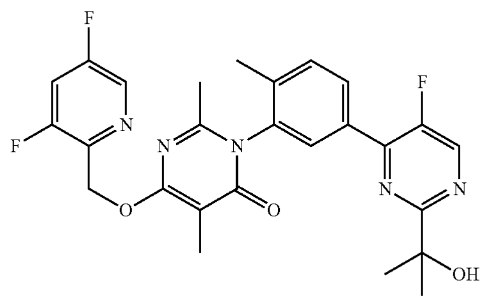 [SMILES: Cc1ccc(-c2nc(C(C)(C)O)ncc2F)cc1-n1c(C)nc(OCc2ncc(F)cc2F)c(C)c1=O] | 6-((3,5-difluoropyridin-2-yl)methoxy)-3-(5-(5-fluoro-2-(2-hydroxypropan-2-yl)pyrimidin-4-yl)-2-methylphenyl)-2,5-dimethylpyrimidin-4(3H)-one |
| 70 | 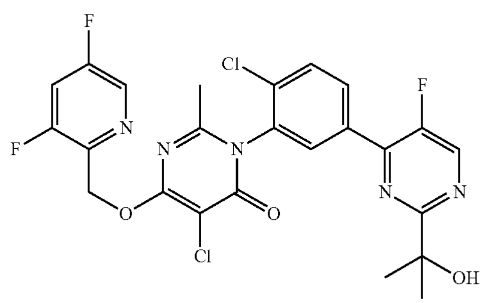 [SMILES: Cc1nc(OCc2ncc(F)cc2F)c(Cl)c(=O)n1-c1cc(-c2nc(C(C)(C)O)ncc2F)ccc1Cl] | 5-chloro-3-(2-chloro-5-(5-fluoro-2-(2-hydroxypropan-2-yl)pyrimidin-4-yl)phenyl)-6-((3,5-difluoropyridin-2-yl)methoxy)-2-methylpyrimidin-4(3H)-one |
| 71 | 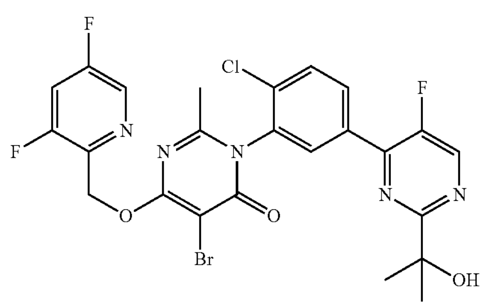 [SMILES: Cc1nc(OCc2ncc(F)cc2F)c(Br)c(=O)n1-c1cc(-c2nc(C(C)(C)O)ncc2F)ccc1Cl] | 5-bromo-3-(2-chloro-5-(5-fluoro-2-(2-hydroxypropan-2-yl)pyrimidin-4-yl)phenyl)-6-((3,5-difluoropyridin-2-yl)methoxy)-2-methylpyrimidin-4(3H)-one |
| 72 | 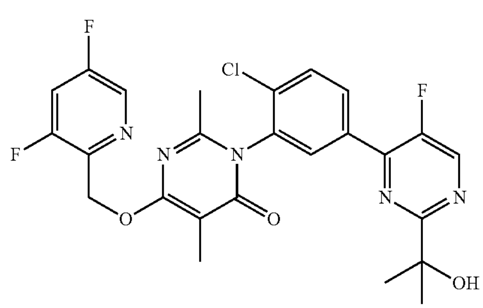 [SMILES: Cc1c(OCc2ncc(F)cc2F)nc(C)n(-c2cc(-c3nc(C(C)(C)O)ncc3F)ccc2Cl)c1=O] | 3-(2-chloro-5-(5-fluoro-2-(2-hydroxypropan-2-yl)pyrimidin-4-yl)phenyl)-6-((3,5-difluoropyridin-2-yl)methoxy)-2,5-dimethylpyrimidin-4(3H)-one |

| Compound | Structure | Name |
|---|---|---|
| 73 | 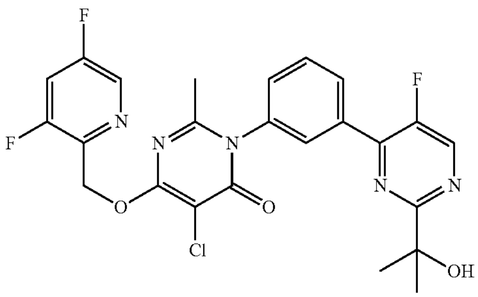 | 5-chloro-6-((3,5-difluoropyridin-2-yl)methoxy)-3-(3-(5-fluoro-2-(2-hydroxypropan-2-yl)pyrimidin-4-yl)phenyl)-2-methylpyrimidin-4(3H)-one |
| 74 | 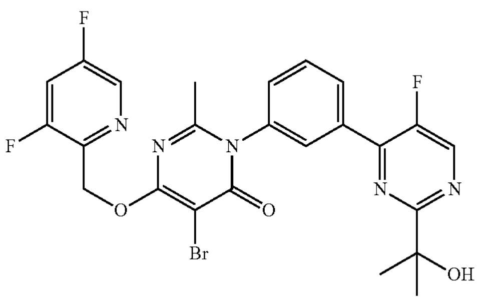 [SMILES: Cc1nc(OCc2ncc(F)cc2F)c(Br)c(=O)n1-c1cccc(-c2nc(C(C)(C)O)ncc2F)c1] | 5-bromo-6-((3,5-difluoropyridin-2-yl)methoxy)-3-(3-(5-fluoro-2-(2-hydroxypropan-2-yl)pyrimidin-4-yl)phenyl)-2-methylpyrimidin-4(3H)-one |
| 75 | 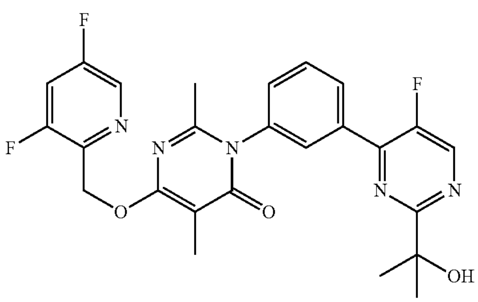 | 6-((3,5-difluoropyridin-2-yl)methoxy)-3-(3-(5-fluoro-2-(2-hydroxypropan-2-yl)pyrimidin-4-yl)phenyl)-2,5-dimethylpyrimidin-4(3H)-one |
| 76 | 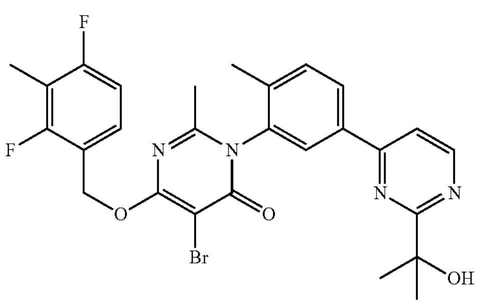 [SMILES: Cc1ccc(-c2ccnc(C(C)(C)O)n2)cc1-n1c(C)nc(OCc2ccc(F)c(C)c2F)c(Br)c1=O] | 5-bromo-6-((2,4-difluoro-3-methylbenzyl)oxy)-3-(5-(2-(2-hydroxypropan-2-yl)pyrimidin-4-yl)-2-methylphenyl)-2-methylpyrimidin-4(3H)-one |
| 77 | 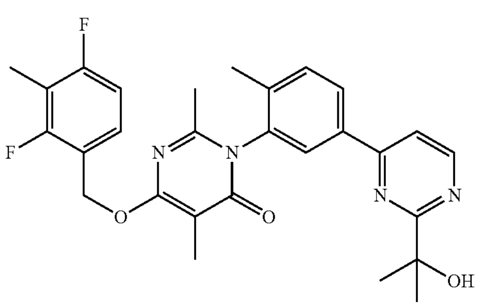 [SMILES: Cc1ccc(-c2ccnc(C(C)(C)O)n2)cc1-n1c(C)nc(OCc2ccc(F)c(C)c2F)c(C)c1=O] | 6-((2,4-difluoro-3-methylbenzyl)oxy)-3-(5-(2-(2-hydroxypropan-2-yl)pyrimidin-4-yl)-2-methylphenyl)-2,5-dimethylpyrimidin-4(3H)-one |

-continued

| Compound | Structure | Name |
|---|---|---|
| 78 | 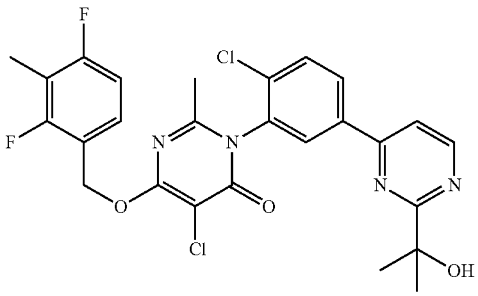 | 5-chloro-3-(2-chloro-5-(2-(2-hydroxypropan-2-yl)pyrimidin-4-yl)phenyl)-6-((2,4-difluoro-3-methylbenzyl)oxy)-2-methylpyrimidin-4(3H)-one |
| 79 | 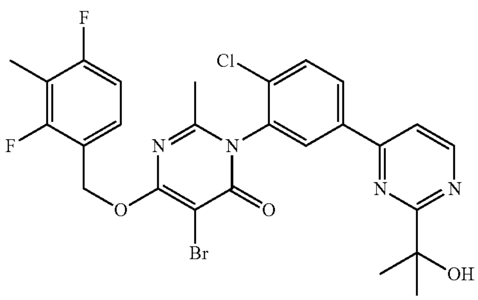 [SMILES: Cc1c(F)ccc(COc2nc(C)n(-c3cc(-c4ccnc(C(C)(C)O)n4)ccc3Cl)c(=O)c2Br)c1F] | 5-bromo-3-(2-chloro-5-(2-(2-hydroxypropan-2-yl)pyrimidin-4-yl)phenyl)-6-((2,4-difluoro-3-methylbenzyl)oxy)-2-methylpyrimidin-4(3H)-one |
| 80 | 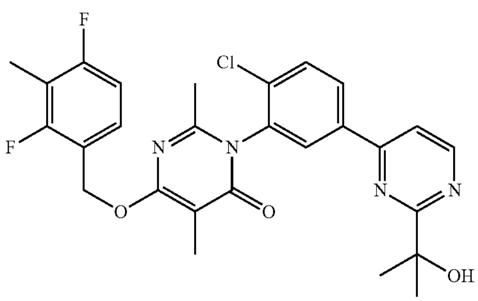 | 3-(2-chloro-5-(2-(2-hydroxypropan-2-yl)pyrimidin-4-yl)phenyl)-6-((2,4-difluoro-3-methylbenzyl)oxy)-2,5-dimethylpyrimidin-4(3H)-one |
| 81 | 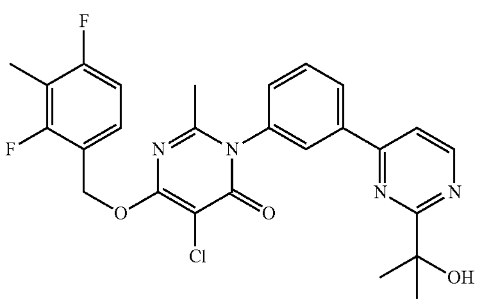 [SMILES: Cc1c(F)ccc(COc2nc(C)n(-c3cccc(-c4ccnc(C(C)(C)O)n4)c3)c(=O)c2Cl)c1F] | 5-chloro-6-((2,4-difluoro-3-methylbenzyl)oxy)-3-(3-(2-(2-hydroxypropan-2-yl)pyrimidin-4-yl)phenyl)-2-methylpyrimidin-4(3H)-one |
| 82 | 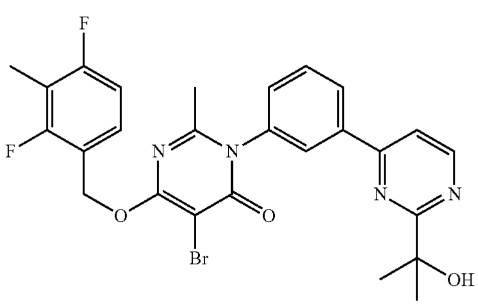 [SMILES: Cc1c(F)ccc(COc2nc(C)n(-c3cccc(-c4ccnc(C(C)(C)O)n4)c3)c(=O)c2Br)c1F] | 5-bromo-6-((2,4-difluoro-3-methylbenzyl)oxy)-3-(3-(2-(2-hydroxypropan-2-yl)pyrimidin-4-yl)phenyl)-2-methylpyrimidin-4(3H)-one |

| Compound | Structure | Name |
|---|---|---|
| 83 | 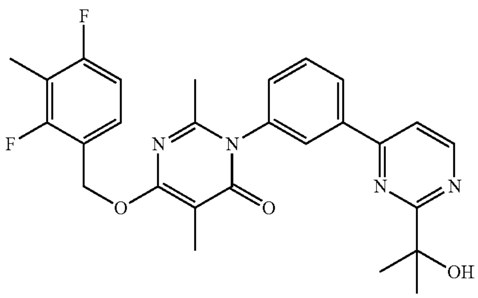 [SMILES: Cc1c(F)ccc(COc2nc(C)n(-c3cccc(-c4ccnc(C(C)(C)O)n4)c3)c(=O)c2C)c1F] | 6-((2,4-difluoro-3-methylbenzyl)oxy)-3-(3-(2-(2-hydroxypropan-2-yl)pyrimidin-4-yl)phenyl)-2,5-dimethylpyrimidin-4(3H)-one |
| 84 | 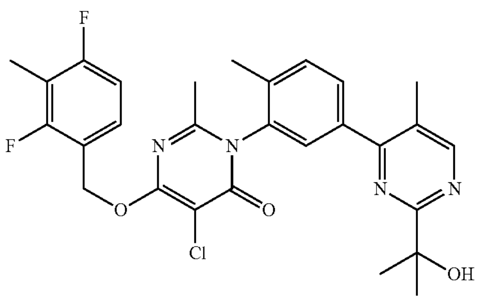 [SMILES: Cc1ccc(-c2nc(C(C)(C)O)ncc2C)cc1-n1c(C)nc(OCc2ccc(F)c(C)c2F)c(Cl)c1=O] | 5-chloro-6-((2,4-difluoro-3-methylbenzyl)oxy)-3-(5-(2-(2-hydroxypropan-2-yl)-5-methylpyrimidin-4-yl)-2-methylphenyl)-2-methylpyrimidin-4(3H)-one |
| 85 | 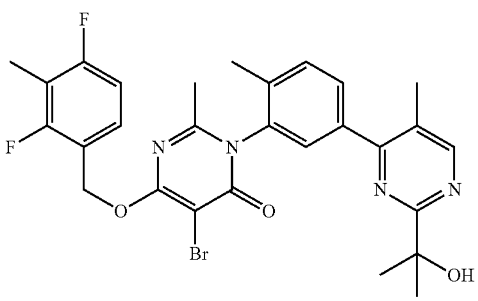 [SMILES: Cc1ccc(-c2nc(C(C)(C)O)ncc2C)cc1-n1c(C)nc(OCc2ccc(F)c(C)c2F)c(Br)c1=O] | 5-bromo-6-((2,4-difluoro-3-methylbenzyl)oxy)-3-(5-(2-(2-hydroxypropan-2-yl)-5-methylpyrimidin-4-yl)-2-methylphenyl)-2-methylpyrimidin-4(3H)-one |
| 86 | 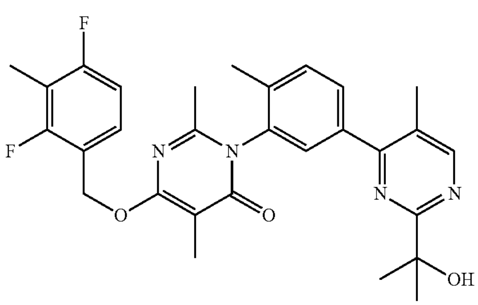 | 6-((2,4-difluoro-3-methylbenzyl)oxy)-3-(5-(2-(2-hydroxypropan-2-yl)-5-methylpyrimidin-4-yl)-2-methylphenyl)-2,5-dimethylpyrimidin-4(3H)-one |
| 87 | 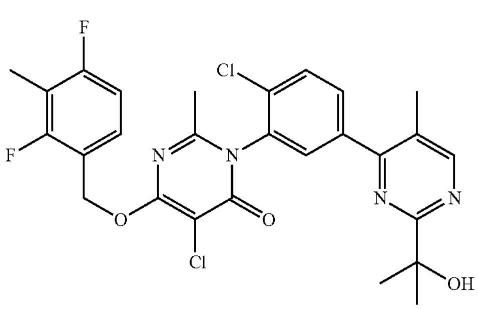 | 5-chloro-3-(2-chloro-5-(2-(2-hydroxypropan-2-yl)-5-methylpyrimidin-4-yl)phenyl)-6-((2,4-difluoro-3-methylbenzyl)oxy)-2-methylpyrimidin-4(3H)-one |

| Compound | Structure | Name |
|---|---|---|
| 88 | 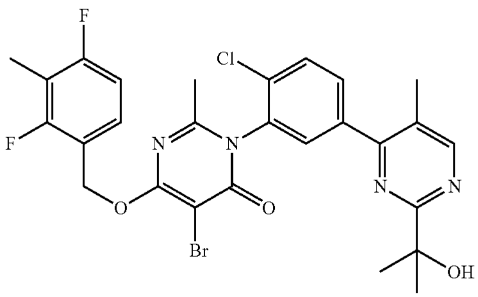 [SMILES: Cc1cnc(C(C)(C)O)nc1-c1ccc(Cl)c(-n2c(C)nc(OCc3ccc(F)c(C)c3F)c(Cl)c2=O)c1] | 5-bromo-3-(2-chloro-5-(2-(2-hydroxypropan-2-yl)-5-methylpyrimidin-4-yl)phenyl)-6-((2,4-difluoro-3-methylbenzyl)oxy)-2-methylpyrimidin-4(3H)-one |
| 89 | 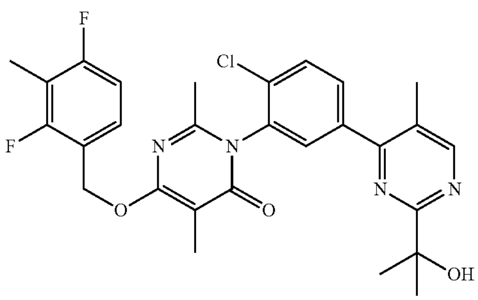 [SMILES: Cc1cnc(C(C)(C)O)nc1-c1ccc(Cl)c(-n2c(C)nc(OCc3ccc(F)c(C)c3F)c(C)c2=O)c1] | 3-(2-chloro-5-(2-(2-hydroxypropan-2-yl)-5-methylpyrimidin-4-yl)phenyl)-6-((2,4-difluoro-3-methylbenzyl)oxy)-2,5-dimethylpyrimidin-4(3H)-one |
| 90 | 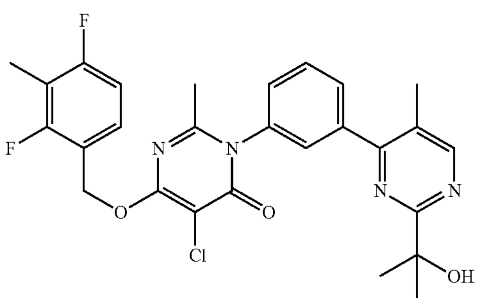 [SMILES: Cc1cnc(C(C)(C)O)nc1-c1cccc(-n2c(C)nc(OCc3ccc(F)c(C)c3F)c(Cl)c2=O)c1] | 5-chloro-6-((2,4-difluoro-3-methylbenzyl)oxy)-3-(3-(2-(2-hydroxypropan-2-yl)-5-methylpyrimidin-4-yl)phenyl)-2-methylpyrimidin-4(3H)-one |
| 91 | 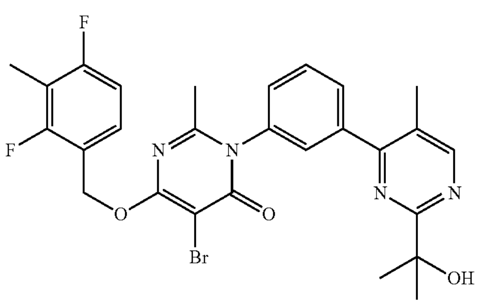 [SMILES: Cc1cnc(C(C)(C)O)nc1-c1cccc(-n2c(C)nc(OCc3ccc(F)c(C)c3F)c(Br)c2=O)c1] | 5-bromo-6-((2,4-difluoro-3-methylbenzyl)oxy)-3-(3-(2-(2-hydroxypropan-2-yl)-5-methylpyrimidin-4-yl)phenyl-2-methylpyrimidin-4(3H)-one |
| 92 | 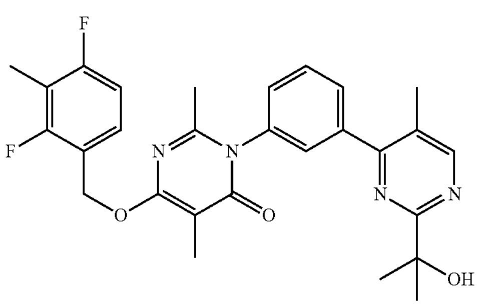 [SMILES: Cc1cnc(C(C)(C)O)nc1-c1cccc(-n2c(C)nc(OCc3ccc(F)c(C)c3F)c(C)c2=O)c1] | 6-((2,4-difluoro-3-methylbenzyl)oxy)-3-(3-(2-(2-hydroxypropan-2-yl)-5-methylpyrimidin-4-yl)phenyl)-2,5-dimethylpyrimidin-4(3H)-one |

| Compound | Structure | Name |
|---|---|---|
| 93 | 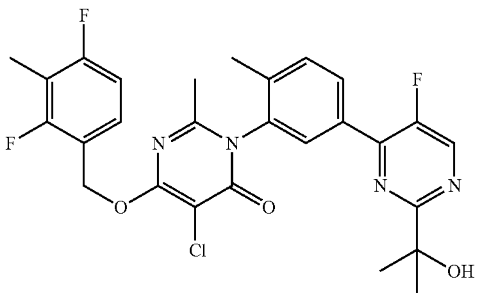 [SMILES: Cc1ccc(-c2nc(C(C)(C)O)ncc2F)cc1-n1c(C)nc(OCc2ccc(F)c(C)c2F)c(Cl)c1=O] | 5-chloro-6-((2,4-difluoro-3-methylbenzyl)oxy)-3-(5-(5-fluoro-2-(2-hydroxypropan-2-yl)pyrimidin-4-yl)-2-methylphenyl)-2-methylpyrimidin-4(3H)-one |
| 94 | 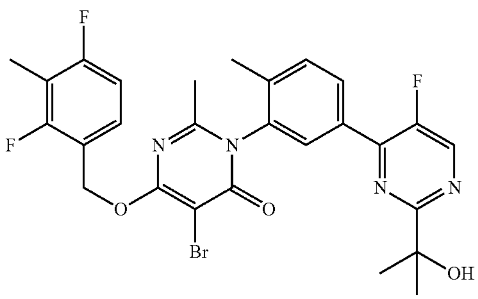 [SMILES: Cc1ccc(-c2nc(C(C)(C)O)ncc2F)cc1-n1c(C)nc(OCc2ccc(F)c(C)c2F)c(Br)c1=O] | 5-bromo-6-((2,4-difluoro-3-methylbenzyl)oxy)-3-(5-(5-fluoro-2-(2-hydroxypropan-2-yl)pyrimidin-4-yl)-2-methylphenyl)-2-methylpyrimidin-4(3H)-one |
| 95 | 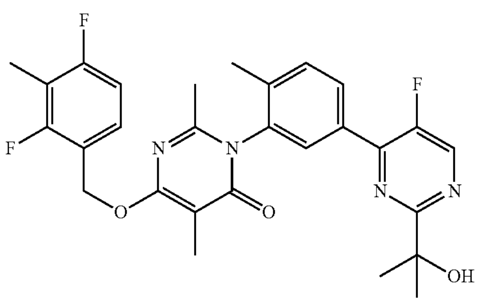 | 6-((2,4-difluoro-3-methylbenzyl)oxy)-3-(5-(5-fluoro-2-(2-hydroxypropan-2-yl)pyrimidin-4-yl)-2-methylphenyl)-2,5-dimethylpyrimidin-4(3H)-one |
| 96 | 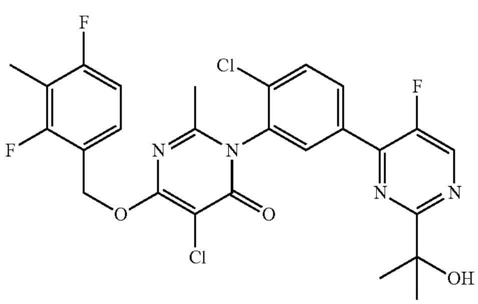 [SMILES: Cc1c(F)ccc(COc2nc(C)n(-c3cc(-c4nc(C(C)(C)O)ncc4F)ccc3Cl)c(=O)c2Cl)c1F] | 5-chloro-3-(2-chloro-5-(5-fluoro-2-(2-hydroxypropan-2-yl)pyrimidin-4-yl)phenyl)-6-((2,4-difluoro-3-methylbenzyl)oxy)-2-methylpyrimidin-4(3H)-one |
| 97 | 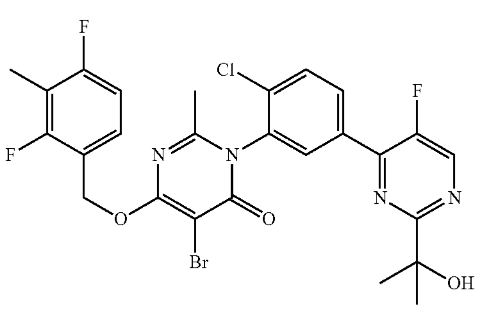 | 5-bromo-3-(2-chloro-5-(5-fluoro-2-(2-hydroxypropan-2-yl)pyrimidin-4-yl)phenyl)-6-((2,4-difluoro-3-methylbenzyl)oxy)-2-methylpyrimidin-4(3H)-one |

| Compound | Structure | Name |
|---|---|---|
| 98 | 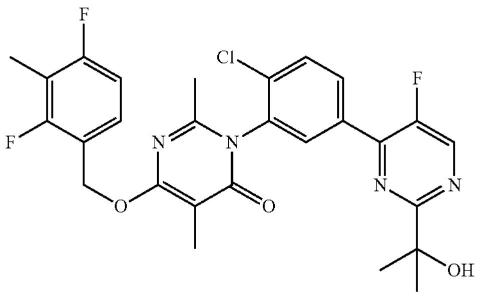 | 3-(2-chloro-5-(5-fluoro-2-(2-hydroxypropan-2-yl)pyrimidin-4-yl)phenyl)-6-((2,4-difluoro-3-methylbenzyl)oxy)-2,5-dimethylpyrimidin-4(3H)-one |
| 99 | 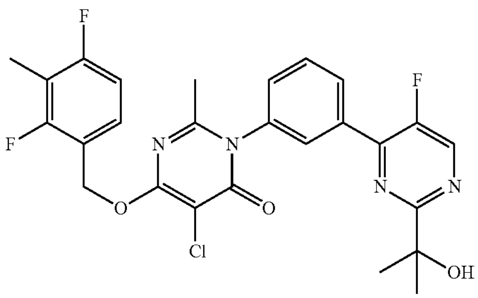 [SMILES: Cc1c(F)ccc(COc2nc(C)n(-c3cccc(-c4nc(C(C)(C)O)ncc4F)c3)c(=O)c2Cl)c1F] | 5-chloro-6-((2,4-difluoro-3-methylbenzyl)oxy)-3-(3-(5-fluoro-2-(2-hydroxypropan-2-yl)pyrimidin-4-yl)phenyl)-2-methylpyrimidin-4(3H)-one |
| 100 | 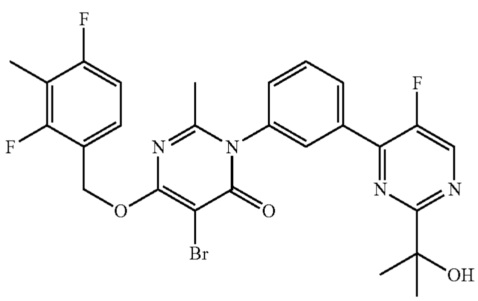 [SMILES: Cc1c(F)ccc(COc2nc(C)n(-c3cccc(-c4nc(C(C)(C)O)ncc4F)c3)c(=O)c2Br)c1F] | 5-bromo-6-((2,4-difluoro-3-methylbenzyl)oxy)-3-(3-(5-fluoro-2-(2-hydroxypropan-2-yl)pyrimidin-4-yl)phenyl)-2-methylpyrimidin-4(3H)-one |
| 101 | 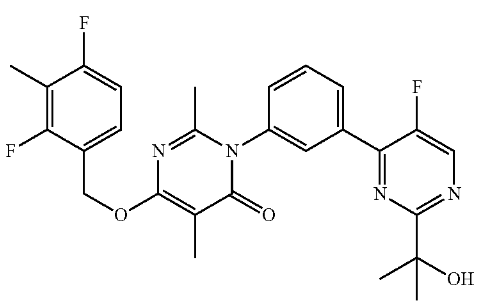 [SMILES: Cc1c(F)ccc(COc2nc(C)n(-c3cccc(-c4nc(C(C)(C)O)ncc4F)c3)c(=O)c2C)c1F] | 6-((2,4-difluoro-3-methylbenzyl)oxy)-3-(3-(5-luoro-2-(2-hydroxypropan-2-yl)pyrimidin-4-yl)phenyl)-2,5-dimethylpyrimidin-4(3H)-one |
| 102 | 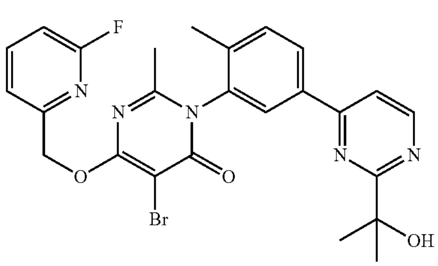 [SMILES: Cc1ccc(-c2ccnc(C(C)(C)O)n2)cc1-n1c(C)nc(OCc2cccc(F)n2)c(Br)c1=O] | 5-bromo-6-((6-fluoropyridin-2-yl)methoxy)-3-(5-(2-(2-hydroxypropan-2-yl)pyrimidin-4-yl)-2-methylphenyl)-2-methylpyrimidin-4(3H)-one |

| Compound | Structure | Name |
|---|---|---|
| 103 | 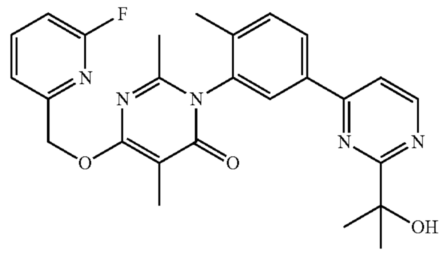 [SMILES: Cc1ccc(-c2ccnc(C(C)(C)O)n2)cc1-n1c(C)nc(OCc2cccc(F)n2)c(C)c1=O] | 6-((6-fluoropyridin-2-yl)methoxy)-3-(5-(2-(2-hydroxypropan-2-yl)pyrimidin-4-yl)-2-methylphenyl)-2,5-dimethylpyrimidin-4(3H)-one |
| 104 | 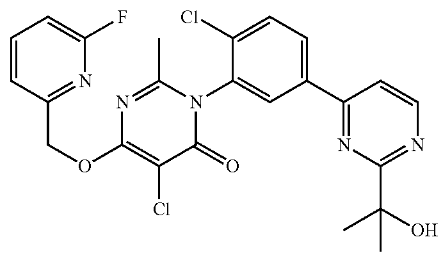 [SMILES: Cc1nc(OCc2cccc(F)n2)c(Cl)c(=O)n1-c1cc(-c2ccnc(C(C)(C)O)n2)ccc1Cl] | 5-chloro-3-(2-chloro-5-(2-(2-hydroxypropan-2-yl)pyrimidin-4-yl)phenyl)-6-((6-fluoropyridin-2-yl)methoxy)-2-methylpyrimidin-4(3H)-one |
| 105 | 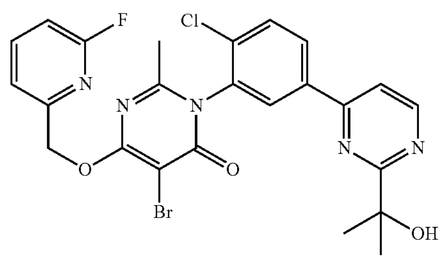 | 5-bromo-3-(2-chloro-5-(2-(2-hydroxypropan-2-yl)pyrimidin-4-yl)phenyl)-6-((6-fluoropyridin-2-yl)methoxy)-2-methylpyrimidin-4(3H)-one |
| 106 | 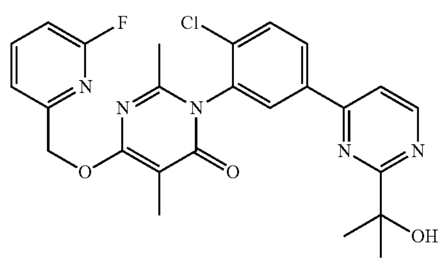 [SMILES: Cc1c(OCc2cccc(F)n2)nc(C)n(-c2cc(-c3ccnc(C(C)(C)O)n3)ccc2Cl)c1=O] | 3-(2-chloro-5-(2-(2-hydroxypropan-2-yl)pyrimidin-4-yl)phenyl)-6-((6-fluoropyridin-2-yl)methoxy)-2,5-dimethylpyrimidin-4(3H)-one |
| 107 | 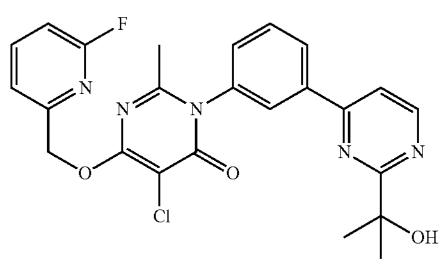 | 5-chloro-6-((6-fluoropyridin-2-yl)methoxy)-3-(3-(2-(2-hydroxypropan-2-yl)pyrimidin-4-yl)phenyl)-2-methylpyrimidin-4(3H)-one |
| 108 | 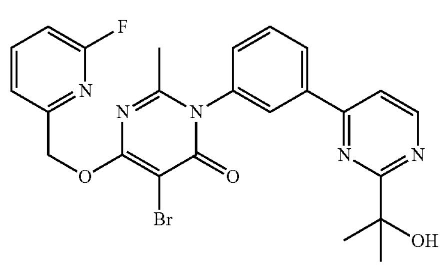 | 5-bromo-6-((6-fluoropyridin-2-yl)methoxy)-3-(3-(2-(2-hydroxypropan-2-yl)pyrimidin-4-yl)phenyl)-2-methylpyrimidin-4(3H)-one |

| Compound | Structure | Name |
|---|---|---|
| 109 | 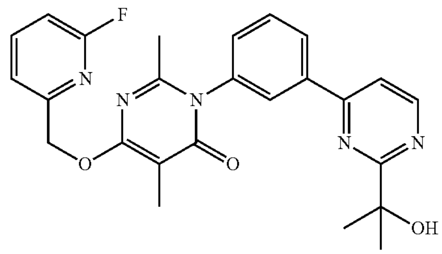 [SMILES: Cc1c(OCc2cccc(F)n2)nc(C)n(-c2cccc(-c3ccnc(C(C)(C)O)n3)c2)c1=O] | 6-((6-fluoropyridin-2-yl)methoxy)-3-(3-(2-(2-hydroxypropan-2-yl)pyrimidin-4-yl)phenyl)-2,5-dimethylpyrimidin-4(3H)-one |
| 110 | 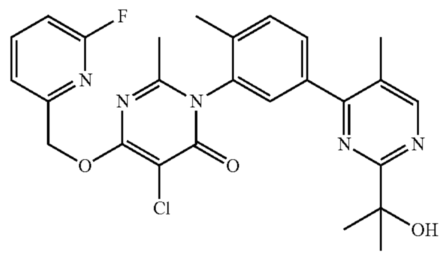 [SMILES: Cc1ccc(-c2nc(C(C)(C)O)ncc2C)cc1-n1c(C)nc(OCc2cccc(F)n2)c(Cl)c1=O] | 5-chloro-6-((6-fluoropyridin-2-yl)methoxy)-3-(5-(2-(2-hydroxypropan-2-yl)-5-methylpyrimidin-4-yl)-2-methylphenyl)-2-methylpyrimidin-4(3H)-one |
| 111 | 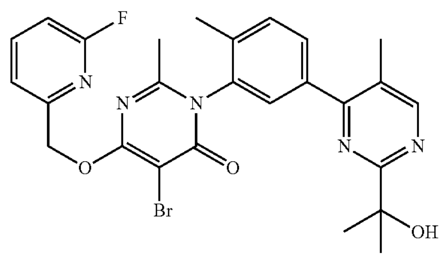 | 5-bromo-6-((6-fluoropyridin-2-yl)methoxy)-3-(5-(2-(2-hydroxypropan-2-yl)-5-methylpyrimidin-4-yl)-2-methylphenyl)-2-methylpyrimidin-4(3H)-one |
| 112 | 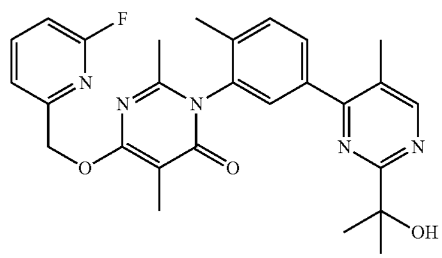 [SMILES: Cc1ccc(-c2nc(C(C)(C)O)ncc2C)cc1-n1c(C)nc(OCc2cccc(F)n2)c(C)c1=O] | 6-((6-fluoropyridin-2-yl)methoxy)-3-(5-(2-(2-hydroxypropan-2-yl)-5-methylpyrimidin-4-yl)-2-methylphenyl)-2,5-dimethylpyrimidin-4(3H)-one |
| 113 | 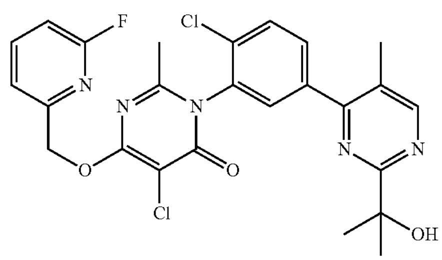 [SMILES: Cc1cnc(C(C)(C)O)nc1-c1ccc(Cl)c(-n2c(C)nc(OCc3cccc(F)n3)c(Cl)c2=O)c1] | 5-chloro-3-(2-chloro-5-(2-(2-hydroxypropan-2-yl)-5-methylpyrimidin-4-yl)phenyl)-6-((6-fluoropyridin-2-yl)methoxy)-2-methylpyrimidin-4(3H)-one |
| 114 | 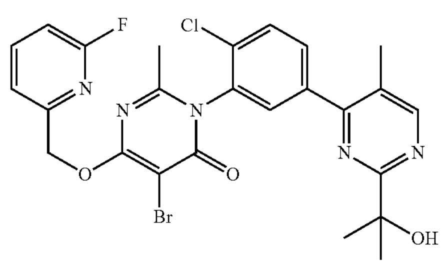 | 5-bromo-3-(2-chloro-5-(2-(2-hydroxypropan-2-yl)-5-methylpyrimidin-4-yl)phenyl)-6-((6-fluoropyridin-2-yl)methoxy)-2-methylpyrimidin-4(3H)-one |

| Compound | Structure | Name |
|---|---|---|
| 115 | 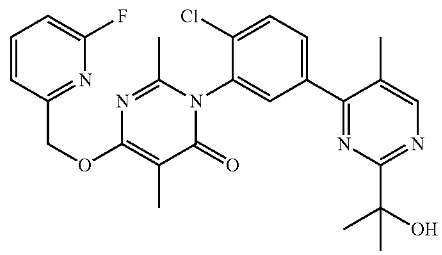 [SMILES: Cc1cnc(C(C)(C)O)nc1-c1ccc(Cl)c(-n2c(C)nc(OCc3cccc(F)n3)c(C)c2=O)c1] | 3-(2-chloro-5-(2-(2-hydroxypropan-2-yl)-5-methylpyrimidin-4-yl)phenyl)-6-((6-fluoropyridin-2-yl)methoxy)-2,5-dimethylpyrimidin-4(3H)-one |
| 116 | 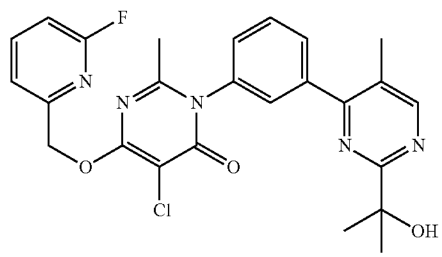 | 5-chloro-6-((6-fluoropyridin-2-yl)methoxy)-3-(3-(2-(2-hydroxypropan-2-yl)-5-methylpyrimidin-4-yl)phenyl)-2-methylpyrimidin-4(3H)-one |
| 117 | 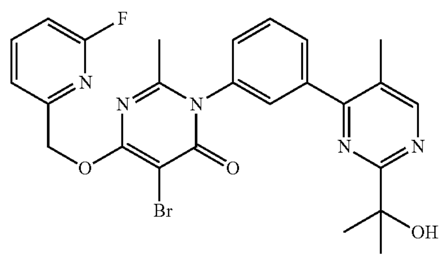 [SMILES: Cc1cnc(C(C)(C)O)nc1-c1cccc(-n2c(C)nc(OCc3cccc(F)n3)c(Cl)c2=O)c1] | 5-bromo-6-((6-fluoropyridin-2-yl)methoxy)-3-(3-(2-(2-hydroxypropan-2-yl)-5-methylpyrimidin-4-yl)phenyl)-2-methylpyrimidin-4(3H)-one |
| 118 | 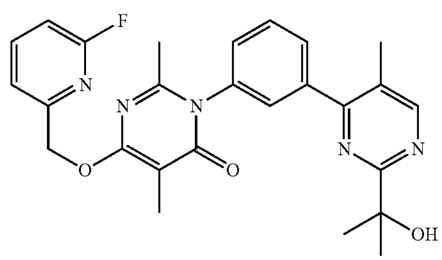 | 6-((6-fluoropyridin-2-yl)methoxy)-3-(3-(2-(2-hydroxypropan-2-yl)-5-methylpyrimidin-4-yl)phenyl)-2,5-dimethylpyrimidin-4(3H)-one |
| 119 | 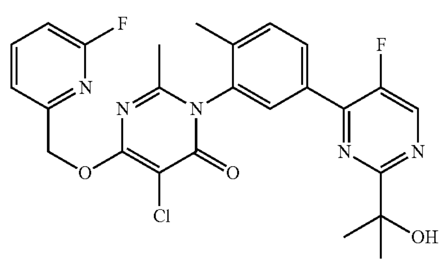 [SMILES: Cc1ccc(-c2nc(C(C)(C)O)ncc2F)cc1-n1c(C)nc(OCc2cccc(F)n2)c(Cl)c1=O] | 5-chloro-3-(5-(5-fluoro-2-(2-hydroxypropan-2-yl)pyrimidin-4-yl)-2-methylphenyl)-6-((6-fluoropyridin-2-yl)methoxy)-2-methylpyrimidin-4(3H)-one |
| 120 | 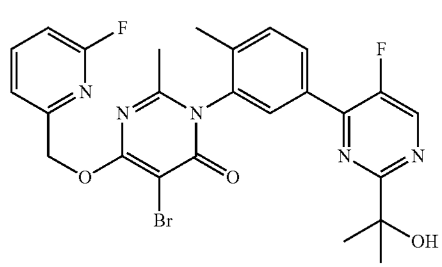 | 5-bromo-3-(5-(5-fluoro-2-(2-hydroxypropan-2-yl)pyrimidin-4-yl)-2-methylphenyl)-6-((6-fluoropyridin-2-yl)methoxy)-2-methylpyrimidin-4(3H)-one |

-continued

| Compound | Structure | Name |
|---|---|---|
| 121 | 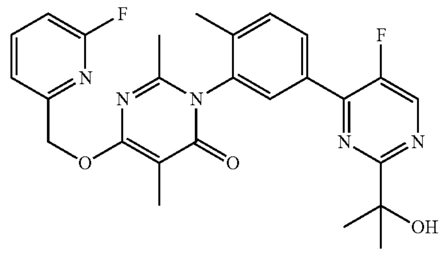 [SMILES: Cc1ccc(-c2nc(C(C)(C)O)ncc2F)cc1-n1c(C)nc(OCc2cccc(F)n2)c(C)c1=O] | 3-(5-(5-fluoro-2-(2-hydroxypropan-2-yl)pyrimidin-4-yl)-2-methylphenyl)-6-((6-fluoropyridin-2-yl)methoxy)-2,5-dimethylpyrimidin-4(3H)-one |
| 122 | 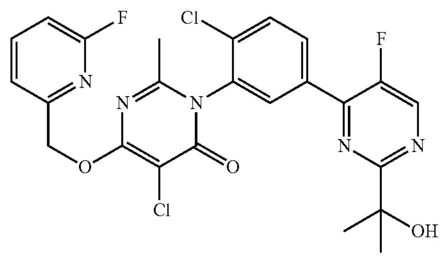 | 5-chloro-3-(2-chloro-5-(5-fluoro-2-(2-hydroxypropan-2-yl)pyrimidin-4-yl)phenyl)-6-((6-fluoropyridin-2-yl)methoxy)-2-methylpyrimidin-4(3H)-one |
| 123 | 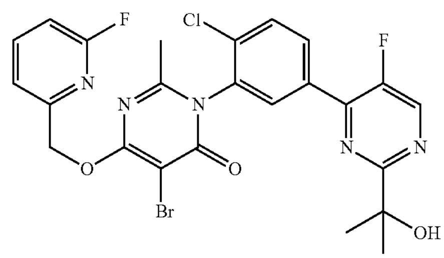 [SMILES: Cc1nc(OCc2cccc(F)n2)c(Br)c(=O)n1-c1cc(-c2nc(C(C)(C)O)ncc2F)ccc1Cl] | 5-bromo-3-(2-chloro-5-(5-fluoro-2-(2-hydroxypropan-2-yl)pyrimidin-4-yl)phenyl)-6-((6-fluoropyridin-2-yl)methoxy)-2-methylpyrimidin-4(3H)-one |
| 124 | 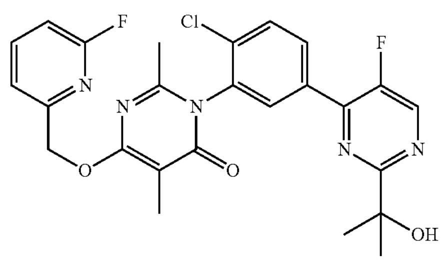 [SMILES: Cc1c(OCc2cccc(F)n2)nc(C)n(-c2cc(-c3nc(C(C)(C)O)ncc3F)ccc2Cl)c1=O] | 3-(2-chloro-5-(5-fluoro-2-(2-hydroxypropan-2-yl)pyrimidin-4-yl)phenyl)-6-((6-fluoropyridin-2-yl)methoxy)-2,5-dimethylpyrimidin-4(3H)-one |
| 125 | 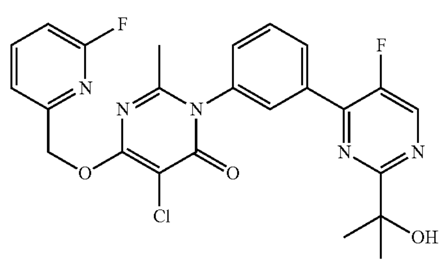 | 5-chloro-3-(3-(5-fluoro-2-(2-hydroxypropan-2-yl)pyrimidin-4-yl)phenyl)-6-((6-fluoropyridin-2-yl)methoxy)-2-methylpyrimidin-4(3H)-one |
| 126 | 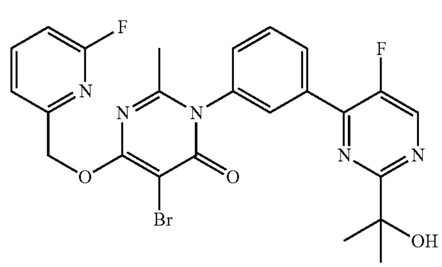 | 5-bromo-3-(3-(5-fluoro-2-(2-hydroxypropan-2-yl)pyrimidin-4-yl)phenyl)-6-((6-fluoropyridin-2-yl)methoxy)-2-methylpyrimidin-4(3H)-one |

-continued

| Compound | Structure | Name |
|---|---|---|
| 127 | 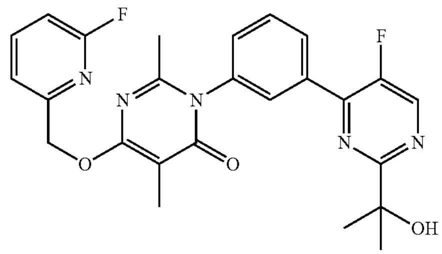 | 3-(3-(5-fluoro-2-(2-hydroxypropan-2-yl)pyrimidin-4-yl)phenyl)-6-((6-fluoropyridin-2-yl)methoxy)-2,5-dimethylpyrimidin-4(3H)-one |
| 128 | 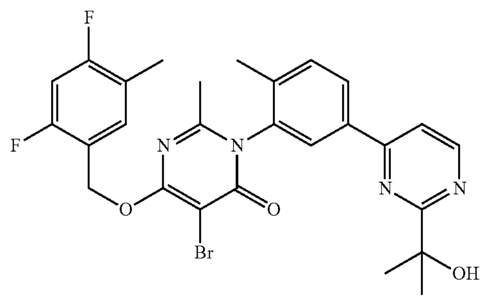 [SMILES: Cc1cc(COc2nc(C)n(-c3cc(-c4ccnc(C(C)(C)O)n4)ccc3C)c(=O)c2Br)c(F)cc1F] | 5-bromo-6-((2,4-difluoro-5-methylbenzyl)oxy)-3-(5-(2-(2-hydroxypropan-2-yl)pyrimidin-4-yl)-2-methylphenyl)-2-methylpyrimidin-4(3H)-one |
| 129 | 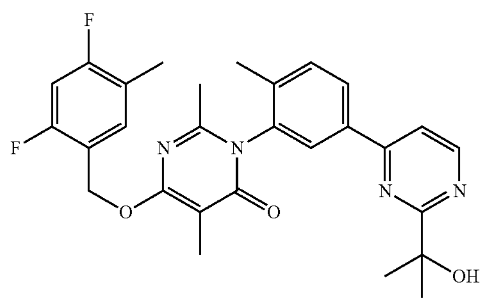 [SMILES: Cc1cc(COc2nc(C)n(-c3cc(-c4ccnc(C(C)(C)O)n4)ccc3C)c(=O)c2C)c(F)cc1F] | 6-((2,4-difluoro-5-methylbenzyl)oxy)-3-(5-(2-(2-hydroxypropan-2-yl)pyrimidin-4-yl)-2-methylphenyl)-2,5-dimethylpyrimidin-4(3H)-one |
| 130 | 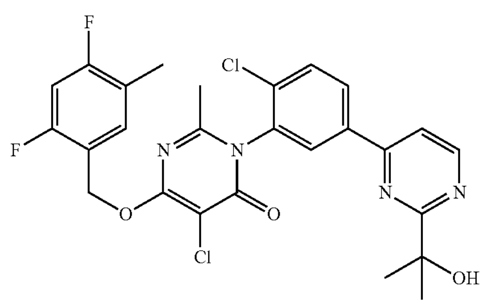 [SMILES: Cc1cc(COc2nc(C)n(-c3cc(-c4ccnc(C(C)(C)O)n4)ccc3Cl)c(=O)c2Cl)c(F)cc1F] | 5-chloro-3-(2-chloro-5-(2-(2-hydroxypropan-2-yl)pyrimidin-4-yl)phenyl)-6-((2,4-difluoro-5-methylbenzyl)oxy)-2-methylpyrimidin-4(3H)-one |
| 131 | 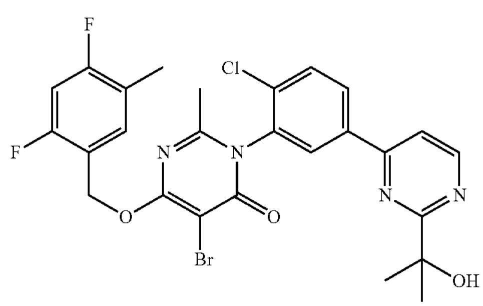 | 5-bromo-3-(2-chloro-5-(2-(2-hydroxypropan-2-yl)pyrimidin-4-yl)phenyl)-6-((2,4-difluoro-5-methylbenzyl)oxy)-2-methylpyrimidin-4(3H)-one |

| Compound | Structure | Name |
|---|---|---|
| 132 | 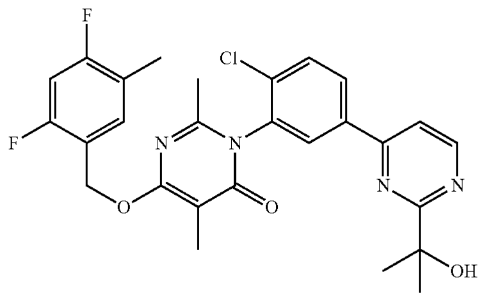 [SMILES: Cc1cc(COc2nc(C)n(-c3cc(-c4ccnc(C(C)(C)O)n4)ccc3Cl)c(=O)c2C)c(F)cc1F] | 3-(2-chloro-5-(2-(2-hydroxypropan-2-yl)pyrimidin-4yl)phenyl)6-((2,4-difluoro-5-methylbenzyl)oxy)-2,5-dimethylpyrimidin-4(3H)-one |
| 133 | 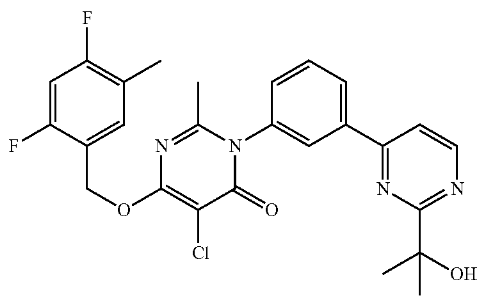 | 5-chloro-6-((2,4-difluoro-5-methylbenzyl)oxy)-3-(3-(2-(2-hydroxypropan-2-yl)pyrimidin-4-yl)phenyl)-2-methylpyrimidin-4(3H)-one |
| 134 | 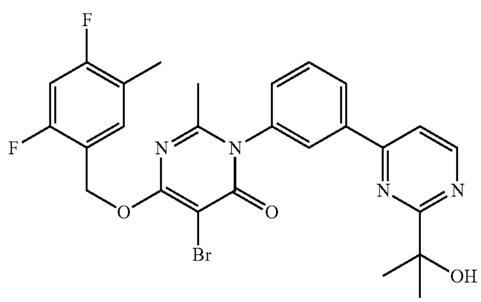 [SMILES: Cc1cc(COc2nc(C)n(-c3cccc(-c4ccnc(C(C)(C)O)n4)c3)c(=O)c2Br)c(F)cc1F] | 5-bromo-6-((2,4-difluoro-5-methylbenzyl)oxy)-3-(3-(2-(2-hydroxypropan-2-yl)pyrimidin-4-yl)phenyl)-2-methylpyrimidin-4(3H)-one |
| 135 | 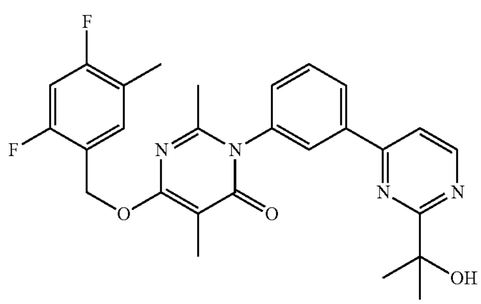 [SMILES: Cc1cc(COc2nc(C)n(-c3cccc(-c4ccnc(C(C)(C)O)n4)c3)c(=O)c2C)c(F)cc1F] | 6-((2,4-difluoro-5-methylbenzyl)oxy)-3-(3-(2-(2-hydroxypropan-2-yl)pyrimidin-4-yl)phenyl)-2,5-dimethylpyrimidin-4(3H)-one |
| 136 | 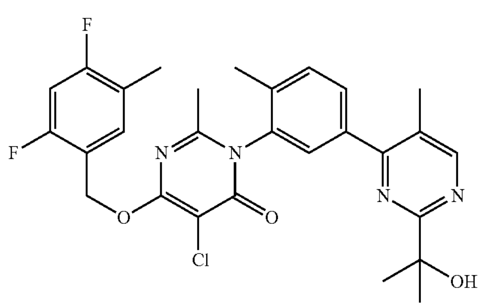 [SMILES: Cc1cc(COc2nc(C)n(-c3cc(-c4nc(C(C)(C)O)ncc4C)ccc3C)c(=O)c2Cl)c(F)cc1F] | 5-chloro-6-((2,4-difluoro-5-methylbenzyl)oxy)-3-(5-(2-(2-hydroxypropan-2-yl)-5-methylpyrimidin-4-yl)-2-methylphenyl)-2-methylpyrimidin-4(3H)-on |

-continued

| Compound | Structure | Name |
|---|---|---|
| 137 | 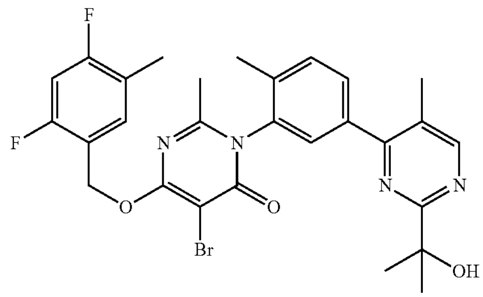 [SMILES: Cc1cc(COc2nc(C)n(-c3cc(-c4nc(C(C)(C)O)ncc4C)ccc3C)c(=O)c2Br)c(F)cc1F] | 5-bromo-6-((2,4-difluoro-5-methylbenzyl)oxy)-3-(5-(2-(2-hydroxypropan-2-yl)-5-methylpyrimidin-4-yl)-2-methylphenyl)-2-methylpyrimidin-4(3H)-one |
| 138 | 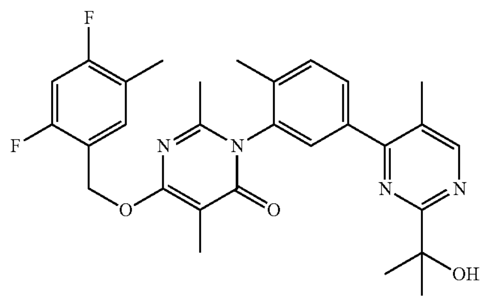 [SMILES: Cc1cc(COc2nc(C)n(-c3cc(-c4nc(C(C)(C)O)ncc4C)ccc3C)c(=O)c2C)c(F)cc1F] | 6-((2,4-difluoro-5-methylbenzyl)oxy)-3-(5-(2-(2-hydroxypropan-2-yl)-5-methylpyrimidin-4-yl)-2-methylphenyl)-2,5-dimethylpyrimidin-4(3H)-one |
| 139 | 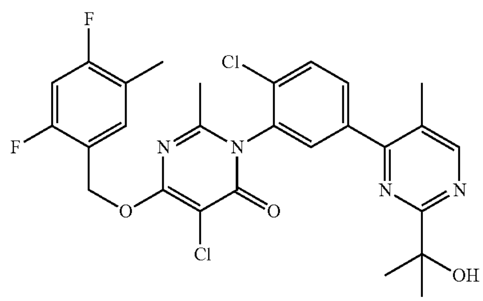 [SMILES: Cc1cc(COc2nc(C)n(-c3cc(-c4nc(C(C)(C)O)ncc4C)ccc3Cl)c(=O)c2Cl)c(F)cc1F] | 5-chloro-3-(2-chloro-5-(2-(2-hydroxypropan-2-yl)-5-methylpyrimidin-4-yl)phenyl)-6-((2,4-difluoro-5-methylbenzyl)oxy)-2-methylpyrimidin-4(3H)-one |
| 140 | 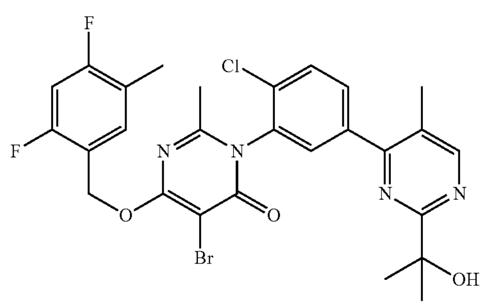 [SMILES: Cc1cc(COc2nc(C)n(-c3cc(-c4nc(C(C)(C)O)ncc4C)ccc3Cl)c(=O)c2Br)c(F)cc1F] | 5-bromo-3-(2-chloro-5-(2-(2-hydroxypropan-2-yl)-5-methylpyrimidin-4-yl)phenyl)-6-((2,4-difluoro-5-methylbenzyl)oxy)-2-methylpyrimidin-4(3H)-one |
| 141 | 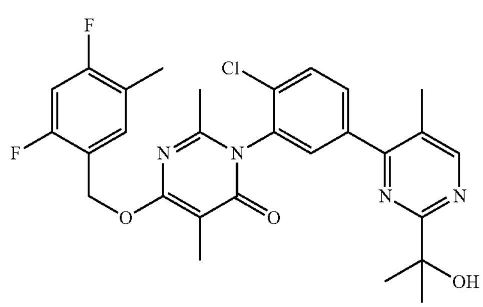 | 3-(2-chloro-5-(2-(2-hydroxypropan-2-yl)-5-methylpyrimidin-4-yl)phenyl)-6-((2,4-difluoro-5-methylbenzyl)oxy)-2,5-dimethylpyrimidin-4(3H)-one |

-continued

| Compound | Structure | Name |
|---|---|---|
| 142 | 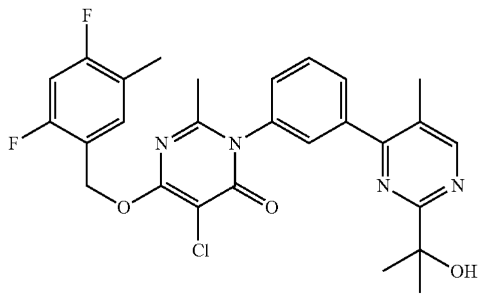 [SMILES: Cc1cc(COc2nc(C)n(-c3cccc(-c4nc(C(C)(C)O)ncc4C)c3)c(=O)c2Cl)c(F)cc1F] | 5-chloro-6-((2,4-difluoro-5-methylbenzyl)oxy)-3-(3-(2-(2-hydroxypropan-2-yl)-5-methylpyrimidin-4-yl)phenyl)-2-methylpyrimidin-4(3H)-one |
| 143 | 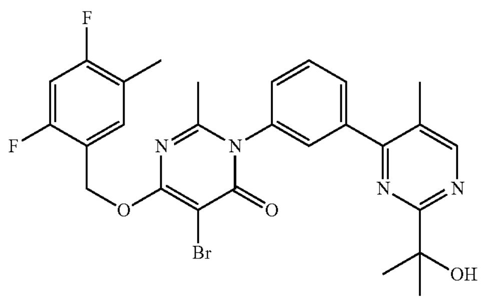 [SMILES: Cc1cc(COc2nc(C)n(-c3cccc(-c4nc(C(C)(C)O)ncc4C)c3)c(=O)c2Br)c(F)cc1F] | 5-bromo-6-((2,4-difluoro-5-methylbenzyl)oxy)-3-(3-(2-(2-hydroxypropan-2-yl)-5-methylpyrimidin-4-yl)phenyl)-2-methylpyrimidin-4(3H)-one |
| 144 | 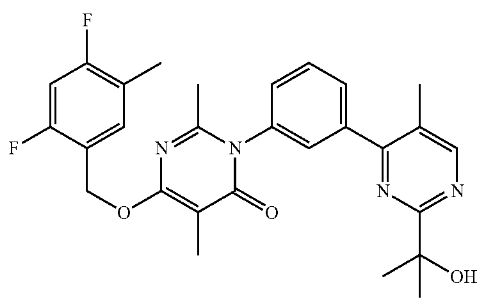 [SMILES: Cc1cc(COc2nc(C)n(-c3cccc(-c4nc(C(C)(C)O)ncc4C)c3)c(=O)c2C)c(F)cc1F] | 6-((2,4-difluoro-5-methylbenzyl)oxy)-3-(3-(2-(2-hydroxypropan-2-yl)-5-methylpyrimidin-4-yl)phenyl)-2,5-dimethylpyrimidin-4(3H)-one |
| 145 | 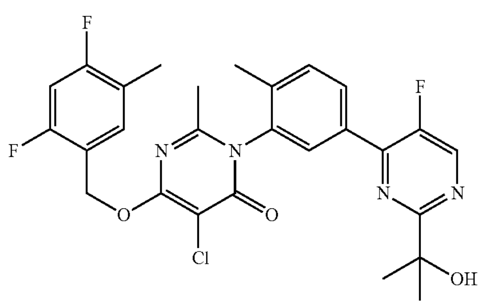 [SMILES: Cc1cc(COc2nc(C)n(-c3cc(-c4nc(C(C)(C)O)ncc4F)ccc3C)c(=O)c2Cl)c(F)cc1F] | 5-chloro-6-((2,4-difluoro-5-methylbenzyl)oxy)-3-(5-(5-fluoro-2-(2-hydroxypropan-2-yl)pyrimidin-4-yl)-2-methylphenyl)-2-methylpyrimidin-4(3H)-one |
| 146 | 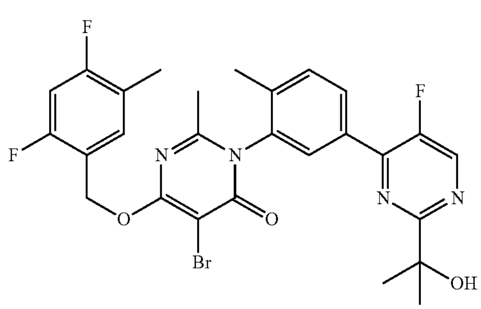 | 5-bromo-6-((2,4-difluoro-5-methylbenzyl)oxy)-3-(5-(5-fluoro-2-(2-hydroxypropan-2-yl)pyrimidin-4-yl)-2-methylphenyl)-2-methylpyrimidin-4(3H)-one |

-continued

| Compound | Structure | Name |
|---|---|---|
| 147 | 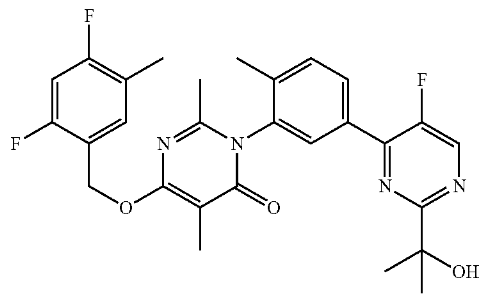 | 6-((2,4-difluoro-5-methylbenzyl)oxy)-3-(5-(5-fluoro-2-(2-hydroxypropan-2-yl)pyrimidin-4-yl)-2-methylphenyl)-2,5-dimethylpyrimidin-4(3H)-one |
| 148 | 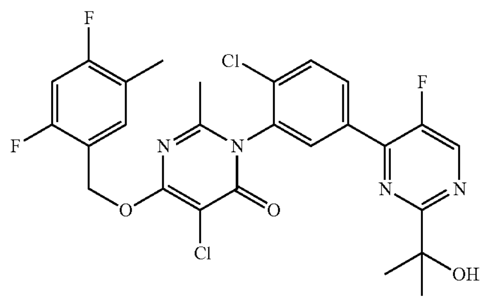 [SMILES: Cc1cc(COc2nc(C)n(-c3cc(-c4nc(C(C)(C)O)ncc4F)ccc3Cl)c(=O)c2Cl)c(F)cc1F] | 5-chloro-3-(2-chloro-5-(5-fluoro-2-(2-hydroxypropan-2-yl)pyrimidin-4-yl)phenyl)-6-((2,4-difluoro-5-methylbenzyl)oxy)-2-methylpyrimidin-4(3H)-one |
| 149 | 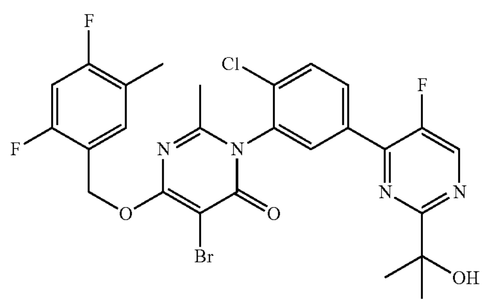 [SMILES: Cc1cc(COc2nc(C)n(-c3cc(-c4nc(C(C)(C)O)ncc4F)ccc3Cl)c(=O)c2Br)c(F)cc1F] | 5-bromo-3-(2-chloro-5-(5-fluoro-2-(2-hydroxypropan-2-yl)pyrimidin-4-yl)phenyl)-6-((2,4-difluoro-5-methylbenzyl)oxy)-2-methylpyrimidin-4(3H)-one |
| 150 | 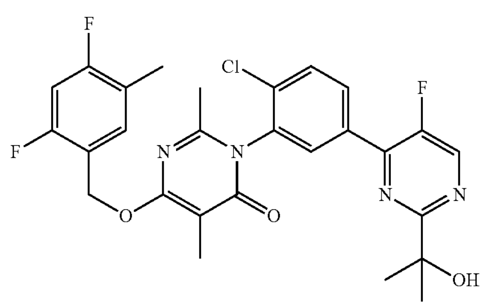 [SMILES: Cc1cc(COc2nc(C)n(-c3cc(-c4nc(C(C)(C)O)ncc4F)ccc3Cl)c(=O)c2C)c(F)cc1F] | 3-(2-chloro-5-(5-fluoro-2-(2-hydroxypropan-2-yl)pyrimidin-4-yl)phenyl)-6-((2,4-difluoro-5-methylbenzyl)oxy)-2,5-dimethylpyrimidin-4(3H)-one |
| 151 | 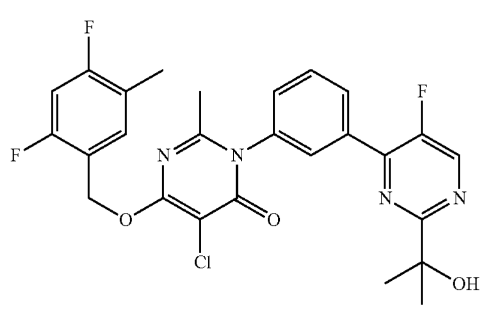 [SMILES: Cc1cc(COc2nc(C)n(-c3cccc(-c4nc(C(C)(C)O)ncc4F)c3)c(=O)c2Cl)c(F)cc1F] | 5-chloro-6-((2,4-difluoro-5-methylbenzyl)oxy)-3-(3-(5-fluoro-2-(2-hydroxypropan-2-yl)pyrimidin-4-yl)phenyl)-2-methylpyrimidin-4(3H)-one |

| Compound | Structure | Name |
|---|---|---|
| 152 | 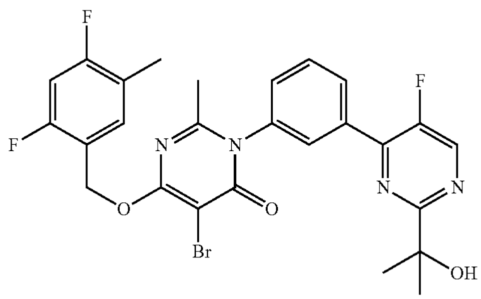 [SMILES: Cc1cc(COc2nc(C)n(-c3cccc(-c4nc(C(C)(C)O)ncc4F)c3)c(=O)c2Br)c(F)cc1F] | 5-bromo-6-((2,4-difluoro-5-methylbenzyl)oxy)-3-(3-(5-fluoro-2-(2-hydroxypropan-2-yl)pyrimidin-4-yl)phenyl)-2-methylpyrimidin-4(3H)-one |
| 153 | 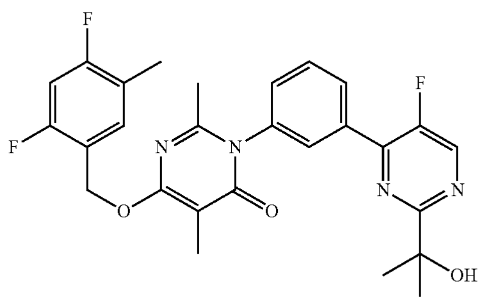 | 6-((2,4-difluoro-5-methylbenzyl)oxy)-3-(3-(5-fluoro-2-(2-hydroxypropan-2-yl)pyrimidin-4-yl)phenyl)-2,5-dimethylpyrimidin-4(3H)-one |
| 154 | 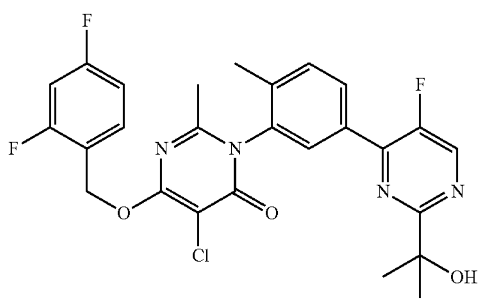 | 5-chloro-6-((2,4-difluorobenzyl)oxy)-3-(5-(5-fluoro-2-(2-hydroxypropan-2-yl)pyrimidin-4-yl)-2-methylphenyl)-2-methylpyrimidin-4(3H)-one |
| 155 | 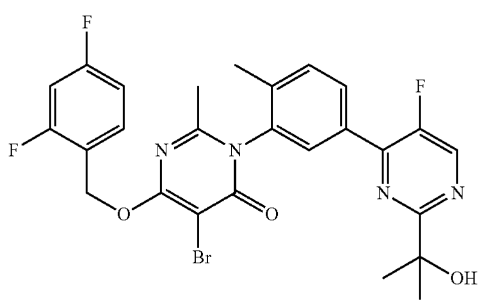 | 5-bromo-6-((2,4-difluorobenzyl)oxy)-3-(5-(5-fluoro-2-(2-hydroxypropan-2-yl)pyrimidin-4-yl)-2-methylphenyl)-2-methylpyrimidin-4(3H)-one |
| 156 | 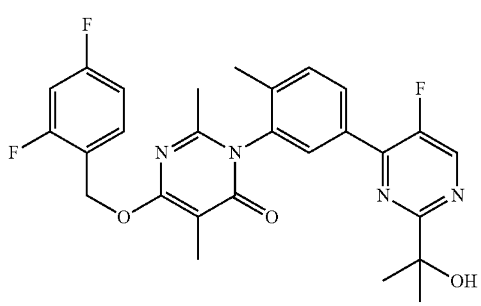 | 6-((2,4-difluorobenzyl)oxy)-3-(5-(5-fluoro-2-(2-hydroxypropan-2-yl)pyrimidin-4-yl)-2-methylphenyl)-2,5-dimethylpyrimidin-4(3H)-one |

| Compound | Structure | Name |
|---|---|---|
| 157 | 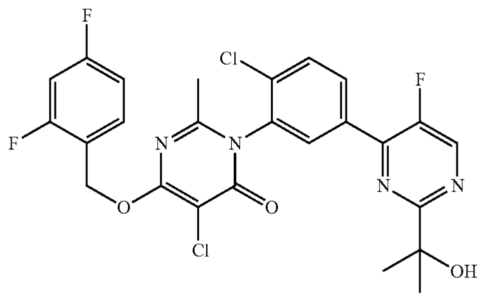 [SMILES: Cc1ccc(-c2nc(C(C)(C)O)ncc2F)cc1-n1c(C)nc(OCc2ccc(F)cc2F)c(Cl)c1=O] | 5-chloro-3-(2-chloro-5-(5-fluoro-2-(2-hydroxypropan-2-yl)pyrimidin-4-yl)phenyl)-6-((2,4-difluorobenzyl)oxy)-2-methylpyrimidin-4(3H)-one |
| 158 | 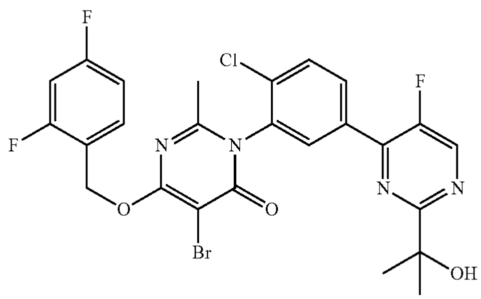 [SMILES: Cc1ccc(-c2nc(C(C)(C)O)ncc2F)cc1-n1c(C)nc(OCc2ccc(F)cc2F)c(Br)c1=O] | 5-bromo-3-(2-chloro-5-(5-fluoro-2-(2-hydroxypropan-2-yl)pyrimidin-4-yl)phenyl)-6-((2,4-difluorobenzyl)oxy)-2-methylpyrimidin-4(3H)-one |
| 159 | 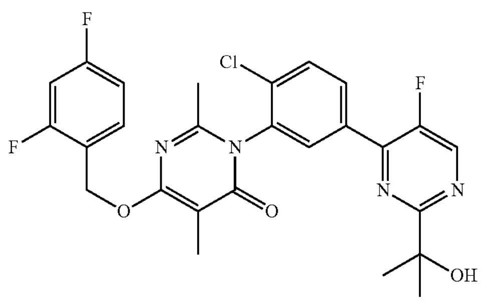 [SMILES: Cc1c(OCc2ccc(F)cc2F)nc(C)n(-c2cc(-c3nc(C(C)(C)O)ncc3F)ccc2Cl)c1=O] | 3-(2-chloro-5-(5-fluoro-2-(2-hydroxypropan-2-yl)primidin-4-yl)phenyl)-6-((2,4-difluorobenzyl)oxy)-2,5-dimethylpyrimidin-4(3H)-one |
| 160 | 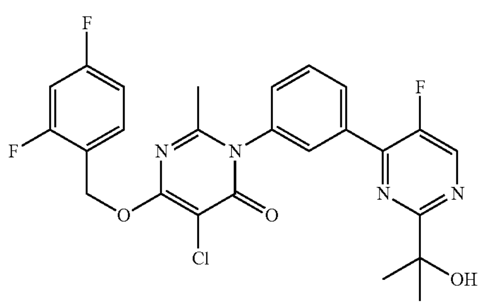 [SMILES: Cc1nc(OCc2ccc(F)cc2F)c(Cl)c(=O)n1-c1cccc(-c2nc(C(C)(C)O)ncc2F)c1] | 5-chloro-6-((2,4-difluorobenzyl)oxy)-3-(3-(5-fluoro-2-(2-hydroxypropan-2-yl)pyrimidin-4-yl)phenyl)-2-methylpyrimidin-4(3H)-one |
| 161 | 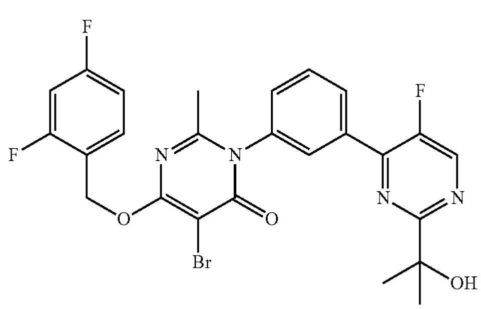 | 5-bromo-6-((2,4-difluorobenzyl)oxy)-3-(3-(5-fluoro-2-(2-hydroxypropan-2-yl)pyrimidin-4-yl)phenyl)-2-methylpyrimidin-4(3H)-one |

-continued

| Compound | Structure | Name |
|---|---|---|
| 162 | 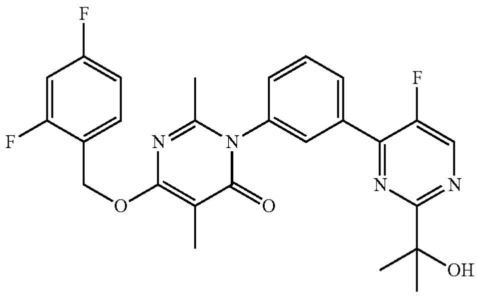 [SMILES: Cc1c(OCc2ccc(F)cc2F)nc(C)n(-c2cccc(-c3nc(C(C)(C)O)ncc3F)c2)c1=O] | 6-((2,4-difluorobenzyl)oxy)-3-(3-(5-fluoro-2-(2-hydroxypropan-2-yl)pyrimidin-4-yl)phenyl)-2,5-dimethylpyrimidin-4(3H)-one |
| 163 | 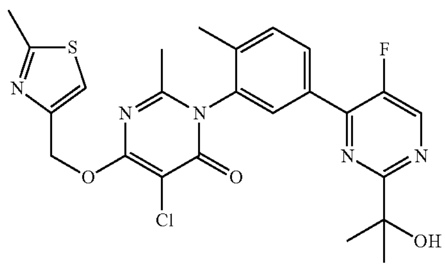 [SMILES: Cc1nc(COc2nc(C)n(-c3cc(-c4nc(C(C)(C)O)ncc4F)ccc3C)c(=O)c2Cl)cs1] | 5-chloro-3-(5-(5-fluoro-2-(2-hydroxypropan-2-yl)pyrimidin-4-yl)-2-methylphenyl)-2-methyl-6-((2-methylthiazol-4-yl)methoxy)pyrimidin-4(3H)-one |
| 164 | 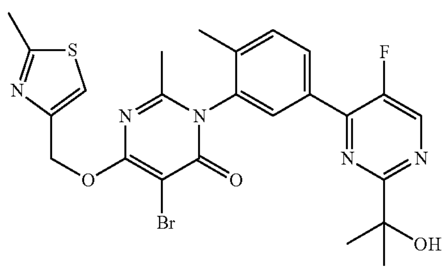 | 5-bromo-3-(5-(5-fluoro-2-(2-hydroxypropan-2-yl)pyrimidin-4-yl)-2-methylphenyl)-2-methyl-6-((2-methylthiazol-4-yl)methoxy)pyrimidin-4(3H)-one |
| 165 | 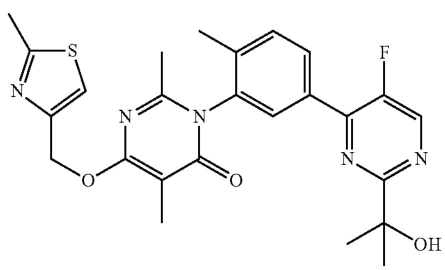 [SMILES: Cc1nc(COc2nc(C)n(-c3cc(-c4nc(C(C)(C)O)ncc4F)ccc3C)c(=O)c2C)cs1] | 3-(5-(5-fluoro-2-(2-hydroxypropan-2-yl)pyrimidin-4-yl)-2-methylphenyl)-2,5-dimethyl-6-((2-methylthiazol-4-yl)methoxy)pyrimidin-4(3H)-one |
| 166 | 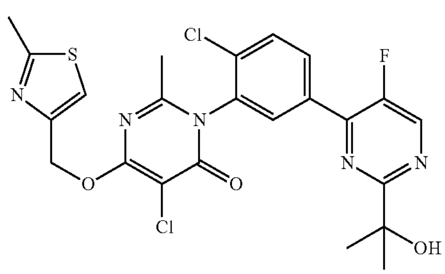 | 5-chloro-3-(2-chloro-5-(5-fluoro-2-(2-hydroxypropan-2-yl)pyrimidin-4-yl)phenyl)-2-methyl-6-((2-methylthiazol-4-yl)methoxy)pyrimidin-4(3H)-one |

-continued

| Compound | Structure | Name |
|---|---|---|
| 167 | 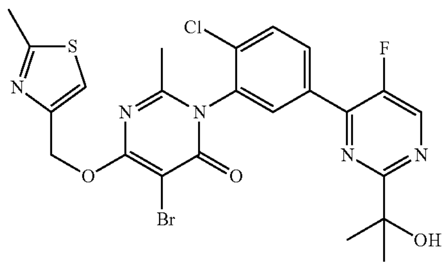 [SMILES: Cc1nc(COc2nc(C)n(-c3cc(-c4nc(C(C)(C)O)ncc4F)ccc3Cl)c(=O)c2Cl)cs1] | 5-bromo-3-(2-chloro-5-(5-fluoro-2-(2-hydroxypropan-2-yl)pyrimidin-4-yl)phenyl)-2-methyl-6-((2-methylthiazol-4-yl)methoxy)pyrimidin-4(3H)-one |
| 168 | 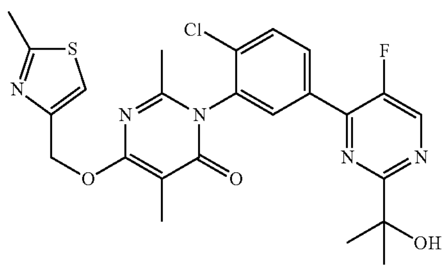 [SMILES: Cc1nc(COc2nc(C)n(-c3cc(-c4nc(C(C)(C)O)ncc4F)ccc3Cl)c(=O)c2C)cs1] | 3-(2-chloro-5-(5-fluoro-2-(2-hydroxypropan-2-yl)pyrimidin-4-yl)phenyl)-2,5-dimethyl-6-((2-methylthiazol-4-yl)methoxy)pyrimidin-4(3H)-one |
| 169 | 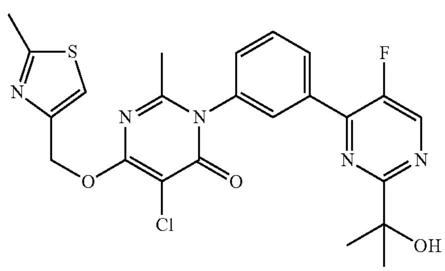 [SMILES: Cc1nc(COc2nc(C)n(-c3cccc(-c4nc(C(C)(C)O)ncc4F)c3)c(=O)c2Cl)cs1] | 5-chloro-3-(3-(5-fluoro-2-(2-hydroxypropan-2-yl)pyrimidin-4-yl)phenyl)-2-methyl-6-((2-methylthiazol-4-yl)methoxy)pyrimidin-4(3H)-one |
| 170 | 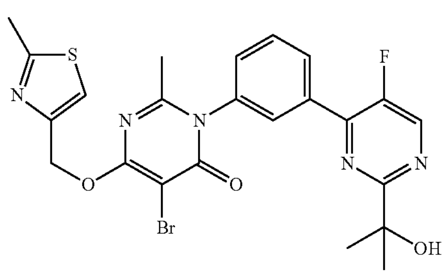 | 5-bromo-3-(3-(5-fluoro-2-(2-hydroxypropan-2-yl)pyrimidin-4-yl)phenyl)-2-methyl-6-((2-methylthiazol-4-yl)methoxy)pyrimidin-4(3H)-one |
| 171 | 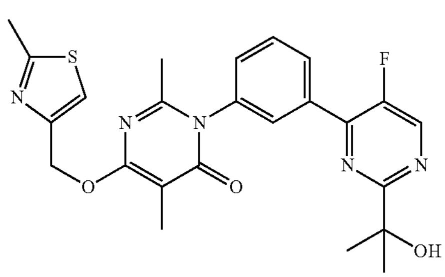 | 3-(3-(5-fluoro-2-(2-hydroxypropan-2-yl)pyrimidin-4-yl)phenyl)-2,5-dimethyl-6-((2-methylthiazol-4-yl)methoxy)pyrimidin-4(3H)-one |

| Compound | Structure | Name |
|---|---|---|
| 172 | 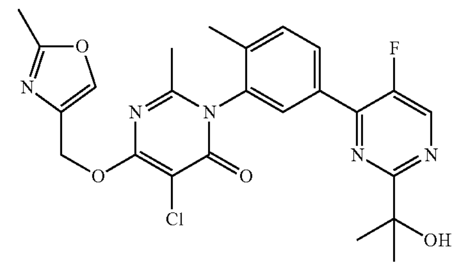 | 5-chloro-3-(5-(5-fluoro-2-(2-hydroxypropan-2-yl)pyrimidin-4-yl)-2-methylphenyl)-2-methyl-6-((2-methyloxazol-4-yl)methoxy)pyrimidin-4(3H)-one |
| 173 | 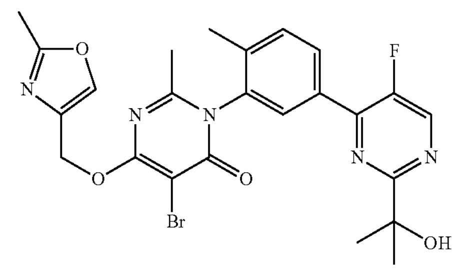 [SMILES: Cc1nc(COc2nc(C)n(-c3cc(-c4nc(C(C)(C)O)ncc4F)ccc3C)c(=O)c2Br)co1] | 5-bromo-3-(5-(5-fluoro-2-(2-hydroxypropan-2-yl)pyrimidin-4-yl)-2-methylphenyl)-2-methyl-6-((2-methyloxazol-4-yl)methoxy)pyrimidin-4(3H)-one |
| 174 | 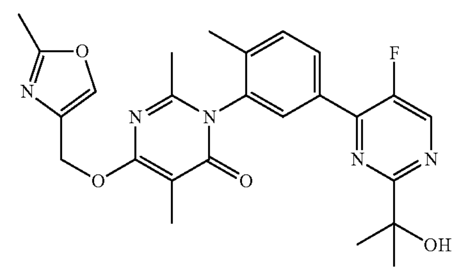 [SMILES: Cc1nc(COc2nc(C)n(-c3cc(-c4nc(C(C)(C)O)ncc4F)ccc3C)c(=O)c2C)co1] | 3-(5-(5-fluoro-2-(2-hydroxypropan-2-yl)pyrimidin-4-yl)-2-methylphenyl)-2,5-dimethyl-6-((2-methyloxazol-4-yl)methoxy)pyrimidin-4(3H)-one |
| 175 | 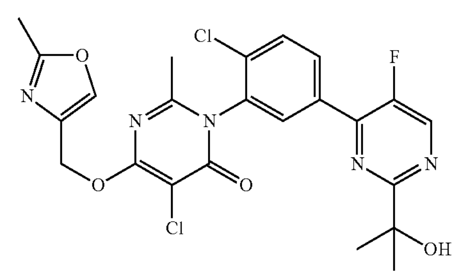 [SMILES: Cc1nc(COc2nc(C)n(-c3cc(-c4nc(C(C)(C)O)ncc4F)ccc3Cl)c(=O)c2Cl)co1] | 5-chloro-3-(2-chloro-5-(5-fluoro-2-(2-hydroxypropan-2-yl)pyrimidin-4-yl)phenyl)-2-methyl-6-((2-methyloxazol-4-yl)methoxy)pyrimidin-4(3H)-one |
| 176 | 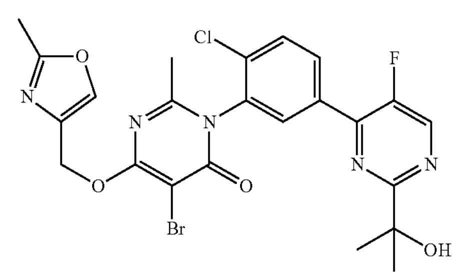 [SMILES: Cc1nc(COc2nc(C)n(-c3cc(-c4nc(C(C)(C)O)ncc4F)ccc3Cl)c(=O)c2Br)co1] | 5-bromo-3-(2-chloro-5-(5-fluoro-2-(2-hydroxypropan-2-yl)pyrimidin-4-yl)phenyl)-2-methyl-6-((2-methyloxazol-4-yl)methoxy)pyrimidin-4(3H)-one |

| Compound | Structure | Name |
| --- | --- | --- |
| 177 | 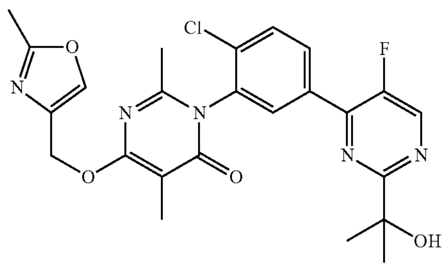 | 3-(2-chloro-5-(5-fluoro-2-(2-hydroxypropan-2-yl)pyrimidin-4-yl)phenyl)-2,5-dimethyl-6-((2-methyloxazol-4-yl)methoxy)pyrimidin-4(3H)-one |
| 178 | 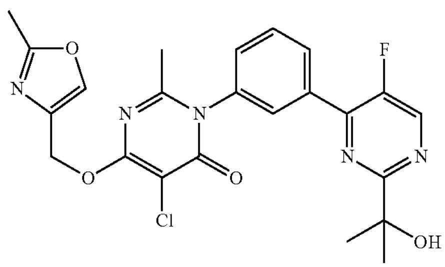 | 5-chloro-3-(3-(5-fluoro-2-(2-hydroxypropan-2-yl)pyrimidin-4-yl)phenyl)-2-methyl-6-((2-methyloxazol-4-yl)methoxy)pyrimidin-4(3H)-one |
| 179 | 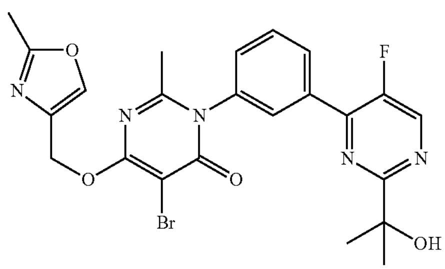 [SMILES: Cc1nc(COc2nc(C)n(-c3cccc(-c4nc(C(C)(C)O)ncc4F)c3)c(=O)c2Br)co1] | 5-bromo-3-(3-(5-fluoro-2-(2-hydroxypropan-2-yl)pyrimidin-4-yl)phenyl)-2-methyl-6-((2-methyloxazol-4-yl)methoxy)pyrimidin-4(3H)-one |
| 180 | 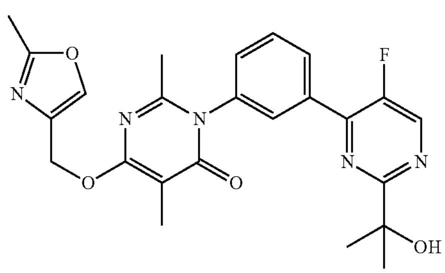 [SMILES: Cc1nc(COc2nc(C)n(-c3cccc(-c4nc(C(C)(C)O)ncc4F)c3)c(=O)c2C)co1] | 3-(3-(5-fluoro-2-(2-hydroxypropan-2-yl)pyrimidin-4-yl)phenyl)-2,5-dimethyl-6-((2-methyloxazol-4-yl)methoxy)pyrimidin-4(3H)-one |
| 181 | 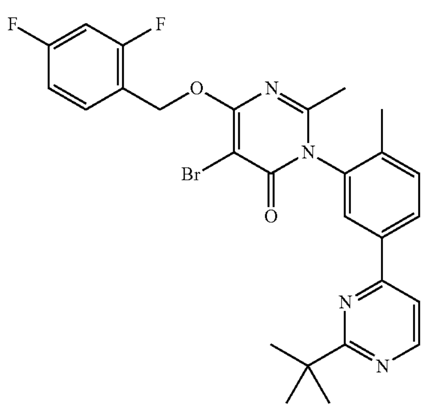 [SMILES: Cc1ccc(-c2ccnc(C(C)(C)C)n2)cc1-n1c(C)nc(OCc2ccc(F)cc2F)c(Br)c1=O] | 5-bromo-3-(5-(2-(tert-butyl)pyrimidin-4-yl)-2-methylphenyl)-6-((2,4-difluorobenzyl)oxy)-2-methylpyrimidin-4(3H)-one |

-continued

| Compound | Structure | Name |
|---|---|---|
| 182 | 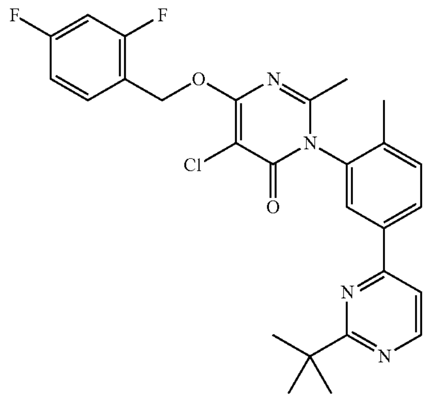 [SMILES: Cc1ccc(-c2ccnc(C(C)(C)C)n2)cc1-n1c(C)nc(OCc2ccc(F)cc2F)c(Cl)c1=O] | 3-(5-(2-(tert-butyl)pyrimidin-4-yl)-2-methylphenyl)-5-chloro-6-((2,4-difluorobenzyl)oxy)-2-methylpyrimidin-4(3H)-one |
| 183 | 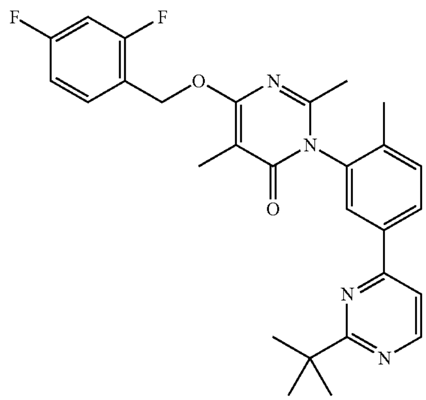 [SMILES: Cc1ccc(-c2ccnc(C(C)(C)C)n2)cc1-n1c(C)nc(OCc2ccc(F)cc2F)c(C)c1=O] | 3-(5-(2-(tert-butyl)pyrimidin-4-yl)-2-methylphenyl)-6-((2,4-difluorobenzyl)oxy)-2,5-dimethylpyrimidin-4(3H)-one |
| 184 | 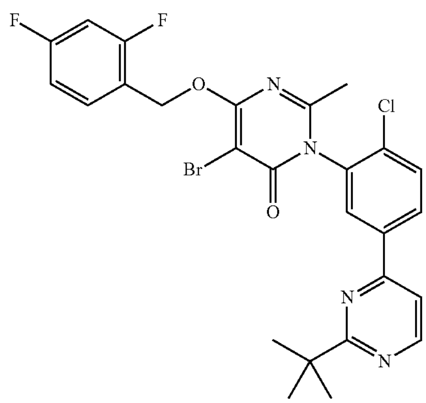 [SMILES: Cc1nc(OCc2ccc(F)cc2F)c(Cl)c(=O)n1-c1cc(-c2ccnc(C(C)(C)C)n2)ccc1Cl] | 5-bromo-3-(5-(2-(tert-butyl)pyrimidin-4-yl)-2-chlorophenyl)-6-((2,4-difluorobenzyl)oxy)-2-methylpyrimidin-4(3H)-one |
| 185 | 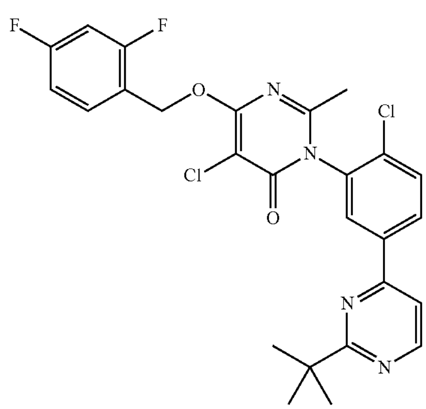 | 3-(5-(2-(tert-butyl)pyrimidin-4-yl)-2-chlorophenyl)-5-chloro-6-((2,4-difluorobenzyl)oxy)-2-methylpyrimidin-4(3H)-one |

-continued

| Compound | Structure | Name |
|---|---|---|
| 186 | 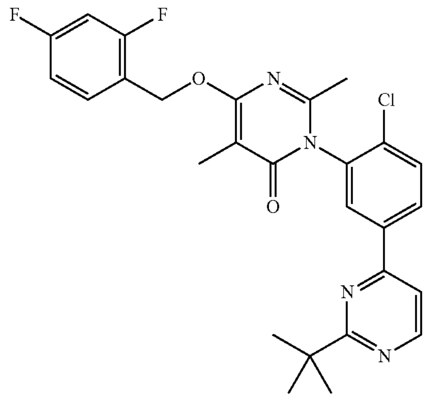 [SMILES: Cc1c(OCc2ccc(F)cc2F)nc(C)n(-c2cc(-c3ccnc(C(C)(C)C)n3)ccc2Cl)c1=O] | 3-(5-(2-(tert-butyl)pyrimidin-4-yl)-2-chlorophenyl)-6-((2,4-difluorobenzyl)oxy)-2,5-dimethylpyrimidin-4(3H)-one |
| 187 | 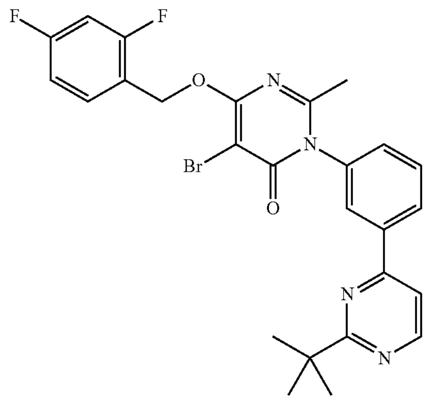 [SMILES: Cc1nc(OCc2ccc(F)cc2F)c(Br)c(=O)n1-c1cccc(-c2ccnc(C(C)(C)C)n2)c1] | 5-bromo-3-(3-(2-(tert-butyl)pyrimidin-4-yl)phenyl)-6-((2,4-difluorobenzyl)oxy)-2-methylpyrimidin-4(3H)-one |
| 188 | 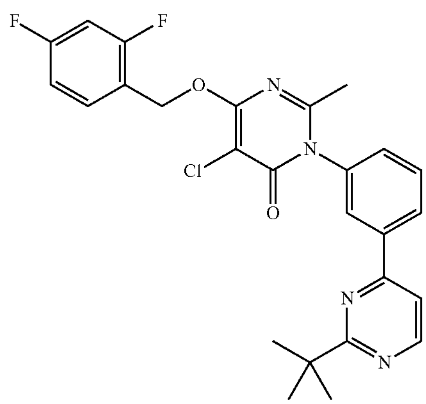 [SMILES: Cc1nc(OCc2ccc(F)cc2F)c(Cl)c(=O)n1-c1cccc(-c2ccnc(C(C)(C)C)n2)c1] | 3-(3-(2-(tert-butyl)pyrimidin-4-yl)phenyl)-5-chloro-6-((2,4-difluorobenzyl)oxy)-2-methylpyrimidin-4(3H)-one |
| 189 | 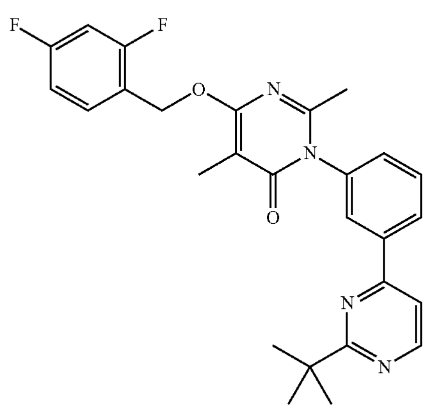 [SMILES: Cc1c(OCc2ccc(F)cc2F)nc(C)n(-c2cccc(-c3ccnc(C(C)(C)C)n3)c2)c1=O] | 3-(3-(2-(tert-butyl)pyrimidin-4-yl)phenyl)-6-((2,4-difluorobenzyl)oxy)-2,5-dimethylpyrimidin-4(3H)-one |

-continued

| Compound | Structure | Name |
|---|---|---|
| 190 | 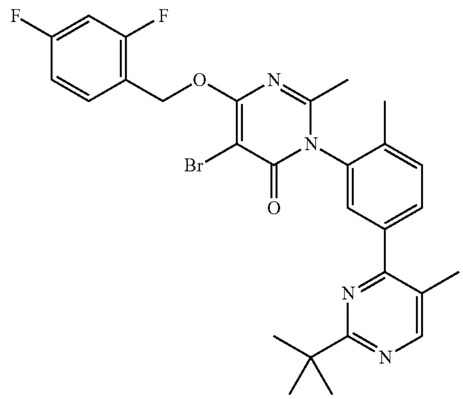 [SMILES: Cc1ccc(-c2nc(C(C)(C)C)ncc2C)cc1-n1c(C)nc(OCc2ccc(F)cc2F)c(Br)c1=O] | 5-bromo-3-(5-(2-(tert-butyl)-5-methylpyrimidin-4-yl)-2-methylphenyl)-6-((2,4-difluorobenzyl)oxy)-2-methylpyrimidin-4(3H)-one |
| 191 | 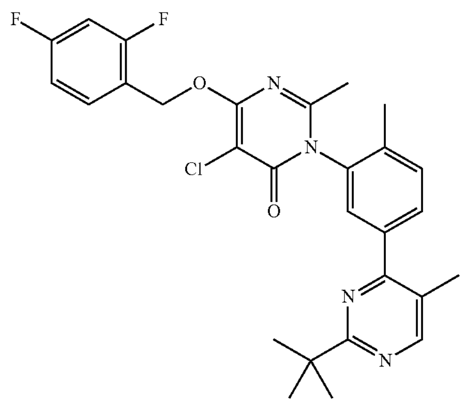 [SMILES: Cc1ccc(-c2nc(C(C)(C)C)ncc2C)cc1-n1c(C)nc(OCc2ccc(F)cc2F)c(Cl)c1=O] | 3-(5-(2-(tert-butyl)-5-methylpyrimidin-4-yl)-2-methylphenyl)-5-chloro-6-((2,4-difluorobenzyl)oxy)-2-methylpyrimidin-4(3H)-one |
| 192 | 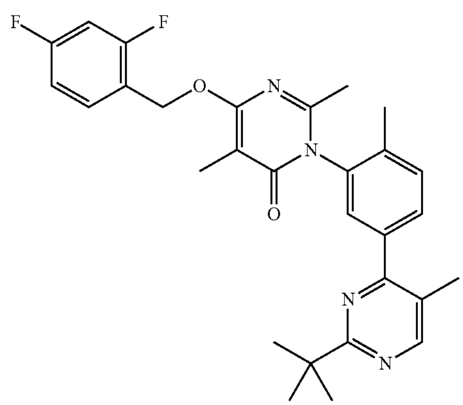 [SMILES: Cc1ccc(-c2nc(C(C)(C)C)ncc2C)cc1-n1c(C)nc(OCc2ccc(F)cc2F)c(C)c1=O] | 3-(5-(2-(tert-butyl)-5-methylpyrimidin-4-yl)-2-methylphenyl)-6-((2,4-difluorobenzyl)oxy)-2,5-dimethylpyrimidin-4(3H)-one |
| 193 | 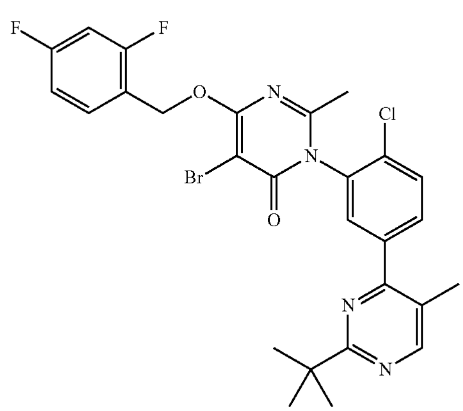 [SMILES: Cc1cnc(C(C)(C)C)nc1-c1ccc(Cl)c(-n2c(C)nc(OCc3ccc(F)cc3F)c(Br)c2=O)c1] | 5-bromo-3-(5-(2-(tert-butyl)-5 methylpyrimidin-4-yl)-2-chlorophenyl)-6-((2,4-difluorobenzyl)oxy)-2-methylpyrimidin-4(3H)-one |

| Compound | Structure | Name |
|---|---|---|
| 194 | 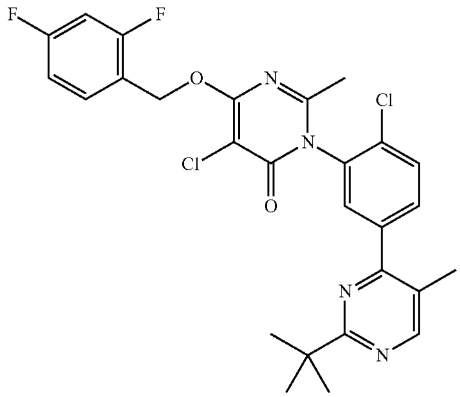 [SMILES: Cc1cnc(C(C)(C)C)nc1-c1ccc(Cl)c(-n2c(C)nc(OCc3ccc(F)cc3F)c(Cl)c2=O)c1] | 3-(5-(2-(tert-butyl)-5-methylpyrimidin-4-yl)-2-chlorophenyl)-5-chloro-6-((2,4-difluorobenzyl)oxy)-2-methylpyrimidin-4(3H)-one |
| 195 | 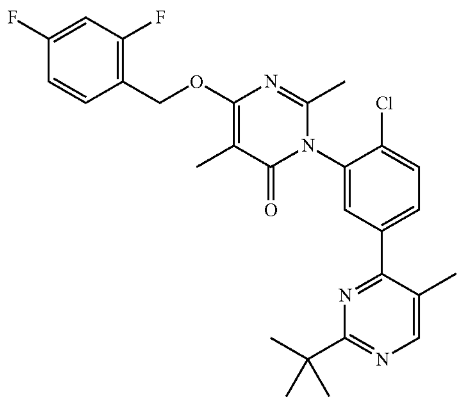 [SMILES: Cc1cnc(C(C)(C)C)nc1-c1ccc(Cl)c(-n2c(C)nc(OCc3ccc(F)cc3F)c(C)c2=O)c1] | 3-(5-(2-(tert-butyl)-5-methylpyrimidin-4-yl)-2-chlorophenyl)-6-((2,4-difluorobenzyl)oxy)-2,5-dimethylpyrimidin-4(3H)-one |
| 196 | 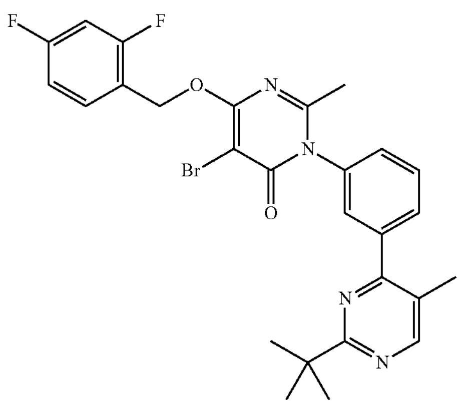 [SMILES: Cc1cnc(C(C)(C)C)nc1-c1cccc(-n2c(C)nc(OCc3ccc(F)cc3F)c(Br)c2=O)c1] | 5-bromo-3-(3-(2-(tert-butyl)-5-methylpyrimidin-4-yl)phenyl)-6-((2,4-difluorobenzyl)oxy)-2-methylpyrimidin-4(3H)-one |
| 197 | 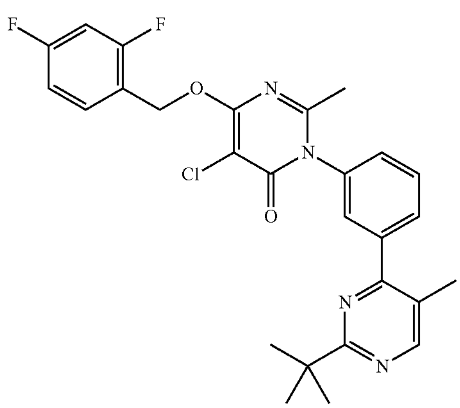 [SMILES: Cc1cnc(C(C)(C)C)nc1-c1cccc(-n2c(C)nc(OCc3ccc(F)cc3F)c(Cl)c2=O)c1] | 3-(3-(2-(tert-butyl)-5-methylpyrimidin-4-yl)phenyl)-5-chloro-6-((2,4-difluorobenzyl)oxy)-2-methylpyrimidin-4(3H)-one |

| Compound | Structure | Name |
|---|---|---|
| 198 | 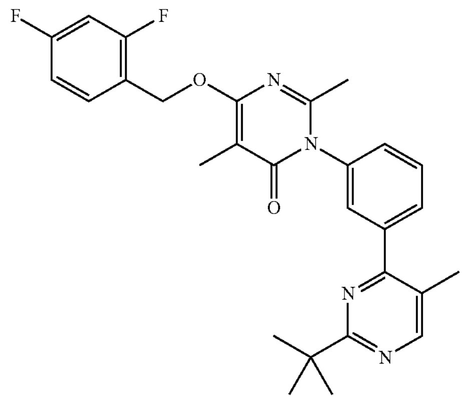 [SMILES: Cc1cnc(C(C)(C)C)nc1-c1cccc(-n2c(C)nc(OCc3ccc(F)cc3F)c(C)c2=O)c1] | 3-(3-(2-(tert-butyl)-5-methylpyrimidin-4-yl)phenyl)-6-((2,4-difluorobenzyl)oxy)-2,5-dimethylpyrimidin-4(3H)-one |
| 199 | 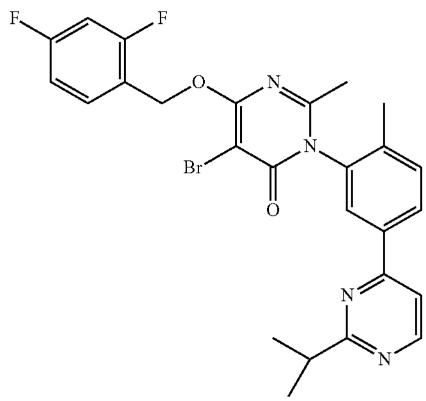 [SMILES: Cc1ccc(-c2ccnc(C(C)C)n2)cc1-n1c(C)nc(OCc2ccc(F)cc2F)c(Br)c1=O] | 5-bromo-6-((2,4-difluorobenzyl)oxy)-3-(5-(2-isopropylpyrimidin-4-yl)-2-methylphenyl)-2-methylpyrimidin-4(3H)-one |
| 200 | 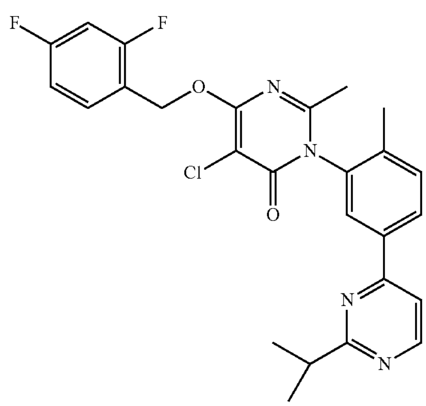 [SMILES: Cc1ccc(-c2ccnc(C(C)C)n2)cc1-n1c(C)nc(OCc2ccc(F)cc2F)c(Cl)c1=O] | 5-chloro-6-((2,4-difluorobenzyl)oxy)-3-(5-(2-isopropylpyrimidin-4-yl)-2-methylphenyl)-2-methylpyrimidin-4(3H)-one |
| 201 | 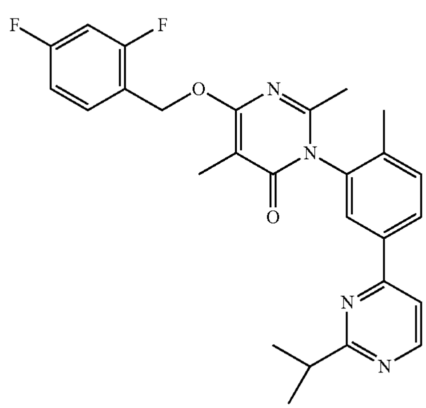 [SMILES: Cc1ccc(-c2ccnc(C(C)C)n2)cc1-n1c(C)nc(OCc2ccc(F)cc2F)c(C)c1=O] | 6-((2,4-difluorobenzyl)oxy)-3-(5-(2-isopropylpyrimidin-4-yl)-2-methylphenyl)-2,5-dimethylpyrimidin-4(3H)-one |

| Compound | Structure | Name |
|---|---|---|
| 202 | 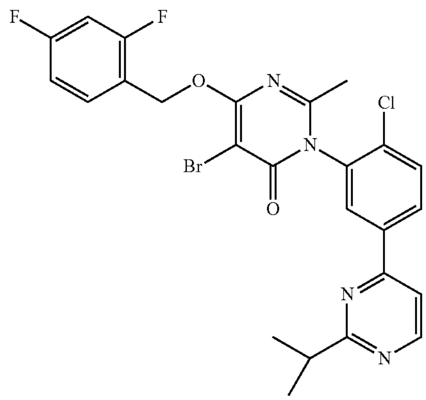 [SMILES: Cc1nc(OCc2ccc(F)cc2F)c(Br)c(=O)n1-c1cc(-c2ccnc(C(C)C)n2)ccc1Cl] | 5-bromo-3-(2-chloro-5-(2-isopropylpyrimidin-4-yl)phenyl)-6-((2,4-difluorobenzyl)oxy)-2-methylpyrimidin-4(3H)-one |
| 203 | 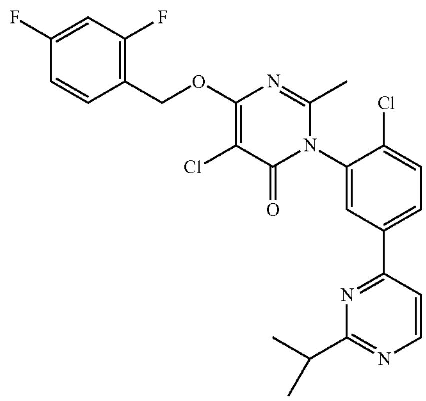 [SMILES: Cc1nc(OCc2ccc(F)cc2F)c(Cl)c(=O)n1-c1cc(-c2ccnc(C(C)C)n2)ccc1Cl] | 5-chloro-3-(2-chloro-5-(2-isopropylpyrimidin-4-yl)phenyl)-6-((2,4-difluorobenzyl)oxy)-2-methylpyrimidin-4(3H)-one |
| 204 | 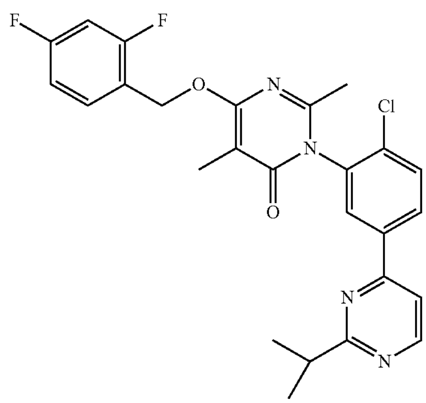 [SMILES: Cc1c(OCc2ccc(F)cc2F)nc(C)n(-c2cc(-c3ccnc(C(C)C)n3)ccc2Cl)c1=O] | 3-(2-chloro-5-(2-isopropylpyrimidin-4-yl)phenyl)-6-((2,4-difluorobenzyl)oxy)-2,5-dimethylpyrimidin-4(3H)-one |
| 205 | 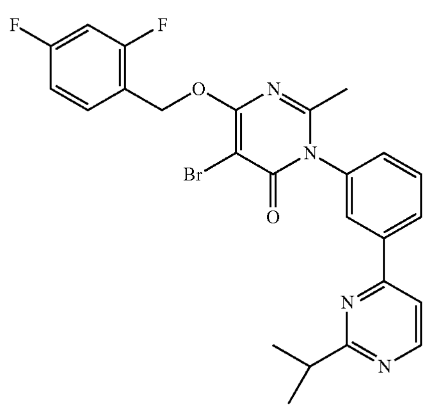 [SMILES: Cc1nc(OCc2ccc(F)cc2F)c(Br)c(=O)n1-c1cccc(-c2ccnc(C(C)C)n2)c1] | 5-bromo-6-((2,4-difluorobenzyl)oxy)-3-(3-(2-isopropylpyrimidin-4-yl)phenyl)-2-methylpyrimidin-4(3H)-one |

-continued

| Compound | Structure | Name |
|---|---|---|
| 206 | 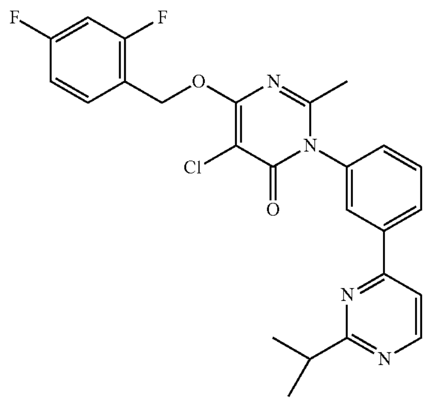 [SMILES: Cc1nc(OCc2ccc(F)cc2F)c(Cl)c(=O)n1-c1cccc(-c2ccnc(C(C)C)n2)c1] | 5-chloro-6-((2,4-difluorobenzyl)oxy)-3-(3-(2-isopropylpyrimidin-4-yl)phenyl)-2-methylpyrimidin-4(3H)-one |
| 207 | 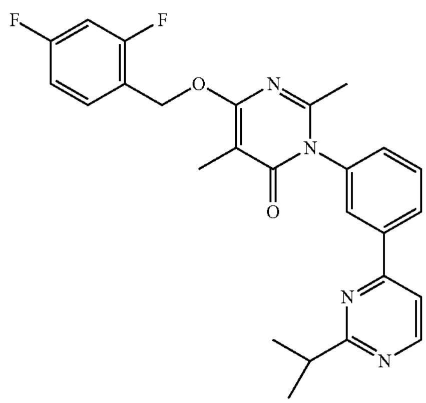 [SMILES: Cc1c(OCc2ccc(F)cc2F)nc(C)n(-c2cccc(-c3ccnc(C(C)C)n3)c2)c1=O] | 6-((2,4-difluorobenzyl)oxy)-3-(3-(2-isopropylpyrimidin-4-yl)phenyl)-2,5-dimethylpyrimidin-4(3H)-one |
| 208 | 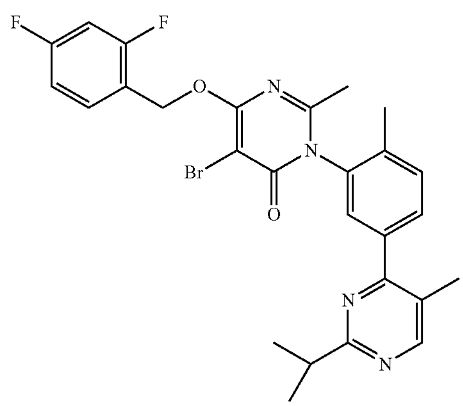 [SMILES: Cc1ccc(-c2nc(C(C)C)ncc2C)cc1-n1c(C)nc(OCc2ccc(F)cc2F)c(Br)c1=O] | 5-bromo-6-((2,4-difluorobenzyl)oxy)-3-(5-(2-isopropyl-5-methylpyrimidin-4-yl)-2-methylphenyl)-2-methylpyrimidin-4(3H)-one |
| 209 | 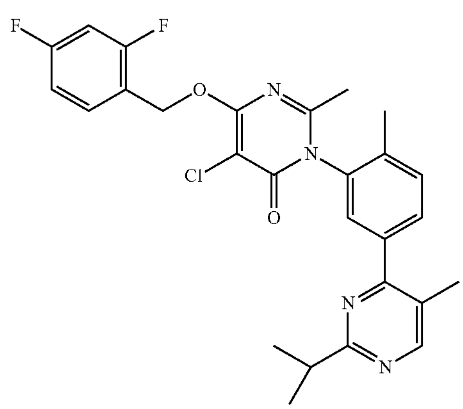 [SMILES: Cc1ccc(-c2nc(C(C)C)ncc2C)cc1-n1c(C)nc(OCc2ccc(F)cc2F)c(Cl)c1=O] | 5-chloro-6-((2,4-difluorobenzyl)oxy)-3-(5-(2-isopropyl-5-methylpyrimidin-4-yl)-2-methylphenyl)-2-methylpyrimidin-4(3H)-one |

-continued

| Compound | Structure | Name |
|---|---|---|
| 210 | 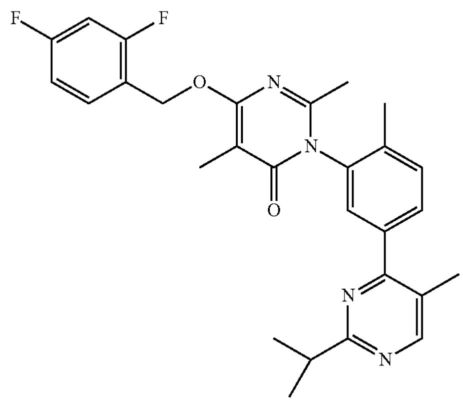 [SMILES: Cc1ccc(-c2nc(C(C)C)ncc2C)cc1-n1c(C)nc(OCc2ccc(F)cc2F)c(C)c1=O] | 6-((2,4-difluorobenzyl)oxy)-3-(5-(2-isopropyl-5-methylpyrimidin-4-yl)-2-methylphenyl)-2,5-dimethylpyrimidin-4(3H)-one |
| 211 | 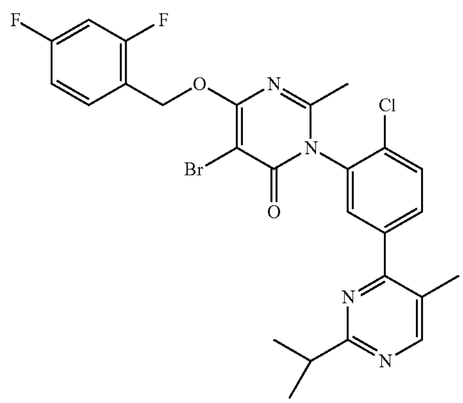 [SMILES: Cc1cnc(C(C)C)nc1-c1ccc(Cl)c(-n2c(C)nc(OCc3ccc(F)cc3F)c(Br)c2=O)c1] | 5-bromo-3-(2-chloro-5-(2-isopropyl-5-methylpyrimidin-4-yl)phenyl)-6-((2,4-difluorobenzyl)oxy)-2-methylpyrimidin-4(3H)-one |
| 212 | 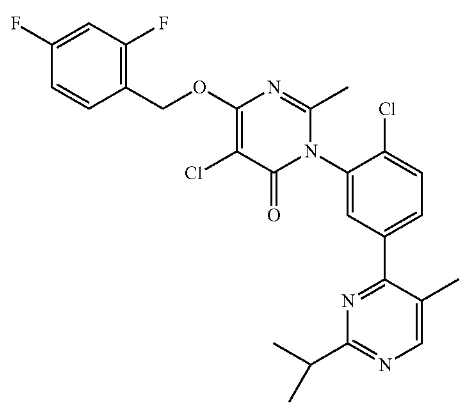 [SMILES: Cc1cnc(C(C)C)nc1-c1ccc(Cl)c(-n2c(C)nc(OCc3ccc(F)cc3F)c(Cl)c2=O)c1] | 5-chloro-3-(2-chloro-5-(2-isopropyl-5-methylpyrimidin-4-yl)phenyl)-6-((2,4-difluorobenzyl)oxy)-2-methylpyrimidin-4(3H)-one |
| 213 | 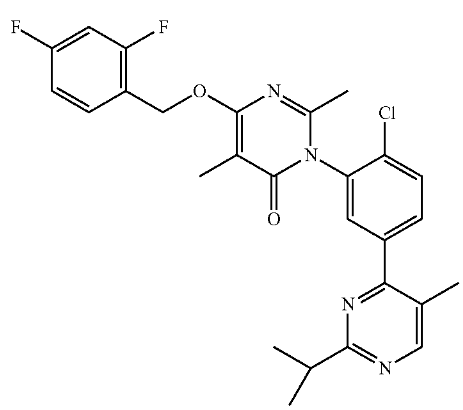 [SMILES: Cc1cnc(C(C)C)nc1-c1ccc(Cl)c(-n2c(C)nc(OCc3ccc(F)cc3F)c(C)c2=O)c1] | 3-(2-chloro-5-(2-isopropyl-5-methylpyrimidin-4-yl)phenyl)-6-((2,4-difluorobenzyl)oxy)-2,5-dimethylpyrimidin-4(3H)-one |

-continued

| Compound | Structure | Name |
|---|---|---|
| 214 | 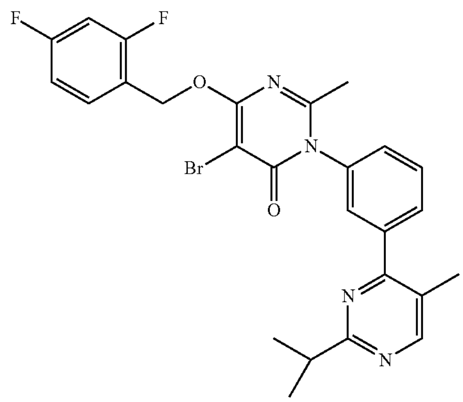 [SMILES: Cc1cnc(C(C)C)nc1-c1cccc(-n2c(C)nc(OCc3ccc(F)cc3F)c(Br)c2=O)c1] | 5-bromo-6-((2,4-difluorobenzyl)oxy)-3-(3-(2-isopropyl-5-methylpyrimidin-4-yl)phenyl)-2-methylpyrimidin-4(3H)-one |
| 215 | 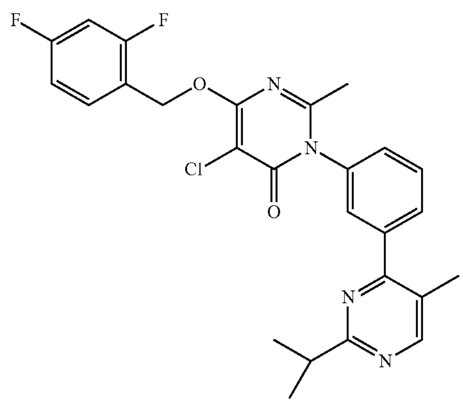 [SMILES: Cc1cnc(C(C)C)nc1-c1cccc(-n2c(C)nc(OCc3ccc(F)cc3F)c(Cl)c2=O)c1] | 5-chloro-6-((2,4-difluorobenzyl)oxy)-3-(3-(2-isopropyl-5-methylpyrimidin-4-yl)phenyl)-2-methylpyrimidin-4(3H)-one |
| 216 | 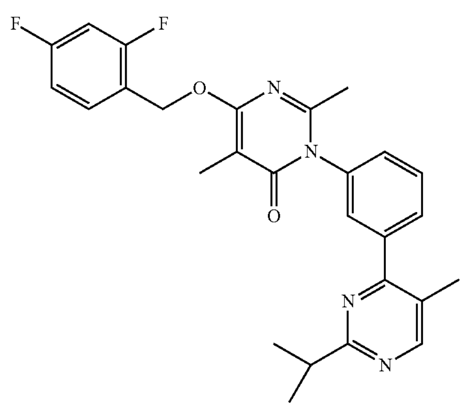 [SMILES: Cc1cnc(C(C)C)nc1-c1cccc(-n2c(C)nc(OCc3ccc(F)cc3F)c(C)c2=O)c1] | 6-((2,4-difluorobenzyl)oxy)-3-(3-(2-isopropyl-5-methylpyrimidin-4-yl)phenyl)-2,5-dimethylpyrimidin-4(3H)-one |
| 217 | 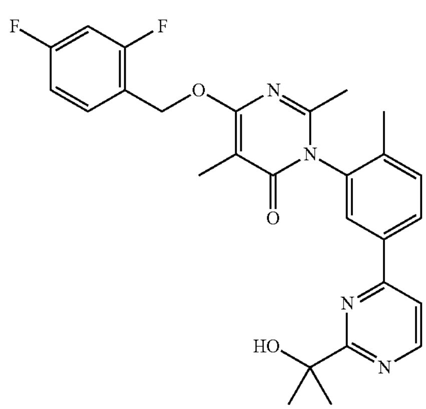 [SMILES: Cc1ccc(-c2ccnc(C(C)(C)O)n2)cc1-n1c(C)nc(OCc2ccc(F)cc2F)c(C)c1=O] | 6-((2,4-difluorobenzyl)oxy)-3-(5-(2-(2-hydroxypropan-2-yl)pyrimidin-4-yl)-2-methylphenyl)-2,5-dimethylpyrimidin-4(3H)-one |

| Compound | Structure | Name |
|---|---|---|
| 218 | 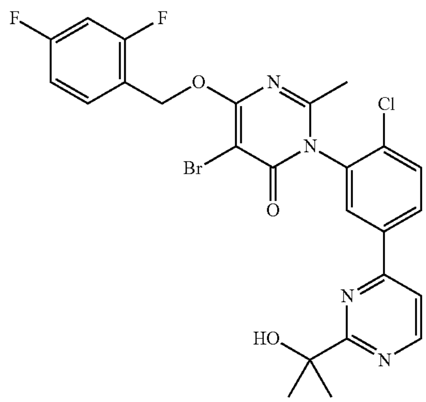 [SMILES: Cc1nc(OCc2ccc(F)cc2F)c(Br)c(=O)n1-c1cc(-c2ccnc(C(C)(C)O)n2)ccc1Cl] | 5-bromo-3-(2-chloro-5-(2-(2-hydroxypropan-2-yl)pyrimidin-4-yl)phenyl)-6-((2,4-difluorobenzyl)oxy)-2-methylpyrimidin-4(3H)-one |
| 219 | 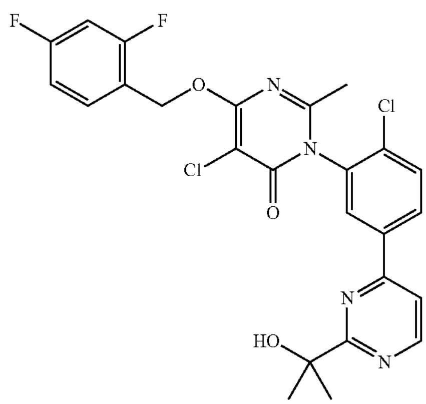 [SMILES: Cc1nc(OCc2ccc(F)cc2F)c(Cl)c(=O)n1-c1cc(-c2ccnc(C(C)(C)O)n2)ccc1Cl] | 5-chloro-3-(2-chloro-5-(2-(2-hydroxypropan-2-yl)pyrimidin-4-yl)phenyl)-6-((2,4-difluorobenzyl)oxy)-2-methylpyrimidin-4(3H)-one |
| 220 | 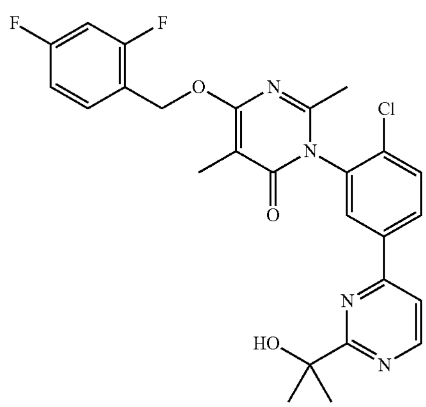 [SMILES: Cc1c(OCc2ccc(F)cc2F)nc(C)n(-c2cc(-c3ccnc(C(C)(C)O)n3)ccc2Cl)c1=O] | 3-(2-chloro-5-(2-(2-hydroxypropan-2-yl)pyrimidin-4-yl)phenyl)-6-((2,4-difluorobenzyl)oxy)-2,5-dimethylpyrimidin-4(3H)-one |
| 221 | 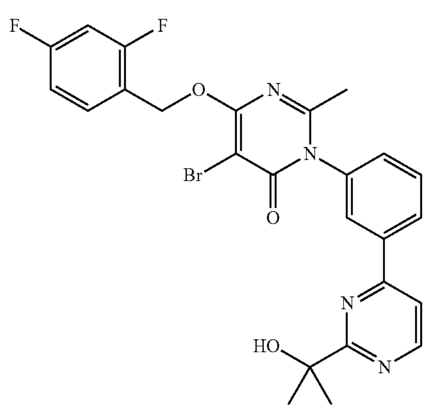 | 5-bromo-6-((2,4-difluorobenzyl)oxy)-3-(3-(2-(2-hydroxypropan-2-yl)pyrimidin-4-yl)phenyl)-2-methylpyrimidin-4(3H)-one |

| Compound | Structure | Name |
|---|---|---|
| 222 | 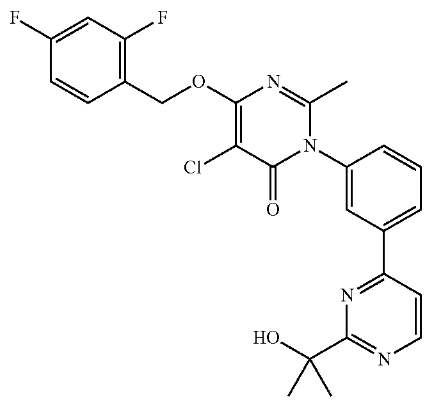 [SMILES: Cc1nc(OCc2ccc(F)cc2F)c(Cl)c(=O)n1-c1cccc(-c2ccnc(C(C)(C)O)n2)c1] | 5-chloro-6-((2,4-difluorobenzyl)oxy)-3-(3-(2-(2-hydroxypropan-2-yl)pyrimidin-4-yl)phenyl)-2-methylpyrimidin-4(3H)-one |
| 223 | 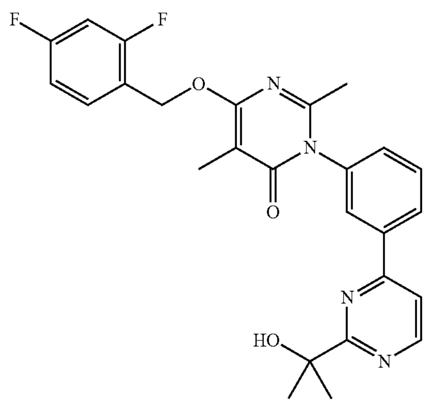 [SMILES: Cc1c(OCc2ccc(F)cc2F)nc(C)n(-c2cccc(-c3ccnc(C(C)(C)O)n3)c2)c1=O] | 6-((2,4-difluorobenzyl)oxy)-3-(3-(2-(2-hydroxypropan-2-yl)pyrimidin-4-yl)phenyl)-2,5-dimethylpyrimidin-4(3H)-one |
| 224 | 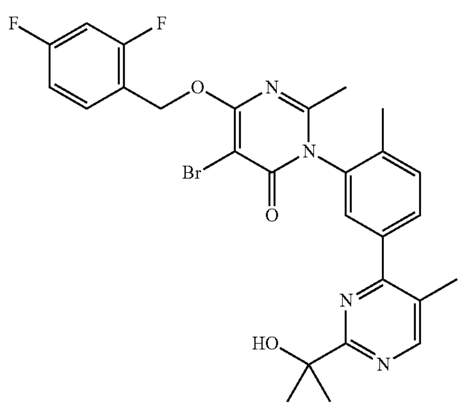 | 5-bromo-6-((2,4-difluorobenzyl)oxy)-3-(5-(2-(2-hydroxypropan-2-yl)-5-methylpyrimidin-4-yl)-2-methylphenyl)-2-methylpyrimidin-4(3H)-one |
| 225 | 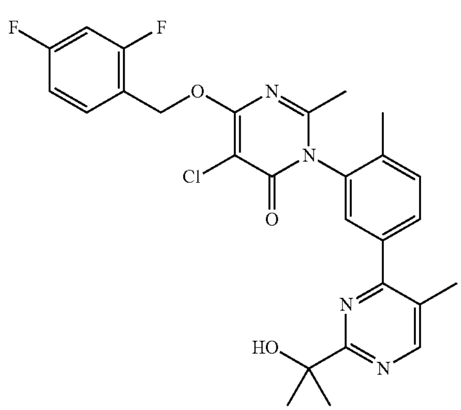 [SMILES: Cc1ccc(-c2nc(C(C)(C)O)ncc2C)cc1-n1c(C)nc(OCc2ccc(F)cc2F)c(Cl)c1=O] | 5-chloro-6-((2,4-difluorobenzyl)oxy)-3-(5-(2-(2-hydroxypropan-2-yl)-5-methylpyrimidin-4-yl)-2-methylphenyl)-2-methylpyrimidin-4(3H)-one |

| Compound | Structure | Name |
|---|---|---|
| 226 | 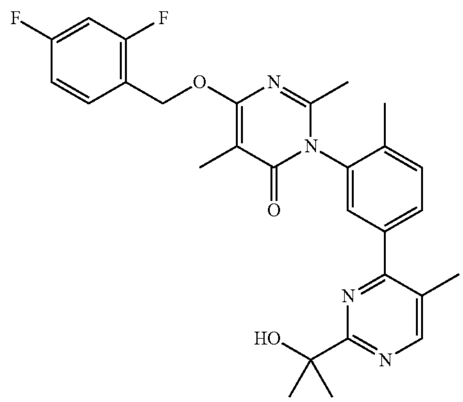 [SMILES: Cc1ccc(-c2nc(C(C)(C)O)ncc2C)cc1-n1c(C)nc(OCc2ccc(F)cc2F)c(C)c1=O] | 6-((2,4-difluorobenzyl)oxy)-3-(5-(2-(2-hydroxypropan-2-yl)-5-methylpyrimidin-4-yl)-2-methylphenyl)-2,5-dimethylpyrimidin-4(3H)-one |
| 227 | 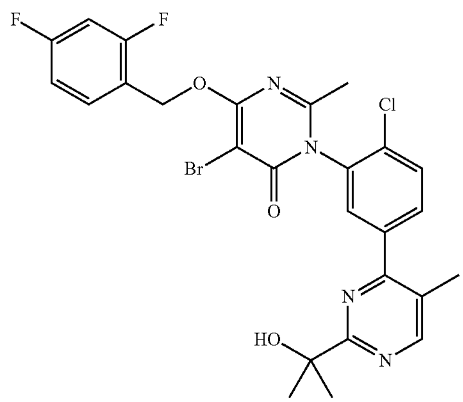 [SMILES: Cc1cnc(C(C)(C)O)nc1-c1ccc(Cl)c(-n2c(C)nc(OCc3ccc(F)cc3F)c(Cl)c2=O)c1] | 5-bromo-3-(2-chloro-5-(2-(2-hydroxypropan-2-yl)-5-methylpyrimidin-4-yl)phenyl)-6-((2,4-difluorobenzyl)oxy)-2-methylpyrimidin-4(3H)-one |
| 228 | 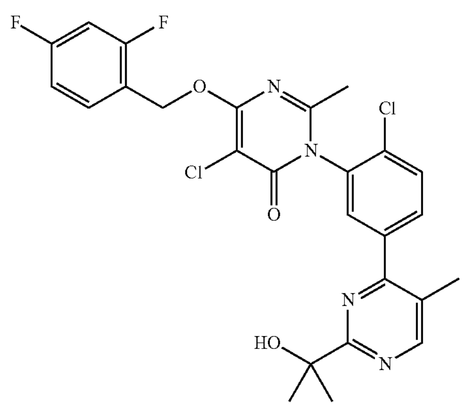 | 5-chloro-3-(2-chloro-5-(2-(2-hydroxypropan-2-yl)-5-methylpyrimidin-4-yl)phenyl)-6-((2,4-difluorobenzyl)oxy)-2-methylpyrimidin-4(3H)-one |
| 229 | 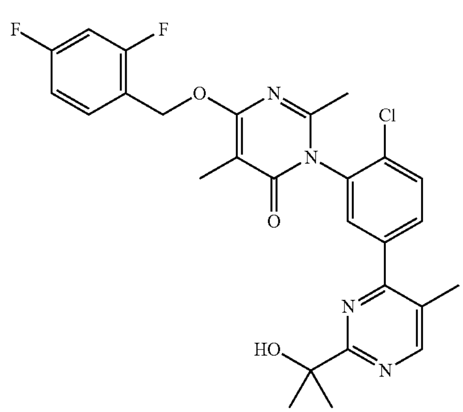 [SMILES: Cc1cnc(C(C)(C)O)nc1-c1ccc(Cl)c(-n2c(C)nc(OCc3ccc(F)cc3F)c(C)c2=O)c1] | 3-(2-chloro-5-(2-(2-hydroxypropan-2-yl)-5-methylpyrimidin-4-yl)phenyl)-6-((2,4-difluorobenzyl)oxy)-2,5-dimethylpyrimidin-4(3H)-one |

-continued

| Compound | Structure | Name |
|---|---|---|
| 230 | 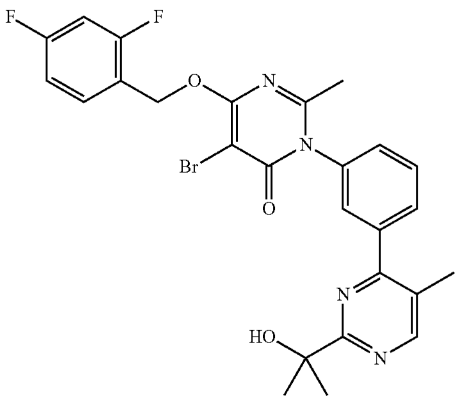 [SMILES: Cc1cnc(C(C)(C)O)nc1-c1cccc(-n2c(C)nc(OCc3ccc(F)cc3F)c(Cl)c2=O)c1] | 5-bromo-6-((2,4-difluorobenzyl)oxy)-3-(3-(2-(2-hydroxypropan-2-yl)-5-methylpyrimidin-4-yl)phenyl)-2-methylpyrimidin-4(3H)-one |
| 231 | 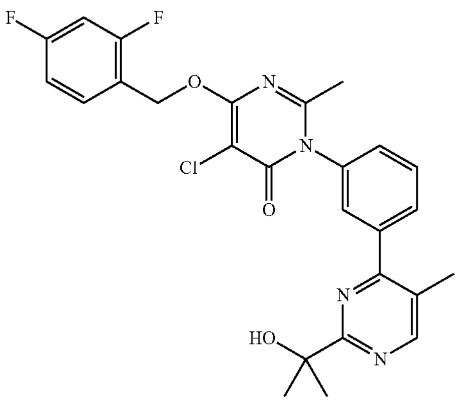 | 5-chloro-6-((2,4-difluorobenzyl)oxy)-3-(3-(2-(2-hydroxypropan-2-yl)-5-methylpyrimidin-4-yl)phenyl)-2-methylpyrimidin-4(3H)-one |
| 232 | 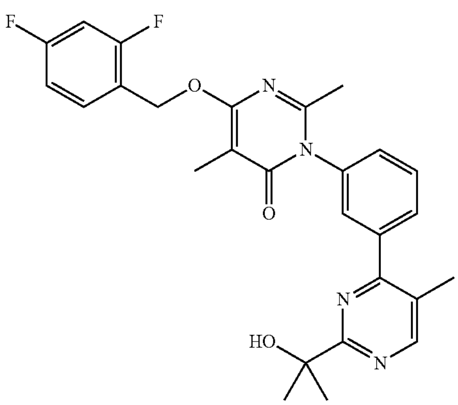 [SMILES: Cc1cnc(C(C)(C)O)nc1-c1cccc(-n2c(C)nc(OCc3ccc(F)cc3F)c(C)c2=O)c1] | 6-((2,4-difluorobenyl)oxy)-3-(3-(2-(2-hydroxypropan-2-yl)-5-methylpyrimidin-4-yl)phenyl)-2,5-dimethylpyrimidin-4(3H)-one |
| 233 | 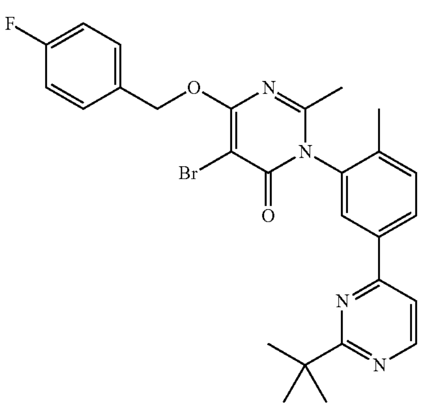 [SMILES: Cc1ccc(-c2ccnc(C(C)(C)C)n2)cc1-n1c(C)nc(OCc2ccc(F)cc2)c(Br)c1=O] | 5-bromo-3-(5-(2-(tert-butyl)pyrimidin-4-yl)-2-methykohenyl)-6-((4-fluorobenzyl)oxy)-2-methylpyrimidin-4(3H)-one |

-continued

| Compound | Structure | Name |
|---|---|---|
| 234 | 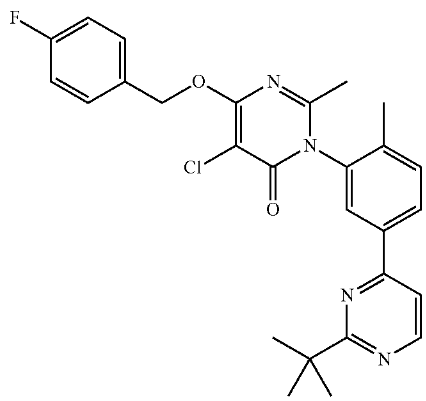 [SMILES: Cc1ccc(-c2ccnc(C(C)(C)C)n2)cc1-n1c(C)nc(OCc2ccc(F)cc2)c(Cl)c1=O] | 3-(5-(2-(tert-butyl)pyrimidin-4-yl)-2-methylphenyl)-5-chloro-6-((4-fluorobenzyl)oxy)-2-methylpyrimidin-4(3H)-one |
| 235 | 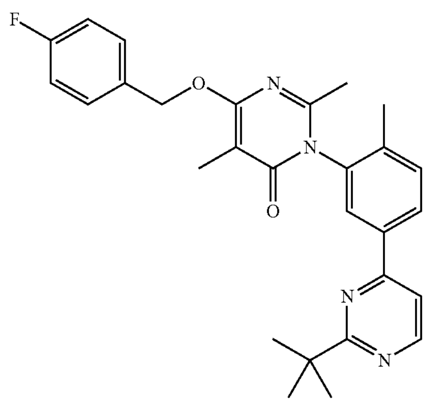 [SMILES: Cc1ccc(-c2ccnc(C(C)(C)C)n2)cc1-n1c(C)nc(OCc2ccc(F)cc2)c(C)c1=O] | 3-(5-(2-(tert-butyl)pyrimidin-4-yl)-2-methylphenyl)-6-((4-fluorobenzyl)oxy)-2,5-dimethylpyrimidin-4(3H)-one |
| 236 | 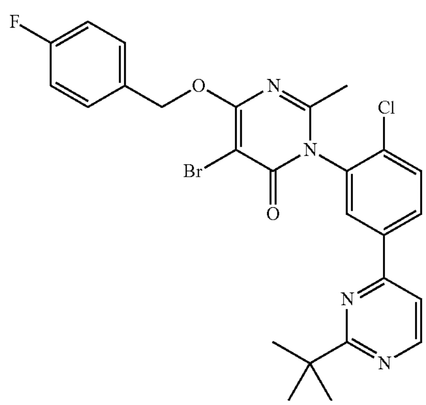 [SMILES: Cc1nc(OCc2ccc(F)cc2)c(Br)c(=O)n1-c1cc(-c2ccnc(C(C)(C)C)n2)ccc1Cl] | 5-bromo-3-(5-(2-(tert-butyl)pyrimidin-4-yl)-2-chlorophenyl)-6-((4-fluorobenzyl)oxy)-2-methylpyrimidin-4(3H)-one |
| 237 | 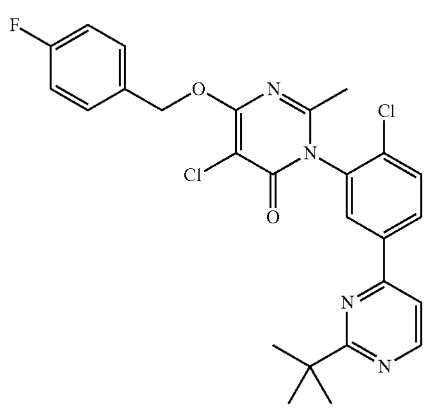 [SMILES: Cc1nc(OCc2ccc(F)cc2)c(Cl)c(=O)n1-c1cc(-c2ccnc(C(C)(C)C)n2)ccc1Cl] | 3-(5-(2-(tert-butyl)pyrimidin-4-yl)-2-chlorophenyl)-5-chloro-6-((4-fluorobenzyl)oxy)-2-methylpyrimidin-4(3H)-one |

| Compound | Structure | Name |
|---|---|---|
| 238 | 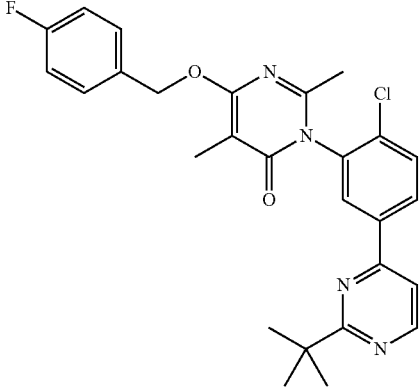 | 3-(5-(2-(tert-butyl)pyrimidin-4-yl)-2-chlorophenyl)-6-((4-fluorobenzyl)oxy)-2,5-dimethylpyrimidin-4(3H)-one |
| 239 | 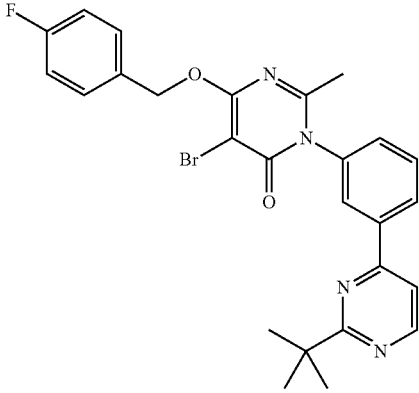 [SMILES: Cc1nc(OCc2ccc(F)cc2)c(Br)c(=O)n1-c1cccc(-c2ccnc(C(C)(C)C)n2)c1] | 5-bromo-3-(3-(2-(tert-butyl)pyrimidin-4-yl)phenyl)-6-((4-fluorobenzyl)oxy)-2-methylpyrimidin-4(3H)-one |
| 240 | 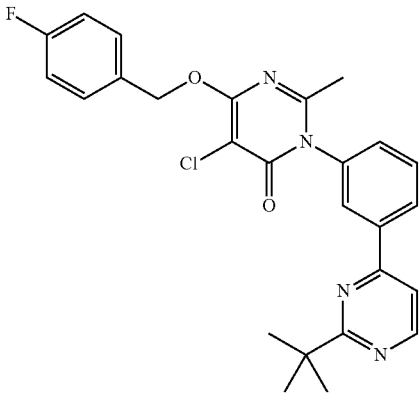 [SMILES: Cc1nc(OCc2ccc(F)cc2)c(Cl)c(=O)n1-c1cccc(-c2ccnc(C(C)(C)C)n2)c1] | 3-(3-(2-(tert-butyl)pyrimidin-4-yl)phenyl)-5-chloro-6-((4-fluorobenzyl)oxy)-2-methylpyrimidin-4(3H)-one |
| 241 | 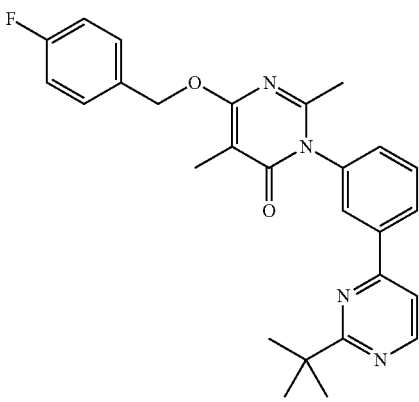 [SMILES: Cc1c(OCc2ccc(F)cc2)nc(C)n(-c2cccc(-c3ccnc(C(C)(C)C)n3)c2)c1=O] | 3-(3-(2-(tert-butyl)pyrimidin-4-yl)phenyl)-6-((4-fluorobenzyl)oxy)-2,5-dimethylpyrimidin-4(3H)-one |

| Compound | Structure | Name |
|---|---|---|
| 242 | 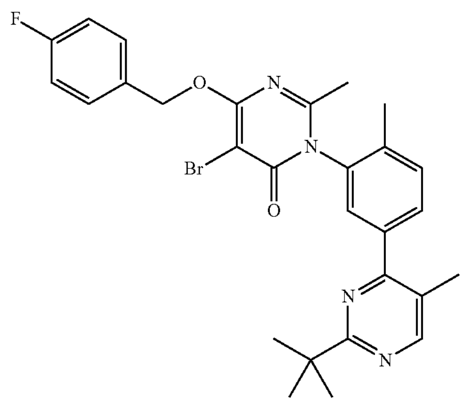 [SMILES: Cc1ccc(-c2nc(C(C)(C)C)ncc2C)cc1-n1c(C)nc(OCc2ccc(F)cc2)c(Br)c1=O] | 5-bromo-3-(5-(2-(tert-butyl)-5-methylpyrimidin-4-yl)-2-methylphenyl)-6-((4-fluorobenzyl)oxy)-2-methylpyrimidin-4(3H)-one |
| 243 | 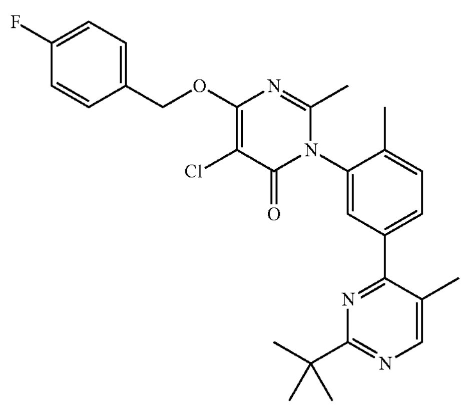 [SMILES: Cc1ccc(-c2nc(C(C)(C)C)ncc2C)cc1-n1c(C)nc(OCc2ccc(F)cc2)c(Cl)c1=O] | 3-(5-(2-(tert-butyl)-5-methylpyrimidin-4-yl)-2-methylphenyl)-5-chloro-6-((4-fluorobenzyl)oxy)-2-methylpyrimidin-4(3H)-one |
| 244 | 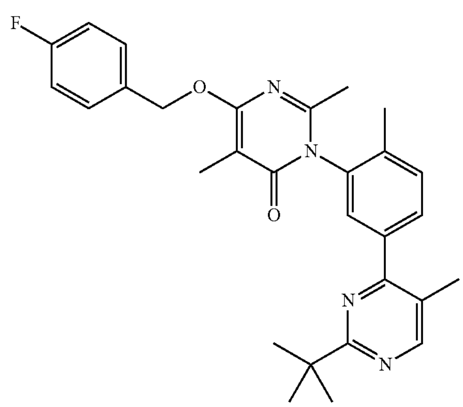 [SMILES: Cc1ccc(-c2nc(C(C)(C)C)ncc2C)cc1-n1c(C)nc(OCc2ccc(F)cc2)c(C)c1=O] | 3-(5-(2-(tert-butyl)-5-methylpyrimidin-4-yl)-2-methylphenyl)-6-((4-fluorobenzyl)oxy)-2,5-dimethylpyrimidin-4(3H)-one |
| 245 | 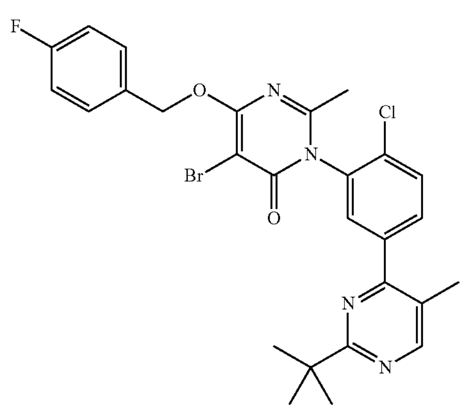 [SMILES: Cc1cnc(C(C)(C)C)nc1-c1ccc(Cl)c(-n2c(C)nc(OCc3ccc(F)cc3)c(Br)c2=O)c1] | 5-bromo-3-(5-(2-(tert-butyl)-5-methylpyrimidin-4-yl)-2-chlorophenyl)-6-((4-fluorobenzyl)oxy)-2-methylpyrimidin-4(3H)-one |

-continued

| Compound | Structure | Name |
|---|---|---|
| 246 | 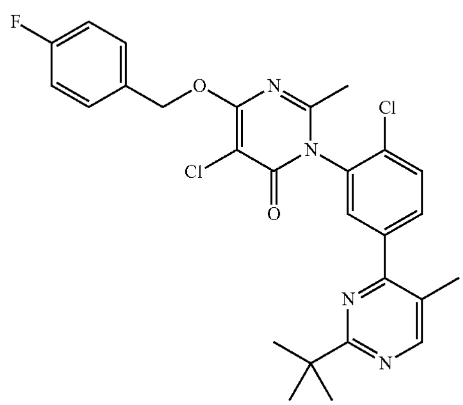 [SMILES: Cc1cnc(C(C)(C)C)nc1-c1ccc(Cl)c(-n2c(C)nc(OCc3ccc(F)cc3)c(Cl)c2=O)c1] | 3-(5-(2-(tert-butyl)-5-methylpyrimidin-4-yl)-2-chlorophenyl)-5-chloro-6-((4-fluorobenzyl)oxy)-2-methylpyrimidin-4(3H)-one |
| 247 | 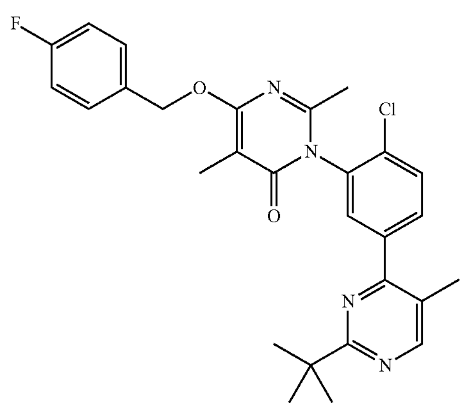 [SMILES: Cc1cnc(C(C)(C)C)nc1-c1ccc(Cl)c(-n2c(C)nc(OCc3ccc(F)cc3)c(C)c2=O)c1] | 3-(5-(2-(tert-butyl)-5-methylpyrimidin-4-yl)-2-chlorophenyl)-6-((4-fluorobenzyl)oxy)-2,5-dimethylpyrimidin-4(3H)-one |
| 248 | 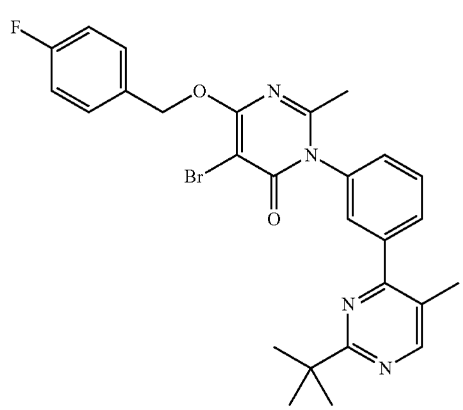 [SMILES: Cc1cnc(C(C)(C)C)nc1-c1cccc(-n2c(C)nc(OCc3ccc(F)cc3)c(Br)c2=O)c1] | 5-bromo-3-(3-(2-(tert-butyl)-5-methylpyrimidin-4-yl)phenyl)-6-((4-fluorobenzyl)oxy)-2-methylpyrimidin-4(3H)-one |
| 249 | 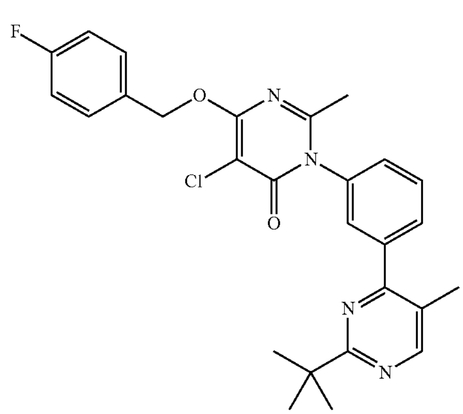 [SMILES: Cc1cnc(C(C)(C)C)nc1-c1cccc(-n2c(C)nc(OCc3ccc(F)cc3)c(Cl)c2=O)c1] | 3-(3-(2-(tert-butyl)-5-methylpyrimidin-4-yl)phenyl)-5-chloro-6-((4-fluorobenzyl)oxy)-2-methylpyrimidin-4(3H)-one |

-continued

| Compound | Structure | Name |
|---|---|---|
| 250 | 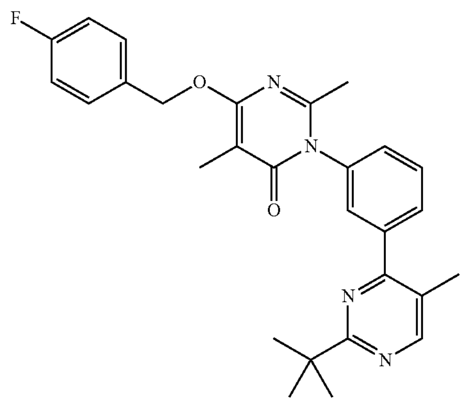 [SMILES: Cc1cnc(C(C)(C)C)nc1-c1cccc(-n2c(C)nc(OCc3ccc(F)cc3)c(C)c2=O)c1] | 3-(3-(2-(tert-butyl)-5-methylpyrimidin-4-yl)phenyl)-6-((4-fluorobenzyl)oxy)-2,5-dimethylpyrimidin-4(3H)-one |
| 251 | 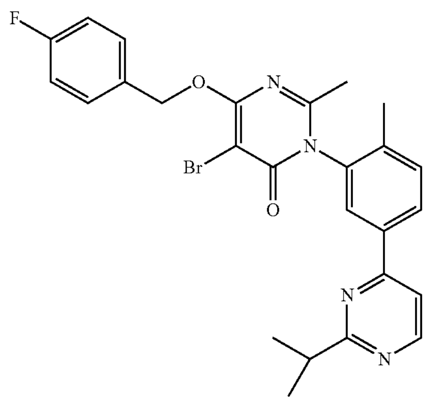 [SMILES: Cc1ccc(-c2ccnc(C(C)C)n2)cc1-n1c(C)nc(OCc2ccc(F)cc2)c(Br)c1=O] | 5-bromo-6-((4-fluorobenzyl)oxy)-3-(5-(2-isopropylpyrimidin-4-yl)-2-methylphenyl)-2-methylpyrimidin-4(3H)-one |
| 252 | 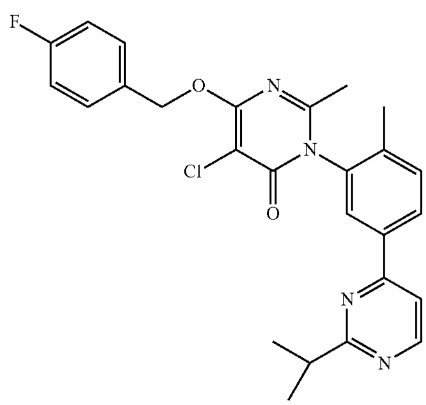 [SMILES: Cc1ccc(-c2ccnc(C(C)C)n2)cc1-n1c(C)nc(OCc2ccc(F)cc2)c(Cl)c1=O] | 5-chloro-6-((4-fluorobenzyl)oxy)-3-(5-(2-isopropylpyrimidin-4-yl)-2-methylphenyl)-2-methylpyrimidin-4(3H)-one |
| 253 | 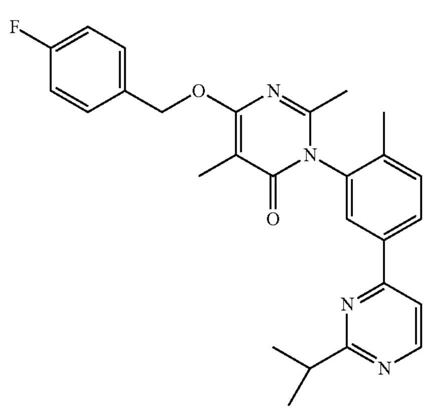 [SMILES: Cc1ccc(-c2ccnc(C(C)C)n2)cc1-n1c(C)nc(OCc2ccc(F)cc2)c(C)c1=O] | 6-((4-fluorobenzyl)oxy)-3-(5-(2-isopropylpyrimidin-4-yl)-2-methylphenyl)-2,5-dimethylpyrimidin-4(3H)-one |

| Compound | Structure | Name |
|---|---|---|
| 254 | 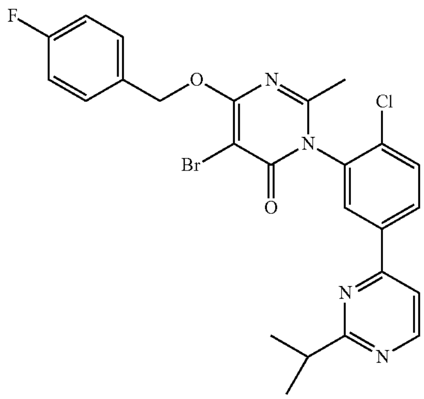 | 5-bromo-3-(2-chloro-5-(2-isopropylpyrimidin-4-yl)phenyl)-6-((4-fluorobenzyl)oxy)-2-methylpyrimidin-4(3H)-one |
| 255 | 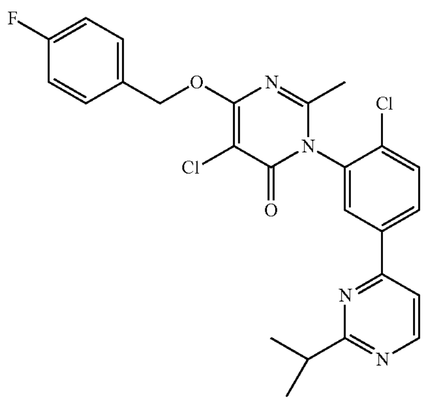 [SMILES: Cc1nc(OCc2ccc(F)cc2)c(Cl)c(=O)n1-c1cc(-c2ccnc(C(C)C)n2)ccc1Cl] | 5-chloro-3-(2-chloro-5-(2-isopropylpyrimidin-4-yl)phenyl)-6-((4-fluorobenzyl)oxy)-2-methylpyrimidin-4(3H)-one |
| 256 | 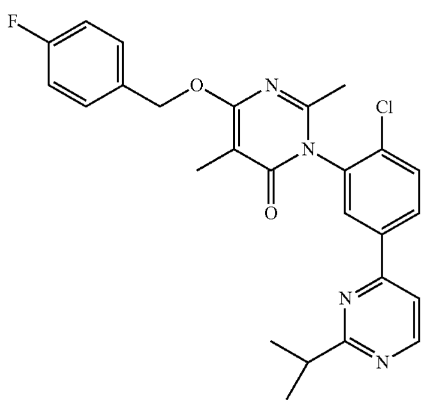 [SMILES: Cc1c(OCc2ccc(F)cc2)nc(C)n(-c2cc(-c3ccnc(C(C)C)n3)ccc2Cl)c1=O] | 3-(2-chloro-5-(2-isopropylpyrimidin-4-yl)phenyl)-6-((4-fluorobenzyl)oxy)-2,5-dimethylpyrimidin-4(3H)-one |
| 257 | 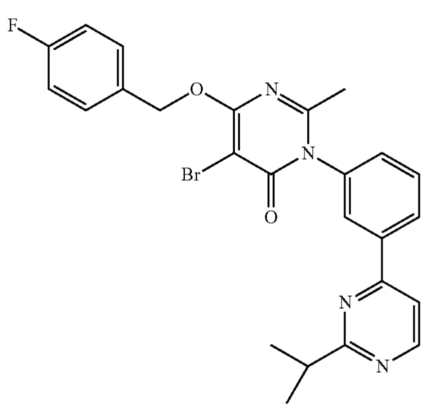 [SMILES: Cc1nc(OCc2ccc(F)cc2)c(Br)c(=O)n1-c1cccc(-c2ccnc(C(C)C)n2)c1] | 5-bromo-6-((4-fluorobenzyl)oxy)-3-(3-(2-isopropylpyrimidin-4-yl)phenyl)-2-methylpyrimidin-4(3H)-one |

-continued

| Compound | Structure | Name |
|---|---|---|
| 258 | 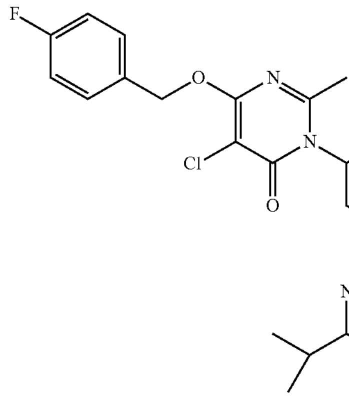 | 5-chloro-6-((4-fluorobenzyl)oxy)-3-(3-(2-isopropylpyrimidin-4-yl)phenyl)-2-methylpyrimidin-4(3H)-one |
| 259 | 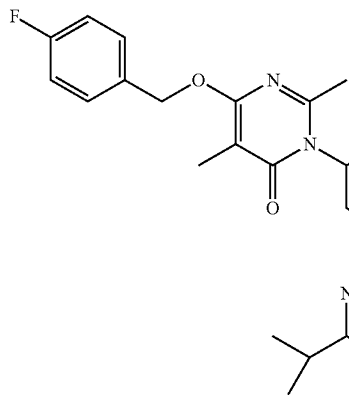 | 6-((4-fluorobenzyl)oxy)-3-(3-(2-isopropylpyrimidin-4-yl)phenyl)-2,5-dimethylpyrimidin-4(3H)-one |
| 260 | 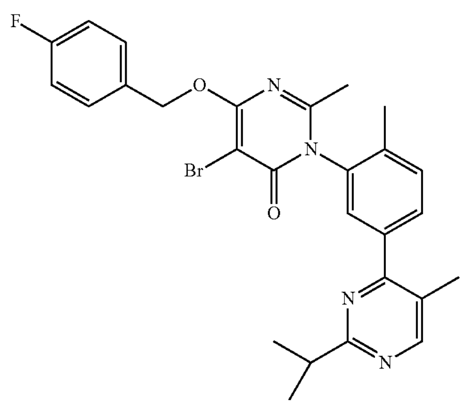 [SMILES: Cc1ccc(-c2nc(C(C)C)ncc2C)cc1-n1c(C)nc(OCc2ccc(F)cc2)c(Br)c1=O] | 5-bromo-6-((4-fluorobenzyl)oxy)-3-(5-(2-isopropyl-5-methylpyrimidin-4-yl)-2-methylphenyl)-2-methylpyrimidin-4(3H)-one |
| 261 | 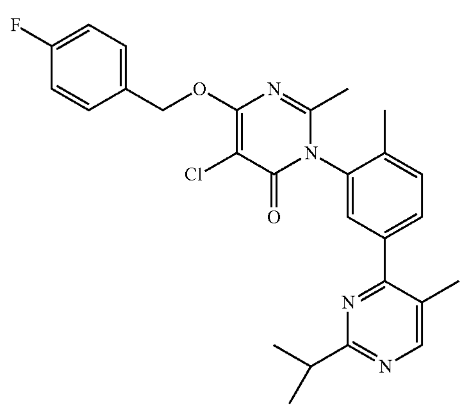 [SMILES: Cc1ccc(-c2nc(C(C)C)ncc2C)cc1-n1c(C)nc(OCc2ccc(F)cc2)c(Cl)c1=O] | 5-chloro-6-((4-fluorobenzyl)oxy)-3-(5-(2-isopropyl-5-methylpyrimidin-4-yl)-2-methylphenyl)-2-methylpyrimidin-4(3H)-one |

-continued

| Compound | Structure | Name |
|---|---|---|
| 262 | 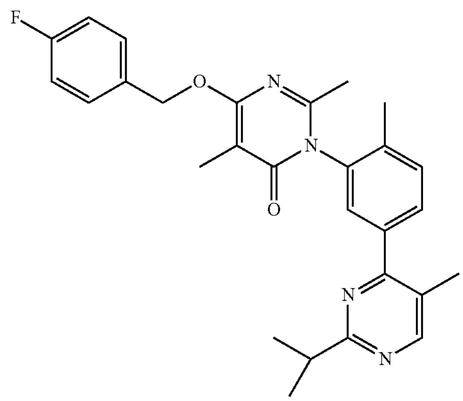 [SMILES: Cc1ccc(-c2nc(C(C)C)ncc2C)cc1-n1c(C)nc(OCc2ccc(F)cc2)c(C)c1=O] | 6-((4-fluorobenzyl)oxy)-3-(5-(2-isopropyl-5-methylpyrimidin-4-yl)-2-methylphenyl)-2,5-dimethylpyrimidin-4(3H)-one |
| 263 | 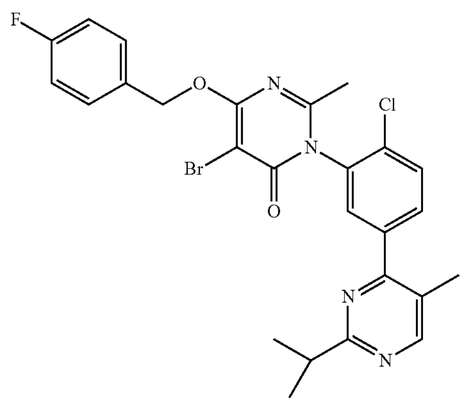 [SMILES: Cc1cnc(C(C)C)nc1-c1ccc(Cl)c(-n2c(C)nc(OCc3ccc(F)cc3)c(Br)c2=O)c1] | 5-bromo-3-(2-chloro-5-(2-isopropyl-5-methylpyrimidin-4-yl)phenyl)-6-((4-fluorobenzyl)oxy)-2-methylpyrimidin-4(3H)-one |
| 264 | 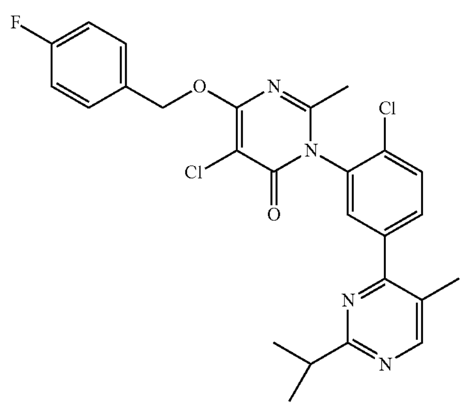 [SMILES: Cc1cnc(C(C)C)nc1-c1ccc(Cl)c(-n2c(C)nc(OCc3ccc(F)cc3)c(Cl)c2=O)c1] | 5-chloro-3-(2-chloro-5-(2-isopropyl-5-methylpyrimidin-4-yl)phenyl)-6-((4-fluorobenzyl)oxy)-2-methylpyrimidin-4(3H)-one |
| 265 | 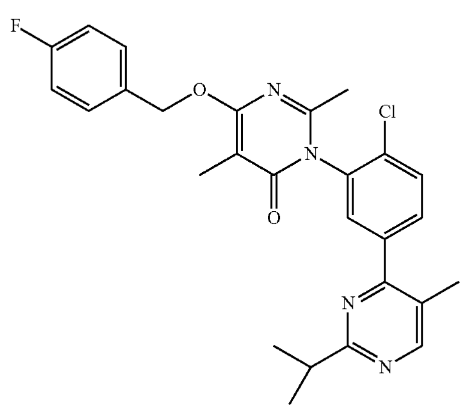 [SMILES: Cc1cnc(C(C)C)nc1-c1ccc(Cl)c(-n2c(C)nc(OCc3ccc(F)cc3)c(C)c2=O)c1] | 3-(2-chloro-5-(2-isopropyl-5-methylpyrimidin-4-yl)phenyl)-6-((4-fluorobenzyl)oxy)-2,5-dimethylpyrimidin-4(3H)-one |

-continued

| Compound | Structure | Name |
|---|---|---|
| 266 | 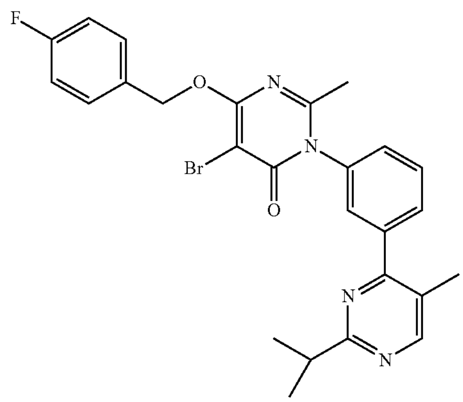 [SMILES: Cc1cnc(C(C)C)nc1-c1cccc(-n2c(C)nc(OCc3ccc(F)cc3)c(Br)c2=O)c1] | 5-bromo-6-((4-fluorobenzyl)oxy)-3-(3-(2-isopropyl-5-methylpyrimidin-4-yl)phenyl)-2-methylpyrimidin-4(3H)-one |
| 267 | 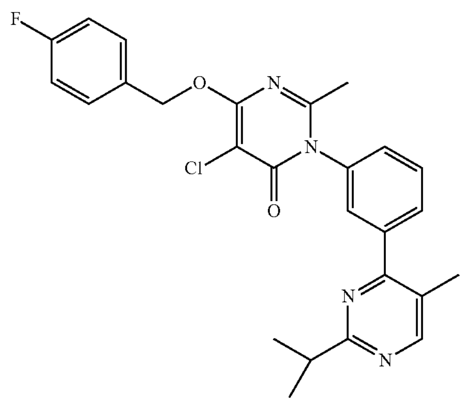 [SMILES: Cc1cnc(C(C)C)nc1-c1cccc(-n2c(C)nc(OCc3ccc(F)cc3)c(Cl)c2=O)c1] | 5-chloro-6-((4-fluorobenzyl)oxy)-3-(3-(2-isopropyl-5-methylpyrimidin-4-yl)phenyl)-2-methylpyrimidin-4(3H)-one |
| 268 | 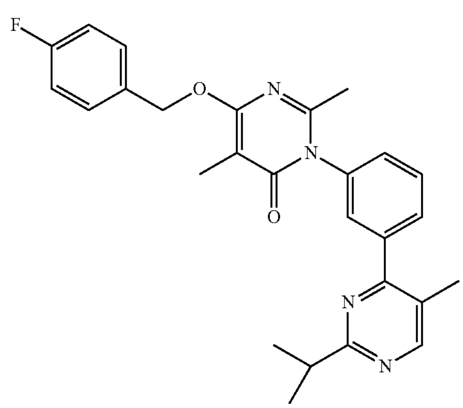 [SMILES: Cc1cnc(C(C)C)nc1-c1cccc(-n2c(C)nc(OCc3ccc(F)cc3)c(C)c2=O)c1] | 6-((4-fluorobenzyl)oxy)-3-(3-(2-isopropyl-5-methylpyrimidin-4-yl)phenyl)-2,5-dimethylpyrimidin-4(3H)-one |
| 269 | 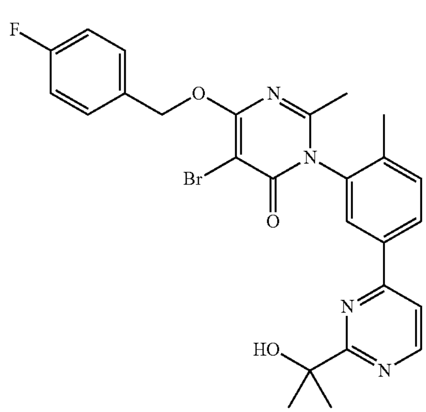 [SMILES: Cc1ccc(-c2ccnc(C(C)(C)O)n2)cc1-n1c(C)nc(OCc2ccc(F)cc2)c(Br)c1=O] | 5-bromo-6-((4-fluorobenzyl)oxy)-3-(5-(2-(2-hydroxypropan-2-yl)pyrimidin-4-yl)-2-methylphenyl)-2-methylpyrimidin-4(3H)-one |

-continued

| Compound | Structure | Name |
|---|---|---|
| 270 | 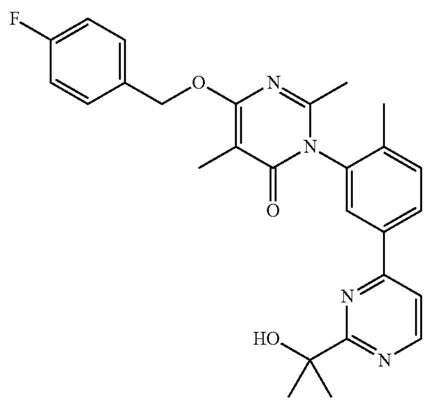 [SMILES: Cc1ccc(-c2ccnc(C(C)(C)O)n2)cc1-n1c(C)nc(OCc2ccc(F)cc2)c(C)c1=O] | 6-((4-fluorobenzyl)oxy)-3-(5-(2-(2-hydroxypropan-2-yl)pyrimidin-4-yl)-2-methylphenyl)-2,5-dimethylpyrimidin-4(3H)-one |
| 271 | 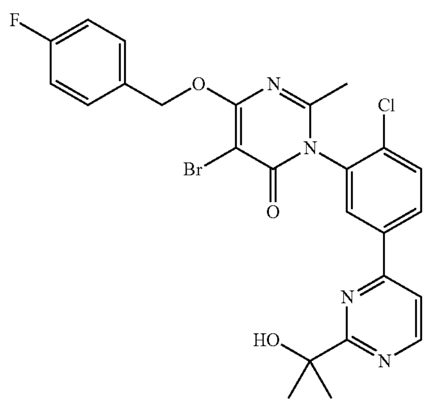 [SMILES: Cc1nc(OCc2ccc(F)cc2)c(Br)c(=O)n1-c1cc(-c2ccnc(C(C)(C)O)n2)ccc1Cl] | 5-bromo-3-(2-chloro-5-(2-(2-hydroxypropan-2-yl)pyrimidin-4-yl)phenyl)-6-((4-fluorobenzyl)oxy)-2-methylpyrimidin-4(3H)-one |
| 272 | 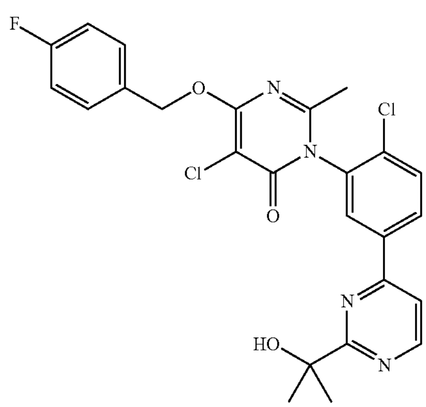 [SMILES: Cc1nc(OCc2ccc(F)cc2)c(Cl)c(=O)n1-c1cc(-c2ccnc(C(C)(C)O)n2)ccc1Cl] | 5-chloro-3-(2-chloro-5-(2-(2-hydroxypropan-2-yl)pyrimidin-4-yl)phenyl)-6-((4-fluorobenzyl)oxy)-2-methylpyrimidin-4(3H)-one |
| 273 | 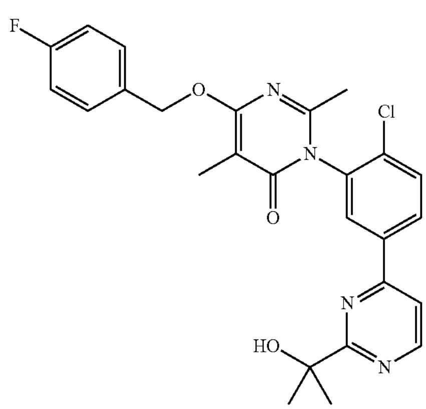 | 3-(2-chloro-5-(2-(2-hydroxypropan-2-yl)pyrimidin-4-yl)phenyl)-6-((4-fluorobenzyl)oxy)-2,5-dimethylpyrimidin-4(3H)-one |

-continued

| Compound | Structure | Name |
|---|---|---|
| 274 | 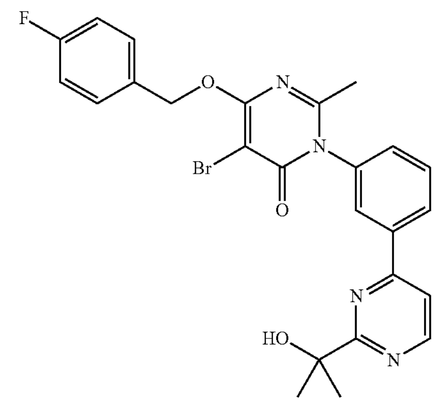 [SMILES: Cc1nc(OCc2ccc(F)cc2)c(Br)c(=O)n1-c1cccc(-c2ccnc(C(C)(C)O)n2)c1] | 5-bromo-6-((4-fluorobenzyl)oxy)-3-(3-(2-(2-hydroxypropan-2-yl)pyrimidin-4-yl)phenyl)-2-methylpyrimidin-4(3H)-one |
| 275 | 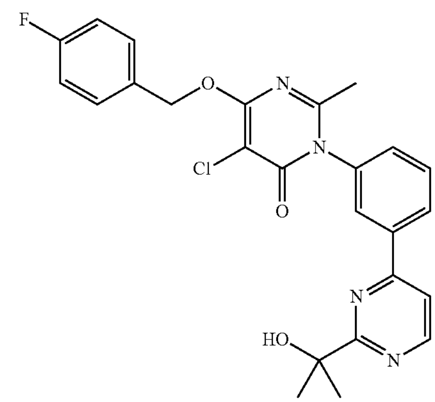 [SMILES: Cc1nc(OCc2ccc(F)cc2)c(Cl)c(=O)n1-c1cccc(-c2ccnc(C(C)(C)O)n2)c1] | 5-chloro-6-((4-fluorobenzyl)oxy)-3-(3-(2-(2-hydroxypropan-2-yl)pyrimidin-4-yl)phenyl)-2-methylpyrimidin-4(3H)-one |
| 276 | 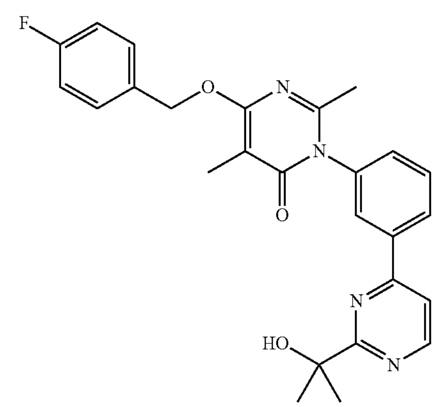 [SMILES: Cc1c(OCc2ccc(F)cc2)nc(C)n(-c2cccc(-c3ccnc(C(C)(C)O)n3)c2)c1=O] | 6-((4-fluorobenzyl)oxy)-3-(3-(2-(2-hydroxypropan-2-yl)pyrimidin-4-yl)phenyl)-2,5-dimethylpyrimidin-4(3H)-one |
| 277 | 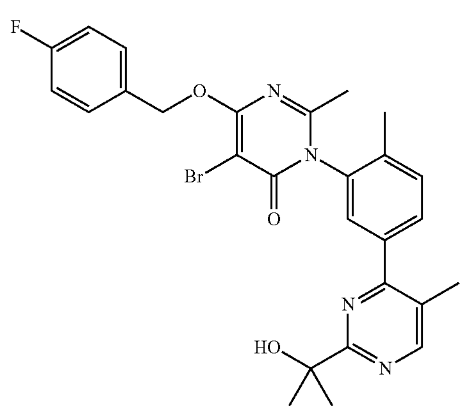 [SMILES: Cc1ccc(-c2nc(C(C)(C)O)ncc2C)cc1-n1c(C)nc(OCc2ccc(F)cc2)c(Br)c1=O] | 5-bromo-6-((4-fluorobenzyl)oxy)-3-(5-(2-(2-hydroxypropan-2-yl)-5-methylpyrimidin-4-yl)-2-methylphenyl)-2-methylpyrimidin-4(3H)-one |

| Compound | Structure | Name |
|---|---|---|
| 278 | 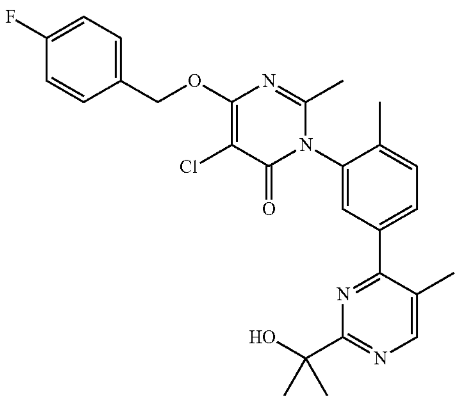 [SMILES: Cc1ccc(-c2nc(C(C)(C)O)ncc2C)cc1-n1c(C)nc(OCc2ccc(F)cc2)c(Cl)c1=O] | 5-chloro-6-((4-fluorobenzyl)oxy)-3-(5-(2-(2-hydroxypropan-2-yl)-5-methylpyrimidin-4-yl)-2-methylphenyl)-2-methylpyrimidin-4(3H)-one |
| 279 | 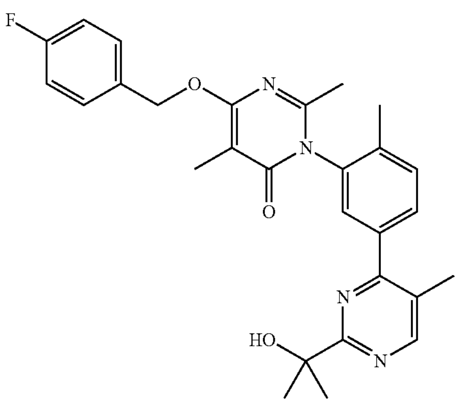 [SMILES: Cc1ccc(-c2nc(C(C)(C)O)ncc2C)cc1-n1c(C)nc(OCc2ccc(F)cc2)c(C)c1=O] | 6-((4-fluorobenzyl)oxy)-3-(5-(2-(2-hydroxypropan-2-yl)-5-methylpyrimidin-4-yl)-2-methylphenyl)-2,5-dimethylpyrimidin-4(3H)-one |
| 280 | 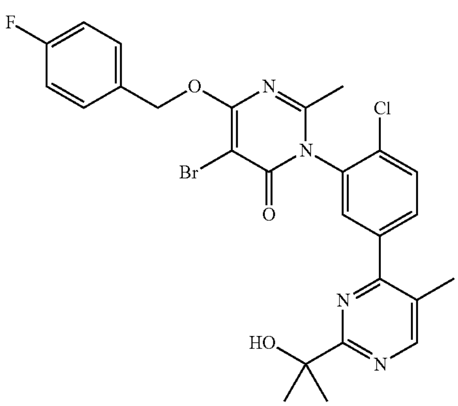 [SMILES: Cc1cnc(C(C)(C)O)nc1-c1ccc(Cl)c(-n2c(C)nc(OCc3ccc(F)cc3)c(Br)c2=O)c1] | 5-bromo-3-(2-chloro-5-(2-(2-hydroxypropan-2-yl)-5-methylpyrimidin-4-yl)phenyl)-6-((4-fluorobenzyl)oxy)-2-methylpyrimidin-4(3H)-one |
| 281 | 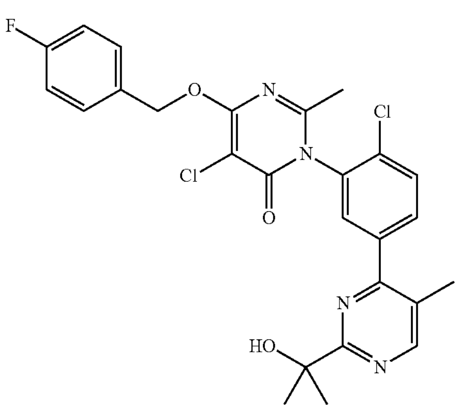 [SMILES: Cc1cnc(C(C)(C)O)nc1-c1ccc(Cl)c(-n2c(C)nc(OCc3ccc(F)cc3)c(Cl)c2=O)c1] | 5-chloro-3-(2-chloro-5-(2-(2-hydroxypropan-2-yl)-5-methylpyrimidin-4-yl)phenyl)-6-((4-fluorobenzyl)oxy)-2-methylpyrimidin-4(3H)-one |

-continued

| Compound | Structure | Name |
|---|---|---|
| 282 | 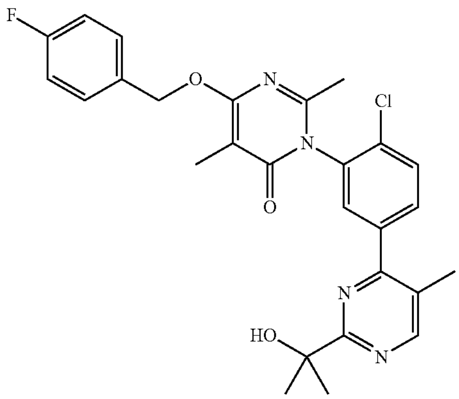 [SMILES: Cc1cnc(C(C)(C)O)nc1-c1ccc(Cl)c(-n2c(C)nc(OCc3ccc(F)cc3)c(C)c2=O)c1] | 3-(2-chloro-5-(2-(2-hydroxypropan-2-yl)-5-methylpyrimidin-4-yl)phenyl)-6-((4-fluorobenzyl)oxy)-2,5-dimethylpyrimidin-4(3H)-one |
| 283 | 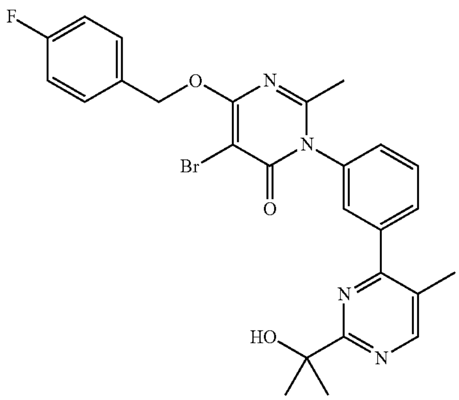 | 5-bromo-6-((4-fluorobenzyl)oxy)-3-(3-(2-(2-hydroxypropan-2-yl)-5-methylpyrimidin-4-yl)phenyl)-2-methylpyrimidin-4(3H)-one |
| 284 | 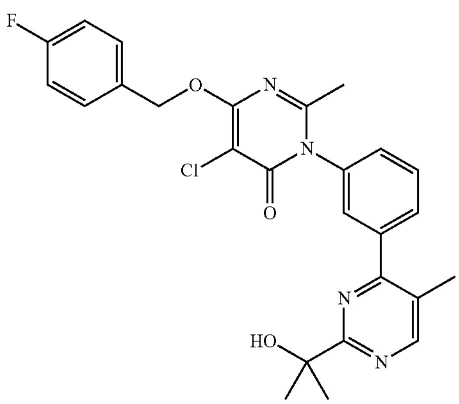 [SMILES: Cc1cnc(C(C)(C)O)nc1-c1cccc(-n2c(C)nc(OCc3ccc(F)cc3)c(Cl)c2=O)c1] | 5-chloro-6-((4-fluorobenzyl)oxy)-3-(3-(2-(2-hydroxypropan-2-yl)-5-methylpyrimidin-4-yl)phenyl)-2-methylpyrimidin-4(3H)-one |
| 285 | 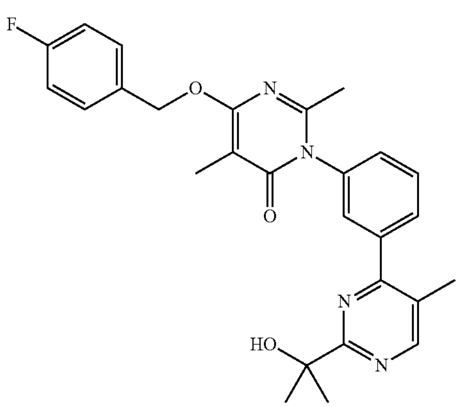 [SMILES: Cc1cnc(C(C)(C)O)nc1-c1cccc(-n2c(C)nc(OCc3ccc(F)cc3)c(C)c2=O)c1] | 6-((4-fluorobenzyl)oxy)-3-(3-(2-(2-hydroxypropan-2-yl)-5-methylpyrimidin-4-yl)phenyl)-2,5-dimethylpyrimidin-4(3H)-one |

-continued

| Compound | Structure | Name |
|---|---|---|
| 286 | 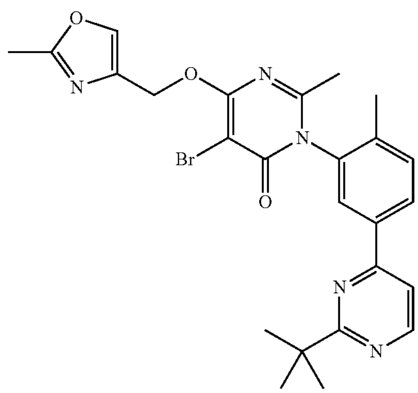 [SMILES: Cc1nc(COc2nc(C)n(-c3cc(-c4ccnc(C(C)(C)C)n4)ccc3C)c(=O)c2Br)co1] | 5-bromo-3-(5-(2-(tert-butyl)pyrimidin-4-yl)-2-methylphenyl)-2-methyl-6-((2-methyloxazol-4-yl)methoxy)pyrimidin-4(3H)-one |
| 287 | 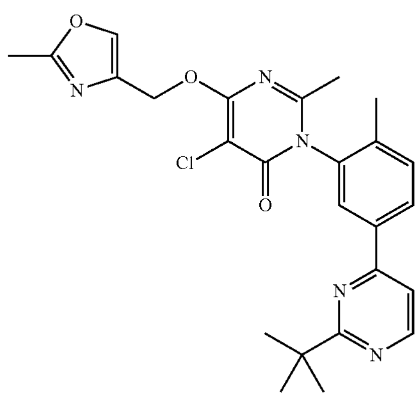 [SMILES: Cc1nc(COc2nc(C)n(-c3cc(-c4ccnc(C(C)(C)C)n4)ccc3C)c(=O)c2Cl)co1] | 3-(5-(2-(tert-butyl)pyrimidin-4-yl)-2-methylphenyl)-5-chloro-2-methyl-6-((2-methyloxazol-4-yl)methoxy)pyrimidin-4(3H)-one |
| 288 | 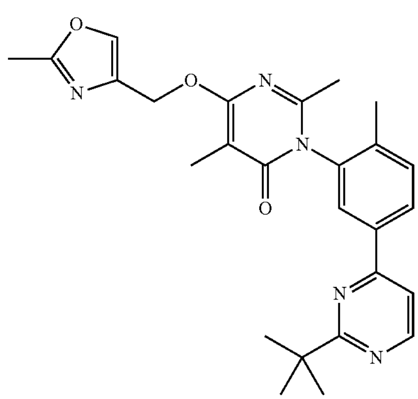 | 3-(5-(2-(tert-butyl)pyrimidin-4-yl)-2-methylphenyl)-2,5-dimethyl-6-((2-methyloxazol-4-yl)methoxy)pyrimidin-4(3H)-one |
| 289 | 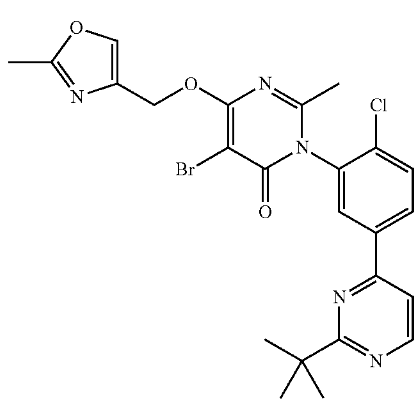 | 5-bromo-3-(5-(2-(tert-butyl)pyrimidin-4-yl)-2-chlorophenyl)-2-methyl-6-((2-methyloxazol-4-yl)methoxy)pyrimidin-4(3H)-one |

-continued

| Compound | Structure | Name |
|---|---|---|
| 290 | 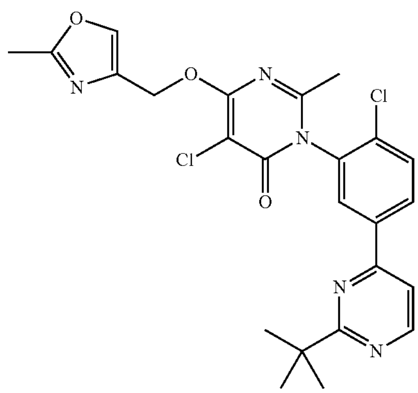 [SMILES: Cc1nc(COc2nc(C)n(-c3cc(-c4ccnc(C(C)(C)C)n4)ccc3Cl)c(=O)c2Cl)co1] | 3-(5-(2-(tert-butyl)pyrimidin-4-yl)-2-chlorophenyl)-5-chloro-2-methyl-6-((2-methyloxazol-4-yl)methoxy)pyrimidin-4(3H)-one |
| 291 | 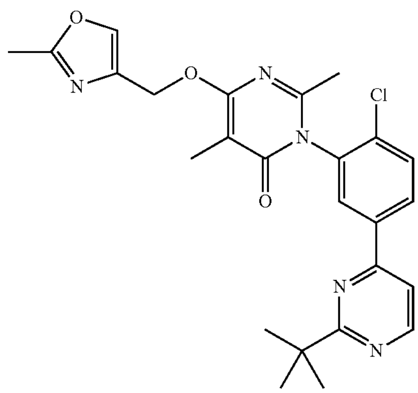 | 3-(5-(2-(tert-butyl)pyrimidin-4-yl)-2-chlorophenyl)-2,5-dimethyl-6-((2-methyloxazol-4-yl)methoxy)pyrimidin-4(3H)-one |
| 292 | 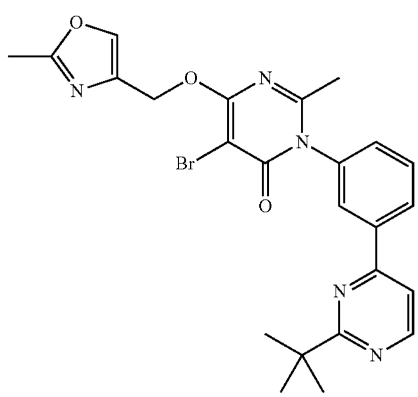 [SMILES: Cc1nc(COc2nc(C)n(-c3cccc(-c4ccnc(C(C)(C)C)n4)c3)c(=O)c2Br)co1] | 5-bromo-3-(3-(2-(tert-butyl)pyrimidin-4-yl)phenyl)-2-methyl-6-((2-methyloxazol-4-yl)methoxy)pyrimidin-4(3H)-one |
| 293 | 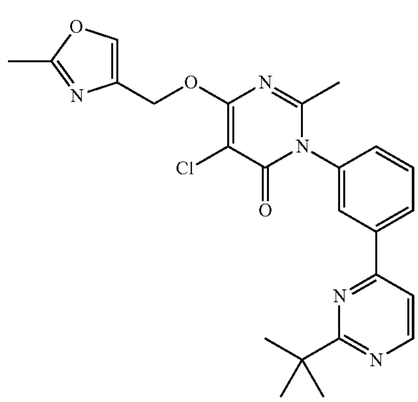 [SMILES: Cc1nc(COc2nc(C)n(-c3cccc(-c4ccnc(C(C)(C)C)n4)c3)c(=O)c2Cl)co1] | 3-(3-(2-(tert-butyl)pyrimidin-4-yl)phenyl)-5-chloro-2-methyl-6-((2-methyloxazol-4-yl)methoxy)pyrimidin-4(3H)-one |

-continued

| Compound | Structure | Name |
|---|---|---|
| 294 | 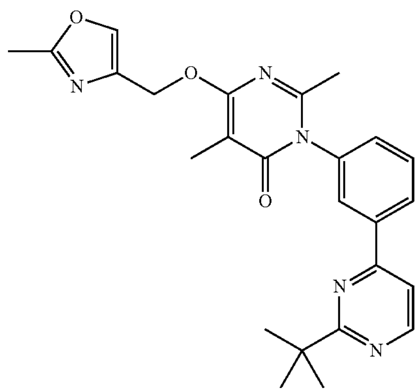 [SMILES: Cc1nc(COc2nc(C)n(-c3cccc(-c4ccnc(C(C)(C)C)n4)c3)c(=O)c2C)co1] | 3-(3-(2-(tert-butyl)pyrimidin-4-yl)phenyl)-2,5-dimethyl-6-((2-methyloxazol-4-yl)methoxy)pyrimidin-4(3H)-one |
| 295 | 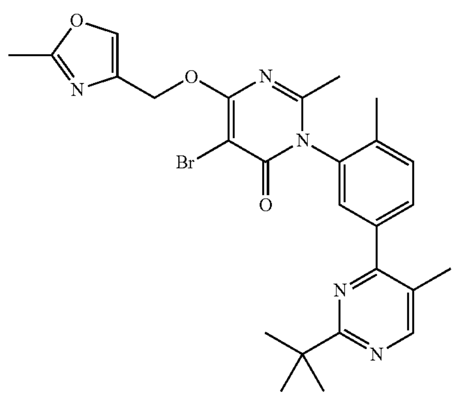 | 5-bromo-3-(5-(2-(tert-butyl)-5-methylpyrimidin-4-yl)-2-methylphenyl)-2-methyl-6-((2-methyloxazol-4-yl)methoxy)pyrimidin-4(3H)-one |
| 296 | 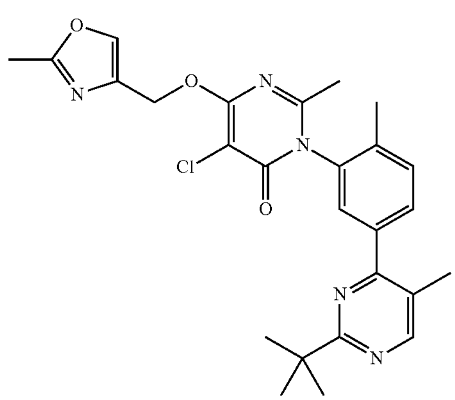 | 3-(5-(2-(tert-butyl)-5-methylpyrimidin-4-yl)-2-methylphenyl)-5-chloro-2-methyl-6-((2-methyloxazol-4-yl)methoxy)pyrimidin-4(3H)-one |
| 297 | 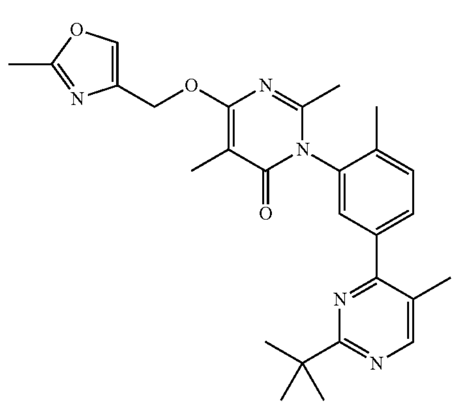 | 3-(5-(2-(tert-butyl)-5-methylpyrimidin-4-yl)-2-methylphenyl)-2,5-dimethyl-6-((2-methyloxazol-4-yl)methoxy)pyrimidin-4(3H)-one |

-continued

| Compound | Structure | Name |
|---|---|---|
| 298 | 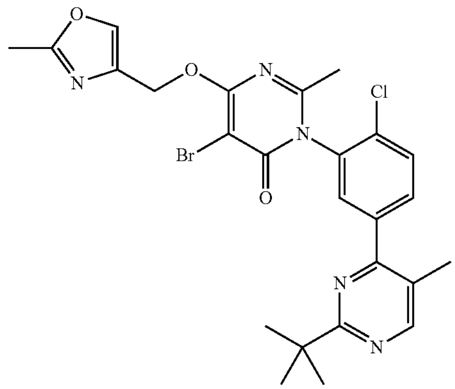 | 5-bromo-3-(5-(2-(tert-butyl)-5-methylpyrimidin-4-yl)-2-chlorophenyl)-2-methyl-6-((2-methyloxazol-4-yl)methoxy)pyrimidin-4(3H)-one |
| 299 | 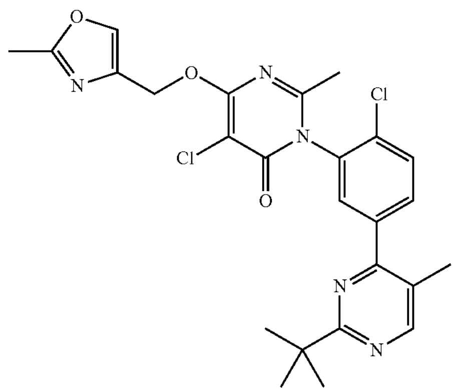 | 3-(5-(2-(tert-butyl)-5-methylpyrimidin-4-yl)-2-chlorophenyl)-5-chloro-2-methyl-6-((2-methyloxazol-4-yl)methoxy)pyrimidin-4(3H)-one |
| 300 | 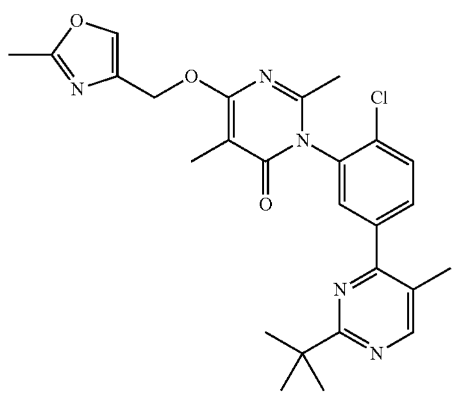 | 3-(5-(2-(tert-butyl)-5-methylpyrimidin-4-yl)-2-chlorophenyl)-2,5-dimethyl-6-((2-methyloxazol-4-yl)methoxy)pyrimidin-4(3H)-one |
| 301 | 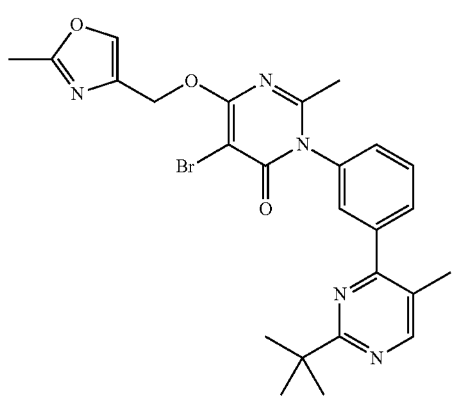 | 5-bromo-3-(3-(2-(tert-butyl)-5-methylpyrimidin-4-yl)phenyl)-2-methyl-6-((2-methyloxazol-4-yl)methoxy)pyrimidin-4(3H)-one |

| Compound | Structure | Name |
|---|---|---|
| 302 | 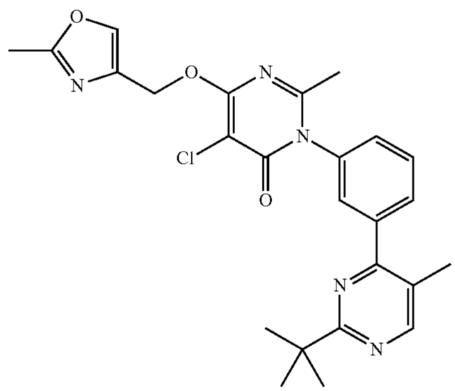 | 3-(3-(2-(tert-butyl)-5-methylpyrimidin-4-yl)phenyl)-5-chloro-2-methyl-6-((2-methyloxazol-4-yl)methoxy)pyrimidin-4(3H)-one |
| 303 | 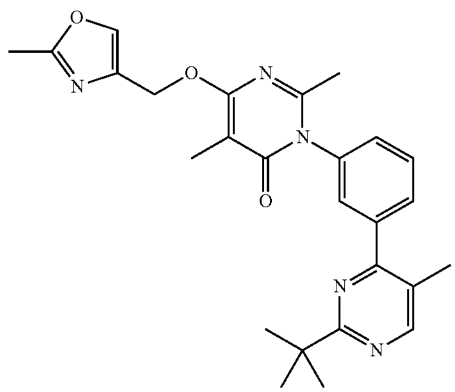 | 3-(3-(2-(tert-butyl)-5-methylpyrimidin-4-yl)phenyl)-2,5-dimethyl-6-((2-methyloxazol-4-yl)methoxy)pyrimidin-4(3H)-one |
| 304 | 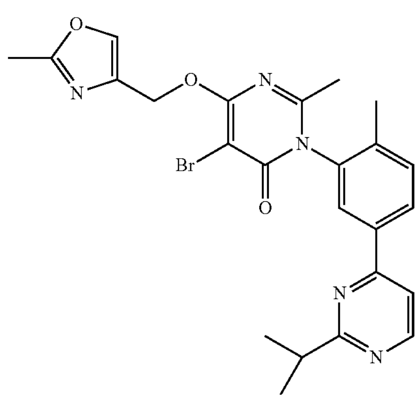 | 5-bromo-3-(5-(2-isopropylpyrimidin-4-yl)-2-methylphenyl)-2-methyl-6-((2-methyloxazol-4-yl)methoxy)pyrimidin-4(3H)-one |
| 305 | 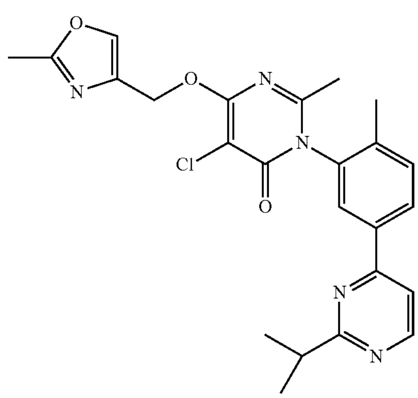 [SMILES: Cc1nc(COc2nc(C)n(-c3cc(-c4ccnc(C(C)C)n4)ccc3C)c(=O)c2Cl)co1] | 5-chloro-3-(5-(2-isopropylpyrimidin-4-yl)-2-methylphenyl)-2-methyl-6-((2-methyloxazol-4-yl)methoxy)pyrimidin-4(3H)-one |

-continued

| Compound | Structure | Name |
|---|---|---|
| 306 | 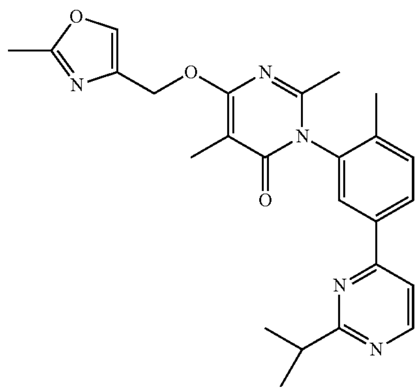 [SMILES: Cc1nc(COc2nc(C)n(-c3cc(-c4ccnc(C(C)C)n4)ccc3C)c(=O)c2C)co1] | 3-(5-(2-isopropylpyrimidin-4-yl)-2-methylphenyl)-2,5-dimethyl-6-((2-methyloxazol-4-yl)methoxy)pyrimidin-4(3H)-one |
| 307 | 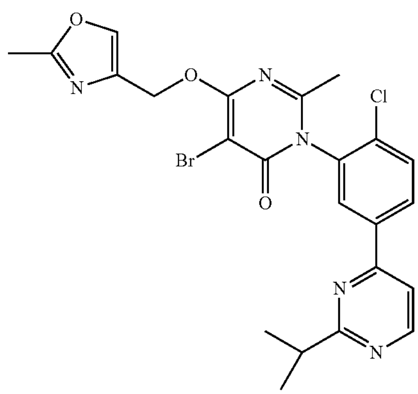 | 5-bromo-3-(2-chloro-5-(2-isopropylpyrimidin-4-yl)phenyl)-2-methyl-6-((2-methyloxazol-4-yl)methoxy)pyrimidin-4(3H)-one |
| 308 | 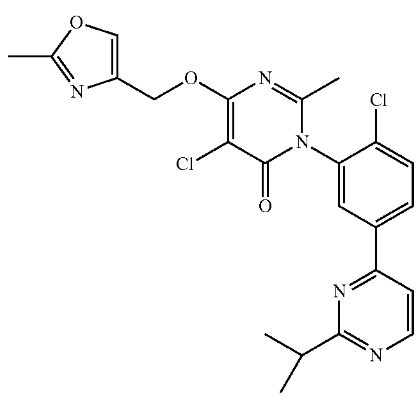 [SMILES: Cc1nc(COc2nc(C)n(-c3cc(-c4ccnc(C(C)C)n4)ccc3Cl)c(=O)c2Cl)co1] | 5-chloro-3-(2-chloro-5-(2-isopropylpyrimidin-4-yl)phenyl)-2-methyl-6-((2-methyloxazol-4-yl)methoxy)pyrimidin-4(3H)-one |
| 309 | 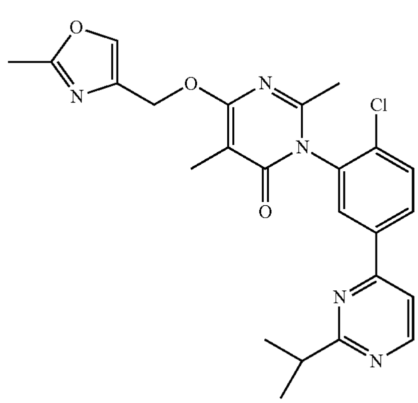 [SMILES: Cc1nc(COc2nc(C)n(-c3cc(-c4ccnc(C(C)C)n4)ccc3Cl)c(=O)c2C)co1] | 3-(2-chloro-5-(2-isopropylpyrimidin-4-yl)phenyl)-2,5-dimethyl-6-((2-methyloxazol-4-yl)methoxy)pyrimidin-4(3H)-one |

| Compound | Structure | Name |
|---|---|---|
| 310 | 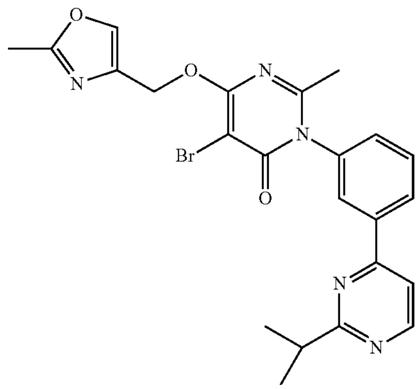 [SMILES: Cc1nc(COc2nc(C)n(-c3cccc(-c4ccnc(C(C)C)n4)c3)c(=O)c2Cl)co1] | 5-bromo-3-(3-(2-isopropylpyrimidin-4-yl)phenyl)-2-methyl-6-((2-methyloxazol-4-yl)methoxy)pyrimidin-4(3H)-one |
| 311 | 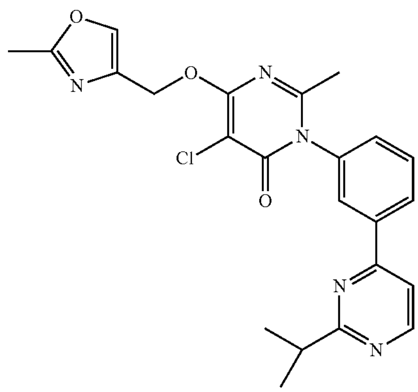 | 5-chloro-3-(3-(2-isopropylpyrimidin-4-yl)phenyl)-2-methyl-6-((2-methyloxazol-4-yl)methoxy)pyrimidin-4(3H)-one |
| 312 | 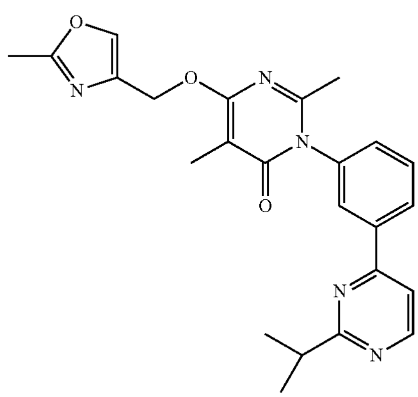 [SMILES: Cc1nc(COc2nc(C)n(-c3cccc(-c4ccnc(C(C)C)n4)c3)c(=O)c2C)co1] | 3-(3-(2-isopropylpyrimidin-4-yl)phenyl)-2,5-dimethyl-6-((2-methyloxazol-4-yl)methoxy)pyrimidin-4(3H)-one |
| 313 | 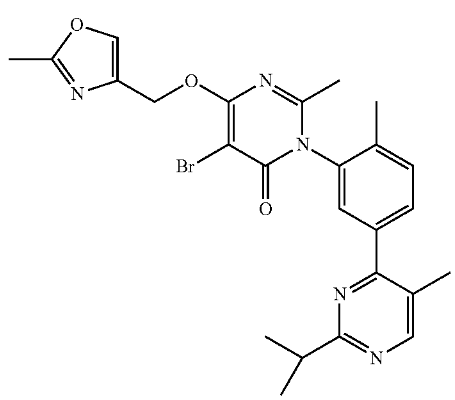 | 5-bromo-3-(5-(2-isopropyl-5-methylpyrimidin-4-yl)-2-methylphenyl)-2-methyl-6-((2-methyloxazol-4-yl)methoxy)pyrimidin-4(3H)-one |

-continued

| Compound | Structure | Name |
|---|---|---|
| 314 | 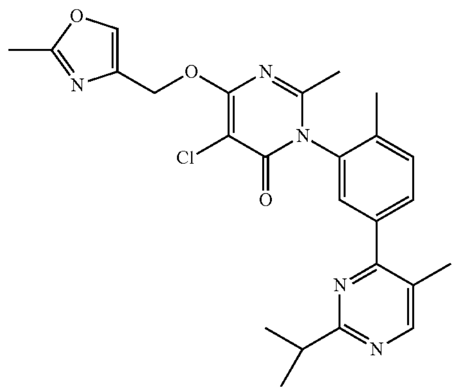 | 5-chloro-3-(5-(2-isopropyl-5-methylpyrimidin-4-yl)-2-methylphenyl)-2-methyl-6-((2-methyloxazol-4-yl)methoxy)pyrimidin-4(3H)-one |
| 315 | 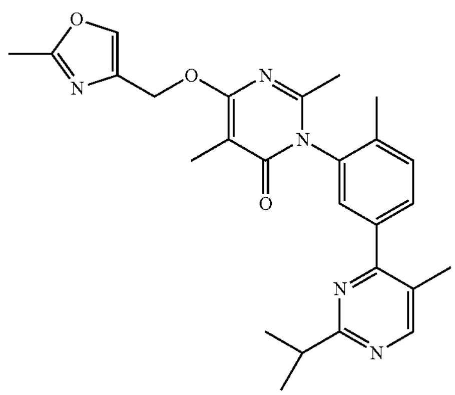 | 3-(5-(2-isopropyl-5-methylpyrimidin-4-yl)-2-methylphenyl)-2,5-dimethyl-6-((2-methyloxazol-4-yl)methoxy)pyrimidin-4(3H)-one |
| 316 | 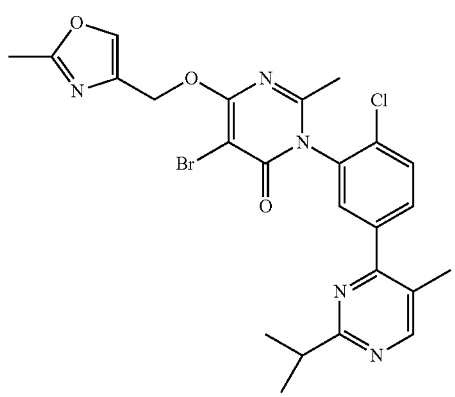 | 5-bromo-3-(2-chloro-5-(2-isopropyl-5-methylpyrimidin-4-yl)phenyl)-2-methyl-6-((2-methyloxazol-4-yl)methoxy)pyrimidin-4(3H)-one |
| 317 | 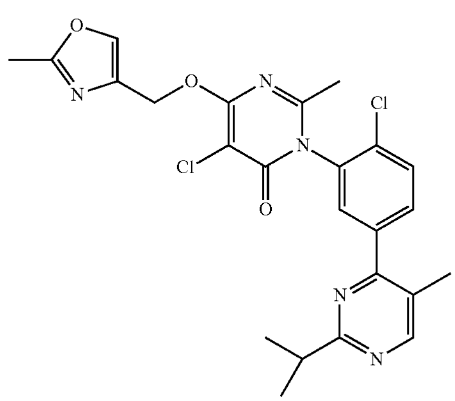 | 5-chloro-3-(2-chloro-5-(2-isopropyl-5-methylpyrimidin-4-yl)phenyl)-2-methyl-6-((2-methyloxazol-4-yl)methoxy)pyrimidin-4(3H)-one |

-continued

| Compound | Structure | Name |
|---|---|---|
| 318 | 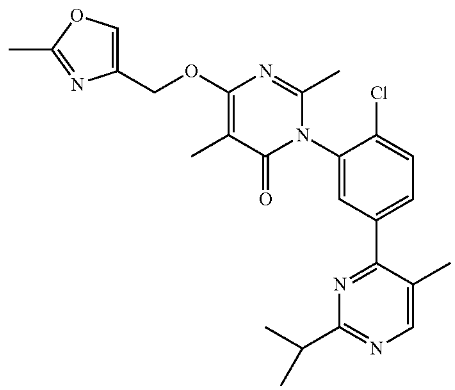 | 3-(2-chloro-5-(2-isopropyl-5-methylpyrimidin-4-yl)phenyl)-2,5-dimethyl-6-((2-methyloxazol-4-yl)methoxy)pyrimidin-4(3H)-one |
| 319 | 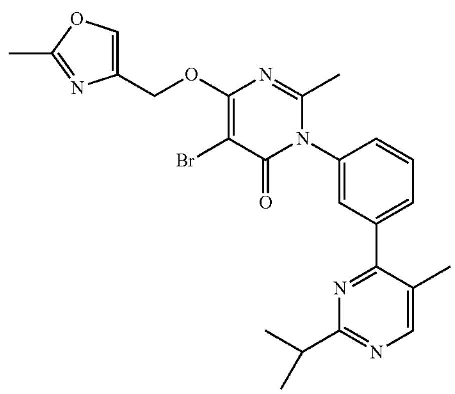 | 5-bromo-3-(3-(2-isopropyl-5-methylpyrimidin-4-yl)phenyl)-2-methyl-6-((2-methyloxazol-4-yl)methoxy)pyrimidin-4(3H)-one |
| 320 | 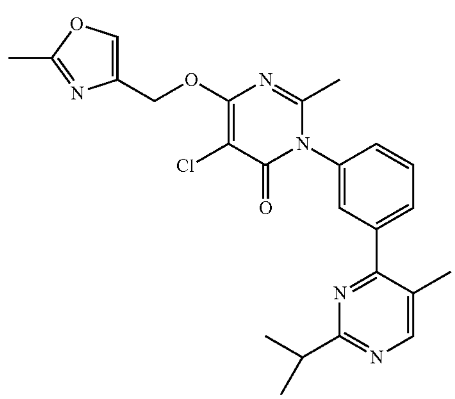 | 5-chloro-3-(3-(2-isopropyl-5-methylpyrimidin-4-yl)phenyl)-2-methyl-6-((2-methyloxazol-4-yl)methoxy)pyrimidin-4(3H)-one |
| 321 | 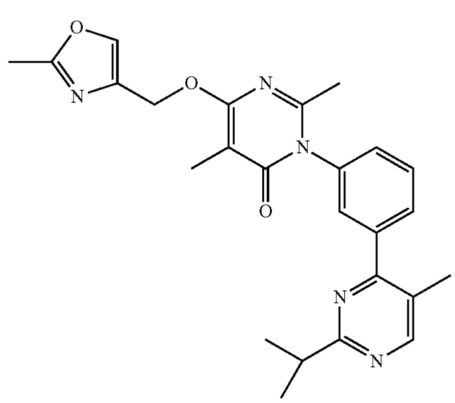 | 3-(3-(2-isopropyl-5-methylpyrimidin-4-yl)phenyl)-2,5-dimethyl-6-((2-methyloxazol-4-yl)methoxy)pyrimidin-4(3H)-one |

-continued

| Compound | Structure | Name |
|---|---|---|
| 322 | 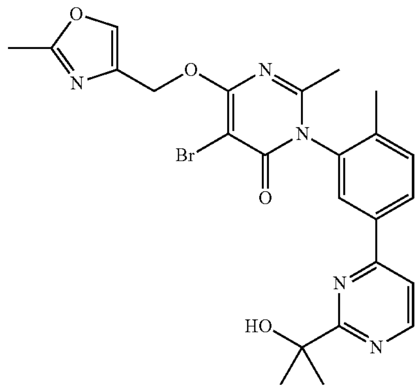 [SMILES: Cc1nc(COc2nc(C)n(-c3cc(-c4ccnc(C(C)(C)O)n4)ccc3C)c(=O)c2Br)co1] | 5-bromo-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one |
| 323 | 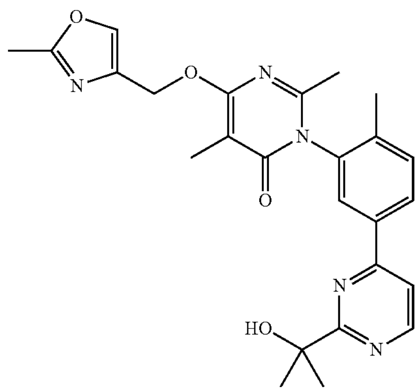 | 3-(5-(2-(2-hydroxypropan-2-yl)pyrimidin-4-yl)-2-methylphenyl)2,5-dimethyl-6-((2-methyloxazol-4-yl)methoxy)pyrimidin-4(3H)-one |
| 324 | 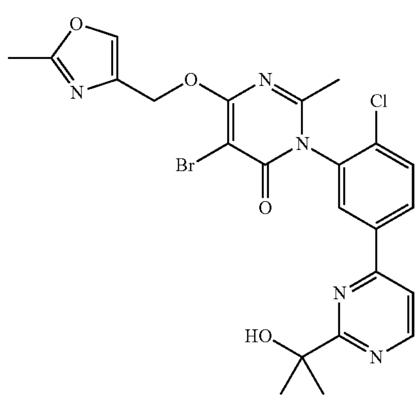 [SMILES: Cc1nc(COc2nc(C)n(-c3cc(-c4ccnc(C(C)(C)O)n4)ccc3Cl)c(=O)c2Br)co1] | 5-bromo-3-(2-chloro-5-(2-(2-hydroxypropan-2-yl)pyrimidin-4-yl)phenyl)-2-methyl-6-((2-methyloxazol-4-yl)methoxy)pyrimidin-4(3H)-one |
| 325 | 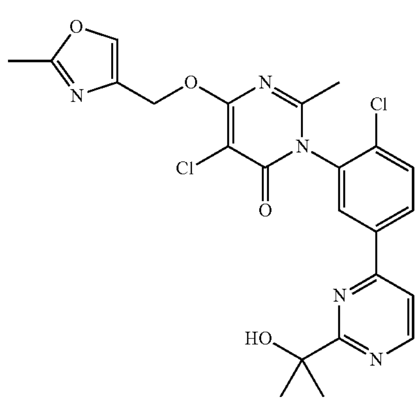 [SMILES: Cc1nc(COc2nc(C)n(-c3cc(-c4ccnc(C(C)(C)O)n4)ccc3Cl)c(=O)c2Cl)co1] | 5-chloro-3-(2-chloro-5-(2-(2-hydroxypropan-2-yl)pyrimidin-4-yl)phenyl)-2-methyl-6-((2-methyloxazol-4-yl)methoxy)pyrimidin-4(3H)-one |

| Compound | Structure | Name |
|---|---|---|
| 326 | 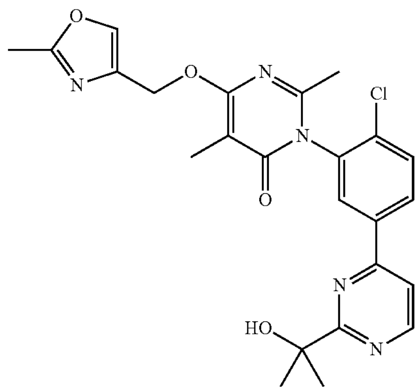 [SMILES: Cc1nc(COc2nc(C)n(-c3cc(-c4ccnc(C(C)(C)O)n4)ccc3Cl)c(=O)c2C)co1] | 3-(2-chloro-5-(2-(2-hydroxypropan-2-yl)pyrimidin-4-yl)phenyl)-2,5-dimethyl-6-((2-methyloxazol-4-yl)methoxy)pyrimidin-4(3H)-one |
| 327 | 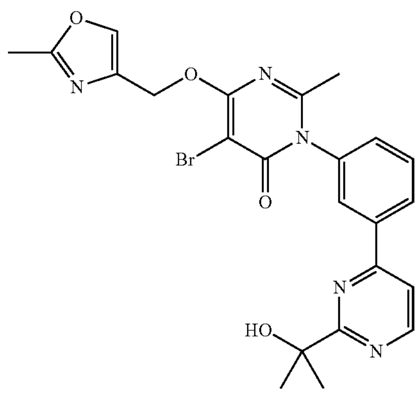 [SMILES: Cc1nc(COc2nc(C)n(-c3cccc(-c4ccnc(C(C)(C)O)n4)c3)c(=O)c2Br)co1] | 5-bromo-3-(3-(2-(2-hydroxypropan-2-yl)pyrimidin-4-yl)phenyl)-2-methyl-6-((2-methyloxazol-4-yl)methoxy)pyrimidin-4(3H)-one |
| 328 | 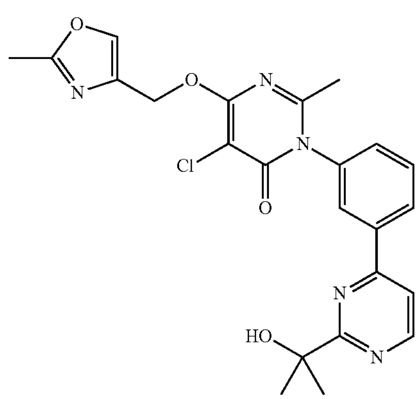 [SMILES: Cc1nc(COc2nc(C)n(-c3cccc(-c4ccnc(C(C)(C)O)n4)c3)c(=O)c2Cl)co1] | 5-chloro-3-(3-(2-(2-hydroxypropan-2-yl)pyrimidin-4-yl)phenyl)-2-methyl-6-((2-methyloxazol-4-yl)methoxy)pyrimidin-4(3H)-one |
| 329 | 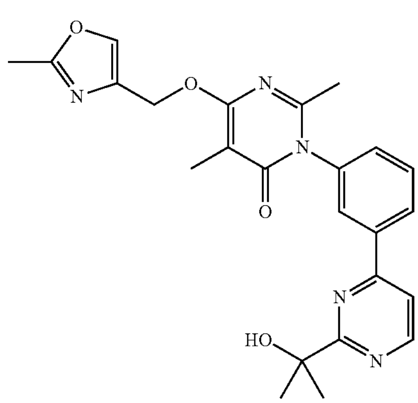 [SMILES: Cc1nc(COc2nc(C)n(-c3cccc(-c4ccnc(C(C)(C)O)n4)c3)c(=O)c2C)co1] | 3-(3-(2-(2-hydroxypropan-2-yl)pyrimidin-4-yl)phenyl)-2,5-dimethyl-6-((2-methyloxazol-4-yl)methoxy)pyrimidin-4(3H)-one |

| Compound | Structure | Name |
|---|---|---|
| 330 | 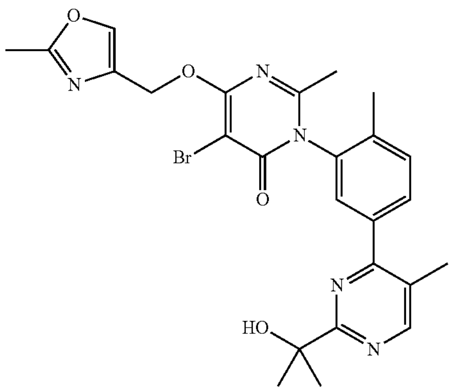 | 5-bromo-3-(5-(2-(2-hydroxypropan-2-yl)-5-methylpyrimidin-4-yl)-2-methylphenyl)-2-methyl-6-((2-methyloxazol-4-yl)methoxy)pyrimidin-4(3H)-one |
| 331 | 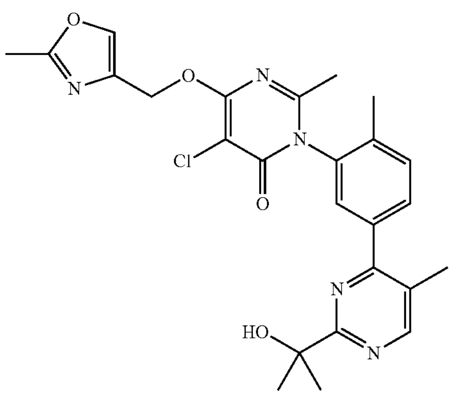 | 5-chloro-3-(5-(2-(2-hydroxypropan-2-yl)-5-methylpyrimidin-4-yl)-2-methylphenyl)-2-methyl-6-((2-methyloxazol-4-yl)methoxy)pyrimidin-4(3H)-one |
| 332 | 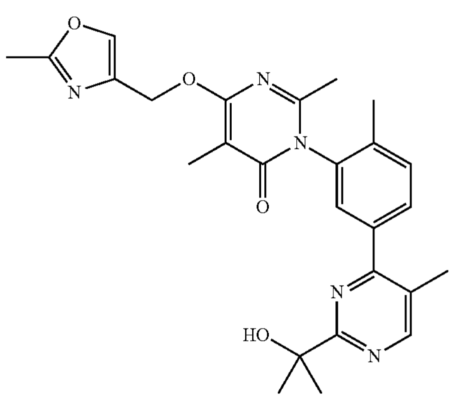 | 3-(5-(2-(2-hydroxypropan-2-yl)-5-methylpyrimidin-4-yl)-2-methylphenyl)-2,5-dimethyl-6-((2-methyloxazol-4-yl)methoxy)pyrimidin-4(3H)-one |
| 333 | 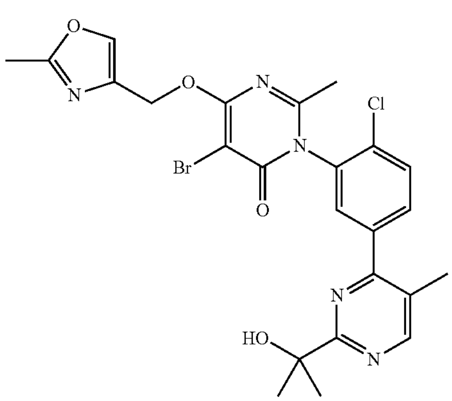 | 5-bromo-3-(2-chloro-5-(2-(2-hydroxypropan-2-yl)-5-methylpyrimidin-4-yl)phenyl)-2-methyl-6-((2-methyloxazol-4-yl)methoxy)pyrimidin-4(3H)-one |

-continued

| Compound | Structure | Name |
|---|---|---|
| 334 | 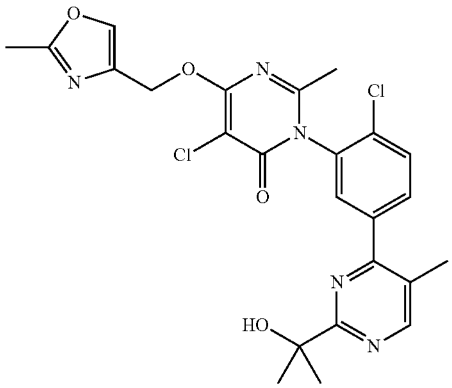 | 5-chloro-3-(2-chloro-5-(2-(2-hydroxypropan-2-yl)-5-methylpyrimidin-4-yl)phenyl)-2-methyl-6-((2-methyloxazol-4-yl)methoxy)pyrimidin-4(3H)-one |
| 335 | 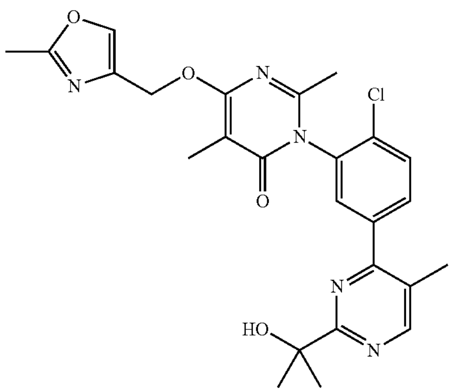 | 3-(2-chloro-5-(2-(2-hydroxypropan-2-yl)-5-methylpyrimidin-4-yl)phenyl)-2,5-dimethyl-6-42-methyloxazol-4-yl)methoxy)pyrimidin-4(3H)-one |
| 336 | 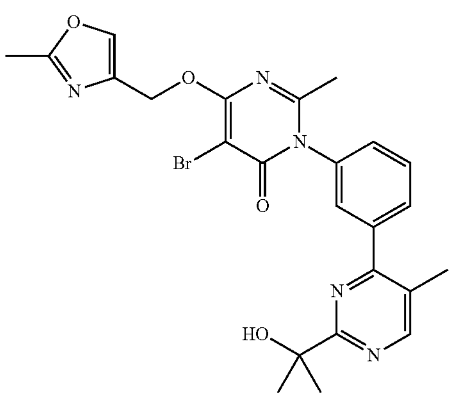 | 5-bromo-3-(3-(2-(2-hydroxypropan-2-yl)-5-methylpyrimidin-4-yl)phenyl)-2-methyl-6-((2-methyloxazol-4-yl)methoxy)pyrimidin-4(3H)-one |
| 337 | 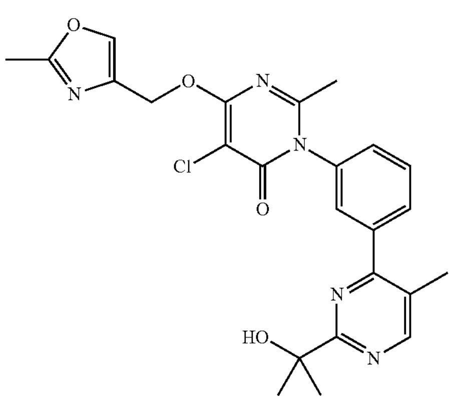 | 5-chloro-3-(3-(2-(2-hydroxypropan-2-yl)-5-methylpyrimidin-4-yl)phenyl)-2-methyl-6-((2-methyloxazol-4-yl)methoxy)pyrimidin-4(3H)-one |

| Compound | Structure | Name |
|---|---|---|
| 338 | 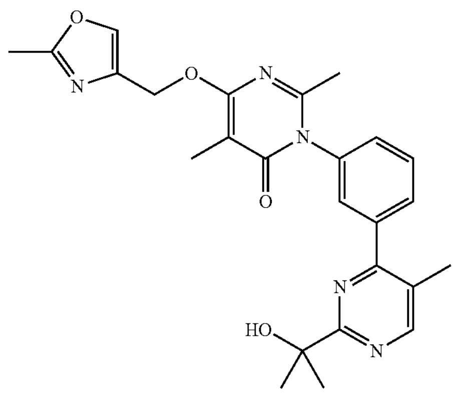 | 3-(3-(2-(2-hydroxypropan-2-yl)-5-methylpyrimidin-4-yl)phenyl)-2,5-dimethyl-6-((2-methyloxazol-4-yl)methoxy)pyrimidin-4(3H)-one |
| 339 | 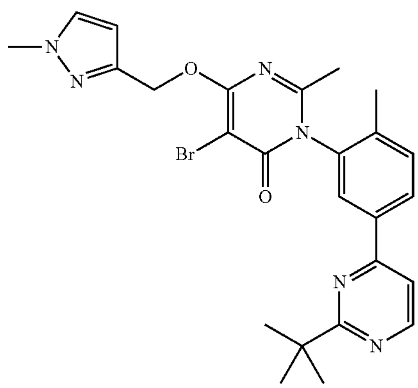 [SMILES: Cc1ccc(-c2ccnc(C(C)(C)C)n2)cc1-n1c(C)nc(OCc2ccn(C)n2)c(Br)c1=O] | 5-bromo-3-(5-(2-(tert-butyl)pyrimidin-4-yl)-2-methylphenyl)-2-methyl-6-((1-methyl-1H-pyrazol-3-yl)methoxy)pyrimidin-4(3H)-one |
| 340 | 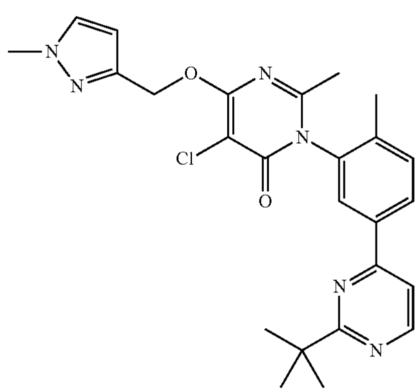 [SMILES: Cc1ccc(-c2ccnc(C(C)(C)C)n2)cc1-n1c(C)nc(OCc2ccn(C)n2)c(Cl)c1=O] | 3-(5-(2-(tert-butyl)pyrimidin-4-yl)-2-methylphenyl)-5-chloro-2-methyl-6-((1-methyl-1H-pyrazol-3-yl)methoxy)pyrimidin-4(3H)-one |
| 341 | 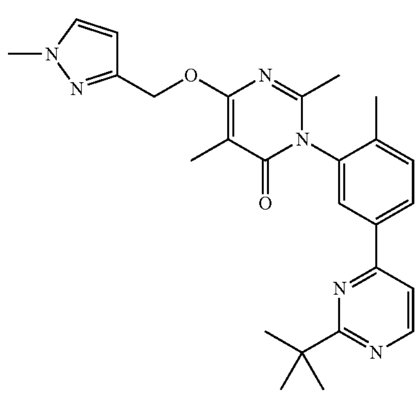 [SMILES: Cc1ccc(-c2ccnc(C(C)(C)C)n2)cc1-n1c(C)nc(OCc2ccn(C)n2)c(C)c1=O] | 3-(5-(2-(tert-butyl)pyrimidin-4-yl)-2-methylphenyl)-2,5-dimethyl-6-((1-methyl-1H-pyrazol-3-yl)methoxy)pyrimidin-4(3H)-one |

| Compound | Structure | Name |
|---|---|---|
| 342 | 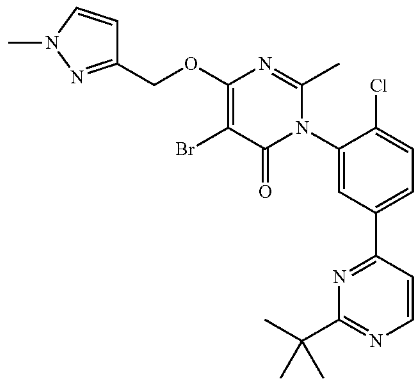 [SMILES: Cc1nc(OCc2ccn(C)n2)c(Br)c(=O)n1-c1cc(-c2ccnc(C(C)(C)C)n2)ccc1Cl] | 5-bromo-3-(5-(2-(tert-butyl)pyrimidin-4-yl)-2-chlorophenyl)-2-methyl-6-((1-methyl-1H-pyrazol-3-yl)methoxy)pyrimidin-4(3H)-one |
| 343 | 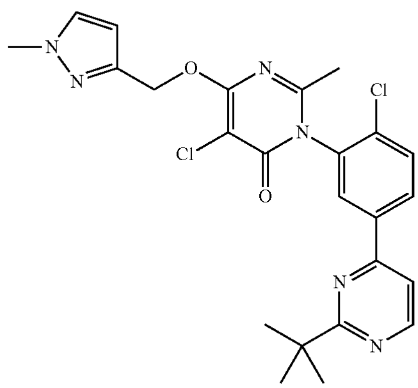 [SMILES: Cc1nc(OCc2ccn(C)n2)c(Cl)c(=O)n1-c1cc(-c2ccnc(C(C)(C)C)n2)ccc1Cl] | 3-(5-(2-(tert-butyl)pyrimidin-4-yl)-2-chlorophenyl)-5-chloro-2-methyl-6-((1-methyl-1H-pyrazol-3-yl)methoxy)pyrimidin-4(3H)-one |
| 344 | 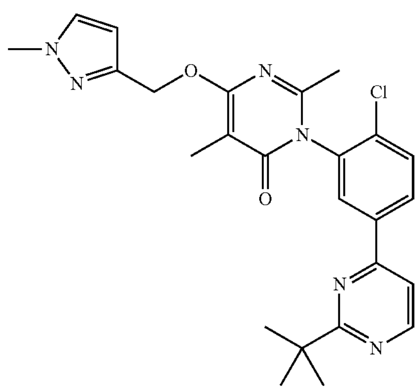 [SMILES: Cc1c(OCc2ccn(C)n2)nc(C)n(-c2cc(-c3ccnc(C(C)(C)C)n3)ccc2Cl)c1=O] | 3-(5-(2-(tert-butyl)pyrimidin-4-yl)-2-chlorophenyl)-2,5-dimethyl-6-((1-methyl-1H-pyrazol-3-yl)methoxy)pyrimidin-4(3H)-one |
| 345 | 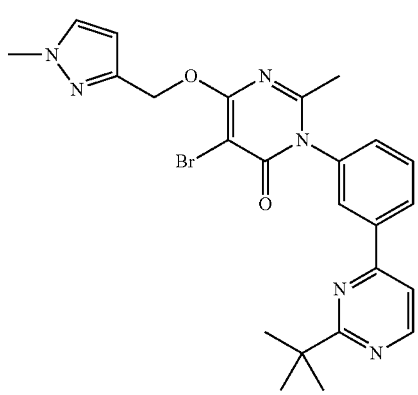 [SMILES: Cc1nc(OCc2ccn(C)n2)c(Br)c(=O)n1-c1cccc(-c2ccnc(C(C)(C)C)n2)c1] | 5-bromo-3-(3-(2-(tert-butyl)pyrimidin-4-yl)phenyl)-2-methyl-6-((1-methyl-1H-pyrazol-3-yl)methoxy)pyrimidin-4(3H)-one |

-continued

| Compound | Structure | Name |
|---|---|---|
| 346 | 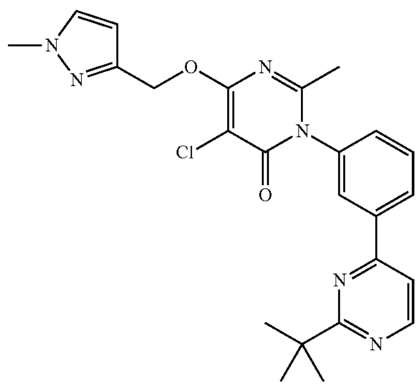 [SMILES: Cc1nc(OCc2ccn(C)n2)c(Cl)c(=O)n1-c1cccc(-c2ccnc(C(C)(C)C)n2)c1] | 3-(3-(2-(tert-butyl)pyrimidin-4-yl)phenyl)-5-chloro-2-methyl-6-((1-methyl-1H-pyrazol-3-yl)methoxy)pyrimidin-4(3H)-one |
| 347 | 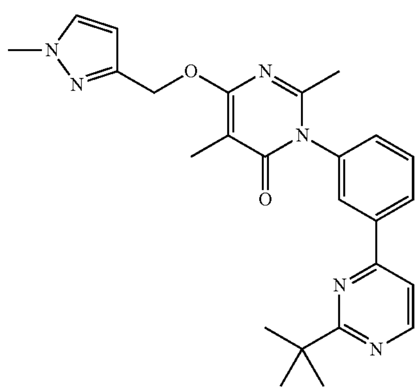 [SMILES: Cc1c(OCc2ccn(C)n2)nc(C)n(-c2cccc(-c3ccnc(C(C)(C)C)n3)c2)c1=O] | 3-(3-(2-(tert-butyl)pyrimidin-4-yl)phenyl)-2,5-dimethyl-6-((1-methyl-1H-pyrazol-3-yl)methoxy)pyrimidin-4(3H)-one |
| 348 | 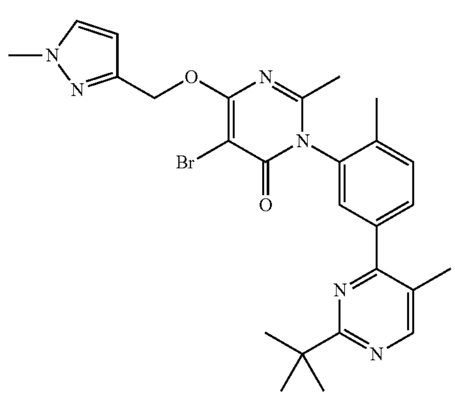 | 5-bromo-3-(5-(2-(tert-butyl)-5-methylpyrimidin-4-yl)-2-methylphenyl)-2-methyl-6-((1-methyl-1H-pyrazol-3-yl)methoxy)pyrimidin-4(3H)-one |
| 349 | 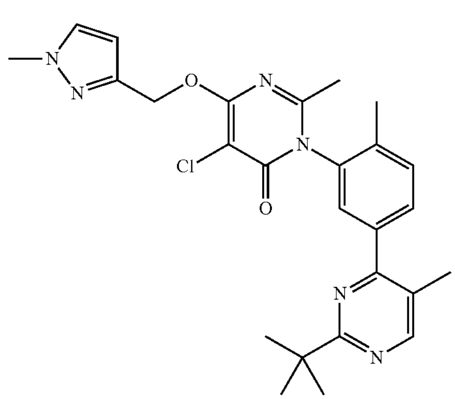 | 3-(5-(2-(tert-butyl)-5-methylpyrimidin-4-yl)-2-methylphenyl)-5-chloro-2-methyl-6-((1-methyl-1H-pyrazol-3-yl)methoxy)pyrimidin-4(3H)-one |

-continued

| Compound | Structure | Name |
|---|---|---|
| 350 | 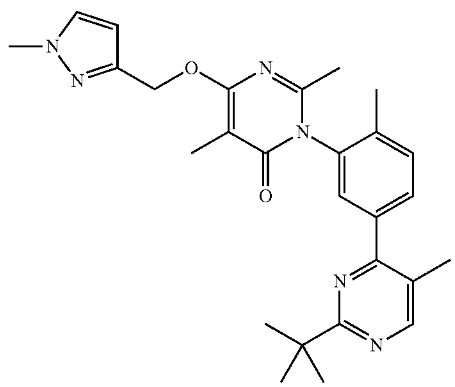 | 3-(5-(2-(tert-butyl)-5-methylpyrimidin-4-yl)-2-methylphenyl)-2,5-dimethyl-6-((1-methyl-1H-pyrazol-3-yl)methoxy)pyrimidin-4(3H)-one |
| 351 | 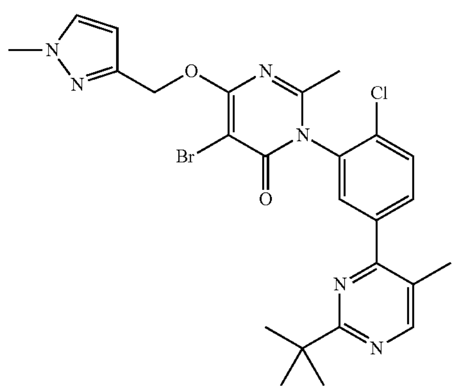 | 5-bromo-3-(5-(2-(tert-butyl)-5-methylprimidin-4-yl)-2-chlorophenyl)-2-methyl-6-((1-methyl-1H-pyrazol-3-yl)methoxy)pyrimidin-4(3H)-one |
| 352 | 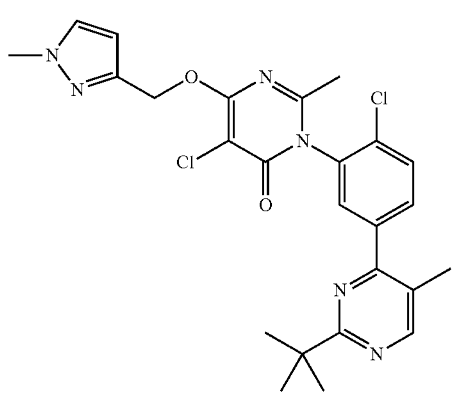 | 3-(5-(2-(tert-butyl)-5-methylpyrimidin-4-yl)-2-chlorophenyl)-5-chloro-2-methyl-6-((1-methyl-1H-pyrazol-3-yl)methoxy)pyrimidin-4(3H)-one |
| 353 | 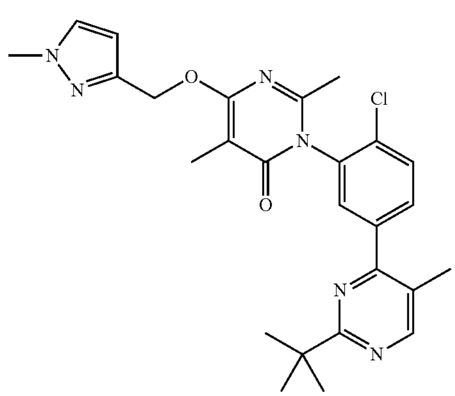 | 3-(5-(2-(tert-butyl)-5-methylpyrimidin-4-yl)-2-chlorophenyl)-2,5-dimethyl-6-((1-methyl-1H-pyrazol-3-yl)methoxy)pyrimidin-4(3H)-one |

-continued

| Compound | Structure | Name |
|---|---|---|
| 354 | 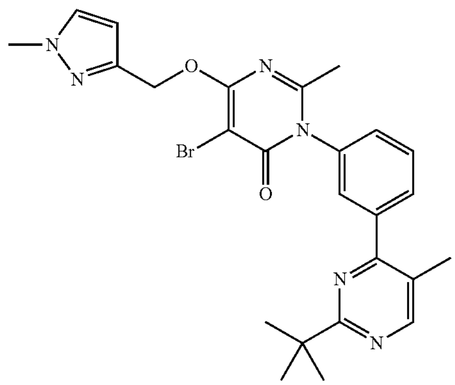 | 5-bromo-3-(3-(2-(tert-butyl)-5-methylpyrimidin-4-yl)phenyl)-2-methyl-6-((1-methyl-1H-pyrazol-3-yl)methoxy)pyrimidin-4(3H)-one |
| 355 | 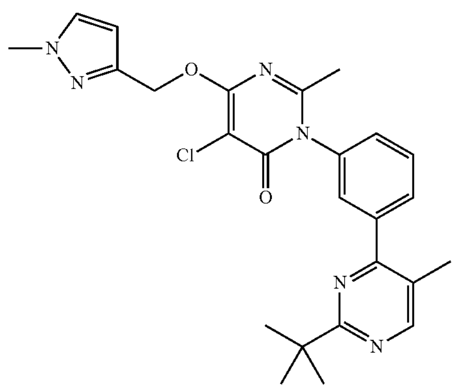 | 3-(3-(2-(tert-butyl)-5-methylpyrimidin-4-yl)phenyl)-5-chloro-2-methyl-6-((1-methyl-1H-pyrazol-3-yl)methoxy)pyrimidin-4(3H)-one |
| 356 | 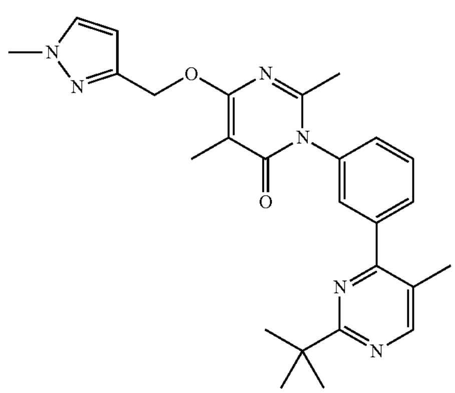 | 3-(3-(2-(tert-butyl)-5-methylpyrimidin-4-yl)phenyl)-2,5-dimethyl-6-((1-methyl-1H-pyrazol-3-yl)methoxy)pyrimidin-4(3H)-one |
| 357 | 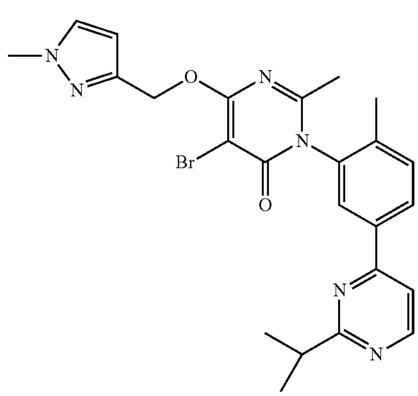 [SMILES: Cc1ccc(-c2ccnc(C(C)C)n2)cc1-n1c(C)nc(OCc2ccn(C)n2)c(Br)c1=O] | 5-bromo-3-(5-(2-isopropylpyrimidin-4-yl)-2-methylphenyl)-2-methyl-6-((1-methyl-1H-pyrazol-3-yl)methoxy)pyrimidin-4(3H)-one |

-continued

| Compound | Structure | Name |
|---|---|---|
| 358 | 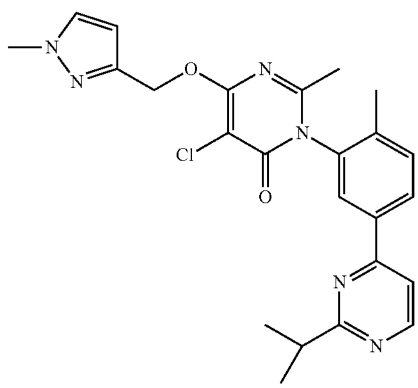 [SMILES: Cc1ccc(-c2ccnc(C(C)C)n2)cc1-n1c(C)nc(OCc2ccn(C)n2)c(Cl)c1=O] | 5-chloro-3-(5-(2-isopropylpyrimidin-4-yl)-2-methylphenyl)-2-methyl-6-((1-methyl-1H-pyrazol-3-yl)methoxy)pyrimidin-4(3H)-one |
| 359 | 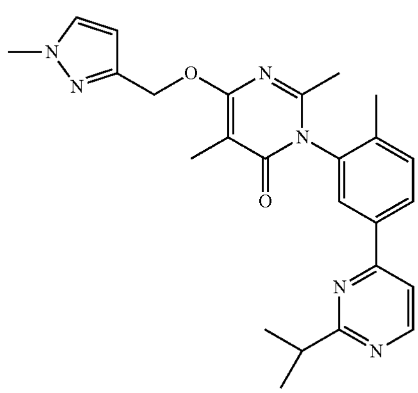 [SMILES: Cc1ccc(-c2ccnc(C(C)C)n2)cc1-n1c(C)nc(OCc2ccn(C)n2)c(C)c1=O] | 3-(5-(2-isopropylpyrimidin-4-yl)-2-methylphenyl)-2,5-dimethyl-6-((1-methyl-1H-pyrazol-3-yl)methoxy)pyrimidin-4(3H)-one |
| 360 | 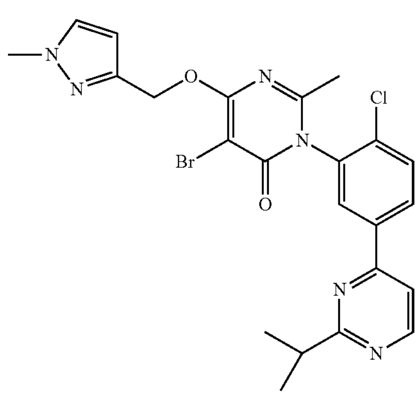 | 5-bromo-3-(2-chloro-5-(2-isopropylpyrimidin-4-yl)phenyl)-2-methyl-6-((1-methyl-1H-pyrazol-3-yl)methoxy)pyrimidin-4(3H)-one |
| 361 | 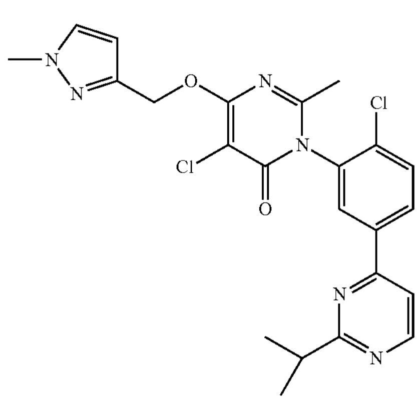 [SMILES: Cc1nc(OCc2ccn(C)n2)c(Cl)c(=O)n1-c1cc(-c2ccnc(C(C)C)n2)ccc1Cl] | 5-chloro-3-(2-chloro-5-(2-isopropylpyrimidin-4-yl)phenyl)-2-methyl-6-((1-methyl-1H-pyrazol-3-yl)methoxy)pyrimidin-4(3H)-one |

-continued

| Compound | Structure | Name |
|---|---|---|
| 362 | 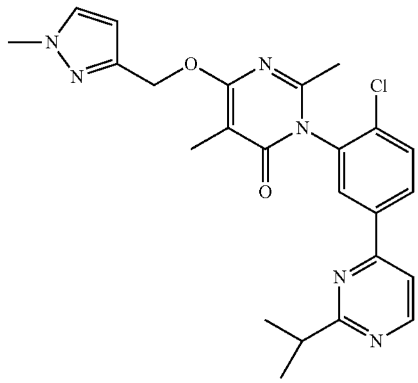 | 3-(2-chloro-5-(2-isopropylpyrimidin-4-yl)phenyl)-2,5-dimethyl-6-((1-methyl-1H-pyrazol-3-yl)methoxy)pyrimidin-4(3H)-one |
| 363 | 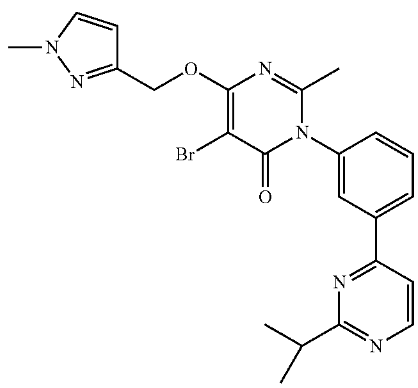 | 5-bromo-3-(3-(2-isopropylpyrimidin-4-yl)phenyl)-2-methyl-6-((1-methyl-1H-pyrazol-3-yl)methoxy)pyrimidin-4(3H)-one |
| 364 | 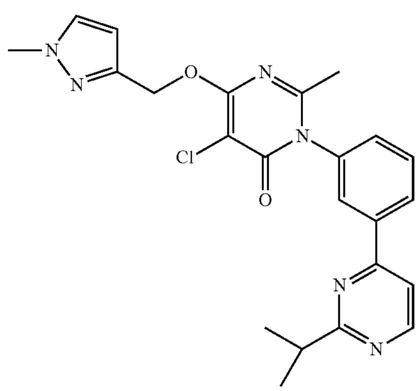 [SMILES: Cc1nc(OCc2ccn(C)n2)c(Cl)c(=O)n1-c1cccc(-c2ccnc(C(C)C)n2)c1] | 5-chloro-3-(3-(2-isopropylpyrimidin-4-yl)phenyl)-2-methyl-6-((1-methyl-1H-pyrazol-3-yl)methoxy)pyrimidin-4(3H)-one |
| 365 | 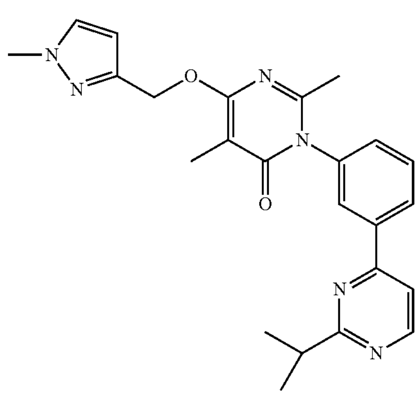 [SMILES: Cc1c(OCc2ccn(C)n2)nc(C)n(-c2cccc(-c3ccnc(C(C)C)n3)c2)c1=O] | 3-(3-(2-isopropylpyrimidin-4-yl)phenyl)-2,5-dimethyl-6-((1-methyl-1H-pyrazol-3-yl)methoxy)pyrimidin-4(3H)-one |

-continued

| Compound | Structure | Name |
|---|---|---|
| 366 | 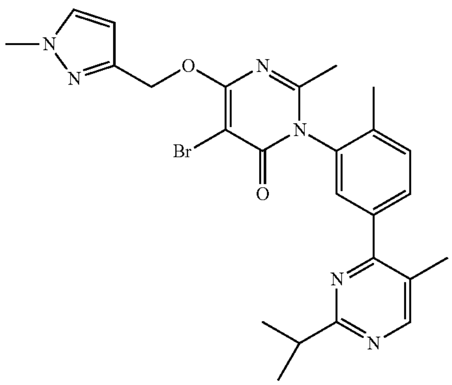 | 5-bromo-3-(5-(2-isopropyl-5-methylpyrimidin-4-yl)-2-methylphenyl)-2-methyl-6-((1-methyl-1H-pyrazol-3-yl)methoxy)pyrimidin-4(3H)-one |
| 367 | 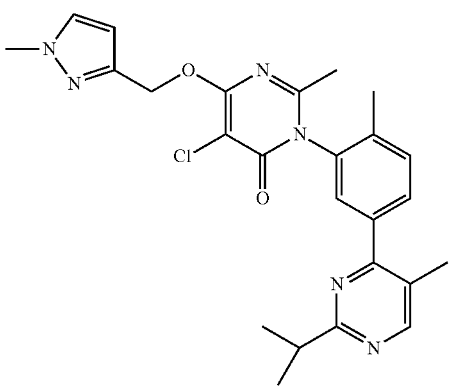 | 5-chloro-3-(5-(2-isopropyl-5-methylpyrimidin-4-yl)-2-methylphenyl)-2-methyl-6-((1-methyl-1H-pyrazol-3-yl)methoxy)pyrimidin-4(3H)-one |
| 368 | 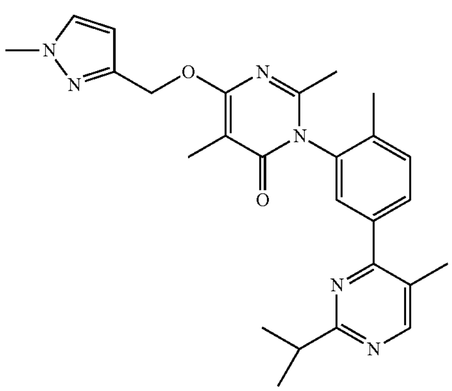 | 3-(5-(2-isopropyl-5-methylpyrimidin-4-yl)-2-methylphenyl)-2,5-dimethyl-6-((1-methyl-1H-pyrazol-3-yl)methoxy)pyrimidin-4(3H)-one |
| 369 | 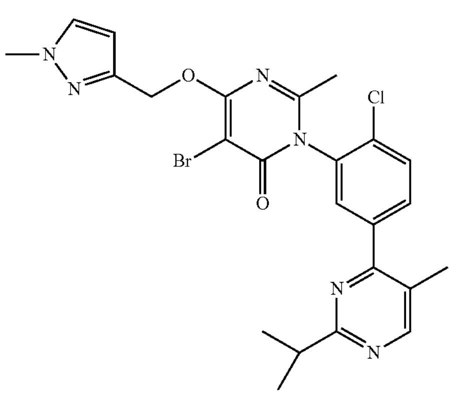 | 5-bromo-3-(2-chloro-5-(2-isopropyl-5-methylpyrimidin-4-yl)phenyl)-2-methyl-6-((1-methyl-1H-pyrazol-3-yl)methoxy)pyrimidin-4(3H)-one |

| Compound | Structure | Name |
|---|---|---|
| 370 | 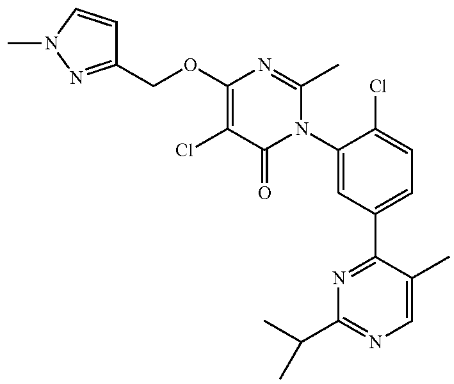 | 5-chloro-3-(2-chloro-5-(2-isopropyl-5-methylpyrimidin-4-yl)phenyl)-2-methyl-6-((1-methyl-1H-pyrazol-3-yl)methoxy)pyrimidin-4(3H)-one |
| 371 | 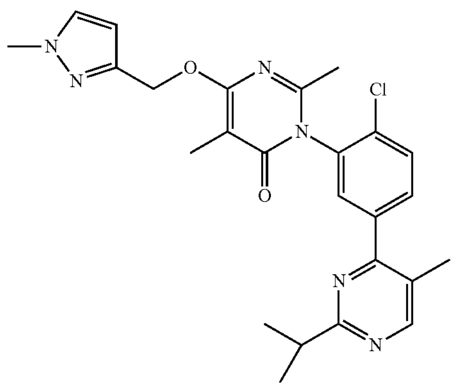 | 3-(2-chloro-5-(2-isopropyl-5-methylpyrimidin-4-yl)phenyl)-2,5-dimethyl-6-((1-methyl-1H-pyrazol-3-yl)methoxy)pyrimidin-4(3H)-one |
| 372 | 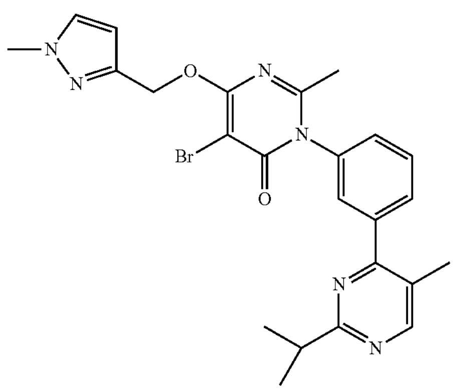 | 5-bromo-3-(3-(2-isopropyl-5-methylpyrimidin-4-yl)phenyl)-2-methyl-6-((1-methyl-1H-pyrazol-3-yl)methoxy)pyrimidin-4(3H)-one |
| 373 | 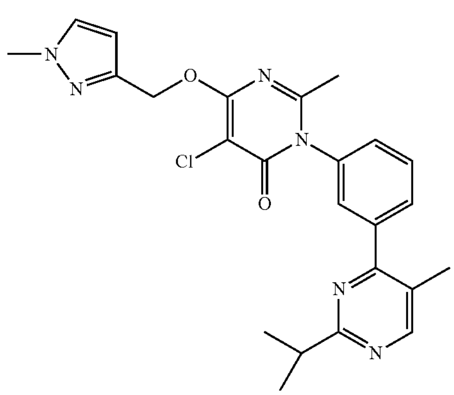 | 5-chloro-3-(3-(2-isopropyl-5-methylpyrimidin-4-yl)phenyl)-2-methyl-6-((1-methyl-1H-pyrazol-3-yl)methoxy)pyrimidin-4(3H)-one |

| Compound | Structure | Name |
|---|---|---|
| 374 | 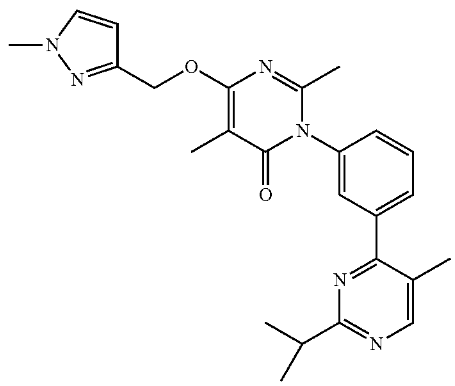 | 3-(3-(2-isopropyl-5-methylpyrimidin-4-yl)phenyl)-2,5-dimethyl-6-((1-methyl-1H-pyrazol-3-yl)methoxy)pyrimidin-4(3H)-one |
| 375 | 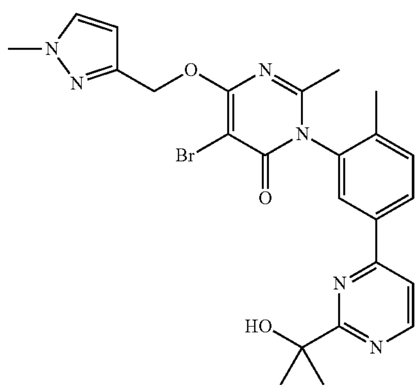 [SMILES: Cc1ccc(-c2ccnc(C(C)(C)O)n2)cc1-n1c(C)nc(OCc2ccn(C)n2)c(Br)c1=O] | 5-bromo-3-(5-(2-(2-hydroxypropan-2-yl)pyrimidin-4-yl)-2-methylphenyl)-2-methyl-6-((1-methyl-1H-pyrazol-3-yl)methoxy)pyrimidin-4(3H)-one |
| 376 | 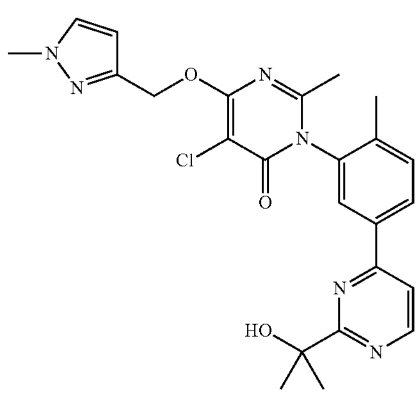 [SMILES: Cc1ccc(-c2ccnc(C(C)(C)O)n2)cc1-n1c(C)nc(OCc2ccn(C)n2)c(Cl)c1=O] | 5-chloro-3-(5-(2-(2-hydroxypropan-2-yl)pyrimidin-4-yl)-2-methylphenyl)-2-methyl-6-((1-methyl-1H-pyrazol-3-yl)methoxy)pyrimidin-4(3H)-one |
| 377 | 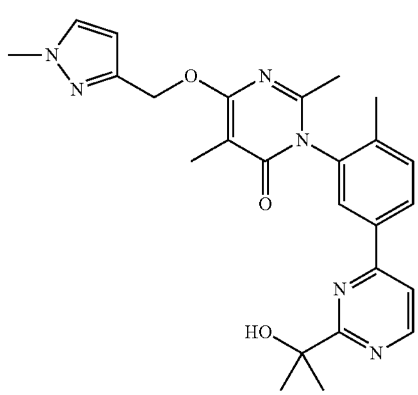 | 3-(5-(2-(2-hydroxypropan-2-yl)pyrimidin-4-yl)-2-methylphenyl)-2,5-dimethyl-6-((1-methyl-1H-pyrazol-3-yl)methoxy)pyrimidin-4(3H)-one |

-continued

| Compound | Structure | Name |
|---|---|---|
| 378 | 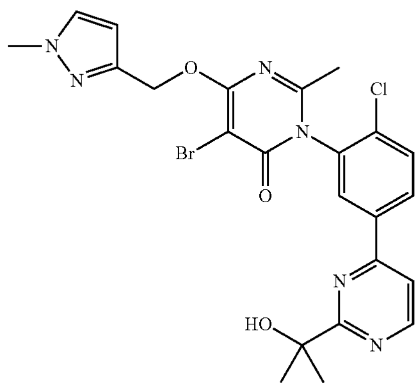 [SMILES: Cc1nc(OCc2ccn(C)n2)c(Br)c(=O)n1-c1cc(-c2ccnc(C(C)(C)O)n2)ccc1Cl] | 5-bromo-3-(2-chloro-5-(2-(2-hydroxypropan-2-yl)pyrimidin-4-yl)phenyl)-2-methyl-6-((1-methyl-1H-pyrazol-3-yl)methoxy)pyrimidin-4(3H)-one |
| 379 | 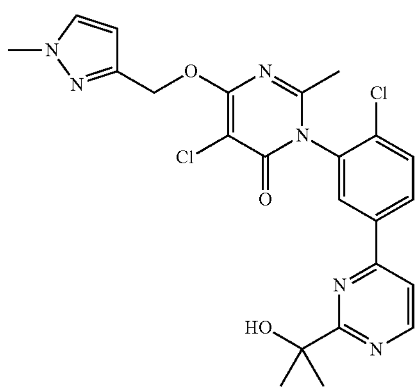 [SMILES: Cc1nc(OCc2ccn(C)n2)c(Cl)c(=O)n1-c1cc(-c2ccnc(C(C)(C)O)n2)ccc1Cl] | 5-chloro-3-(2-chloro-5-(2-(2-hydroxypropan-2-yl)pyrimidin-4-yl)phenyl)-2-methyl-6-((1-methyl-1H-pyrazol-3-yl)methoxy)pyrimidin-4(3H)-one |
| 380 | 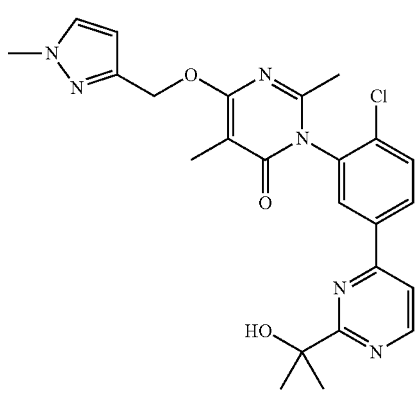 [SMILES: Cc1c(OCc2ccn(C)n2)nc(C)n(-c2cc(-c3ccnc(C(C)(C)O)n3)ccc2Cl)c1=O] | 3-(2-chloro-5-(2-(2-hydroxypropan-2-yl)pyrimidin-4-yl)phenyl)-2,5-dimethyl-64(1-methyl-1H-pyrazol-3-yl)methoxy)pyrimidin-4(3H)-one |
| 381 | 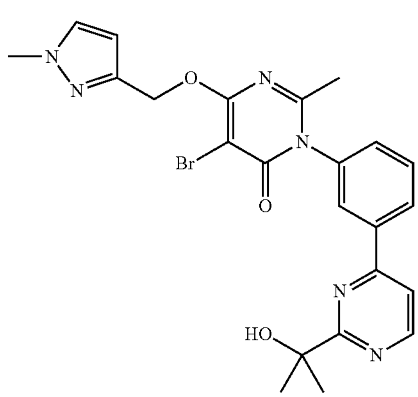 [SMILES: Cc1nc(OCc2ccn(C)n2)c(Br)c(=O)n1-c1cccc(-c2ccnc(C(C)(C)O)n2)c1] | 5-bromo-3-(3-(2-(2-hydroxypropan-2-yl)pyrimidin-4-yl)phenyl)-2-methyl-6-((1-methyl-1H-pyrazol-3-yl)methoxy)pyrimidin-4(3H)-one |

-continued

| Compound | Structure | Name |
|---|---|---|
| 382 | 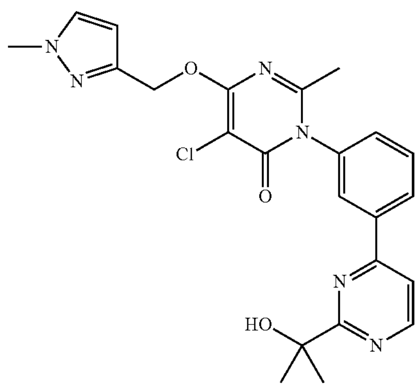 [SMILES: Cc1nc(OCc2ccn(C)n2)c(Cl)c(=O)n1-c1cccc(-c2ccnc(C(C)(C)O)n2)c1] | 5-chloro-3-(3-(2-(2-hydroxypropan-2-yl)pyrimidin-4-yl)phenyl)-2-methyl-6-((1-methyl-1H-pyrazol-3-yl)methoxy)pyrimidin-4(3H)-one |
| 383 | 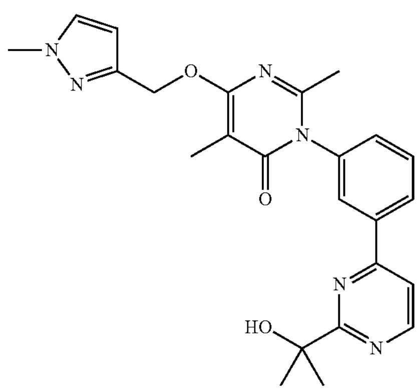 [SMILES: Cc1c(OCc2ccn(C)n2)nc(C)n(-c2cccc(-c3ccnc(C(C)(C)O)n3)c2)c1=O] | 3-(3-(2-(2-hydroxypropan-2-yl)pyrimidin-4-yl)phenyl)-2,5-dimethyl-6-((1-methyl-1H-pyrazol-3-yl)methoxy)pyrimidin-4(3H)-one |
| 384 | 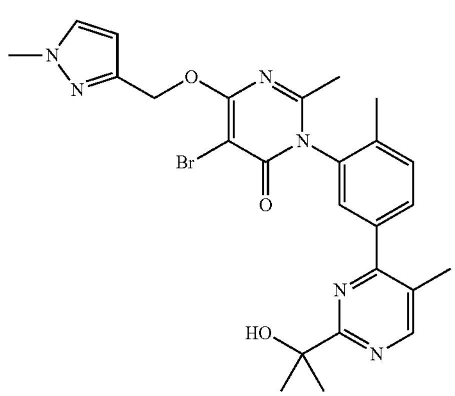 | 5-bromo-3-(5-(2-(2-hydroxypropan-2-yl)-5-methylpyrimidin-4-yl)-2-methylphenyl)-2-methyl-6-((1-methyl-1H-pyrazol-3-yl)methoxy)pyrimidin-4(3H)-one |
| 385 | 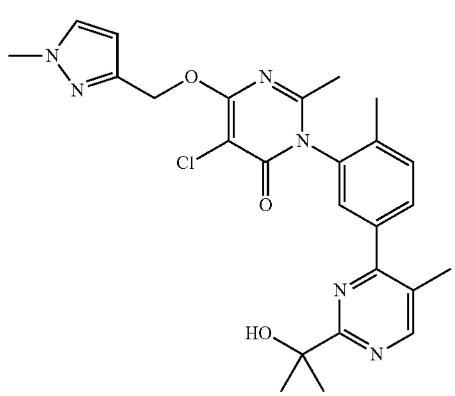 | 5-chloro-3-(5-(2-(2-hydroxypropan-2-yl)-5-methylpyrimidin-4-yl)-2-methylphenyl)-2-methyl-6-((1-methyl-1H-pyrazol-3-yl)methoxy)pyrimidin-4(3H)-one |

| Compound | Structure | Name |
|---|---|---|
| 386 | 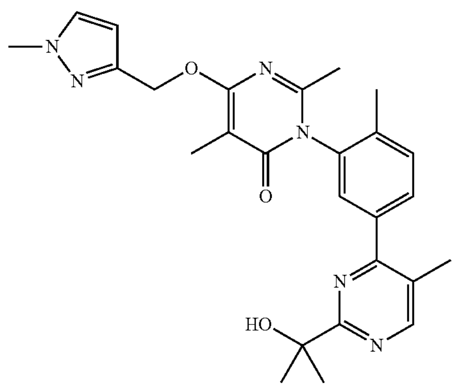 | 3-(5-(2-(2-hydroxypropan-2-yl)-5-methylpyrimidin-4-yl)-2-methylphenyl)-2,5-dimethyl-6-((1-methyl-1H-pyrazol-3-yl)methoxy)pyrimidin-4(3H)-one |
| 387 | 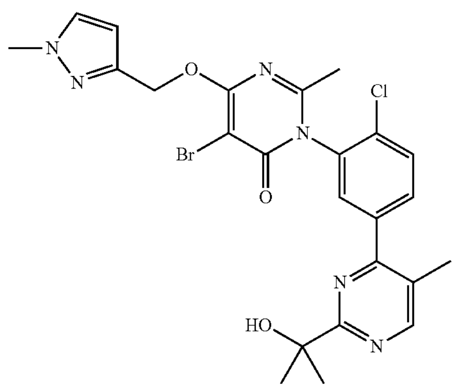 | 5-bromo-3-(2-chloro-5-(2-(2-hydroxypropan-2-yl)5-methylprimidin-4yl)phenyl)-2-methyl-6-((1-methyl-1H-pyrazol-3-yl)methoxy)pyrimidin-4(3H)-one |
| 388 | 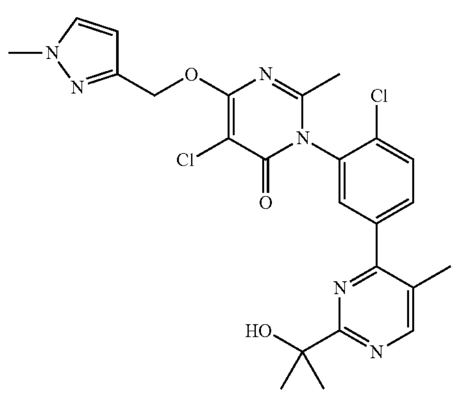 | 5-chloro-3-(2-chloro-5-(2-(2-hydroxypropan-2-yl)-5-methylpyrimidin-4-yl)phenyl)-2-methyl-6-((1-methyl-1H-pyrazol-3-yl)methoxy)pyrimidin-4(3H)-one |
| 389 | 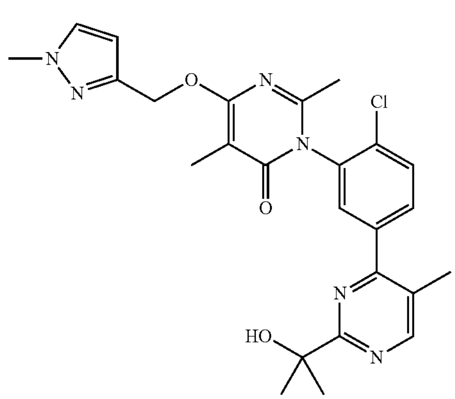 | 3-(2-chloro-5-(2-(2-hydroxypropan-2-yl)-5-methylprimidin-4-yl)phenyl)2,5-dimethyl-6-((1-methyl-1H-pyrazol-3-yl)methoxy)pyrimidin-4(3H)-one |

| Compound | Structure | Name |
|---|---|---|
| 390 | 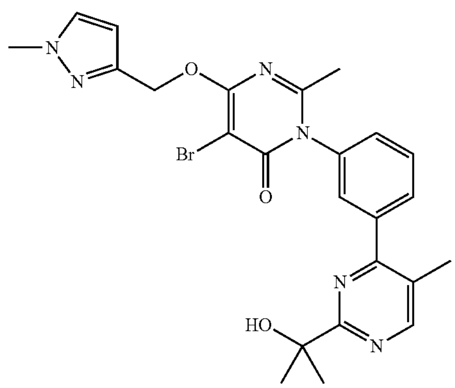 | 5-bromo-3-(3-(2-(2-hydroxypropan-2-yl)-5-methylpyrimidin-4-yl)phenyl)-2-methyl-6-((1-methyl-1H-pyrazol-3-yl)methoxy)pyrimidin-4(3H)-one |
| 391 | 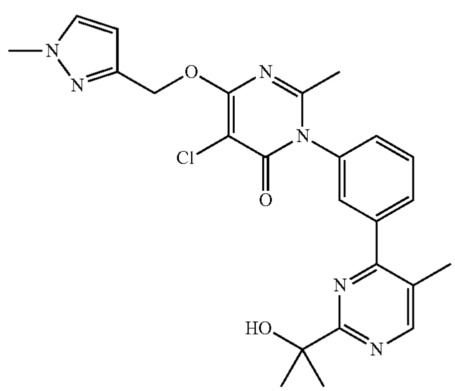 | 5-chloro-3-(3-(2-(2-hydroxypropan-2-yl)-5-methylpyrimidin-4-yl)phenyl)-2-methyl-6-((1-methyl-1H-pyrazol-3-yl)methoxy)pyrimidn-4(3H)-one |
| 392 | 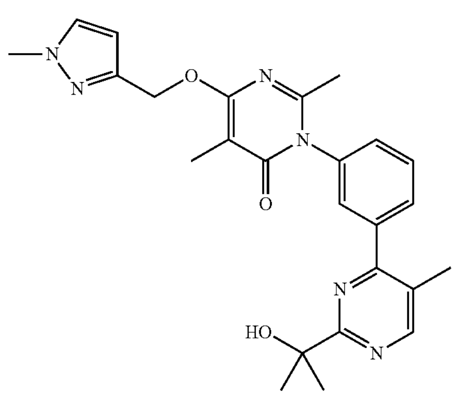 | 3-(3-(2-(2-hydroxypropan-2-yl)-5-methylpyrimidin-4-yl)phenyl)-2,5-dimethyl-6-((1-methyl-1H-pyrazol-3-yl)methoxy)pyrimidin-4(3H)-one |
| 393 | 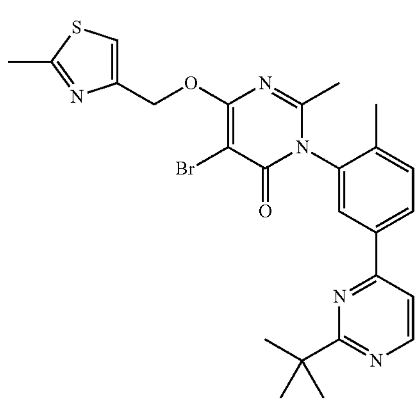 | 5-bromo-3-(5-(2-(tert-butyl)pyrimidin-4-yl)-2-methylphenyl)-2-methyl-6-((2-methylthiazol-4-yl)methoxy)pyrimidin-4(3H)-one |

| Compound | Structure | Name |
|---|---|---|
| 394 | 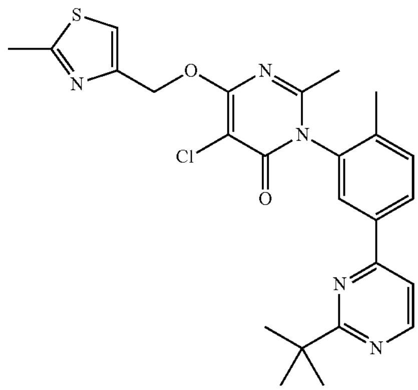 | 3-(5-(2-(tert-butyl)pyrimidin-4-yl)-2-methylphenyl)-5-chloro-2-methyl-6-((2-methylthiazol-4-yl)methoxy)pyrimidin-4(3H)-one |
| 395 | 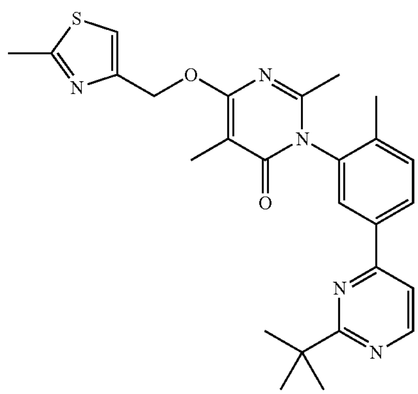 | 3-(5-(2-(tert-butyl)pyrimidin-4-yl)-2-methylphenyl)-2,5-dimethyl-6-((2-methylthiazol-4-yl)methoxy)pyrimidin-4(3H)-one |
| 396 | 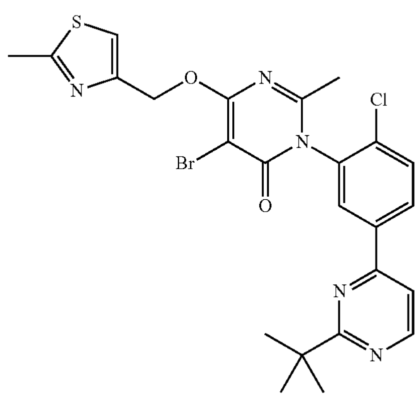 | 5-bromo-3-(5-(2-(tert-butyl)pyrimidin-4-yl)-2-chlorophenyl)-2-methyl-6-((2-methylthiazol-4-yl)methoxy)pyrimidin-4(3H)-one |
| 397 | 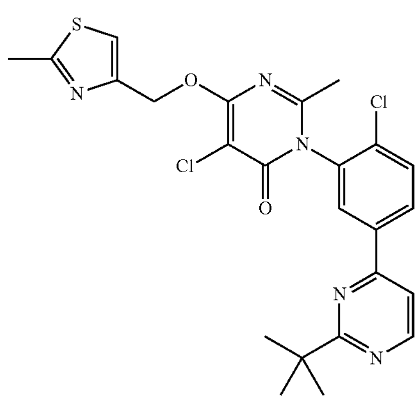 [SMILES: Cc1nc(COc2nc(C)n(-c3cc(-c4ccnc(C(C)(C)C)n4)ccc3Cl)c(=O)c2Cl)cs1] | 3-(5-(2-(tert-butyl)pyrimidin-4-yl)-2-chlorophenyl)-5-chloro-2-methyl-6-((2-methylthiazol-4-yl)methoxy)pyrimidin-4(3H)one |

| Compound | Structure | Name |
|---|---|---|
| 398 | 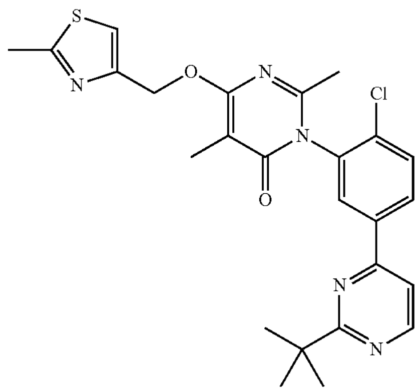 [SMILES: Cc1nc(COc2nc(C)n(-c3cc(-c4ccnc(C(C)(C)C)n4)ccc3Cl)c(=O)c2C)cs1] | 3-(5-(2-(tert-butyl)pyrimidin-4-yl)-2-chlorophenyl)-2,5-dimethyl-6-((2-methylthiazol-4-yl)methoxy)pyrimidin-4(3H)-one |
| 399 | 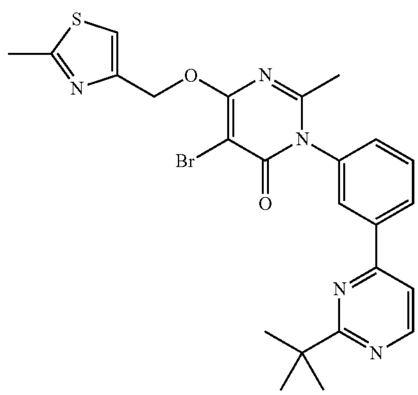 [SMILES: Cc1nc(COc2nc(C)n(-c3cccc(-c4ccnc(C(C)(C)C)n4)c3)c(=O)c2Br)cs1] | 5-bromo-3-(3-(2-(tert-butyl)pyrimidin-4-yl)phenyl)-2-methyl-6-((2-methylthiazol-4-yl)methoxy)pyrimidin-4(3H)-one |
| 400 | 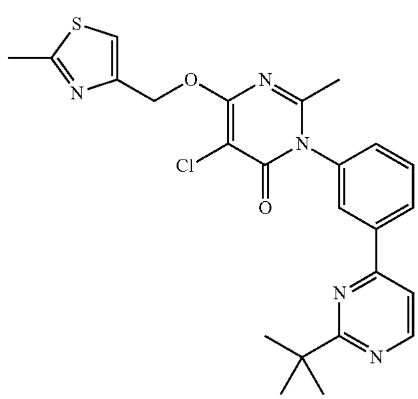 | 3-(3-(2-(tert-butyl)pyrimidin-4-yl)phenyl)-5-chloro-2-methyl-6-((2-methylthiazol-4-yl)methoxy)pyrimidin-4(3H)-one |
| 401 | 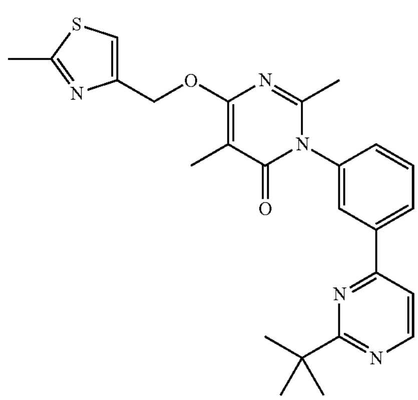 | 3-(3-(2-(tert-butyl)pyrimidin-4-yl)phenyl)-2,5-dimethyl-6-((2-methylthiazol-4-yl)methoxy)pyrimidin-4(3H)-one |

| Compound | Structure | Name |
|---|---|---|
| 402 | 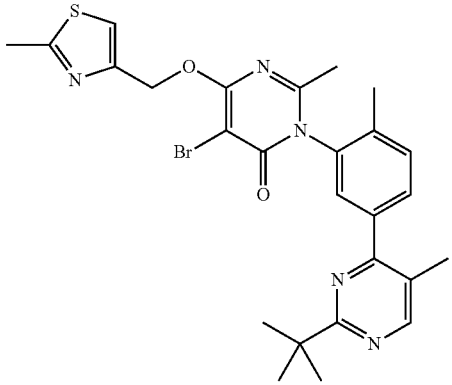 | 5-bromo-3-(5-(2-(tert-butyl)-5-methylpyrimidin-4-yl)-2-methylphenyl)-2-methyl-6-((2-methylthiazol-4-yl)methoxy)pyrimidin-4(3H)-one |
| 403 | 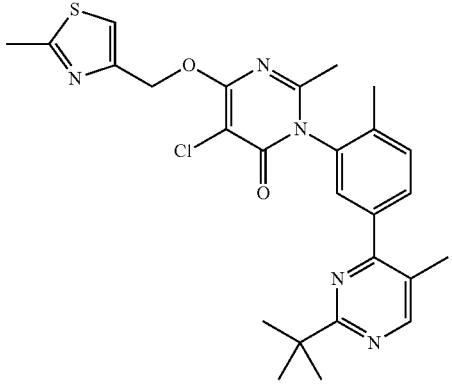 | 3-(5-(2-(tert-butyl)-5-methylpyrimidin-4-yl)-2-methylphenyl)-5-chloro-2-methyl-6-((2-methylthiazol-4-yl)methoxy)pyrimidin-4(3H)-one |
| 404 | 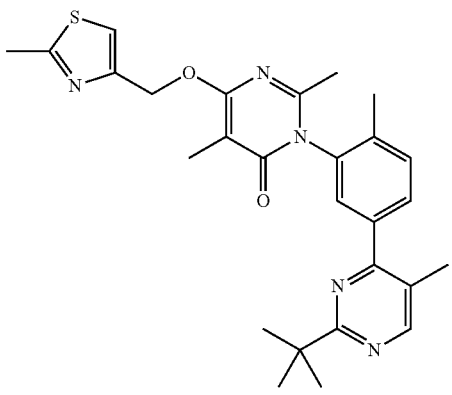 | 3-(5-(2-(tert-butyl)-5-methylpyrimidin-4-yl)-2-methylphenyl)-2,5-dimethyl-6-((2-methylthiazol-4-yl)methoxy)pyrimidin-4(3H)-one |
| 405 | 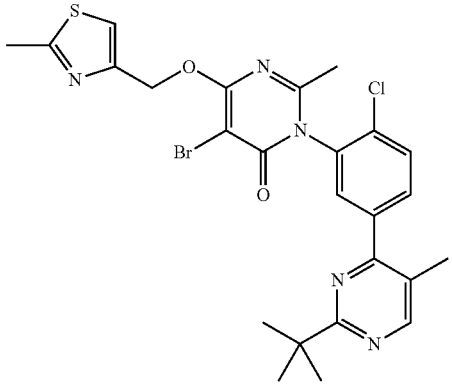 | 5-bromo-3-(5-(2-(tert-butyl)-5-methylpyrimidin-4-yl)-2-chlorophenyl)-2-methyl-6-((2-methylthiazol-4-yl)methoxy)pyrimidin-4(3H)-one |

-continued

| Compound | Structure | Name |
|---|---|---|
| 406 | 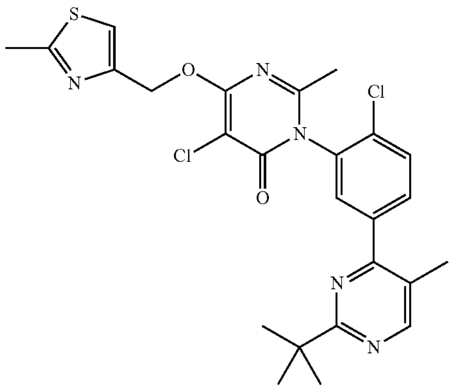 | 3-(5-(2-(tert-butyl)-5-methylpyrimidin-4-yl)-2-chlorophenyl)-5-chloro-2-methyl-6-((2-methylthiazol-4-yl)methoxy)pyrimidin-4(3H)-one |
| 407 | 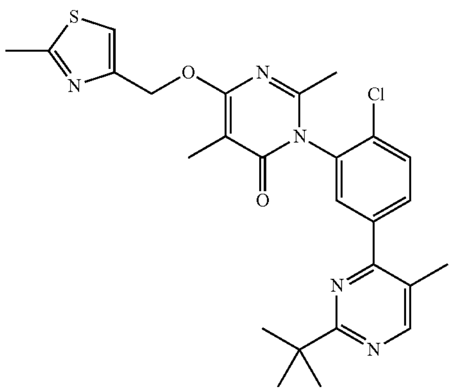 | 3-(5-(2-(tert-butyl)-5-methylpyrimidin-4-yl)-2-chlorophenyl)-2,5-dimethyl-6-((2-methylthiazol-4-yl)methoxy)pyrimidin-4(3H)-one |
| 408 | 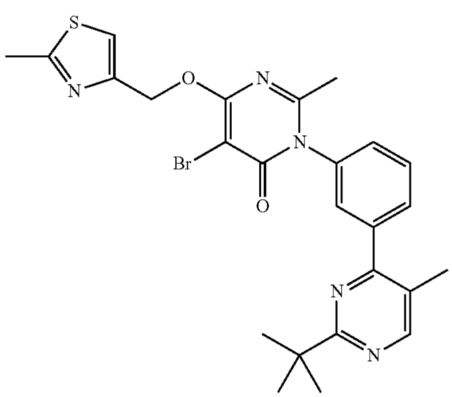 | 5-bromo-3-(3-(2-(tert-butyl)-5-methylpyrimidin-4-yl)phenyl)-2-methyl-6-((2-methylthiazol-4-yl)methoxy)pyrimidin-4(3H)-one |
| 409 | 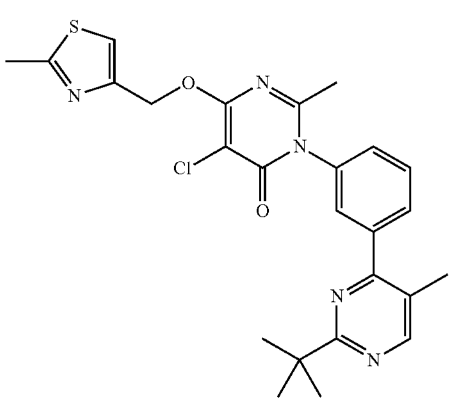 | 3-(3-(2-(tert-butyl)-5-methylpyrimidin-4-yl)phenyl)-5-chloro-2-methyl-6-((2-methylthiazol-4-yl)methoxy)pyrimidin-4(3H)-one |

-continued

| Compound | Structure | Name |
|---|---|---|
| 410 | 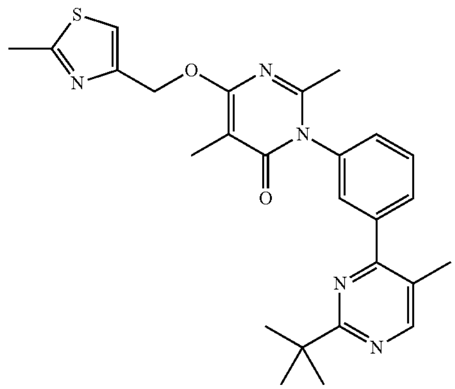 | 3-(3-(2-(tert-butyl)-5-methylpyrimidin-4-yl)phenyl)-2,5-dimethyl-6-((2-methylthiazol-4-yl)methoxy)pyrimidin-4(3H)-one |
| 411 | 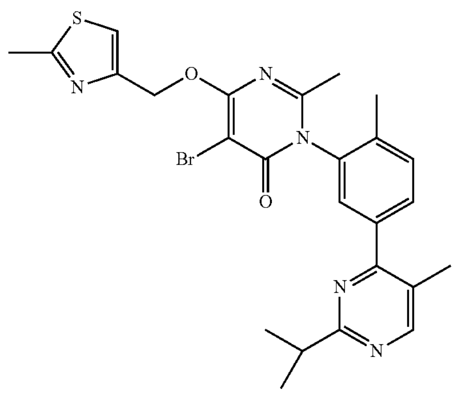 | 5-bromo-3-(5-(2-isopropylpyrimidin-4-yl)-2-methylphenyl)-2-methyl-6-((2-methylthiazol-4-yl)methoxy)pyrimidin-4(3H)-one |
| 412 | 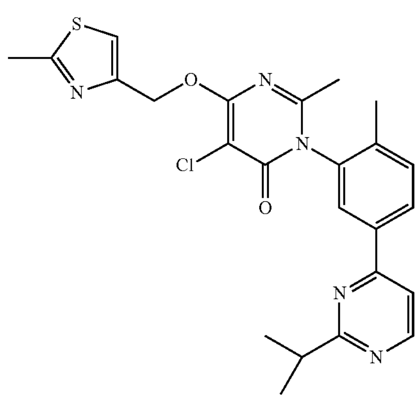 [SMILES: Cc1nc(COc2nc(C)n(-c3cc(-c4ccnc(C(C)C)n4)ccc3C)c(=O)c2Cl)cs1] | 5-chloro-3-(5-(2-isopropylpyrimidin-4-yl)-2-methylphenyl)-2-methyl-6-((2-methylthiazol-4-yl)methoxy)pyrimidin-4(3H)-one |
| 413 | 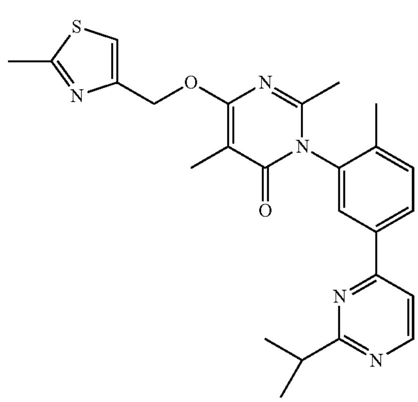 [SMILES: Cc1nc(COc2nc(C)n(-c3cc(-c4ccnc(C(C)C)n4)ccc3C)c(=O)c2C)cs1] | 3-(5-(2-isopropylpyrimidin-4-yl)-2-methylphenyl)-2,5-dimethyl-6-((2-methylthiazol-4-yl)methoxy)pyrimidin-4(3H)-one |

-continued

| Compound | Structure | Name |
|---|---|---|
| 414 | 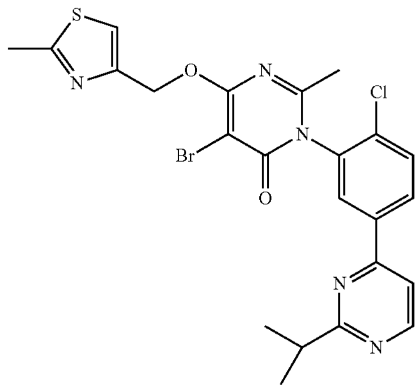 [SMILES: Cc1nc(COc2nc(C)n(-c3cc(-c4ccnc(C(C)C)n4)ccc3Cl)c(=O)c2Br)cs1] | 5-bromo-3-(2-chloro-5-(2-isopropylpyrimidin-4-yl)phenyl)-2-methyl-6-((2-methylthiazol-4-yl)methoxy)pyrimidin-4(3H)-one |
| 415 | 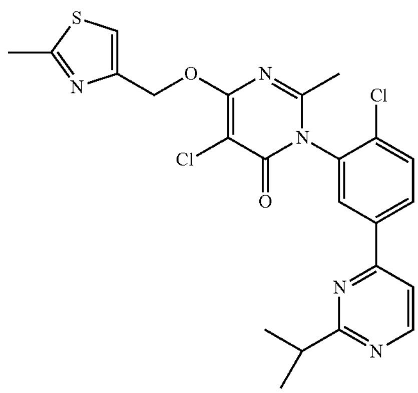 | 5-chloro-3-(2-chloro-5-(2-isopropylpyrimidin-4-yl)phenyl)-2-methyl-6-((2-methylthiazol-4-yl)methoxy)pyrimidin-4(3H)-one |
| 416 | 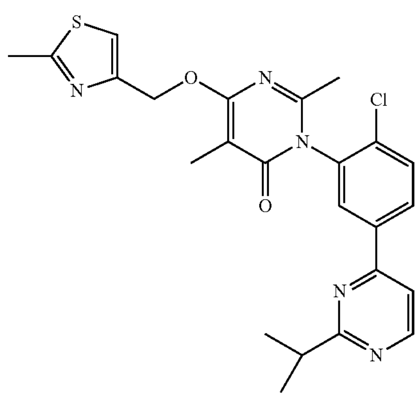 [SMILES: Cc1nc(COc2nc(C)n(-c3cc(-c4ccnc(C(C)C)n4)ccc3Cl)c(=O)c2C)cs1] | 3-(2-chloro-5-(2-isopropylpyrimidin-4-yl)phenyl)-2,5-dimethyl-6-((2-methylthiazol-4-yl)methoxy)pyrimidin-4(3H)-one |
| 417 | 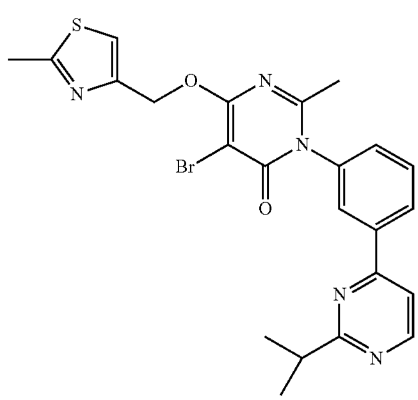 | 5-bromo-3-(3-(2-isopropylpyrimidin-4-yl)phenyl)-2-methyl-6-((2-methylthiazol-4-yl)methoxy)pyrimidin-4(3H)-one |

-continued

| Compound | Structure | Name |
|---|---|---|
| 418 | 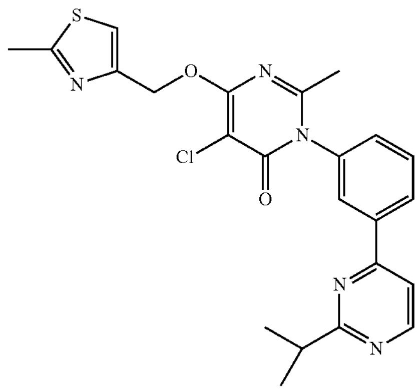 [SMILES: Cc1nc(COc2nc(C)n(-c3cccc(-c4ccnc(C(C)C)n4)c3)c(=O)c2Cl)cs1] | 5-chloro-3-(3-(2-isopropylpyrimidin-4-yl)phenyl)-2-methyl-6-((2-methylthiazol-4-yl)methoxy)pyrimidin-4(3H)-one |
| 419 | 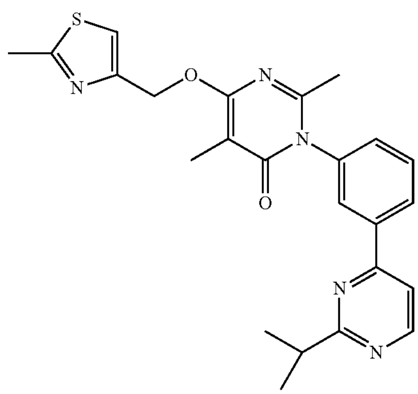 | 3-(3-(2-isopropylpyrimidin-4-yl)phenyl)-2,5-dimethyl-6-((2-methylthiazol-4-yl)methoxy)pyrimidin-4(3H)-one |
| 420 | 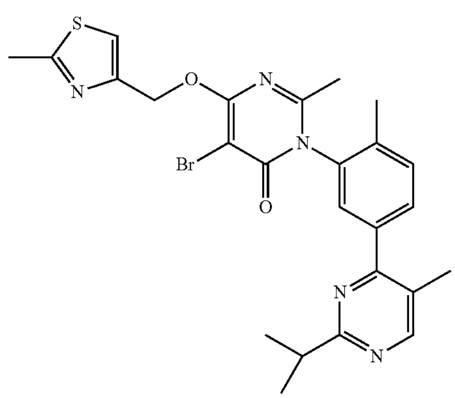 | 5-bromo-3-(5-(2-isopropyl-5-methylpyrimidin-4-yl)-2-methylphenyl)-2-methyl-6-((2-methylthiazol-4-yl)methoxy)pyrimidin-4(3H)-one |
| 421 | 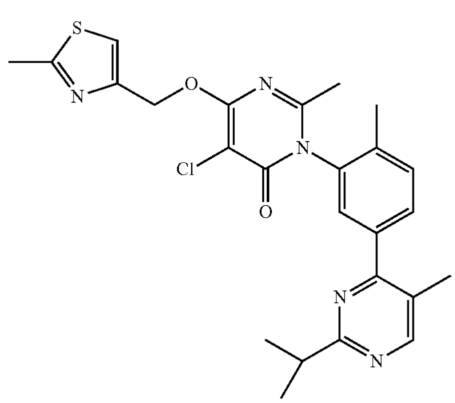 | 5-chloro-3-(5-(2-isopropyl-5-methylpyrimidin-4-yl)-2-methylphenyl)-2-methyl-6-((2-methylthiazol-4-yl)methoxy)pyrimidin-4(3H)-one |

-continued

| Compound | Structure | Name |
|---|---|---|
| 422 | 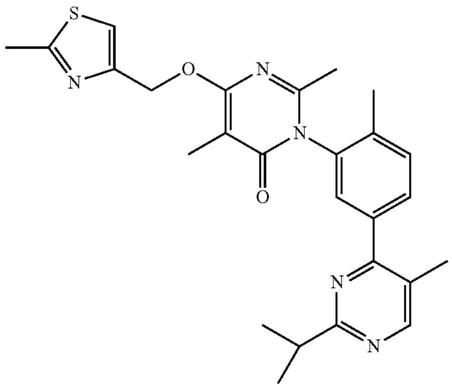 | 3-(5-(2-isopropyl-5-methylpyrimidin-4-yl)-2-methylphenyl)-2,5-dimethyl-6-((2-methylthiazol-4-yl)methoxy)pyrimidin-4(3H)-one |
| 423 | 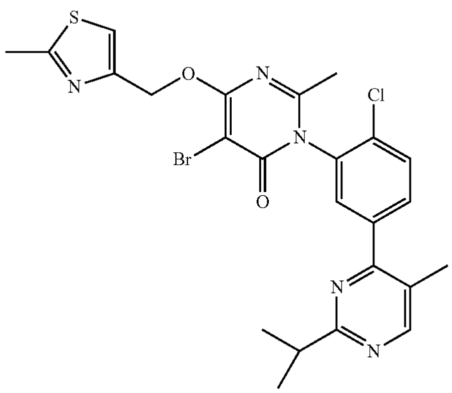 | 5-bromo-3-(2-chloro-5-(2-isopropyl-5-methylpyrimidin-4-yl)phenyl)-2-methyl-6-((2-methylthiazol-4-yl)methoxy)pyrimidin-4(3H)-one |
| 424 | 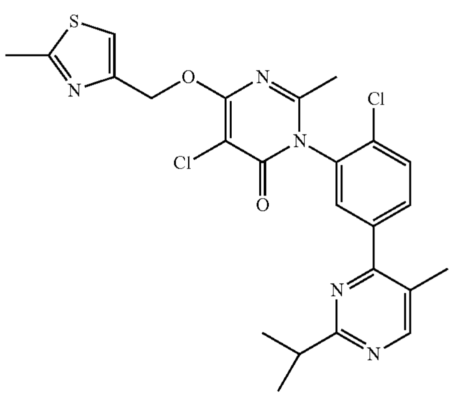 | 5-chloro-3-(2-chloro-5-(2-isopropyl-5-methylpyrimidin-4-yl)phenyl)-2-methyl-6-((2-methylthiazol-4-yl)methoxy)pyrimidin-4(3H)-one |
| 425 | 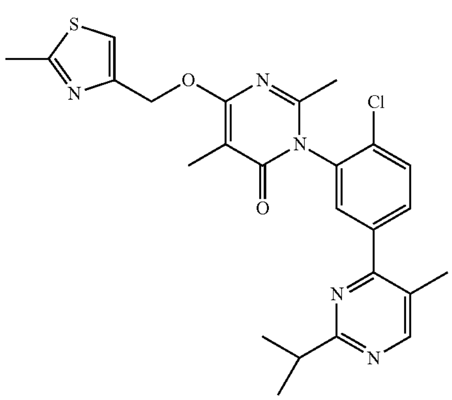 | 3-(2-chloro-5-(2-isopropyl-5-methylpyrimidin-4-yl)phenyl)-2,5-dimethyl-6-((2-methylthiazol-4-yl)methoxy)pyrimidin-4(3H)-one |

-continued

| Compound | Structure | Name |
|---|---|---|
| 426 | 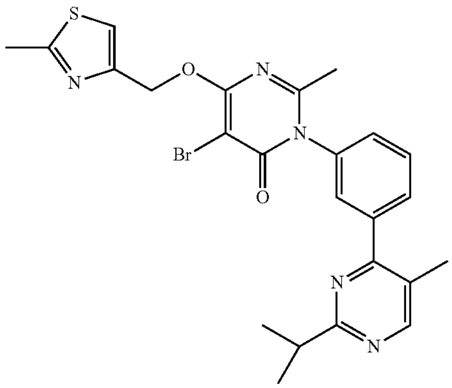 | 5-bromo-3-(3-(2-isopropyl-5-methylpyrimidin-4-yl)phenyl)-2-methyl-6-((2-methylthiazol-4-yl)methoxy)pyrimidin-4(3H)-one |
| 427 | 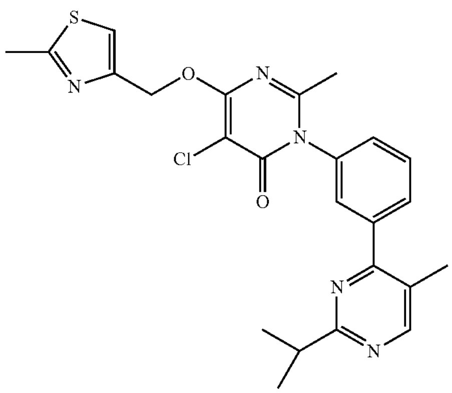 | 5-chloro-3-(3-(2-isopropyl-5-methylpyrimidin-4-yl)phenyl)-2-methyl-6-((2-methylthiazol-4-yl)methoxy)pyrimidin-4(3H)-one |
| 428 | 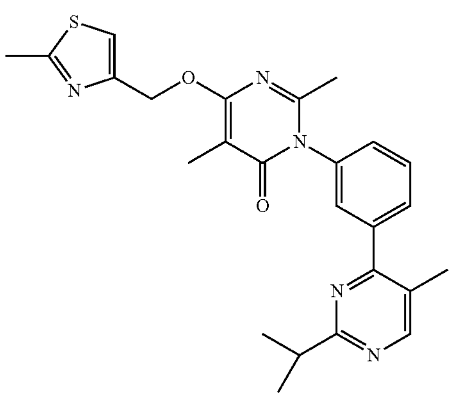 | 3-(3-(2-isopropyl-5-methylpyrimidin-4-yl)phenyl)-2,5-dimethyl-6-((2-methylthiazol-4-yl)methoxy)pyrimidin-4(3H)-one |
| 429 | 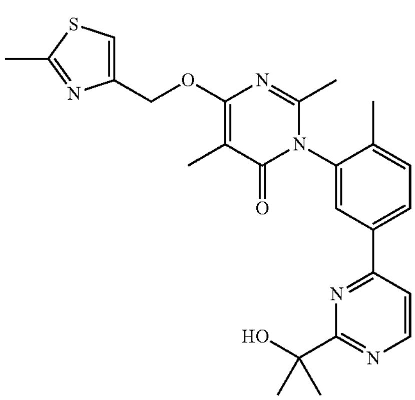 [SMILES: Cc1nc(COc2nc(C)n(-c3cc(-c4ccnc(C(C)(C)O)n4)ccc3C)c(=O)c2C)cs1] | 3-(5-(2-(2-hydroxypropan-2-yl)pyrimidin-4-yl)-2-methylphenyl)-2,5-dimethyl-6-((2-methylthiazol-4-yl)methoxy)pyrimidin-4(3H)-one |

| Compound | Structure | Name |
|---|---|---|
| 430 | 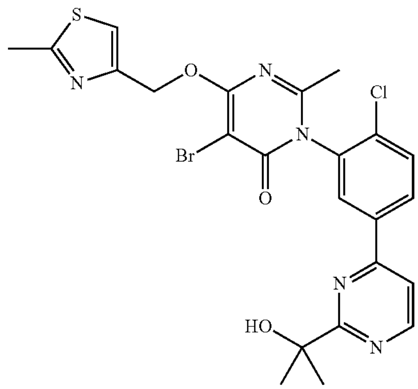 [SMILES: Cc1nc(COc2nc(C)n(-c3cc(-c4ccnc(C(C)(C)O)n4)ccc3Cl)c(=O)c2Br)cs1] | 5-bromo-3-(2-chloro-5-(2-(2-hydroxypropan-2-yl)pyrimidin-4-yl)phenyl)-2-methyl-6-((2-methylthiazol-4-yl)methoxy)pyrimidin-4(3H)-one |
| 431 | 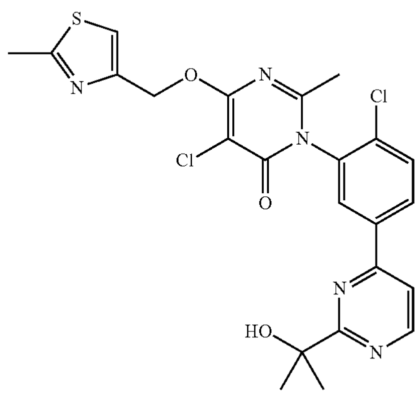 | 5-chloro-3-(2-chloro-5-(2-(2-hydroxypropan-2-yl)pyrimidin-4-yl)phenyl)-2-methyl-6-((2-methylthiazol-4-yl)methoxy)pyrimidin-4(3H)-one |
| 432 | 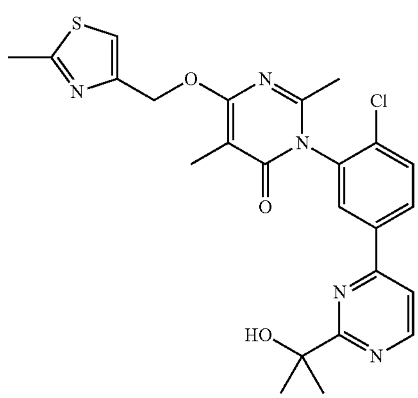 | 3-(2-chloro-5-(2-(2-hydroxypropan-2-yl)pyrimidin-4-yl)phenyl)-2,5-dimethyl-6-((2-methylthiazol-4-yl)methoxy)pyrimidin-4(3H)-one |
| 433 | 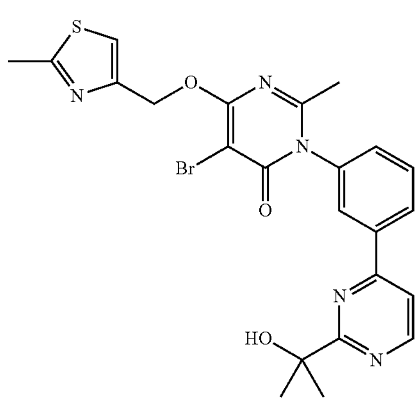 [SMILES: Cc1nc(COc2nc(C)n(-c3cccc(-c4ccnc(C(C)(C)O)n4)c3)c(=O)c2Br)cs1] | 5-bromo-3-(3-(2-(2-hydroxypropan-2-yl)pyrimidin-4-yl)phenyl)-2-methyl-6-((2-methylthiazol-4-yl)methoxy)pyrimidin-4(3H)-one |

| Compound | Structure | Name |
|---|---|---|
| 434 | 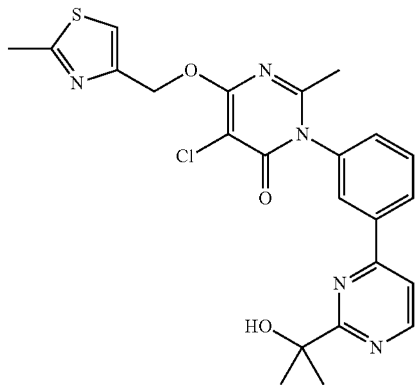 | 5-chloro-3-(3-(2-(2-hydroxypropan-2-yl)pyrimidin-4-yl)phenyl)-2-methyl-6-((2-methylthiazol-4-yl)methoxy)pyrimidin-4(3H)-one |
| 435 | 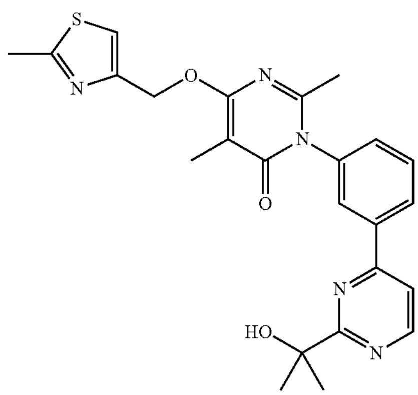 | 3-(3-(2-(2-hydroxypropan-2-yl)pyrimidin-4-yl)phenyl)-2,5-dimethyl-6-((2-methylthiazol-4-yl)methoxy)pyrimidin-4(3H)-one |
| 436 | 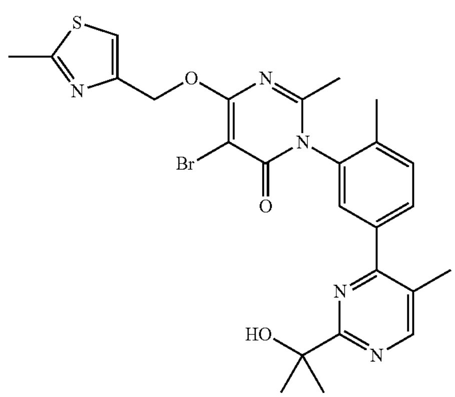 | 5-bromo-3-(5-(2-(2-hydroxypropan-2-yl)-5-methylpyrimidin-4-yl)-2-methylphenyl)-2-methyl-6-((2-methylthiazol-4-yl)methoxy)pyrimidin-4(3H)-one |
| 437 | 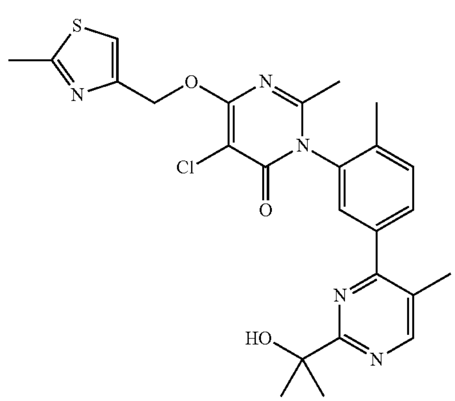 | 5-chloro-3-(5-(2-(2-hydroxypropan-2-yl)-5-methylpyrimidin-4-yl)-2-methylphenyl)-2-methyl-6-((2-methylthiazol-4-yl)methoxy)pyrimidin-4(3H)-one |

-continued

| Compound | Structure | Name |
|---|---|---|
| 438 | 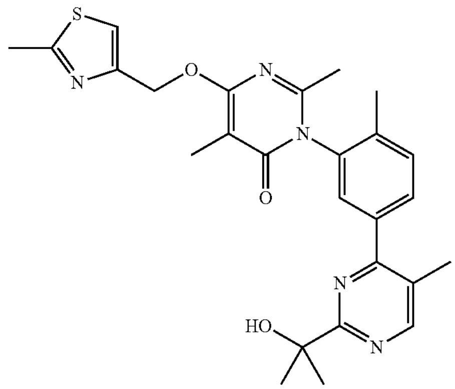 | 3-(5-(2-(2-hydroxypropan-2-yl)-5-methylpyrimidin-4-yl)-2-methylphenyl)-2,5-dimethyl-6-((2-methylthiazol-4-yl)methoxy)pyrimidin-4(3H)-one |
| 439 | 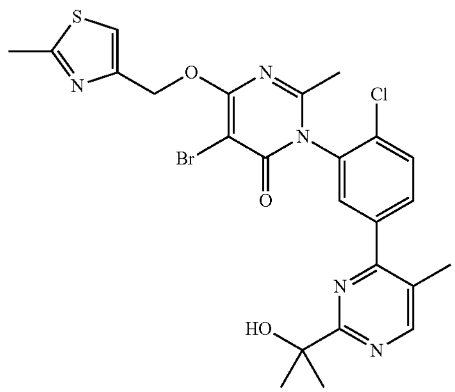 | 5-bromo-3-(2-chloro-5-(2-(2-hydroxypropan-2-yl)-5-methylpyrimidin-4-yl)phenyl)-2-methyl-6-((2-methylthiazol-4-yl)methoxy)pyrimidin-4(3H)-one |
| 440 | 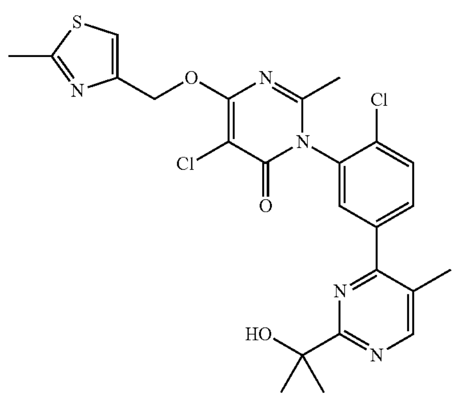 | 5-chloro-3-(2-chloro-5-(2-(2-hydroxypropan-2-yl)-5-methylpyrimidin-4-yl)phenyl)-2-methyl-6-((2-methylthiazol-4-yl)methoxy)pyrimidin-4(3H)-one |
| 441 | 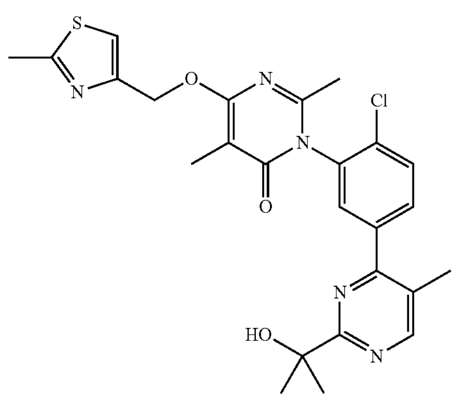 | 3-(2-chloro-5-(2-(2-hydroxypropan-2-yl)-5-methylpyrimidin-4-yl)phenyl)-2,5-dimethyl-6-((2-methylthiazol-4-yl)methoxy)pyrimidin-4(3H)-one |

-continued

| Compound | Structure | Name |
|---|---|---|
| 442 | 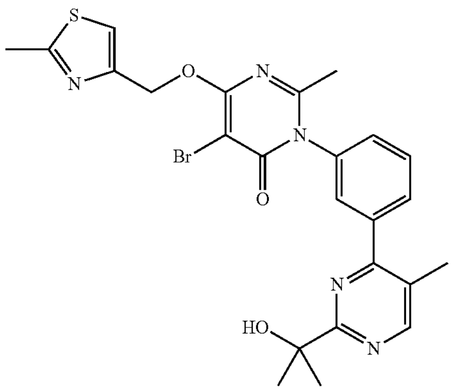 | 5-bromo-3-(3-(2-(2-hydroxypropan-2-yl)-5-methylpyrimidin-4-yl)phenyl)-2-methyl-6-((2-methylthiazol-4-yl)methoxy)pyrimidin-4(3H)-one |
| 443 | 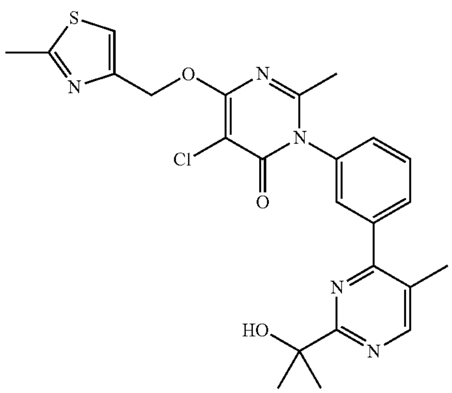 | 5-chloro-3-(3-(2-(2-hydroxypropan-2-yl)-5-methylpyrimidin-4-yl)phenyl)-2-methyl-6-((2-methylthiazol-4-yl)methoxy)pyrimidin-4(3H)-one |
| 444 | 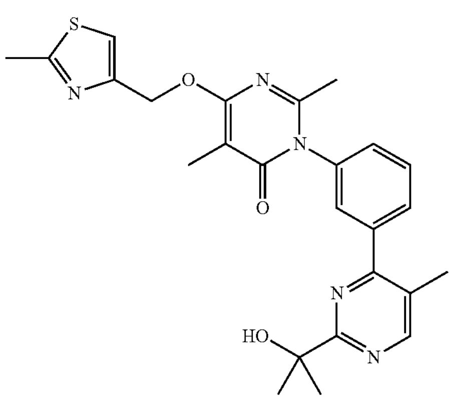 | 3-(3-(2-(2-hydroxypropan-2-yl)-5-methylpyrimidin-4-yl)phenyl)-2,5-dimethyl-6-((2-methylthiazol-4-yl)methoxy)pyrimidin-4(3H)-one |
| 445 | 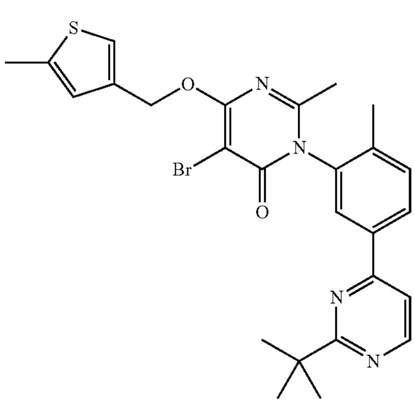 [SMILES: Cc1cc(COc2nc(C)n(-c3cc(-c4ccnc(C(C)(C)C)n4)ccc3C)c(=O)c2Br)cs1] | 5-bromo-3-(5-(2-(tert-butyl)pyrimidin-4-yl)-2-methylphenyl)-2-methyl-6-((5-methylthiophen-3-yl)methoxy)pyrimidin-4(3H)-one |

-continued

| Compound | Structure | Name |
|---|---|---|
| 446 | 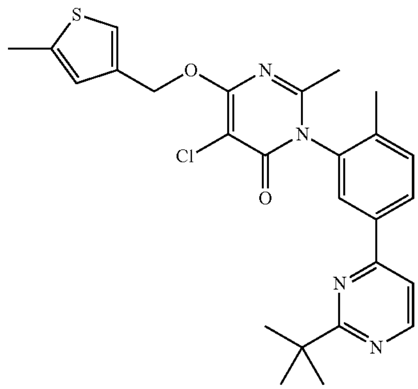 [SMILES: Cc1cc(COc2nc(C)n(-c3cc(-c4ccnc(C(C)(C)C)n4)ccc3C)c(=O)c2Cl)cs1] | 3-(5-(2-(tert-butyl)pyrimidin-4-yl)-2-methylphenyl)-5-chloro-2-methyl-6-((5-methylthiophen-3-yl)methoxy)pyrimidin-4(3H)-one |
| 447 | 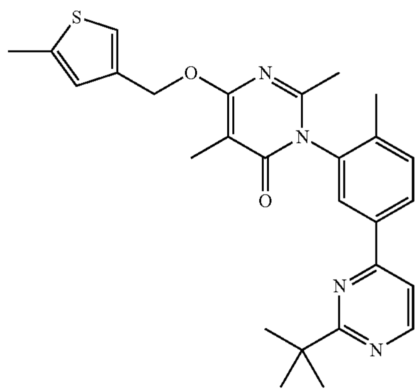 [SMILES: Cc1cc(COc2nc(C)n(-c3cc(-c4ccnc(C(C)(C)C)n4)ccc3C)c(=O)c2C)cs1] | 3-(5-(2-(tert-butyl)pyrimidin-4-yl)-2-methylphenyl)-2,5-dimethyl-6-((5-methylthiophen-3-yl)methoxy)pyrimidin-4(3H)-one |
| 448 | 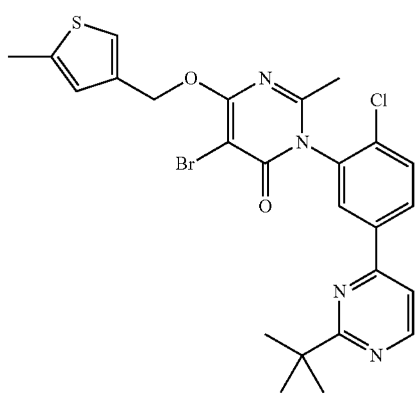 [SMILES: Cc1cc(COc2nc(C)n(-c3cc(-c4ccnc(C(C)(C)C)n4)ccc3Cl)c(=O)c2Br)cs1] | 5-bromo-3-(5-(2-(tert-butyl)pyrimidin-4-yl)-2-chlorophenyl)-2-methyl-6-((5-methylthiophen-3-yl)methoxy)pyrimidin-4(3H)-one |
| 449 | 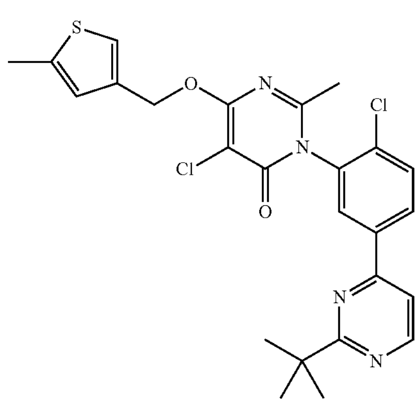 [SMILES: Cc1cc(COc2nc(C)n(-c3cc(-c4ccnc(C(C)(C)C)n4)ccc3Cl)c(=O)c2Cl)cs1] | 3-(5-(2-(tert-butyl)pyrimidin-4-yl)-2-chlorophenyl)-5-chloro-2-methyl-6-((5-methylthiophen-3-yl)methoxy)pyrimidin-4(3H)-one |

| Compound | Structure | Name |
|---|---|---|
| 450 | 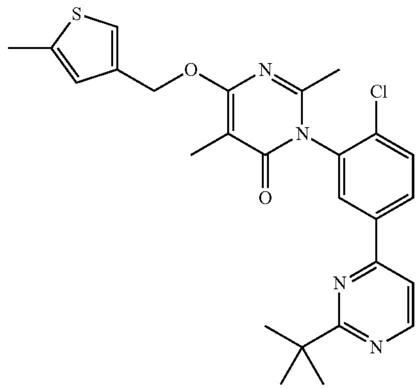 [SMILES: Cc1cc(COc2nc(C)n(-c3cc(-c4ccnc(C(C)(C)C)n4)ccc3Cl)c(=O)c2C)cs1] | 3-(5-(2-(tert-butyl)pyrimidin-4-yl)-2-chlorophenyl)-2,5-dimethyl-6-((5-methylthiophen-3-yl)methoxy)pyrimidin-4(3H)-one |
| 451 | 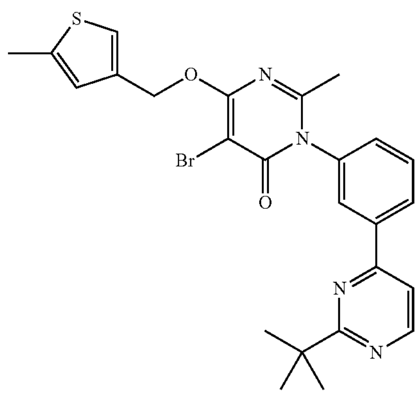 | 5-bromo-3-(3-(2-(tert-butyl)pyrimidin-4-yl)phenyl)-2-methyl-6-((5-methylthiophen-3-yl)methoxy)pyrimidin-4(3H)-one |
| 452 | 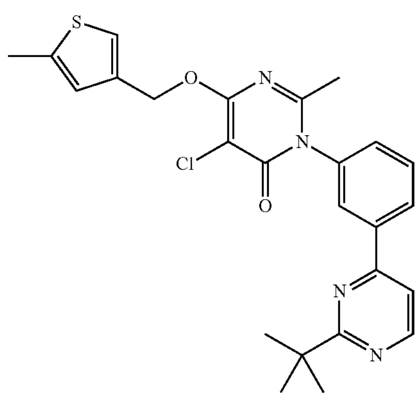 [SMILES: Cc1cc(COc2nc(C)n(-c3cccc(-c4ccnc(C(C)(C)C)n4)c3)c(=O)c2Cl)cs1] | 3-(3-(2-(tert-butyl)pyrimidin-4-yl)phenyl)-5-chloro-2-methyl-6-((5-methylthiophen-3-yl)methoxy)pyrimidin-4(3H)-one |
| 453 | 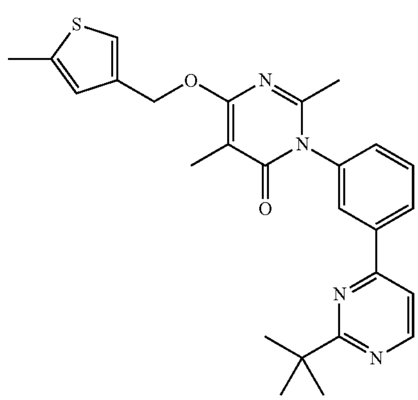 [SMILES: Cc1cc(COc2nc(C)n(-c3cccc(-c4ccnc(C(C)(C)C)n4)c3)c(=O)c2C)cs1] | 3-(3-(2-(tert-butyl)pyrimidin-4-yl)phenyl)-2,5-dimethyl-6-((5-methylthiophen-3-yl)methoxy)pyrimidin-4(3H)-one |

-continued

| Compound | Structure | Name |
|---|---|---|
| 454 | 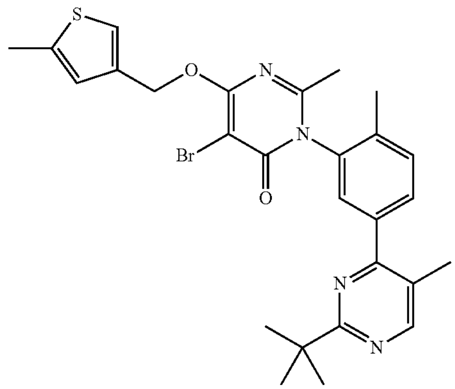 | 5-bromo-3-(5-(2-(tert-butyl)-5-methylpyrimidin-4-yl)-2-methylphenyl)-2-methyl-6-((5-methylthiophen-3-yl)methoxy)pyrimidin-4(3H)-one |
| 455 | 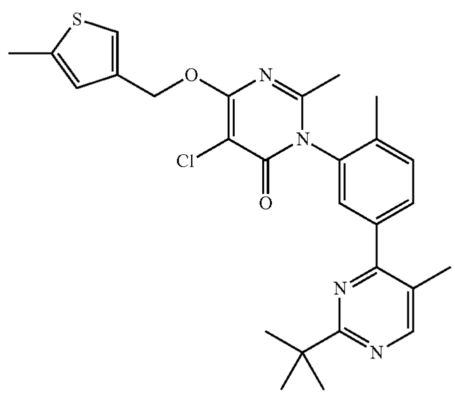 | 3-(5-(2-(tert-butyl)-5-methylpyrimidin-4-yl)-2-methylphenyl)-5-chloro-2-methyl-6-((5-methylthiophen-3-yl)methoxy)pyrimidin-4(3H)-one |
| 456 | 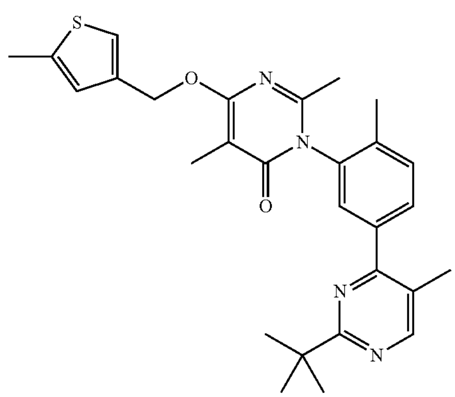 | 3-(5-(2-(tert-butyl)-5-methylpyrimidin-4-yl)-2-methylphenyl)-2,5-dimethyl-6-((5-methylthiophen-3-yl)methoxy)pyrimidin-4(3H)-one |
| 457 | 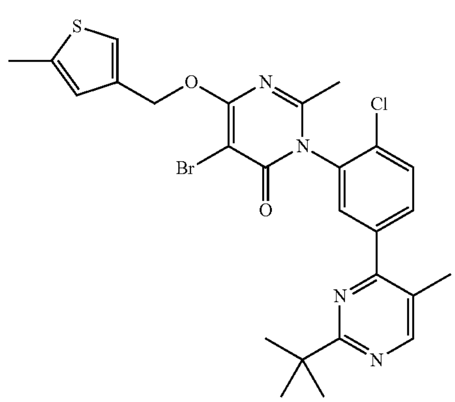 | 5-bromo-3-(5-(2-(tert-butyl)-5-methylpyrimidin-4-yl)-2-chlorophenyl)-2-methyl-6-((5-methylthiophen-3-yl)methoxy)pyrimidin-4(3H)-one |

| Compound | Structure | Name |
|---|---|---|
| 458 | 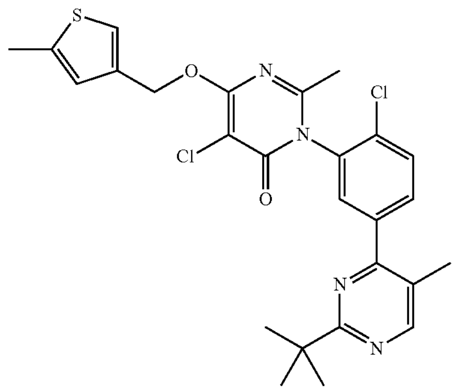 | 3-(5-(2-(tert-butyl)-5-methylpyrimidin-4-yl)-2-chlorophenyl)-5-chloro-2-methyl-6-((5-methylthiophen-3-yl)methoxy)pyrimidin-4(3H)-one |
| 459 | 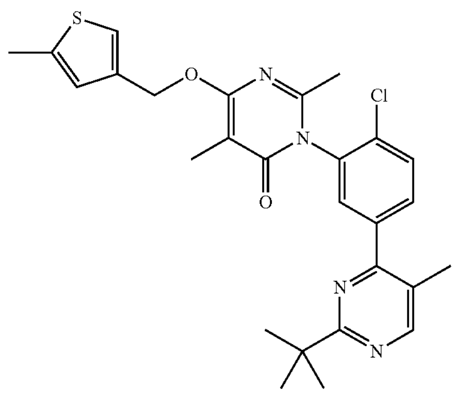 | 3-(5-(2-(tert-butyl)-5-methylpyrimidin-4-yl)-2-chlorophenyl)-2,5-dimethyl-6-((5-methylthiophen-3-yl)methoxy)pyrimidin-4(3H)-one |
| 460 | 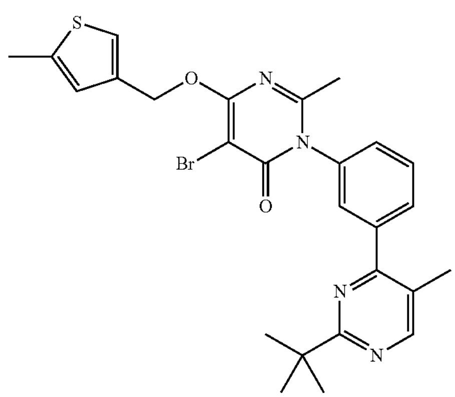 | 5-bromo-3-(3-(2-(tert-butyl)-5-methylpyrimidin-4-yl)phenyl)-2-methyl-6-((5-methylthiophen-3-yl)methoxy)pyrimidin-4(3H)-one |
| 461 | 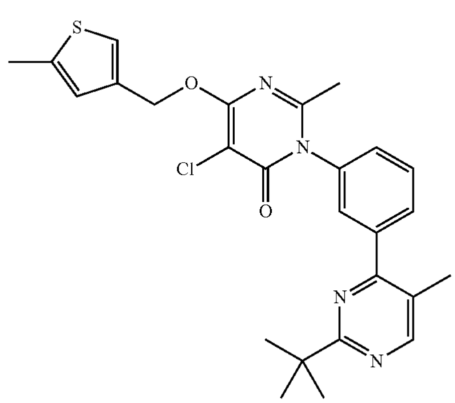 | 3-(3-(2-(tert-butyl)-5-methylpyrimidin-4-yl)phenyl)-5-chloro-2-methyl-6-((5-methylthiophen-3-yl)methoxy)pyrimidin-4(3H)-one |

-continued

| Compound | Structure | Name |
|---|---|---|
| 462 | 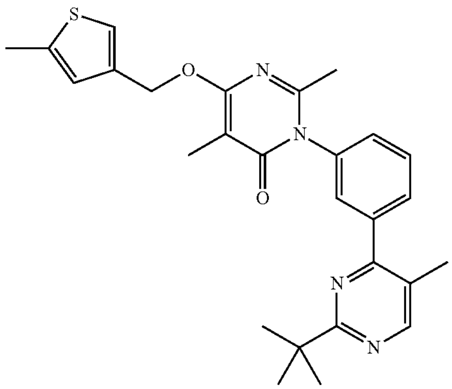 | 3-(3-(2-(tert-butyl)-5-methylpyrimidin-4-yl)phenyl)-2,5-dimethyl-6-((5-methylthiophen-3-yl)methoxy)pyrimidin-4(3H)-one |
| 463 | 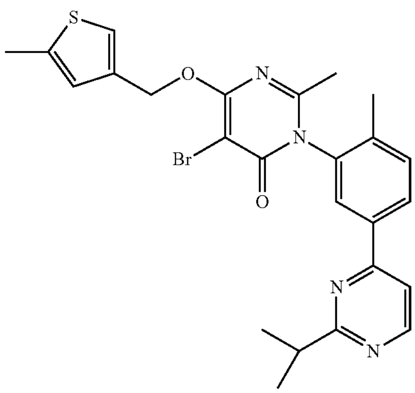 [SMILES: Cc1cc(COc2nc(C)n(-c3cc(-c4ccnc(C(C)C)n4)ccc3C)c(=O)c2Br)cs1] | 5-bromo-3-(5-(2-isopropylpyrimidin-4-yl)-2-methylphenyl)-2-methyl-6-((5-methylthiophen-3-yl)methoxy)pyrimidin-4(3H)-one |
| 464 | 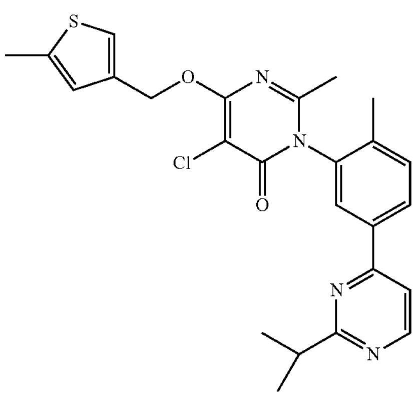 [SMILES: Cc1cc(COc2nc(C)n(-c3cc(-c4ccnc(C(C)C)n4)ccc3C)c(=O)c2Cl)cs1] | 5-chloro-3-(5-(2-isopropylpyrimidin-4-yl)-2-methylphenyl)-2-methyl-6-((5-methylthiophen-3-yl)methoxy)pyrimidin-4(3H)-one |
| 465 | 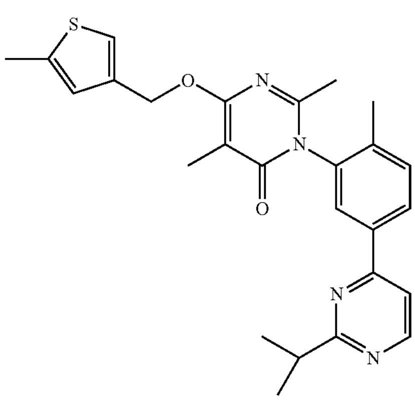 [SMILES: Cc1cc(COc2nc(C)n(-c3cc(-c4ccnc(C(C)C)n4)ccc3C)c(=O)c2C)cs1] | 3-(5-(2-isopropylpyrimidin-4-yl)-2-methylphenyl)-2,5-dimethyl-6-((5-methylthiophen-3-yl)methoxy)pyrimidin-4(3H)-one |

| Compound | Structure | Name |
|---|---|---|
| 466 | 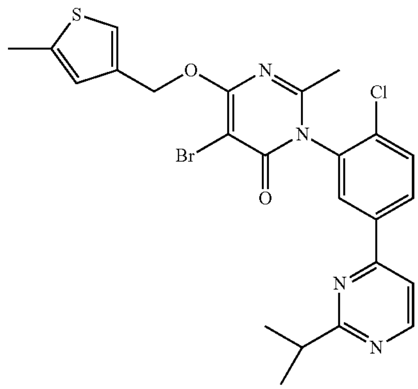 | 5-bromo-3-(2-chloro-5-(2-isopropylpyrimidin-4-yl)phenyl)-2-methyl-6-((5-methylthiophen-3-yl)methoxy)pyrimidin-4(3H)-one |
| 467 | 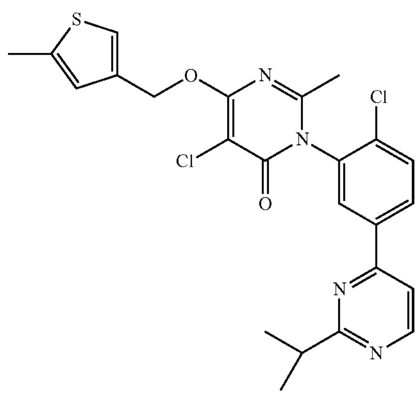 [SMILES: Cc1cc(COc2nc(C)n(-c3cc(-c4ccnc(C(C)C)n4)ccc3Cl)c(=O)c2Cl)cs1] | 5-chloro-3-(2-chloro-5-(2-isopropylpyrimidin-4-yl)phenyl)-2-methyl-6-((5-methylthiophen-3-yl)methoxy)pyrimidin-4(3H)-one |
| 468 | 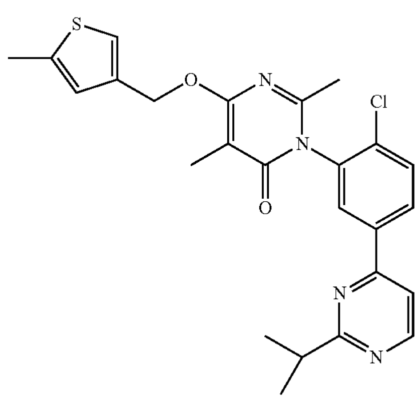 [SMILES: Cc1cc(COc2nc(C)n(-c3cc(-c4ccnc(C(C)C)n4)ccc3Cl)c(=O)c2C)cs1] | 3-(2-chloro-5-(2-isopropylpyrimidin-4-yl)phenyl)-2,5-dimethyl-6-((5-methylthiophen-3-yl)methoxy)pyrimidin-4(3H)-one |
| 469 | 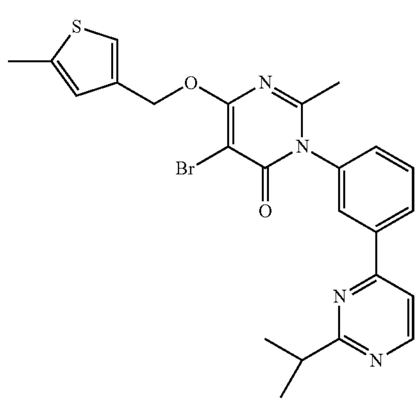 [SMILES: Cc1cc(COc2nc(C)n(-c3cccc(-c4ccnc(C(C)C)n4)c3)c(=O)c2Br)cs1] | 5-bromo-3-(3-(2-isopropylpyrimidin-4-yl)phenyl)-2-methyl-6-((5-methylthiophen-3-yl)methoxy)pyrimidin-4(3H)-one |

| Compound | Structure | Name |
|---|---|---|
| 470 | 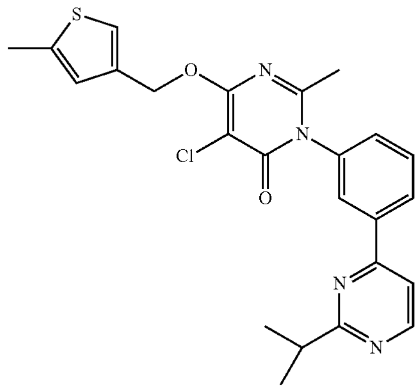 [SMILES: Cc1cc(COc2nc(C)n(-c3cccc(-c4ccnc(C(C)C)n4)c3)c(=O)c2Cl)cs1] | 5-chloro-3-(3-(2-isopropylpyrimidin-4-yl)phenyl)-2-methyl-6-((5-methylthiophen-3-yl)methoxy)pyrimidin-4(3H)-one |
| 471 | 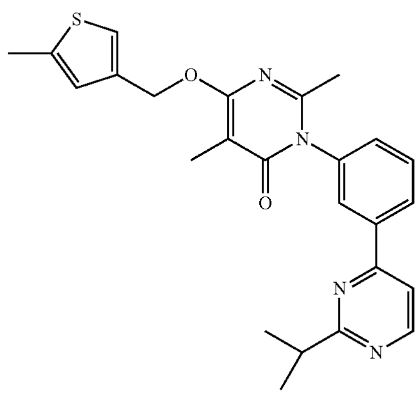 [SMILES: Cc1cc(COc2nc(C)n(-c3cccc(-c4ccnc(C(C)C)n4)c3)c(=O)c2C)cs1] | 3-(3-(2-isopropylpyrimidin-4-yl)phenyl)-2,5-dimethyl-6-((5-methylthiophen-3-yl)methoxy)pyrimidin-4(3H)-one |
| 472 | 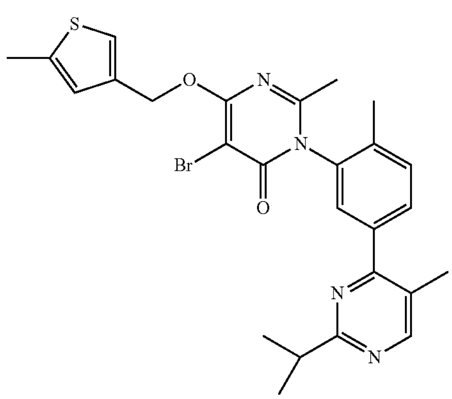 | 5-bromo-3-(5-(2-isopropyl-5-methylpyrimidin-4-yl)-2-methylphenyl)-2-methyl-6-((5-methylthiophen-3-yl)methoxy)pyrimidin-4(3H)-one |
| 473 | 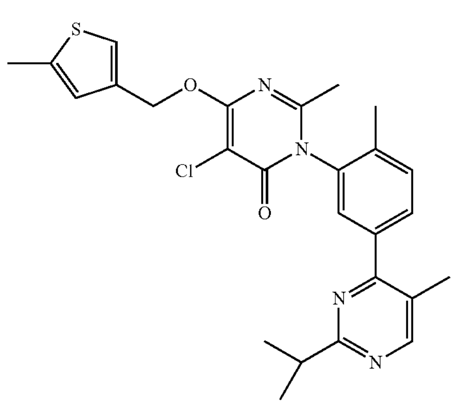 | 5-chloro-3-(5-(2-isopropyl-5-methylpyrimidin-4-yl)-2-methylphenyl)-2-methyl-6-((5-methylthiophen-3-yl)methoxy)pyrimidin-4(3H)-one |

| Compound | Structure | Name |
|---|---|---|
| 474 | 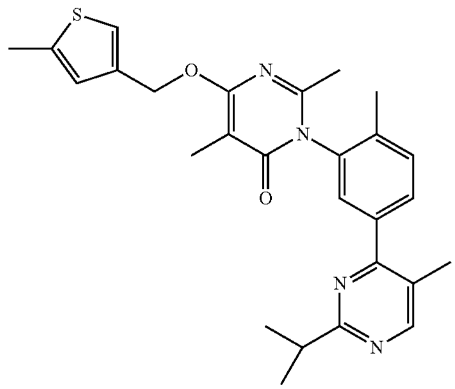 | 3-(5-(2-isopropyl-5-methylpyrimidin-4-yl)-2-methylphenyl)-2,5-dimethyl-6-((5-methylthiophen-3-yl)methoxy)pyrimidin-4(3H)-one |
| 475 | 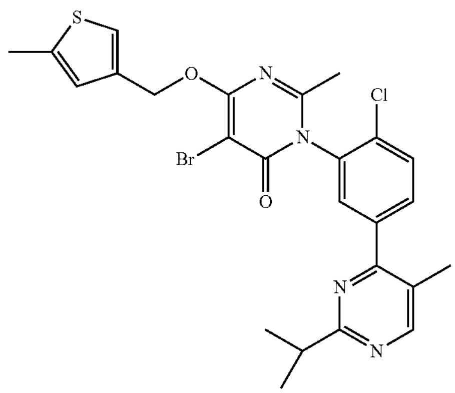 | 5-bromo-3-(2-chloro-5-(2-isopropyl-5-methylpyrimidin-4-yl)phenyl)-2-methyl-6-((5-methylthiophen-3-yl)methoxy)pyrimidin-4(3H)-one |
| 476 | 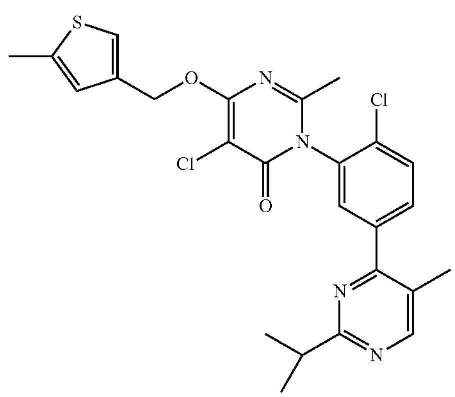 | 5-chloro-3-(2-chloro-5-(2-isopropyl-5-methylpyrimidin-4-yl)phenyl)-2-methyl-6-((5-methylthiophen-3-yl)methoxy)pyrimidin-4(3H)-one |
| 477 | 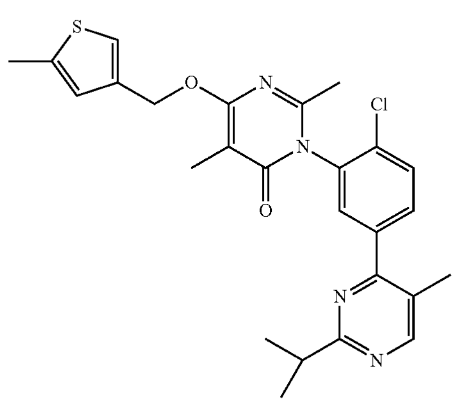 | 3-(2-chloro-5-(2-isopropyl-5-methylpyrimidin-4-yl)phenyl)-2,5-dimethyl-6-((5-methylthiophen-3-yl)methoxy)pyrimidin-4(3H)-one |

| Compound | Structure | Name |
|---|---|---|
| 478 | 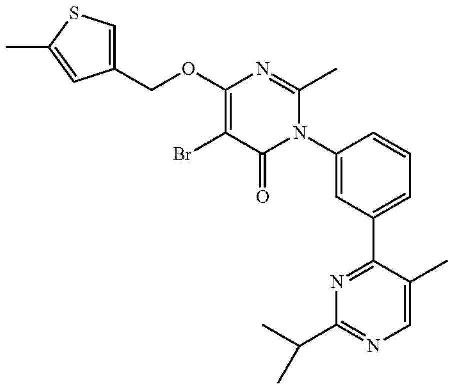 | 5-bromo-3-(3-(2-isopropyl-5-methylpyrimidin-4-yl)phenyl)-2-methyl-6-((5-methylthiophen-3-yl)methoxy)pyrimidin-4(3H)-one |
| 479 | 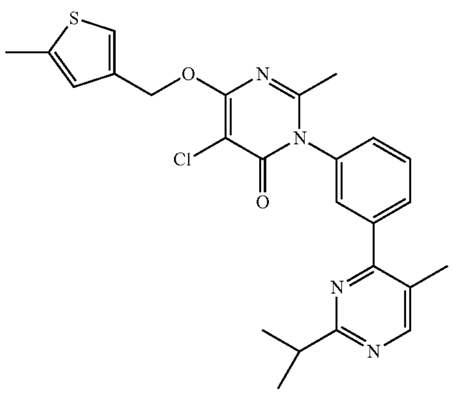 | 5-chloro-3-(3-(2-isopropyl-5-methylpyrimidin-4-yl)phenyl)-2-methyl-6-((5-methylthiophen-3-yl)methoxy)pyrimidin-4(3H)-one |
| 480 | 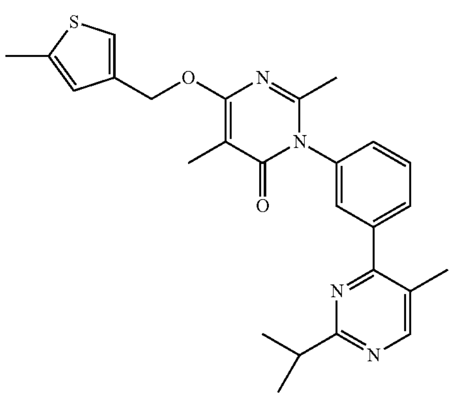 | 3-(3-(2-isopropyl-5-methylpyrimidin-4-yl)phenyl)-2,5-dimethyl-6-((5-methylthiophen-3-yl)methoxy)pyrimidin-4(3H)-one |
| 481 | 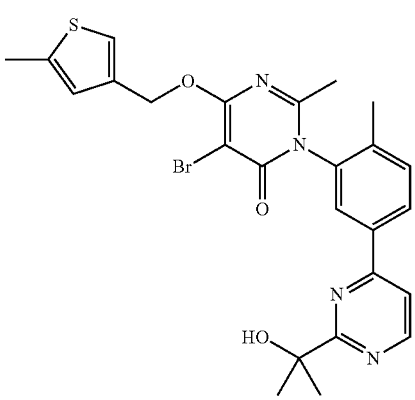 [SMILES: Cc1cc(COc2nc(C)n(-c3cc(-c4ccnc(C(C)(C)O)n4)ccc3C)c(=O)c2Cl)cs1] | 5-bromo-3-(5-(2-(2-hydroxypropan-2-yl)pyrimidin-4-yl)-2-methylphenyl)-2-methyl-6-((5-methylthiophen-3-yl)methoxy)pyrimidin-4(3H)-one |

-continued

| Compound | Structure | Name |
|---|---|---|
| 482 | 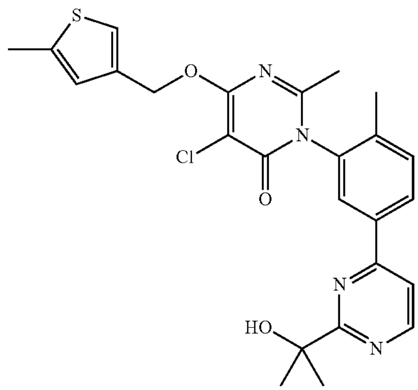 | 5-chloro-3-(5-(2-(2-hydroxypropan-2-yl)pyrimidin-4-yl)-2-methylphenyl)-2-methyl-6-((5-methylthiophen-3-yl)methoxy)pyrimidin-4(3H)-one |
| 483 | 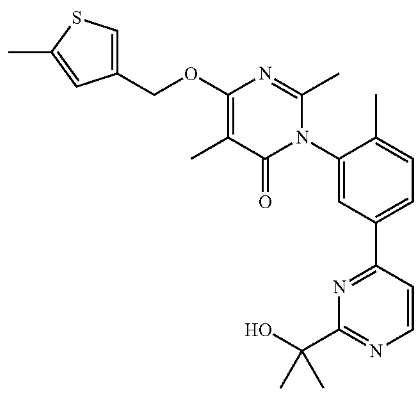 | 3-(5-(2-(2-hydroxypropan-2-yl)pyrimidin-4-yl)-2-methylphenyl)-2,5-dimethyl-6-((5-methylthiophen-3-yl)methoxy)pyrimidin-4(3H)-one |
| 484 | 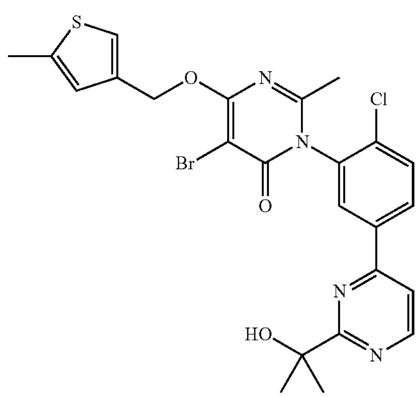 [SMILES: Cc1cc(COc2nc(C)n(-c3cc(-c4ccnc(C(C)(C)O)n4)ccc3Cl)c(=O)c2Br)cs1] | 5-bromo-3-(2-chloro-5-(2-(2-hydroxypropan-2-yl)pyrimidin-4-yl)phenyl)-2-methyl-6-((5-methylthiophen-3-yl)methoxy)pyrimidin-4(3H)-one |
| 485 | 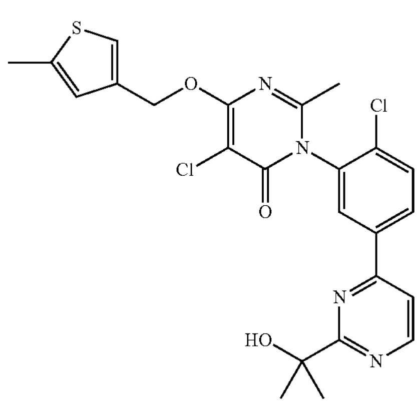 | 5-chloro-3-(2-chloro-5-(2-(2-hydroxypropan-2-yl)pyrimidin-4-yl)phenyl)-2-methyl-6-((5-methylthiophen-3-yl)methoxy)pyrimidin-4(3H)-one |

| Compound | Structure | Name |
|---|---|---|
| 486 | 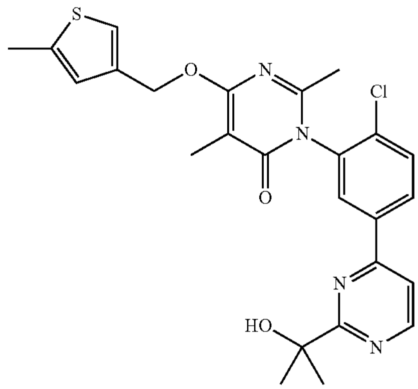 [SMILES: Cc1cc(COc2nc(C)n(-c3cc(-c4ccnc(C(C)(C)O)n4)ccc3Cl)c(=O)c2C)cs1] | 3-(2-chloro-5-(2-(2-hydroxypropan-2-yl)pyrimidin-4-yl)phenyl)-2,5-dimethyl-6-((5-methylthiophen-3-yl)methoxy)pyrimidin-4(3H)-one |
| 487 | 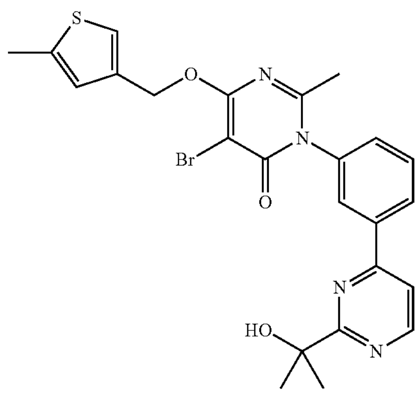 | 5-bromo-3-(3-(2-(2-hydroxypropan-2-yl)pyrimidin-4-yl)phenyl)-2-methyl-6-((5 methylthiophen-3-yl)methoxy)pyrimidin-4(3H)-one |
| 488 | 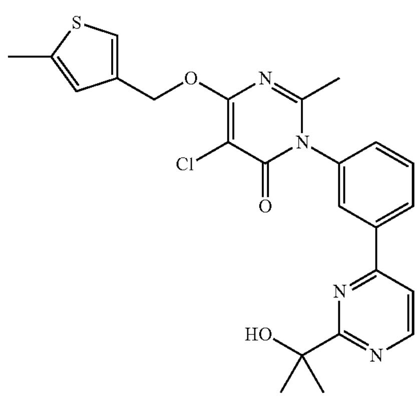 | 5-chloro-3-(3-(2-(2-hydroxypropan-2-yl)pyrimidin-4-yl)phenyl)-2-methyl-6-((5-methylthiophen-3-yl)methoxy)pyrimidin-4(3H)-one |
| 489 | 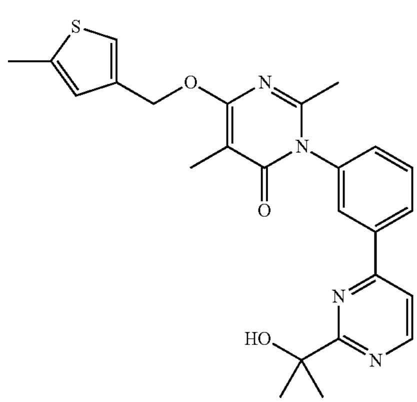 [SMILES: Cc1cc(COc2nc(C)n(-c3cccc(-c4ccnc(C(C)(C)O)n4)c3)c(=O)c2C)cs1] | 3-(3-(2-(2-hydroxypropan-2-yl)pyrimidin-4-yl)phenyl)-2,5-dimethyl-6-((5-methylthiophen-3-yl)methoxy)pyrimidin-4(3H)-one |

| Compound | Structure | Name |
|---|---|---|
| 490 | 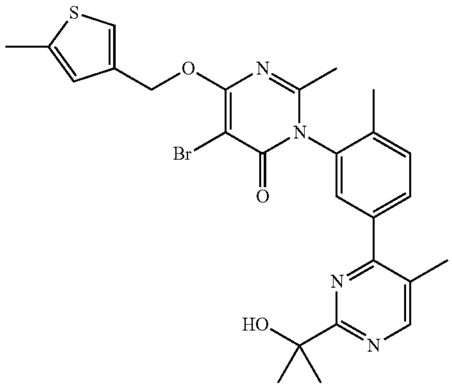 | 5-bromo-3-(5-(2-(2-hydroxypropan-2-yl)-5-methylpyrimidin-4-yl)-2-methylphenyl)-2-methyl-6-((5-methylthiophen-3-yl)methoxy)pyrimidin-4(3H)-one |
| 491 | 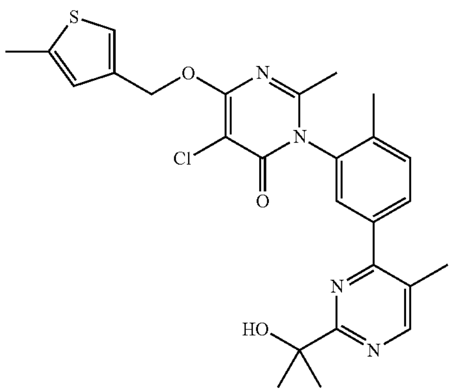 | 5-chloro-3-(5-(2-(2-hydroxypropan-2-yl)-5-methylpyrimidin-4-yl)-2-methylphenyl)-2-methyl-6-((5-methylthiophen-3-yl)methoxy)pyrimidin-4(3H)-one |
| 492 | 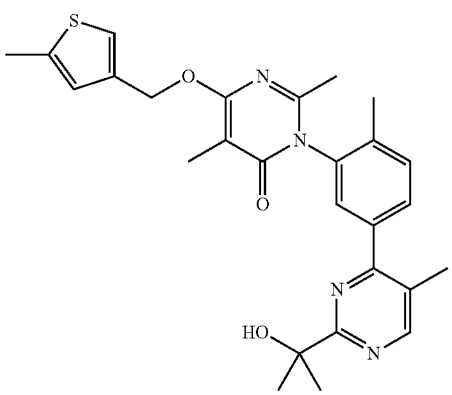 | 3-(5-(2-(2-hydroxypropan-2-yl)-5-methylpyrimidin-4-yl)-2-methylphenyl)-2,5-dimethyl-6-((5-methylthiophen-3-yl)methoxy)pyrimidin-4(3H)-one |
| 493 | 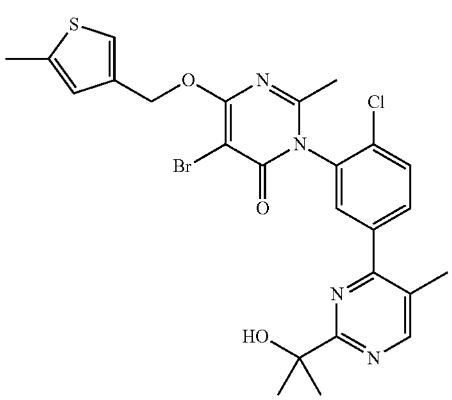 | 5-bromo-3-(2-chloro-5-(2-(2-hydroxypropan-2-yl)-5-methylpyrimidin-4-yl)phenyl)-2-methyl-6-((5-methylthiophen-3-yl)methoxy)pyrimidin-4(3H)-one |

| Compound | Structure | Name |
|---|---|---|
| 494 | 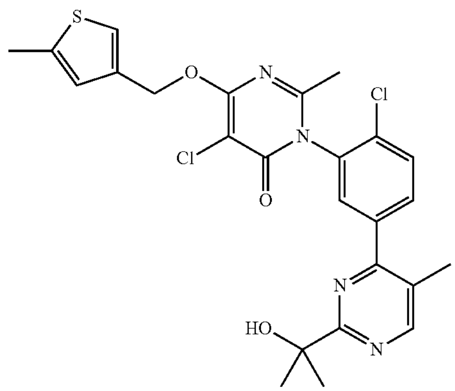 | 5-chloro-3-(2-chloro-5-(2-(2-hydroxypropan-2-yl)-5-methylpyrimidin-4-yl)phenyl)-2-methyl-6-((5-methylthiophen-3-yl)methoxy)pyrimidin-4(3H)-one |
| 495 | 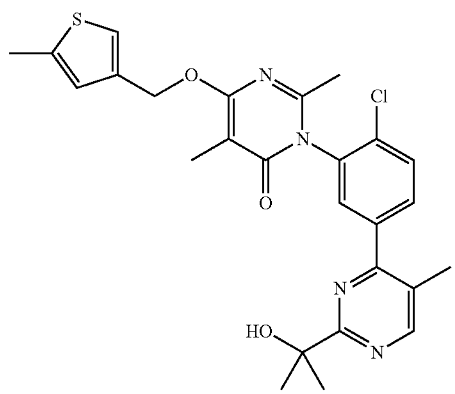 | 3-(2-chloro-5-(2-(2-hydroxypropan-2-yl)-5-methylpyrimidin-4-yl)phenyl)-2,5-dimethyl-6-((5-methylthiophen-3-yl)methoxy)pyrimidin-4(3H)-one |
| 496 | 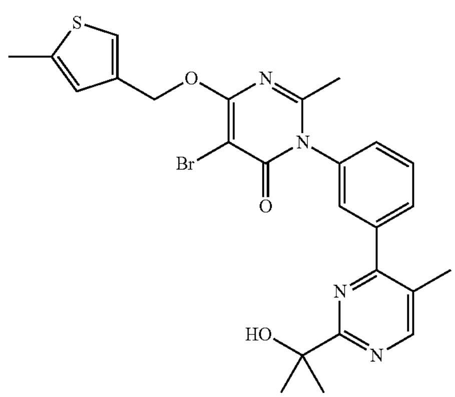 | 5-bromo-3-(3-(2-(2-hydroxypropan-2-yl)-5-methylpyrimidin-4-yl)phenyl)-2-methyl-6-((5-methylthiophen-3-yl)methoxy)pyrimidin-4(3H)-one |
| 497 | 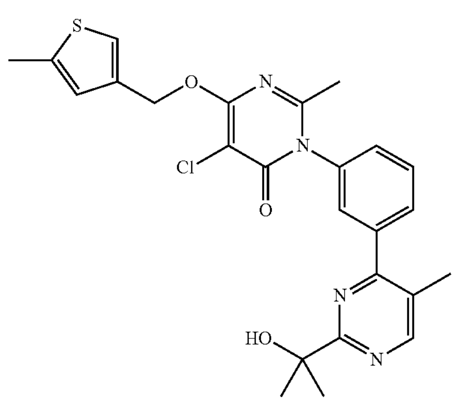 | 5-chloro-3-(3-(2-(2-hydroxypropan-2-yl)-5-methylpyrimidin-4-yl)phenyl)-2-methyl-6-((5-methylthiophen-3-yl)methoxy)pyrimidin-4(3H)-one |

-continued

| Compound | Structure | Name |
|---|---|---|
| 498 | 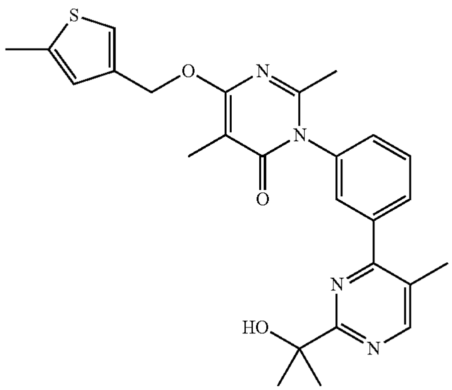 | 3-(3-(2-(2-hydroxypropan-2-yl)-5-methylpyrimidin-4-yl)phenyl)-2,5-dimethyl-6-((5-methylthiophen-3-yl)methoxy)pyrimidin-4(3H)-one |
| 499 | 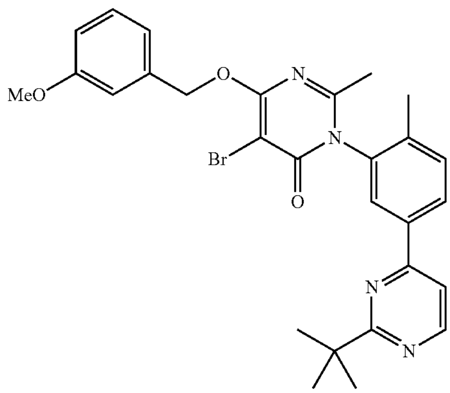 [SMILES: COc1cccc(COc2nc(C)n(-c3cc(-c4ccnc(C(C)(C)C)n4)ccc3C)c(=O)c2Br)c1] | 5-bromo-3-(5-(2-(tert-butyl)pyrimidin-4-yl)-2-methylphenyl)-6-((3-methoxybenzyl)oxy)-2-methylpyrimidin-4(3H)-one |
| 500 | 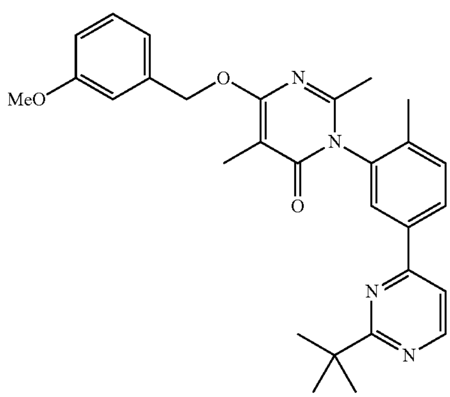 | 3-(5-(2-(tert-butyl)pyrimidin-4-yl)-2-methylphenyl)-6-((3-methoxybenzyl)oxy)-2,5-dimethylpyrimidin-4(3H)-one |
| 501 | 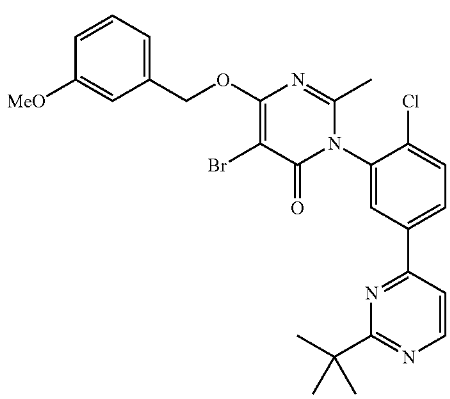 [SMILES: COc1cccc(COc2nc(C)n(-c3cc(-c4ccnc(C(C)(C)C)n4)ccc3Cl)c(=O)c2Br)c1] | 5-bromo-3-(5-(2-(tert-butyl)pyrimidin-4-yl)-2-chlorophenyl)-6-((3-methoxybenzyl)oxy)-2-methylpyrimidin-4(3H)-one |

-continued

| Compound | Structure | Name |
|---|---|---|
| 502 | 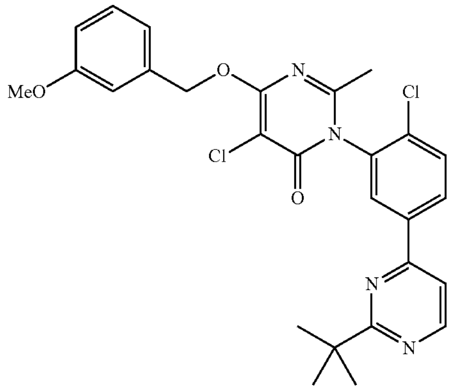 [SMILES: COc1cccc(COc2nc(C)n(-c3cc(-c4ccnc(C(C)(C)C)n4)ccc3Cl)c(=O)c2Cl)c1] | 3-(5-(2-(tert-butyl)pyrimidin-4-yl)-2-chlorophenyl)-5-chloro-6-((3-methoxybenzyl)oxy)-2-methylpyrimidin-4(3H)-one |
| 503 | 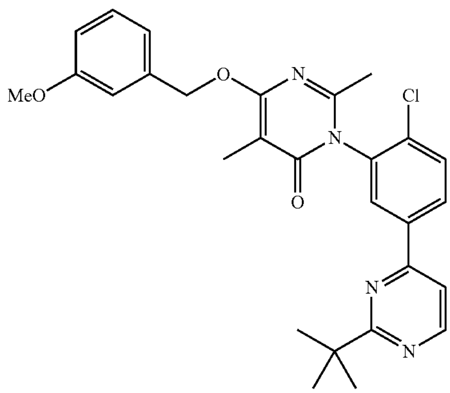 [SMILES: COc1cccc(COc2nc(C)n(-c3cc(-c4ccnc(C(C)(C)C)n4)ccc3Cl)c(=O)c2C)c1] | 3-(5-(2-(tert-butyl)pyrimidin-4-yl)-2-chlorophenyl)-6-((3-methoxybenzyl)oxy)-2,5-dimethylpyrimidin-4(3H)-one |
| 504 | 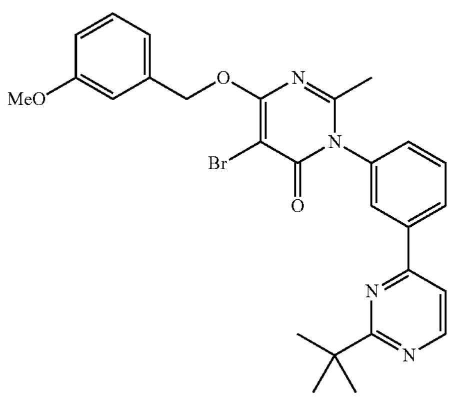 [SMILES: COc1cccc(COc2nc(C)n(-c3cccc(-c4ccnc(C(C)(C)C)n4)c3)c(=O)c2Br)c1] | 5-bromo-3-(3-(2-(tert-butyl)pyrimidin-4-yl)phenyl)-6-((3-methoxybenzyl)oxy)-2-methylpyrimidin-4(3H)-one |
| 505 | 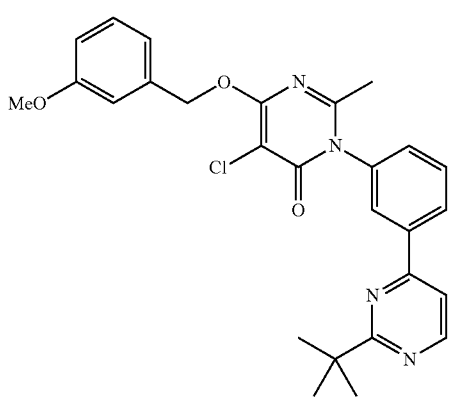 [SMILES: COc1cccc(COc2nc(C)n(-c3cccc(-c4ccnc(C(C)(C)C)n4)c3)c(=O)c2Cl)c1] | 3-(3-(2-(tert-butyl)pyrimidin-4-yl)phenyl)-5-chloro-6-((3-methoxybenzyl)oxy)-2-methylpyrimidin-4(3H)-one |

| Compound | Structure | Name |
|---|---|---|
| 506 | 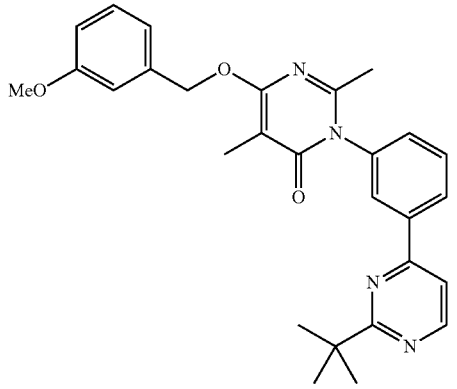 [SMILES: COc1cccc(COc2nc(C)n(-c3cccc(-c4ccnc(C(C)(C)C)n4)c3)c(=O)c2C)c1] | 3-(3-(2-(tert-butyl)pyrimidin-4-yl)phenyl)-6-((3-methoxybenzyl)oxy)-2,5-dimethylpyrimidin-4(3H)-one |
| 507 | 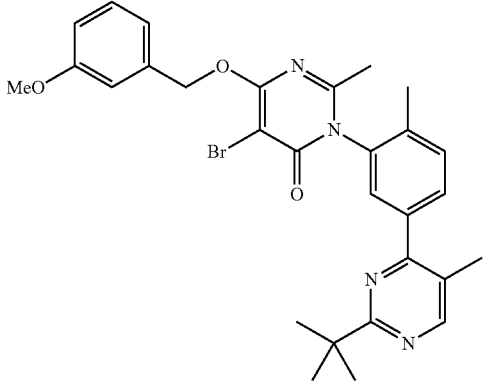 [SMILES: COc1cccc(COc2nc(C)n(-c3cc(-c4nc(C(C)(C)C)ncc4C)ccc3C)c(=O)c2Br)c1] | 5-bromo-3-(5-(2-(tert-butyl)-5-methylpyrimidin-4-yl)-2-methylphenyl)-6-((3-methoxybenzyl)oxy)-2-methylpyrimidin-4(3H)-one |
| 508 | 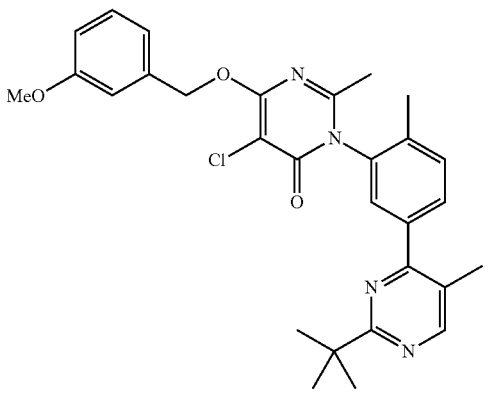 [SMILES: COc1cccc(COc2nc(C)n(-c3cc(-c4nc(C(C)(C)C)ncc4C)ccc3C)c(=O)c2Cl)c1] | 3-(5-(2-(tert-butyl)-5-methylpyrimidin-4-yl)-2-methylphenyl)-5-chloro-6-((3-methoxybenzyl)oxy)-2-methylpyrimidin-4(3H)-one |
| 509 | 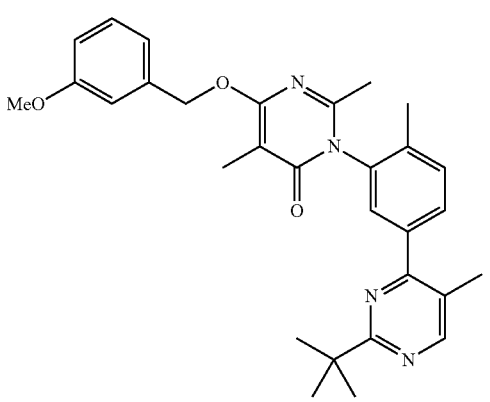 [SMILES: COc1cccc(COc2nc(C)n(-c3cc(-c4nc(C(C)(C)C)ncc4C)ccc3C)c(=O)c2C)c1] | 3-(5-(2-(tert-butyl)-5-methylpyrimidin-4-yl)-2-methylphenyl)-6-((3-methoxybenzyl)oxy)-2,5-dimethylpyrimidin-4(3H)-one |

-continued

| Compound | Structure | Name |
|---|---|---|
| 510 | 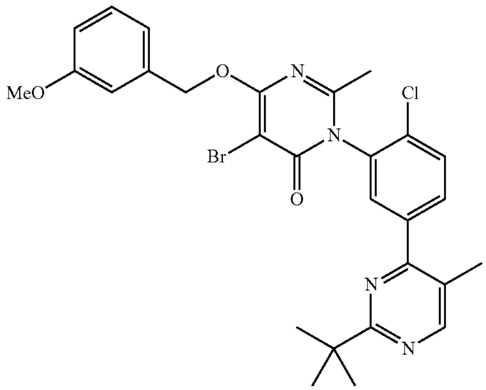 | 5-bromo-3-(5-(2-(tert-butyl)-5-methylpyrimidin-4-yl)-2-chlorophenyl)-6-((3-methoxybenzyl)oxy)-2-methylpyrimidin-4(3H)-one |
| 511 | 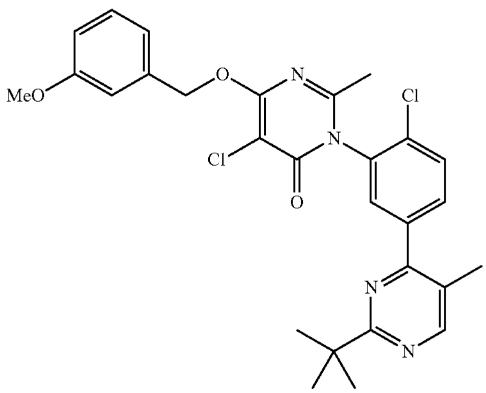 | 3-(5-(2-(tert-butyl)-5-methylpyrimidin-4-yl)-2-chlorophenyl)-5-chloro-6-((3-methoxybenzyl)oxy)-2-methylpyrimidin-4(3H)-one |
| 512 | 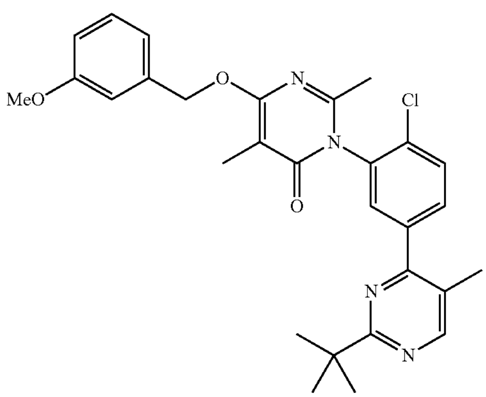 | 3-(5-(2-(tert-butyl)-5-methylpyrimidin-4-yl)-2-chlorophenyl)-6-((3-methoxybenzyl)oxy)-2,5-dimethylpyrimidin-4(3H)-one |
| 513 | 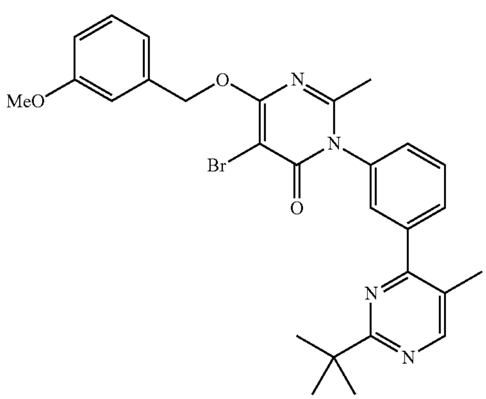 [SMILES: COc1cccc(COc2nc(C)n(-c3cccc(-c4nc(C(C)(C)C)ncc4C)c3)c(=O)c2Cl)c1] | 5-bromo-3-(3-(2-(tert-butyl)-5-methylpyrimidin-4-yl)phenyl)-6-((3-methoxybenzyl)oxy)-2-methylpyrimidin-4(3H)-one |

-continued

| Compound | Structure | Name |
|---|---|---|
| 514 | 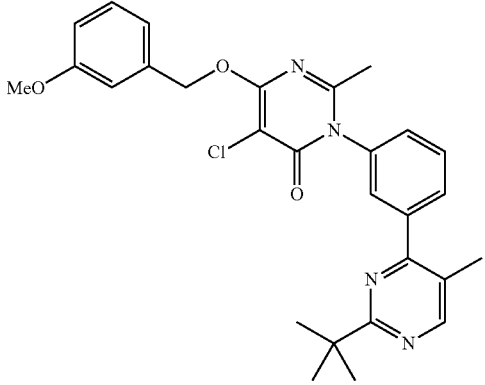 | 3-(3-(2-(tert-butyl)-5-methylpyrimidin-4-yl)phenyl)-5-chloro-6-((3-methoxybenzyl)oxy)-2-methylpyrimidin-4(3H)-one |
| 515 | 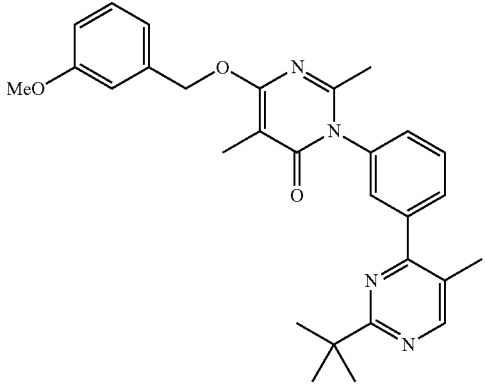 [SMILES: COc1cccc(COc2nc(C)n(-c3cccc(-c4nc(C(C)(C)C)ncc4C)c3)c(=O)c2C)c1] | 3-(3-(2-(tert-butyl)-5-methylpyrimidin-4-yl)phenyl)-6-((3-methoxybenzyl)oxy)-2,5-dimethylpyrimidin-4(3H)-one |
| 516 | 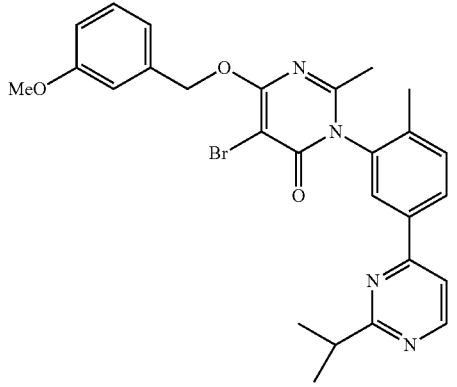 [SMILES: COc1cccc(COc2nc(C)n(-c3cc(-c4ccnc(C(C)C)n4)ccc3C)c(=O)c2Br)c1] | 5-bromo-3-(5-(2-isopropylpyrimidin-4-yl)-2-methylphenyl)-6-((3-methoxybenzyl)oxy)-2-methylpyrimidin-4(3H)-one |
| 517 | 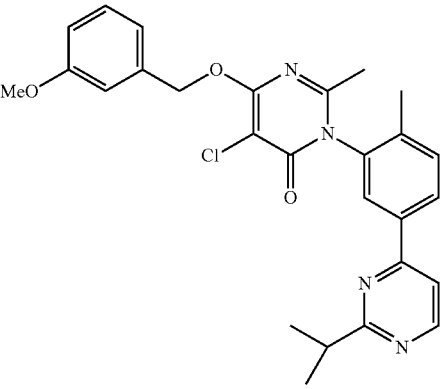 [SMILES: COc1cccc(COc2nc(C)n(-c3cc(-c4ccnc(C(C)C)n4)ccc3C)c(=O)c2Cl)c1] | 5-chloro-3-(5-(2-isopropylpyrimidin-4-yl)-2-methylphenyl)-6-((3-methoxybenzyl)oxy)-2-methylpyrimidin-4(3H)-one |

-continued

| Compound | Structure | Name |
|---|---|---|
| 518 | 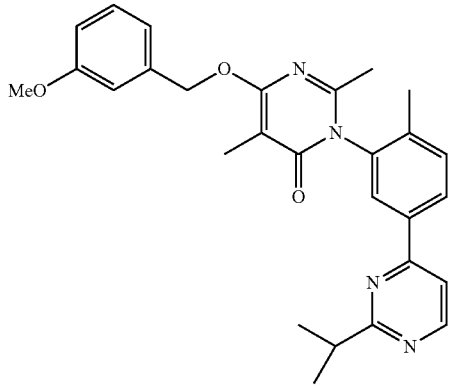 [SMILES: COc1cccc(COc2nc(C)n(-c3cc(-c4ccnc(C(C)C)n4)ccc3C)c(=O)c2C)c1] | 3-(5-(2-isopropylpyrimidin-4-yl)-2-methylphenyl)-6-((3-methoxybenzyl)oxy)-2,5-dimethylpyrimidin-4(3H)-one |
| 519 | 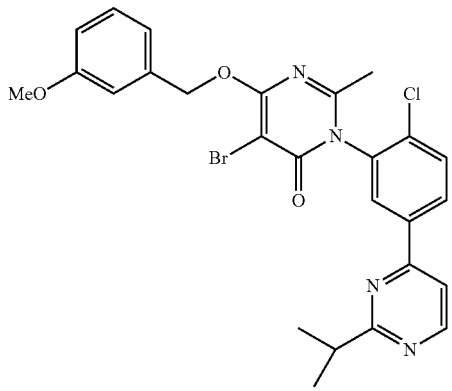 [SMILES: COc1cccc(COc2nc(C)n(-c3cc(-c4ccnc(C(C)C)n4)ccc3Cl)c(=O)c2Br)c1] | 5-bromo-3-(2-chloro-5-(2-isopropylpyrimidin-4-yl)phenyl)-6-((3-methoxybenzyl)oxy)-2-methylpyrimidin-4(3H)-one |
| 520 | 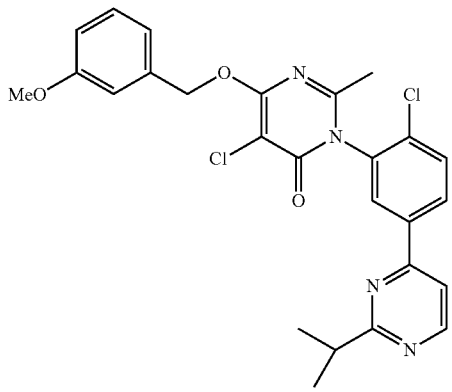 | 5-chloro-3-(2-chloro-5-(2-isopropylpyrimidin-4-yl)phenyl)-6-((3-methoxybenzyl)oxy)-2-methylpyrimidin-4(3H)-one |
| 521 | 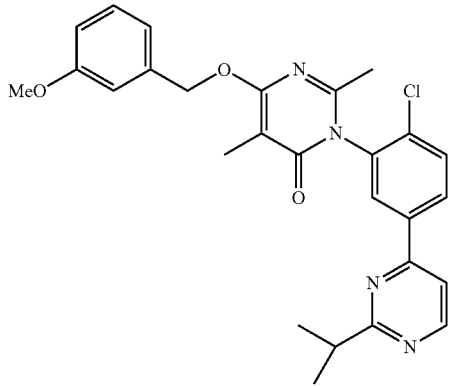 [SMILES: COc1cccc(COc2nc(C)n(-c3cc(-c4ccnc(C(C)C)n4)ccc3Cl)c(=O)c2C)c1] | 3-(2-chloro-5-(2-isopropylpyrimidin-4-yl)phenyl)-6-((3-methoxybenzyl)oxy)-2,5-dimethylpyrimidin-4(3H)-one |

| Compound | Structure | Name |
|---|---|---|
| 522 | 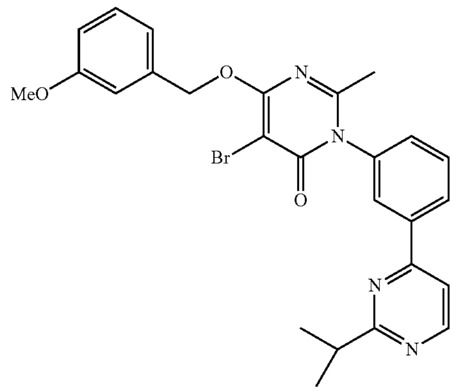 [SMILES: COc1cccc(COc2nc(C)n(-c3cccc(-c4ccnc(C(C)C)n4)c3)c(=O)c2Br)c1] | 5-bromo-3-(3-(2-isopropylpyrimidin-4-yl)phenyl)-6-((3-methoxybenzyl)oxy)-2-methylpyrimidin-4(3H)-one |
| 523 | 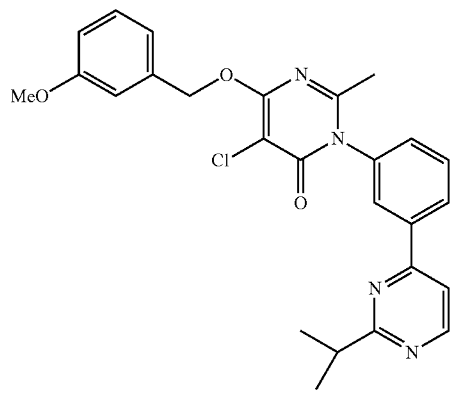 [SMILES: COc1cccc(COc2nc(C)n(-c3cccc(-c4ccnc(C(C)C)n4)c3)c(=O)c2Cl)c1] | 5-chloro-3-(3-(2-isopropylpyrimidin-4-yl)phenyl)-6-((3-methoxybenzyl)oxy)-2-methylpyrimidin-4(3H)-one |
| 524 | 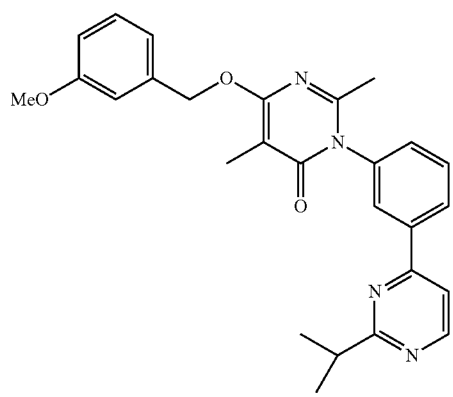 [SMILES: COc1cccc(COc2nc(C)n(-c3cccc(-c4ccnc(C(C)C)n4)c3)c(=O)c2C)c1] | 3-(3-(2-isopropylpyrimidin-4-yl)phenyl)-6-((3-methoxybenzyl)oxy)-2,5-dimethylpyrimidin-4(3H)-one |
| 525 | 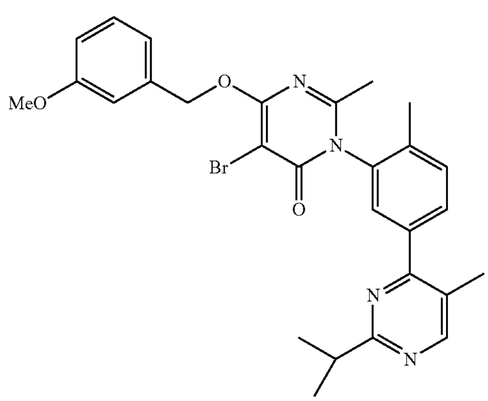 [SMILES: COc1cccc(COc2nc(C)n(-c3cc(-c4nc(C(C)C)ncc4C)ccc3C)c(=O)c2Cl)c1] | 5-bromo-3-(5-(2-isopropyl-5-methylpyrimidin-4-yl)-2-methylphenyl)-6-((3-methoxybenzyl)oxy)-2-methylpyrimidin-4(3H)-one |

-continued

| Compound | Structure | Name |
|---|---|---|
| 526 | 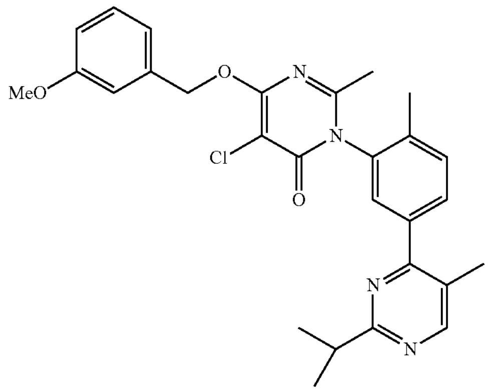 | 5-chloro-3-(5-(2-isopropyl-5-methylpyrimidin-4-yl)-2-methylphenyl)-6-((3-methoxybenzyl)oxy)-2-methylpyrimidin-4(3H)-one |
| 527 | 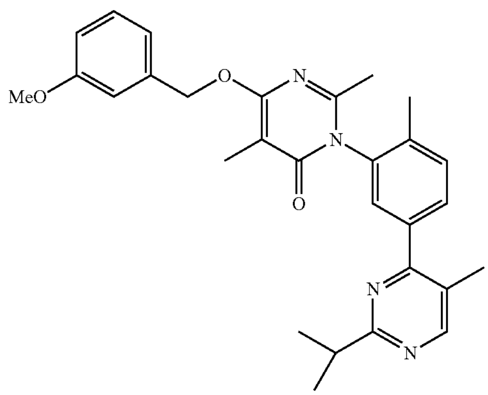 [SMILES: COc1cccc(COc2nc(C)n(-c3cc(-c4nc(C(C)C)ncc4C)ccc3C)c(=O)c2C)c1] | 3-(5-(2-isopropyl-5-methylpyrimidin-4-yl)-2-methylphenyl)-6-((3-methoxybenzyl)oxy)-2,5-dimethylpyrimidin-4(3H)-one |
| 528 | 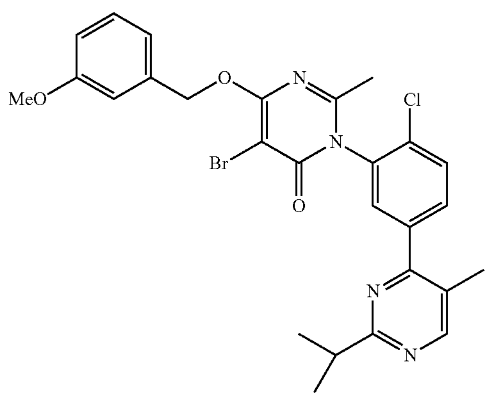 | 5-bromo-3-(2-chloro-5-(2-isopropyl-5-methylpyrimidin-4-yl)phenyl)-6-((3-methoxybenzyl)oxy)-2-methylpyrimidin-4(3H)-one |
| 529 | 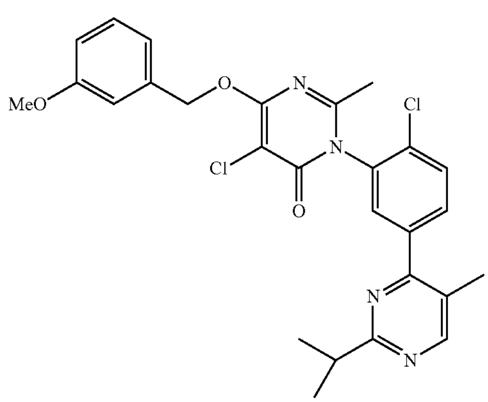 | 5-chloro-3-(2-chloro-5-(2-isopropyl-5-methylpyrimidin-4-yl)phenyl)-6-((3-methoxybenzyl)oxy)-2-methylpyrimidin-4(3H)-one |

-continued

| Compound | Structure | Name |
|---|---|---|
| 530 | 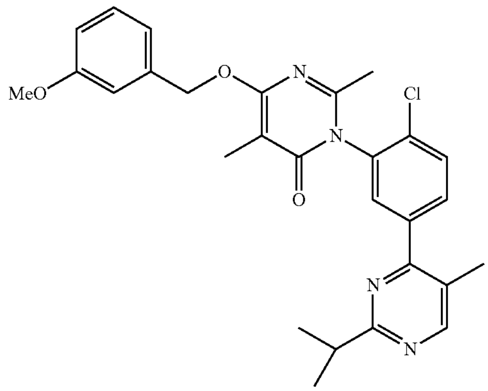 | 3-(2-chloro-5-(2-isopropyl-5-methylpyrimidin-4-yl)phenyl)-6-((3-methoxybenzyl)oxy)-2,5-dimethylpyrimidin-4(3H)-one |
| 531 | 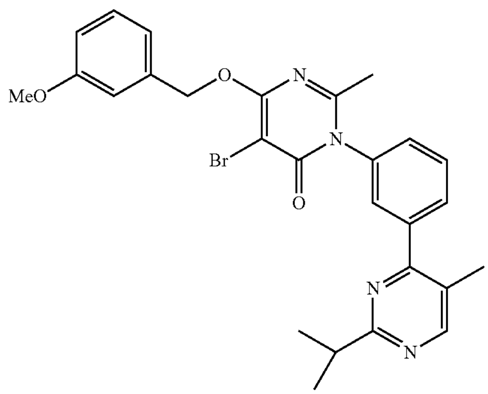 [SMILES: COc1cccc(COc2nc(C)n(-c3cccc(-c4nc(C(C)C)ncc4C)c3)c(=O)c2Cl)c1] | 5-bromo-3-(3-(2-isopropyl-5-methylpyrimidin-4-yl)phenyl)-6-((3-methoxybenzyl)oxy)-2-methylpyrimidin-4(3H)-one |
| 532 | 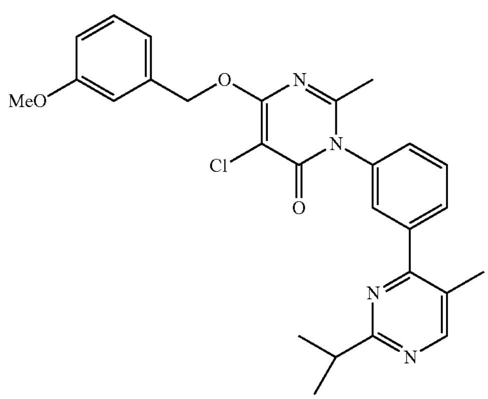 | 5-chloro-3-(3-(2-isopropyl-5-methylpyrimidin-4-yl)phenyl)-6-((3-methoxybenzyl)oxy)-2-methylpyrimidin-4(3H)-one |
| 533 | 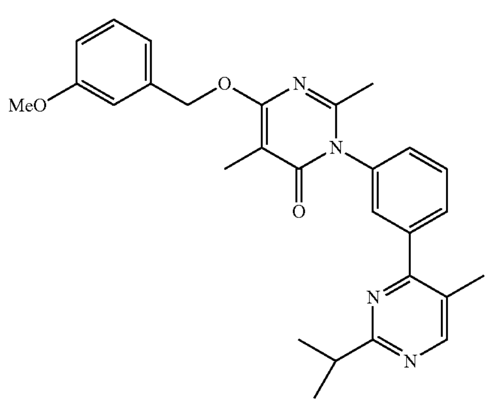 [SMILES: COc1cccc(COc2nc(C)n(-c3cccc(-c4nc(C(C)C)ncc4C)c3)c(=O)c2C)c1] | 3-(3-(2-isopropyl-5-methylpyrimidin-4-yl)phenyl)-6-((3-methoxybenzyl)oxy)-2,5-dimethylpyrimidin-4(3H)-one |

-continued

| Compound | Structure | Name |
|---|---|---|
| 534 | 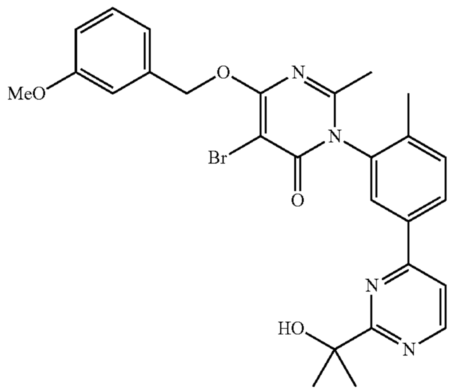 [SMILES: COc1cccc(COc2nc(C)n(-c3cc(-c4ccnc(C(C)(C)O)n4)ccc3C)c(=O)c2Br)c1] | 5-bromo-3-(5-(2-(2-hydroxypropan-2-yl)pyrimidin-4-yl)-2-methylphenyl)-6-((3-methoxybenzyl)oxy)-2-methylpyrimidin-4(3H)-one |
| 535 | 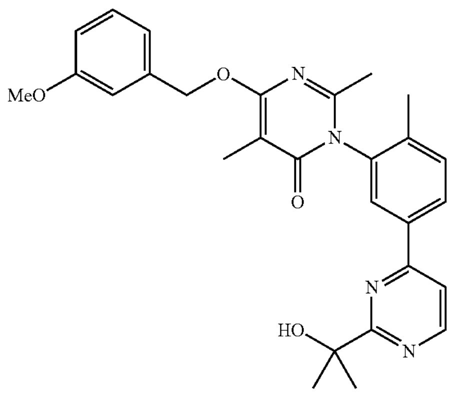 [SMILES: COc1cccc(COc2nc(C)n(-c3cc(-c4ccnc(C(C)(C)O)n4)ccc3C)c(=O)c2C)c1] | 3-(5-(2-(2-hydroxypropan-2-yl)pyrimidin-4-yl)-2-methylphenyl)-6-((3-methoxybenzyl)oxy)-2,5-dimethylpyrimidin-4(3H)-one |
| 536 | 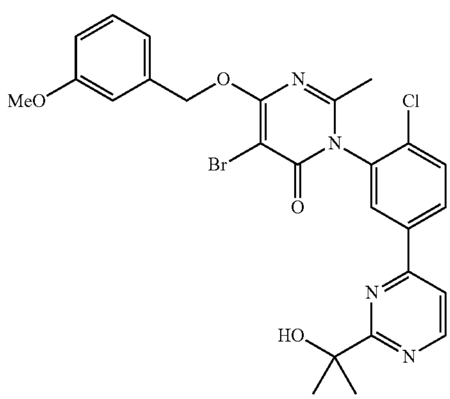 | 5-bromo-3-(2-chloro-5-(2-(2-hydroxypropan-2-yl)pyrimidin-4-yl)phenyl)-6-((3-methoxybenzyl)oxy)-2-methylpyrimidin-4(3H)-one |
| 537 | 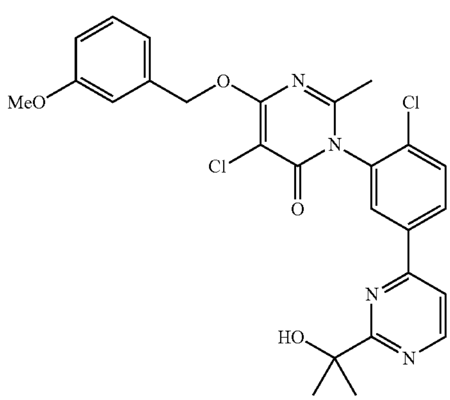 [SMILES: COc1cccc(COc2nc(C)n(-c3cc(-c4ccnc(C(C)(C)O)n4)ccc3Cl)c(=O)c2Cl)c1] | 5-chloro-3-(2-chloro-5-(2-(2-hydroxypropan-2-yl)pyrimidin-4-yl)phenyl)-6-((3-methoxybenzyl)oxy)-2-methylpyrimidin-4(3H)-one |

-continued

| Compound | Structure | Name |
|---|---|---|
| 538 | 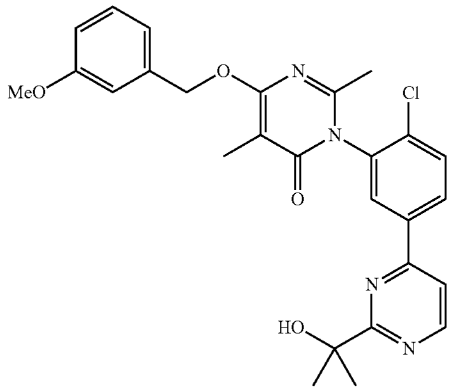 [SMILES: COc1cccc(COc2nc(C)n(-c3cc(-c4ccnc(C(C)(C)O)n4)ccc3Cl)c(=O)c2C)c1] | 3-(2-chloro-5-(2-(2-hydroxypropan-2-yl)pyrimidin-4-yl)phenyl)-6-((3-methoxybenzyl)oxy)-2,5-dimethylpyrimidin-4(3H)-one |
| 539 | 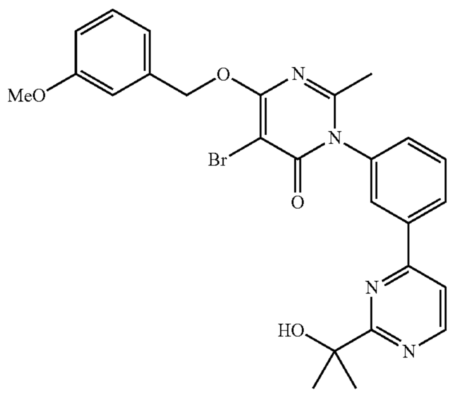 | 5-bromo-3-(3-(2-(2-hydroxypropan-2-yl)pyrimidin-4-yl)phenyl)-6-((3-methoxybenzyl)oxy)-2-methylpyrimidin-4(3H)-one |
| 540 | 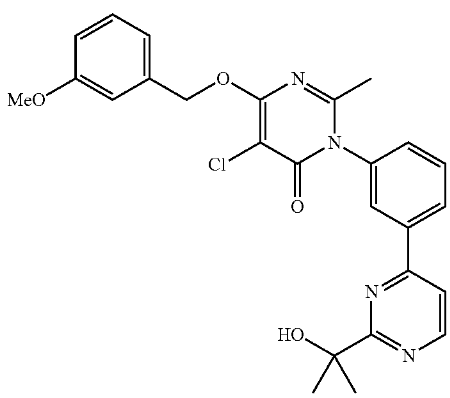 [SMILES: COc1cccc(COc2nc(C)n(-c3cccc(-c4ccnc(C(C)(C)O)n4)c3)c(=O)c2Cl)c1] | 5-chloro-3-(3-(2-(2-hydroxypropan-2-yl)pyrimidin-4-yl)phenyl)-6-((3-methoxybenzyl)oxy)-2-methylpyrimidin-4(3H)-one |
| 541 | 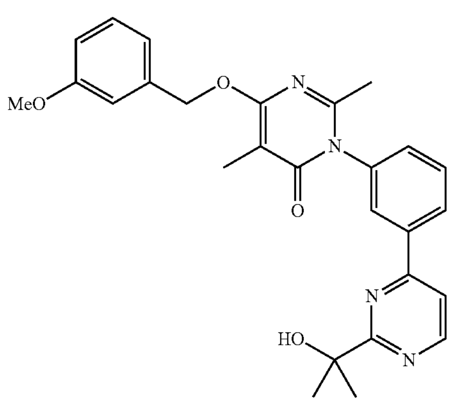 [SMILES: COc1cccc(COc2nc(C)n(-c3cccc(-c4ccnc(C(C)(C)O)n4)c3)c(=O)c2C)c1] | 3-(3-(2-(2-hydroxypropan-2-yl)pyrimidin-4-yl)phenyl)-6-((3-methoxybenzyl)oxy)-2,5-dimethylpyrimidin-4(3H)-one |

| Compound | Structure | Name |
|---|---|---|
| 542 | 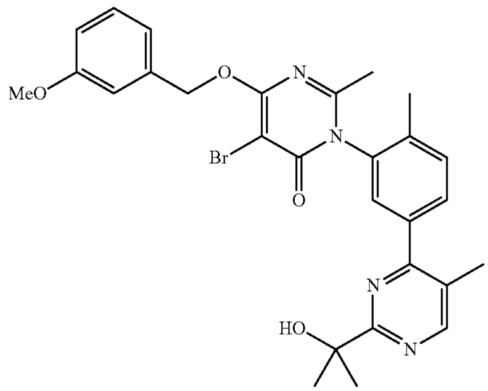 [SMILES: COc1cccc(COc2nc(C)n(-c3cc(-c4nc(C(C)(C)O)ncc4C)ccc3C)c(=O)c2Br)c1] | 5-bromo-3-(5-(2-(2-hydroxypropan-2-yl)-5-methylpyrimidin-4-yl)-2-methylphenyl)-6-((3-methoxybenzyl)oxy)-2-methylpyrimidin-4(3H)-one |
| 543 | 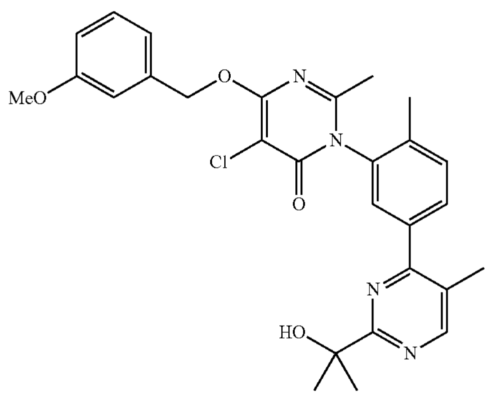 [SMILES: COc1cccc(COc2nc(C)n(-c3cc(-c4nc(C(C)(C)O)ncc4C)ccc3C)c(=O)c2Cl)c1] | 5-chloro-3-(5-(2-(2-hydroxypropan-2-yl)-5-methylpyrimidin-4-yl)-2-methylphenyl)-6-((3-methoxybenzyl)oxy)-2-methylpyrimidin-4(3H)-one |
| 544 | 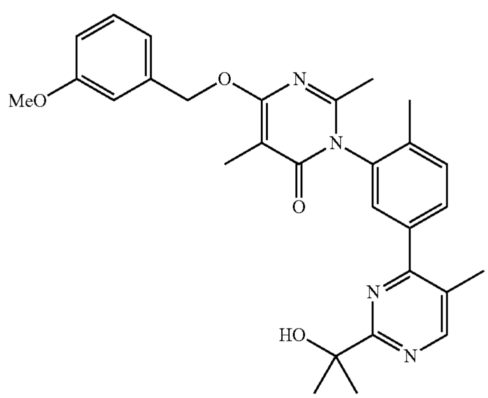 [SMILES: COc1cccc(COc2nc(C)n(-c3cc(-c4nc(C(C)(C)O)ncc4C)ccc3C)c(=O)c2C)c1] | 3-(5-(2-(2-hydroxypropan-2-yl)-5-methylpyrimidin-4-yl)-2-methylphenyl)-6-((3-methoxybenzyl)oxy)-2,5-dimethylpyrimidin-4(3H)-one |
| 545 | 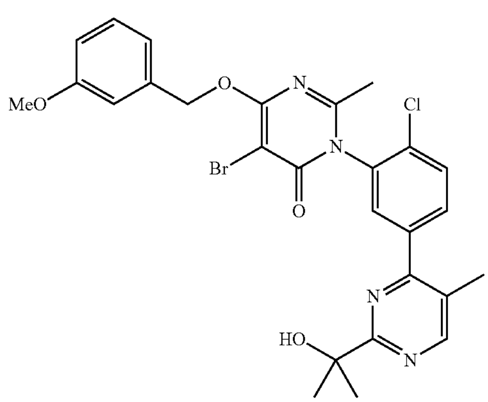 [SMILES: COc1cccc(COc2nc(C)n(-c3cc(-c4nc(C(C)(C)O)ncc4C)ccc3Cl)c(=O)c2Cl)c1] | 5-bromo-3-(2-chloro-5-(2-(2-hydroxypropan-2-yl)-5-methylpyrimidin-4-yl)phenyl)-6-((3-methoxybenzyl)oxy)-2-methylpyrimidin-4(3H)-one |

| Compound | Structure | Name |
|---|---|---|
| 546 | 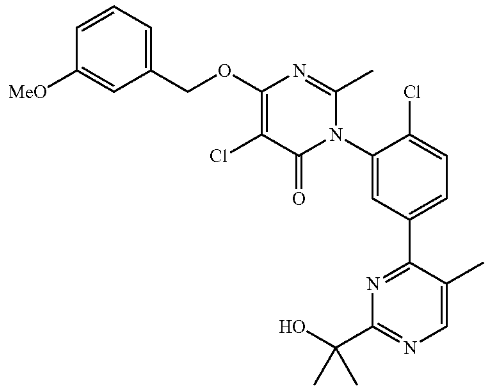 | 5-chloro-3-(2-chloro-5-(2-(2-hydroxypropan-2-yl)-5-methylpyrimidin-4-yl)phenyl)-6-((3-methoxybenzyl)oxy)-2-methylpyrimidin-4(3H)-one |
| 547 | 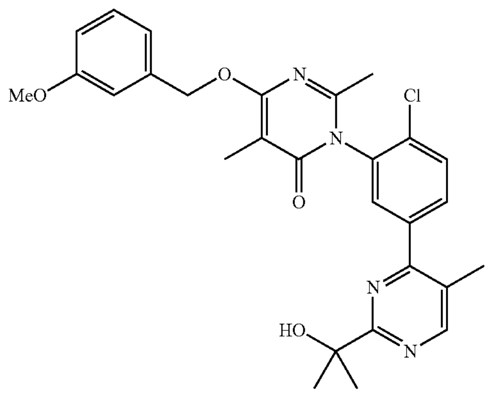 | 3-(2-chloro-5-(2-(2-hydroxypropan-2-yl)-5-methylpyrimidin-4-yl)phenyl)-6-((3-methoxybenzyl)oxy)-2,5-dimethylpyrimidin-4(3H)-one |
| 548 | 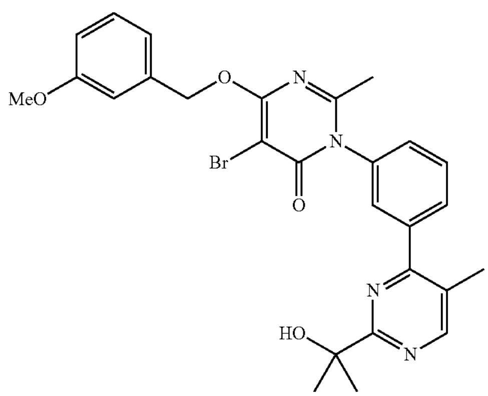 [SMILES: COc1cccc(COc2nc(C)n(-c3cccc(-c4nc(C(C)(C)O)ncc4C)c3)c(=O)c2Br)c1] | 5-bromo-3-(3-(2-(2-hydroxypropan-2-yl)-5-methylpyrimidin-4-yl)phenyl)-6-((3-methoxybenzyl)oxy)-2-methylpyrimidin-4(3H)-one |
| 549 | 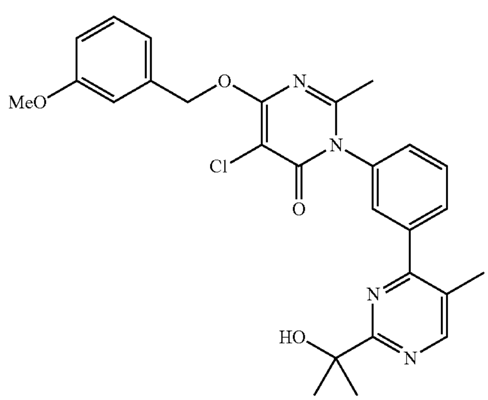 [SMILES: COc1cccc(COc2nc(C)n(-c3cccc(-c4nc(C(C)(C)O)ncc4C)c3)c(=O)c2Cl)c1] | 5-chloro-3-(3-(2-(2-hydroxypropan-2-yl)-5-methylpyrimidin-4-yl)phenyl)-6-((3-methoxybenzyl)oxy)-2-methylpyrimidin-4(3H)-one |

| Compound | Structure | Name |
|---|---|---|
| 550 | 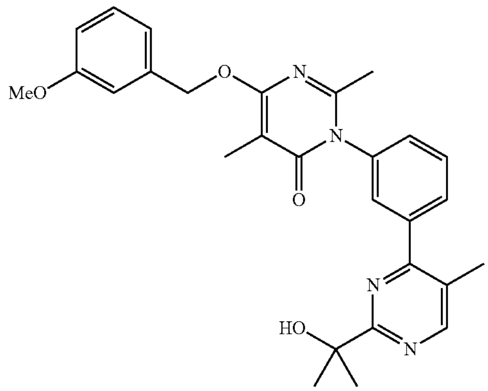 [SMILES: COc1cccc(COc2nc(C)n(-c3cccc(-c4nc(C(C)(C)O)ncc4C)c3)c(=O)c2C)c1] | 3-(3-(2-(2-hydroxypropan-2-yl)-5-methylpyrimidin-4-yl)phenyl)-6-((3-methoxybenzyl)oxy)-2,5-dimethylpyrimidin-4(3H)-one |
| 551 | 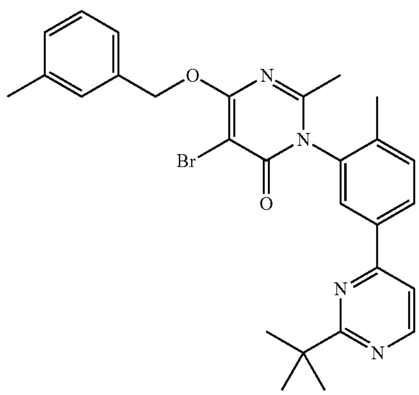 [SMILES: Cc1cccc(COc2nc(C)n(-c3cc(-c4ccnc(C(C)(C)C)n4)ccc3C)c(=O)c2Br)c1] | 5-bromo-3-(5-(2-(tert-butyl)pyrimidin-4-yl)-2-methylphenyl)-2-methyl-6-((3-methylbenzyl)oxy)pyrimidin-4(3H)-one |
| 552 | 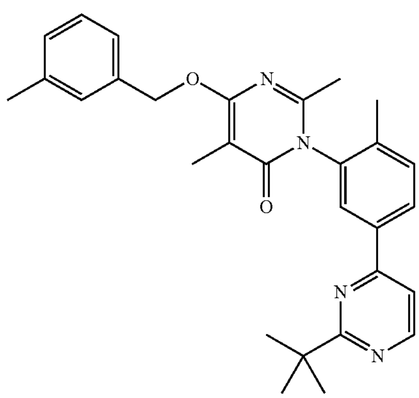 [SMILES: Cc1cccc(COc2nc(C)n(-c3cc(-c4ccnc(C(C)(C)C)n4)ccc3C)c(=O)c2C)c1] | 3-(5-(2-(tert-butyl)pyrimidin-4-yl)-2-methylphenyl)-2,5-dimethyl-6-((3-methylbenzyl)oxy)pyrimidin-4(3H)-one |
| 553 | 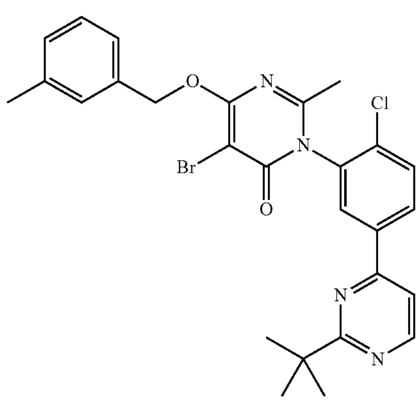 | 5-bromo-3-(5-(2-(tert-butyl)pyrimidin-4-yl)-2-chlorophenyl)-2-methyl-6-((3-methylbenzyl)oxy)pyrimidin-4(3H)-one |

| Compound | Structure | Name |
|---|---|---|
| 554 | 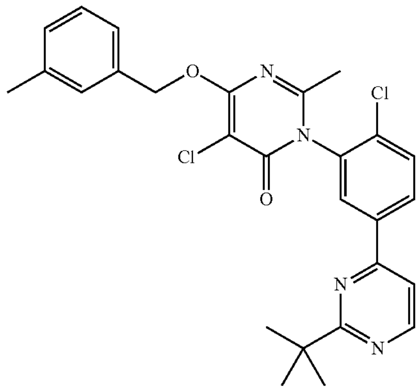 | 3-(5-(2-(tert-butyl)pyrimidin-4-yl)-2-chlorophenyl)-5-chloro-2-methyl-6-((3-methylbenzyl)oxy)pyrimidin-4(3H)-one |
| 555 | 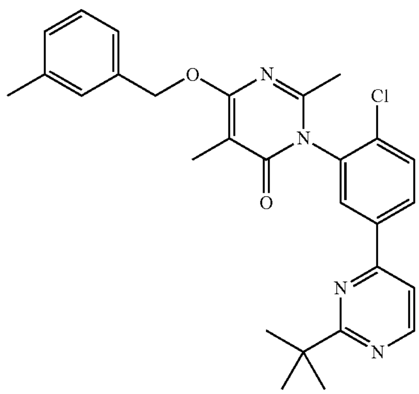 [SMILES: Cc1cccc(COc2nc(C)n(-c3cc(-c4ccnc(C(C)(C)C)n4)ccc3Cl)c(=O)c2C)c1] | 3-(5-(2-(tert-butyl)pyrimidin-4-yl)-2-chlorophenyl)-2,5-dimethyl-6-((3-methylbenzyl)oxy)pyrimidin-4(3H)-one |
| 556 | 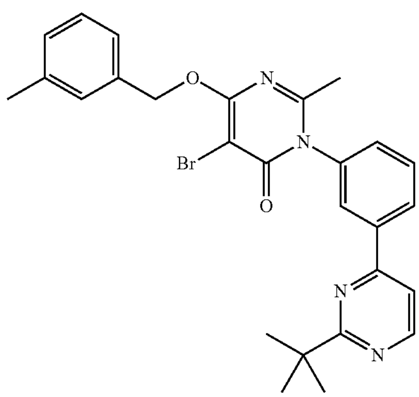 [SMILES: Cc1cccc(COc2nc(C)n(-c3cccc(-c4ccnc(C(C)(C)C)n4)c3)c(=O)c2Br)c1] | 5-bromo-3-(3-(2-(tert-butyl)pyrimidin-4-yl)phenyl)-2-methyl-6-((3-methylbenzyl)oxy)pyrimidin-4(3H)-one |
| 557 | 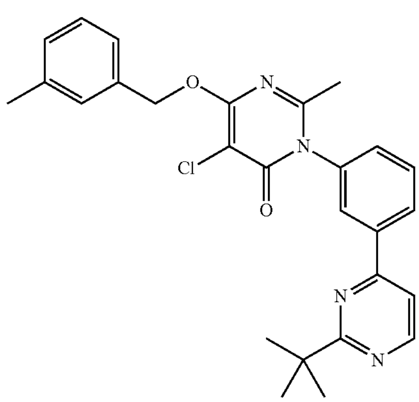 | 3-(3-(2-(tert-butyl)pyrimidin-4-yl)phenyl)-5-chloro-2-methyl-6-((3-methylbenzyl)oxy)pyrimidin-4(3H)-one |

| Compound | Structure | Name |
|---|---|---|
| 558 | 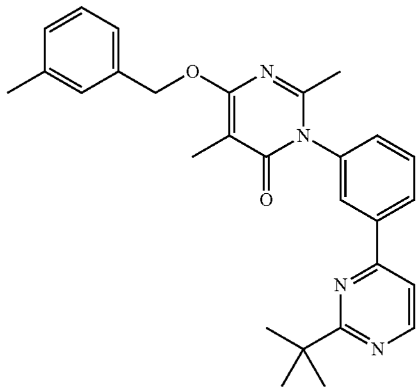 | 3-(3-(2-(tert-butyl)pyrimidin-4-yl)phenyl)-2,5-dimethyl-6-((3-methylbenzyl)oxy)pyrimidin-4(3H)-one |
| 559 | 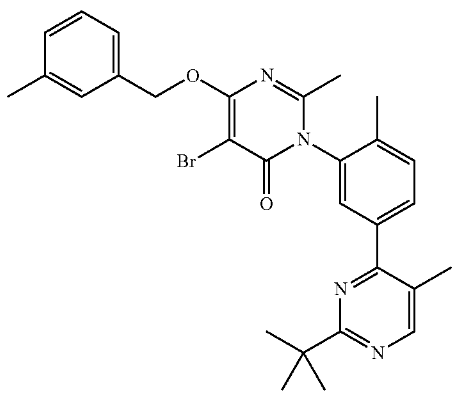 | 5-bromo-3-(5-(2-(tert-butyl)-5-methylpyrimidin-4-yl)-2-methylphenyl)-2-methyl-6-((3-methylbenzyl)oxy)pyrimidin-4(3H)-one |
| 560 | 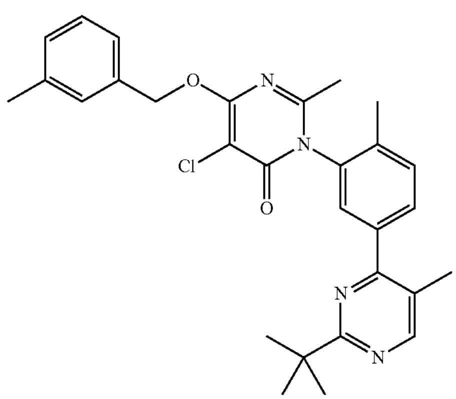 | 3-(5-(2-(tert-butyl)-5-methylpyrimidin-4-yl)-2-methylphenyl)-5-chloro-2-methyl-6-((3-methylbenzyl)oxy)pyrimidin-4(3H)-one |
| 561 | 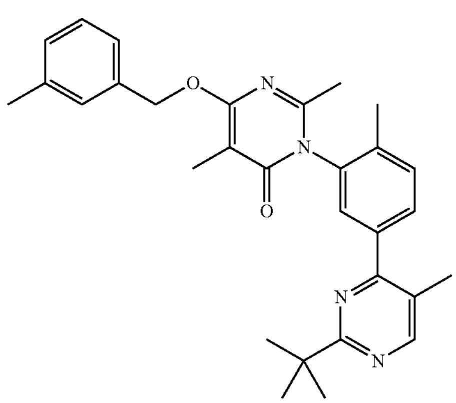 | 3-(5-(2-(tert-butyl)-5-methylpyrimidin-4-yl)-2-methylphenyl)-2,5-dimethyl-6-((3-methylbenzyl)oxy)pyrimidin-4(3H)-one |

| Compound | Structure | Name |
|---|---|---|
| 562 | 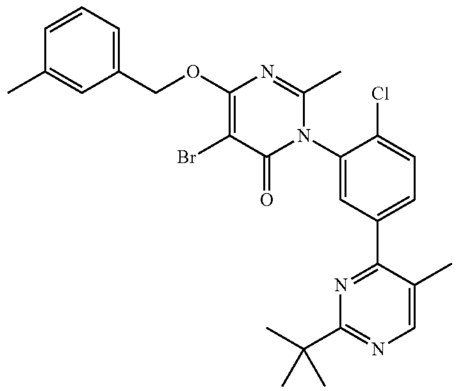 | 5-bromo-3-(5-(2-(tert-butyl)-5-methylpyrimidin-4-yl)-2-chlorophenyl)-2-methyl-6-((3-methylbenzyl)oxy)pyrimidin-4(3H)-one |
| 563 | 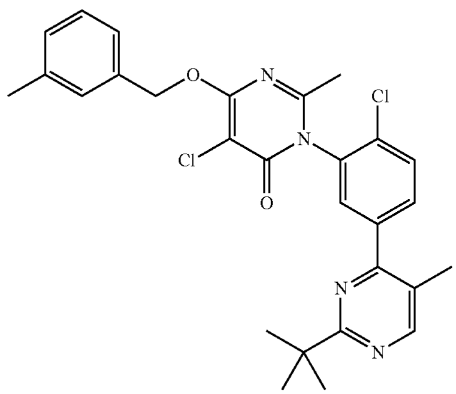 | 3-(5-(2-(tert-butyl)-5-methylpyrimidin-4-yl)-2-chlorophenyl)-5-chloro-2-methyl-6-((3-methylbenzyl)oxy)pyrimidin-4(3H)-one |
| 564 | 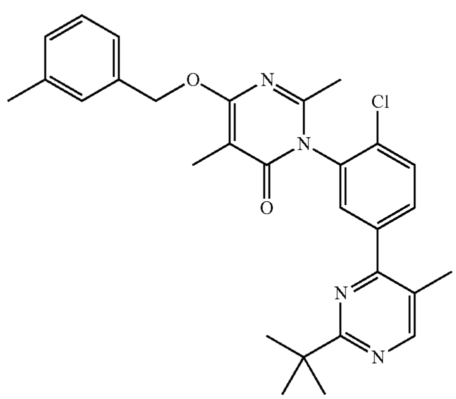 | 3-(5-(2-(tert-butyl)-5-methylpyrimidin-4-yl)-2-chlorophenyl)-2,5-dimethyl-6-((3-methylbenzyl)oxy)pyrimidin-4(3H)-one |
| 565 | 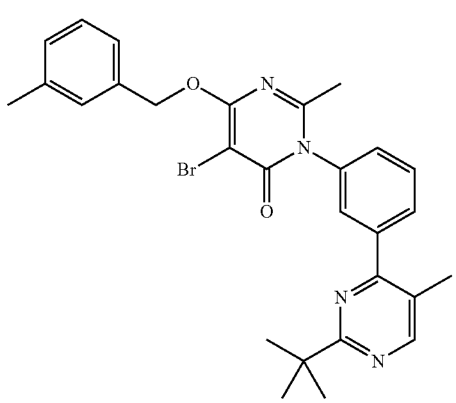 | 5-bromo-3-(3-(2-(tert-butyl)-5-methylpyrimidin-4-yl)phenyl)-2-methyl-6-((3-methylbenzyl)oxy)pyrimidin-4(3H)-one |

| Compound | Structure | Name |
|---|---|---|
| 566 | 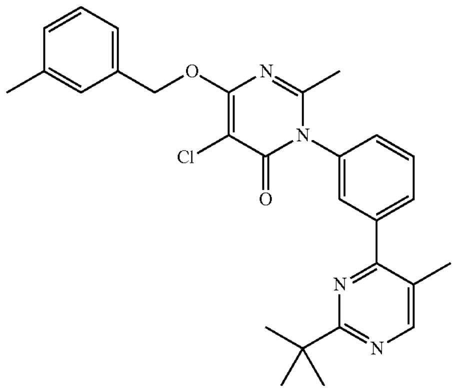 | 3-(3-(2-(tert-butyl)-5-methylpyrimidin-4-yl)phenyl)-5-chloro-2-methyl-6-((3-methylbenzyl)oxy)pyrimidin-4(3H)-one |
| 567 | 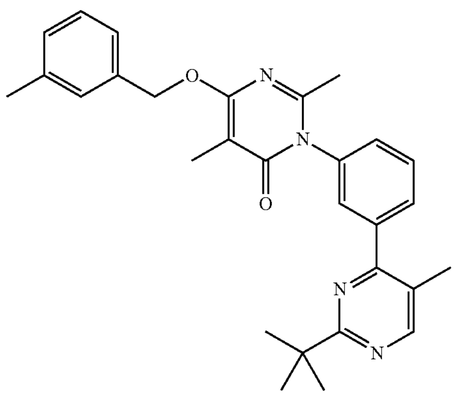 | 3-(3-(2-(tert-butyl)-5-methylpyrimidin-4-yl)phenyl)-2,5-dimethyl-6-((3-methylbenzyl)oxy)pyrimidin-4(3H)-one |
| 568 | 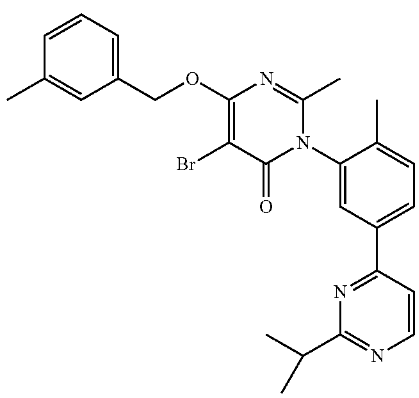 | 5-bromo-3-(5-(2-isopropylpyrimidin-4-yl)-2-methylphenyl)-2-methyl-6-((3-methylbenzyl)oxy)pyrimidin-4(3H)-one |
| 569 | 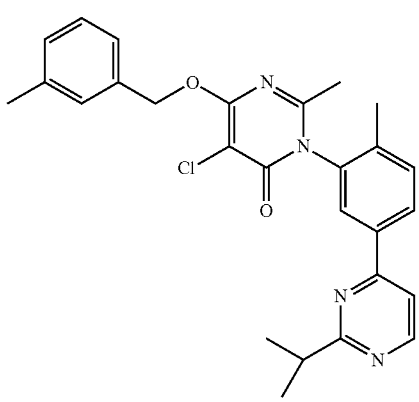 [SMILES: Cc1cccc(COc2nc(C)n(-c3cc(-c4ccnc(C(C)C)n4)ccc3C)c(=O)c2Cl)c1] | 5-chloro-3-(5-(2-isopropylpyrimidin-4-yl)-2-methylphenyl)-2-methyl-6-((3-methylbenzyl)oxy)pyrimidin-4(3H)-one |

| Compound | Structure | Name |
|---|---|---|
| 570 | 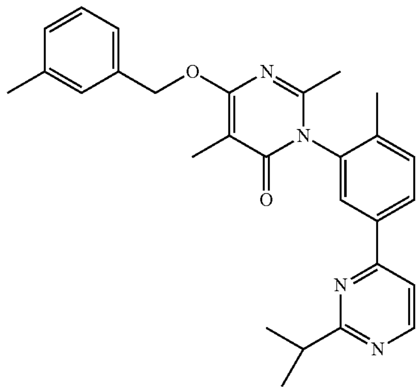 | 3-(5-(2-isopropylpyrimidin-4-yl)-2-methylphenyl)-2,5-dimethyl-6-((3-methylbenzyl)oxy)pyrimidin-4(3H)-one |
| 571 | 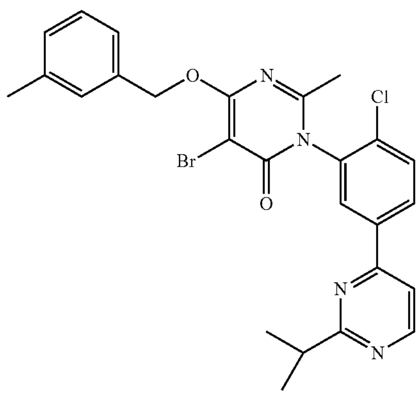 [SMILES: Cc1cccc(COc2nc(C)n(-c3cc(-c4ccnc(C(C)C)n4)ccc3Cl)c(=O)c2Cl)c1] | 5-bromo-3-(2-chloro-5-(2-isopropylpyrimidin-4-yl)phenyl)-2-methyl-6-((3-methylbenzyl)oxy)pyrimidin-4(3H)-one |
| 572 | 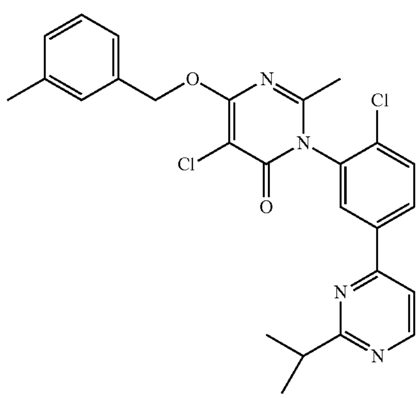 | 5-chloro-3-(2-chloro-5-(2-isopropylpyrimidin-4-yl)phenyl)-2-methyl-6-((3-methylbenzyl)oxy)pyrimidin-4(3H)-one |
| 573 | 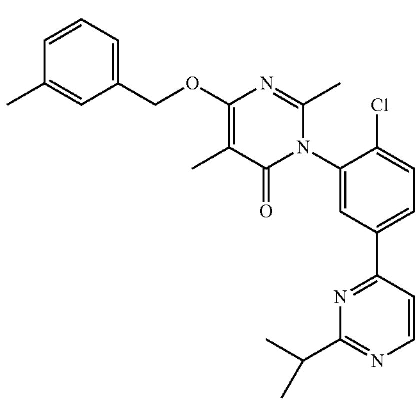 [SMILES: Cc1cccc(COc2nc(C)n(-c3cc(-c4ccnc(C(C)C)n4)ccc3Cl)c(=O)c2C)c1] | 3-(2-chloro-5-(2-isopropylpyrimidin-4-yl)phenyl)-2,5-dimethyl-6-((3-methylbenzyl)oxy)pyrimidin-4(3H)-one |

-continued

| Compound | Structure | Name |
|---|---|---|
| 574 | 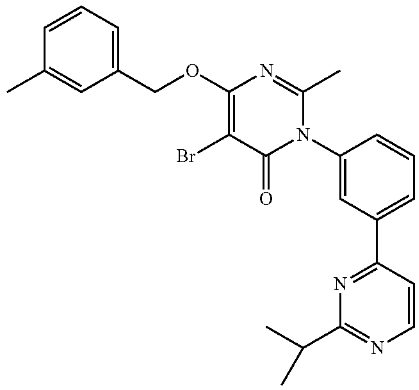 [SMILES: Cc1cccc(COc2nc(C)n(-c3cccc(-c4ccnc(C(C)C)n4)c3)c(=O)c2Cl)c1] | 5-bromo-3-(3-(2-isopropylpyrimidin-4-yl)phenyl)-2-methyl-6-((3-methylbenzyl)oxy)pyrimidin-4(3H)-one |
| 575 | 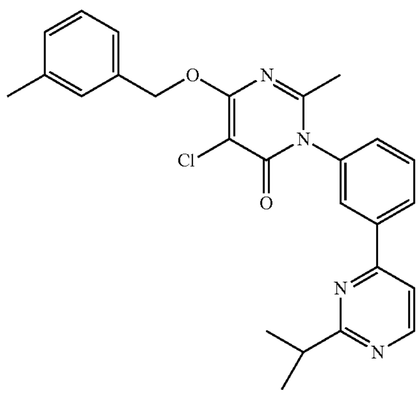 | 5-chloro-3-(3-(2-isopropylpyrimidin-4-yl)phenyl)-2-methyl-6-((3-methylbenzyl)oxy)pyrimidin-4(3H)-one |
| 576 | 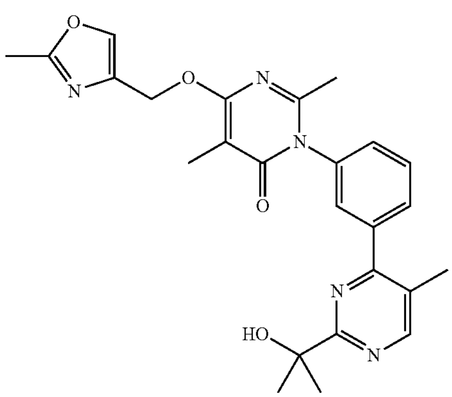 | 3-(3-(2-isopropylpyrimidin-4-yl)phenyl)-2,5-dimethyl-6-((3-methylbenzyl)oxy)pyrimidin-4(3H)-one |
| 577 | 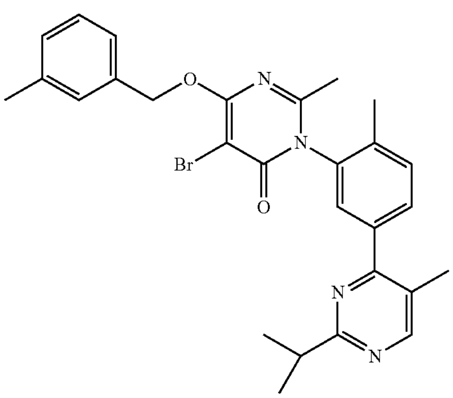 | 5-bromo-3-(5-(2-isopropyl-5-methylpyrimidin-4-yl)-2-methylphenyl)-2-methyl-6-((3-methylbenzyl)oxy)pyrimidin-4(3H)-one |

-continued

| Compound | Structure | Name |
|---|---|---|
| 578 | 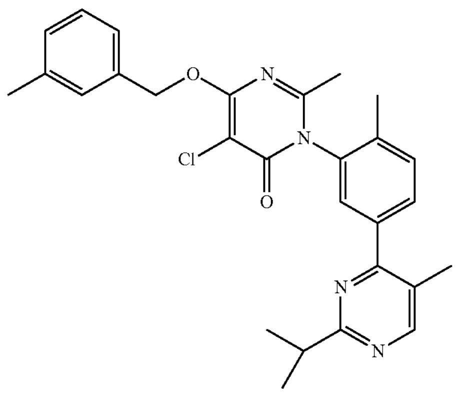 | 5-chloro-3-(5-(2-isopropyl-5-methylpyrimidin-4-yl)-2-methylphenyl)-2-methyl-6-((3-methylbenzyl)oxy)pyrimidin-4(3H)-one |
| 579 | 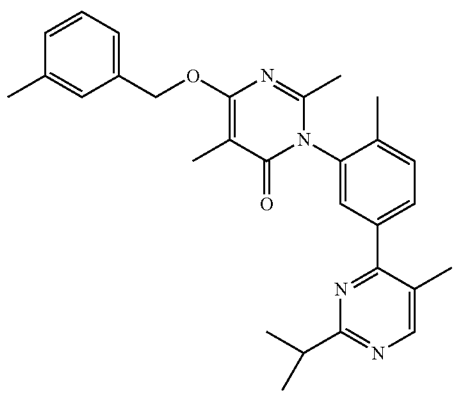 | 3-(5-(2-isopropyl-5-methylpyrimidin-4-yl)-2-methylphenyl)-2,5-dimethyl-6-((3-methylbenzyl)oxy)pyrimidin-4(3H)-one |
| 580 | 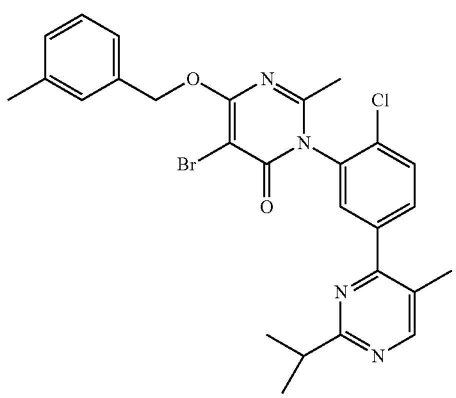 | 5-bromo-3-(2-chloro-5-(2-isopropyl-5-methylpyrimidin-4-yl)phenyl)-2-methyl-6-((3-methylbenzyl)oxy)pyrimidin-4(3H)-one |
| 581 | 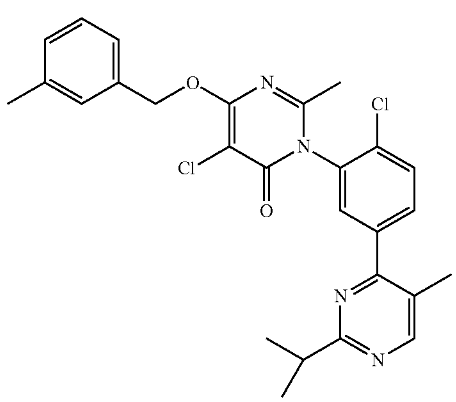 | 5-chloro-3-(2-chloro-5-(2-isopropyl-5-methylpyrimidin-4-yl)phenyl)-2-methyl-6-((3-methylbenzyl)oxy)pyrimidin-4(3H)-one |

-continued

| Compound | Structure | Name |
|---|---|---|
| 582 | 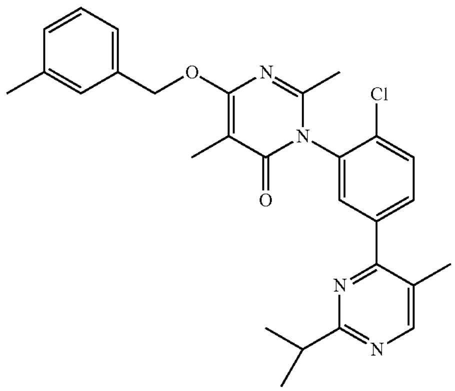 | 3-(2-chloro-5-(2-isopropyl-5-methylpyrimidin-4-yl)phenyl)-2,5-dimethyl-6-((3-methylbenzyl)oxy)pyrimidin-4(3H)-one |
| 583 | 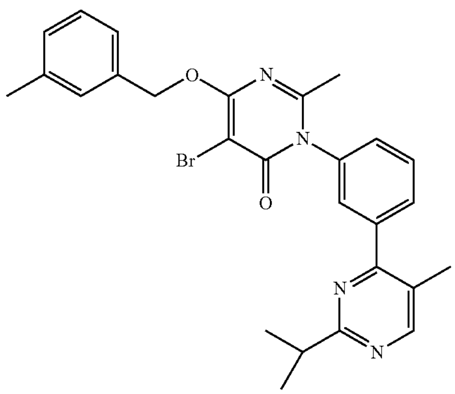 | 5-bromo-3-(3-(2-isopropyl-5-methylpyrimidin-4-yl)phenyl)-2-methyl-6-((3-methylbenzyl)oxy)pyrimidin-4(3H)-one |
| 584 | 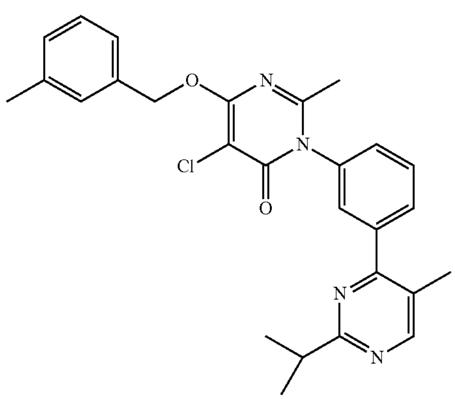 | 5-chloro-3-(3-(2-isopropyl-5-methylpyrimidin-4-yl)phenyl)-2-methyl-6-((3-methylbenzyl)oxy)pyrimidin-4(3H)-one |
| 585 | 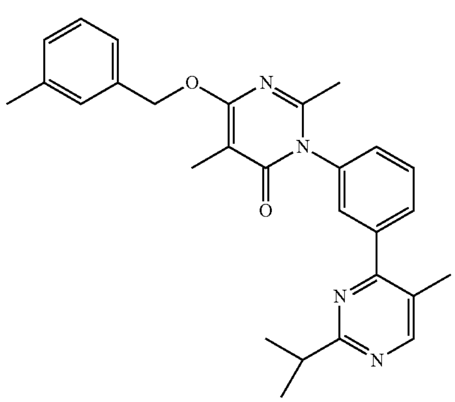 | 3-(3-(2-isopropyl-5-methylpyrimidin-4-yl)phenyl)-2,5-dimethyl-6-((3-methylbenzyl)oxy)pyrimidin-4(3H)-one |

| Compound | Structure | Name |
|---|---|---|
| 586 | 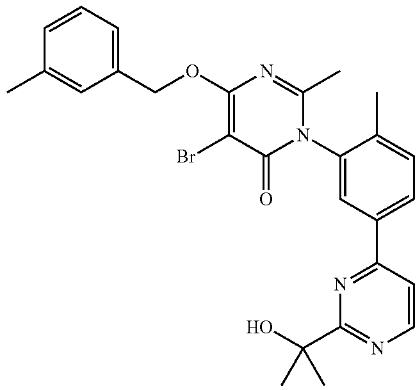 [SMILES: Cc1cccc(COc2nc(C)n(-c3cc(-c4ccnc(C(C)(C)O)n4)ccc3C)c(=O)c2Br)c1] | 5-bromo-3-(5-(2-(2-hydroxypropan-2-yl)pyrimidin-4-yl)-2-methylphenyl)-2-methyl-6-((3-methylbenzyl)oxy)pyrimidin-4(3H)-one |
| 587 | 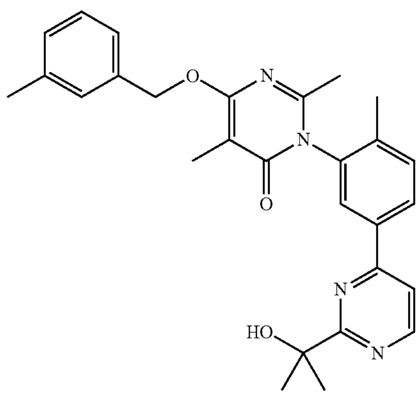 [SMILES: Cc1cccc(COc2nc(C)n(-c3cc(-c4ccnc(C(C)(C)O)n4)ccc3C)c(=O)c2C)c1] | 3-(5-(2-(2-hydroxypropan-2-yl)pyrimidin-4-yl)-2-methylphenyl)-2,5-dimethyl-6-((3-methylbenzyl)oxy)pyrimidin-4(3H)-one |
| 588 | 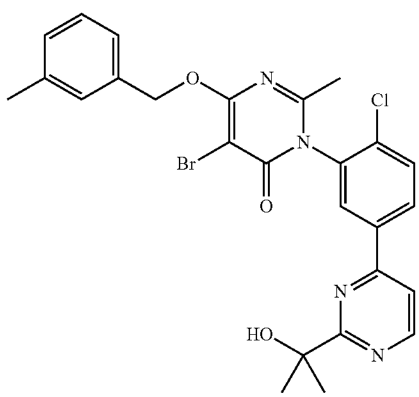 [SMILES: Cc1cccc(COc2nc(C)n(-c3cc(-c4ccnc(C(C)(C)O)n4)ccc3Cl)c(=O)c2Br)c1] | 5-bromo-3-(2-chloro-5-(2-(2-hydroxypropan-2-yl)pyrimidin-4-yl)phenyl)-2-methyl-6-((3-methylbenzyl)oxy)pyrimidin-4(3H)-one |
| 589 | 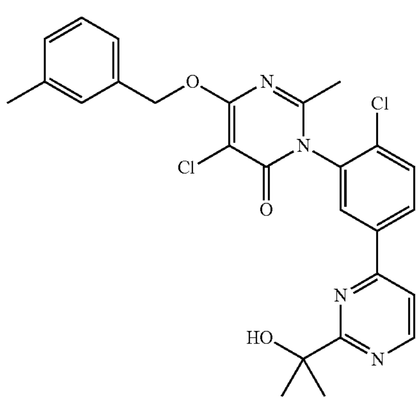 [SMILES: Cc1cccc(COc2nc(C)n(-c3cc(-c4ccnc(C(C)(C)O)n4)ccc3Cl)c(=O)c2Cl)c1] | 5-chloro-3-(2-chloro-5-(2-(2-hydroxypropan-2-yl)pyrimidin-4-yl)phenyl)-2-methyl-6-((3-methylbenzyl)oxy)pyrimidin-4(3H)-one |

| Compound | Structure | Name |
|---|---|---|
| 590 | 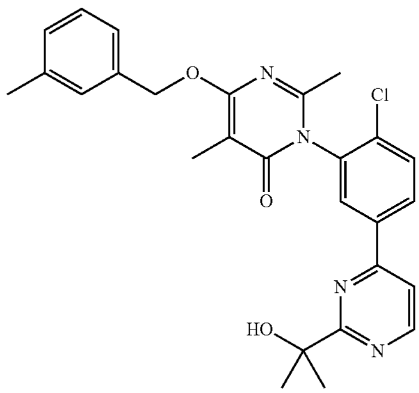 | 3-(2-chloro-5-(2-(2-hydroxypropan-2-yl)pyrimidin-4-yl)phenyl)-2,5-dimethyl-6-((3-methylbenzyl)oxy)pyrimidin-4(3H)-one |
| 591 | 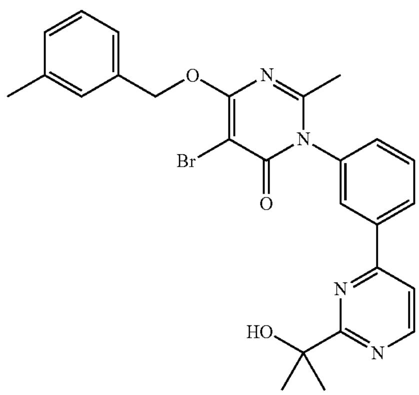 | 5-bromo-3-(3-(2-(2-hydroxypropan-2-yl)pyrimidin-4-yl)phenyl)-2-methyl-6-((3-methylbenzyl)oxy)pyrimidin-4(3H)-one |
| 592 | 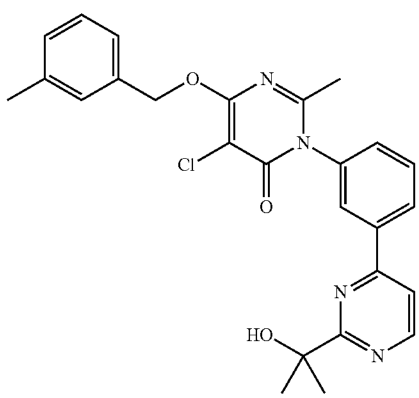 [SMILES: Cc1cccc(COc2nc(C)n(-c3cccc(-c4ccnc(C(C)(C)O)n4)c3)c(=O)c2Cl)c1] | 5-chloro-3-(3-(2-(2-hydroxypropan-2-yl)pyrimidin-4-yl)phenyl)-2-methyl-6-((3-methylbenzyl)oxy)pyrimidin-4(3H)-one |
| 593 | 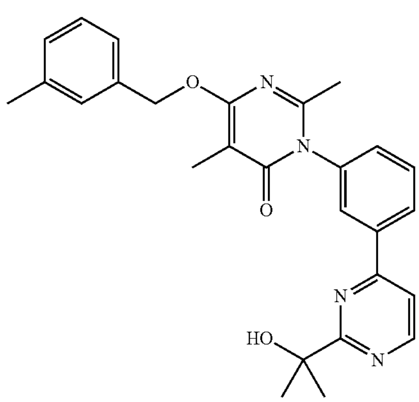 [SMILES: Cc1cccc(COc2nc(C)n(-c3cccc(-c4ccnc(C(C)(C)O)n4)c3)c(=O)c2C)c1] | 3-(3-(2-(2-hydroxypropan-2-yl)pyrimidin-4-yl)phenyl)-2,5-dimethyl-6-((3-methylbenzyl)oxy)pyrimidin-4(3H)-one |

-continued

| Compound | Structure | Name |
|---|---|---|
| 594 | 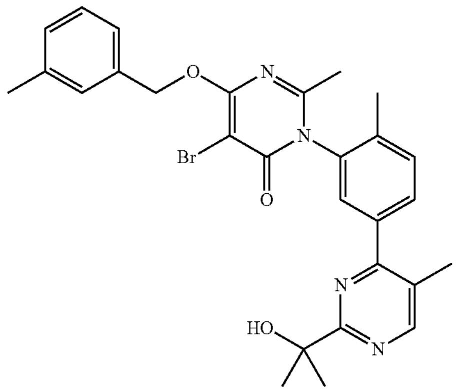 | 5-bromo-3-(5-(2-(2-hydroxypropan-2-yl)-5-methylpyrimidin-4-yl)-2-methylphenyl)-2-methyl-6-((3-methylbenzyl)oxy)pyrimidin-4(3H)-one |
| 595 | 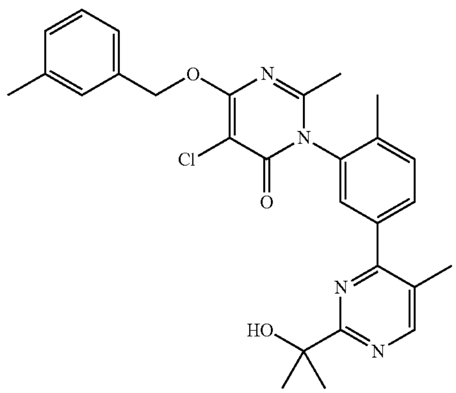 | 5-chloro-3-(5-(2-(2-hydroxypropan-2-yl)-5-methylpyrimidin-4-yl)-2-methylphenyl)-2-methyl-6-((3-methylbenzyl)oxy)pyrimidin-4(3H)-one |
| 596 | 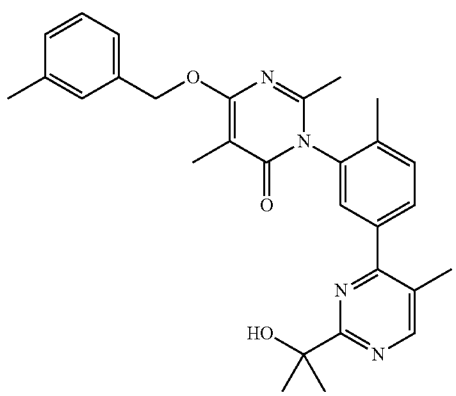 | 3-(5-(2-(2-hydroxypropan-2-yl)-5-methylpyrimidin-4-yl)-2-methylphenyl)-2,5-dimethyl-6-((3-methylbenzyl)oxy)pyrimidin-4(3H)-one |
| 597 | 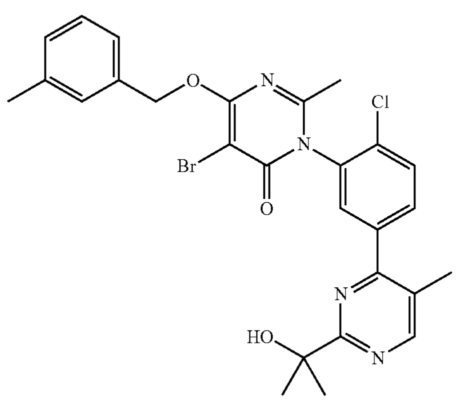 | 5-bromo-3-(2-chloro-5-(2-(2-hydroxypropan-2-yl)-5-methylpyrimidin-4-yl)phenyl)-2-methyl-6-((3-methylbenzyl)oxy)pyrimidin-4(3H)-one |

| Compound | Structure | Name |
|---|---|---|
| 598 | 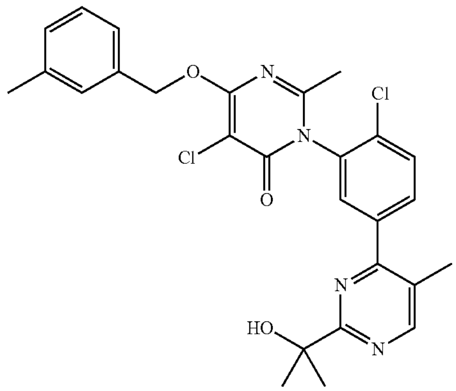 | 5-chloro-3-(2-chloro-5-(2-(2-hydroxypropan-2-yl)-5-methylpyrimidin-4-yl)phenyl)-2-methyl-6-((3-methylbenzyl)oxy)pyrimidin-4(3H)-one |
| 599 | 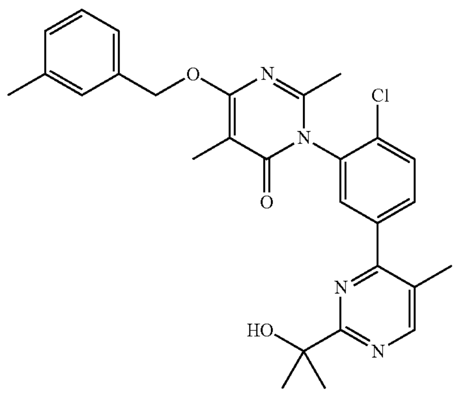 | 3-(2-chloro-5-(2-(2-hydroxypropan-2-yl)-5-methylpyrimidin-4-yl)phenyl)-2,5-dimethyl-6-((3-methylbenzyl)oxy)pyrimidin-4(3H)-one |
| 600 | 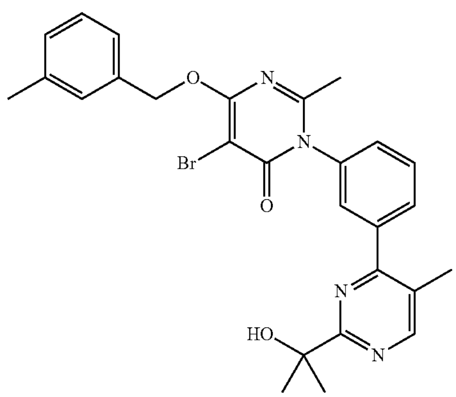 | 5-bromo-3-(3-(2-(2-hydroxypropan-2-yl)-5-methylpyrimidin-4-yl)phenyl)-2-methyl-6-((3-methylbenzyl)oxy)pyrimidin-4(3H)-one |
| 601 | 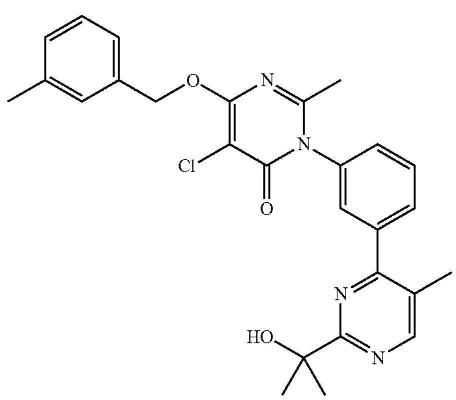 | 5-chloro-3-(3-(2-(2-hydroxypropan-2-yl)-5-methylpyrimidin-4-yl)phenyl)-2-methyl-6-((3-methylbenzyl)oxy)pyrimidin-4(3H)-one |

| Compound | Structure | Name |
|---|---|---|
| 602 | 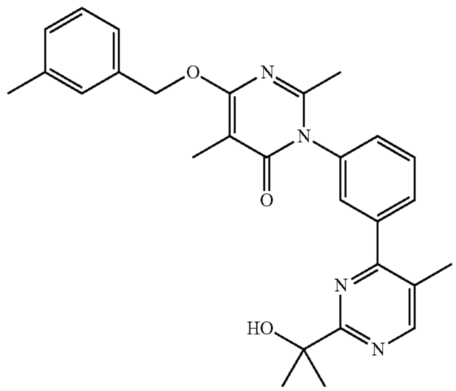 | 3-(3-(2-(2-hydroxypropan-2-yl)-5-methylpyrimidin-4-yl)phenyl)-2,5-dimethyl-6-((3-methylbenzyl)oxy)pyrimidin-4(3H)-one |
| 603 | 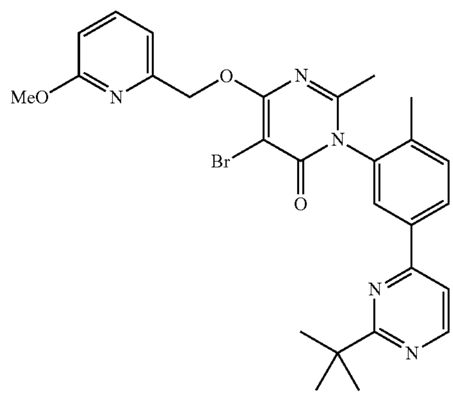 [SMILES: COc1cccc(COc2nc(C)n(-c3cc(-c4ccnc(C(C)(C)C)n4)ccc3C)c(=O)c2Br)n1] | 5-bromo-3-(5-(2-(tert-butyl)pyrimidin-4-yl)-2-methylphenyl)-6-((6-methoxypyridin-2-yl)methoxy)-2-methylpyrimidin-4(3H)-one |
| 604 | 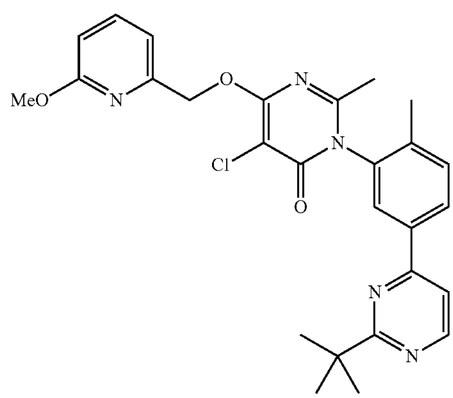 | 3-(5-(2-(tert-butyl)pyrimidin-4-yl)-2-methylphenyl)-5-chloro-6-((6-methoxypyridin-2-yl)methoxy)-2-methylpyrimidin-4(3H)-one |
| 605 | 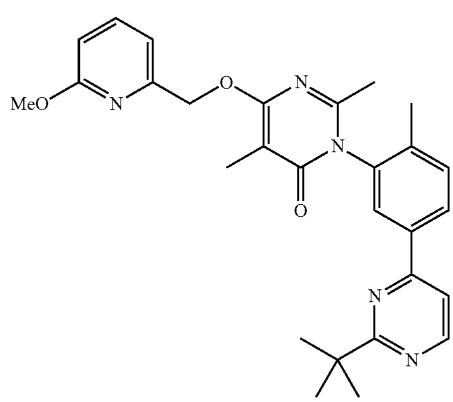 [SMILES: COc1cccc(COc2nc(C)n(-c3cc(-c4ccnc(C(C)(C)C)n4)ccc3C)c(=O)c2C)n1] | 3-(5-(2-(tert-butyl)pyrimidin-4-yl)-2-methylphenyl)-6-((6-methoxypyridin-2-yl)methoxy)-2,5-dimethylpyrimidin-4(3H)-one |

-continued

| Compound | Structure | Name |
|---|---|---|
| 606 | 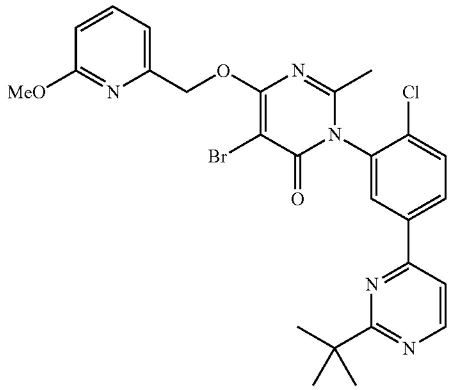 | 5-bromo-3-(5-(2-(tert-butyl)pyrimidin-4-yl)-2-chlorophenyl)-6-((6-methoxypyridin-2-yl)methoxy)-2-methylpyrimidin-4(3H)-one |
| 607 | 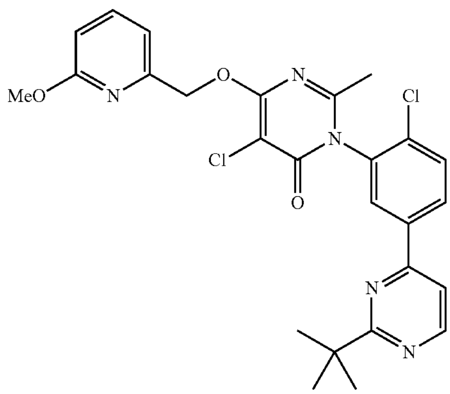 [SMILES: COc1cccc(COc2nc(C)n(-c3cc(-c4ccnc(C(C)(C)C)n4)ccc3Cl)c(=O)c2Cl)n1] | 3-(5-(2-(tert-butyl)pyrimidin-4-yl)-2-chlorophenyl)-5-chloro-6-((6-methoxypyridin-2-yl)methoxy)-2-methylpyrimidin-4(3H)-one |
| 608 | 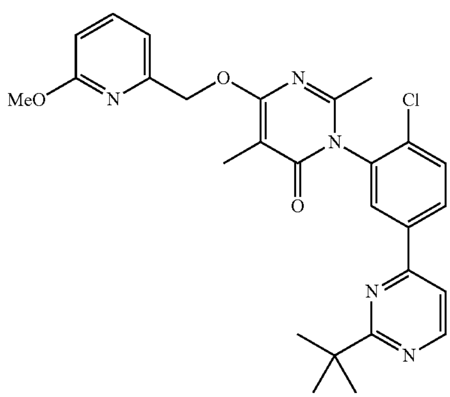 [SMILES: COc1cccc(COc2nc(C)n(-c3cc(-c4ccnc(C(C)(C)C)n4)ccc3Cl)c(=O)c2C)n1] | 3-(5-(2-(tert-butyl)pyrimidin-4-yl)-2-chlorophenyl)-6-((6-methoxypyridin-2-yl)methoxy)-2,5-dimethylpyrimidin-4(3H)-one |
| 609 | 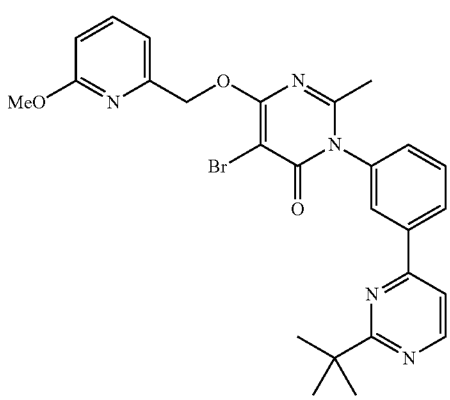 [SMILES: COc1cccc(COc2nc(C)n(-c3cccc(-c4ccnc(C(C)(C)C)n4)c3)c(=O)c2Br)n1] | 5-bromo-3-(3-(2-(tert-butyl)pyrimidin-4-yl)phenyl)-6-((6-methoxypyridin-2-yl)methoxy)-2-methylpyrimidin-4(3H)-one |

| Compound | Structure | Name |
|---|---|---|
| 610 | 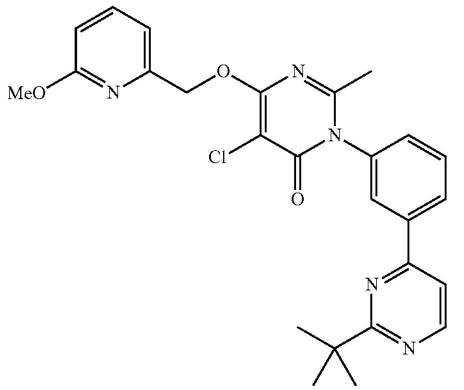 [SMILES: COc1cccc(COc2nc(C)n(-c3cccc(-c4ccnc(C(C)(C)C)n4)c3)c(=O)c2Cl)n1] | 3-(3-(2-(tert-butyl)pyrimidin-4-yl)phenyl)-5-chloro-6-((6-methoxypyridin-2-yl)methoxy)-2-methylpyrimidin-4(3H)-one |
| 611 | 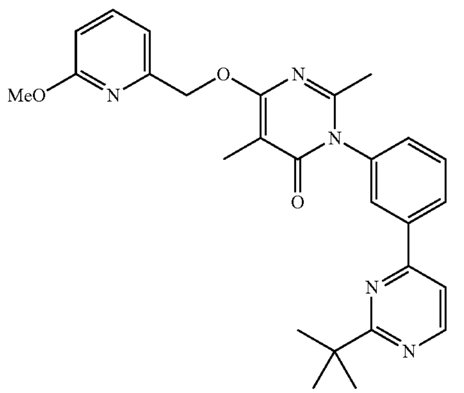 | 3-(3-(2-(tert-butyl)pyrimidin-4-yl)phenyl)-6-((6-methoxypyridin-2-yl)methoxy)-2,5-dimethylpyrimidin-4(3H)-one |
| 612 | 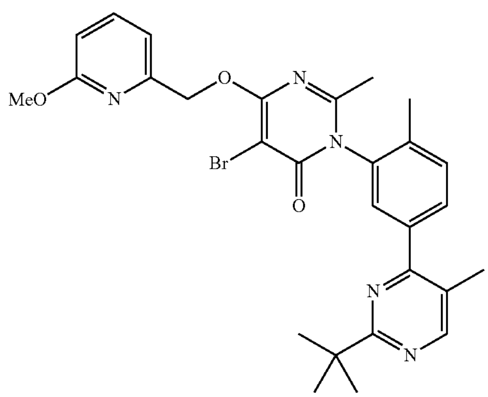 [SMILES: COc1cccc(COc2nc(C)n(-c3cc(-c4nc(C(C)(C)C)ncc4C)ccc3C)c(=O)c2Br)n1] | 5-bromo-3-(5-(2-(tert-butyl)-5-methylpyrimidin-4-yl)-2-methylphenyl)-6-((6-methoxypyridin-2-yl)methoxy)-2-methylpyrimidin-4(3H)-one |
| 613 | 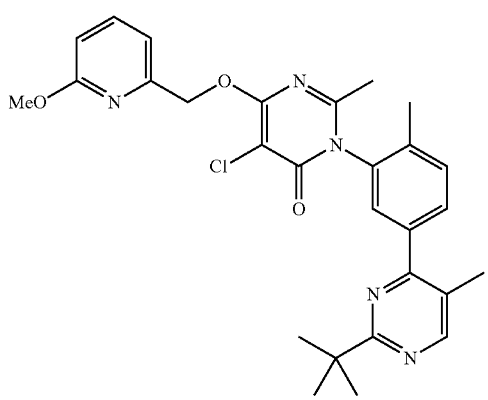 [SMILES: COc1cccc(COc2nc(C)n(-c3cc(-c4nc(C(C)(C)C)ncc4C)ccc3C)c(=O)c2Cl)n1] | 3-(5-(2-(tert-butyl)-5-methylpyrimidin-4-yl)-2-methylphenyl)-5-chloro-6-((6-methoxypyridin-2-yl)methoxy)-2-methylpyrimidin-4(3H)-one |

-continued

| Compound | Structure | Name |
|---|---|---|
| 614 | 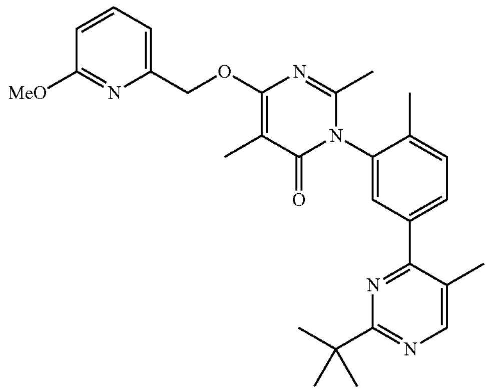 [SMILES: COc1cccc(COc2nc(C)n(-c3cc(-c4nc(C(C)(C)C)ncc4C)ccc3C)c(=O)c2C)n1] | 3-(5-(2-(tert-butyl)-5-methylpyrimidin-4-yl)-2-methylphenyl)-6-((6-methoxypyridin-2-yl)methoxy)-2,5-dimethylpyrimidin-4(3H)-one |
| 615 | 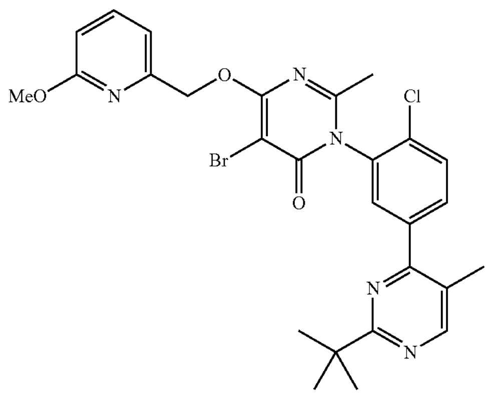 [SMILES: COc1cccc(COc2nc(C)n(-c3cc(-c4nc(C(C)(C)C)ncc4C)ccc3Cl)c(=O)c2Cl)n1] | 5-bromo-3-(5-(2-(tert-butyl)-5-methylpyrimidin-4-yl)-2-chlorophenyl)-6-((6-methoxypyridin-2-yl)methoxy)-2-methylpyrimidin-4(3H)-one |
| 616 | 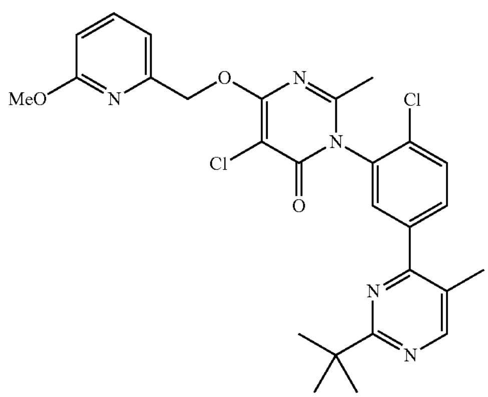 | 3-(5-(2-(tert-butyl)-5-methylpyrimidin-4-yl)-2-chlorophenyl)-5-chloro-6-((6-methoxypyridin-2-yl)methoxy)-2-methylpyrimidin-4(3H)-one |
| 617 | 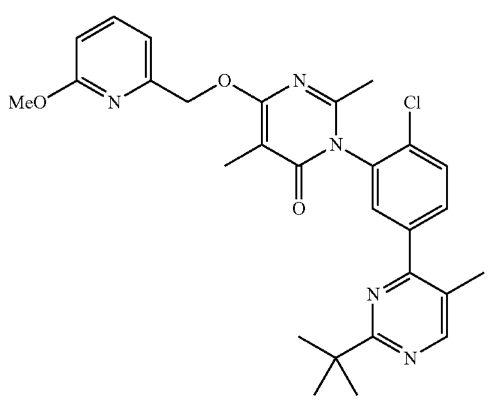 [SMILES: COc1cccc(COc2nc(C)n(-c3cc(-c4nc(C(C)(C)C)ncc4C)ccc3Cl)c(=O)c2C)n1] | 3-(5-(2-(tert-butyl)-5-methylpyrimidin-4-yl)-2-chlorophenyl)-6-((6-methoxypyridin-2-yl)methoxy)-2,5-dimethylpyrimidin-4(3H)-one |

-continued

| Compound | Structure | Name |
|---|---|---|
| 618 | 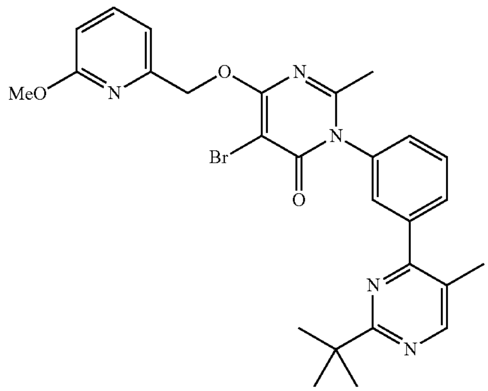 [SMILES: COc1cccc(COc2nc(C)n(-c3cccc(-c4nc(C(C)(C)C)ncc4C)c3)c(=O)c2Cl)n1] | 5-bromo-3-(3-(2-(tert-butyl)-5-methylpyrimidin-4-yl)phenyl)-6-((6-methoxypyridin-2-yl)methoxy)-2-methylpyrimidin-4(3H)-one |
| 619 | 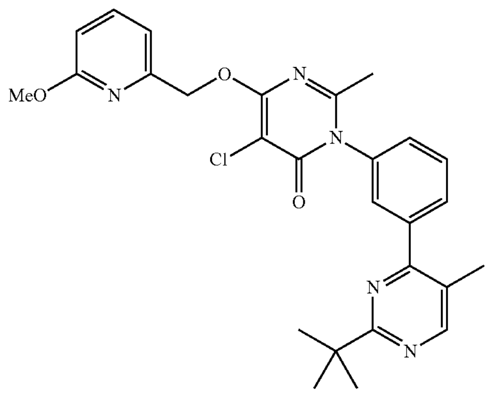 | 3-(3-(2-(tert-butyl)-5-methylpyrimidin-4-yl)phenyl)-5-chloro-6-((6-methoxypyridin-2-yl)methoxy)-2-methylpyrimidin-4(3H)-one |
| 620 | 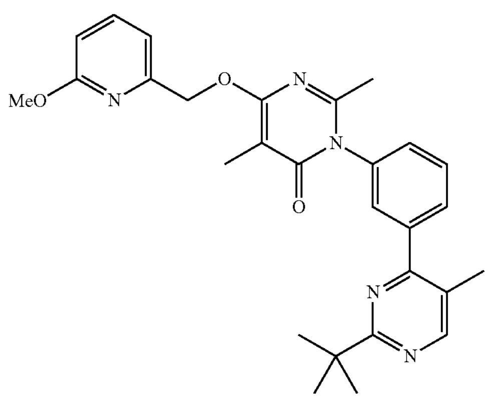 [SMILES: COc1cccc(COc2nc(C)n(-c3cccc(-c4nc(C(C)(C)C)ncc4C)c3)c(=O)c2C)n1] | 3-(3-(2-(tert-butyl)-5-methylpyrimidin-4-yl)phenyl)-6-((6-methoxypyridin-2-yl)methoxy)-2,5-dimethylpyrimidin-4(3H)-one |
| 621 | 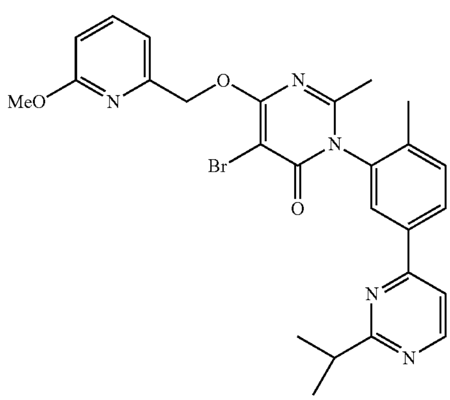 [SMILES: COc1cccc(COc2nc(C)n(-c3cc(-c4ccnc(C(C)C)n4)ccc3C)c(=O)c2Br)n1] | 5-bromo-3-(5-(2-isopropylpyrimidin-4-yl)-2-methylphenyl)-6-((6-methoxypyridin-2-yl)methoxy)-2-methylpyrimidin-4(3H)-one |

| Compound | Structure | Name |
|---|---|---|
| 622 | 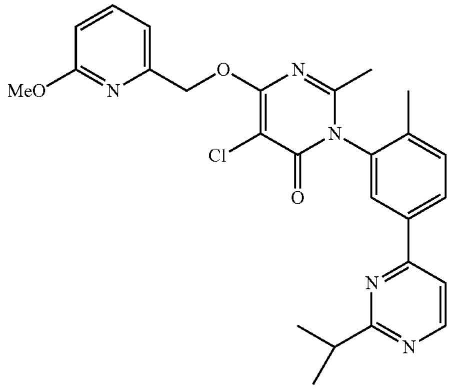 [SMILES: COc1cccc(COc2nc(C)n(-c3cc(-c4ccnc(C(C)C)n4)ccc3C)c(=O)c2Cl)n1] | 5-chloro-3-(5-(2-isopropylpyrimidin-4-yl)-2-methylphenyl)-6-((6-methoxypyridin-2-yl)methoxy)-2-methylpyrimidin-4(3H)-one |
| 623 | 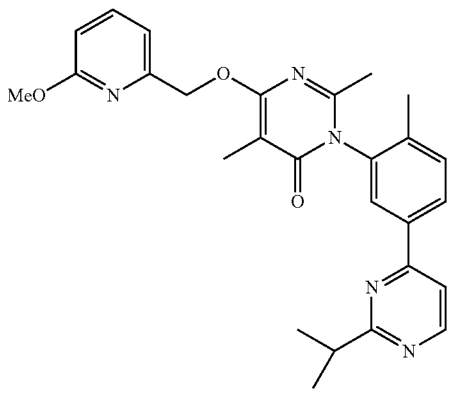 [SMILES: COc1cccc(COc2nc(C)n(-c3cc(-c4ccnc(C(C)C)n4)ccc3C)c(=O)c2C)n1] | 3-(5-(2-isopropylpyrimidin-4-yl)-2-methylphenyl)-6-((6-methoxypyridin-2-yl)methoxy)-2,5-dimethylpyrimidin-4(3H)-one |
| 624 | 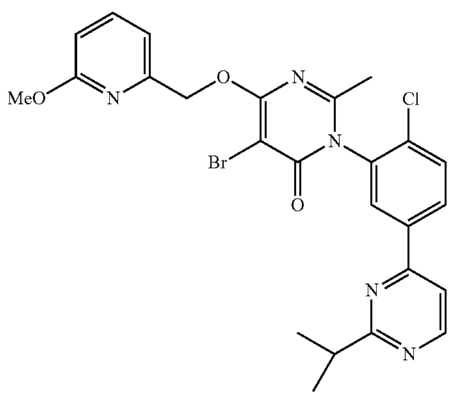 [SMILES: COc1cccc(COc2nc(C)n(-c3cc(-c4ccnc(C(C)C)n4)ccc3Cl)c(=O)c2Br)n1] | 5-bromo-3-(2-chloro-5-(2-isopropylpyrimidin-4-yl)phenyl)-6-((6-methoxypyridin-2-yl)methoxy)-2-methylpyrimidin-4(3H)-one |
| 625 | 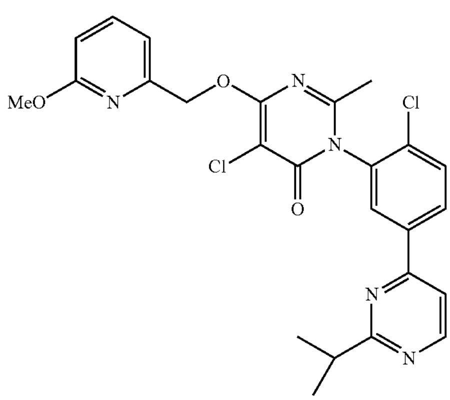 [SMILES: COc1cccc(COc2nc(C)n(-c3cc(-c4ccnc(C(C)C)n4)ccc3Cl)c(=O)c2Cl)n1] | 5-chloro-3-(2-chloro-5-(2-isopropylpyrimidin-4-yl)phenyl)-6-((6-methoxypyridin-2-yl)methoxy)-2-methylpyrimidin-4(3H)-one |

| Compound | Structure | Name |
|---|---|---|
| 626 | 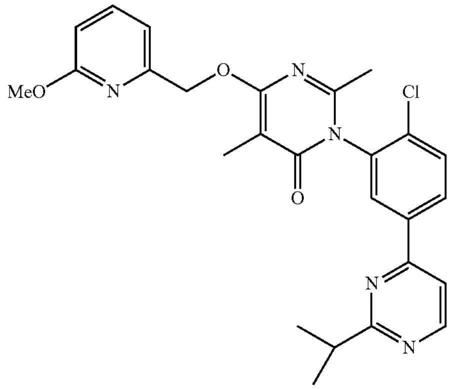 [SMILES: COc1cccc(COc2nc(C)n(-c3cc(-c4ccnc(C(C)C)n4)ccc3Cl)c(=O)c2C)n1] | 3-(2-chloro-5-(2-isopropylpyrimidin-4-yl)phenyl)-6-((6-methoxypyridin-2-yl)methoxy)-2,5-dimethylpyrimidin-4(3H)-one |
| 627 | 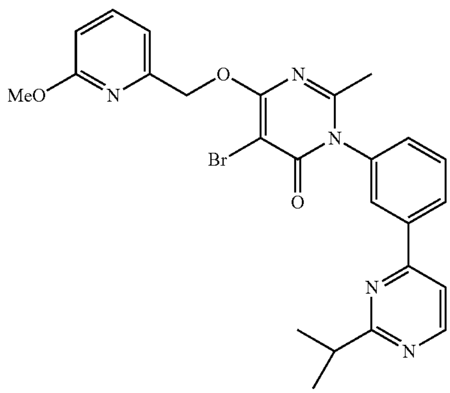 [SMILES: COc1cccc(COc2nc(C)n(-c3cccc(-c4ccnc(C(C)C)n4)c3)c(=O)c2Br)n1] | 5-bromo-3-(3-(2-isopropylpyrimidin-4-yl)phenyl)-6-((6-methoxypyridin-2-yl)methoxy)-2-methylpyrimidin-4(3H)-one |
| 628 | 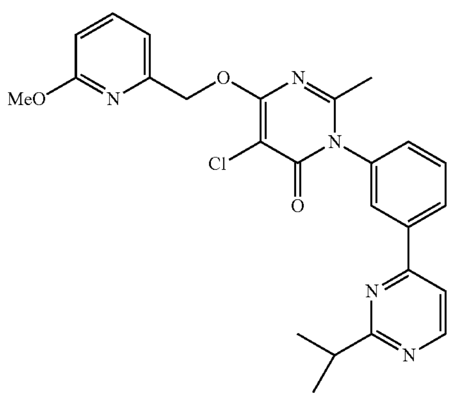 | 5-chloro-3-(3-(2-isopropylpyrimidin-4-yl)phenyl)-6-((6-methoxypyridin-2-yl)methoxy)-2-methylpyrimidin-4(3H)-one |
| 629 | 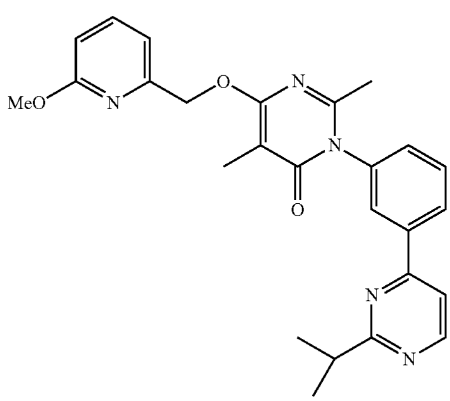 [SMILES: COc1cccc(COc2nc(C)n(-c3cccc(-c4ccnc(C(C)C)n4)c3)c(=O)c2C)n1] | 3-(3-(2-isopropylpyrimidin-4-yl)phenyl)-6-((6-methoxypyridin-2-yl)methoxy)-2,5-dimethylpyrimidin-4(3H)-one |

| Compound | Structure | Name |
|---|---|---|
| 630 | 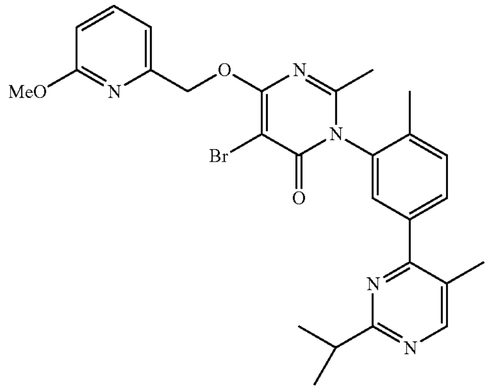 [SMILES: COc1cccc(COc2nc(C)n(-c3cc(-c4nc(C(C)C)ncc4C)ccc3C)c(=O)c2Br)n1] | 5-bromo-3-(5-(2-isopropyl-5-methylpyrimidin-4-yl)-2-methylphenyl)-6-((6-methoxypyridin-2-yl)methoxy)-2-methylpyrimidin-4(3H)-one |
| 631 | 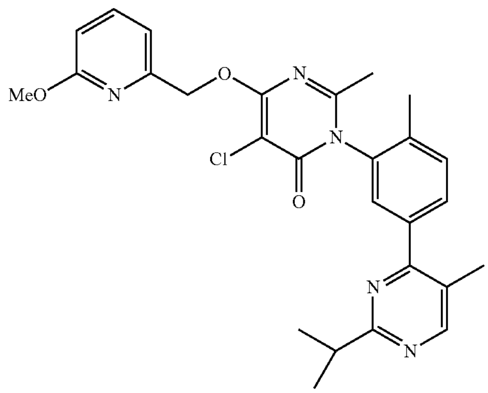 [SMILES: COc1cccc(COc2nc(C)n(-c3cc(-c4nc(C(C)C)ncc4C)ccc3C)c(=O)c2Cl)n1] | 5-chloro-3-(5-(2-isopropyl-5-methylpyrimidin-4-yl)-2-methylphenyl)-6-((6-methoxypyridin-2-yl)methoxy)-2-methylpyrimidin-4(3H)-one |
| 632 | 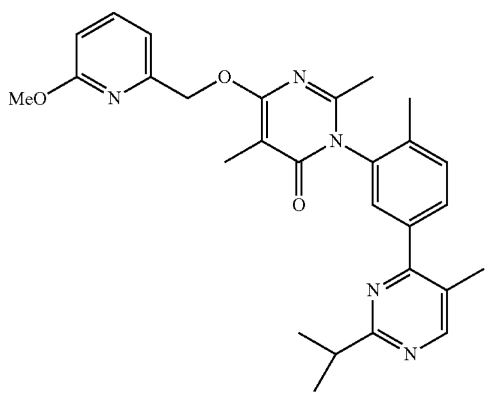 [SMILES: COc1cccc(COc2nc(C)n(-c3cc(-c4nc(C(C)C)ncc4C)ccc3C)c(=O)c2C)n1] | 3-(5-(2-isopropyl-5-methylpyrimidin-4-yl)-2-methylphenyl)-6-((6-methoxypyridin-2-yl)methoxy)-2,5-dimethylpyrimidin-4(3H)-one |
| 633 | 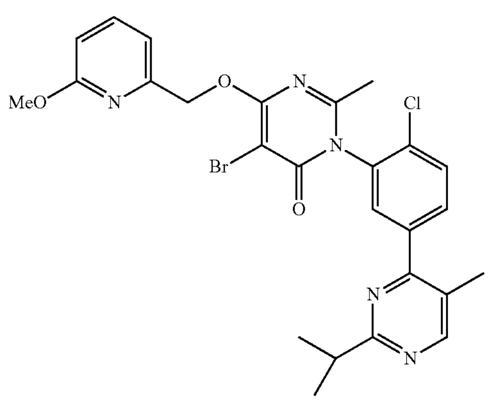 [SMILES: COc1cccc(COc2nc(C)n(-c3cc(-c4nc(C(C)C)ncc4C)ccc3Cl)c(=O)c2Cl)n1] | 5-bromo-3-(2-chloro-5-(2-isopropyl-5-methylpyrimidin-4-yl)phenyl)-6-((6-methoxypyridin-2-yl)methoxy)-2-methylpyrimidin-4(3H)-one |

| Compound | Structure | Name |
|---|---|---|
| 634 | 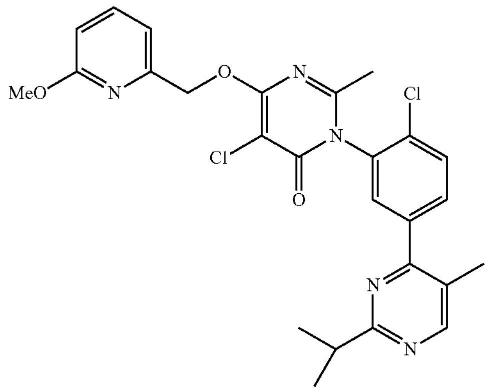 | 5-chloro-3-(2-chloro-5-(2-isopropyl-5-methylpyrimidin-4-yl)phenyl)-6-((6-methoxypyridin-2-yl)methoxy)-2-methylpyrimidin-4(3H)-one |
| 635 | 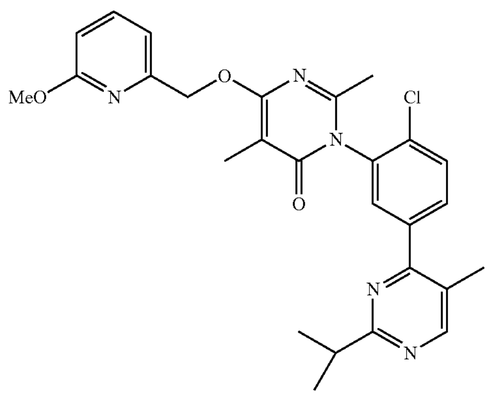 [SMILES: COc1cccc(COc2nc(C)n(-c3cc(-c4nc(C(C)C)ncc4C)ccc3Cl)c(=O)c2C)n1] | 3-(2-chloro-5-(2-isopropyl-5-methylpyrimidin-4-yl)phenyl)-6-((6-methoxypyridin-2-yl)methoxy)-2,5-dimethylpyrimidin-4(3H)-one |
| 636 | 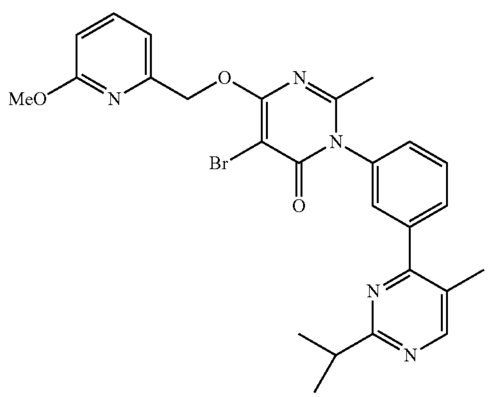 | 5-bromo-3-(3-(2-isopropyl-5-methylpyrimidin-4-yl)phenyl)-6-((6-methoxypyridin-2-yl)methoxy)-2-methylpyrimidin-4(3H)-one |
| 637 | 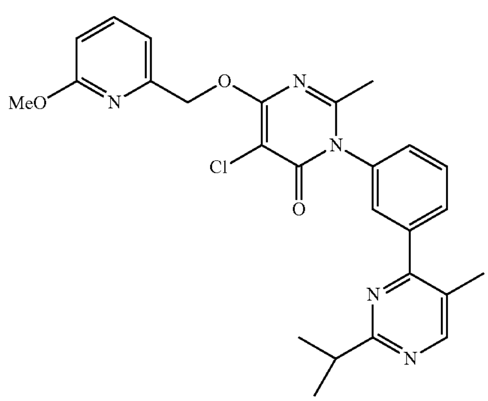 [SMILES: COc1cccc(COc2nc(C)n(-c3cccc(-c4nc(C(C)C)ncc4C)c3)c(=O)c2Cl)n1] | 5-chloro-3-(3-(2-isopropyl-5-methylpyrimidin-4-yl)phenyl)-6-((6-methoxypyridin-2-yl)methoxy)-2-methylpyrimidin-4(3H)-one |

| Compound | Structure | Name |
|---|---|---|
| 638 | 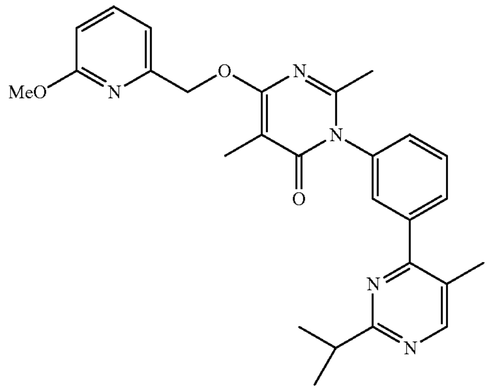 [SMILES: COc1cccc(COc2nc(C)n(-c3cccc(-c4nc(C(C)C)ncc4C)c3)c(=O)c2C)n1] | 3-(3-(2-isopropyl-5-methylpyrimidin-4-yl)phenyl)-6-((6-methoxypyridin-2-yl)methoxy)-2,5-dimethylpyrimidin-4(3H)-one |
| 639 | 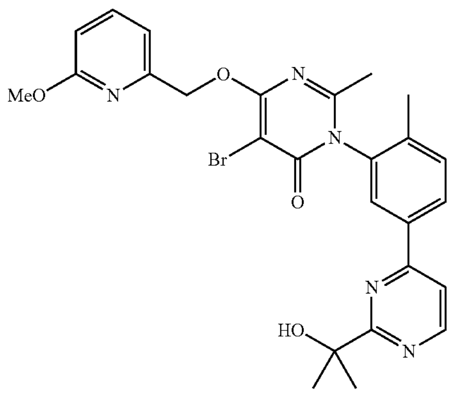 [SMILES: COc1cccc(COc2nc(C)n(-c3cc(-c4ccnc(C(C)(C)O)n4)ccc3C)c(=O)c2Br)n1] | 5-bromo-3-(5-(2-(2-hydroxypropan-2-yl)pyrimidin-4-yl)-2-methylphenyl)-6-((6-methoxypyridin-2-yl)methoxy)-2-methylpyrimidin-4(3H)-one |
| 640 | 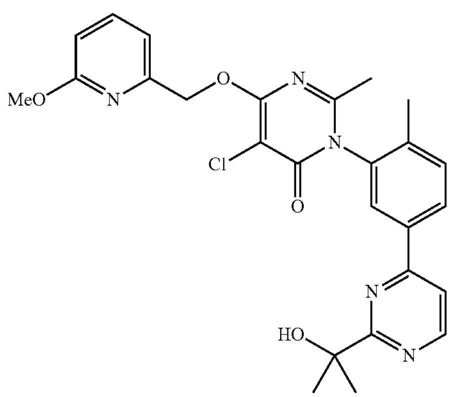 [SMILES: COc1cccc(COc2nc(C)n(-c3cc(-c4ccnc(C(C)(C)O)n4)ccc3C)c(=O)c2Cl)n1] | 5-chloro-3-(5-(2-(2-hydroxypropan-2-yl)pyrimidin-4-yl)-2-methylphenyl)-6-((6-methoxypyridin-2-yl)methoxy)-2-methylpyrimidin-4(3H)-one |
| 641 | 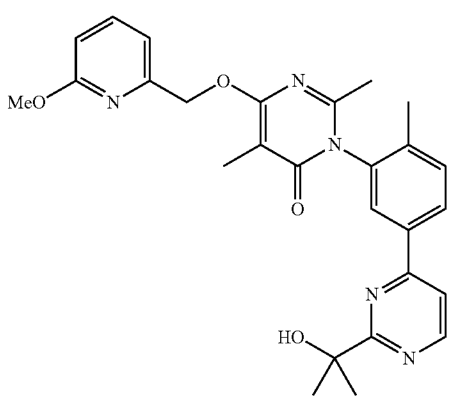 [SMILES: COc1cccc(COc2nc(C)n(-c3cc(-c4ccnc(C(C)(C)O)n4)ccc3C)c(=O)c2C)n1] | 3-(5-(2-(2-hydroxypropan-2-yl)pyrimidin-4-yl)-2-methylphenyl)-6-((6-methoxypyridin-2-yl)methoxy)-2,5-dimethylpyrimidin-4(3H)-one |

| Compound | Structure | Name |
|---|---|---|
| 642 | 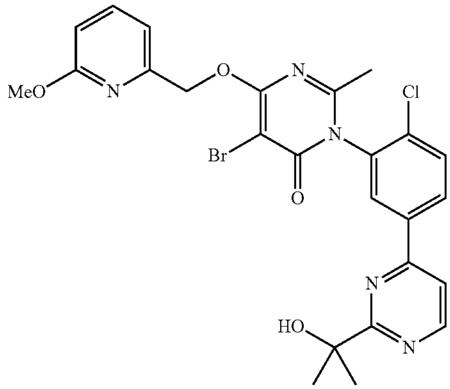 [SMILES: COc1cccc(COc2nc(C)n(-c3cc(-c4ccnc(C(C)(C)O)n4)ccc3Cl)c(=O)c2Br)n1] | 5-bromo-3-(2-chloro-5-(2-(2-hydroxypropan-2-yl)pyrimidin-4-yl)phenyl)-6-((6-methoxypyridin-2-yl)methoxy)-2-methylpyrimidin-4(3H)-one |
| 643 | 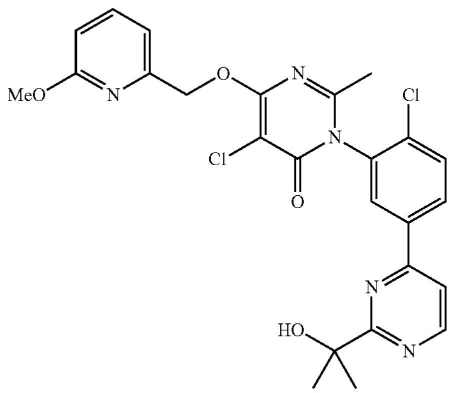 [SMILES: COc1cccc(COc2nc(C)n(-c3cc(-c4ccnc(C(C)(C)O)n4)ccc3Cl)c(=O)c2Cl)n1] | 5-chloro-3-(2-chloro-5-(2-(2-hydroxypropan-2-yl)pyrimidin-4-yl)phenyl)-6-((6-methoxypyridin-2-yl)methoxy)-2-methylpyrimidin-4(3H)-one |
| 644 | 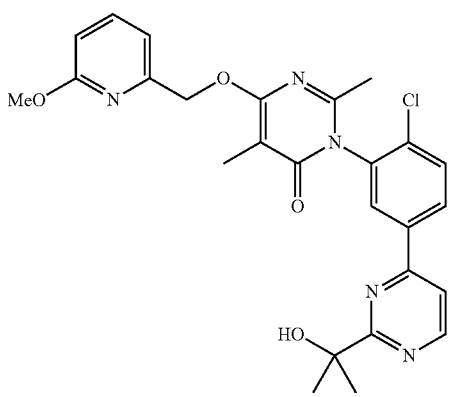 [SMILES: COc1cccc(COc2nc(C)n(-c3cc(-c4ccnc(C(C)(C)O)n4)ccc3Cl)c(=O)c2C)n1] | 3-(2-chloro-5-(2-(2-hydroxypropan-2-yl)pyrimidin-4-yl)phenyl)-6-((6-methoxypyridin-2-yl)methoxy)-2,5-dimethylpyrimidin-4(3H)-one |
| 645 | 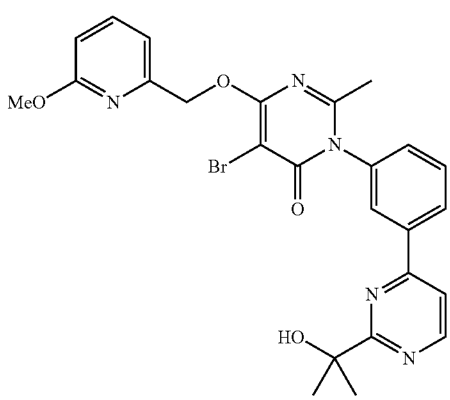 [SMILES: COc1cccc(COc2nc(C)n(-c3cccc(-c4ccnc(C(C)(C)O)n4)c3)c(=O)c2Br)n1] | 5-bromo-3-(3-(2-(2-hydroxypropan-2-yl)pyrimidin-4-yl)phenyl)-6-((6-methoxypyridin-2-yl)methoxy)-2-methylpyrimidin-4(3H)-one |

-continued

| Compound | Structure | Name |
|---|---|---|
| 646 | 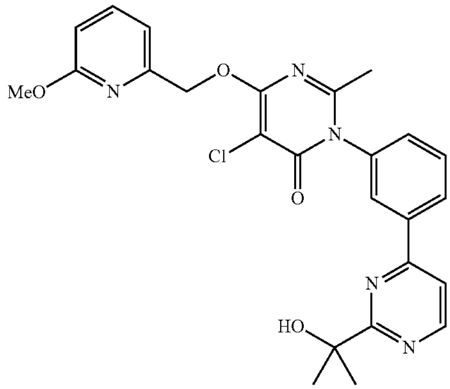 | 5-chloro-3-(3-(2-(2-hydroxypropan-2-yl)pyrimidin-4-yl)phenyl)-6-((6-methoxypyridin-2-yl)methoxy)-2-methylpyrimidin-4(3H)-one |
| 647 | 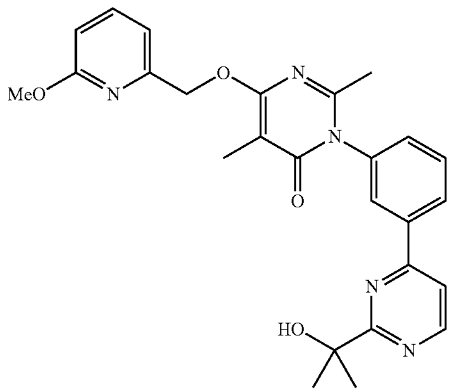 [SMILES: COc1cccc(COc2nc(C)n(-c3cccc(-c4ccnc(C(C)(C)O)n4)c3)c(=O)c2C)n1] | 3-(3-(2-(2-hydroxypropan-2-yl)pyrimidin-4-yl)phenyl)-6-((6-methoxypyridin-2-yl)methoxy)-2,5-dimethylpyrimidin-4(3H)-one |
| 648 | 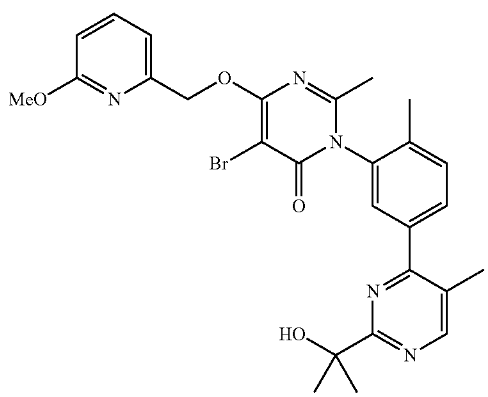 [SMILES: COc1cccc(COc2nc(C)n(-c3cc(-c4nc(C(C)(C)O)ncc4C)ccc3C)c(=O)c2Cl)n1] | 5-bromo-3-(5-(2-(2-hydroxypropan-2-yl)-5-methylpyrimidin-4-yl)-2-methylphenyl)-6-((6-methoxypyridin-2-yl)methoxy)-2-methylpyrimidin-4(3H)-one |
| 649 | 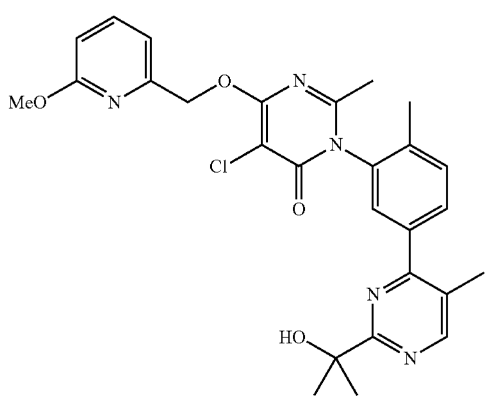 | 5-chloro-3-(5-(2-(2-hydroxypropan-2-yl)-5-methylpyrimidin-4-yl)-2-methylphenyl)-6-((6-methoxypyridin-2-yl)methoxy)-2-methylpyrimidin-4(3H)-one |

-continued

| Compound | Structure | Name |
|---|---|---|
| 650 | 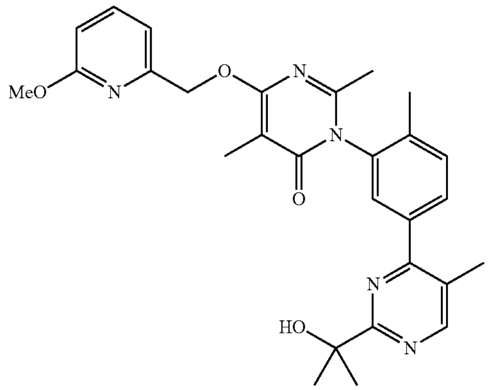 [SMILES: COc1cccc(COc2nc(C)n(-c3cc(-c4nc(C(C)(C)O)ncc4C)ccc3C)c(=O)c2C)n1] | 3-(5-(2-(2-hydroxypropan-2-yl)-5-methylpyrimidin-4-yl)-2-methylphenyl)-6-((6-methoxypyridin-2-yl)methoxy)-2,5-dimethylpyrimidin-4(3H)-one |
| 651 | 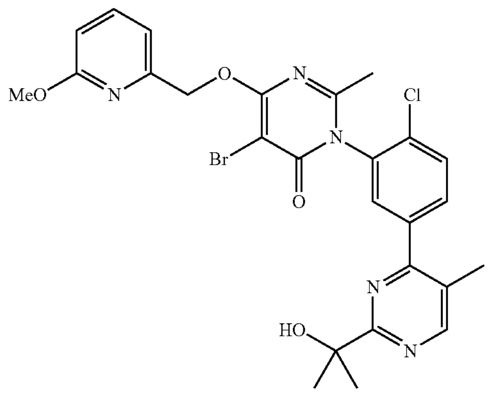 | 5-bromo-3-(2-chloro-5-(2-(2-hydroxypropan-2-yl)-5-methylpyrimidin-4-yl)phenyl)-6-((6-methoxypyridin-2-yl)methoxy)-2-methylpyrimidin-4(3H)-one |
| 652 | 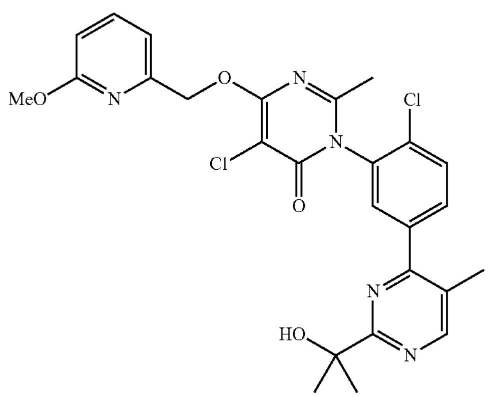 [SMILES: COc1cccc(COc2nc(C)n(-c3cc(-c4nc(C(C)(C)O)ncc4C)ccc3Cl)c(=O)c2Cl)n1] | 5-chloro-3-(2-chloro-5-(2-(2-hydroxypropan-2-yl)-5-methylpyrimidin-4-yl)phenyl)-6-((6-methoxypyridin-2-yl)methoxy)-2-methylpyrimidin-4(3H)-one |
| 653 | 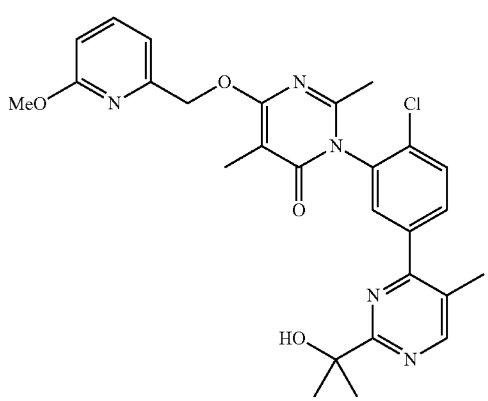 | 3-(2-chloro-5-(2-(2-hydroxypropan-2-yl)-5-methylpyrimidin-4-yl)phenyl)-6-((6-methoxypyridin-2-yl)methoxy)-2,5-dimethylpyrimidin-4(3H)-one |

| Compound | Structure | Name |
|---|---|---|
| 654 | 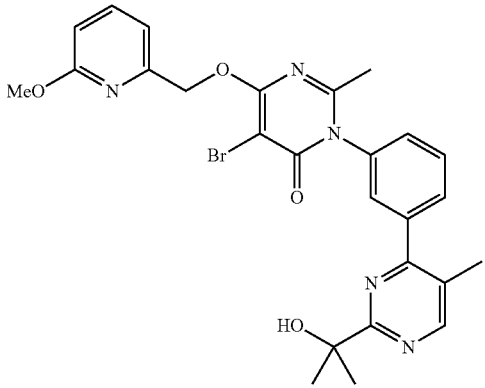 | 5-bromo-3-(3-(2-(2-hydroxypropan-2-yl)-5-methylpyrimidin-4-yl)phenyl)-6-((6-methoxypyridin-2-yl)methoxy)-2-methylpyrimidin-4(3H)-one |
| 655 | 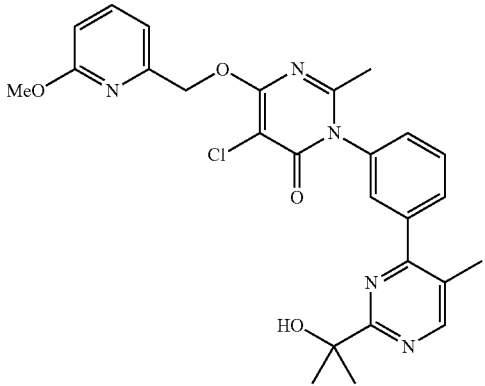 [SMILES: COc1cccc(COc2nc(C)n(-c3cccc(-c4nc(C(C)(C)O)ncc4C)c3)c(=O)c2Cl)n1] | 5-chloro-3-(3-(2-(2-hydroxypropan-2-yl)-5-methylpyrimidin-4-yl)phenyl)-6-((6-methoxypyridin-2-yl)methoxy)-2-methylpyrimidin-4(3H)-one |
| 656 | 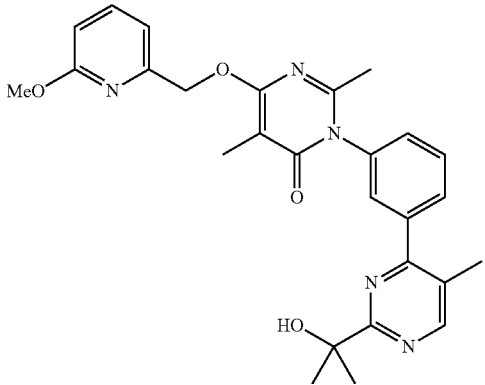 [SMILES: COc1cccc(COc2nc(C)n(-c3cccc(-c4nc(C(C)(C)O)ncc4C)c3)c(=O)c2C)n1] | 3-(3-(2-(2-hydroxypropan-2-yl)-5-methylpyrimidin-4-yl)phenyl)-6-((6-methoxypyridin-2-yl)methoxy)-2,5-dimethylpyrimidin-4(3H)-one |
| 657 | 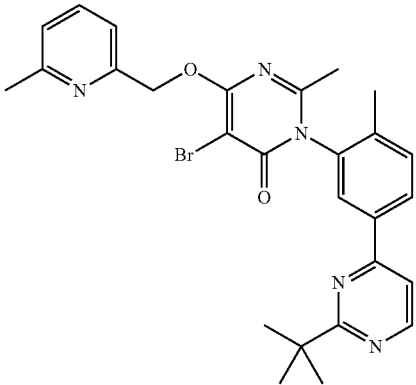 [SMILES: Cc1cccc(COc2nc(C)n(-c3cc(-c4ccnc(C(C)(C)C)n4)ccc3C)c(=O)c2Br)n1] | 5-bromo-3-(5-(2-(tert-butyl)pyrimidin-4-yl)-2-methylphenyl)-2-methyl-6-((6-methylpyridin-2-yl)methoxy)pyrimidin-4(3H)-one |

-continued

| Compound | Structure | Name |
|---|---|---|
| 658 | 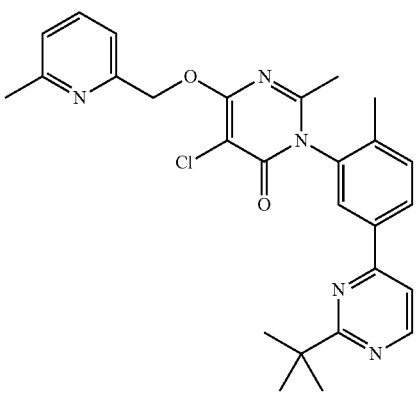 | 3-(5-(2-(tert-butyl)pyrimidin-4-yl)-2-methylphenyl)-5-chloro-2-methyl-6-((6-methylpyridin-2-yl)methoxy)pyrimidin-4(3H)-one |
| 659 | 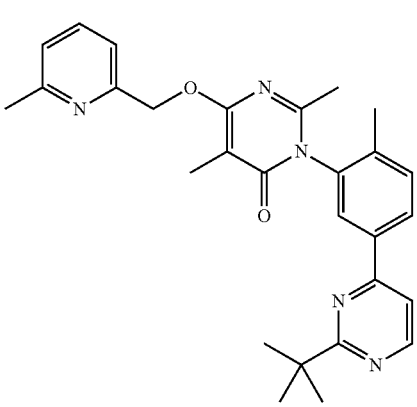 [SMILES: Cc1cccc(COc2nc(C)n(-c3cc(-c4ccnc(C(C)(C)C)n4)ccc3C)c(=O)c2C)n1] | 3-(5-(2-(tert-butyl)pyrimidin-4-yl)-2-methylphenyl)-2,5-dimethyl-6-((6-methylpyridin-2-yl)methoxy)pyrimidin-4(3H)-one |
| 660 | 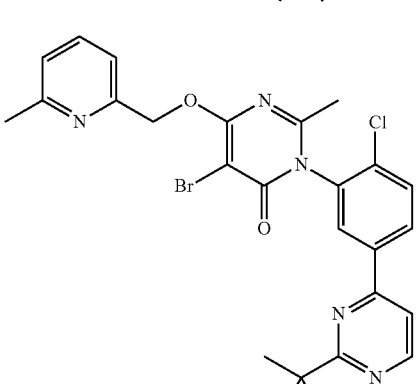 | 5-bromo-3-(5-(2-(tert-butyl)pyrimidin-4-yl)-2-chlorophenyl)-2-methyl-6-((6-methylpyridin-2-yl)methoxy)pyrimidin-4(3H)-one |
| 661 | 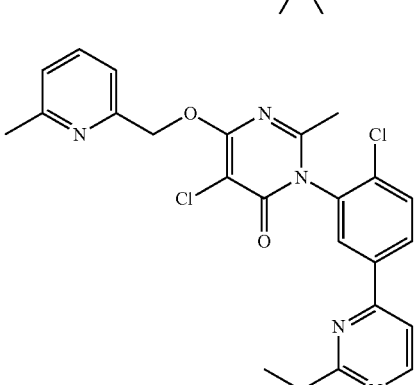 | 3-(5-(2-(tert-butyl)pyrimidin-4-yl)-2-chlorophenyl)-5-chloro-2-methyl-6-((6-methylpyridin-2-yl)methoxy)pyrimidin-4(3H)-one |

| Compound | Structure | Name |
|---|---|---|
| 662 | 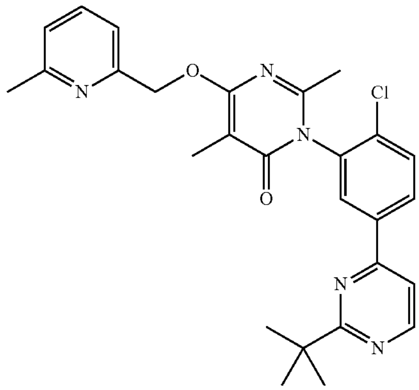 [SMILES: Cc1cccc(COc2nc(C)n(-c3cc(-c4ccnc(C(C)(C)C)n4)ccc3Cl)c(=O)c2C)n1] | 3-(5-(2-(tert-butyl)pyrimidin-4-yl)-2-chlorophenyl)-2,5-dimethyl-6-((6-methylpyridin-2-yl)methoxy)pyrimidin-4(3H)-one |
| 663 | 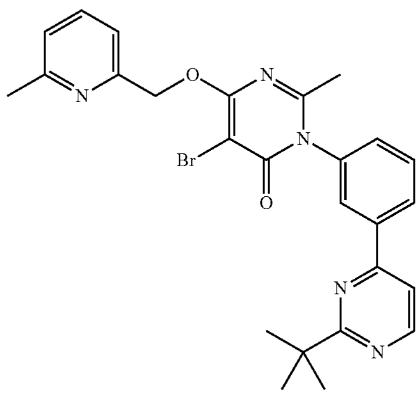 [SMILES: Cc1cccc(COc2nc(C)n(-c3cccc(-c4ccnc(C(C)(C)C)n4)c3)c(=O)c2Cl)n1] | 5-bromo-3-(3-(2-(tert-butyl)pyrimidin-4-yl)phenyl)-2-methyl-6-((6-methylpyridin-2-yl)methoxy)pyrimidin-4(3H)-one |
| 664 | 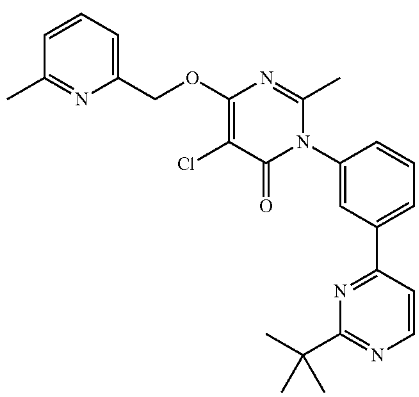 | 3-(3-(2-(tert-butyl)pyrimidin-4-yl)phenyl)-5-chloro-2-methyl-6-((6-methylpyridin-2-yl)methoxy)pyrimidin-4(3H)-one |
| 665 | 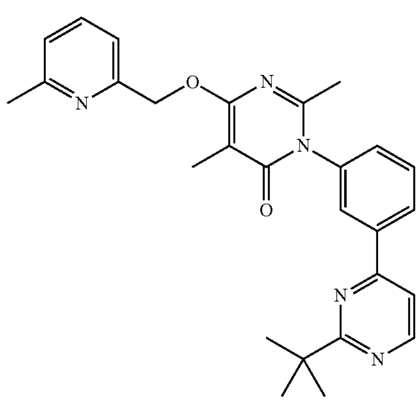 [SMILES: Cc1cccc(COc2nc(C)n(-c3cccc(-c4ccnc(C(C)(C)C)n4)c3)c(=O)c2C)n1] | 3-(3-(2-(tert-butyl)pyrimidin-4-yl)phenyl)-2,5-dimethyl-6-((6-methylpyridin-2-yl)methoxy)pyrimidin-4(3H)-one |

| Compound | Structure | Name |
|---|---|---|
| 666 | 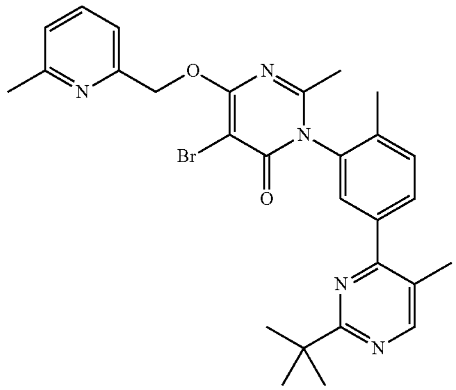 | 5-bromo-3-(5-(2-(tert-butyl)-5-methylpyrimidin-4-yl)-2-methylphenyl)-2-methyl-6-((6-methylpyridin-2-yl)methoxy)pyrimidin-4(3H)-one |
| 667 | 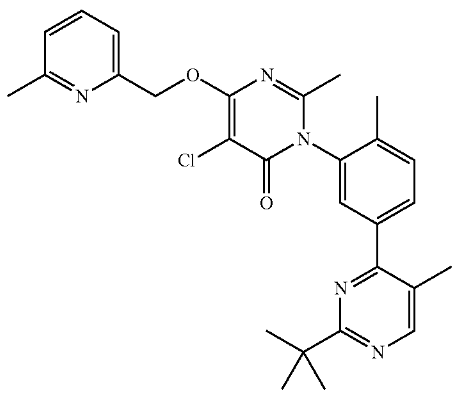 | 3-(5-(2-(tert-butyl)-5-methylpyrimidin-4-yl)-2-methylphenyl)-5-chloro-2-methyl-6-((6-methylpyridin-2-yl)methoxy)pyrimidin-4(3H)-one |
| 668 | 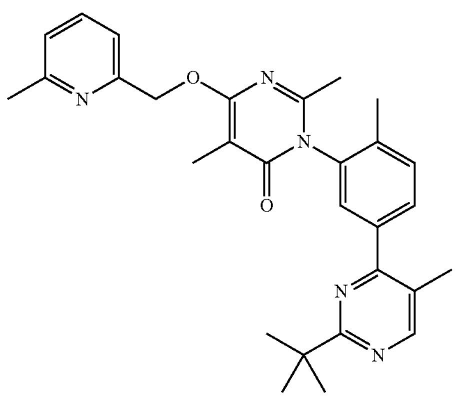 | 3-(5-(2-(tert-butyl)-5-methylpyrimidin-4-yl)-2-methylphenyl)-2,5-dimethyl-6-((6-methylpyridin-2-yl)methoxy)pyrimidin-4(3H)-one |
| 669 | 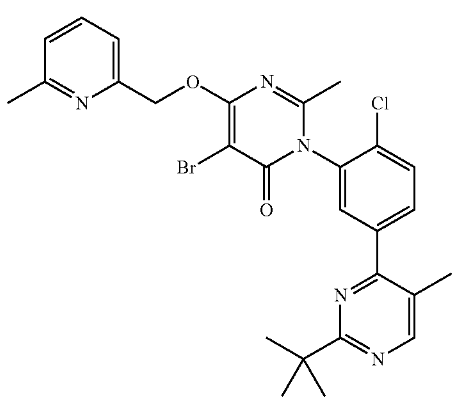 | 5-bromo-3-(5-(2-(tert-butyl)-5-methylpyrimidin-4-yl)-2-chlorophenyl)-2-methyl-6-((6-methylpyridin-2-yl)methoxy)pyrimidin-4(3H)-one |

-continued

| Compound | Structure | Name |
|---|---|---|
| 670 | 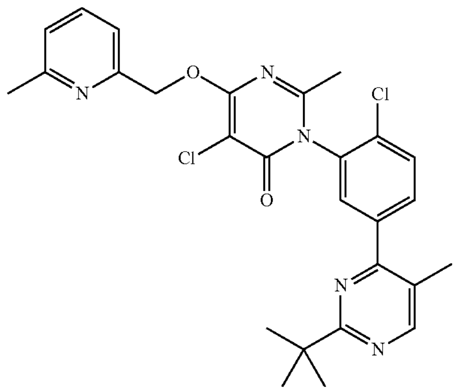 | 3-(5-(2-(tert-butyl)-5-methylpyrimidin-4-yl)-2-chlorophenyl)-5-chloro-2-methyl-6-((6-methylpyridin-2-yl)methoxy)pyrimidin-4(3H)-one |
| 671 | 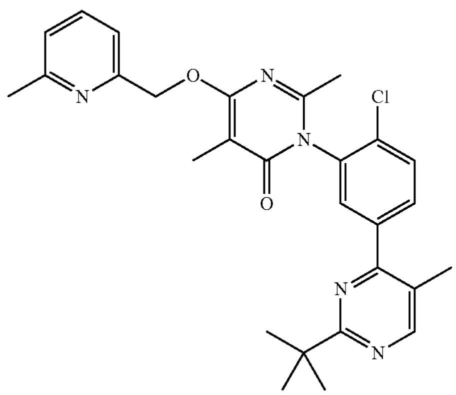 | 3-(5-(2-(tert-butyl)-5-methylpyrimidin-4-yl)-2-chlorophenyl)-2,5-dimethyl-6-((6-methylpyridin-2-yl)methoxy)pyrimidin-4(3H)-one |
| 672 | 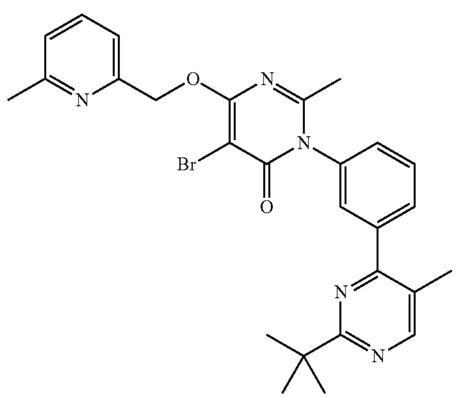 | 5-bromo-3-(3-(2-(tert-butyl)-5-methylpyrimidin-4-yl)phenyl)-2-methyl-6-((6-methylpyridin-2-yl)methoxy)pyrimidin-4(3H)-one |
| 673 | 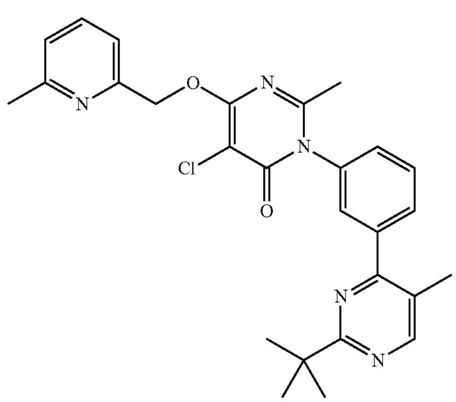 | 3-(3-(2-(tert-butyl)-5-methylpyrimidin-4-yl)phenyl)-5-chloro-2-methyl-6-((6-methylpyridin-2-yl)methoxy)pyrimidin-4(3H)-one |

-continued

| Compound | Structure | Name |
|---|---|---|
| 674 | 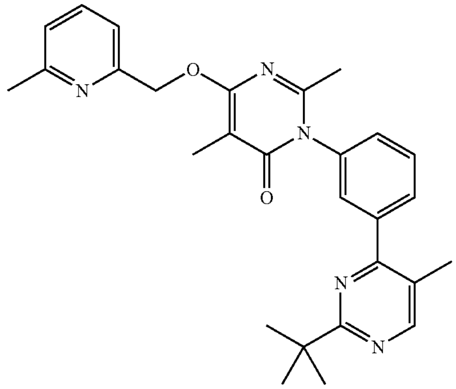 | 3-(3-(2-(tert-butyl)-5-methylpyrimidin-4-yl)phenyl)-2,5-dimethyl-6-((6-methylpyridin-2-yl)methoxy)pyrimidin-4(3H)-one |
| 675 | 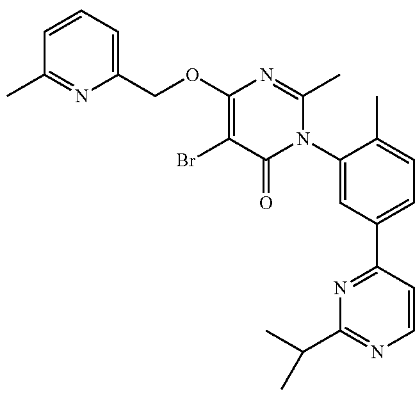 [SMILES: Cc1cccc(COc2nc(C)n(-c3cc(-c4ccnc(C(C)C)n4)ccc3C)c(=O)c2Cl)n1] | 5-bromo-3-(5-(2-isopropylpyrimidin-4-yl)-2-methylphenyl)-2-methyl-6-((6-methylpyridin-2-yl)methoxy)pyrimidin-4(3HY)-one |
| 676 | 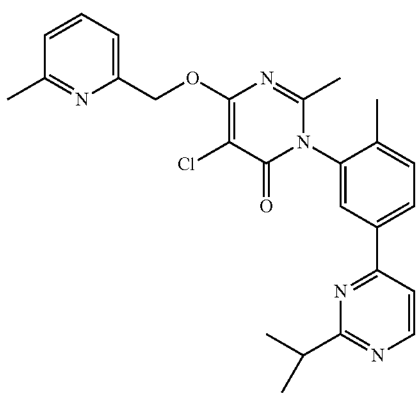 | 5-chloro-3-(5-(2-isopropylpyrimidin-4-yl)-2-methylphenyl)-2-methyl-6-((6-methylpyridin-2-yl)methoxy)pyrimidin-4(3H)-one |
| 677 | 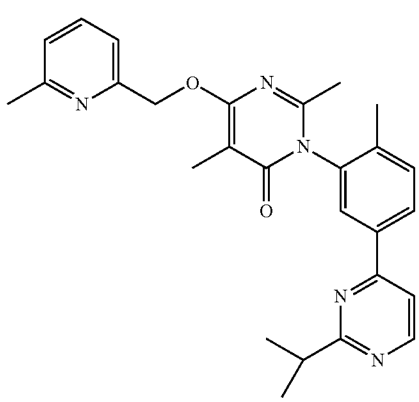 [SMILES: Cc1cccc(COc2nc(C)n(-c3cc(-c4ccnc(C(C)C)n4)ccc3C)c(=O)c2C)n1] | 3-(5-(2-isopropylpyrimidin-4-yl)-2-methylphenyl)-2,5-dimethyl-6-((6-methylpyridin-2-yl)methoxy)pyrimidin-4(3H)-one |

| Compound | Structure | Name |
|---|---|---|
| 678 | 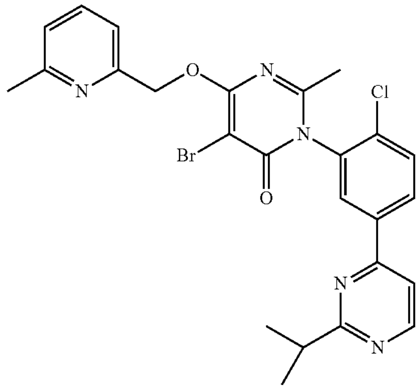 | 5-bromo-3-(2-chloro-5-(2-isopropylpyrimidin-4-yl)phenyl)-2-methyl-6-((6-methylpyridin-2-yl)methoxy)pyrimidin-4(3H)-one |
| 679 | 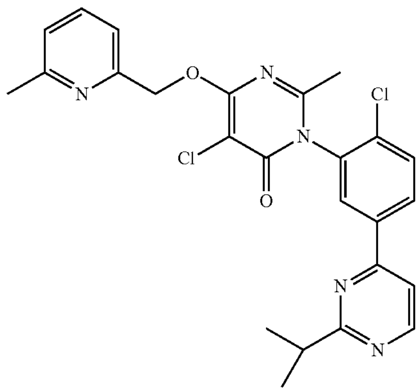 | 5-chloro-3-(2-chloro-5-(2-isopropylpyrimidin-4-yl)phenyl)-2-methyl-6-((6-methylpyridin-2-yl)methoxy)pyrimidin-4(3H)-one |
| 680 | 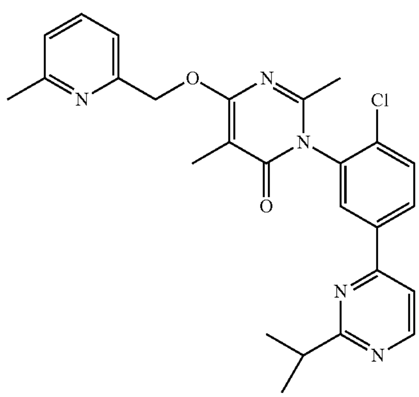 | 3-(2-chloro-5-(2-isopropylpyrimidin-4-yl)phenyl)-2,5-dimethyl-6-((6-methylpyridin-2-yl)methoxy)pyrimidin-4(3H)-one |
| 681 | 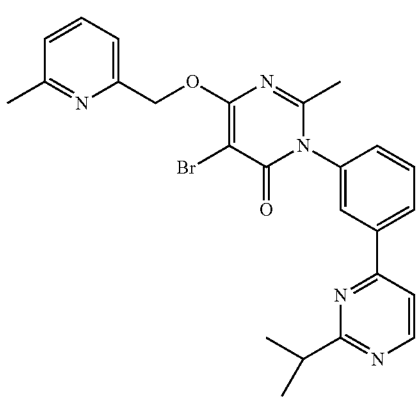 | 5-bromo-3-(3-(2-isopropylpyrimidin-4-yl)phenyl)-2-methyl-6-((6-methylpyridin-2-yl)methoxy)pyrimidin-4(3H)-one |

-continued

| Compound | Structure | Name |
|---|---|---|
| 682 | 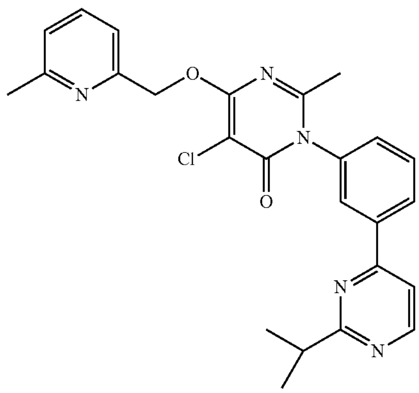 [SMILES: Cc1cccc(COc2nc(C)n(-c3cccc(-c4ccnc(C(C)C)n4)c3)c(=O)c2Cl)n1] | 5-chloro-3-(3-(2-isopropylpyrimidin-4-yl)phenyl)-2-methyl-6-((6-methylpyridin-2-yl)methoxy)pyrimidin-4(3H)-one |
| 683 | 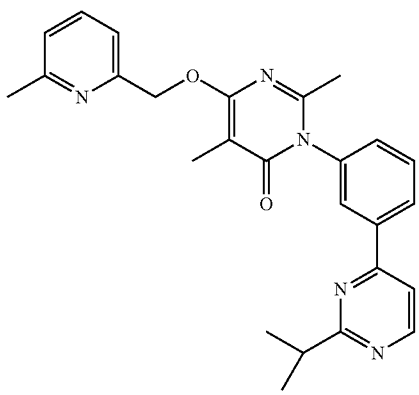 [SMILES: Cc1cccc(COc2nc(C)n(-c3cccc(-c4ccnc(C(C)C)n4)c3)c(=O)c2C)n1] | 3-(3-(2-isopropylpyrimidin-4-yl)phenyl)-2,5-dimethyl-6-((6-methylpyridin-2-yl)methoxy)pyrimidin-4(3H)-one |
| 684 | 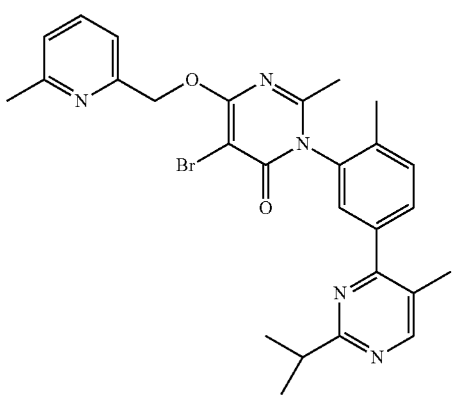 | 5-bromo-3-(5-(2-isopropyl-5-methylpyrimidin-4-yl)-2-methylphenyl)-2-methyl-6-((6-methylpyridin-2-yl)methoxy)pyrimidin-4(3H)-one |
| 685 | 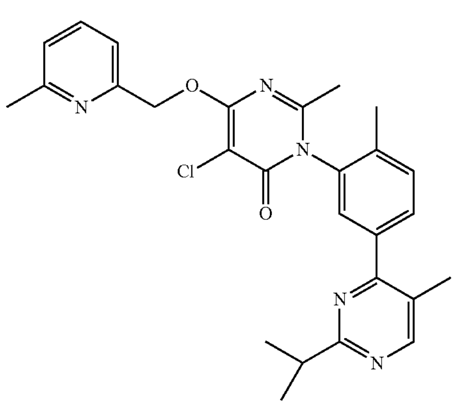 | 5-chloro-3-(5-(2-isopropyl-5-methylpyrimidin-4-yl)-2-methylphenyl)-2-methyl-6-((6-methylpyridin-2-yl)methoxy)pyrimidin-4(3H)-one |

-continued

| Compound | Structure | Name |
|---|---|---|
| 686 | 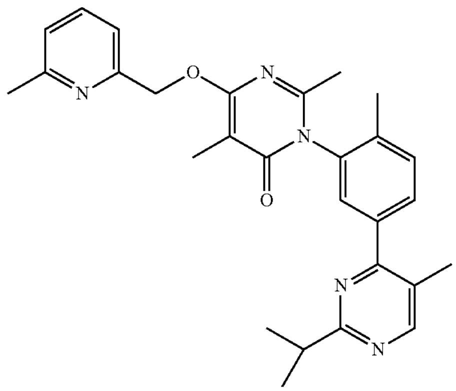 | 3-(5-(2-isopropyl-5-methylpyrimidin-4-yl)-2-methylphenyl)-2,5-dimethyl-6-((6-methylpyridin-2-yl)methoxy)pyrimidin-4(3H)-one |
| 687 | 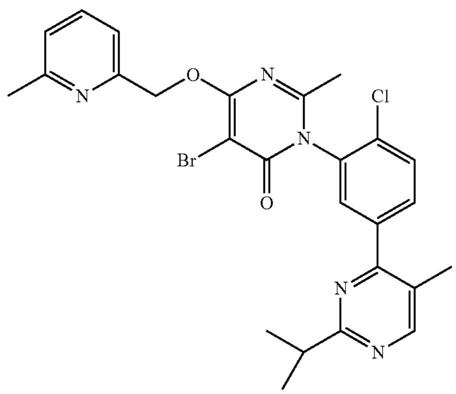 | 5-bromo-3-(2-chloro-5-(2-isopropyl-5-methylpyrimidin-4-yl)phenyl)-2-methyl-6-((6-methylpyridin-2-yl)methoxy)pyrimidin-4(3H)-one |
| 688 | 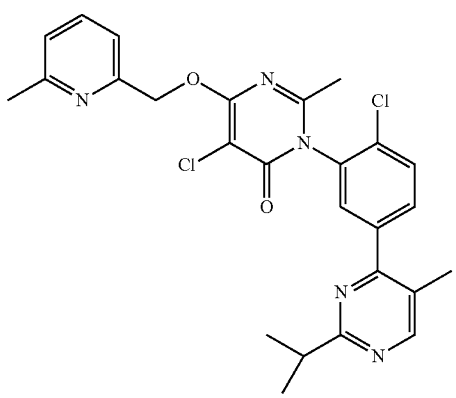 | 5-chloro-3-(2-chloro-5-(2-isopropyl-5-methylpyrimidin-4-yl)phenyl)-2-methyl-6-((6-methylpyridin-2-yl)methoxy)pyrimidin-4(3H)-one |
| 689 | 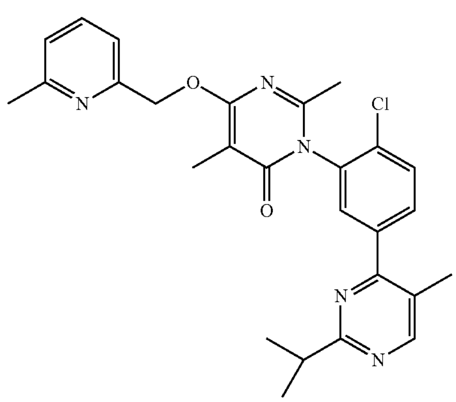 | 3-(2-chloro-5-(2-isopropyl-5-methylpyrimidin-4-yl)phenyl)-2,5-dimethyl-6-((6-methylpyridin-2-yl)methoxy)pyrimidin-4(3H)-one |

| Compound | Structure | Name |
|---|---|---|
| 690 | 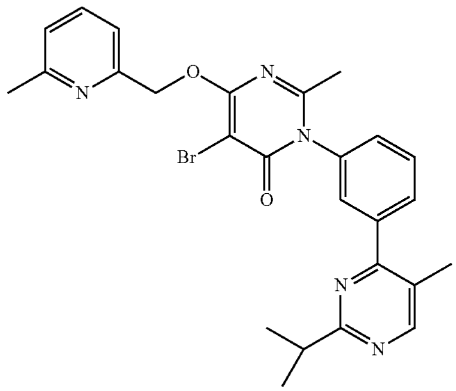 | 5-bromo-3-(3-(2-isopropyl-5-methylpyrimidin-4-yl)phenyl)-2-methyl-6-((6-methylpyridin-2-yl)methoxy)pyrimidin-4(3H)-one |
| 691 | 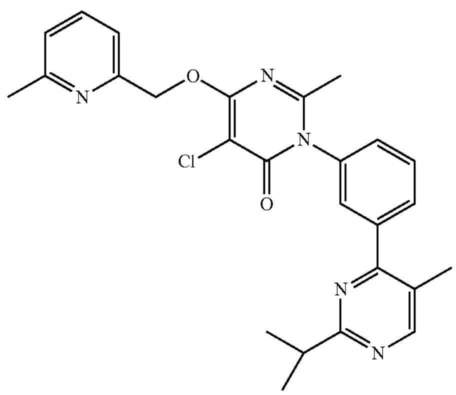 | 5-chloro-3-(3-(2-isopropyl-5-methylpyrimidin-4-yl)phenyl)-2-methyl-6-((6-methylpyridin-2-yl)methoxy)pyrimidin-4(3H)-one |
| 692 | 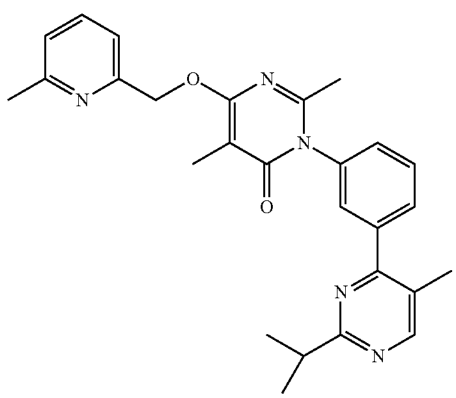 | 3-(3-(2-isopropyl-5-methylpyrimidin-4-yl)phenyl)-2,5-dimethyl-6-((6-methylpyridin-2-yl)methoxy)pyrimidin-4(3H)-one |
| 693 | 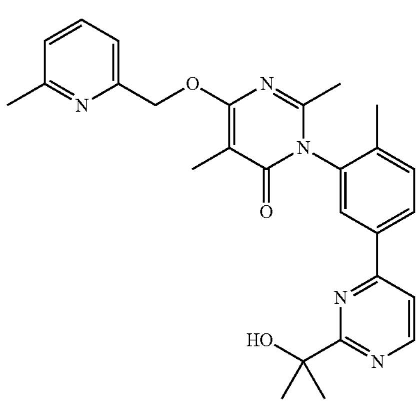 [SMILES: Cc1cccc(COc2nc(C)n(-c3cc(-c4ccnc(C(C)(C)O)n4)ccc3C)c(=O)c2C)n1] | 3-(5-(2-(2-hydroxypropan-2-yl)pyrimidin-4-yl)-2-methylphenyl)-2,5-dimethyl-6-((6-methylpyridin-2-yl)methoxy)pyrimidin-4(3H)-one |

| Compound | Structure | Name |
|---|---|---|
| 694 | 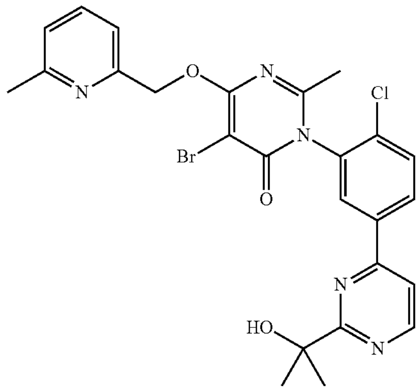 [SMILES: Cc1cccc(COc2nc(C)n(-c3cc(-c4ccnc(C(C)(C)O)n4)ccc3Cl)c(=O)c2Br)n1] | 5-bromo-3-(2-chloro-5-(2-(2-hydroxypropan-2-yl)pyrimidin-4-yl)phenyl)-2-methyl-6-((6-methylpyridin-2-yl)methoxy)pyrimidin-4(3H)-one |
| 695 | 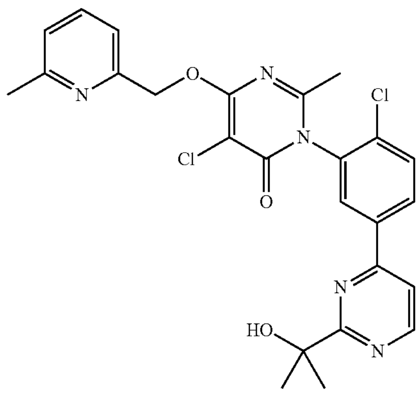 | 5-chloro-3-(2-chloro-5-(2-(2-hydroxypropan-2-yl)pyrimidin-4-yl)phenyl)-2-methyl-6-((6-methylpyridin-2-yl)methoxy)pyrimidin-4(3H)-one |
| 696 | 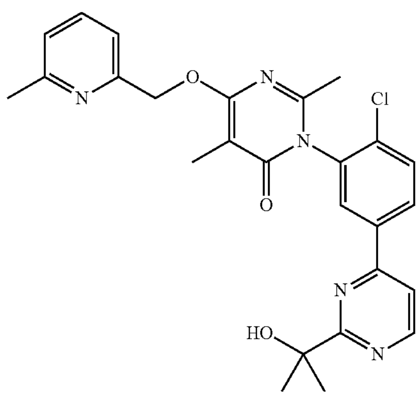 [SMILES: Cc1cccc(COc2nc(C)n(-c3cc(-c4ccnc(C(C)(C)O)n4)ccc3Cl)c(=O)c2C)n1] | 3-(2-chloro-5-(2-(2-hydroxypropan-2-yl)pyrimidin-4-yl)phenyl)-2,5-dimethyl-6-((6-methylpyridin-2-yl)methoxy)pyrimidin-4(3H)-one |
| 697 | 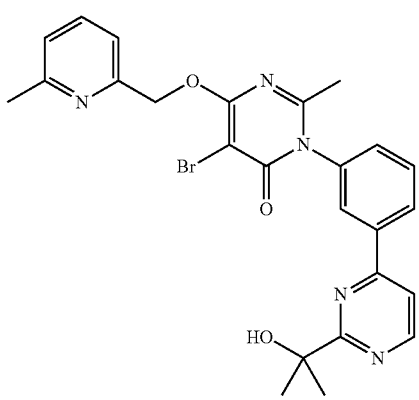 | 5-bromo-3-(3-(2-(2-hydroxypropan-2-yl)pyrimidin-4-yl)phenyl)-2-methyl-6-((6-methylpyridin-2-yl)methoxy)pyrimidin-4(3H)-one |

-continued

| Compound | Structure | Name |
|---|---|---|
| 698 | 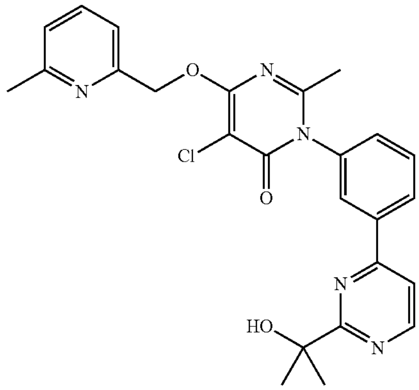 | 5-chloro-3-(3-(2-(2-hydroxypropan-2-yl)pyrimidin-4-yl)phenyl)-2-methyl-6-((6-methylpyridin-2-yl)methoxy)pyrimidin-4(3H)-one |
| 699 | 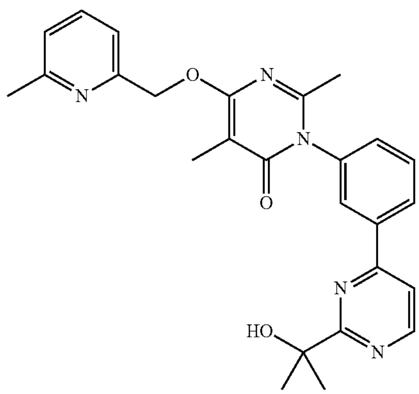 [SMILES: Cc1cccc(COc2nc(C)n(-c3cccc(-c4ccnc(C(C)(C)O)n4)c3)c(=O)c2C)n1] | 3-(3-(2-(2-hydroxypropan-2-yl)pyrimidin-4-yl)phenyl)-2,5-dimethyl-6-((6-methylpyridin-2-yl)methoxy)pyrimidin-4(3H)-one |
| 700 | 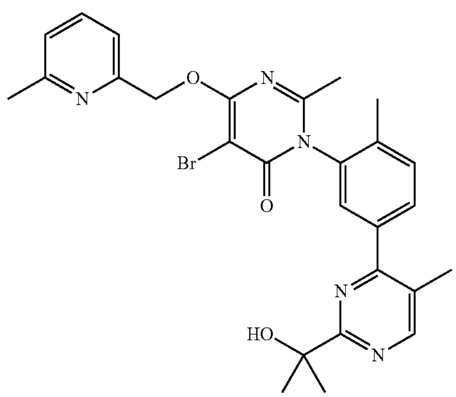 | 5-bromo-3-(5-(2-(2-hydroxypropan-2-yl)-5-methylpyrimidin-4-yl)-2-methylphenyl)-2-methyl-6-((6-methylpyridin-2-yl)methoxy)pyrimidin-4(3H)-one |
| 701 | 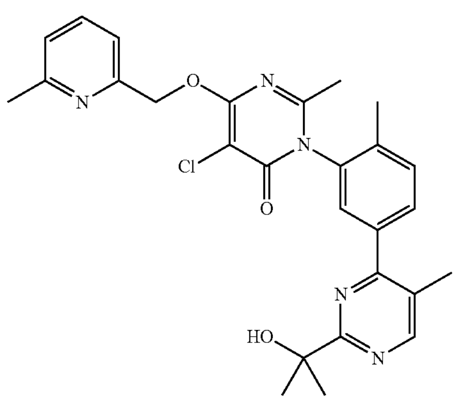 | 5-chloro-3-(5-(2-(2-hydroxypropan-2-yl)-5-methylpyrimidin-4-yl)-2-methylphenyl)-2-methyl-6-((6-methylpyridin-2-yl)methoxy)pyrimidin-4(3H)-one |

-continued

| Compound | Structure | Name |
|---|---|---|
| 702 | 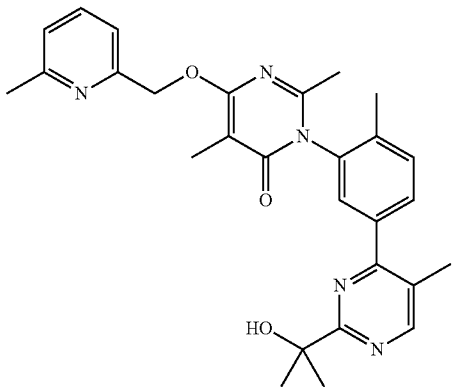 | 3-(5-(2-(2-hydroxypropan-2-yl)-5-methylpyrimidin-4-yl)-2-methylphenyl)-2,5-dimethyl-6-((6-methylpyridin-2-yl)methoxy)pyrimidin-4(3H)-one |
| 703 | 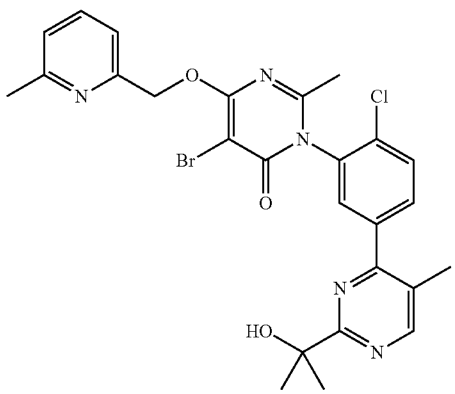 | 5-bromo-3-(2-chloro-5-(2-(2-hydroxypropan-2-yl)-5-methylpyrimidin-4-yl)phenyl)-2-methyl-6-((6-methylpyridin-2-yl)methoxy)pyrimidin-4(3H)-one |
| 704 | 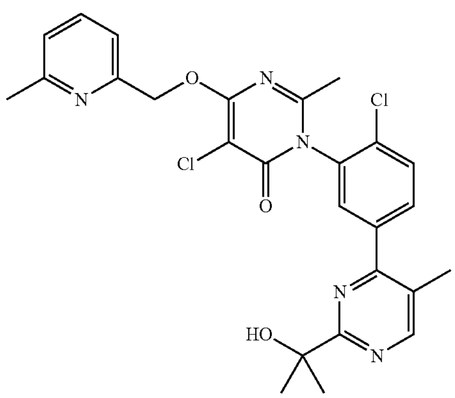 | 5-chloro-3-(2-chloro-5-(2-(2-hydroxypropan-2-yl)-5-methylpyrimidin-4-yl)phenyl)-2-methyl-6-((6-methylpyridin-2-yl)methoxy)pyrimidin-4(3H)-one |
| 705 | 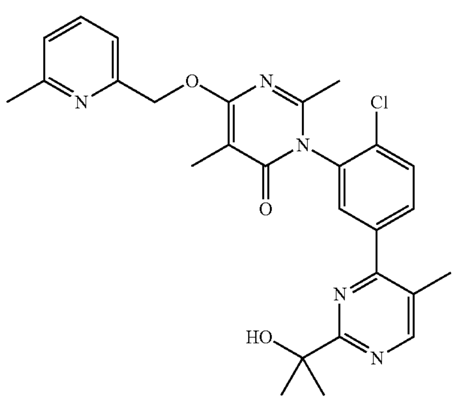 | 3-(2-chloro-5-(2-(2-hydroxypropan-2-yl)-5-methylpyrimidin-4-yl)phenyl)-2,5-dimethyl-6-((6-methylpyridin-2-yl)methoxy)pyrimidin-4(3H)-one |

-continued

| Compound | Structure | Name |
|---|---|---|
| 706 | 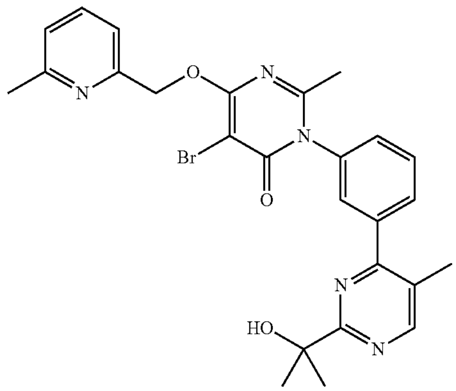 | 5-bromo-3-(3-(2-(2-hydroxypropan-2-yl)-5-methylpyrimidin-4-yl)phenyl)-2-methyl-6-((6-methylpyridin-2-yl)methoxy)pyrimidin-4(3H)-one |
| 707 | 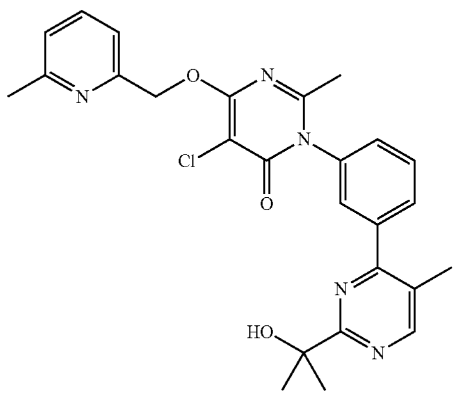 | 5-chloro-3-(3-(2-(2-hydroxypropan-2-yl)-5-methylpyrimidin-4-yl)phenyl)-2-methyl-6-((6-methylpyridin-2-yl)methoxy)pyrimidin-4(3H)-one |
| 708 | 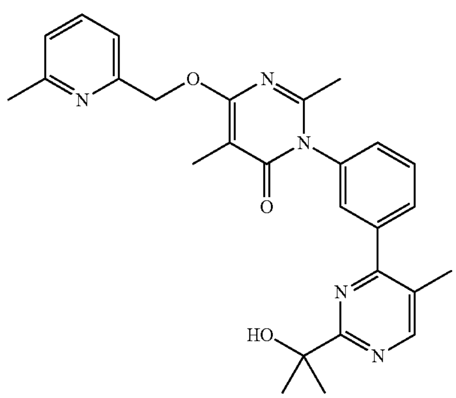 | 3-(3-(2-(2-hydroxypropan-2-yl)-5-methylpyrimidin-4-yl)phenyl)-2,5-dimethyl-6-((6-methylpyridin-2-yl)methoxy)pyrimidin-4(3H)-one |
| 709 | 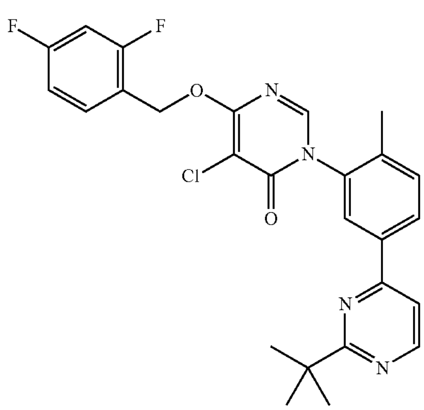 [SMILES: Cc1ccc(-c2ccnc(C(C)(C)C)n2)cc1-n1cnc(OCc2ccc(F)cc2F)c(Cl)c1=O] | 3-(5-(2-(tert-butyl)pyrimidin-4-yl)-2-methylphenyl)-5-chloro-6-((2,4-difluorobenzyl)oxy)pyrimidin-4(3H)-one |

-continued

| Compound | Structure | Name |
|---|---|---|
| 710 | 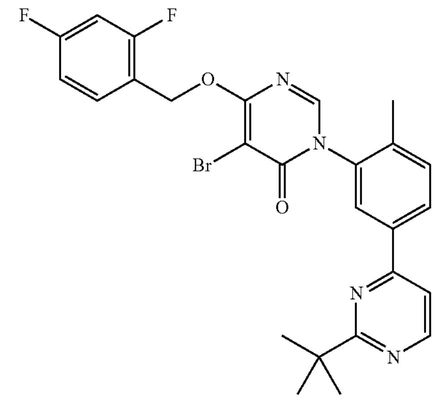 [SMILES: Cc1ccc(-c2ccnc(C(C)(C)C)n2)cc1-n1cnc(OCc2ccc(F)cc2F)c(Br)c1=O] | 5-bromo-3-(5-(2-(tert-butyl)pyrimidin-4-yl)-2-methylphenyl)-6-((2,4-difluorobenzyl)oxy)pyrimidin-4(3H)-one |
| 711 | 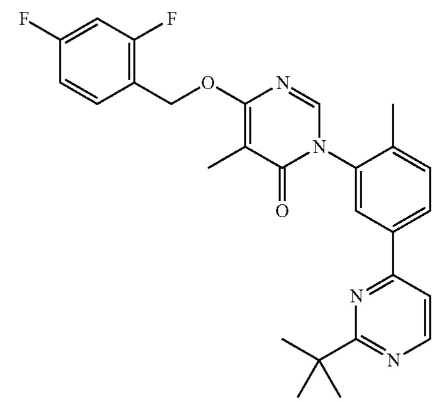 [SMILES: Cc1ccc(-c2ccnc(C(C)(C)C)n2)cc1-n1cnc(OCc2ccc(F)cc2F)c(C)c1=O] | 3-(5-(2-(tert-butyl)pyrimidin-4-yl)-2-methylphenyl)-6-((2,4-difluorobenzyl)oxy)-5-methylpyrimidin-4(3H)-one |
| 712 | 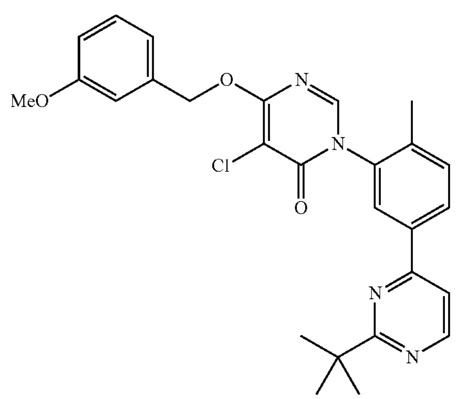 [SMILES: COc1cccc(COc2ncn(-c3cc(-c4ccnc(C(C)(C)C)n4)ccc3C)c(=O)c2Cl)c1] | 3-(5-(2-(tert-butyl)pyrimidin-4-yl)-2-methylphenyl)-5-chloro-6-((3-methoxybenzyl)oxy)pyrimidin-4(3H)-one |
| 713 | 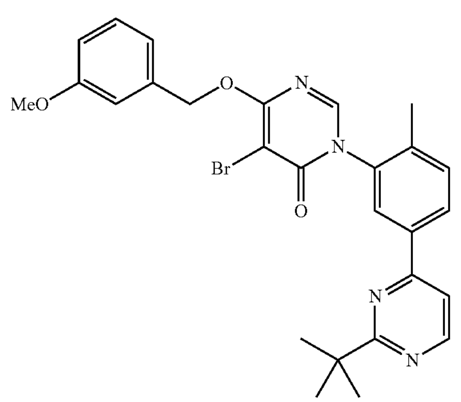 [SMILES: COc1cccc(COc2ncn(-c3cc(-c4ccnc(C(C)(C)C)n4)ccc3C)c(=O)c2Br)c1] | 5-bromo-3-(5-(2-(tert-butyl)pyrimidin-4-yl)-2-methylphenyl)-6-((3-methoxybenzyl)oxy)pyrimidin-4(3H)-one |

| Compound | Structure | Name |
|---|---|---|
| 714 | 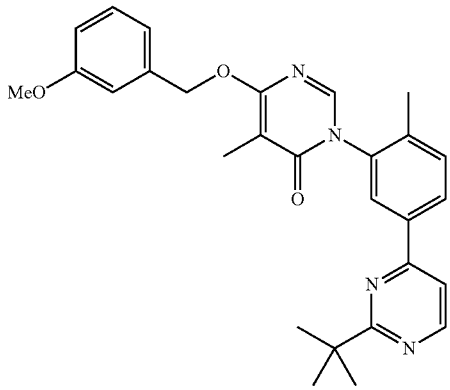 [SMILES: COc1cccc(COc2ncn(-c3cc(-c4ccnc(C(C)(C)C)n4)ccc3C)c(=O)c2C)c1] | 3-(5-(2-(tert-butyl)pyrimidin-4-yl)-2-methylphenyl)-6-((3-methoxybenzyl)oxy)-5-methylpyrimidin-4(3H)-one |
| 715 | 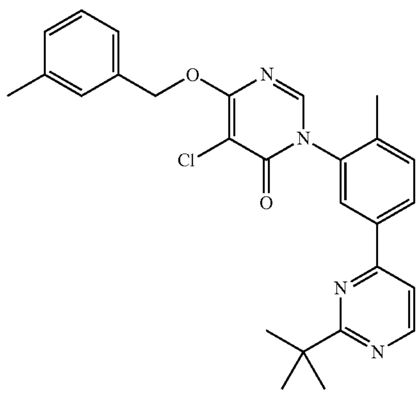 [SMILES: Cc1cccc(COc2ncn(-c3cc(-c4ccnc(C(C)(C)C)n4)ccc3C)c(=O)c2Br)c1] | 3-(5-(2-(tert-butyl)pyrimidin-4-yl)-2-methylphenyl)-5-chloro-6-((3-methylbenzyl)oxy)pyrimidin-4(3H)-one |
| 716 | 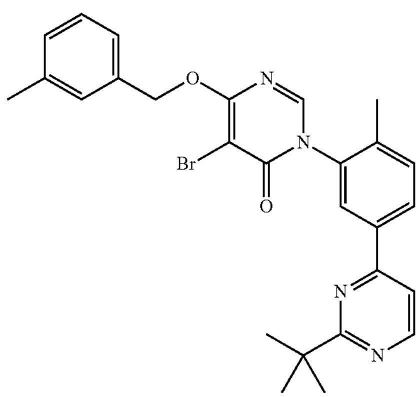 | 5-bromo-3-(5-(2-(tert-butyl)pyrimidin-4-yl)-2-methylphenyl)-6-((3-methylbenzyl)oxy)pyrimidin-4(3H)-one |
| 717 | 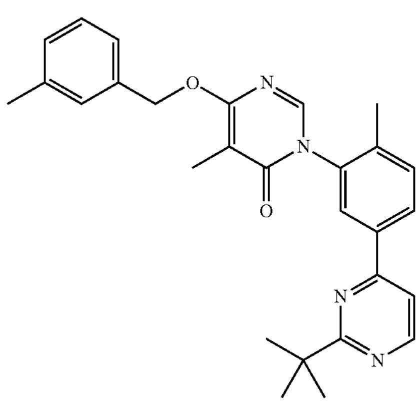 [SMILES: Cc1cccc(COc2ncn(-c3cc(-c4ccnc(C(C)(C)C)n4)ccc3C)c(=O)c2C)c1] | 3-(5-(2-(tert-butyl)pyrimidin-4-yl)-2-methylphenyl)-5-methyl-6-((3-methylbenzyl)oxy)pyrimidin-4(3H)-one |

| Compound | Structure | Name |
|---|---|---|
| 718 | 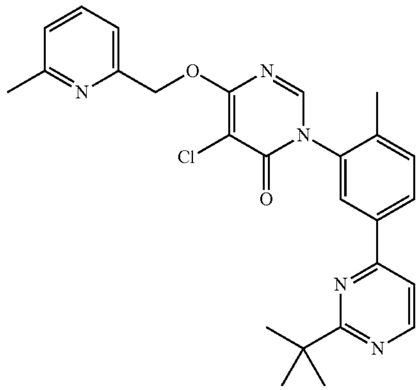 [SMILES: Cc1cccc(COc2ncn(-c3cc(-c4ccnc(C(C)(C)C)n4)ccc3C)c(=O)c2Cl)n1] | 3-(5-(2-(tert-butyl)pyrimidin-4-yl)-2-methylphenyl)-5-chloro-6-((6-methylpyridin-2-yl)methoxy)pyrimidin-4(3H)-one |
| 719 | 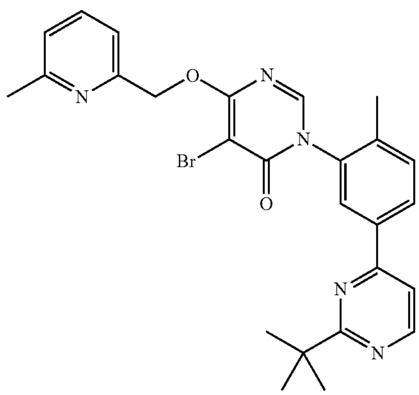 | 5-bromo-3-(5-(2-(tert-butyl)pyrimidin-4-yl)-2-methylphenyl)-6-((6-methylpyridin-2-yl)methoxy)pyrimidin-4(3H)-one |
| 720 | 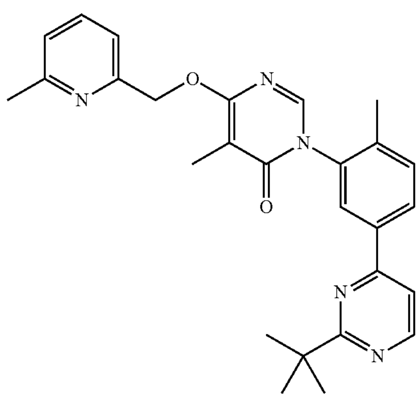 [SMILES: Cc1cccc(COc2ncn(-c3cc(-c4ccnc(C(C)(C)C)n4)ccc3C)c(=O)c2C)n1] | 3-(5-(2-(tert-butyl)pyrimidin-4-yl)-2-methylphenyl)-5-methyl-6-((6-methylpyridin-2-yl)methoxy)pyrimidin-4(3H)-one |
| 721 | 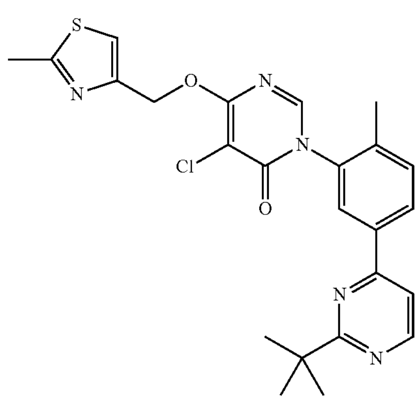 | 3-(5-(2-(tert-butyl)pyrimidin-4-yl)-2-methylphenyl)-5-chloro-6-((2-methylthiazol-4-yl)methoxy)pyrimidin-4(3H)-one |

-continued

| Compound | Structure | Name |
|---|---|---|
| 722 | 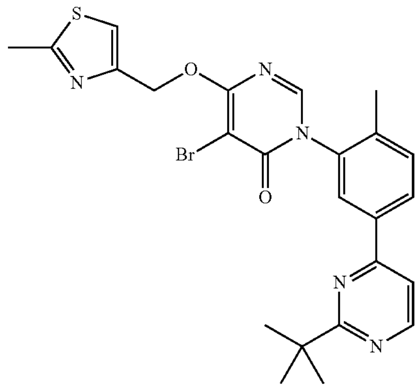 | 5-bromo-3-(5-(2-(tert-butyl)pyrimidin-4-yl)-2-methylphenyl)-6-((2-methylthiazol-4-yl)methoxy)pyrimidin-4(3H)-one |
| 723 | 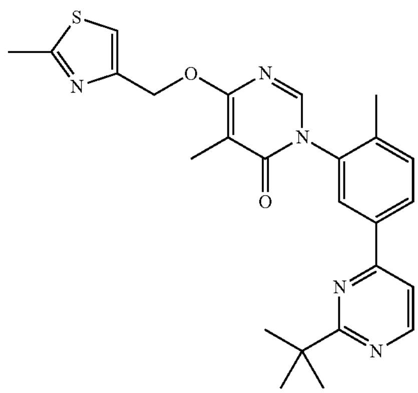 | 3-(5-(2-(tert-butyl)pyrimidin-4-yl)-2-methylphenyl)-5-methyl-6-((2-methylthiazol-4-yl)methoxy)pyrimidin-4(3H)-one |
| 724 | 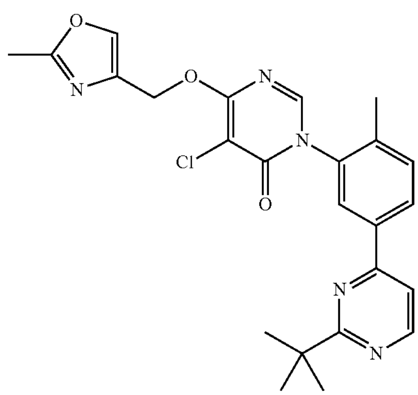 | 3-(5-(2-(tert-butyl)pyrimidin-4-yl)-2-methylphenyl)-5-chloro-6-((2-methyloxazol-4-yl)methoxy)pyrimidin-4(3H)-one |
| 725 | 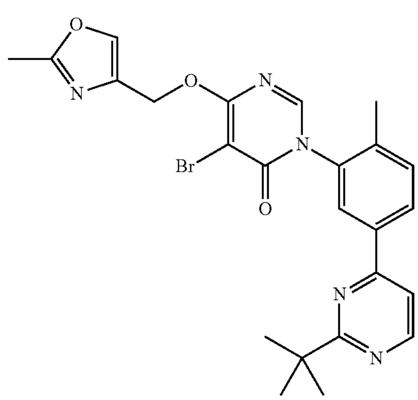 | 5-bromo-3-(5-(2-(tert-butyl)pyrimidin-4-yl)-2-methylphenyl)-6-((2-methyloxazol-4-yl)methoxy)pyrimidin-4(3H)-one |

-continued

| Compound | Structure | Name |
|---|---|---|
| 726 | 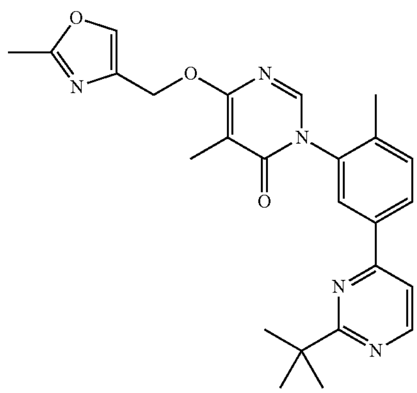 [SMILES: Cc1nc(COc2ncn(-c3cc(-c4ccnc(C(C)(C)C)n4)ccc3C)c(=O)c2C)co1] | 3-(5-(2-(tert-butyl)pyrimidin-4-yl)-2-methylphenyl)-5-methyl-6-((2-methyloxazol-4-yl)methoxy)pyrimidin-4(3H)-one |
| 727 | 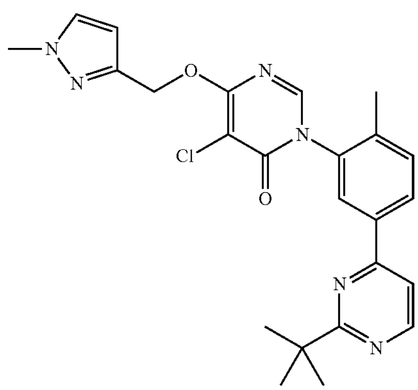 [SMILES: Cc1ccc(-c2ccnc(C(C)(C)C)n2)cc1-n1cnc(OCc2ccn(C)n2)c(Cl)c1=O] | 3-(5-(2-(tert-butyl)pyrimidin-4-yl)-2-methylphenyl)-5-chloro-6-((1-methyl-1H-pyrazol-3-yl)methoxy)pyrimidin-4(3H)-one |
| 728 | 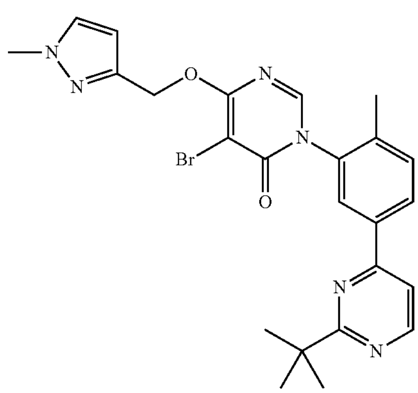 [SMILES: Cc1ccc(-c2ccnc(C(C)(C)C)n2)cc1-n1cnc(OCc2ccn(C)n2)c(Br)c1=O] | 5-bromo-3-(5-(2-(tert-butyl)pyrimidin-4-yl)-2-methylphenyl)-6-((1-methyl-1H-pyrazol-3-yl)methoxy)pyrimidin-4(3H)-one |
| 729 | 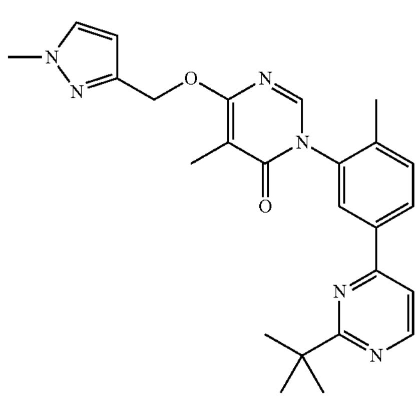 [SMILES: Cc1ccc(-c2ccnc(C(C)(C)C)n2)cc1-n1cnc(OCc2ccn(C)n2)c(C)c1=O] | 3-(5-(2-(tert-butyl)pyrimidin-4-yl)-2-methylphenyl)-5-methyl-6-((1-methyl-1H-pyrazol-3-yl)methoxy)pyrimidin-4(3H)-one |

-continued

| Compound | Structure | Name |
|---|---|---|
| 730 | 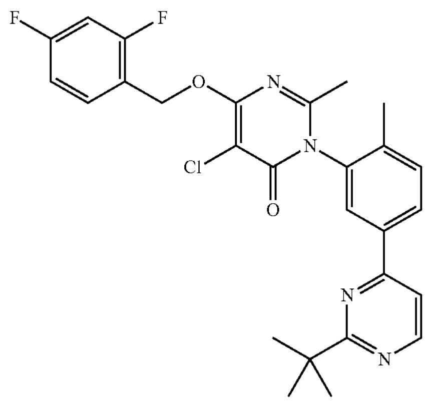 [SMILES: Cc1ccc(-c2ccnc(C(C)(C)C)n2)cc1-n1c(C)nc(OCc2ccc(F)cc2F)c(Cl)c1=O] | 3-(5-(2-(tert-butyl)pyrimidin-4-yl)-2-methylphenyl)-5-chloro-6-((2,4-difluorobenzyl)oxy)-2-methylpyrimidin-4(3H)-one |
| 731 | 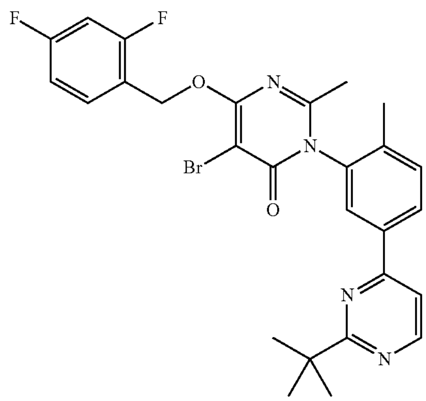 | 5-bromo-3-(5-(2-(tert-butyl)pyrimidin-4-yl)-2-methylphenyl)-6-((2,4-difluorobenzyl)oxy)-2-methylpyrimidin-4(3H)-one |
| 732 | 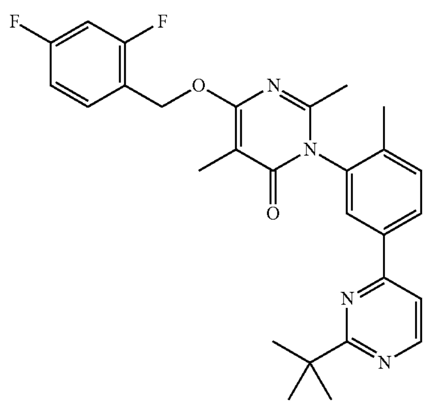 [SMILES: Cc1ccc(-c2ccnc(C(C)(C)C)n2)cc1-n1c(C)nc(OCc2ccc(F)cc2F)c(C)c1=O] | 3-(5-(2-(tert-butyl)pyrimidin-4-yl)-2-methylphenyl)-6-((2,4-difluorobenzyl)oxy)-2,5-dimethylpyrimidin-4(3H)-one |
| 733 | 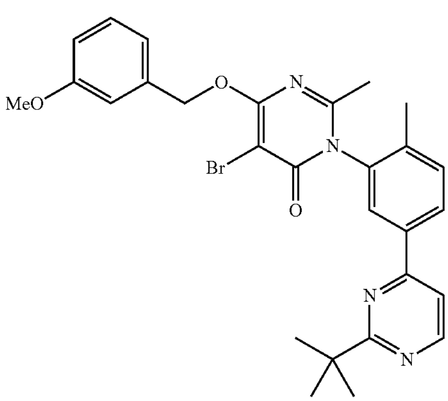 [SMILES: COc1cccc(COc2nc(C)n(-c3cc(-c4ccnc(C(C)(C)C)n4)ccc3C)c(=O)c2Br)c1] | 5-bromo-3-(5-(2-(tert-butyl)pyrimidin-4-yl)-2-methylphenyl)-6-((3-methoxybenzyl)oxy)-2-methylpyrimidin-4(3H)-one |

| Compound | Structure | Name |
|---|---|---|
| 734 | 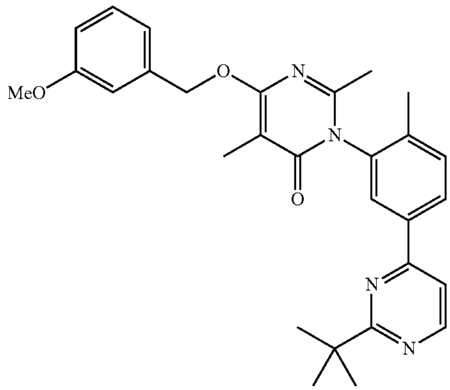 [SMILES: COc1cccc(COc2nc(C)n(-c3cc(-c4ccnc(C(C)(C)C)n4)ccc3C)c(=O)c2C)c1] | 3-(5-(2-(tert-butyl)pyrimidin-4-yl)-2-methylphenyl)-6-((3-methoxybenzyl)oxy)-2,5-dimethylpyrimidin-4(3H)-one |
| 735 | 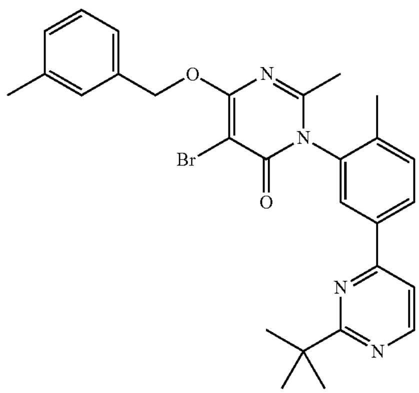 [SMILES: Cc1cccc(COc2nc(C)n(-c3cc(-c4ccnc(C(C)(C)C)n4)ccc3C)c(=O)c2Br)c1] | 5-bromo-3-(5-(2-(tert-butyl)pyrimidin-4-yl)-2-methylphenyl)-2-methyl-6-((3-methylbenzyl)oxy)pyrimidin-4(3H)-one |
| 736 | 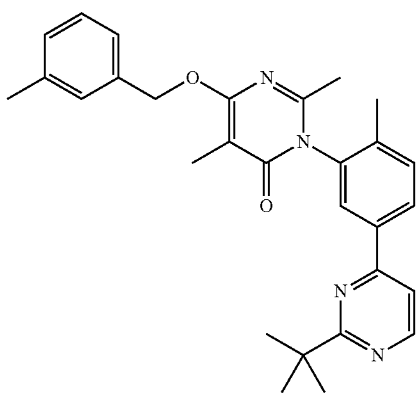 [SMILES: Cc1cccc(COc2nc(C)n(-c3cc(-c4ccnc(C(C)(C)C)n4)ccc3C)c(=O)c2C)c1] | 3-(5-(2-(tert-butyl)pyrimidin-4-yl)-2-methylphenyl)-2,5-dimethyl-6-((3-methylbenzyl)oxy)pyrimidin-4(3H)-one |
| 737 | 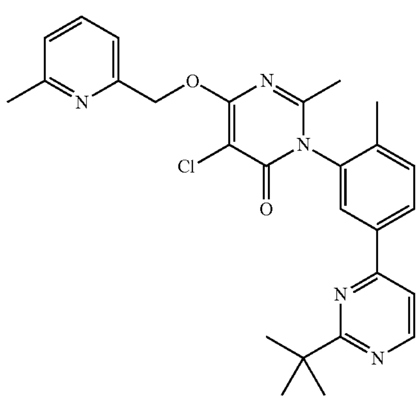 [SMILES: Cc1cccc(COc2nc(C)n(-c3cc(-c4ccnc(C(C)(C)C)n4)ccc3C)c(=O)c2Cl)n1] | 3-(5-(2-(tert-butyl)pyrimidin-4-yl)-2-methylphenyl)-5-chloro-2-methyl-6-((6-methylpyridin-2-yl)methoxy)pyrimidin-4(3H)-one |

-continued

| Compound | Structure | Name |
|---|---|---|
| 738 | 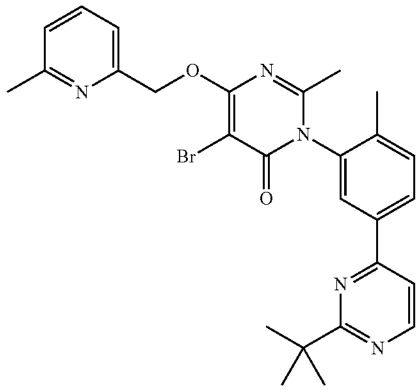 | 5-bromo-3-(5-(2-(tert-butyl)pyrimidin-4-yl)-2-methylphenyl)-2-methyl-6-((6-methylpyridin-2-yl)methoxy)pyrimidin-4(3H)-one |
| 739 | 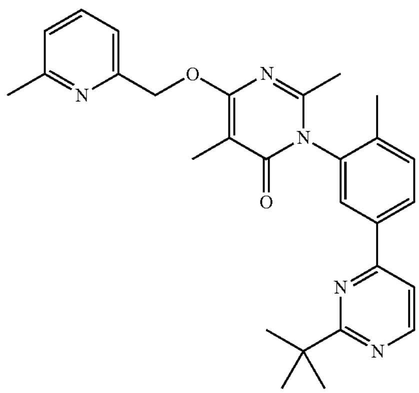 [SMILES: Cc1cccc(COc2nc(C)n(-c3cc(-c4ccnc(C(C)(C)C)n4)ccc3C)c(=O)c2C)n1] | 3-(5-(2-(tert-butyl)pyrimidin-4-yl)-2-methylphenyl)-2,5-dimethyl-6-((6-methylpyridin-2-yl)methoxy)pyrimidin-4(3H)-one |
| 740 | 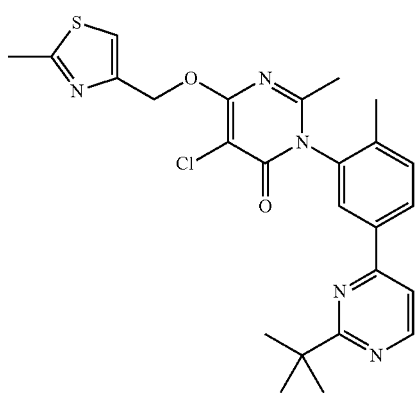 [SMILES: Cc1nc(COc2nc(C)n(-c3cc(-c4ccnc(C(C)(C)C)n4)ccc3C)c(=O)c2Cl)cs1] | 3-(5-(2-(tert-butyl)pyrimidin-4-yl)-2-methylphenyl)-5-chloro-2-methyl-6-((2-methylthiazol-4-yl)methoxy)pyrimidin-4(3H)-one |
| 741 | 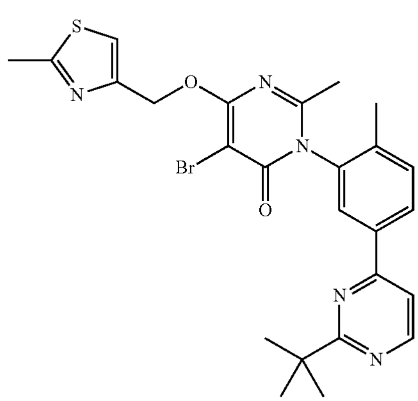 [SMILES: Cc1nc(COc2nc(C)n(-c3cc(-c4ccnc(C(C)(C)C)n4)ccc3C)c(=O)c2Br)cs1] | 5-bromo-3-(5-(2-(tert-butyl)pyrimidin-4-yl)-2-methylphenyl)-2-methyl-6-((2-methylthiazol-4-yl)methoxy)pyrimidin-4(3H)-one |

| Compound | Structure | Name |
|---|---|---|
| 742 | 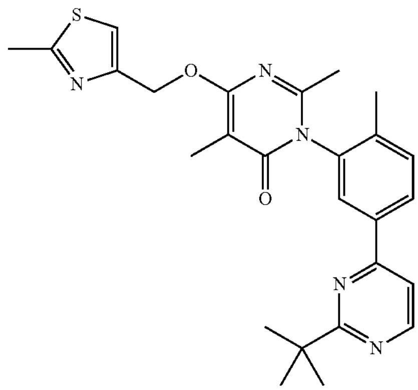 | 3-(5-(2-(tert-butyl)pyrimidin-4-yl)-2-methylphenyl)-2,5-dimethyl-6-((2-methylthiazol-4-yl)methoxy)pyrimidin-4(3H)-one |
| 743 | 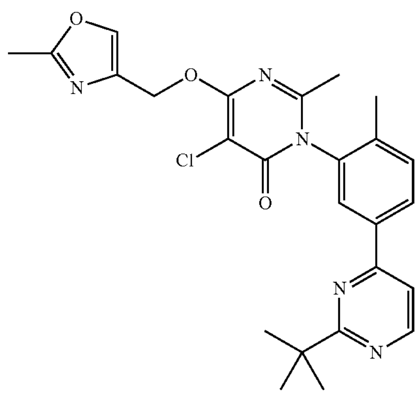 [SMILES: Cc1nc(COc2nc(C)n(-c3cc(-c4ccnc(C(C)(C)C)n4)ccc3C)c(=O)c2Cl)co1] | 3-(5-(2-(tert-butyl)pyrimidin-4-yl)-2-methylphenyl)-5-chloro-2-methyl-6-((2-methyloxazol-4-yl)methoxy)pyrimidin-4(3H)-one |
| 744 | 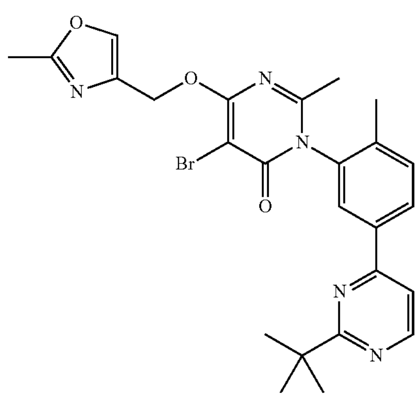 [SMILES: Cc1nc(COc2nc(C)n(-c3cc(-c4ccnc(C(C)(C)C)n4)ccc3C)c(=O)c2Br)co1] | 5-bromo-3-(5-(2-(tert-butyl)pyrimidin-4-yl)-2-methylphenyl)-2-methyl-6-((2-methyloxazol-4-yl)methoxy)pyrimidin-4(3H)-one |
| 745 | 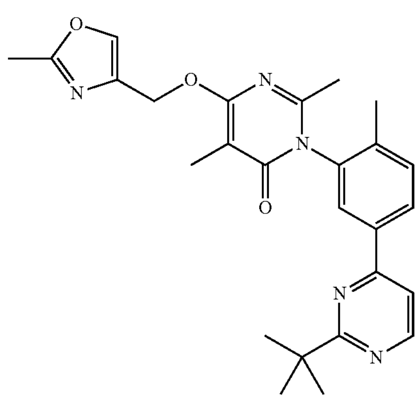 [SMILES: Cc1nc(COc2nc(C)n(-c3cc(-c4ccnc(C(C)(C)C)n4)ccc3C)c(=O)c2C)co1] | 3-(5-(2-(tert-butyl)pyrimidin-4-yl)-2-methylphenyl)-2,5-dimethyl-6-((2-methyloxazol-4-yl)methoxy)pyrimidin-4(3H)-one |

| Compound | Structure | Name |
|---|---|---|
| 746 | 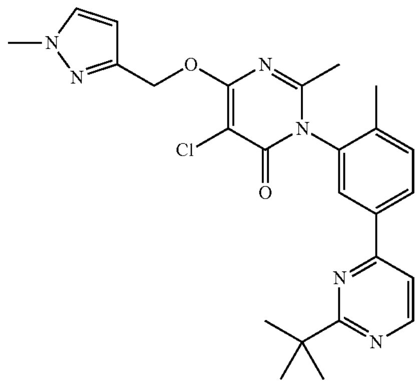 [SMILES: Cc1ccc(-c2ccnc(C(C)(C)C)n2)cc1-n1c(C)nc(OCc2ccn(C)n2)c(Cl)c1=O] | 3-(5-(2-(tert-butyl)pyrimidin-4-yl)-2-methylphenyl)-5-chloro-2-methyl-6-((1-methyl-1H-pyrazol-3-yl)methoxy)pyrimidin-4(3H)-one |
| 747 | 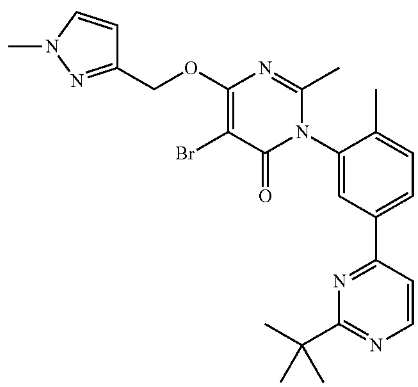 | 5-bromo-3-(5-(2-(tert-butyl)pyrimidin-4-yl)-2-methylphenyl)-2-methyl-6-((1-methyl-1H-pyrazol-3-yl)methoxy)pyrimidin-4(3H)-one |
| 748 | 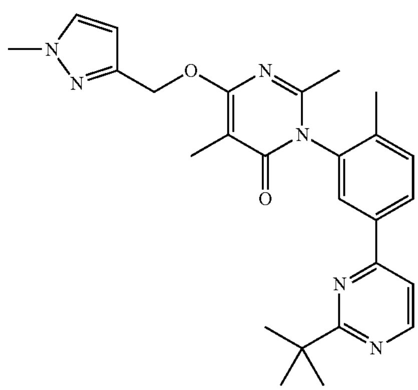 [SMILES: Cc1ccc(-c2ccnc(C(C)(C)C)n2)cc1-n1c(C)nc(OCc2ccn(C)n2)c(C)c1=O] | 3-(5-(2-(tert-butyl)pyrimidin-4-yl)-2-methylphenyl)-2,5-dimethyl-6-((1-methyl-1H-pyrazol-3-yl)methoxy)pyrimidin-4(3H)-one |
| 749 | 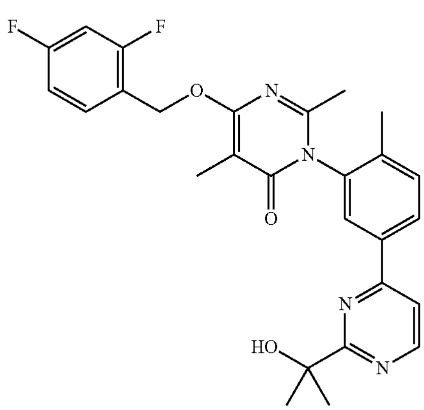 [SMILES: Cc1ccc(-c2ccnc(C(C)(C)O)n2)cc1-n1c(C)nc(OCc2ccc(F)cc2F)c(C)c1=O] | 6-((2,4-difluorobenzyl)oxy)-3-(5-(2-(2-hydroxypropan-2-yl)pyrimidin-4-yl)-2-methylphenyl)-2,5-dimethylpyrimidin-4(3H)-one |

| Compound | Structure | Name |
|---|---|---|
| 750 | 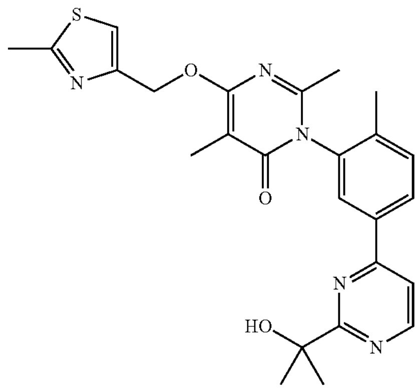 [SMILES: Cc1nc(COc2nc(C)n(-c3cc(-c4ccnc(C(C)(C)O)n4)ccc3C)c(=O)c2C)cs1] | 3-(5-(2-(2-hydroxypropan-2-yl)pyrimidin-4-yl)-2-methylphenyl)-2,5-dimethyl-6-((2-methylthiazol-4-yl)methoxy)pyrimidin-4(3H)-one |
| 751 | 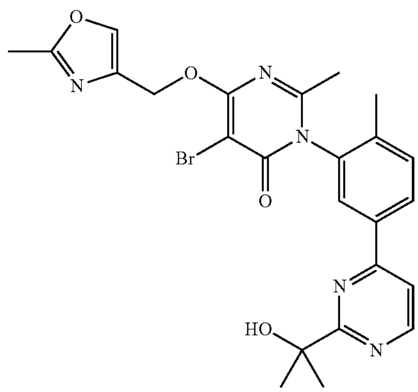 [SMILES: Cc1nc(COc2nc(C)n(-c3cc(-c4ccnc(C(C)(C)O)n4)ccc3C)c(=O)c2Br)co1] | 5-bromo-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one |
| 752 | 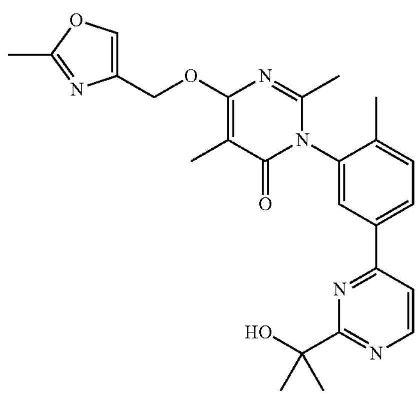 | 3-(5-(2-(2-hydroxypropan-2-yl)pyrimidin-4-yl)-2-methylphenyl)-2,5-dimethyl-6-((2-methyloxazol-4-yl)methoxy)pyrimidin-4(3H)-one |
| 753 | 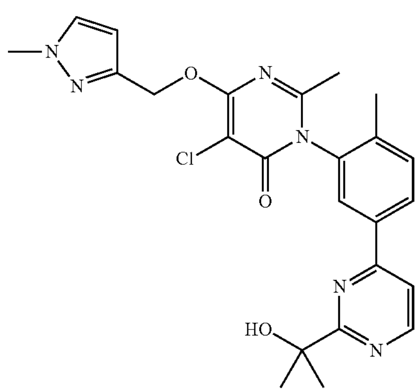 [SMILES: Cc1ccc(-c2ccnc(C(C)(C)O)n2)cc1-n1c(C)nc(OCc2ccn(C)n2)c(Cl)c1=O] | 5-chloro-3-(5-(2-(2-hydroxypropan-2-yl)pyrimidin-4-yl)-2-methylphenyl)-2-methyl-6-((1-methyl-1H-pyrazol-3-yl)methoxy)pyrimidin-4(3H)-one |

| Compound | Structure | Name |
|---|---|---|
| 754 | 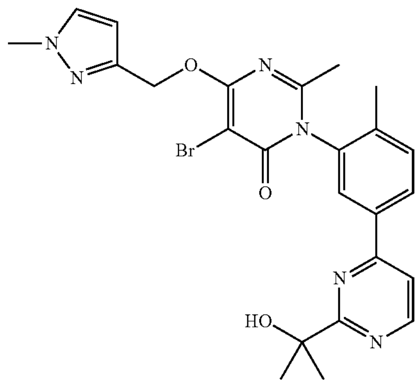 [SMILES: Cc1ccc(-c2ccnc(C(C)(C)O)n2)cc1-n1c(C)nc(OCc2ccn(C)n2)c(Br)c1=O] | 5-bromo-3-(5-(2-(2-hydroxypropan-2-yl)pyrimidin-4-yl)-2-methylphenyl)-2-methyl-6-((1-methyl-1H-pyrazol-3-yl)methoxy)pyrimidin-4(3H)-one |
| 755 | 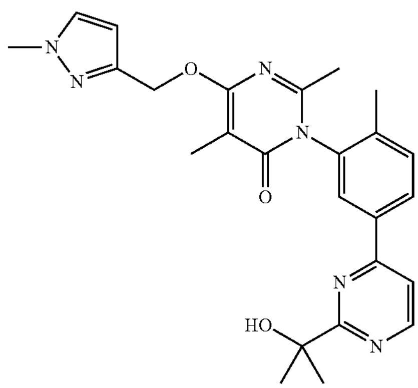 [SMILES: Cc1ccc(-c2ccnc(C(C)(C)O)n2)cc1-n1c(C)nc(OCc2ccn(C)n2)c(C)c1=O] | 3-(5-(2-(2-hydroxypropan-2-yl)pyrimidin-4-yl)-2-methylphenyl)-2,5-dimethyl-6-((1-methyl-1H-pyrazol-3-yl)methoxy)pyrimidin-4(3H)-one |

In another embodiment, there is provided a class of compounds which are intermediates to product compounds of Formula (I), such intermediates having the structure of Formula (III):

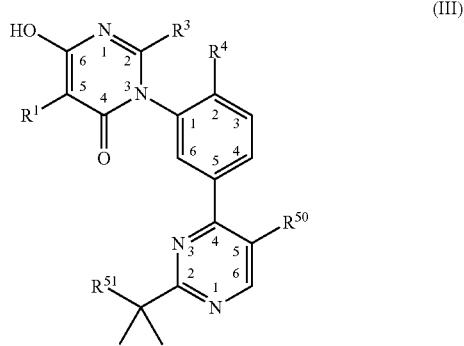

(III)

and a pharmaceutically acceptable salt or solvate thereof, wherein: $R^1$ is selected from the group consisting of methyl, ethyl, chloro and bromo; $R^3$ is selected from the group consisting of —H and methyl; $R^4$ is selected from the group consisting of —H, methyl and chloro; $R^{50}$ is selected from the group consisting of —H, $C_{1-3}$alkyl and halo; and $R^{51}$ is selected from the group consisting of —H, $C_{1-3}$alkyl, hydroxyl, amino and thiol.

In another embodiment of Formula (III), $R^1$ is selected from the group consisting of methyl, chloro and bromo; $R^3$ is methyl; $R^4$ is selected from the group consisting —H, methyl and chloro; $R^{50}$ is selected from the group consisting —H, methyl and fluoro; and $R^{51}$ is selected from the group consisting of —H, methyl and hydroxyl.

A non-limiting example of a Formula (III) compound is 5-chloro-6-hydroxy-3-{5-[2-(1-hydroxy-1-methyl-ethyl)-pyrimidin-4-yl]-2-methyl-phenyl}-2-methyl-3H-pyrimidin-4-one and pharmaceutically acceptable salts or solvates thereof.

In another embodiment, there is provided a class of compounds which are intermediates to product compounds of Formula (I), such intermediates having the structure of Formula (IV):

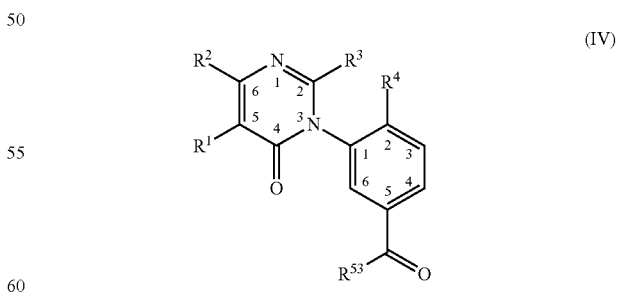

(IV)

and a pharmaceutically acceptable salt or solvate thereof, wherein: $R^1$ is selected from the group consisting of —H, $C_{1-5}$alkyl, bromo, chloro and fluoro; $R^2$ is $C_{1-5}$alkoxy optionally substituted with one or more substituents independently selected from the group consisting of $C_{1-6}$cycloalkyl, aryl and heterocyclyl; wherein the $C_{1-6}$cycloalkyl, aryl or heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl; $R^3$ is selected from the group consisting of —H and $C_{1-5}$alkyl; $R^4$ is selected from the group consisting of —H, $C_{1-5}$alkyl, chloro, bromo and fluoro; and $R^{53}$ is selected from the group consisting of

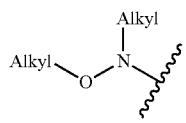

or alkynyl.

In another embodiment of Formula (IV), $R^1$ is selected from the group consisting of methyl, ethyl, bromo and chloro; $R^2$ is $C_{1-3}$alkoxy optionally substituted with one or more substituents selected from the group consisting of five- or six-membered cycloalkyl, phenyl and five- or six-membered heterocyclyl; wherein the five- or six-membered cycloalkyl, phenyl or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl; $R^3$ is selected from the group consisting of —H and $C_{1-3}$alkyl; $R^4$ is selected from the group consisting of —H, methyl and chloro; and $R^{53}$ is selected from the group consisting of

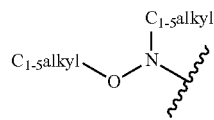

or $C_{2-5}$alkynyl. Preferred $C_{1-5}$alkyl is methyl.

In another embodiment of Formula (IV), $R^1$ is selected from the group consisting of methyl, ethyl, bromo and chloro; $R^2$ is methoxy optionally substituted with five- or six-membered cycloalkyl, phenyl, or five- or six-membered heterocyclyl; wherein the five- or six-membered cycloalkyl, phenyl, or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl; $R^3$ is selected from the group consisting of —H and $C_{1-3}$alkyl; $R^4$ is selected from the group consisting of —H, methyl and chloro; and $R^{53}$ is selected from the group consisting of

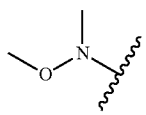

or ethynyl.

In another embodiment, there is provided a compound having the structure of Formula (V):

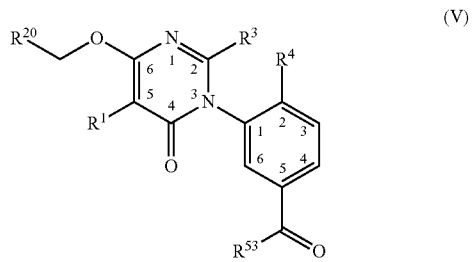

and a pharmaceutically acceptable salt or solvate thereof, wherein: $R^1$ is selected from the group consisting of methyl, ethyl, bromo and chloro; $R^3$ is selected from the group consisting of —H and $C_{1-3}$alkyl; $R^4$ is selected from the group consisting of —H, methyl and chloro; $R^{20}$ is phenyl substituted with one or more substituents selected from the group consisting of $C_{1-3}$alkyl, $C_{1-3}$alkoxy, amido, carboxy, formyl, carbamido, cyano, halo and halo$C_{1-3}$alkyl; or $R^{20}$ is five- or six-membered heteroaryl substituted with one or more substituents selected from the group consisting of $C_{1-3}$ alkyl, $C_{1-3}$alkoxy, $C_{1-5}$alkyl-O—$C_{1-5}$alkyl, amido, carboxy, formyl, carbamido, cyano, halo and halo$C_{1-3}$alkyl; and $R^{53}$ is selected from the group consisting of

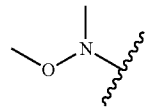

or ethynyl.

In another embodiment of Formula (V), $R^1$ is selected from the group consisting of methyl, bromo and chloro; $R^3$ is methyl; $R^4$ is selected from the group consisting —H, methyl and chloro; $R^{20}$ is phenyl substituted with one or more substituents selected from the group consisting of methyl, methoxy, amido, carboxy, formyl, carbamido, cyano and fluoro; or $R^{20}$ is selected from the group consisting thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl and triazinyl, wherein the thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl or triazinyl is substituted with one or more substituents selected from the group consisting of methyl, methoxy, amido, carboxy, formyl, carbamido, cyano, fluoro and trifluoromethyl; and $R^{53}$ is selected from the group consisting of

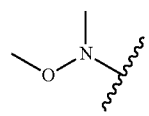

or ethynyl.

In another embodiment of Formula (V), $R^1$ is selected from the group consisting of chloro and bromo; $R^3$ is methyl; $R^4$ is methyl; $R^{20}$ is phenyl substituted with one or more substituents selected from the group consisting of methyl, methoxy and fluoro; or $R^{20}$ is selected from the group consisting pyridinyl, oxazolyl and thiazolyl, wherein the pyridinyl, oxazolyl or thiazolyl is substituted with one or more substituents selected from the group consisting of methyl, methoxy, fluoro and trifluoromethyl; and $R^{53}$ is selected from the group consisting of

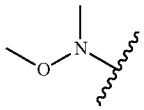 [SMILES: *N(C)OC]

or ethynyl.

In another embodiment of Formula (V), $R^1$ is selected from the group consisting of chloro and bromo; $R^3$ is methyl; $R^4$ is methyl; $R^{20}$ is selected from the group consisting of methoxyphenyl, methylphenyl, fluorophenyl, difluorophenyl and methyldifluorophenyl; or $R^{20}$ is selected from the group consisting methylpyridinyl, fluoropyridinyl, difluoropyridinyl, trifluoromethylpyridinyl, methyloxazolyl and methylthiazolyl; and $R^{53}$ is selected from the group consisting of

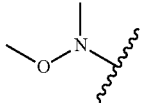

or ethynyl.

In another embodiment of Formula (V), $R^1$ is selected from the group consisting of chloro and bromo; $R^3$ is methyl; $R^4$ is methyl; $R^{20}$ is selected from the group consisting of 3-methoxyphenyl; 3-methylphenyl; 2,4-difluorophenyl; 4-fluorophenyl; 2,4-difluoro-3-methylphenyl; 2,4-difluoro-5-methylphenyl; 6-fluoropyridin-2-yl; 6-methylpyridin-2-yl; 6-(trifluoromethyl)pyridin-2-yl; 3,5-difluoropyridin-2-yl; 2-methyloxazol-4-yl and 2-methylthiazol-4-yl; and $R^{53}$ is selected from the group consisting of

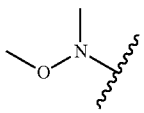

or ethynyl.

Non-limiting examples of Formula (V) compounds include the following compounds and pharmaceutically acceptable salts or solvates thereof: 3-[5-chloro-4-(4-methoxy-benzyloxy)-2-methyl-6-oxo-6H-pyrimidin-1-yl]-N-methoxy-4,N-dimethyl-benzamide; 5-chloro-6-(4-methoxy-benzyloxy)-2-methyl-3-(2-methyl-5-propynoyl-phenyl)-3H-pyrimidin-4-one; 3-[5-bromo-4-(2,4-difluoro-benzyloxy)-2-methyl-6-oxo-6H-pyrimidin-1-yl]-N-methoxy-4,N-dimethyl-benzamide; 5-bromo-6-(2,4-difluoro-benzyloxy)-2-methyl-3-(2-methyl-5-propynoyl-phenyl)-3H-pyrimidin-4-one; 3-[5-chloro-4-(2,4-difluoro-benzyloxy)-2-methyl-6-oxo-6H-pyrimidin-1-yl]-N-methoxy-4,N-dimethyl-benzamide; 5-chloro-6-(2,4-difluoro-benzyloxy)-2-methyl-3-(2-methyl-5-propynoyl-phenyl)-3H-pyrimidin-4-one; 3-[5-chloro-4-(4-fluoro-benzyloxy)-2-methyl-6-oxo-6H-pyrimidin-1-yl]-N-methoxy-4,N-dimethyl-benzamide; 5-chloro-6-(4-fluoro-benzyloxy)-2-methyl-3-(2-methyl-5-propynoyl-phenyl)-3H-pyrimidin-4-one; 3-[5-chloro-2-methyl-4-(3-methyl-benzyloxy)-6-oxo-6H-pyrimidin-1-yl]-N-methoxy-4,N-dimethyl-benzamide; 5-chloro-2-methyl-6-(3-methyl-benzyloxy)-3-(2-methyl-5-propynoyl-phenyl)-3H-pyrimidin-4-one; 3-[5-chloro-4-(3-methoxy-benzyloxy)-2-methyl-6-oxo-6H-pyrimidin-1-yl]-N-methoxy-4,N-dimethyl-benzamide; 5-chloro-6-(3-methoxy-benzyloxy)-2-methyl-3-(2-methyl-5-propynoyl-phenyl)-3H-pyrimidin-4-one; 3-[5-bromo-2-methyl-4-(2-methyl-thiazol-4-ylmethoxy)-6-oxo-6H-pyrimidin-1-yl]-N-methoxy-4,N-dimethyl-benzamide; 5-bromo-2-methyl-3-(2-methyl-5-propynoyl-phenyl)-6-(2-methyl-thiazol-4-ylmethoxy)-3H-pyrimidin-4-one; 3-[5-chloro-2-methyl-4-(2-methyl-thiazol-4-ylmethoxy)-6-oxo-6H-pyrimidin-1-yl]-N-methoxy-4,N-dimethyl-benzamide; 5-chloro-2-methyl-3-(2-methyl-5-propynoyl-phenyl)-6-(2-methyl-thiazol-4-ylmethoxy)-3H-pyrimidin-4-one; 3-[5-bromo-2-methyl-4-(6-methyl-pyridin-2-ylmethoxy)-6-oxo-6H-pyrimidin-1-yl]-N-methoxy-4,N-dimethyl-benzamide; 5-bromo-2-methyl-3-(2-methyl-5-propynoyl-phenyl)-6-(6-methyl-pyridin-2-ylmethoxy)-3H-pyrimidin-4-one; 3-[5-chloro-2-methyl-4-(6-methyl-pyridin-2-ylmethoxy)-6-oxo-6H-pyrimidin-1-yl]-N-methoxy-4,N-dimethyl-benzamide; 5-chloro-2-methyl-3-(2-methyl-5-propynoyl-phenyl)-6-(6-methyl-pyridin-2-ylmethoxy)-3H-pyrimidin-4-one; 3-[5-chloro-2-methyl-6-oxo-4-(6-trifluoromethyl-pyridin-2-ylmethoxy)-6H-pyrimidin-1-yl]-N-methoxy-4,N-dimethyl-benzamide; 5-chloro-2-methyl-3-(2-methyl-5-propynoyl-phenyl)-6-(6-trifluoromethyl-pyridin-2-ylmethoxy)-3H-pyrimidin-4-one; 3-[5-chloro-4-(6-fluoro-pyridin-2-ylmethoxy)-2-methyl-6-oxo-6H-pyrimidin-1-yl]-N-methoxy-4,N-dimethyl-benzamide; and 5-chloro-6-(6-fluoro-pyridin-2-ylmethoxy)-2-methyl-3-(2-methyl-5-propynoyl-phenyl)-3H-pyrimidin-4-one.

The present invention further comprises methods for treating a condition in a subject having or susceptible to having such a condition, by administering to the subject a therapeutically-effective amount of one or more compounds as described above. In one embodiment, the treatment is preventative treatment. In another embodiment, the treatment is palliative treatment. In another embodiment, the treatment is restorative treatment.

The conditions that can be treated in accordance with the present invention include, but are not limited to, autoimmune disorders, chronic inflammatory disorders, acute inflammatory disorders, auto-inflammatory disorders, pain, atherosclerosis, diabetes, fibrotic diseases, metabolic disorders, cancer, neoplasia, leukemia, and lymphoma.

In some embodiments the methods described herein are used to treat patients with disorders arising from dysregulated cytokine, enzymes and/or inflammatory mediator production, stability, secretion, posttranslational processing. Examples of cytokines that may be dysregulated include interleukins 1, 2, 6, 8, 10, 12, 17, 22 and 23 along with tumor necrosis factor alpha and interferons alpha, beta and gamma. Examples of inflammatory mediators that may be dysregulated include nitric oxide, prostaglandins and leukotrienes. Examples of enzymes include cyclo-oxygenase, nitric oxide synthase and matrixmetalloprotease.

In some embodiments the methods described herein are used to treat patients with dysregulated p38 activity, activation, biosynthesis or pathway function.

In some embodiments, the methods are used to treat a patient suffering from an autoimmune disorder, chronic and/or acute inflammatory disorder and/or auto-inflammatory disorder. Examples of disorders include, but are not limited to colitis, multiple sclerosis, arthritis, rheumatoid arthritis, osteoarthritis, juvenile arthritis, psoriatic arthritis, cryopyrin associated periodic syndromes, Muckle-Wells Syndrome, Familial Cold Auto-inflammatory Syndrome, neonatal-onset multisystem inflammatory disease, TNF receptor associated periodic syndrome, acute pancreatitis, chronic pancreatitis, atherosclerosis, inflammatory bowel disease, Crohn's disease, ulcerative colitis, Diabetes mellitus type 1, Diabetes mellitus type 2, diabetic retinopathy, Still's disease, multiple sclerosis, vasculitis, sarcoidosis, pulmonary inflammation, acute respiratory distress syndrome, chronic obstructive pulmonary disease (COPD), asthma, wet and dry age-related macular degeneration, autoimmune hemolytic syndromes, autoimmune hepatitis, autoimmune neuropathy, autoimmune ovarian failure, autoimmune orchitis, autoimmune thrombocytopenia, reactive arthritis, ankylosing spondylitis, silicone implant associated autoimmune disease, Sjogren's syndrome, Familial Mediterranean Fever, systemic lupus erythematosus, vasculitis syndromes (such as, for example, giant cell arteritis, Behcet's disease & Wegener's granulomatosis), Vitiligo, secondary hematologic manifestation of autoimmune diseases (such as, for example, anemias), drug-induced autoimmunity, Hashimoto's thyroiditis, hypophysitis, idiopathic thrombocytic pupura, metal-induced autoimmunity, myasthenia gravis, pemphigus, autoimmune deafness (including, for example, Meniere's disease), Goodpasture's syndrome, Graves' disease, HW-related autoimmune syndromes and Gullain-Barre disease. Examples of inflammatory conditions include, but are not limited to sepsis, septic shock, endotoxic shock, exotoxin-induced toxic shock, gram negative sepsis, toxic shock syndrome, glomerulonephritis, peritonitis, interstitial cystitis, psoriasis, atopic dermatitis, hypoxia-induced inflammations, vasculitis, graft vs. host reaction (i.e., graft vs. host disease), allograft rejections (e.g., acute allograft rejection, and chronic allograft rejection), early transplantation rejection (e.g., acute allograft rejection), reperfusion injury, acute pain, chronic pain, neuropathic pain, Fibromyalgia, pancreatitis, chronic infections, meningitis, encephalitis, myocarditis, gingivitis, post-surgical trauma, tissue injury, traumatic brain injury, hepatitis, enterocolitis, sinusitis, uveitis, ocular inflammation, optic neuritis, gastric ulcers, esophagitis, peritonitis, periodontitis, dermatomyositis, gastritis, myositis, polymyalgia, pneumonia, bronchitis, inflammation associated with infection and antibiotic-induced clostridium difficile infection. Fibrotic diseases, for instance, metabolic disorders, including but not limited to, obesity, steroid-resistance, glucose intolerance and metabolic syndrome.

In some embodiments, the methods described herein can be used to treat a patient suffering from neoplasia. Examples of these conditions include, but are not limited to, angiogenesis, multiple myeloma, leukemia, B cell lymphoma, T cell lymphoma, mast cell tumors, lymphoma, Hodgkin's disease, cancer of the bone, mouth/pharynx, oesophagus, larynx, stomach, intestine, colon, rectum, lung, liver, pancreas, nerve, brain, head and neck, throat, ovary, uterus, prostate, testis, bladder, kidney, breast non-small cell lung carcinoma, melanoma, skin cancer, teratoma, rhabdomyosarcoma, glioma, metastatic and bone disorders.

In some embodiments, the disease associated with dysregulated p38 include cardiovascular and cerebrovascular diseases, including but not limited to, atherosclerosis, restenosis of an atherosclerotic coronary artery, acute coronary syndrome, myocardial infarction, cardiac-allograft vasculopathy and stroke; central nervous system disorders with an inflammatory or apoptotic component, Alzheimer's disease, Parkinson's disease, Huntington's disease, amyotrophic lateral sclerosis, spinal cord injury, neuronal ischemia and peripheral neuropathy.

The term patient refers to both humans and non-human animals with the above-mentioned conditions. Non-human animals could be companion animals such as canine and feline species.

Suitable subjects to be treated according to the present invention include mammalian subjects. Mammals according to the present disclosure include, but are not limited to, human, canine, feline, bovine, caprine, equine, ovine, porcine, rodents, lagomorphs, and primates, and encompass mammals in utero. Subjects may be of either gender and at any stage of development.

The compounds of the present invention are generally administered in a therapeutically effective amount.

The compounds of the present invention can be administered by any suitable route in the form of a pharmaceutical composition adapted to such a route, and in a dose effective for the treatment intended. Therapeutically effective doses of the compounds of the present invention required to prevent or arrest the progress of, or to treat the medical condition, are readily ascertained by one of ordinary skill in the art using preclinical and clinical approaches familiar to the medicinal arts.

The compounds of the present invention may be administered orally, including by swallowing, so that the compound enters the gastrointestinal tract, or absorbed into the blood stream directly from the mouth (e.g., buccal or sublingual administration).

Suitable compositions for oral administration include solid formulations such as tablets, lozenges and capsules, which can contain liquids, gels, or powders.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable lubricants, for use in a tablet, may be present in amounts from about 0.1% to about 5% by weight, and include calcium, zinc or magnesium stearate, sodium stearyl fumarate and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet, may be present in amounts from about 0.1% to about 3% by weight, and include polysorbate 80, sodium dodecyl sulfate, talc and silicon dioxide.

Compounds of the present invention may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compounds of the present invention may be administered topically to the skin or transdermally. Formulations for this topical administration can include lotions, solutions, creams, gels, hydrogels, ointments, foams, implants, and patches. Pharmaceutically acceptable carriers for topical administration formulations can include water, alcohol, mineral oil, glycerin, and polyethylene glycol. Topical administration can also be performed by electroporation, iontophoresis, phonophoresis and the like.

Compositions for topical administration may be formulated as immediate or modified release, including delayed or sustained release.

The compounds of the present invention can be used, alone or in combination with other pharmaceutically active compounds, to treat various conditions such as those previously described above. The compound of the present invention and other pharmaceutically active compound(s) can be administered simultaneously (either in the same dosage form or in separate dosage forms) or sequentially. Accordingly, in one embodiment, the present invention comprises methods for treating a disease by administering to the subject a therapeutically-effective amount of one or more compounds of the present invention and one or more additional pharmaceutically active compounds.

In another embodiment, the present invention comprises a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, anti-atherosclerotic drugs, immunosuppressive drugs, immunomodulatory drugs, cytostatic drugs, angiogenesis inhibitors, kinase inhibitors, cytokine blockers and inhibitors of cell adhesion molecules.

p38 inhibitor compositions described herein are also optionally used in combination with other therapeutic reagents that are selected for their therapeutic value for the condition to be treated In general, the compositions described herein and, in embodiments where combinational therapy is employed, other agents do not have to be administered in the same pharmaceutical composition, and, because of different physical and chemical characteristics, are optionally administered by different routes.

The initial administration is generally made according to established protocols, and then, based upon the observed effects, the dosage, modes of administration and times of administration subsequently modified. In certain instances, it is appropriate to administer a p38 inhibitor composition as described herein, in combination with another therapeutic agent. By way of example only, if one of the side effects experienced by a patient upon receiving a p38 inhibitor composition as described herein is rash, then it is appropriate to administer an anti-histamine agent in combination with the initial therapeutic agent. Or, by way of example only, the therapeutic effectiveness of a p38 inhibitor is enhanced by administration of another therapeutic agent (which also includes a therapeutic regimen) that also has therapeutic benefit. In any case, regardless of the disease, disorder or condition being treated, the overall benefit experienced by the patient is either simply additive of the two therapeutic agents or the patient experiences a therapeutic benefit, such as a therapeutic enhancement, or increase in therapeutic index, or reduction in side-effects, or reduction in required effective drug dose, or combinations thereof.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a p38 inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

In another embodiment, a p38 inhibitor is optionally used in combination with procedures that provide additional therapeutic benefit to the patient, e.g., a therapeutic enhancement, or increase in therapeutic index, or reduction in side-effects, or reduction in required effective drug dose, or combinations thereof. A p38 inhibitor and the additional therapy(ies) are optionally administered before, during or after the occurrence of a disease or condition, and the timing of administering the composition containing a p38 inhibitor varies in some embodiments. Thus, for example, a p38 inhibitor is used as a prophylactic and is administered continuously to subjects with a propensity to develop conditions or diseases in order to prevent the occurrence of the disease or condition. A p38 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A p38 inhibitor can be used in combination with drugs from the following classes: (1) anti-inflammatory agents, such as NSAIDs, immunosuppressive drugs, immunomodulatory drugs; (2) anti-neoplastic drugs, such as cytostatic drugs (which can also be anti-proliferative agents), angiogenesis inhibitors, biological agents, steroids, vitamin D3 analogs, retinoids, other kinase inhibitors, cytokine blockers, corticosteroids and inhibitors of cell adhesion molecules. Where a subject is suffering from or at risk of suffering from atherosclerosis or a condition that is associated with atherosclerosis, a p38 inhibitor composition described herein is optionally used together with one or more agents or methods for treating atherosclerosis or a condition that is associated with atherosclerosis in any combination. Examples of therapeutic agents/treatments for treating atherosclerosis or a condition that is associated with atherosclerosis include, but are not limited to, torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol and clofibrate.

Where a subject is suffering from or at risk of suffering from an inflammatory condition, a p38 inhibitor composition described herein is optionally used together with one or more agents or methods for treating an inflammatory condition in any combination. Examples of anti-inflammatory therapeutic agents/treatments for treating an autoimmune and/or inflammatory condition include, but are not limited to any of the following: corticosteroids, nonsteroidal antiinflammatory drugs (NSAID) (e.g., ibuprofen, naproxen, acetominophen, aspirin, fenoprofen, flurbiprofen, ketoprofen, oxaprozin, diclofenac sodium, diclofenac potassium, etodolac, indomethacin, ketorolac, sulindac, tolmetin, meclofenamate, mefenamic acid, nabumetone, piroxicam, COX-2 inhibitors (e.g., celecoxib), immunosuppressants (e.g. methotrexate, leflunomide, azathioprine, cyclosporine, tacrolimus and cyclophosphamide, CD20 blockers (Rituximab), tumor necrosis factor (TNF) blockers (e.g., etanercept, infliximab and adalimumab), Abatacept (CTLA4-Ig) and interleukin-1 receptor antagonists (e.g. Anakinra, interleukin 6 inhibitors (e.g. Actemra), interleukin 17 inhibitors (e.g. AIN457), Janus kinase inhibitors (e.g., Tasocitinib), syk inhibitors (e.g., R788), chloroquine and its derivatives.

For use in cancer and neoplastic diseases a p38 inhibitor is optimally used together with one or more of the following classes of drugs: wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, proteosome inhibitor, chemotherapy agent, or glucose reduction agent.

The present disclosure also provides kits that are suitable for use in performing the methods of treatment or prevention described above. In one embodiment, the kit contains a first dosage form comprising one or more of the compounds of the present invention and a container for the dosage, in quantities sufficient to carry out the methods of the present invention.

The invention also embraces a pharmaceutical composition comprising a therapeutically effective amount of a compound of Formula (II) or a pharmaceutically acceptable salt thereof, and a pharmaceutically acceptable carrier.

In another embodiment, the invention embraces a composition comprising a pharmaceutically acceptable carrier and a therapeutically effective amount of a first active pharmaceutical ingredient in combination with a second active pharmaceutical ingredient, wherein the first active pharmaceutical ingredient is a compound of Formula (II) or a pharmaceutically acceptable salt thereof, and wherein the second active pharmaceutical ingredient is selected from the group consisting of anti-inflammatory drugs, anti-neoplastic drugs, anti-atherosclerotic drugs, and drugs for treating airway tissue hypersensitivity.

In another embodiment, the second active pharmaceutical ingredient is one or more anti-inflammatory drugs, selected from the group consisting of NSAIDs, immunomodulatory drugs and tumor necrosis factor α (TNFα) blockers.

NSAIDs suitable for use in the present invention include one or more of the following: ibuprofen, naproxen, acetominophen, aspirin, fenoprofen, flurbiprofen, ketoprofen, oxaprozin, diclofenac sodium, diclofenac potassium, etodolac, indomethacin, ketorolac, sulindac, tolmetin, meclofenamate, mefenamic acid, nabumetone, piroxicam and celecoxib.

Immunomodulatory drugs suitable for use in the present invention include one or more of the following: methotrexate, leflunomide, azathioprine, cyclosporine, tacrolimus and cyclophosphamide and rituximab.

TNFα blockers suitable for use in the present invention include one or more of the following: etanercept, infliximab and adalimumab.

In another embodiment, the second active pharmaceutical ingredient is one or more anti-neoplastic drugs, selected from the group consisting of cytostatic drugs, angiogenesis inhibitors, steroids, kinase inhibitors, cytokine blockers and inhibitors of cell adhesion molecules.

Cytostatic drugs suitable for use in the present invention include one or more of the following: cyclophosphamide, doxorubicin, vincristine and prednisone.

Angiogenesis inhibitors suitable for use in the present invention include etaracizumab and/or cilengitide.

Steroids suitable for use in the present invention include one or more of the following: corticosteroids, prednisone, prednisolone, methylprednisolone, dexamethasone, hydrocortisone, cortisone, betamethasone and triamcinolone.

Kinase inhibitors suitable for use in the present invention include one or more of the following: afatanib, axitinib, bosutinib, crizotinib, dabrafanib, dasatinib, erlotinib, fostamatinib, gefitinib, imatinib, lapatinib, nilotinib, pazopanib, ruxolitinib, selumetinib, sorafanib, sunitinib, tofasitinib, trametinib, vandetinib, vemurafenib, AV-292 and PCI-32756.

Cytokine blockers suitable for use in the present invention include one or more of the following: anakinra, canakinumab, rilonacept, tocilizumab, AIN457 and ustekinumab.

An inhibitor of cell adhesion molecules suitable for use in the present invention is catumaxomab.

In another embodiment, the second active pharmaceutical ingredient is one or more anti-atherosclerotic drugs, selected from the group consisting of atorvastatin, fluvastatin, lovastatin, pravastatin, rosuvastatin and simvastatin.

In another embodiment, the second active pharmaceutical ingredient is one or more drugs for treating airway tissue hypersensitivity, selected from the group consisting of $\beta_2$ agonists, anticholinergic drugs, corticosteroids, phosphodiesterase inhibitors, leukotriene modulators, methyl xanthines and anti-infectives.

$\beta_2$ agonists suitable for use in the present invention include one or more of the following: salbutamol, terbutaline, salmeterol, isoetharine and formoterol.

Anticholinergic drugs suitable for use in the present invention include ipratropium and/or tiotropium.

Corticosteroids suitable for use in the present invention include one or more of the following: budesonide, flunisolide, fluticasone, triamcinalone, beclomethasone, ciclesonide, mometasone and prednisone.

Phosphodiesterase inhibitors suitable for use in the present invention include theophylline and/or roflumilast.

Leukotriene modulators suitable for use in the present invention include montelukast and/or zafirlukast.

Methyl xanthines suitable for use in the present invention include theophylline and/or dyphylline.

Anti-infectives suitable for use in the present invention include one or more of the following: metronidazole, vancomycin, rifamixin and fidaxomicin.

General Synthetic Preparations

The compounds of the present invention can be prepared via the synthetic routes shown in Schemes I-IX below. These schemes are representative and the syntheses of these compounds are not limited to the illustrated routes.

Scheme I: Preparation of C-2 pyrimidinones having mono-substituted pyrimidine (Route A).

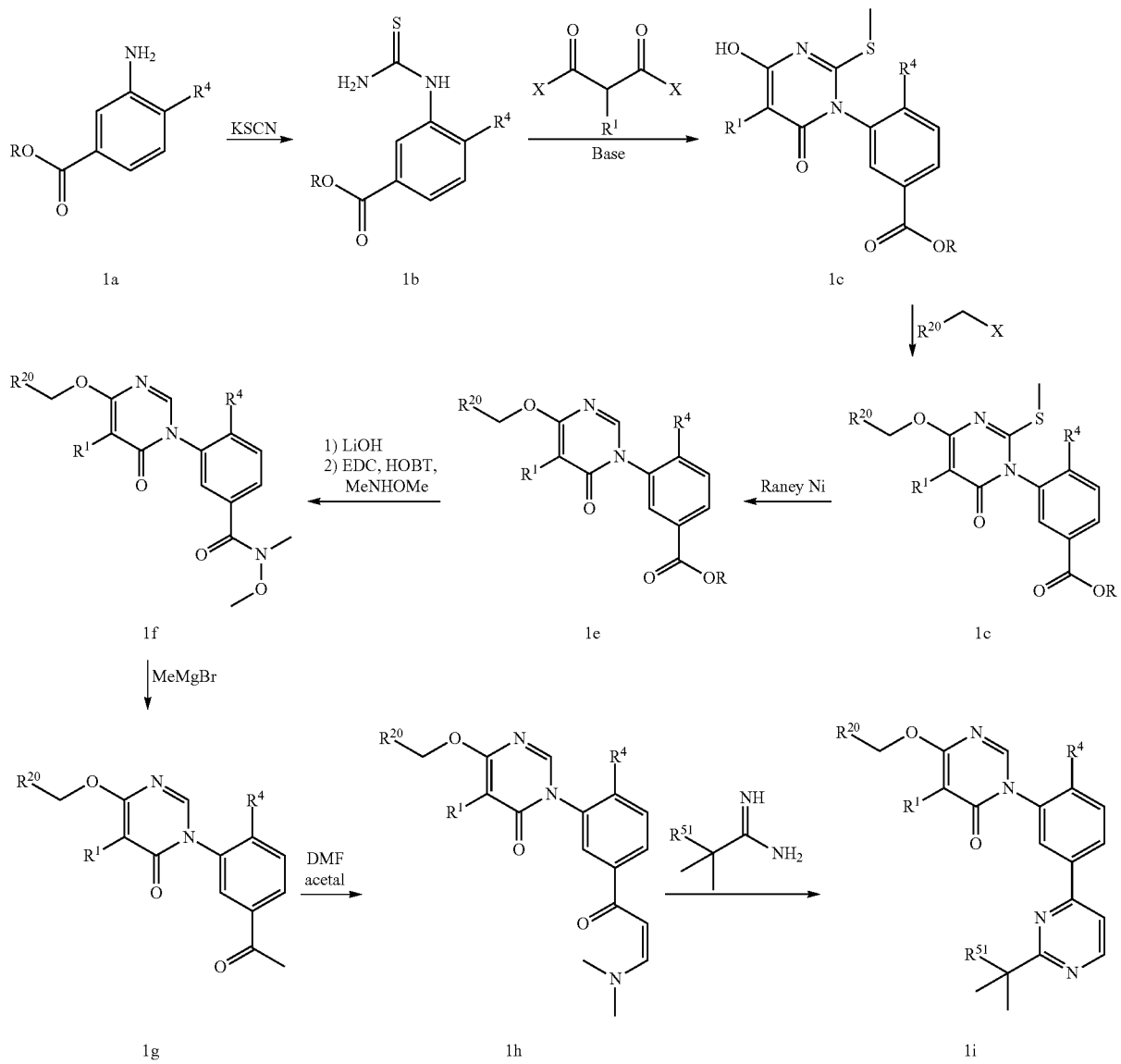

R = $C_{1-4}$alkyl
$R^1$ = methyl or ethyl

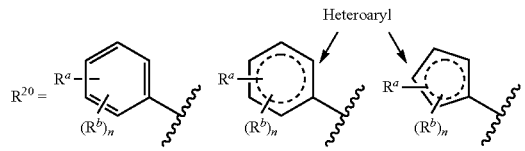

$R^a$ = $C_{1-3}$alkyl, $C_{1-3}$alkoxy, cyano, halo or trihaloalkyl
$R^b$ = $C_{1-3}$alkyl, $C_{1-3}$alkoxy, cyano, halo or trihaloalkyl
n = 0, 1 or 2
$R^4$ = H, methyl or chloro
$R^{51}$ = H, $C_{1-3}$alkyl, hydroxyl or thiol
X = halo As shown in Scheme I, acylation of substituted aniline (1a) with potassium thioisocyanate affords a thiourea (1b). Condensation of (1b) with a substituted malonate derivative in the presence of base followed by the addition of methyl iodide generates the thiomethyl pyrimidinone product (1c). Alkylation with a substituted halide affords the alkylated pyrimidinone (1d). Treatment of (1d) with Raney nickel provides the des-thiomethyl pyrimidinone (1e). Conversion of (1e) to the Weinreb amide (1f) followed by addition of methyl Grignard affords the methyl ketone (1g). Condensation of (1g) with a dimethyl formamide acetal generates the enamino ketone intermediate (1h) which is then condensed with a substituted amidine to afford the target C-2 H pyrimidinone (1i).

Scheme II: Preparation of C-2 H pyrimidinones having mono-substituted pyrimidine (Route B).

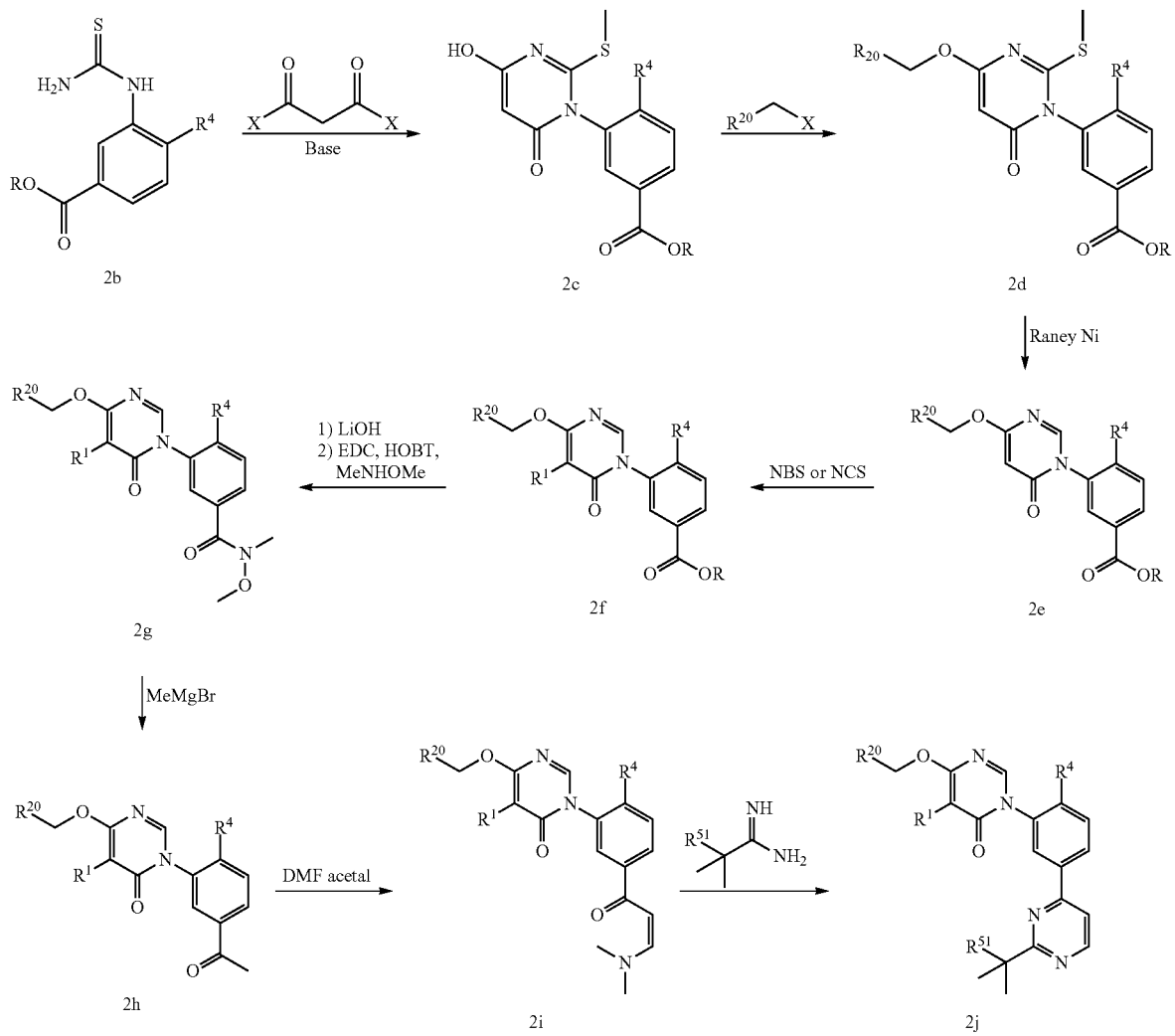

-continued

R = C₁₋₄alkyl
R¹ = bromo or chloro

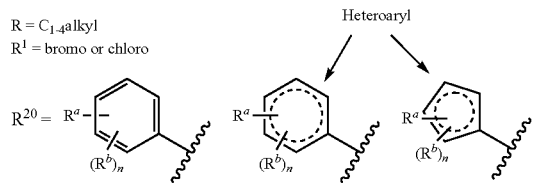

$R^a$ = C₁₋₃alkyl, C₁₋₃alkoxy, cyano, halo or trihaloalkyl
$R^b$ = C₁₋₃alkyl, C₁₋₃alkoxy, cyano, halo or trihaloalkyl
n = 0, 1 or 2
R⁴ = H, methyl or chloro
R⁵¹ = H, C₁₋₃alkyl, hydroxyl or thiol
X = halo As shown in Scheme II, thiourea (2b) is condensed with an unsubstituted malonate derivative in the presence of base to afford the thiomethylpyrimidinone (2c). Alkylation with a substituted halide affords the alkylated pyrimidinone (2d). Raney nickel mediated reduction of (2d) provides the des-thiomethylpyrimidinone (2e). Halogenation of (2e) with either N-bromo or N-chlorosuccinimide (NBS or NCS) generates the halogenated pyrimidinone (2f). Hydrolysis of (2f) followed by coupling of the thus formed acid with methoxy methylamine produces the Weinreb amide (2g). Treatment of (2g) with methyl magnesium bromide affords the methyl ketone (2h). Condensation of the methyl ketone with an acetal of dimethylformamide generates the enamino ketone (2i). Reaction of (2i) with a substituted amidine yields the C-2 H pyrimidinone (2j).

Scheme III: Preparation of C-2 substituted pyrimidinones having mono-substituted pyrimidine (Route A).

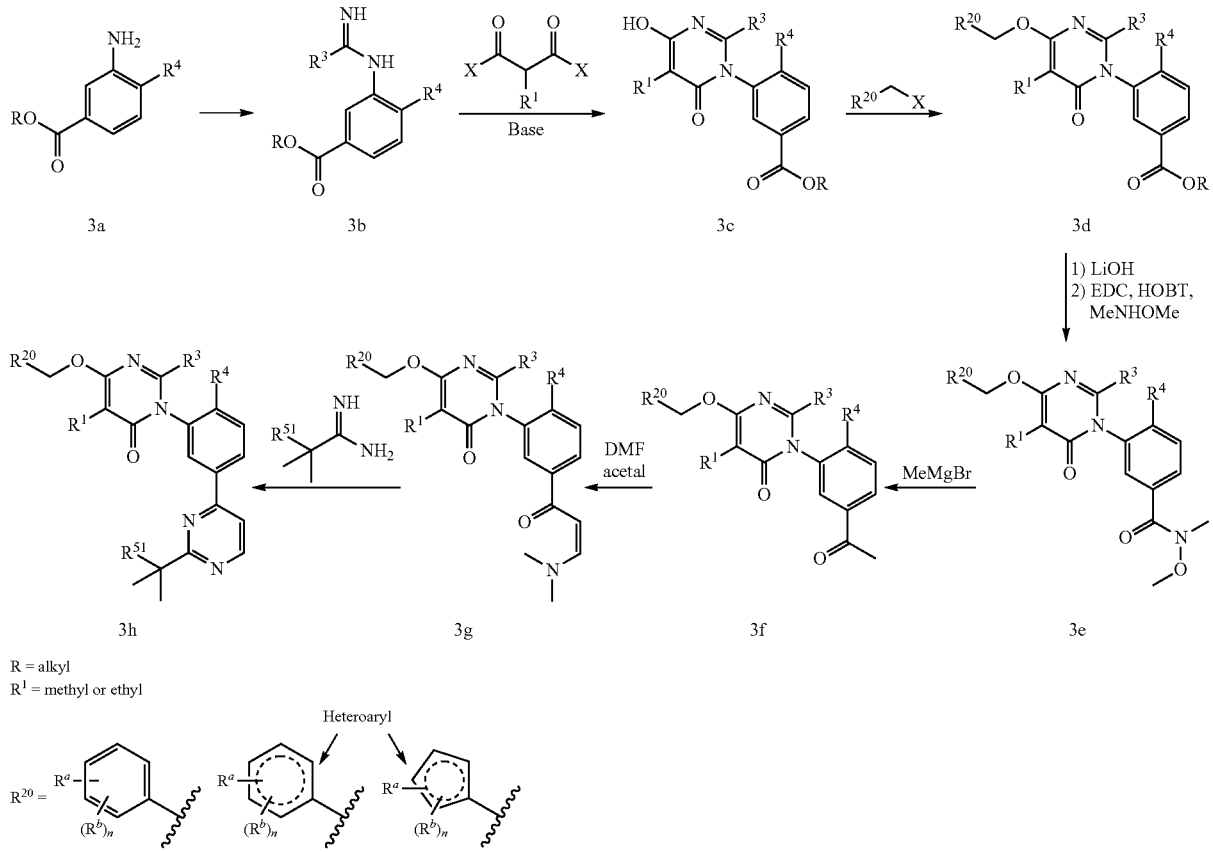

R = alkyl
R¹ = methyl or ethyl $R^a$ = C₁₋₃alkyl, C₁₋₃alkoxy, cyano, halo or trihaloalkyl
$R^b$ = C₁₋₃alkyl, C₁₋₃alkoxy, cyano, halo or trihaloalkyl
n = 0, 1 or 2
R³ = methyl or ethyl
R⁴ = H, methyl or chloro
R⁵¹ = H, C₁₋₃alkyl, hydroxyl or thiol
X = halo As shown in Scheme III, reaction of a substituted aniline (3a) with an appropriate amidine transfer reagent or a substituted nitrile provides the amidine (3b). Condensation of (3b) with a substituted malonate derivative in the presence of base generates the hydroxy pyrimidinone product (3c). Alkylation with a substituted halide affords the alkylated pyrimidinone (3d). Conversion of (3d) to the Weinreb amide (3e) followed by addition of methyl Grignard affords the methyl ketone (3f). Condensation of 3f with a dimethyl formamide acetal generates the enamino ketone intermediate (3g) which is then condensed with a substituted amidine to afford the target C-2 alkyl pyrimidinone (3h).

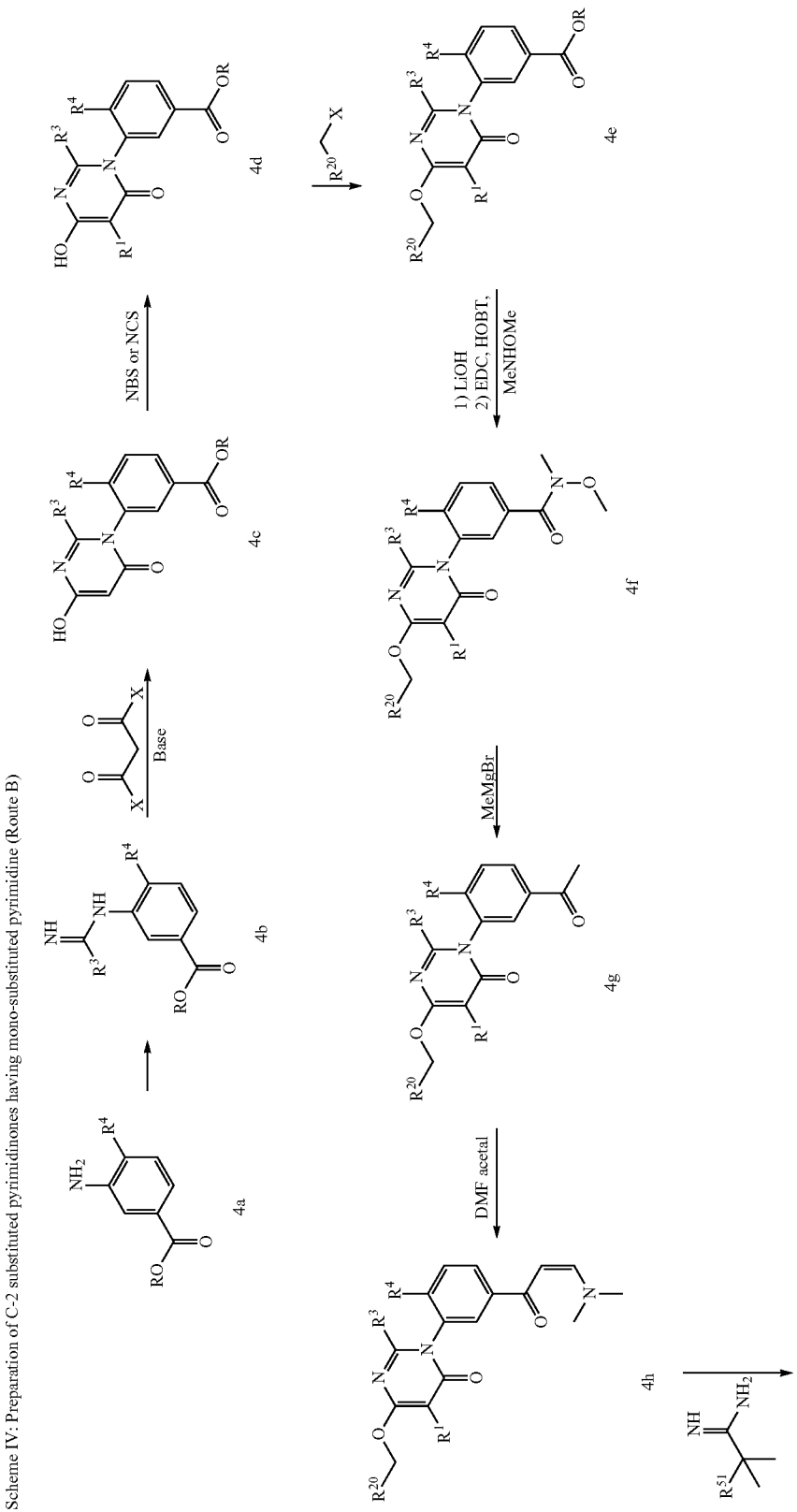

-continued
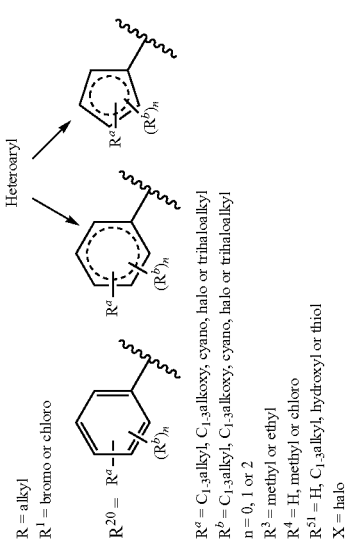
4i
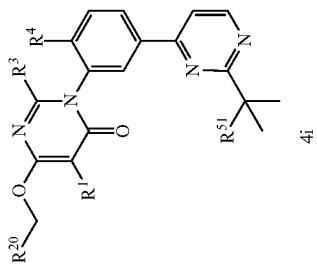
R = alkyl
$R^1$ = bromo or chloro
$R^{20}$ = 
$R^a$ = $C_{1-3}$alkyl, $C_{1-3}$alkoxy, cyano, halo or trihaloalkyl
$R^b$ = $C_{1-3}$alkyl, $C_{1-3}$alkoxy, cyano, halo or trihaloalkyl
n = 0, 1 or 2
$R^3$ = methyl or ethyl
$R^4$ = H, methyl or chloro
$R^{51}$ = H, $C_{1-3}$alkyl, hydroxyl or thiol
X = halo As shown in Scheme IV, reaction of a substituted aniline (4a) with an appropriate amidine transfer reagent or a substituted nitrile provides the amidine (4b). Condensation of (4b) with an unsubstituted malonate derivative in the presence of base generates the hydroxy pyrimidinone product (4c). Halogenation with a substituted halide affords the halogenated pyrimidinone (4d). Alkylation of (4d) provides the alkylated pyrimidinone (4e). Conversion of (4e) to the Weinreb amide (4f) followed by addition of methyl Grignard affords the methyl ketone (4g). Condensation of (4g) with a dimethyl formamide acetal generates the enamino ketone intermediate (4h) which is then condensed with a substituted amidine to afford the target C-2 alkyl pyrimidinone (4i).

Scheme V: Preparation of C-2 substituted pyrimidinones having mono-substituted pyrimidine (Route C)

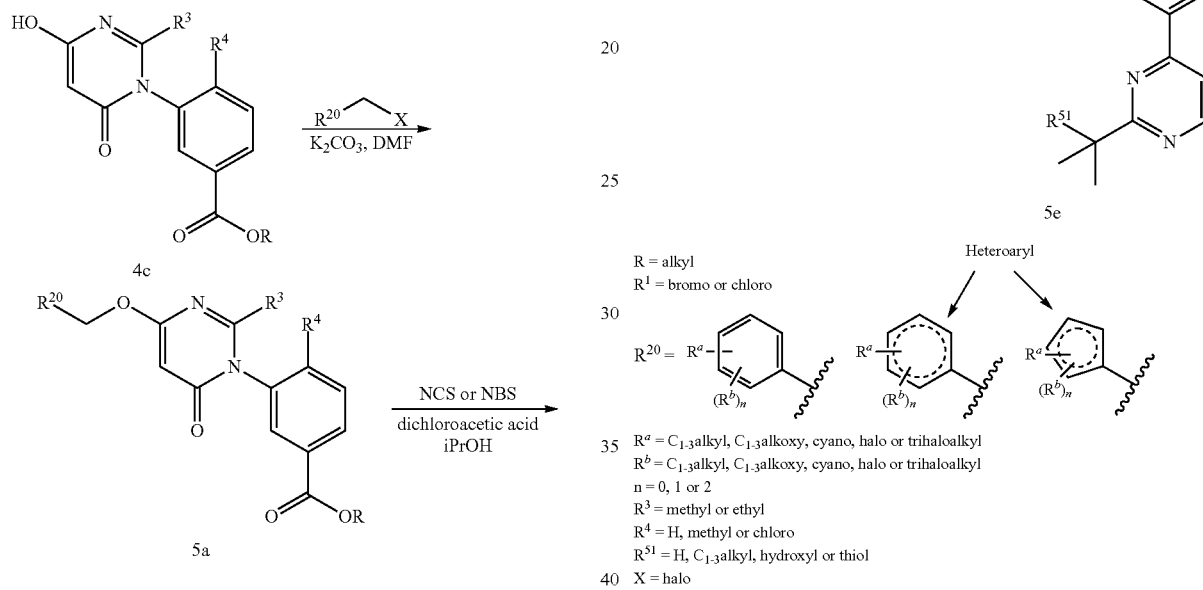

R = alkyl
$R^1$ = bromo or chloro

Heteroaryl $R^{20}$ =

$R^a$ = $C_{1-3}$alkyl, $C_{1-3}$alkoxy, cyano, halo or trihaloalkyl
$R^b$ = $C_{1-3}$alkyl, $C_{1-3}$alkoxy, cyano, halo or trihaloalkyl
n = 0, 1 or 2
$R^3$ = methyl or ethyl
$R^4$ = H, methyl or chloro
$R^{51}$ = H, $C_{1-3}$alkyl, hydroxyl or thiol
X = halo As shown in Scheme V, alkylation of phenol (4c) with the desired arylmethyl halide or heteroarylmethyl halide provides (5a). Reaction of (5a) with NCS or NBS affords the halogenated pyrimidinone (5b). Conversion of (5b) to the intermediate carboxylic acid and then to the Weinreb amide using standard coupling conditions gives (5c). Reaction of (5c) with ethynyl Grignard affords the alkynyl ketone (5d). Condensation of (5d) with a 2-substituted formamidine generates the desired pyrimidinone (5e).

Scheme VI: Preparation of C-2 substituted pyrimidinones having mono-substituted pyrimidine (Route D)

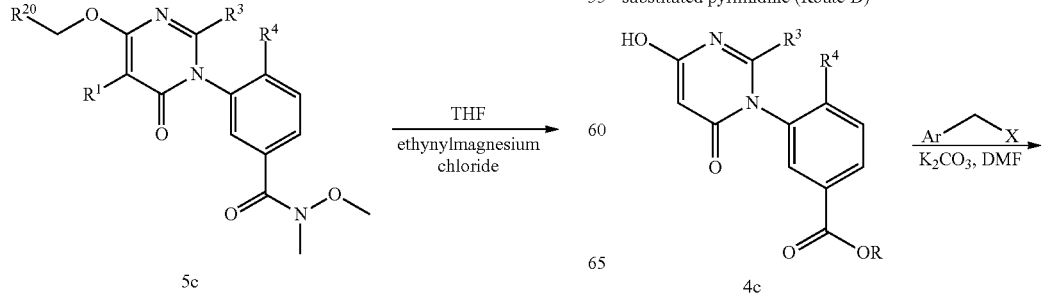

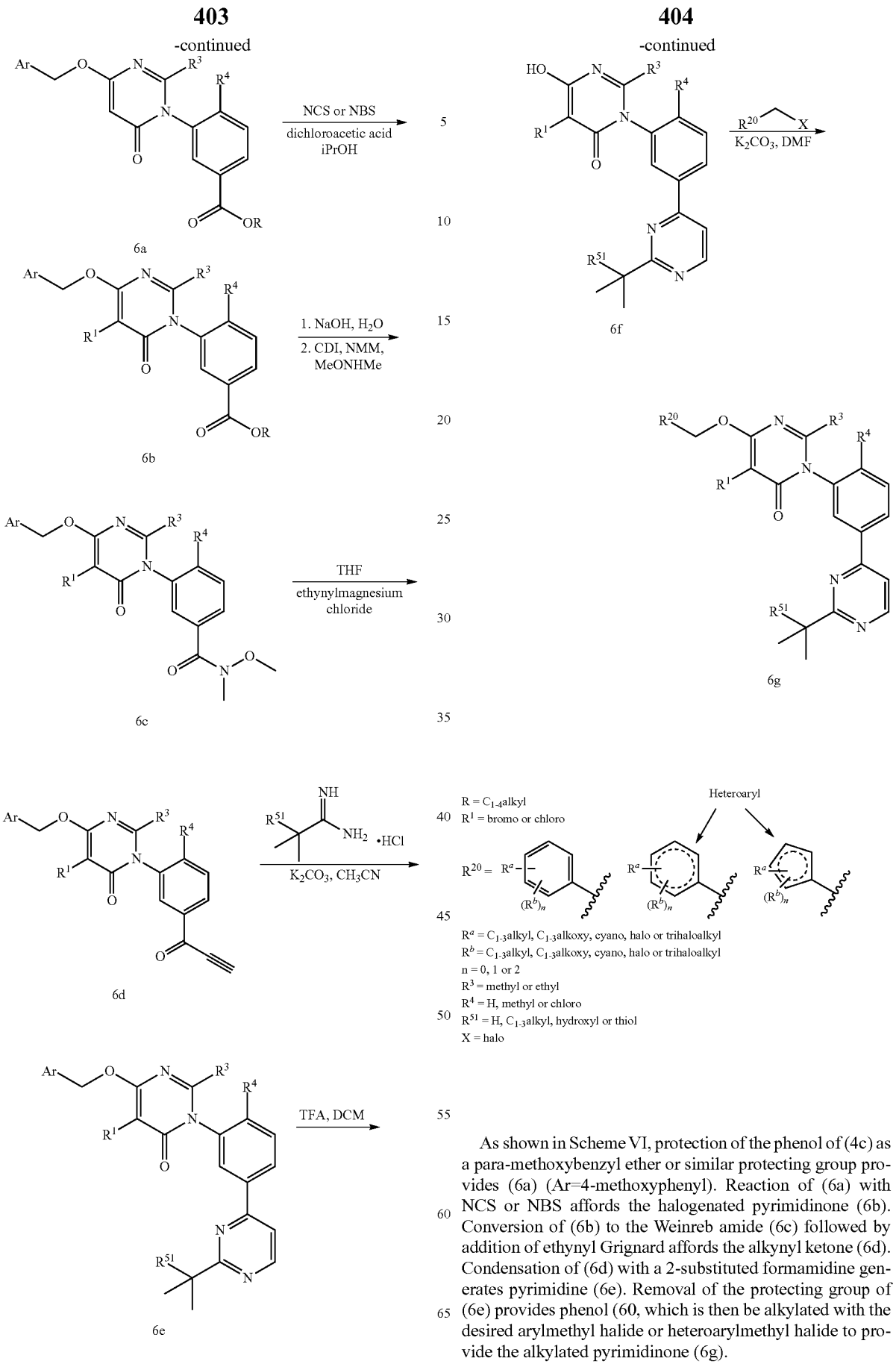

As shown in Scheme VI, protection of the phenol of (4c) as a para-methoxybenzyl ether or similar protecting group provides (6a) (Ar=4-methoxyphenyl). Reaction of (6a) with NCS or NBS affords the halogenated pyrimidinone (6b). Conversion of (6b) to the Weinreb amide (6c) followed by addition of ethynyl Grignard affords the alkynyl ketone (6d). Condensation of (6d) with a 2-substituted formamidine generates pyrimidine (6e). Removal of the protecting group of (6e) provides phenol (6f), which is then be alkylated with the desired arylmethyl halide or heteroarylmethyl halide to provide the alkylated pyrimidinone (6g).

Scheme VII: Preparation of C-2 substituted pyrimidinones having di-substituted pyrimidine (Route A)

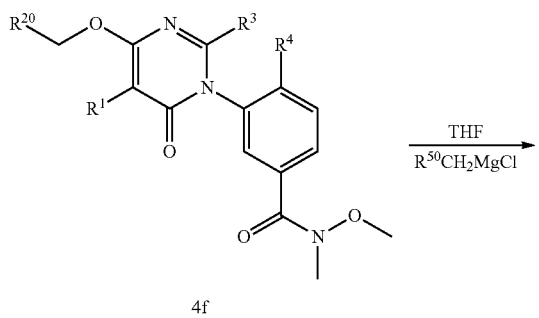

4f

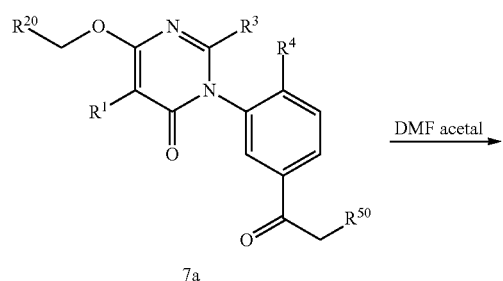

7a

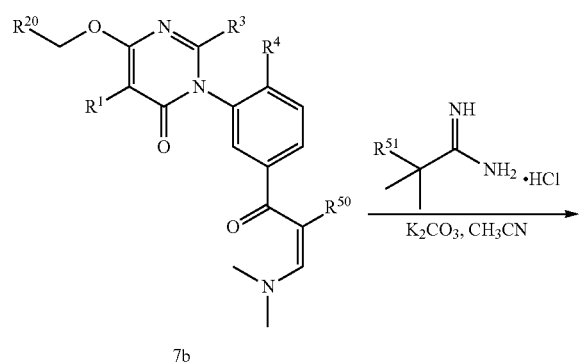

7b

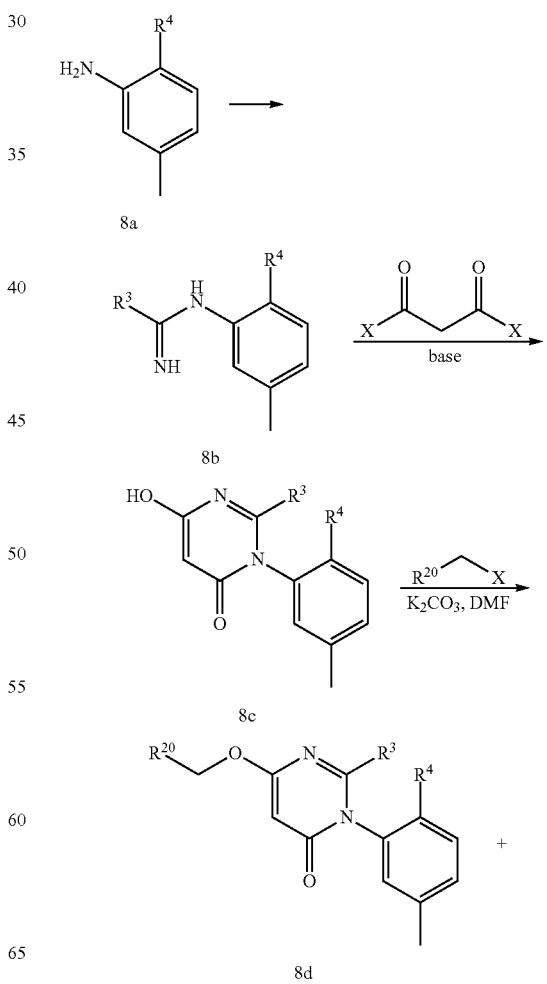

7c

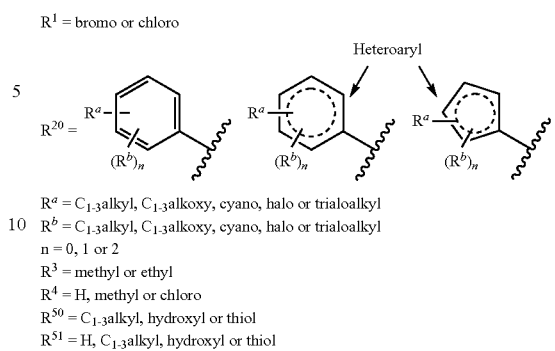

$R^1$ = bromo or chloro
$R^a$ = $C_{1-3}$alkyl, $C_{1-3}$alkoxy, cyano, halo or trialoalkyl
$R^b$ = $C_{1-3}$alkyl, $C_{1-3}$alkoxy, cyano, halo or trialoalkyl
n = 0, 1 or 2
$R^3$ = methyl or ethyl
$R^4$ = H, methyl or chloro
$R^{50}$ = $C_{1-3}$alkyl, hydroxyl or thiol
$R^{51}$ = H, $C_{1-3}$alkyl, hydroxyl or thiol As shown in Scheme VII, reaction of Weinreb amide (4f) with a substituted-methyl Grignard reagent affords ketone (7a). Condensation of (7a) with dimethyl formamide acetal generates the enamino ketone intermediate (7b) which is condensed with a substituted amidine to afford the target C-2 alkyl pyrimidinone (7c).

Scheme VIII: Preparation of C-2 substituted pyrimidinone having di-Substituted pyrimidine (Route B)

8a

8b

8c

8d

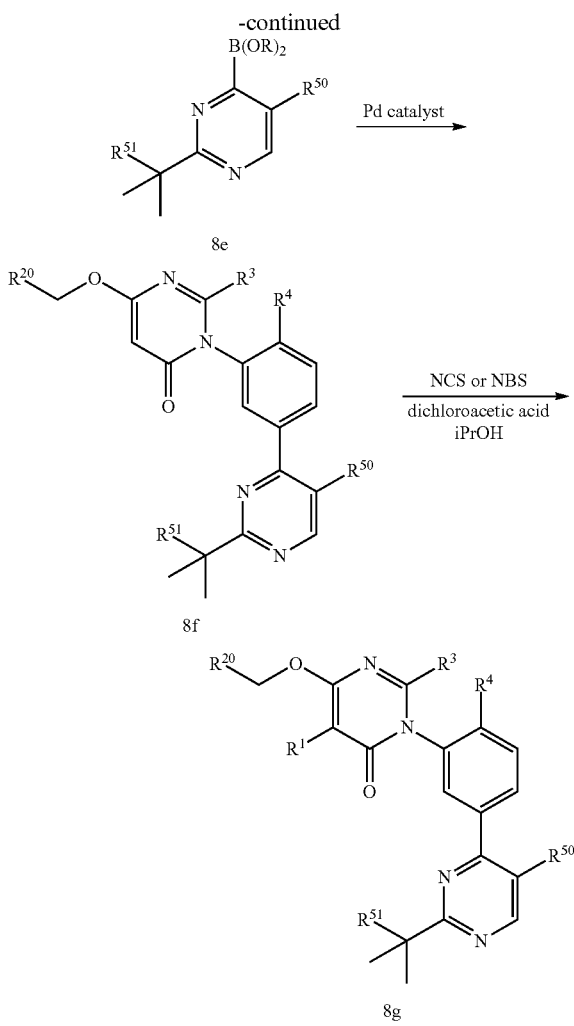

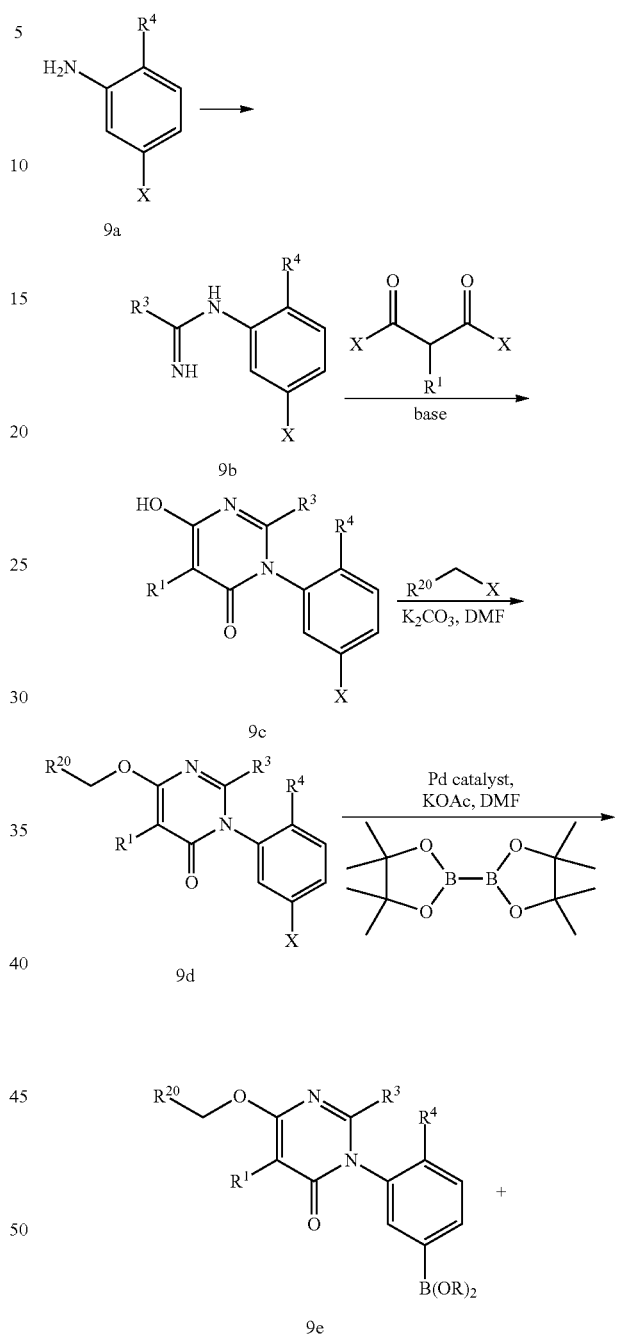

Scheme IX: Preparation of C-2 substituted pyrimidinones having di-substituted pyrimidine (Route C)

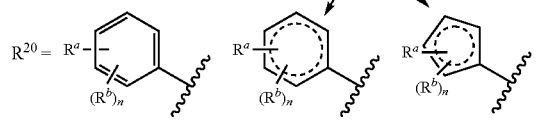

R = alkyl
R[1] = bromo or chloro

R[a] = C$_{1-3}$alkyl, C$_{1-3}$alkoxy, cyano, halo or trihaloalkyl
R[b] = C$_{1-3}$alkyl, C$_{1-3}$alkoxy, cyano, halo or trihaloalkyl
n = 0, 1 or 2
R[3] = methyl or ethyl
R[4] = H, methyl or chloro
R[50] = C$_{1-3}$alkyl or halo
R[51] = H, C$_{1-3}$alkyl, hydroxyl or thiol
X = halo

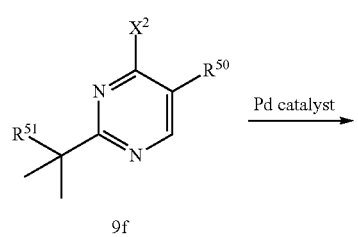

As shown in Scheme VIII, reaction of substituted aniline (8a) with an appropriate amidine transfer reagent or a substituted nitrile provides the amidine (8b). Condensation of (8b) with an unsubstituted malonate derivative in the presence of base generates the hydroxy-pyrimidinone product (8c). Alkylation of (8c) with the desired arylmethyl halide or heteroarylmethyl halide provides pyrimidinone (8d). Reaction of (8d) with boronic ester (8e) under Suzuki conditions using a palladium catalyst affords (8f). Halogenation with NBS or NCS affords the target C-2 alkyl pyrimidinone (8g). Alternatively (8d) may be halogenated with NCS or NBS and then the Suzuki reaction carried out to provide (8g) directly.

409
-continued

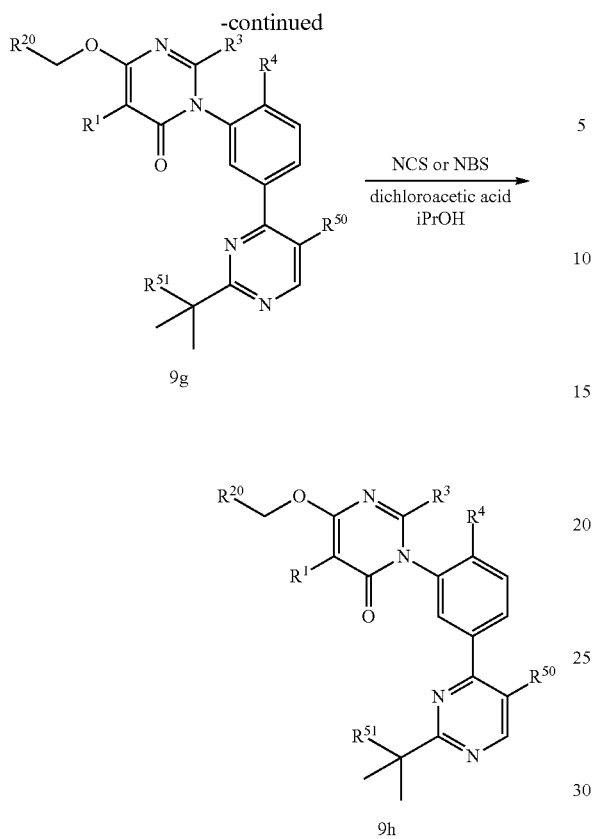

9g

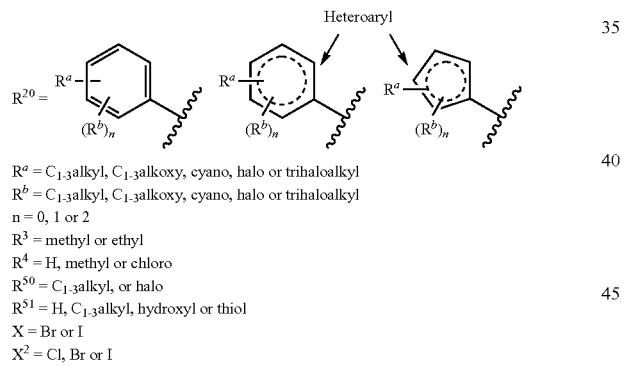

R = alkyl
R¹ = H, methyl, ethyl, bromo or chloro

[three heteroaryl/aryl structures for R²⁰]

$R^a$ = $C_{1-3}$alkyl, $C_{1-3}$alkoxy, cyano, halo or trihaloalkyl
$R^b$ = $C_{1-3}$alkyl, $C_{1-3}$alkoxy, cyano, halo or trihaloalkyl
n = 0, 1 or 2
$R^3$ = methyl or ethyl
$R^4$ = H, methyl or chloro
$R^{50}$ = $C_{1-3}$alkyl, or halo
$R^{51}$ = H, $C_{1-3}$alkyl, hydroxyl or thiol
X = Br or I
$X^2$ = Cl, Br or I As shown in Scheme IX, reaction of substituted aniline (9a, X=I or Br) with an appropriate amidine transfer reagent or a substituted nitrile provides amidine (9b). Condensation of (9b) with a malonate derivative in the presence of base generates the hydroxy-pyrimidinone product (9c). Alkylation of (9c) with the desired arylmethyl halide or heteroarylmethyl halide provides pyrimidinone (9d). Reaction of (9d) with the bis(pinacolato)diboron reagent (J. Med. Chem. 2006, 5671) provides borate ester (9e). Reaction of boronic ester (9e) with halo (9f) ($X^2$=Cl, Br or I) under Suzuki conditions using a palladium catalyst affords (9g). If R¹ on (9g) is hydrogen, the corresponding chloro or bromo analogs may be prepared by halogenation with either NBS or NCS to afford the targeted C-2 alkyl pyrimidinone (9h). Alternatively, (9d) with a hydrogen at R¹, may be directly halogenated with NCS or NBS to give the corresponding analog which is then be subjected to the Suzuki reaction to provide (9g) directly.

410

Protecting Groups:

Acetyl (Ac)
Acylals (diacetates) e.g.,

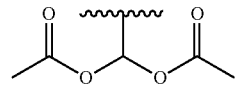 [SMILES: *C(OC(C)=O)OC(C)=O]

Benzoyl (Bz)
Benzyl (Bn, Bnl)
Benzyl esters, e.g.,

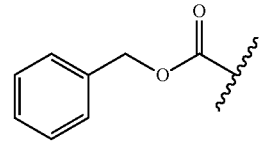 [SMILES: *C(=O)OCc1ccccc1]

Methoxytrityl (MMT),
Dimethoxytrityl (DMT) and
Triphenylmehyl or Trityl (Tr)

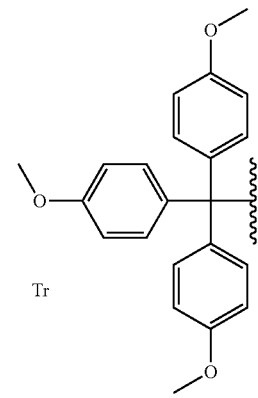 [SMILES: *C(c1ccc(OC)cc1)(c1ccc(OC)cc1)c1ccc(OC)cc1]

Tr

Dithianes, e.g., 1,3-propanedithiol
Ethoxyethyl ether
Methoxymethyl ether (MOM)

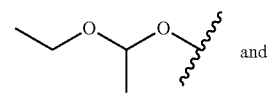 [SMILES: *OC(C)OCC] and

Methyl ester
Methylthiomethyl ethers, e.g.,

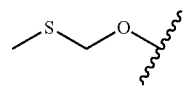

Oxazolines, e.g.,

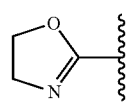

p-Methoxybenzyl carbonyl (Moz or MeOZ)
p-Methoxybenzyl ether (PMB)

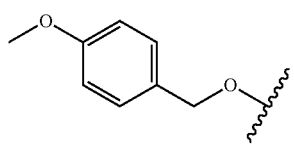 [SMILES: *OCc1ccc(OC)cc1]

Silyl groups, e.g., trimethylsilyl (TMS), tert-
butyldimethylsilyl (TBDMS), tri-iso-
propylsilyloxymethyl (TOM), triisopropylsilyl (TIPS)
and Trimethylsilylethoxymethyl (SEM)
tert-Butyloxycarbonyl (BOC or tBOC)
Tetrahydropyranyl ether (THP),

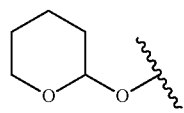 [SMILES: *OC1CCCCO1]

Tosyl (Ts or Tos)

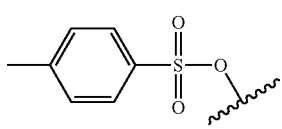 [SMILES: *OS(=O)(=O)c1ccc(C)cc1]

β-Methoxyethoxymethyl ether (MEM)

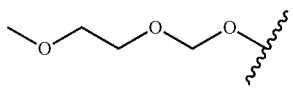 [SMILES: *OCOCCOC]

(4-nitrophenyl)sulfonyl (Nosyl)

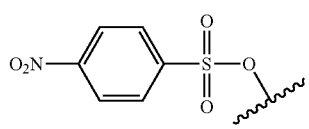 [SMILES: *OS(=O)(=O)c1ccc([N+](=O)[O-])cc1]

Preparation of Compound Intermediates

5-Chloro-6-hydroxy-3-{5-[2-(1-hydroxy-1-methyl-ethyl)-pyrimidin-4-yl]-2-methyl-phenyl}-2-methyl-3H-pyrimidin-4-one (Intermediate 1)

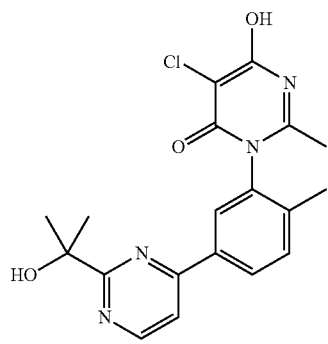 [SMILES: Cc1ccc(-c2ccnc(C(C)(C)O)n2)cc1-n1c(C)nc(O)c(Cl)c1=O]

Step A: Preparation of thioacetimidic acid naphthalen-2-ylmethyl ester

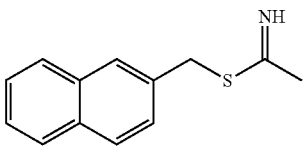

To a solution of thioacetamide (3.3 g, 44 mmol) in chloroform (100 mL) was added 2-bromomethylnaphthylene (9.7 g, 44 mmol) and heated to reflux for two hours. The resulting white solid was collected by vacuum filtration (9.18 g, 71% yield). MS (M+H): 296

Step B: Preparation of 3-acetimidoylamino-4-methyl-benzoic acid methyl ester

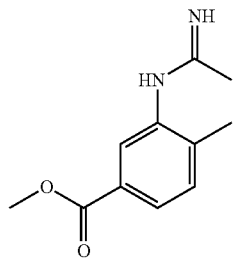

To a solution of methyl 3-amino-4-methyl benzoate (2.8 g, 16.9 mmol) in ethanol (50 mL), cooled using an ice bath, was added thioacetimidic acid naphthalen-2-ylmethyl ester from Step A (5.0 g, 16.9 mmol). The reaction was stirred at 60° C. for two hours. The reaction was returned to ambient temperature and the solvent was removed in vacuo. The remaining residue was dissolved into ethyl acetate and washed with water. The aqueous layer was treated with 1M NaOH until the pH was adjusted to 9. The aqueous layer was extracted with ethyl acetate, washed with brine and dried over MgSO$_4$. Following filtration, the solution was concentrated in vacuo to provide the methyl amidine as a white solid (1.39 g, 40% yield). MS (M+H): 207

Step C: Preparation of 3-[1-(2-methoxycarbonyl-acetylamino)-ethylideneamino]-4-methyl-benzoic acid methyl ester

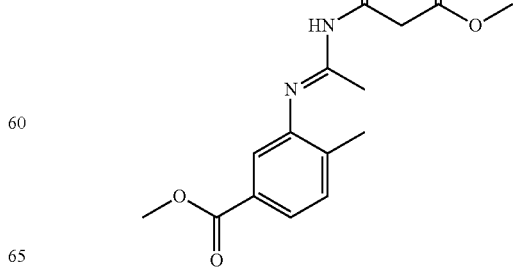

To a solution of 3-acetimidoylamino-4-methyl-benzoic acid methyl ester from Step B (1.39 g, 6.7 mmol) in dichloromethane (20 mL), cooled using an ice/brine water bath, was added 4-methylmorpholine (1.11 mL, 10.1 mmol) and methyl malonyl chloride (1.08 mL, 10.1 mmol). The reaction was allowed to warm to ambient temperature and stirred for eighteen hours. The reaction was quenched with saturated sodium bicarbonate, extracted with ethyl acetate, washed with brine and dried over magnesium sulfate. The slurry was filtered and concentrated to provide the product as an orange oil (2.2 g, quantitative yield). MS (M+H): 307

Step D: Preparation of 3-(4-hydroxy-2-methyl-6-oxo-6H-pyrimidin-1-yl)-4-methyl-benzoic acid methyl ester (Intermediate 2)

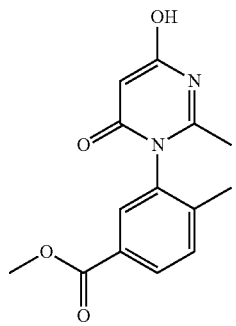

To a solution of 3-[1-(2-methoxycarbonyl-acetylamino)-ethylideneamino]-4-methyl-benzoic acid methyl ester from Step C (2.0 g, 6.7 mmol) in 1,4-dioxane (10 mL) was added 1,8-diazabicyclo[5.4.0]undec-7-ene (0.5 mL, 3.35 mmol) and the solution was heated at 60° C. for one hour. The solution was returned to ambient temperature and concentrated in vacuo to provide the phenol as an orange oil (1.8 g, quantitative yield) and used without purification. MS (M+H): 275

Step E: Preparation of 3-[4-(4-methoxy-benzyloxy)-2-methyl-6-oxo-6H-pyrimidin-1-yl]-4-methyl-benzoic acid methyl ester

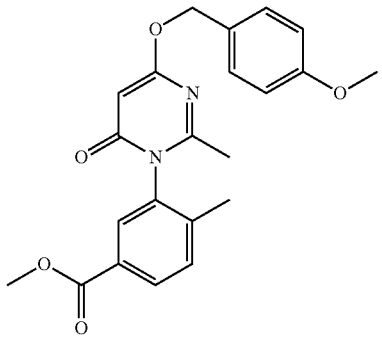

To a solution of 3-(4-hydroxy-2-methyl-6-oxo-6H-pyrimidin-1-yl)-4-methyl-benzoic acid methyl ester from Step D (800 mg, 66% purity, 1.93 mmol) in N,N-dimethylformamide (3 mL) was added 4-methoxybenzyl chloride (0.26 mL, 1.93 mmol), potassium carbonate (666 mg, 4.82 mmol) and 18-crown-6 (80 mg). The slurry was heated at 60° C. for two hours. The solution was allowed to cool to ambient temperature and was partitioned between ethyl acetate and water. The organic layer was washed with water and brine and dried over magnesium sulfate. The slurry was filtered and concentrated to a brown oil. Normal phase chromatography (ethyl acetate/heptane) provided the alkylated product as a white solid (170 mg, 22% yield). MS (M+H): 395

Step F: Preparation of 3-[5-chloro-4-(4-methoxy-benzyloxy)-2-methyl-6-oxo-6H-pyrimidin-1-yl]-4-methyl-benzoic acid methyl ester (Intermediate 3)

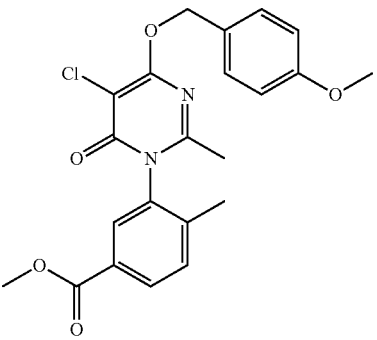

To a solution of 3-[4-(4-methoxy-benzyloxy)-2-methyl-6-oxo-6H-pyrimidin-1-yl]-4-methyl-benzoic acid methyl ester from Step E (2.4 g, 6.26 mmol), in isopropanol (10 mL) was added dichloroacetic acid (0.2 mL) and N-chlorosuccinimide (916 mg, 6.88 mmol). The solution was stirred at ambient temperature for one hour and then stirred for two hours at 30° C. The solution was concentrated in vacuo and the residue was partitioned between ethyl acetate and water. The organic layer was washed with water and brine and dried over magnesium sulfate. The slurry was filtered and concentrated to provide a crude orange oil. Normal phase chromatography (ethyl acetate/heptane) provided the chloro compound (400 mg, 15% yield). MS (M+H): 429

Step G: Preparation of 3-[5-chloro-4-(4-methoxy-benzyloxy)-2-methyl-6-oxo-6H-pyrimidin-1-yl]-N-methoxy-4,N-dimethyl-benzamide

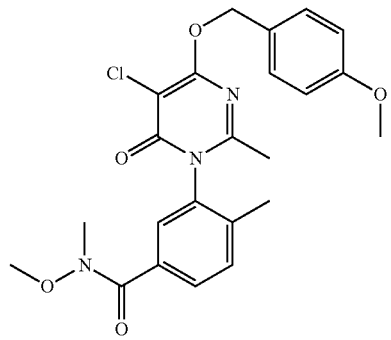

To a solution of 3-[5-chloro-4-(4-methoxy-benzyloxy)-2-methyl-6-oxo-6H-pyrimidin-1-yl]-4-methyl-benzoic acid methyl ester from Step F (12.6 g, 29.5 mmol) in tetrahydrofuran (20 mL) was added 2N sodium hydroxide until hydrolysis was complete as monitored by HPLC. The solution was concentrated in vacuo and the aqueous residue was acidified to pH=3 using 1M hydrochloric acid. The solution was extracted with ethyl acetate. The organic layer was washed with water and brine and dried over magnesium sulfate. The slurry was filtered and concentrated to provide the acid as an orange semi-solid. The intermediate acid was suspended into tetrahydrofuran (30 mL) and 2-chloro-4,6-dimethoxy-1,3,5-triazine (6.21 g, 35.4 mmol) and 4-methylmorpholine (6.5 mL, 59.0 mmol) were added. After thirty minutes of stifling, N,O-dimethylhydroxylamine HCl (4.31 g, 44.2 mmol) was added and stirring continued for eighteen hours. The reaction was concentrated in vacuo and the residue was partitioned between ethyl acetate and water. The organic layer was washed with water and brine and dried over magnesium sulfate. The slurry was filtered and concentrated to an orange oil. The crude material was purified using normal phase chromatography (ethyl acetate/heptane) to provide the dimethylhydroxy amide (6.9 g, 51%). MS (M+H): 458

Step H: Preparation of 5-chloro-6-(4-methoxy-benzyloxy)-2-methyl-3-(2-methyl-5-propynoyl-phenyl)-3H-pyrimidin-4-one

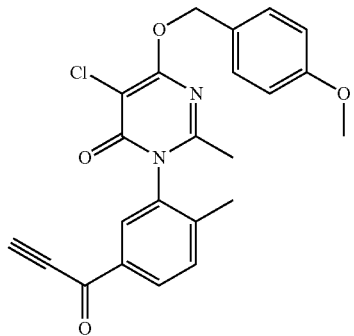 [SMILES: C#CC(=O)c1ccc(C)c(-n2c(C)nc(OCc3ccc(OC)cc3)c(Cl)c2=O)c1]

To a solution of 3-[5-chloro-4-(4-methoxy-benzyloxy)-2-methyl-6-oxo-6H-pyrimidin-1-yl]-N-methoxy-4,N-dimethyl-benzamide of Step G (2.0 g, 4.4 mmol) in tetrahydrofuran (20 mL), cooled on an ice bath, was added ethynylmagnesium chloride, 0.5M in tetrahydrofuran, (22 mL, 10.9 mmol) in a dropwise manner. After the addition was complete the reaction was allowed to return to ambient temperature and was stirred for eighteen hours. The reaction was quenched via dropwise addition into ice cold 1M HCl. The resulting solution was extracted with ethyl acetate, washed with saturated ammonium chloride, water and brine. The solution was dried over magnesium sulfate, filtered and concentrated to give a dark red oil. The crude material was purified using normal phase chromatography (ethyl acetate/heptane) to provide the ethynyl ketone (660 mg, 35% yield). MS (M+H): 423

Step I: Preparation of 5-chloro-3-{5-[2-(1-hydroxy-1-methyl-ethyl)-pyrimidin-4-yl]-2-methyl-phenyl}-6-(4-methoxy-benzyloxy)-2-methyl-3H-pyrimidin-4-one

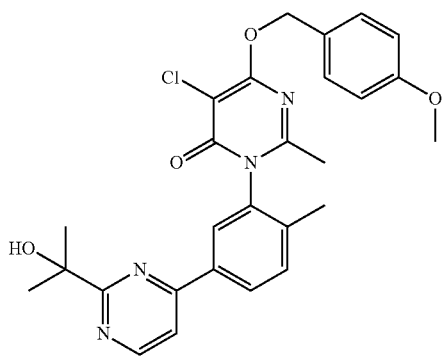 [SMILES: COc1ccc(COc2nc(C)n(-c3cc(-c4ccnc(C(C)(C)O)n4)ccc3C)c(=O)c2Cl)cc1]

To a solution of 5-chloro-6-(4-methoxy-benzyloxy)-2-methyl-3-(2-methyl-5-propynoyl-phenyl)-3H-pyrimidin-4-one from Step H (660 mg, 1.56 mmol) in acetonitrile (3 mL) was added 2-hydroxy-2-methylpropionamidine HCl (324 mg, 2.34 mmol) and potassium carbonate (645 mg, 4.68 mmol) and heated at 75° C. for eighteen hours. The reaction was returned to ambient temperature and filtered to remove excess salts. The filtrate was concentrated to provide a dark red oil. Normal phase chromatography (ethyl acetate/heptanes) provided the pyrimidine as a yellow oil (336 mg, 42%). MS (M+H): 507

Step J: Preparation of Title Compound (Intermediate 1)

To a solution 5-chloro-3-{5-[2-(1-hydroxy-1-methyl-ethyl)-pyrimidin-4-yl]-2-methyl-phenyl}-6-(4-methoxy-benzyloxy)-2-methyl-3H-pyrimidin-4-one from Step I (661 mg, 1.31 mmol) in dichloromethane (5 mL) was added trifluoroacetic acid (1 mL). The solution was stirred at ambient temperature for one hour. Concentration in vacuo provided the title compound as a yellow solid (assume theoretical yield). MS (M+H): 387

PREPARATION OF EXAMPLE COMPOUNDS

Example 1

Preparation of 5-bromo-6-((2,4-difluorobenzyl)oxy)-3-(5-(2-(2-hydroxypropan-2-yl)pyrimidin-4-yl)-2-methylphenyl)-2-methylpyrimidin-4(3H)-one

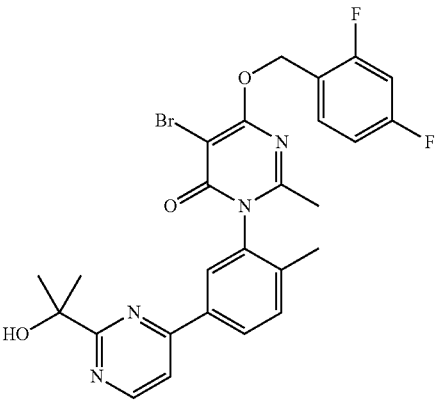 [SMILES: Cc1ccc(-c2ccnc(C(C)(C)O)n2)cc1-n1c(C)nc(OCc2ccc(F)cc2F)c(Br)c1=O]

Step A: Preparation of 3-[4-(2,4-difluoro-benzyloxy)-2-methyl-6-oxo-6H-pyrimidin-1-yl]-4-methyl-benzoic acid methyl ester

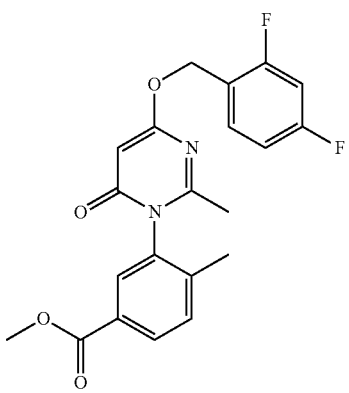 [SMILES: COC(=O)c1ccc(C)c(-n2c(C)nc(OCc3ccc(F)cc3F)cc2=O)c1]

To a solution of Intermediate 2 (500 mg, 1.82 mmol) in N,N-dimethylformamide (2 mL) was added 2,4-difluorobenzyl bromide (0.23 mL, 1.82 mmol), potassium carbonate (376 mg, 2.73 mmol) and 18-crown-6 (40 mg). The slurry was stirred at ambient temperature for one hour. The reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a white semi-solid (260 mg, 36% yield). MS (M+H): 401

Step B: Preparation of 3-[5-bromo-4-(2,4-difluoro-benzyloxy)-2-methyl-6-oxo-6H-pyrimidin-1-yl]-4-methyl-benzoic acid methyl ester

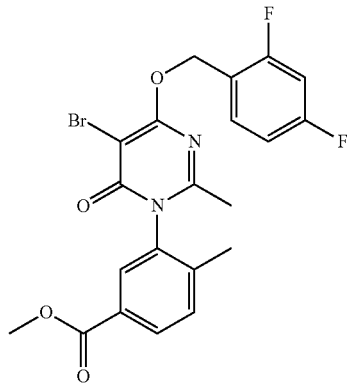 [SMILES: COC(=O)c1ccc(C)c(-n2c(C)nc(OCc3ccc(F)cc3F)c(Br)c2=O)c1]

To a solution of 3-[4-(2,4-difluoro-benzyloxy)-2-methyl-6-oxo-6H-pyrimidin-1-yl]-4-methyl-benzoic acid methyl ester from Step A (440 mg, 1.1 mmol) in dichloromethane (10 mL) was added N-bromosuccinimide (196 mg, 1.1 mmol). The solution was stirred at ambient temperature for two hours. The solution was partitioned between ethyl acetate and water. The organic layer was washed with water and brine and dried over magnesium sulfate. The slurry was filtered and concentrated to provide the bromo compound as a light yellow oil (500 mg, 95%). MS (M, M+2): 479, 481

Step C: Preparation of 3-[5-bromo-4-(2,4-difluoro-benzyloxy)-2-methyl-6-oxo-6H-pyrimidin-1-yl]-4-methyl-benzoic acid

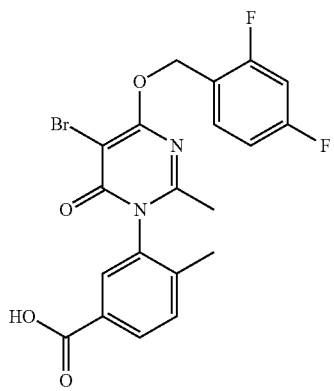 [SMILES: Cc1ccc(C(=O)O)cc1-n1c(C)nc(OCc2ccc(F)cc2F)c(Br)c1=O]

To a solution of 3-[5-bromo-4-(2,4-difluoro-benzyloxy)-2-methyl-6-oxo-6H-pyrimidin-1-yl]-4-methyl-benzoic acid methyl ester from Step B (50 mg, 1.04 mmol) in tetrahydrofuran (3 mL) was added 1N sodium hydroxide (2 mL) and the solution was stirred at ambient temperature for four hours. The solution was concentrated in vacuo and the aqueous residue was acidified to pH=2 using 1M HCl. The solution was extracted with ethyl acetate, washed with water and dried over magnesium sulfate. The slurry was filtered and concentrated to a light yellow semi-solid (470 mg, 97%). MS (M, M+2): 465, 467

Step D: Preparation of 3-[5-bromo-4-(2,4-difluoro-benzyloxy)-2-methyl-6-oxo-6H-pyrimidin-1-yl]-N-methoxy-4,N-dimethyl-benzamide

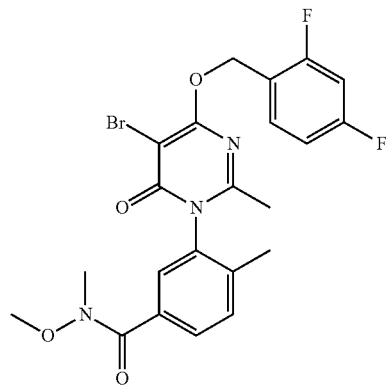 [SMILES: CON(C)C(=O)c1ccc(C)c(-n2c(C)nc(OCc3ccc(F)cc3F)c(Br)c2=O)c1]

To a solution of 3-[5-bromo-4-(2,4-difluoro-benzyloxy)-2-methyl-6-oxo-6H-pyrimidin-1-yl]-4-methyl-benzoic acid from Step C (307 mg, 0.66 mmol) in tetrahydrofuran (2 mL) was added 1,1'-carbonyldiimidazole (162 mg, 1.0 mmol). After stifling at ambient temperature for three hours, N,N-dimethylhydroxylamine HCl (97 mg, 1.0 mmol) and triethylamine (0.18 mL, 1.32 mmol) were added. The solution continued to stir for eighteen hours. The solution was partitioned between ethyl acetate and water. The organic layer was washed with saturated sodium bicarbonate, water, 5% citric acid and brine and dried over magnesium sulfate. The slurry was filtered and concentrated to provide the amide as an oil (86 mg, 26%). MS (M, M+2): 508, 510

Step E: Preparation of 5-bromo-6-(2,4-difluoro-benzyloxy)-2-methyl-3-(2-methyl-5-propynoyl-phenyl)-3H-pyrimidin-4-one

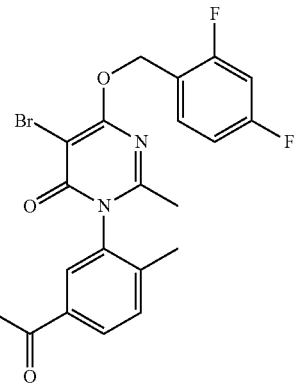

To a solution of 3-[5-bromo-4-(2,4-difluoro-benzyloxy)-2-methyl-6-oxo-6H-pyrimidin-1-yl]-N-methoxy-4,N-dimethyl-benzamide from Step D (86 mg, 0.17 mmol) in tetrahydrofuran (4 mL), cooled using an ice water bath, was added ethynylmagnesium chloride, 0.5M in tetrahydrofuran, (0.5 mL, 0.25 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated to provide the ethynyl ketone which was used without additional purification.

Step F: Preparation of Title Compound

To a solution of the 5-bromo-6-(2,4-difluoro-benzyloxy)-2-methyl-3-(2-methyl-5-propynoyl-phenyl)-3H-pyrimidin-4-one of Step E (80 mg, 0.17 mmol) in acetonitrile (3 mL) was added 2-hydroxy-2-methylpropionamidine HCl (35 mg, 0.25 mmol) and potassium carbonate (70 mg, 0.50 mmol) and the slurry was heated at 75° C. for eighteen hours. The reaction was returned to ambient temperature and filtered to remove excess salts. The filtrate was concentrated and purified via normal phase chromatography (ethyl acetate/heptane) to provide the title compound as a white solid (58 mg, 61% yield). MS (M, M+2): 557, 559; $^1$H NMR (400 MHz, chloroform-d) δ ppm, 1.64 (s, 6H), 2.17 (s, 3H), 2.20 (s, 3H), 5.50-5.60 (m, 2H), 6.87-6.94 (m, 2H), 7.54-7.58 (m, 3H), 7.92 (s, 1H), 8.13 (d, J=7.04 Hz, 1H), 8.77 (d, J=4.30, 1H).

Example 2

Preparation of 5-chloro-6-(2,4-difluoro-benzyloxy)-3-{5-[2-(1-hydroxy-1-methyl-ethyl)-pyrimidin-4-yl]-2-methyl-phenyl}-2-methyl-3H-pyrimidin-4-one

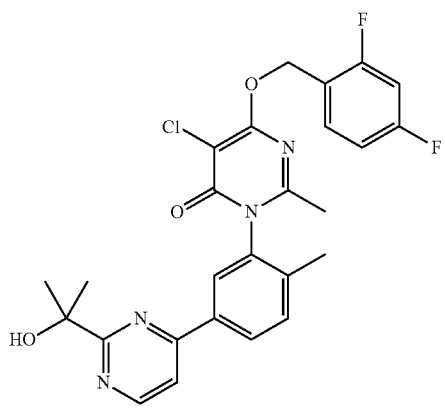

Step A: Preparation of 3-[5-chloro-4-(2,4-difluoro-benzyloxy)-2-methyl-6-oxo-6H-pyrimidin-1-yl]-4-methyl-benzoic acid methyl ester

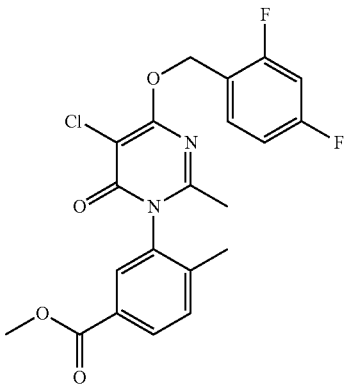 [SMILES: COC(=O)c1ccc(C)c(-n2c(C)nc(OCc3ccc(F)cc3F)c(Cl)c2=O)c1]

To a solution of 3-[4-(2,4-difluoro-benzyloxy)-2-methyl-6-oxo-6H-pyrimidin-1-yl]-4-methyl-benzoic acid methyl ester from Example 1, Step A (260 mg, 0.65 mmol) in isopropanol (5 mL) was added N-chlorosuccinimide (95 mg, 0.71 mmol) and 3 drops of dichloroacetic acid. The solution was heated at 60° C. for three hours. The solution was concentrated in vacuo and the residue was partitioned between ethyl acetate and water. The organic layer was washed with water and brine and dried over magnesium sulfate. The slurry was filtered and concentrated to provide the chlorinated product as a light yellow semi-solid (230 mg, 82%). MS (M+H): 435

Step B: Preparation of 3-[5-chloro-4-(2,4-difluoro-benzyloxy)-2-methyl-6-oxo-6H-pyrimidin-1-yl]-4-methyl-benzoic acid

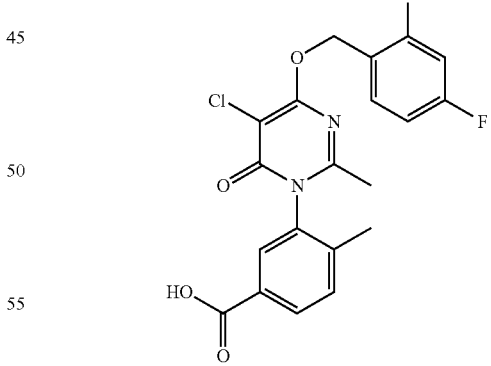

To a solution of 3-[5-chloro-4-(2,4-difluoro-benzyloxy)-2-methyl-6-oxo-6H-pyrimidin-1-yl]-4-methyl-benzoic acid methyl ester from Step A (230 mg, 0.53 mmol) in tetrahydrofuran (3 mL) was added 1N sodium hydroxide (1 mL) and the solution was stirred at ambient temperature for four hours. The solution was concentrated in vacuo and the aqueous residue was acidified to pH=2 using 1M HCl. The solution was extracted with ethyl acetate, washed with water and dried over magnesium sulfate. The slurry was filtered and concentrated to give a light orange semi-solid (230 mg, quantitative yield).

Step C: Preparation of 3-[5-chloro-4-(2,4-difluoro-benzyloxy)-2-methyl-6-oxo-6H-pyrimidin-1-yl]-N-methoxy-4,N-dimethyl-benzamide

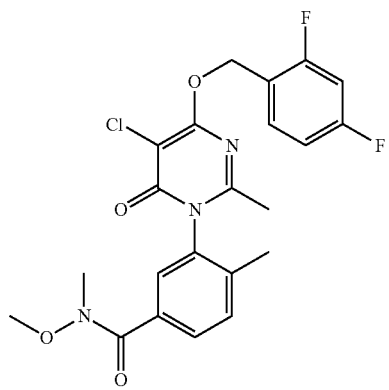 [SMILES: CON(C)C(=O)c1ccc(C)c(-n2c(C)nc(OCc3ccc(F)cc3F)c(Cl)c2=O)c1]

To a solution of 3-[5-chloro-4-(2,4-difluoro-benzyloxy)-2-methyl-6-oxo-6H-pyrimidin-1-yl]-4-methyl-benzoic acid from Step B (230 mg, 0.53 mmol) in tetrahydrofuran (2 mL) was added 1,1'-carbonyldiimidazole (128 mg, 0.79 mmol). After stirring at ambient temperature for three hours, N,N-dimethylhydroxylamine HCl (76 mg, 0.79 mmol) and triethylamine (0.15 mL, 1.06 mmol) were added. The solution continued to stir for eighteen hours. The solution was partitioned between ethyl acetate and water. The organic layer was washed with saturated sodium bicarbonate, water, 5% citric acid and brine and dried over magnesium sulfate. The slurry was filtered and concentrated to provide the amide as a light green oil (160 mg, 65%). MS (M+H): 464

Step D: Preparation of 5-chloro-6-(2,4-difluoro-benzyloxy)-2-methyl-3-(2-methyl-5-propynoyl-phenyl)-3H-pyrimidin-4-one

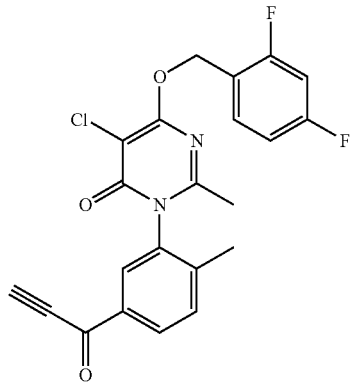 [SMILES: C#CC(=O)c1ccc(C)c(-n2c(C)nc(OCc3ccc(F)cc3F)c(Cl)c2=O)c1]

To a solution of 3-[5-chloro-4-(2,4-difluoro-benzyloxy)-2-methyl-6-oxo-6H-pyrimidin-1-yl]-N-methoxy-4,N-dimethyl-benzamide from Step C (160 mg, 0.34 mmol) in tetrahydrofuran (2 mL), cooled using an ice water bath, was added ethynylmagnesium bromide, 0.5M in tetrahydrofuran, (1.02 mL, 0.51 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was purified using normal phase chromatography (ethyl acetate/heptane) to provide the ethynyl ketone as an oil (20 mg, 14% yield). MS (M+H): 429

Step E: Preparation of Title Compound

To a solution of the 5-chloro-6-(2,4-difluoro-benzyloxy)-2-methyl-3-(2-methyl-5-propynoyl-phenyl)-3H-pyrimidin-4-one of Step D (20 mg, 0.05 mmol) in acetonitrile (1 mL) as added 2-hydroxy-2-methylpropionamidine HCl (9 mg, 0.07 mmol) and potassium carbonate (20 mg, 0.15 mmol) and the slurry was heated at 85° C. for eighteen hours. The reaction was returned to ambient temperature and filtered to remove excess salts. The filtrate was concentrated and purified via normal phase chromatography (ethyl acetate/heptane) to provide the title compound as a white solid (12.5 mg, 50% yield). MS (M+H): 513; $^1$H NMR (400 MHz, chloroform-d) δ ppm, 1.65 (s, 6H), 2.18 (s, 3H), 2.21 (s, 3H), 5.51-5.60 (m, 2H), 6.88-6.97 (m, 2H), 7.55-7.60 (m, 3H), 7.93 (s, 1H), 8.14 (d, J=8.61 Hz, 1H), 8.78 (d, J=5.09, 1H).

Example 3

Preparation of 5-chloro-6-((4-fluorobenzyl)oxy)-3-(5-(2-(2-hydroxypropan-2-yl)pyrimidin-4-yl)-2-methylphenyl)-2-methylpyrimidin-4(3H)-one

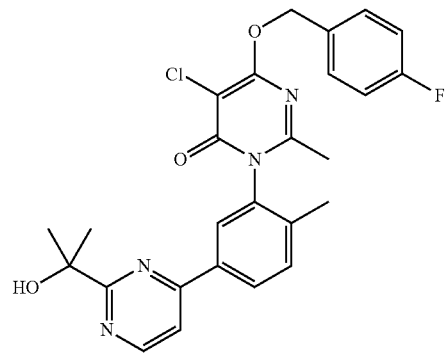 [SMILES: Cc1ccc(-c2ccnc(C(C)(C)O)n2)cc1-n1c(C)nc(OCc2ccc(F)cc2)c(Cl)c1=O]

Step A: Preparation of 3-[5-chloro-4-(4-fluoro-benzyloxy)-2-methyl-6-oxo-6H-pyrimidin-1-yl]-4-methyl-benzoic acid methyl ester

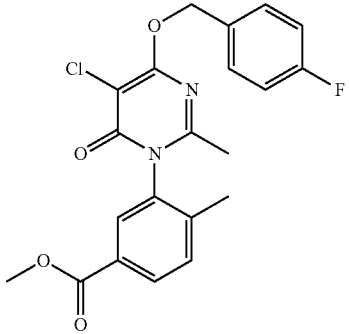 [SMILES: COC(=O)c1ccc(C)c(-n2c(C)nc(OCc3ccc(F)cc3)c(Cl)c2=O)c1]

To a solution of Intermediate 3 (120 mg, 0.39 mmol) in N,N-dimethylformamide (2 mL) was added 4-fluorobenzyl bromide (0.05 mL, 0.39 mmol), potassium carbonate (81 mg, 0.58 mmol) and 18-crown-6 (10 mg). The slurry was stirred at ambient temperature for two hours. The reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a colorless oil. (63 mg, 38% yield). MS (M+H): 417

Step B: Preparation of 3-[5-chloro-4-(4-fluoro-benzyloxy)-2-methyl-6-oxo-6H-pyrimidin-1-yl]-N-methoxy-4,N-dimethyl-benzamide

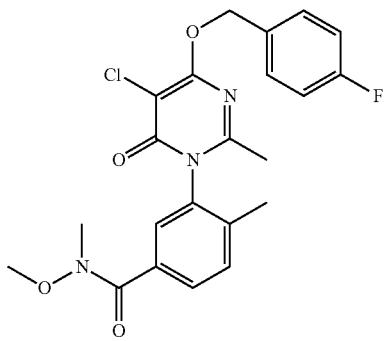 [SMILES: CON(C)C(=O)c1ccc(C)c(-n2c(C)nc(OCc3ccc(F)cc3)c(Cl)c2=O)c1]

To a solution of 3-[5-chloro-4-(4-fluoro-benzyloxy)-2-methyl-6-oxo-6H-pyrimidin-1-yl]-4-methyl-benzoic acid methyl ester from Step A (63 mg, 0.15 mmol) in tetrahydrofuran (1 mL) was added 1N sodium hydroxide (1 mL) and the solution was stirred at ambient temperature for eighteen hours. The solution was concentrated in vacuo and the aqueous residue was acidified to pH=2 using 1M HCl. The solution was extracted with ethyl acetate, washed with water and dried over magnesium sulfate. The slurry was filtered and concentrated to an orange oil used without any additional purification. To a solution of the crude acid in tetrahydrofuran (2 mL) was added 1,1'-carbonyldiimidazole (37 mg, 0.23 mmol). After stifling at ambient temperature for one hour, N,N-dimethylhydroxylamine HCl (22 mg, 0.23 mmol) and triethylamine (0.04 mL, 0.30 mmol) were added. The solution continued to stir for eighteen hours. The solution was partitioned between ethyl acetate and water. The organic layer was washed with saturated sodium bicarbonate, water, and brine and dried over magnesium sulfate. The slurry was filtered and concentrated to provide the amide as a colorless oil (60 mg, 90%). MS (M+H): 446

Step C: Preparation of 5-chloro-6-(4-fluoro-benzyloxy)-2-methyl-3-(2-methyl-5-propynoyl-phenyl)-3H-pyrimidin-4-one

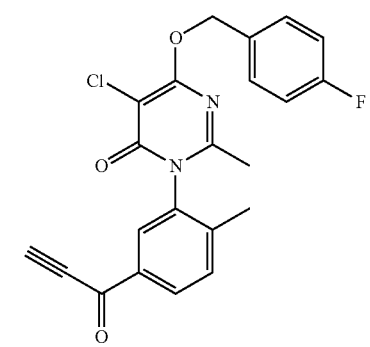 [SMILES: C#CC(=O)c1ccc(C)c(-n2c(C)nc(OCc3ccc(F)cc3)c(Cl)c2=O)c1]

To a solution of 3-[5-chloro-4-(4-fluoro-benzyloxy)-2-methyl-6-oxo-6H-pyrimidin-1-yl]-N-methoxy-4,N-dimethyl-benzamide from Step B (60 mg, 0.14 mmol) in tetrahydrofuran (2 mL), cooled using an ice water bath, was added ethynylmagnesium bromide, 0.5M in tetrahydrofuran, (0.41 mL, 0.21 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was purified using normal phase chromatography (ethyl acetate/heptane) to provide the propynyl ketone as an oil (10 mg, 17%). MS (M+H): 411

Step D: Preparation of Title Compound

To a solution of 5-chloro-6-(4-fluoro-benzyloxy)-2-methyl-3-(2-methyl-5-propynoyl-phenyl)-3H-pyrimidin-4-one of Step C (10 mg, 0.02 mmol) in acetonitrile (1 mL) was added 2-hydroxy-2-methylpropanamidine HCl (5 mg, 0.03 mmol) and potassium carbonate (10 mg, 0.08 mmol) and the slurry was heated at 75° C. for eighteen hours. After cooling to room temperature the reaction was filtered to remove excess salts. The filtrate was concentrated and purified via normal phase chromatography (ethyl acetate/heptane) to provide the title compound as a yellow oil (2.9 mg, 24% yield). MS (M+H): 495

Example 4

Preparation of 3-(5-(2-(tert-butyl)pyrimidin-4-yl)-2-methylphenyl)-5-chloro-2-methyl-6-((3-methylbenzyl)oxy)pyrimidin-4(3H)-one

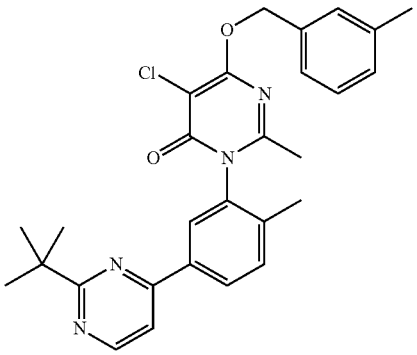 [SMILES: Cc1cccc(COc2nc(C)n(-c3cc(-c4ccnc(C(C)(C)C)n4)ccc3C)c(=O)c2Cl)c1]

Step A: Preparation of 4-methyl-3-[2-methyl-4-(3-methyl-benzyloxy)-6-oxo-6H-pyrimidin-1-yl]-benzoic acid methyl ester

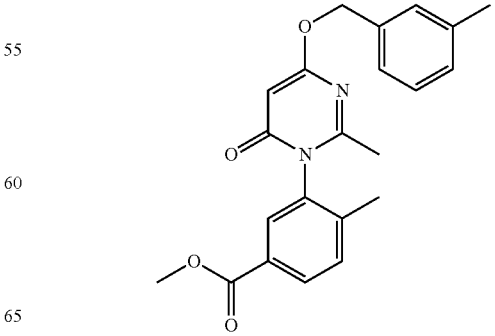

To a solution of Intermediate 2 (460 mg, 1.68 mmol) in N,N-dimethylformamide (2 mL) was added 3-methylbenzyl bromide (0.22 mL, 1.68 mmol), potassium carbonate (350 mg, 2.53 mmol) and 18-crown-6 (40 mg). The slurry was stirred at ambient temperature for one hour. The reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a white semi-solid (138 mg, 22% yield). MS (M+H): 379

Step B: Preparation of 3-[5-chloro-2-methyl-4-(3-methyl-benzyloxy)-6-oxo-6H-pyrimidin-1-yl]-4-methyl-benzoic acid methyl ester

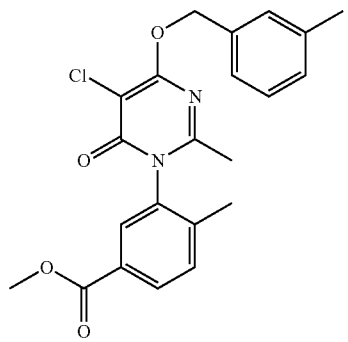

To a solution of 4-methyl-3-[2-methyl-4-(3-methyl-benzyloxy)-6-oxo-6H-pyrimidin-1-yl]-benzoic acid methyl ester from Step A (218 mg, 0.58 mmol) in isopropanol (2 mL) was added N-chlorosuccinimide (84 mg, 0.63 mmol) and 2 drops of dichloroacetic acid. The solution was heated at 60° C. for two hours. The solution was concentrated in vacuo and the residue was partitioned between ethyl acetate and water. The organic layer was washed with water and brine and dried over magnesium sulfate. The slurry was filtered and concentrated to provide the chlorinated product as a light yellow oil (230 mg, 78%). MS (M+H): 413

Step C: Preparation of 3-[5-chloro-2-methyl-4-(3-methyl-benzyloxy)-6-oxo-6H-pyrimidin-1-yl]-4-methyl-benzoic acid

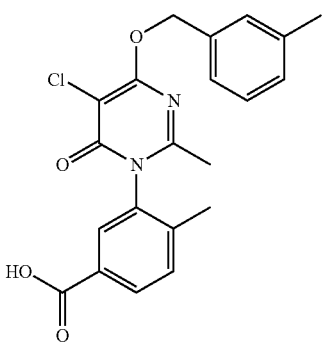 [SMILES: Cc1cccc(COc2nc(C)n(-c3cc(C(=O)O)ccc3C)c(=O)c2Cl)c1]

To a solution of 3-[5-chloro-2-methyl-4-(3-methyl-benzyloxy)-6-oxo-6H-pyrimidin-1-yl]-4-methyl-benzoic acid methyl ester from Step B (230 mg, 0.56 mmol) in tetrahydrofuran (1 mL) was added 1N sodium hydroxide (1 mL) and the solution was stirred at ambient temperature for eighteen hours. The solution was concentrated in vacuo and the aqueous residue was acidified to pH=2 using 1M HCl. The solution was extracted with ethyl acetate, washed with water and dried over magnesium sulfate. The slurry was filtered and concentrated to an orange oil (240 mg, quantitative yield). MS (M+H): 399

Step D: Preparation of 3-[5-chloro-2-methyl-4-(3-methyl-benzyloxy)-6-oxo-6H-pyrimidin-1-yl]-N-methoxy-4,N-dimethyl-benzamide

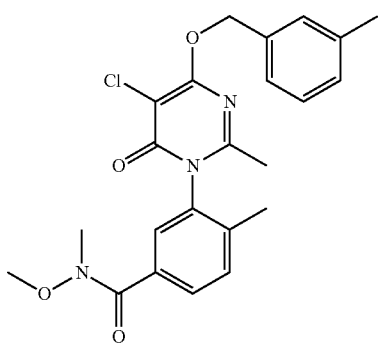

To a solution of 3-[5-chloro-2-methyl-4-(3-methyl-benzyloxy)-6-oxo-6H-pyrimidin-1-yl]-4-methyl-benzoic acid from Step C (220 mg, 0.56 mmol) in tetrahydrofuran (2 mL) was added 1,1'-carbonyldiimidazole (136 mg, 0.84 mmol). After stirring at ambient temperature for one hour, N,N-dimethylhydroxylamine HCl (81 mg, 0.84 mmol) and triethylamine (0.15 mL, 1.12 mmol) were added. The solution continued to stir for eighteen hours. The solution was partitioned between ethyl acetate and water. The organic layer was washed with saturated sodium bicarbonate, water, 5% citric acid and brine and dried over magnesium sulfate. The slurry was filtered and concentrated to provide the amide as a brown oil (193 mg, 78%). MS (M+H): 442

Step E: Preparation of 5-chloro-2-methyl-6-(3-methyl-benzyloxy)-3-(2-methyl-5-propynoyl-phenyl)-3H-pyrimidin-4-one

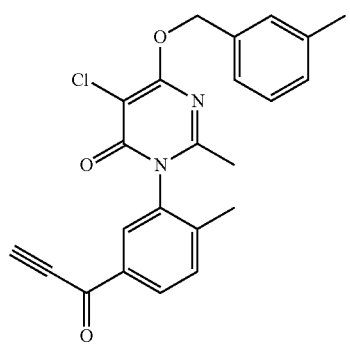 [SMILES: C#CC(=O)c1ccc(C)c(-n2c(C)nc(OCc3cccc(C)c3)c(Cl)c2=O)c1]

To a solution of 3-[5-chloro-2-methyl-4-(3-methyl-benzyloxy)-6-oxo-6H-pyrimidin-1-yl]-N-methoxy -4,N-dimethyl-benzamide from Step D (193 mg, 0.44 mmol) in tetrahydrofuran (3 mL), cooled using an ice water bath, was added ethynylmagnesium bromide, 0.5M in tetrahydrofuran, (1.3 mL, 0.66 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was purified using normal phase chromatography (ethyl acetate/heptane) to provide the ethynyl ketone as a yellow oil (50 mg, 28% yield). MS (M+H): 407

Step F: Preparation of Title Compound

To a solution of 5-chloro-2-methyl-6-(3-methyl-benzyloxy)-3-(2-methyl-5-propynoyl-phenyl)-3H-pyrimidin-4-one of Step E (25 mg, 0.06 mmol) in acetonitrile (2 mL) was added 2,2,2-trimethylamidine HCl (13 mg, 0.09 mmol) and potassium carbonate (25 mg, 0.18 mmol) and the slurry was heated at 75° C. for eighteen hours. The reaction was returned to ambient temperature and filtered to remove excess salts. The filtrate was concentrated and purified via normal phase chromatography (ethyl acetate/heptane) to provide the title compound as a white solid (14.3 mg, 49% yield). MS (M+H): 489; $^1$H NMR (400 MHz, chloroform-d) δ ppm, 1.47 (s, 9H), 2.18 (s, 3H), 2.21 (s, 3H), 2.41 (s, 3H), 5.51-5.53 (m, 2H), 7.18 (s, 1H), 7.26-7.31 (m, 3H), 7.49-7.53 (m, 2H), 7.94 (s, 1H), 8.18 (s, 1H), 8.75 (s, 1H).

Example 5

Preparation of 5-chloro-3-(5-(2-(2-hydroxypropan-2-yl)pyrimidin-4-yl)-2-methylphenyl)-2-methyl-6-((3-methylbenzyl)oxy)pyrimidin-4(3H)-one

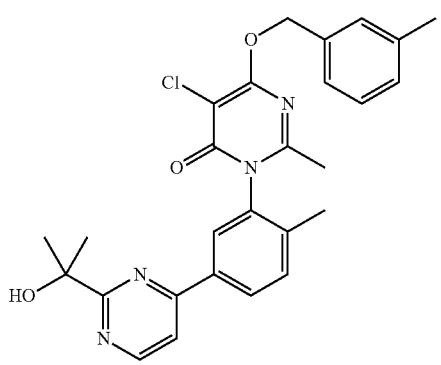 [SMILES: Cc1cccc(COc2nc(C)n(-c3cc(-c4ccnc(C(C)(C)O)n4)ccc3C)c(=O)c2Cl)c1]

To a solution of 5-chloro-2-methyl-6-(3-methyl-benzyloxy)-3-(2-methyl-5-propynoyl-phenyl)-3H-pyrimidin-4-one from Example 4, Step E (25 mg, 0.06 mmol) in acetonitrile (2 mL) was added 2-hydroxy-2-methyl propionamidine HCl (13 mg, 0.09 mmol) and potassium carbonate (25 mg, 0.18 mmol) and the slurry was heated at 75° C. for eighteen hours. The reaction was returned to ambient temperature and filtered to remove excess salts. The filtrate was concentrated and purified via normal phase chromatography (ethyl acetate/heptane) to provide the title compound as a white solid (7.6 mg, 26% yield). MS (M+H): 491; $^1$H NMR (400 MHz, chloroform-d) δ ppm, 1.65 (s, 6H), 2.17 (s, 3H), 2.21 (s, 3H), 2.40 (s, 3H), 5.47-5.56 (m, 2H), 7.17 (s, 1H), 7.26-7.31 (m, 3H), 7.54-7.58 (m, 2H), 7.92 (s, 1H), 8.14 (d, J=7.43 Hz, 1H), 8.76 (d, J=5.08 Hz, 1H).

Example 6

Preparation of 3-[5-(2-tert-butyl-pyrimidin-4-yl)-2-methyl-phenyl]-5-chloro-6-(3-methoxy-benzyloxy)-2-methyl-3H-pyrimidin-4-one

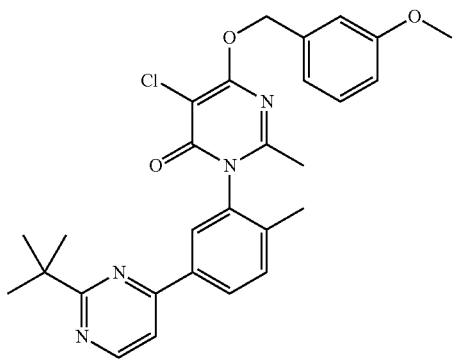 [SMILES: COc1cccc(COc2nc(C)n(-c3cc(-c4ccnc(C(C)(C)C)n4)ccc3C)c(=O)c2Cl)c1]

Step A: Preparation of 3-[4-(3-methoxy-benzyloxy)-2-methyl-6-oxo-6H-pyrimidin-1-yl]-4-methyl-benzoic acid methyl ester

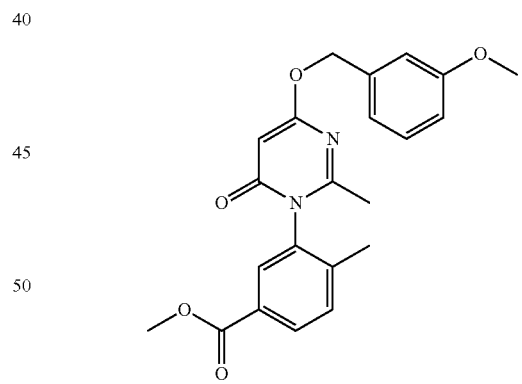

To a solution of Intermediate 2 (460 mg, 1.68 mmol) in N,N-dimethylformamide (2 mL) was added 3-methoxybenzyl bromide (0.23 mL, 1.68 mmol), potassium carbonate (350 mg, 2.53 mmol) and 18-crown-6 (40 mg). The slurry was stirred at ambient temperature for one hour. The reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a white semi-solid (226 mg, 34% yield). MS (M+H): 395

Step B: Preparation of 3-[5-chloro-4-(3-methoxy-benzyloxy)-2-methyl-6-oxo-6H-pyrimidin-1-yl]-4-methyl-benzoic acid methyl ester

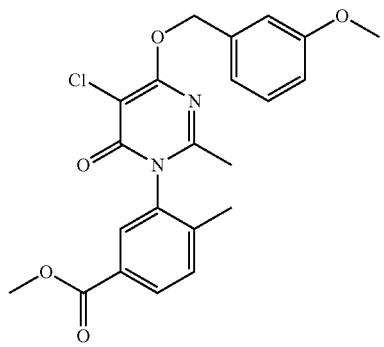

To a solution of 3-[4-(3-methoxy-benzyloxy)-2-methyl-6-oxo-6H-pyrimidin-1-yl]-4-methyl-benzoic acid methyl ester from Step A (226 mg, 0.57 mmol) in isopropanol (2 mL) was added N-chlorosuccinimide (84 mg, 0.63 mmol) and 2 drops of dichloroacetic acid. The solution was heated at 60° C. for two hours. The solution was allowed to cool to room temperature and concentrated in vacuo and the residue was partitioned between ethyl acetate and water. The organic layer was washed with water and brine and dried over magnesium sulfate. The slurry was filtered and concentrated to provide the chlorinated product as a light yellow semi-solid (260 mg, quantitative yield). MS (M+H): 429

Step C: Preparation of 3-[5-chloro-4-(3-methoxy-benzyloxy)-2-methyl-6-oxo-6H-pyrimidin-1-yl]-4-methyl-benzoic acid

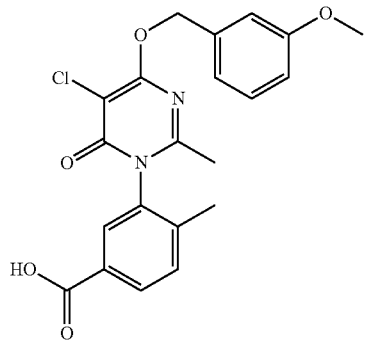 [SMILES: COc1cccc(COc2nc(C)n(-c3cc(C(=O)O)ccc3C)c(=O)c2Cl)c1]

To a solution of 3-[5-chloro-4-(3-methoxy-benzyloxy)-2-methyl-6-oxo-6H-pyrimidin-1-yl]-4-methyl-benzoic acid methyl ester from Step B (260 mg, 0.6 mmol) in tetrahydrofuran (1 mL) was added 1N sodium hydroxide (1 mL) and the solution was stirred at ambient temperature for three hours. The solution was concentrated in vacuo and the aqueous residue was acidified to pH=2 using 1M HCl. The solution was extracted with ethyl acetate, washed with water and dried over magnesium sulfate. The slurry was filtered and concentrated to a yellow oil (230 mg, 92%). MS (M+H): 415

Step D: Preparation of 3-[5-chloro-4-(3-methoxy-benzyloxy)-2-methyl-6-oxo-6H-pyrimidin-1-yl]-N-methoxy-4,N-dimethyl-benzamide

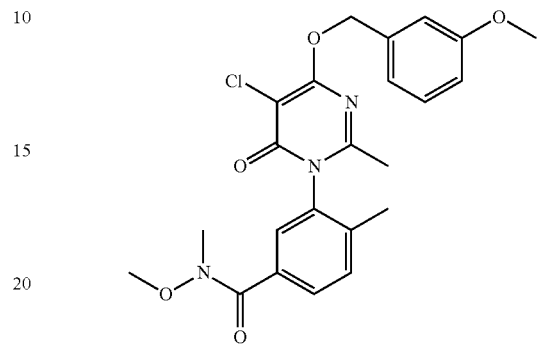

To a solution of 3-[5-chloro-4-(3-methoxy-benzyloxy)-2-methyl-6-oxo-6H-pyrimidin-1-yl]-4-methyl-benzoic acid from step C (230 mg, 0.56 mmol) in tetrahydrofuran (2 mL) was added 1,1'-carbonyldiimidazole (135 mg, 0.83 mmol). After stirring at ambient temperature for three hours, N,N-dimethylhydroxylamine HCl (80 mg, 0.83 mmol) and triethylamine (0.15 mL, 1.12 mmol) were added. The solution continued to stir for eighteen hours. The solution was partitioned between ethyl acetate and water. The organic layer was washed with saturated sodium bicarbonate, water, 5% citric acid and brine and dried over magnesium sulfate. The slurry was filtered and concentrated to provide the amide as a light green oil (200 mg, 78%). MS (M+H): 458

Step E: Preparation of 5-chloro-6-(3-methoxy-benzyloxy)-2-methyl-3-(2-methyl-5-propynoyl-phenyl)-3H-pyrimidin-4-one

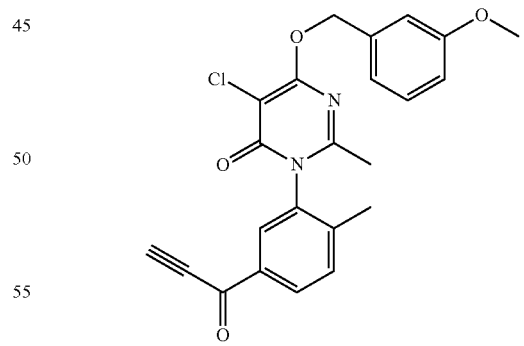

To a solution of 3-[5-chloro-4-(3-methoxy-benzyloxy)-2-methyl-6-oxo-6H-pyrimidin-1-yl]-N-methoxy-4,N-dimethyl-benzamide from Step D (200 mg, 0.44 mmol) in tetrahydrofuran (3 mL), cooled using an ice water bath, was added ethynylmagnesium bromide, 0.5M in tetrahydrofuran, (1.3 mL, 0.66 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was purified using normal phase chromatography (ethyl acetate/heptane) to provide the ethynyl ketone as a yellow oil (65 mg, 35% yield). MS (M+H): 423

Step F: Preparation of Title Compound

To a solution of 5-chloro-6-(3-methoxy-benzyloxy)-2-methyl-3-(2-methyl-5-propynoyl-phenyl)-3H-pyrimidin-4-one of Step E (32.5 mg, 0.08 mmol) in acetonitrile (2 mL) was added 2,2,2-trimethylamidine HCl (16 mg, 0.12 mmol) and potassium carbonate (32 mg, 0.23 mmol) and the slurry was heated at 85° C. for eighteen hours. The reaction was returned to ambient temperature and filtered to remove excess salts. The filtrate was concentrated and purified via normal phase chromatography (ethyl acetate/heptane) to provide the title compound as a white solid (15.7 mg, 40% yield). MS (M+H): 505

Example 7

Preparation of 5-chloro-3-(5-(2-(2-hydroxypropan-2-yl)pyrimidin-4-yl)-2-methylphenyl)-6-((3-methoxybenzyl)oxy)-2-methylpyrimidin-4(3H)-one

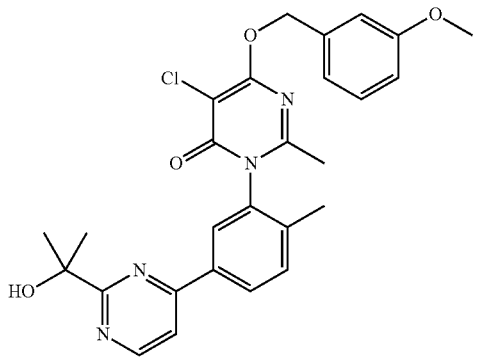 [SMILES: COc1cccc(COc2nc(C)n(-c3cc(-c4ccnc(C(C)(C)O)n4)ccc3C)c(=O)c2Cl)c1]

To a solution of 5-chloro-6-(3-methoxy-benzyloxy)-2-methyl-3-(2-methyl-5-propynoyl-phenyl) -3H-pyrimidin-4-one from Example 6, Step E (32.5 mg, 0.08 mmol) in acetonitrile (1 mL) was added 2-hydroxy-2-methylpropionamidine HCl (16 mg, 0.12 mmol) and potassium carbonate (32 mg, 0.23 mmol) and the slurry was heated at 85° C. for eighteen hours. The reaction was returned to ambient temperature and filtered to remove excess salts. The filtrate was concentrated and purified via normal phase chromatography (ethyl acetate/heptane) to provide the title compound as a white solid (14.4 mg, 37% yield). MS (M+H): 507; $^1$H NMR (400 MHz, chloroform-d) δ ppm, 1.64 (s, 6H), 2.17 (s, 3H), 2.21 (s, 3H), 3.85 (s, 3H), 5.49-5.58 (m, 2H), 6.90 (d, J=7.43, 1H), 7.07 (s, 1H), 7.09 (s, 1H), 7.31-7.35 (m, 1H), 7.54-7.58 (m, 2H), 7.93 (s, 1H), 8.13 (d, J=6.65 Hz, 1H), 8.77 (d, J=5.09, 1H).

Example 8

Preparation of 5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one

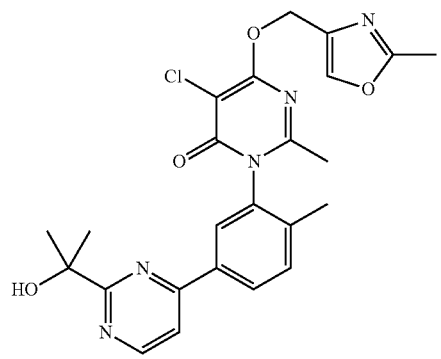 [SMILES: Cc1nc(COc2nc(C)n(-c3cc(-c4ccnc(C(C)(C)O)n4)ccc3C)c(=O)c2Cl)co1]

Step A: Preparation of 4-chloromethyl-2-methyl-oxazole

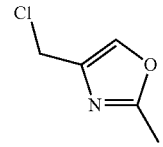

To a solution of acetamide (600 mg, 10.2 mmol) in glacial acetic acid (3 mL) was added 1,3-dichloroactone (1.29 g, 10.2 mmol). The solution was heated at 100° C. overnight. The cooled solution was neutralized using saturated sodium bicarbonate and extracted into ethyl acetate. The organic layer was dried over magnesium sulfate. The material was filtered and concentrated to a dark red oil used without additional purification.

Step B: Preparation of Title Compound

To a solution of Intermediate 1 (509 mg, 1.32 mmol) in N,N-dimethylformamide (5 mL) was added 4-chloromethyl-2-methyl-oxazole from Step A (173 mg, 1.32 mmol), potassium carbonate (273 mg, 1.98 mmol) and 18-crown-6 (40 mg). The slurry was heated at 60° C. for eighteen hours. The reaction was allowed to cool to room temperature and then partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the title compound as a colorless oil. (160 mg, 25% yield). MS (M+H): 482; $^1$H NMR (400 MHz, chloroform-d) δ ppm, 1.64 (s, 6H), 2.17 (s, 3H), 2.20 (s, 3H), 2.50 (s, 3H), 5.40-5.48 (m, 2H), 7.54-7.58 (m, 2H), 7.66 (s, 1H), 7.93 (s, 1H), 8.13 (d, J=8.21 Hz, 1H), 8.77 (d, J=5.08, 1H).

Examples 9 & 10

Chiral Resolution of 5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one

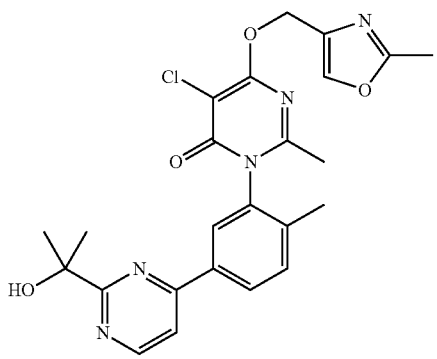

Optical rotations were obtained using an Autopol III polarimeter manufactured by Rudolph Research Analytical using a 1.5 mL cell. Racemic 5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one (Example 8) (160 mg, 0.33 mmol) was separated using supercritical fluid chromatography (Thar 80, preparative SFC, ChiralPak AD-H, 250×30 mmID column) with a mobile phase of carbon dioxide and methanol (0.1% NH$_4$OH). The separation method used an isocratic method of 40% methanol (0.1% NH$_4$OH) with a flow rate of 50 mL/min and a cycle time of 8 min.

Example 9 eluted first at 2.93 minutes yielding 37.3 mg of (−)-5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one. MS (M+H): 482; $^1$H NMR (400 MHz, chloroform-d) δ ppm, 1.64 (s, 6H), 2.17 (s, 3H), 2.20 (s, 3H), 2.50 (s, 3H), 5.40-5.48 (m, 2H), 7.54-7.58 (m, 2H), 7.66 (s, 1H), 7.93 (s, 1H), 8.13 (d, J=8.21 Hz, 1H), 8.77 (d, J=5.08, 1H). $[\alpha]_D^{20}$ −14 (c 0.1, CH$_3$OH).

Example 10 eluted second at 4.22 minutes yielding 33 mg of (+)-5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one. MS (M+H): 482; $^1$H NMR (400 MHz, chloroform-d) δ ppm, 1.64 (s, 6H), 2.17 (s, 3H), 2.20 (s, 3H), 2.50 (s, 3H), 5.40-5.48 (m, 2H), 7.54-7.58 (m, 2H), 7.66 (s, 1H), 7.93 (s, 1H), 8.13 (d, J=8.21 Hz, 1H), 8.77 (d, J=5.08, 1H). $[\alpha]_D^{20}$ +43 (c 0.1, CH$_3$OH).

Example 11

Preparation of 5-bromo-3-(5-(2-(2-hydroxypropan-2-yl)pyrimidin-4-yl)-2-methylphenyl)-2-methyl-6-((2-methylthiazol-4-yl)methoxy)pyrimidin-4(3H)-one

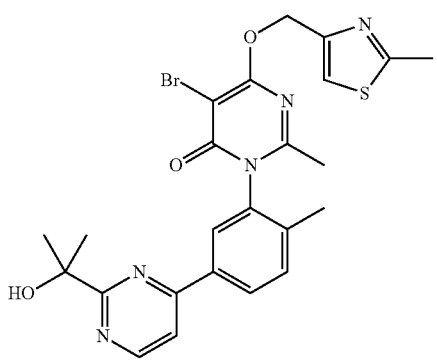 [SMILES: Cc1nc(COc2nc(C)n(-c3cc(-c4ccnc(C(C)(C)O)n4)ccc3C)c(=O)c2Cl)co1]

Step A: Preparation of 4-methyl-3-[2-methyl-4-(2-methyl-thiazol-4-ylmethoxy)-6-oxo-6H-pyrimidin-1-yl]-benzoic acid methyl ester

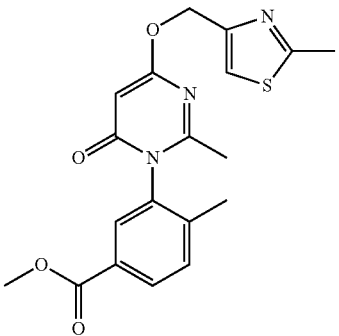

To a solution of Intermediate 2 (530 mg, 1.93 mmol) in N,N-dimethylformamide (2 mL) was added 4-(chloromethyl)-2-methyl-1,3-thiazole HCl (354 mg, 1.93 mmol), potassium carbonate (666 mg, 4.82 mmol) and 18-crown-6 (50 mg). The slurry was heated at 60° C. for three hours. The reaction was returned to ambient temperature and partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a colorless oil. (120 mg, 16% yield). MS (M+H): 386

Step B: Preparation of 3-[5-Bromo-2-methyl-4-(2-methyl-thiazol-4-ylmethoxy)-6-oxo-6H-pyrimidin-1-yl]-4-methyl-benzoic acid methyl ester

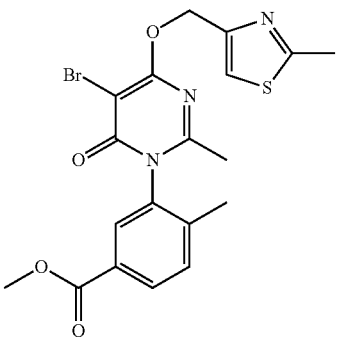

To a solution of 4-methyl-3-[2-methyl-4-(2-methyl-thiazol-4-ylmethoxy)-6-oxo-6H-pyrimidin-1-yl]-benzoic acid methyl ester from Step A (310 mg, 0.81 mmol) in dichloromethane (10 mL) was added N-bromosuccinimide (143 mg, 0.81 mmol) and the solution was stirred at ambient temperature for two hours. The solution was washed with water and brine and dried over magnesium sulfate. The slurry was filtered and concentrated to provide the bromo compound as a yellow oil (338 mg, 90%). MS (M, M+2): 464, 466

Step C: Preparation of 3-[5-bromo-2-methyl-4-(2-methyl-thiazol-4-ylmethoxy)-6-oxo-6H-pyrimidin-1-yl]-N-methoxy-4,N-dimethyl-benzamide

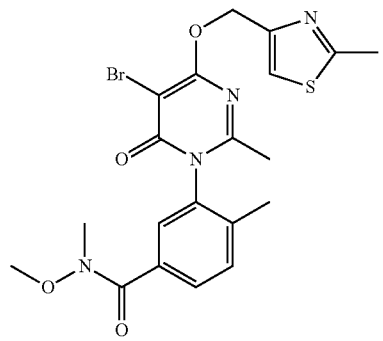

To a solution of 3-[5-bromo-2-methyl-4-(2-methyl-thiazol-4-ylmethoxy)-6-oxo-6H-pyrimidin-1-yl]-4-methyl-benzoic acid methyl ester from Step B (338 mg, 0.73 mmol) in tetrahydrofuran (2 mL) was added 1N sodium hydroxide (1 mL) and the solution stirred at ambient temperature for two hours. The solution was concentrated in vacuo and the aqueous residue was acidified to pH=2 using 1M HCl. The solution was extracted with ethyl acetate, washed with water and dried over magnesium sulfate. The slurry was filtered and concentrated to a brown oil and used without any additional purification. To a solution of the crude acid in tetrahydrofuran (3 mL) was added 1,1'-carbonyldiimidazole (177 mg, 1.1 mmol). After stifling at ambient temperature for one hour, N,N-dimethylhydroxylamine HCl (107 mg, 1.1 mmol) and triethylamine (0.2 mL, 1.46 mmol) were added. The solution continued to stir for eighteen hours. The solution was partitioned between ethyl acetate and water. The organic layer was washed with saturated sodium bicarbonate, water, and brine and dried over magnesium sulfate. The slurry was filtered and concentrated to provide the amide as a yellow oil (71 mg, 20%). MS (M, M+2): 493, 495

Step D: Preparation of 5-bromo-2-methyl-3-(2-methyl-5-propynoyl-phenyl)-6-(2-methyl-thiazol-4-ylmethoxy)-3H-pyrimidin-4-one

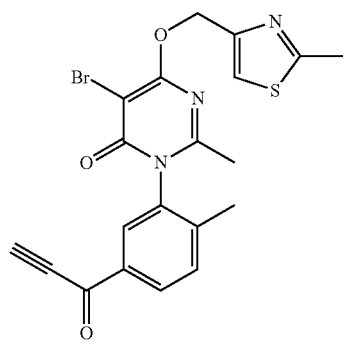 [SMILES: C#CC(=O)c1ccc(C)c(-n2c(C)nc(OCc3csc(C)n3)c(Br)c2=O)c1]

To a solution of 3-[5-bromo-2-methyl-4-(2-methyl-thiazol-4-ylmethoxy)-6-oxo-6H-pyrimidin-1-yl]-N-methoxy-4,N-dimethyl-benzamide from Step C (71 mg, 0.14 mmol) in tetrahydrofuran (2 mL), cooled using an ice water bath, was added ethynylmagnesium chloride, 0.5M in tetrahydrofuran, (0.42 mL, 0.21 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was used without any additional purification.

Step E: Preparation of Title Compound

To a solution of 5-bromo-2-methyl-3-(2-methyl-5-propynoyl-phenyl)-6-(2-methyl-thiazol-4-ylmethoxy)-3H-pyrimidin-4-one of Step D (64 mg, 0.14 mmol) in acetonitrile (1 mL) was added 2-hydroxy-2-methylpropionamidine HCl (30 mg, 0.21 mmol) and potassium carbonate (60 mg, 0.42 mmol) and the slurry was heated at 75° C. for two hours and at ambient temperature for eighteen hours. The reaction was filtered to remove excess salts. The filtrate was concentrated and purified via normal phase chromatography (ethyl acetate/heptane) to provide the title compound as a white solid (30 mg, 39% yield). MS (M, M+2): 542, 544; $^1$H NMR (400 MHz, chloroform-d) δ ppm, 1.64 (s, 6H), 2.16 (s, 3H), 2.21 (s, 3H), 2.76 (s, 3H), 5.59-5.67 (m, 2H), 7.26 (s, 1H), 7.54-7.58 (m, 2H), 7.92 (s, 1H), 8.14 (d, J=8.61, 1H), 8.78 (d, J=5.48, 1H).

Example 12

Preparation of 5-chloro-3-(5-(2-(2-hydroxypropan-2-yl)pyrimidin-4-yl)-2-methylphenyl)-2-methyl-6-((2-methylthiazol-4-yl)methoxy)pyrimidin-4(3H)-one

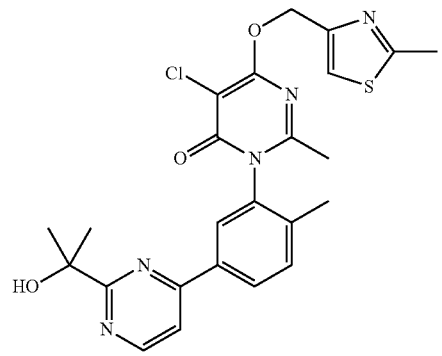 [SMILES: Cc1nc(COc2nc(C)n(-c3cc(-c4ccnc(C(C)(C)O)n4)ccc3C)c(=O)c2Cl)cs1]

Step A: Preparation of 3-[5-chloro-2-methyl-4-(2-methyl-thiazol-4-ylmethoxy)-6-oxo-6H-pyrimidin-1-yl]-4-methyl-benzoic acid methyl ester

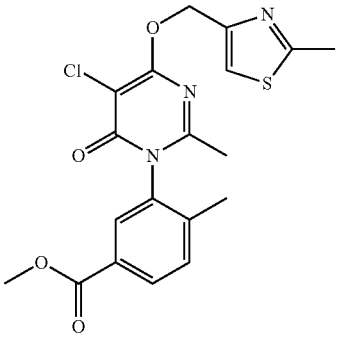

To a solution of 4-methyl-3-[2-methyl-4-(2-methyl-thiazol-4-ylmethoxy)-6-oxo-6H-pyrimidin-1-yl]-benzoic acid methyl ester from Step A, of Example 11 (120 mg, 0.31 mmol) in isopropanol (1.5 mL) was added N-chlorosuccinimide (46 mg, 0.34 mmol) and 2 drops of dichloroacetic acid.

The solution was heated at 60° C. for three hours. The solution was allowed to cool and concentrated in vacuo and the residue was partitioned between ethyl acetate and water. The organic layer was washed with water and brine and dried over magnesium sulfate. The slurry was filtered and concentrated to provide the chlorinated product as colorless oil (125 mg, 96%). MS (M+H): 420

Step B: Preparation of 3-[5-chloro-2-methyl-4-(2-methyl-thiazol-4-ylmethoxy)-6-oxo-6H-pyrimidin-1-yl]-N-methoxy-4,N-dimethyl-benzamide

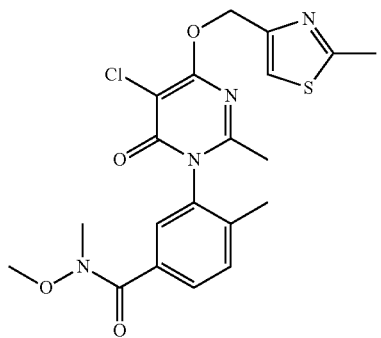

To a solution of 3-[5-chloro-2-methyl-4-(2-methyl-thiazol-4-ylmethoxy)-6-oxo-6H-pyrimidin-1-yl]-4-methyl-benzoic acid methyl ester from Step A (125 mg, 0.30 mmol) in tetrahydrofuran (1 mL) was added 1N sodium hydroxide (1 mL) and the solution stirred at ambient temperature for eighteen hours. The solution was concentrated in vacuo and the aqueous residue was acidified to pH=2 using 1M HCl. The solution was extracted with ethyl acetate, washed with water and dried over magnesium sulfate. The slurry was filtered and concentrated to an orange oil used without any additional purification. To a solution of the crude acid in tetrahydrofuran (2 mL) was added 1,1'-carbonyldiimidazole (72 mg, 0.45 mmol). After stifling at ambient temperature for one hour, N,N-dimethylhydroxylamine HCl (44 mg, 0.45 mmol) and triethylamine (0.08 mL, 0.60 mmol) were added. The solution continued to stir for eighteen hours. The solution was partitioned between ethyl acetate and water. The organic layer was washed with saturated sodium bicarbonate, water, and brine and dried over magnesium sulfate. The slurry was filtered and concentrated to provide the amide as a light brown oil (93 mg, 71%). MS (M+H): 449

Step C: Preparation of 5-chloro-2-methyl-3-(2-methyl-5-propynoyl-phenyl)-6-(2-methyl-thiazol-4-ylmethoxy)-3H-pyrimidin-4-one

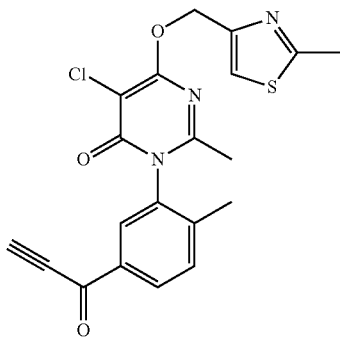 [SMILES: C#CC(=O)c1ccc(C)c(-n2c(C)nc(OCc3csc(C)n3)c(Cl)c2=O)c1]

To a solution of 3-[5-chloro-2-methyl-4-(2-methyl-thiazol-4-ylmethoxy)-6-oxo-6H-pyrimidin-1-yl]-N-methoxy-4,N-dimethyl-benzamide from Step B (93 mg, 0.21 mmol) in tetrahydrofuran (2 mL), cooled using an ice water bath, was added ethynylmagnesium bromide, 0.5M in tetrahydrofuran, (0.62 mL, 0.31 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was used without any additional purification.

Step D: Preparation of Title Compound

To a solution of 5-chloro-2-methyl-3-(2-methyl-5-propynoyl-phenyl)-6-(2-methyl-thiazol-4-ylmethoxy)-3H-pyrimidin-4-one from Step C (87 mg, 0.21 mmol) in acetonitrile (2 mL) was added 2-hydroxy-2-methylpropionamidine HCl (44 mg, 0.32 mmol) and potassium carbonate (87 mg, 0.63 mmol) and the slurry was heated at 75° C. for two hours and at ambient temperature for eighteen hours. The reaction was filtered to remove excess salts. The filtrate was concentrated and purified via normal phase chromatography (ethyl acetate/heptane) to provide the title compound as a white solid (12 mg, 11% yield). MS (M+H): 499; $^1$H NMR (400 MHz, chloroform-d) δ ppm, 1.64 (s, 6H), 2.17 (s, 3H), 2.21 (s, 3H), 2.77 (s, 3H), 5.59-5.68 (m, 2H), 7.26 (s, 1H), 7.55-7.59 (m, 2H), 7.93 (s, 1H), 8.14 (d, J=8.60, 1H), 8.78 (d, J=5.08, 1H).

Example 13

Preparation of 5-bromo-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one

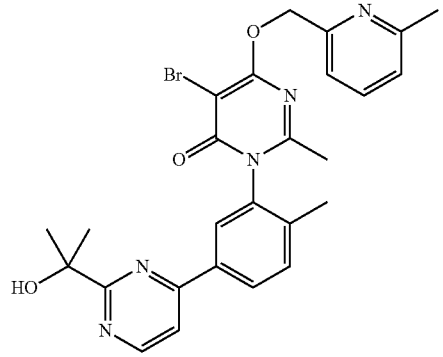

Step A: Preparation of 4-methyl-3-[2-methyl-4-(6-methyl-pyridin-2-ylmethoxy)-6-oxo-6H-pyrimidin-1-yl]-benzoic acid methyl ester

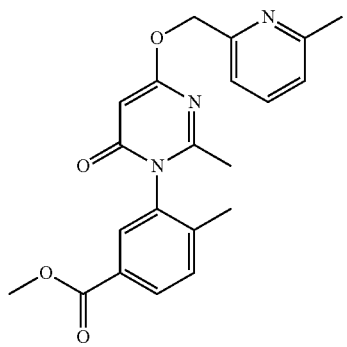

To a solution of Intermediate 2 (460 mg, 1.68 mmol) in N,N-dimethylformamide (2 mL) was added 2-(bromomethyl)-6-methylpyridine (312 mg, 1.68 mmol), potassium carbonate (350 mg, 2.53 mmol) and 18-crown-6 (40 mg). The slurry was stirred at ambient temperature for one hour. The reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a white semi-solid (100 mg, 16% yield). MS (M+H): 380

Step B: Preparation of 3-[5-bromo-2-methyl-4-(6-methyl-pyridin-2-ylmethoxy)-6-oxo-6H-pyrimidin-1-yl]-4-methyl-benzoic acid methyl ester

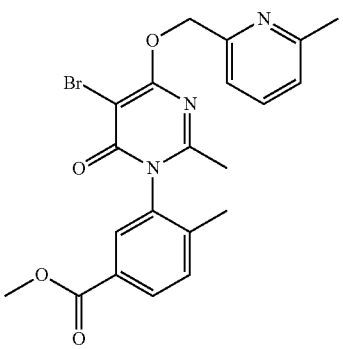

To a solution of 4-methyl-3-[2-methyl-4-(6-methyl-pyridin-2-ylmethoxy)-6-oxo-6H-pyrimidin-1-yl]-benzoic acid methyl ester from Step A (122 mg, 0.32 mmol) in dichloromethane (2 mL) was added N-bromosuccinimide (57 mg, 0.32 mmol). The solution was stirred at ambient temperature for two hours. The solution was washed with water and brine and dried over magnesium sulfate. The slurry was filtered and concentrated to provide the brominated product as colorless oil (148 mg, quantitative yield). MS (M, M+2): 458, 460

Step C: Preparation of 3-[5-bromo-2-methyl-4-(6-methyl-pyridin-2-ylmethoxy)-6-oxo-6H-pyrimidin-1-yl]-N-methoxy-4,N-dimethyl-benzamide

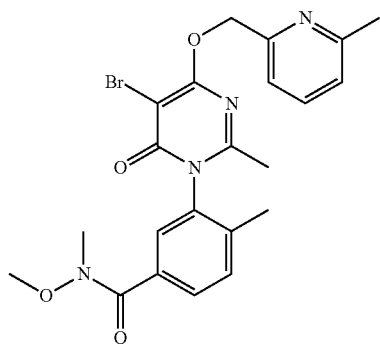

To a solution of 3-[5-bromo-2-methyl-4-(6-methyl-pyridin-2-ylmethoxy)-6-oxo-6H-pyrimidin-1-yl]-4-methyl-benzoic acid methyl ester from Step B (148 mg, 0.31 mmol) in tetrahydrofuran (2 mL) was added 1N sodium hydroxide (1 mL) and the solution stirred at ambient temperature for three hours. The solution was concentrated in vacuo and the aqueous residue acidified to pH=2 using 1M HCl. The solution was extracted with ethyl acetate, washed with water and dried over magnesium sulfate. The slurry was filtered and concentrated to provide a yellow oil used without any additional purification. To a solution of the crude acid in tetrahydrofuran (3 mL) was added 1,1'-carbonyldiimidazole (75 mg, 0.46 mmol). After stifling at ambient temperature for one hour, N,N-dimethylhydroxylamine HCl (45 mg, 0.46 mmol) and triethylamine (0.09 mL, 0.62 mmol) were added. The solution continued to stir for eighteen hours. The solution was partitioned between ethyl acetate and water. The organic layer was washed with saturated sodium bicarbonate, water, and brine and dried over magnesium sulfate. The slurry was filtered and concentrated to provide the amide as a yellow oil (60 mg, 40%). MS (M, M+2): 487, 489

Step D: Preparation of 5-bromo-2-methyl-3-(2-methyl-5-propynoyl-phenyl)-6-(6-methyl-pyridin-2-ylmethoxy)-3H-pyrimidin-4-one

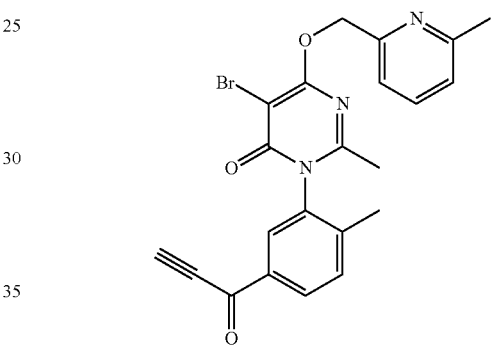

To a solution of 3-[5-bromo-2-methyl-4-(6-methyl-pyridin-2-ylmethoxy)-6-oxo-6H-pyrimidin-1-yl]-N-methoxy-4,N-dimethyl-benzamide from Step C (60 mg, 0.12 mmol) in tetrahydrofuran (2 mL), cooled using an ice water bath, was added ethynylmagnesium chloride, 0.5M in tetrahydrofuran, (0.5 mL, 0.25 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was used without any additional purification.

Step E: Preparation of Title Compound

To a solution of 5-bromo-2-methyl-3-(2-methyl-5-propynoyl-phenyl)-6-(6-methyl-pyridin-2-ylmethoxy)-3H-pyrimidin-4-one of Step D (54 mg, 0.12 mmol) in acetonitrile (1 mL) was added 2-hydroxy-2-methylpropionamidine HCl (25 mg, 0.18 mmol) and potassium carbonate (50 mg, 0.36 mmol) and the slurry was heated at 75° C. for eighteen hours. The reaction was returned to ambient temperature and filtered to remove excess salts. The filtrate was concentrated and purified via normal phase chromatography (ethyl acetate/heptane) to provide the title compound as a light yellow solid (27 mg, 42% yield). MS (M, M+2): 536, 538; $^1$H NMR (400 MHz, chloroform-d) δ ppm, 1.64 (s, 6H), 2.14 (s, 3H), 2.21 (s, 3H), 2.61 (s, 3H), 4.78 (s, 1H), 5.61-5.72 (m, 2H), 7.14 (d, J=7.83 Hz, 1H), 7.43 (d, J=7.44 Hz, 1H), 7.54-7.58 (m, 2H), 7.70 (s, 1H), 7.92 (s, 1H), 8.13 (d, J=7.82 Hz, 1H), 8.77 (d, J=5.09 Hz, 1H).

Example 14

Preparation of 5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one

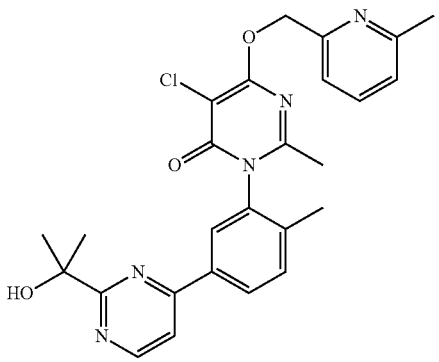 [SMILES: Cc1cccc(COc2nc(C)n(-c3cc(-c4ccnc(C(C)(C)O)n4)ccc3C)c(=O)c2Cl)n1]

Step A: Preparation of 3-[5-chloro-2-methyl-4-(6-methyl-pyridin-2-ylmethoxy)-6-oxo-6H-pyrimidin-1-yl]-4-methyl-benzoic acid methyl ester

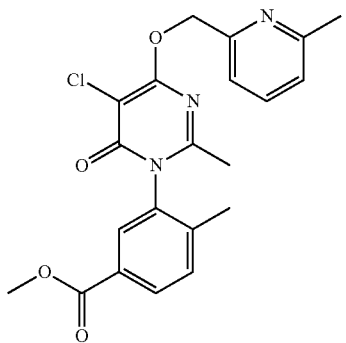

To a solution of 4-methyl-3-[2-methyl-4-(6-methyl-pyridin-2-ylmethoxy)-6-oxo-6H-pyrimidin-1-yl]-benzoic acid methyl ester from Step A, of Example 13 (100 mg, 0.26 mmol) in isopropanol (1 mL) was added N-chlorosuccinimide (39 mg, 0.29 mmol) and 1 drops of dichloroacetic acid. The solution was heated at 60° C. for two hours. The solution was concentrated in vacuo and the residue was partitioned between ethyl acetate and water. The organic layer was washed with water and brine and dried over magnesium sulfate. The slurry was filtered and concentrated to provide the chlorinated product as colorless oil (120 mg, quantitative yield). MS (M+H): 414

Step B: Preparation of 3-[5-chloro-2-methyl-4-(6-methyl-pyridin-2-ylmethoxy)-6-oxo-6H-pyrimidin-1-yl]-N-methoxy-4,N-dimethyl-benzamide

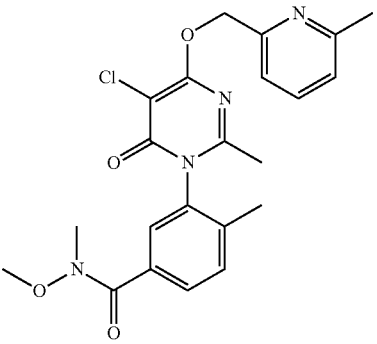

To a solution of 3-[5-chloro-2-methyl-4-(6-methyl-pyridin-2-ylmethoxy)-6-oxo-6H-pyrimidin-1-yl]-4-methyl-benzoic acid methyl ester from Step A (108 mg, 0.26 mmol) in tetrahydrofuran (1 mL) was added 1N sodium hydroxide (1 mL) and the solution stirred at ambient temperature for eighteen hours. The solution was concentrated in vacuo and the aqueous residue was acidified to pH=2 using 1M HCl. The solution was extracted with ethyl acetate, washed with water and dried over magnesium sulfate. The slurry was filtered and concentrated to give an orange oil which was used without any additional purification. To a solution of the crude acid in tetrahydrofuran (2 mL) was added 1,1'-carbonyldiimidazole (63 mg, 0.39 mmol). After stifling at ambient temperature for one hour, N,N-dimethylhydroxylamine HCl (38 mg, 0.39 mmol) and triethylamine (0.07 mL, 0.52 mmol) were added. The solution continued to stir for eighteen hours. The solution was partitioned between ethyl acetate and water. The organic layer was washed with saturated sodium bicarbonate, water, and brine and dried over magnesium sulfate. The slurry was filtered and concentrated to provide the amide as a light brown oil (73 mg, 63%). MS (M+H): 443

Step C: Preparation of 5-chloro-2-methyl-3-(2-methyl-5-propynoyl-phenyl)-6-(6-methyl-pyridin-2-ylmethoxy)-3H-pyrimidin-4-one

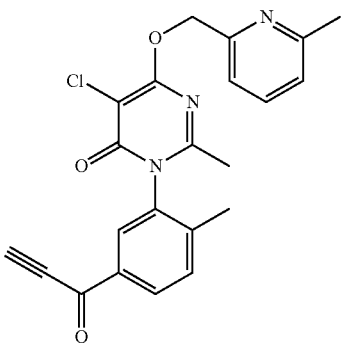 [SMILES: C#CC(=O)c1ccc(C)c(-n2c(C)nc(OCc3cccc(C)n3)c(Cl)c2=O)c1]

To a solution of 3-[5-chloro-2-methyl-4-(6-methyl-pyridin-2-ylmethoxy)-6-oxo-6H-pyrimidin-1-yl]-N-methoxy-4,N-dimethyl-benzamide from Step B (73 mg, 0.16 mmol) in tetrahydrofuran (2 mL), cooled using an ice water bath, was added ethynylmagnesium bromide, 0.5M in tetrahydrofuran, (0.5 mL, 0.25 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was used without any additional purification.

Step D: Preparation of Title Compound

To a solution of 5-chloro-2-methyl-3-(2-methyl-5-propynoyl-phenyl)-6-(6-methyl-pyridin-2-ylmethoxy)-3H-pyrimidin-4-one of Step C (67 mg, 0.16 mmol) in acetonitrile (2 mL) was added 2-hydroxy-2-methylpropionamidine HCl (34 mg, 0.25 mmol) and potassium carbonate (68 mg, 0.49 mmol) and the slurry was heated at 75° C. for eighteen hours. The reaction was returned to ambient temperature and filtered to remove excess salts. The filtrate was concentrated and purified via normal phase chromatography (ethyl acetate/heptane) to provide the title compound as a white solid (9.5 mg, 12% yield). MS (M+H): 492; $^1$H NMR (400 MHz, chloroform-d) δ ppm, 1.64 (s, 6H), 2.14 (s, 3H), 2.21 (s, 3H), 2.60 (s, 3H), 4.79 (s, 1H), 5.61-5.74 (m, 2H), 7.13 (d, J=7.43 Hz, 1H), 7.40 (d, J=7.04 Hz, 1H), 7.54-7.58 (m, 2H), 7.68 (s, 1H), 7.93 (s, 1H), 8.14 (d, J=7.83 Hz, 1H), 8.77 (d, J=5.09 Hz, 1H).

Examples 15 & 16

Chiral Resolution of 5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one

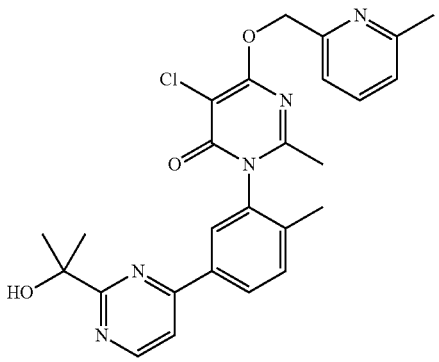 [SMILES: Cc1cccc(COc2nc(C)n(-c3cc(-c4ccnc(C(C)(C)O)n4)ccc3C)c(=O)c2Cl)n1]

Optical rotations were obtained using an Autopol III polarimeter manufactured by Rudolph Research Analytical using a 1.5 mL cell. Racemic 5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one (Example 14)(89 mg, 0.18 mmol) was separated using supercritical fluid chromatography (Thar 80, preparative SFC, ChiralPak AD-20μ, 250×30 mmID column) with a mobile phase of carbon dioxide and ethanol. The separation method used an isocratic method of 45% ethanol with a flow rate of 80 mL/min and a cycle time of 11.5 min.

Example 15 eluted first at 5.13 minutes yielding 20.9 mg of (−)-5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one. MS (M+H): 492; $^1$H NMR (400 MHz, chloroform-d) δ ppm, 1.64 (s, 6H), 2.14 (s, 3H), 2.21 (s, 3H), 2.60 (s, 3H), 4.79 (s, 1H), 5.61-5.74 (m, 2H), 7.13 (d, J=7.43 Hz, 1H), 7.40 (d, J=7.04 Hz, 1H), 7.54-7.58 (m, 2H), 7.68 (s, 1H), 7.93 (s, 1H), 8.14 (d, J=7.83 Hz, 1H), 8.77 (d, J=5.09 Hz, 1H). $[\alpha]_D^{20}$ −11 (c 0.1, CH$_3$OH)

Example 16 eluted second at 7.64 minutes yielding 19.1 mg of (+)-5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one. MS (M+H): 492; $^1$H NMR (400 MHz, chloroform-d) δ ppm, 1.64 (s, 6H), 2.14 (s, 3H), 2.21 (s, 3H), 2.60 (s, 3H), 4.79 (s, 1H), 5.61-5.74 (m, 2H), 7.13 (d, J=7.43 Hz, 1H), 7.40 (d, J=7.04 Hz, 1H), 7.54-7.58 (m, 2H), 7.68 (s, 1H), 7.93 (s, 1H), 8.14 (d, J=7.83 Hz, 1H), 8.77 (d, J=5.09 Hz, 1H). $[\alpha]_D^{20}$ +20 (c 0.1, CH$_3$OH).

Example 17

Preparation of 5-chloro-3-(5-(2-(2-hydroxypropan-2-yl)pyrimidin-4-yl)-2-methylphenyl)-2-methyl-6-((6-(trifluoromethyl)pyridin-2-yl)methoxy)pyrimidin-4(3H)-one

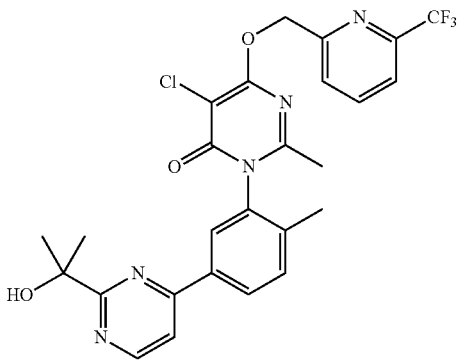 [SMILES: Cc1ccc(-c2ccnc(C(C)(C)O)n2)cc1-n1c(C)nc(OCc2cccc(C(F)(F)F)n2)c(Cl)c1=O]

Step A: Preparation of 3-[5-chloro-2-methyl-6-oxo-4-(6-trifluoromethyl-pyridin-2-ylmethoxy)-6H-pyrimidin-1-yl]-4-methyl-benzoic acid methyl ester

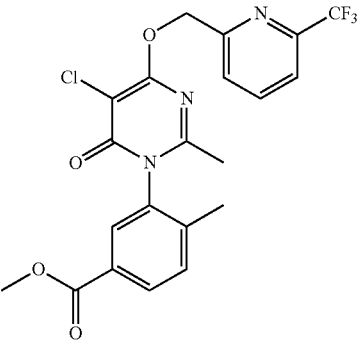 [SMILES: COC(=O)c1ccc(C)c(-n2c(C)nc(OCc3cccc(C(F)(F)F)n3)c(Cl)c2=O)c1]

To a solution of Intermediate 3 (250 mg, 0.81 mmol) in N,N-dimethylformamide (3 mL) was added 2-(chloromethyl)-6-(trifluoromethyl)pyridine (158 mg, 0.81 mmol), potassium carbonate (224 mg, 1.62 mmol) and 18-crown-6 (40 mg). The slurry was heated at 45° C. for eighteen hours. The reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a colorless oil. (110 mg, 29% yield). MS (M+H): 468

Step B: Preparation of 3-[5-chloro-2-methyl-6-oxo-4-(6-trifluoromethyl-pyridin-2-ylmethoxy)-6H-pyrimidin-1-yl]-N-methoxy-4,N-dimethyl-benzamide

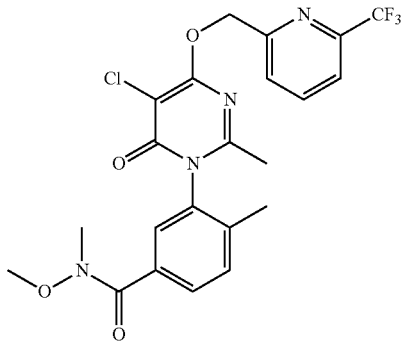 [SMILES: CON(C)C(=O)c1ccc(C)c(-n2c(C)nc(OCc3cccc(C(F)(F)F)n3)c(Cl)c2=O)c1]

To a solution of 3-[5-chloro-2-methyl-6-oxo-4-(6-trifluoromethyl-pyridin-2-ylmethoxy)-6H-pyrimidin-1-yl]-4-methyl-benzoic acid methyl ester from Step A (110 mg, 0.23 mmol) in tetrahydrofuran (1 mL) was added 1N sodium hydroxide (1 mL) and the solution was stirred at ambient temperature for eighteen hours. The solution was concentrated in vacuo and the aqueous residue acidified to pH=2 using 1M HCl. The solution was extracted with ethyl acetate, washed with water and dried over magnesium sulfate. The slurry was filtered and concentrated to give a yellow solid which was used without additional purification. To a solution of the crude acid in tetrahydrofuran (2 mL) was added 1,1'-carbonyldiimidazole (56 mg, 0.35 mmol). After stirring at ambient temperature for one hour, N,N-dimethylhydroxylamine HCl (35 mg, 0.35 mmol) and triethylamine (0.06 mL, 0.46 mmol) were added. The solution continued to stir for eighteen hours. The solution was partitioned between ethyl acetate and water. The organic layer was washed with saturated sodium bicarbonate, water, and brine and dried over magnesium sulfate. The slurry was filtered and concentrated to provide the amide as a colorless oil (53 mg, 46%). MS (M+H): 497

Step C: Preparation of 5-chloro-2-methyl-3-(2-methyl-5-propynoyl-phenyl)-6-(6-trifluoromethyl-pyridin-2-ylmethoxy)-3H-pyrimidin-4-one

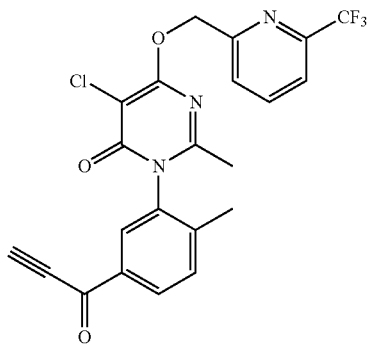 [SMILES: C#CC(=O)c1ccc(C)c(-n2c(C)nc(OCc3cccc(C(F)(F)F)n3)c(Cl)c2=O)c1]

To a solution of 3-[5-chloro-2-methyl-6-oxo-4-(6-trifluoromethyl-pyridin-2-ylmethoxy)-6H-pyrimidin-1-yl]-N-methoxy-4,N-dimethyl-benzamide from Step B (53 mg, 0.11 mmol) in tetrahydrofuran (1.5 mL), cooled using an ice water bath, was added ethynylmagnesium chloride, 0.5M in tetrahydrofuran, (0.3 mL, 0.15 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was used without additional purification.

Step D: Preparation of Title Compound

To a solution of 5-chloro-2-methyl-3-(2-methyl-5-propynoyl-phenyl)-6-(6-trifluoromethyl-pyridin-2-ylmethoxy)-3H-pyrimidin-4-one of Step C (50 mg, 0.11 mmol) in acetonitrile (1 mL) was added 2-hydroxy-2-methylpropionamidine HCl (23 mg, 0.16 mmol) and potassium carbonate (45 mg, 0.33 mmol) and the slurry heated at 75° C. for eighteen hours. After cooling to room temperature the reaction was filtered to remove excess salts. The filtrate was concentrated and purified via normal phase chromatography (ethyl acetate/heptane) to provide the title compound as a yellow oil (19 mg, 32% yield). MS (M+H): 546; $^1$H NMR (400 MHz, chloroform-d) δ ppm, 1.64 (s, 6H), 2.15 (s, 3H), 2.21 (s, 3H), 5.69-5.78 (m, 2H), 7.56-7.59 (m, 2H), 7.66 (d, J=7.43 Hz, 1H), 7.82 (d, J=7.82 Hz, 1H), 7.94-8.00 (m, 2H), 8.14 (d, J=7.43 Hz, 1H), 8.78 (d, J=5.08 Hz, 1H).

Example 18

Preparation of 5-chloro-6-(((6-fluoropyridin-2-yl)methoxy)-3-(5-(2-(2-hydroxypropan-2-yl)pyrimidin-4-yl)-2-methylphenyl)-2-methylpyrimidin-4(3H)-one

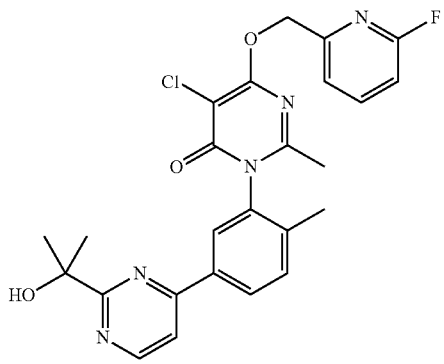 [SMILES: Cc1ccc(-c2ccnc(C(C)(C)O)n2)cc1-n1c(C)nc(OCc2cccc(F)n2)c(Cl)c1=O]

Step A: Preparation of 2-chloromethyl-6-fluoro-pyridine

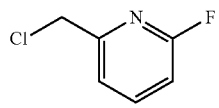

To a solution of 2-fluoro-6-methylpyridine (0.23 mL, 2.2 mmol) in acetonitrile (5 mL) was added N-chlorosuccinimide (440 mg, 3.3 mmol), benzoyl peroxide (14 mg, 0.044 mmol)

and glacial acetic acid (10 uL). The solution was heated at 85° C. for four hours and at ambient temperature for eighteen hours. The solution was partitioned between ethyl acetate and water. The organic layer was washed with water and brine and dried over magnesium sulfate. The material was filtered and concentrated. The crude material was purified using normal phase chromatography (ethyl acetate/heptane) to provide the chloromethyl compound as a colorless oil (240 mg, 75%).

Step B: Preparation of 3-[5-chloro-4-(6-fluoro-pyridin-2-ylmethoxy)-2-methyl-6-oxo-6H-pyrimidin-1-yl]-4-methyl-benzoic acid methyl ester

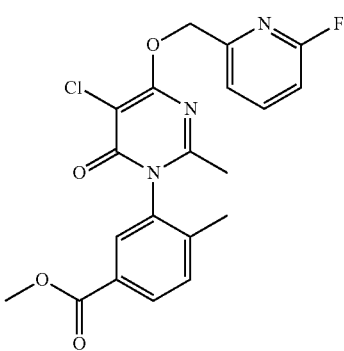 [SMILES: COC(=O)c1ccc(C)c(-n2c(C)nc(OCc3cccc(F)n3)c(Cl)c2=O)c1]

To a solution of Intermediate 3 (250 mg, 0.81 mmol) in N,N-dimethylformamide (3 mL) was added 2-chloromethyl-6-fluoro-pyridine from Step A (118 mg, 0.81 mmol), potassium carbonate (224 mg, 1.62 mmol) and 18-crown-6 (40 mg). The slurry was heated at 45° C. for eighteen hours. After cooling the reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the alkylated product as a white solid. (180 mg, 53% yield). MS (M+H): 418

Step C: Preparation of 3-[5-chloro-4-(6-fluoro-pyridin-2-ylmethoxy)-2-methyl-6-oxo-6H-pyrimidin-1-yl]-N-methoxy-4,N-dimethyl-benzamide

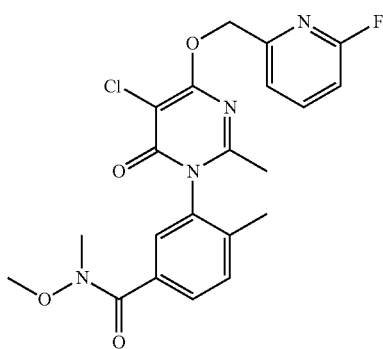 [SMILES: CON(C)C(=O)c1ccc(C)c(-n2c(C)nc(OCc3cccc(F)n3)c(Cl)c2=O)c1]

To a solution of 3-[5-chloro-4-(6-fluoro-pyridin-2-ylmethoxy)-2-methyl-6-oxo-6H-pyrimidin-1-yl]-4-methyl-benzoic acid methyl ester from Step B (180 mg, 0.43 mmol) in tetrahydrofuran (2 mL) was added 1N sodium hydroxide (1 mL) and the solution was stirred at ambient temperature for eighteen hours. The solution was concentrated in vacuo and the aqueous residue was acidified to pH=2 using 1M HCl. The solution was extracted with ethyl acetate, washed with water and dried over magnesium sulfate. The slurry was filtered and concentrated to give a yellow solid which was used without additional purification. To a solution of the crude acid in tetrahydrofuran (2 mL) was added 1,1'-carbonyldiimidazole (105 mg, 0.65 mmol). After stirring at ambient temperature for one hour, N,N-dimethylhydroxylamine HCl (63 mg, 0.65 mmol) and triethylamine (0.12 mL, 0.86 mmol) were added. The solution continued to stir for eighteen hours. The solution was partitioned between ethyl acetate and water. The organic layer was washed with saturated sodium bicarbonate, water, and brine and dried over magnesium sulfate. The slurry was filtered and concentrated to provide the amide as a colorless oil (85 mg, 44%). MS (M+H): 447

Step D: Preparation of 5-chloro-6-(6-fluoro-pyridin-2-ylmethoxy)-2-methyl-3-(2-methyl-5-propynoyl-phenyl)-3H-pyrimidin-4-one

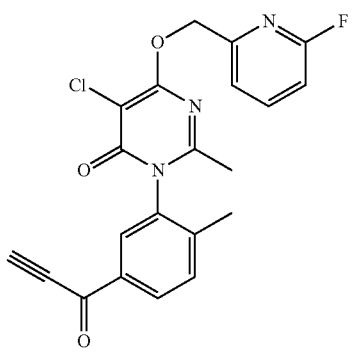 [SMILES: C#CC(=O)c1ccc(C)c(-n2c(C)nc(OCc3cccc(F)n3)c(Cl)c2=O)c1]

To a solution of 3-[5-chloro-4-(6-fluoro-pyridin-2-ylmethoxy)-2-methyl-6-oxo-6H-pyrimidin-1-yl]-N-methoxy-4,N-dimethyl-benzamide from Step C (85 mg, 0.19 mmol) in tetrahydrofuran (2 mL), cooled using an ice water bath, was added ethynylmagnesium chloride, 0.5M in tetrahydrofuran, (0.57 mL, 0.28 mmol) in a drop-wise manner. Additional Grignard reagent was added as necessary to ensure full product formation. After thirty minutes, the reaction was quenched into ice cold water and extracted with ethyl acetate. The organic layer was washed with saturated ammonium chloride, water and brine and dried over magnesium sulfate. The slurry was filtered and concentrated. The crude material was used without additional purification.

Step E: Preparation of Title Compound

To a solution of 5-chloro-6-(6-fluoro-pyridin-2-ylmethoxy)-2-methyl-3-(2-methyl-5-propynoyl-phenyl)-3H-pyrimidin-4-one of Step D (78 mg, 0.19 mmol) in acetonitrile (3 mL) was added 2-hydroxy-2-methylpropionamidine HCl (39 mg, 0.28 mmol) and potassium carbonate (78 mg, 0.57 mmol) and the slurry heated at 75° C. for eighteen hours. After cooling to room temperature the reaction was filtered to remove excess salts. The filtrate was concentrated and purified via normal phase chromatography (ethyl acetate/heptane) to provide the title compound as a yellow oil (29 mg, 31% yield). MS (M+H): 496; $^1$H NMR (400 MHz, chloroform-d) δ ppm, 1.64 (s, 6H), 2.15 (s, 3H), 2.21 (s, 3H), 5.54-5.65 (m, 2H), 6.90 (d, J=7.83 Hz, 1H) 7.48 (d, J=6.65 Hz, 1H), 7.55-7.57 (m, 2H), 7.85-7.93 (m, 2H), 8.14 (d, J=8.22 Hz, 1H), 8.78 (d, J=5.09, 1H).

Example 19

Preparation of 5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one

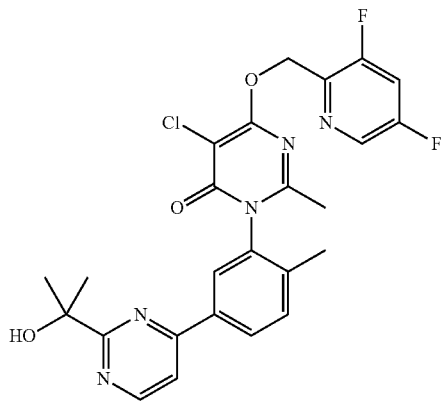

Step A: Preparation of
3,5-difluoro-pyridine-2-carboxylic acid ethyl ester

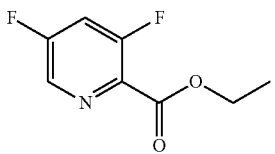

To a suspension of 3,5-difluoropyridine-2-carboxylic acid (2.0 g, 12.6 mmol) in ethanol (5 mL), cooled using an ice water bath, was added thionyl chloride (2 mL) in a dropwise manner. The solution was heated at 60° C. for three hours. The reaction was returned to ambient temperature and was concentrated in vacuo to provide the ethyl ester, hydrochloride salt, as a yellow oil (2.5 g, quantitative yield).

Step B: Preparation of
(3,5-difluoro-pyridin-2-yl)-methanol

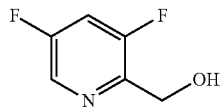

To a solution of 3,5-difluoro-pyridine-2-carboxylic acid ethyl ester of Step A (2.5 g, 12.6 mmol) in ethanol (10 mL), cooled using an ice water bath, was added sodium borohydride (1.43 g, 37.8 mmol) in a portion wise manner. The solution was stirred at 0° C. for thirty minutes and at ambient temperature for two hours. The reaction was returned to 0° C. and saturated ammonium chloride was added dropwise. The solvent was removed in vacuo and the resulting residue was partitioned between ethyl acetate and water. The organic layer was washed with saturated ammonium chloride, water and brine and dried over magnesium sulfate. The slurry was filtered and concentrated to provide the alcohol as a yellow oil (1.8 g, 98%). MS (M+H): 146

Step C: Preparation of
2-chloromethyl-3,5-difluoro-pyridine

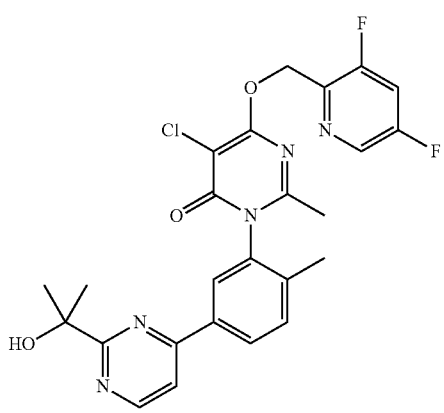 [SMILES: Cc1ccc(-c2ccnc(C(C)(C)O)n2)cc1-n1c(C)nc(OCc2ncc(F)cc2F)c(Cl)c1=O]

To a solution of (3,5-difluoro-pyridin-2-yl)-methanol from Step B (1.8 g, 12.3 mmol) in dichloromethane (20 mL) was added three drops of N,N-dimethylformamide and cooled using an ice water bath. Thionyl chloride (2 mL) was added dropwise and the solution was stirred at ambient temperature for one hour. The solution was concentrated in vacuo to provide the chloro compound as a light brown liquid (1.75 g, 87%).

Step D: Preparation of Title Compound

To a solution of Intermediate 1 (505 mg, 1.31 mmol) in N,N-dimethylformamide (3 mL) was added 2-chloromethyl-3,5-difluoro-pyridine from Step C (214 mg, 1.31 mmol), potassium carbonate (452 mg, 3.27 mmol) and 18-crown-6 (40 mg). The slurry was heated at 60° C. for eighteen hours. After cooling the reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the title compound as a colorless oil (250 mg, 37% yield). MS (M+H): 514; $^1$H NMR (400 MHz, chloroform-d) δ ppm, 1.64 (s, 6H), 2.16 (s, 3H), 2.21 (s, 3H), 5.62-5.72 (m, 2H), 7.28-7.30 (m, 1H), 7.54-7.58 (m, 2H), 7.92 (s, 1H), 8.14 (d, J=8.21 Hz, 1H), 8.40 (s, 1H), 8.78 (d, J=5.47, 1H).

Examples 20 & 21

Chiral Resolution of 5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one Optical rotations were obtained using an Autopol III polarimeter manufactured by Rudolph Research Analytical using a 1.5 mL cell. Racemic 5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one (Example 19) (250 mg, 0.49 mmol) was separated using supercritical fluid chromatography (Thar 80, preparative SFC, ChiralCel OJ-H, 250×30 mmID column) with a mobile phase of carbon dioxide and isopropanol. The separation method used an isocratic method of 30% isopropanol, a flow rate of 60 mL/min and a cycle time of 6.0 min.

Example 20 eluted first at 2.29 minutes yielding 106 mg of (+)-5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one. MS (M+H): 514; $^1$H NMR (400 MHz, chloroform-d) δ ppm, 1.64 (s, 6H), 2.16 (s, 3H), 2.21 (s, 3H), 5.62-5.72 (m, 2H), 7.28-7.30 (m, 1H), 7.54-7.58 (m, 2H), 7.92 (s, 1H), 8.14 (d, J=8.21 Hz, 1H), 8.40 (s, 1H), 8.78 (d, J=5.47, 1H). $[\alpha]_D^{20}$+20 (c 0.1, CH$_3$OH).

Example 21 eluted second at 2.80 minutes yielding 112 mg of (−)-5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one. MS (M+H): 514; $^1$H NMR (400 MHz, chloroform-d) δ ppm, 1.64 (s, 6H), 2.16 (s, 3H), 2.21 (s, 3H), 5.62-5.72 (m, 2H), 7.28-7.30 (m, 1H), 7.54-7.58 (m, 2H), 7.92 (s, 1H), 8.14 (d, J=8.21 Hz, 1H), 8.40 (s, 1H), 8.78 (d, J=5.47, 1H). $[\alpha]_D^{20}$-32 (c 0.1, CH$_3$OH).

Example 22

Preparation of 5-chloro-6-(2,4-difluoro-3-methyl-benzyloxy)-3-{5-[2-(1-hydroxy-1-methyl-ethyl)-pyrimidin-4-yl]-2-methyl-phenyl}-2-methyl-3H-pyrimidin-4-one

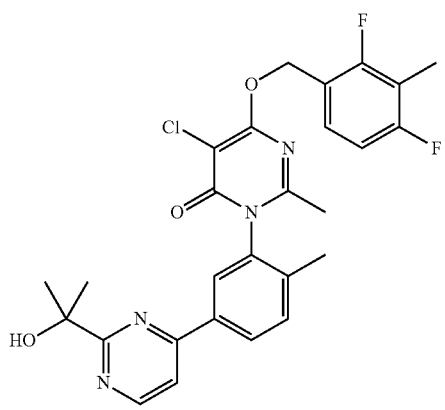

Step A: Preparation of 2,4-difluoro-3-methyl-benzoic acid methyl ester

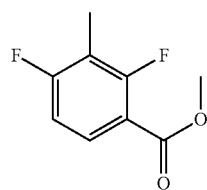

To a suspension of 2,4-difluoro-3-methylbenzoic acid (950 mg, 5.52 mmol) in methanol (10 mL), cooled using an ice water bath, was added thionyl chloride (1 mL) in a dropwise manner. The solution was heated at 60° C. for three hours. The reaction was returned to ambient temperature and was concentrated in vacuo. The residue was partitioned between ethyl acetate and water. The organic layer was washed with water and brine and dried over magnesium sulfate. The slurry was filtered and concentrated to provide the ethyl ester as a yellow oil (1.1 g, 90%). MS (M+H): 187

Step B: Preparation of (2,4-difluoro-3-methyl-phenyl)-methanol

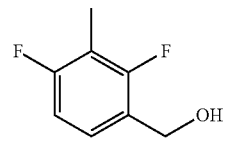

To a solution of 2,4-difluoro-3-methyl-benzoic acid methyl ester from Step A (1.1 g, 5.5 mmol) in tetrahydrofuran (10 mL), cooled to −78° C. using a dry ice/acetone bath, was added lithium aluminum hydride, 1.0M in tetrahydrofuran (10 mL, 10 mmol), in a dropwise manner. The solution was stirred for two hours. The reaction was quenched by dropwise addition of ice-cold saturated sodium bicarbonate solution and was extracted with ethyl acetate. The organic layer was washed with water and brine and dried over magnesium sulfate. The slurry was filtered and concentrated to provide the alcohol as a colorless liquid (1.1 g, quantitative yield).

Step C: Preparation of 1-chloromethyl-2,4-difluoro-3-methyl-benzene

To a solution of (2,4-difluoro-3-methyl-phenyl)-methanol from Step B (1.1 g, 7.0 mmol) in dichloromethane (3 mL), cooled using an ice water bath was added thionyl chloride (2 mL) in a dropwise manner. The solution was stirred at 60° C. for three hours. The reaction was cooled using an ice bath and was quenched by dropwise addition of saturated sodium bicarbonate. The solution was extracted with ethyl acetate, washed with brine and dried over magnesium sulfate. The solution was filtered and concentrated in vacuo to provide the chloro compound as a colorless oil (1.0 g, 81%).

Step D: Preparation of Title Compound

To a solution of Intermediate 1 (50 mg, 0.13 mmol) in N,N-dimethylformamide (1.5 mL) was added 1-chloromethyl-2,4-difluoro-3-methyl-benzene from Step C (23 mg, 0.13 mmol), potassium carbonate (36 mg, 0.26 mmol) and 18-crown-6 (3 mg). The slurry was heated at 60° C. for three hours. After cooling to room temperature, the reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the title compound as a colorless oil (25 mg, 37% yield). MS (M+H): 527; $^1$H NMR (400 MHz, chloroform-d) δ ppm, 1.64 (s, 6H), 2.18 (s, 3H), 2.19 (s, 3H), 2.21 (s, 3H), 5.45-5.59 (m, 2H), 6.88-6.92 (m, 1H), 7.34-7.40 (m, 1H), 7.55-7.58 (m, 2H), 7.93 (s, 1H), 8.14 (d, J=7.83 Hz, 1H), 8.78 (d, J=5.09, 1H).

Example 23

Preparation of 5-chloro-6-((2,4-difluoro-5-methyl-benzyl)oxy)-3-(5-(2-(2-hydroxypropan-2-yl)pyrimidin-4-yl)-2-methylphenyl)-2-methylpyrimidin-4(3H)-one

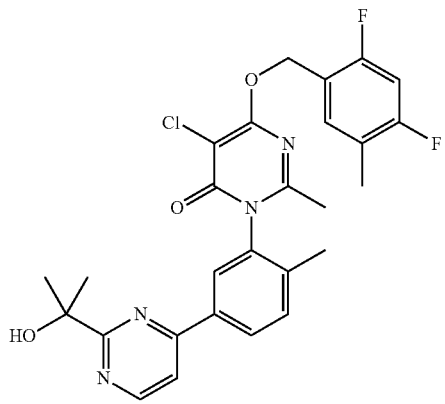

Step A: Preparation of 2,4-difluoro-5-methyl-benzoic acid methyl ester

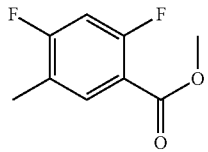

To a suspension of 2,4-difluoro-5-methylbenzoic acid (1.0 g, 5.81 mmol) in methanol (10 mL), cooled using an ice water bath, was added thionyl chloride (1 mL) in a dropwise manner. The solution was heated at 50° C. for three hours. The solution was concentrated in vacuo to provide the ethyl ester as a yellow oil (1.0 g, 92%).

Step B: Preparation of (2,4-difluoro-5-methyl-phenyl)-methanol

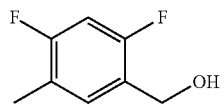

To a solution of 2,4-difluoro-5-methyl-benzoic acid methyl ester from Step A (1.0 g, 5.37 mmol) in tetrahydrofuran (10 mL), cooled to −78° C. using a dry ice/acetone bath, was added lithium aluminum hydride, 1.0M in tetrahydrofuran (10 mL, 10 mmol), in a dropwise manner. The solution was stirred for two hours. The reaction was quenched by dropwise addition of ice-cold saturated sodium bicarbonate solution, allowed to warm to room temperature and was extracted with ethyl acetate. The organic layer was washed with water and brine and dried over magnesium sulfate. The slurry was filtered and concentrated to provide the alcohol as a colorless liquid (1.0 g, quantitative yield).

Step C: Preparation of 1-chloromethyl-2,4-difluoro-5-methyl-benzene

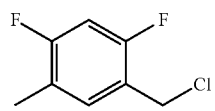

To a solution of (2,4-difluoro-5-methyl-phenyl)-methanol from Step B (1.0 g, 6.3 mmol) in dichloromethane (3 mL), cooled using an ice water bath, was added thionyl chloride (2 mL) in a dropwise manner. The solution was stirred at 60° C. for three hours. The reaction was cooled using an ice bath and was quenched by dropwise addition of saturated sodium bicarbonate. The solution was extracted with ethyl acetate, washed with brine and dried over magnesium sulfate. The solution was filtered and concentrated in vacuo to provide the chloro compound as a yellow liquid (900 mg, 81%).

Step D: Preparation of Title Compound

To a solution of Intermediate 1 (50 mg, 0.13 mmol) in N,N-dimethylformamide (1.5 mL) was added 1-chloromethyl-2,4-difluoro-5-methyl-benzene from Step C (23 mg, 0.13 mmol), potassium carbonate (36 mg, 0.26 mmol) and 18-crown-6 (3 mg). The slurry was heated at 60° C. for five hours. After cooling to room temperature the reaction was partitioned between ethyl acetate and water. The organic layer was washed with water and brine and dried over magnesium sulfate. The slurry was filtered and concentrated in vacuo. The crude material was purified using normal phase chromatography (ethyl acetate/heptane) to provide the title compound as a colorless oil. (27 mg, 39% yield). MS (M+H): 527; $^1$H NMR (400 MHz, chloroform-d) δ ppm, 1.65 (s, 6H), 2.17 (s, 3H), 2.21 (s, 3H), 2.28 (s, 3H), 5.47-5.56 (m, 2H), 6.80-6.84 (m, 1H) 7.34-7.38 (m, 1H), 7.55-7.59 (m, 2H), 7.93 (s, 1H), 8.14 (d, J=7.05 Hz, 1H), 8.78 (d, J=5.09, 1H).

Formulation Examples

The present invention embraces an oral formulation comprising a compound of Formula (II) and pharmaceutically acceptable excipients. A formulation of the present invention may be administered to a human or a canine.

Formulation A may be administered to a human to treat rheumatoid arthritis:

| Formulation A | | |
|---|---|---|
| Components | | (wt %) |
| API (Ex. #21) | (−)-5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one | 10 |

-continued

Formulation A

| Components | | (wt %) |
|---|---|---|
| Bulking agents | Lactose Anhydrous | 10 |
| | Microcrystalline Cellulose | 49 |
| Lubricant | Magnesium Stearate | 1.0 |
| Wetting agent | Sodium Lauryl Sulfate | 5.0 |
| Disintegrant | Polyvinylpyrrolidone | 7.0 |
| Flow aid | Silicon Dioxide | 2.0 |
| Buffer | Succinic Acid | 16 |

Formulation B may be administered to a canine to treat lymphoma:

Formulation B

| Components | | (wt %) |
|---|---|---|
| API (Ex. #9) | (-)-5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one | 10 |
| Bulking agents | Lactose Anhydrous | 10 |
| | Microcrystalline Cellulose | 49 |
| Lubricant | Magnesium Stearate | 1.0 |
| Wetting agent | Sodium Lauryl Sulfate | 5.0 |
| Flow aid | Silicon Dioxide | 2.0 |
| Disintegrant | Sodium Starch Glycolate | 7.0 |
| Buffer | Succinic Acid | 16 |

Formulations A & B Tablet Manufacturing Procedure:
First, sodium lauryl sulfate, lactose anhydrous and silicon dioxide are combined in a bin blender and mixed for about 15 minutes. Next, the active pharmaceutical ingredient (API) and succinic acid are added to the blender and mixed for about 15 minutes. Then, microcrystalline cellulose is added to the blender and mixed for about 15 minutes. Then, disintegrant polyvinylpyrrolidone or sodium starch glycolate is added to the blender and mixed for about 15 minutes. Finally, magnesium stearate is added to the blender and is mixed for about 5 minutes. The resulting powder is roller compacted to produce a uniform mix. The resulting mix is compressed into 100 mg tablets having a tablet hardness of 5-10 Strong-Cobb Units (SCU).

Biological Evaluations

P38 inhibitory potency and P38/MK2 substrate selectivity: The novel, MK2 substrate-selective inhibitory mechanism of compounds is evaluated in enzyme assays that compare inhibitor potency in blocking p38/MK2 versus p38/PRAK induced phosphorylation of an HSP-27 derived peptide substrate. The ability of compounds to inhibit activated phospho-p38α is evaluated using a p38α/MK2 and a p38α/PRAK cascade assay format. The kinase activity of p38α is determined by its ability to phosphorylate and activate GST-MK2 or GST-PRAK. The kinase activity of activated MK2 and PRAK is followed by measuring the phosphorylation of a fluorescently-labeled, peptide substrate based on the sequence of Hsp27 (FITC-KKKALSRQLSVAA). The phosphorylation of the Hsp27 peptide is quantified using IMAP assay technology (Molecular Devices) and the Analyst HT plate reader (LJL Biosystems). Kinase reactions are carried out in a 384-well plate (Corning 3575) in 20 mM HEPES pH 7.5, 10 mM $MgCl_2$, 0.0005% Tween-20, 0.01% BSA, 1 mM DTT, and 2% DMSO. The inhibitor concentration varies between 0.5-30,000 nM, while the Hsp27 peptide substrate and MgATP are held constant at 1 µM and 10 µM, respectively. Activated p38α is added to a final concentration of 20 pM for reactions with 1 nM nonphosphorylated 1 nM GST-MK2. For the p38α/PRAK cascade, unactivated GST-PRAK is held constant at 10 nM while p38α is added to a final concentration of 200 µM. Kinase reactions are incubated at room temperature and quenched after 120 minutes by the addition of 1× Progressive Binding Buffer A containing 1×IMAP beads (IMAP FP Progressive Screening Express Kit, Molecular Devices Catalog Number R8127). Inhibitor potency is calculated by fitting dose-response data to the 4-parameter logistical $IC_{50}$ equation. The substrate selectivity is calculated as a ratio of p38α/PRAK:p38α/MK2 IC50 values. A substrate selective inhibitor will have a p38α/PRAK:p38α/MK2 IC50 ratio of >2 while a classical p38 inhibitor will have a ratio of between 0.5-2. Compounds demonstrated to have substrate selectivity in this assay, are expected to provide a superior therapeutic benefit and better safety profile compared with classical p38 inhibitors in the treatment of p38 kinase mediated diseases. By way of example, the enhanced therapeutic benefit could be associated with a reduction in inhibition of p38 mediated anti-inflammatory functions, such as IL-10 production and TAB1 phosphorylation. An increased safety profile is expected based, for example, on a reduced inhibition of p38 substrates, such as PPARg and CDC25 phosphatase and PLA2 involved in gluconeogenesis and cell cycle regulation, respectively.

Cytokine regulation in human monocytes: The p38 pathway has been shown to be critical for the biosynthesis of a number of proinflammatory cytokines including TNFα, IL-1β and IL-6. Evaluation of the potency and efficacy of p38 inhibitors to block cytokine production is carried out using the human U937 cell line and purified human PBMCs (peripheral blood mononuclear cells). The U937 human pre-monocytic cell line is obtained from the American Type Culture Collection (Rockville, Md.). These cells are differentiated to a monocytic/macrophage phenotype as described by Burnette (Burnette et al., (2009). SD0006: a potent, selective and orally available inhibitor of p38 kinase, Pharmacology 84(1):42-60). Differentiated U937 cells are seeded into 96-well tissue culture plates (200,000 cells/well) in complete media. After 24 hours, the cells are pretreated for 60 minutes in the presence or absence of compound and then stimulated with LPS (lipopolysaccharide) (0.1 µg/mL) for 4 hours. Culture media are then collected for determination of TNFα or IL-6 levels by ELISA. Human PBMCs are isolated from leukopacks as described by Burnette (Burnette et al., (2009), op. cit.). The cells are seeded into 96-well tissue culture plates (200,000 cells/well) in complete media. After a one hour recovery period at 37° C., 5% $CO_2$, the cells are pretreated for 60 minutes in the presence or absence of compound and then stimulated with LPS (0.1 µg/ml) for 18-24 hours. Culture media are then collected for determination of TNFα and IL1β by ELISA. Cytokine concentrations are extrapolated from recombinant protein standard curves using a four-parameter logistic model and solving for $IC_{50}$ after iterating to the best least-squares fit. p38 inhibitors will show a dose dependent inhibition of LPS stimulated TNFα, and IL6 in differentiated U937 cells and a dose dependent inhibition of LPS stimulated TNFα, IL6 and IL1b in human PBMCs. As drugs that down-regulate TNFα, IL6 and IL1b are efficacious in a number of autoimmune, autoinflammatory inflammatory, cardiovascular and oncological diseases, it would be expected that p38 drugs that inhibit these cytokines and other enzymes and mediators of disease will be effective drugs. Species compounds of Formula (I), described hereinabove, evaluated in this assay, are expected to provide a therapeutic benefit in the treatment of p38 kinase mediated diseases, including lymphoma and inflammation.

Compounds were tested in accordance with the above described assays, yielding the $IC_{50}$ values described below:

| Example Number | MW | p38/MK2 $IC_{50}$ (uM) | p38/PRAK $IC_{50}$ (uM) | Selectivity Ratio | PBMC Cell, TNFα $IC_{50}$ (uM) |
|---|---|---|---|---|---|
| 1 | 557 | 0.015 | 0.076 | 5.1 | 0.012 |
| 2 | 512 | 0.015 | 0.083 | 5.5 | 0.0098 |
| 3 | 494 | 0.051 | 0.514 | 10.1 | 0.054 |
| 4 | 488 | 1.02 | 12.9 | 12.6 | 0.101 |
| 5 | 490 | 0.039 | 0.582 | 14.9 | 0.040 |
| 6 | 504 | 1.90 | 11.6 | 6.1 | 0.27 |
| 7 | 506 | 0.062 | 1.49 | 24 | 0.094 |
| 8 Racemic | 481 | 0.121 | 2.19 | 18.1 | 0.158 |
| 9 (−) isomer | 481 | 0.126 | 1.33 | 10.6 | 0.277 |
| 10 (+) isomer | 481 | 19.2 | >30 | >1.56 | ND |
| 11 | 542 | 0.062 | 0.675 | 10.9 | 0.126 |
| 12 | 498 | 0.076 | 1.36 | 17.9 | 0.118 |
| 13 | 536 | 0.083 | 1.28 | 15.4 | 0.140 |
| 14 Racemic | 491 | 0.184 | 3.30 | 17.9 | 0.250 |
| 15 (−) isomer | 491 | 0.052 | 1.23 | 23.6 | 0.070 |
| 16 (+) isomer | 491 | 5.03 | >30 | >6.0 | 3.56 |
| 17 | 545 | 1.70 | >30 | >17.6 | 3.75 |
| 18 | 495 | 0.579 | 7.69 | 13.3 | 0.624 |
| 19 Racemic | 513 | 0.040 | 0.566 | 14.1 | 0.104 |
| 20 (+) isomer | 513 | 5.38 | 15.2 | 2.82 | ND |
| 21 (−) isomer | 513 | 0.033 | 0.252 | 7.63 | 0.096 |
| 22 | 526 | 0.386 | 5.82 | 15.1 | 0.215 |
| 23 | 526 | 0.044 | 0.514 | 11.7 | 0.074 |

Signaling Pathway analysis in LPS stimulated U937 cells: Analysis of the affects of p38 inhibitors on the MAP kinase signaling pathways in U937 cells provides both confirmation of p38 target modulation in a cellular setting and an assessment of the impact of that modulation on other signal transduction pathways. The U937 human pre-monocytic cell line is obtained from the American Type Culture Collection (Rockville, Md.). These cells are differentiated to a monocytic/macrophage phenotype as described by Burnette (Burnette et al, (2009). SD0006: a potent, selective and orally available inhibitor of p38 kinase, Pharmacology 84(1):42-60). Differentiated U937 cells are seeded into 96-well tissue culture plates (200,000 cells/well) in complete media. After 24 hours, the cells are pretreated for 60 minutes in the presence or absence of compound and then stimulated with LPS (0.1 μg/mL) for 30 minutes. The media is removed and the cells are washed with Dulbeccos Phosphate Buffered Saline. The cells are then lysed in MSD Tris lysis buffer and analyzed for phospho-HSP27 (Ser 82) (target biomarker) and phospho-JNK (impact on other MAPK pathway) using MesoScale Discovery kits. The degree of target phosphorylation is calculated as a percent of the stimulated control and $IC_{50}$ are determined using a four-parameter logistic fit. Historically, classical p38 inhibitors show inhibition of LPS stimulated HSP27 phosphorylation and up-regulation of JNK phosphorylation. A substrate selective p38 inhibitor will still show dose-dependent inhibition of LPS stimulated phospho-HSP27 but its effects on the JNK pathway are anticipated to be significantly reduced compared to a classical inhibitor. The biological consequence of reduced elevation of proinflammatory JNK pathway activation by p38 substrate selective inhibitors should be an enhanced level of efficacy and improved safety in the treatment of autoimmune, autoinflammatory, inflammatory, cardiovascular, CNS, oncologial and other diseases. Species compounds of Formula (I), described hereinabove, evaluated in this assay, are expected to provide a therapeutic benefit in the treatment of p38 kinase mediated diseases, including lymphoma and rheumatoid arthritis.

IL1β induced prostaglandin production in Rheumatoid arthritis synovial fibroblasts (RASF): Rheumatoid arthritis synovial fibroblasts (RASF) are derived from the inflamed synovium of a female RA patient who was undergoing total knee replacement. Synovial tissue is teased away from adjacent cartilage and dispersed into single cells with collagenase. Cells are expanded and banked. RASF cells are further cultured as described by Burnette (Burnette, et al. (2009), op. cit.). RASF cells are seeded into 96-well tissue culture plates ($5\times10^4$ cells/well) in complete growth medium. After 24 hours, the medium is replaced with fresh growth medium containing 1% FBS. Cells are treated with serial concentrations (30,000-0.01 nM) of compound or dimethyl-sulfoxide (DMSO) vehicle control for 1 hour then stimulated with 1 ng/mL IL-1β (R&D Systems, Minneapolis, Minn.) for 18-20 hours at 37° C. and conditioned media is collected. PGE2 levels in the cultured media are quantitated by ELISA (Cayman Chemical, Ann Arbor, Mich.). Classical p38 inhibitors have been shown to dose-dependently inhibit IL-1b stimulated PGE2 production in RASF cells and substrate selective inhibitors should demonstrate the same inhibition. Downregulation of PGE2 should result in reduced inflammation and pain associated with autoimmune and inflammatory disease states as well as oncological, CNS, cardiovascular and other diseases. Species compounds of Formula (I), described hereinabove, evaluated in this assay, are expected to provide a therapeutic benefit in the treatment of p38 kinase mediated diseases, including lymphoma and rheumatoid arthritis.

Substrate selectivity in HUVEC cells: When a compound is identified from the biochemical characterization step with selective inhibition of p38/MK2, it is next placed into a cell-based assay to verify enzyme to cell translatability. These assays utilize human umbilical vein endothelial cells (HUVEC) to demonstrate inhibition of Hsp27 phosphorylation (a biomarker of p38/MK2 activation) while sparing production of tissue factor (TF), which is linked to another downstream substrate of p38, MSK. In a 96-well format, adherent HUVEC (at 5 passages or less) are treated for 1 hour with serially-diluted compounds, including a non-selective p38 inhibitor as a reference, or vehicle for controls. For Hsp27 phosphorylation, cells are stimulated with 500 pg/mL IL-1β for 0.5 hours, media is removed, cells are lysed, and phospho-Hsp27 in the lysate is quantitated by enzyme-linked immunosorbent assay (ELISA) (Life Technologies, Carlsbad, Calif.). The procedure for TF release is a similar ELISA-based assay (American Diagnostica, Stanford, Conn.), except that IL-1β stimulation proceeds for 5 hours. The ratio of TF inhibition IC50:HSP27 phosphorylation inhibition IC50 is defined as the substrate selectivity index in these cells. Compounds with indices of >2 are considered substrate selective and should demonstrate enhanced efficacy and improved safety compared with classical p38 inhibitors with ratios <2. Species compounds of Formula (I), described hereinabove, when evaluated in this assay, are expected to provide a therapeutic benefit in the treatment of p38 kinase mediated diseases, including lymphoma and autoinflammatory disease.

Canine B cell growth regulation: p38 inhibitors have been shown to uniquely inhibit canine B cell proliferation and survival. This selective effect on canine B cells may be exploited in therapeutic treatment for canine B cell lymphoma, a fatal disease that impacts >40,000 companion animals in the United States. Quantitation of impact of p38 inhibitors on B cell growth is a cellular indicator of efficacy in B cell lymphoma. Species compounds of Formula (I), described hereinabove, evaluated in this assay are expected to provide a therapeutic benefit in the treatment of p38 kinase mediated diseases, such as lymphoma. These assays utilize beagle dog spleens obtained with protocols approved by the Saint Louis University Animal Care and Use Committee in collaboration with Seventh Wave Laboratories. Leukocytes are isolated from splenocytes by centrifugation through Histopaque 1077. To evaluate effect on proliferation, leukocytes are cultured for 48 hours in 96-well plates in the presence of vehicle or test compounds. Cells are stimulated with LPS for TLR4 stimulation, *Staphylococcus aureus* B cell mitogen, or concanavalin-A T cell mitogen, then proliferation is quantitated with a BRDU incorporation ELISA (Roche, Mannheim, Germany). For apoptosis experiments, leukocytes are plated on 96-well polypropylene U bottom plates and treated with p38 MAPK inhibitors or staurosporine (as a positive control) for up to 24 hours in the absence or presence of actinomycin D or cycloheximide (if needed to increase apoptosis rate). Apoptosis is determined using Caspase-Glo 3/7 luminescent assay (Promega, Madison, Wis.). In both assays, values generated after incubation with increasing concentrations of the inhibitors are compared to a negative control without inhibitors.

LPS Induced TNFα Production in rats: Rats are fasted eighteen hours prior to oral dosing, and allowed free access to water throughout the experiment. Each treatment group consists of five animals. Compounds are prepared as a suspension in a vehicle consisting of 0.5% methylcellulose, (Sigma Aldrich, St. Louis, Mo.) and 0.025% Tween 20 (Sigma Aldrich). Administration of the compound or vehicle is by oral gavage in a volume of 1 mL. Each experiment utilizes two vehicle groups to control for intra-experiment variability. Administration of LPS (*E. coli* serotype 0111:B4, Sigma Aldrich) occurs, four hours after test compound administration, by intravenous injection at a dose of 1 mg/kg in 0.5 mL sterile saline (Baxter Healthcare, Deerfield, Ill.). Blood is collected in serum separator tubes via cardiac puncture ninety minutes after LPS injection, a time point corresponding to maximal TNFα and IL-1β production. After clotting, serum is withdrawn and stored at −20° C. and IL-1β and TNFα levels quantitated by ELISA (Burnette, et al. (2009), op. cit.). Compounds that inhibit IL-1β and TNFα levels in this assay will be expected to be efficacious in diseases associated with enhanced secretion, production, activity, stability of these inflammatory cytokines. Species compounds of Formula (I), described hereinabove, when evaluated in this assay, are expected to provide a therapeutic benefit in the treatment of p38 kinase mediated diseases, including lymphoma and inflammation.

Liver Microsomal Stability Assay: The in vitro metabolic stability of compounds of the present invention will be evaluated in two species, using pooled liver microsomes derived from male Beagle dogs (Xenotech), and separately, using pooled microsomes derived from human liver (Xenotech). Drug stability in liver microsomes can be predictive of drug stability in vivo. Test compounds (1 μM) will be incubated, in triplicate, in liver microsomes at 37° C. in the presence of 1 mM NADPH. Reactions will be stopped at 0, 5, 10, 15, 20 and 30 minutes by addition of organic solvent (e.g., acetonitrile, methanol). Samples will be analyzed for the rate of disappearance of test compound using HPLC (Shimadzu Prominence System with Thermo Hypercarb DASH-HTS column) and triple quadropole mass spectrometry (AB Sciex 4000 QTrap LC/MS/MS System). Elimination rate constant, half-life and intrinsic clearance will be calculated from results.

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

What is claimed is:
1. A compound, or pharmaceutically acceptable salt of a compound, of Formula (I):

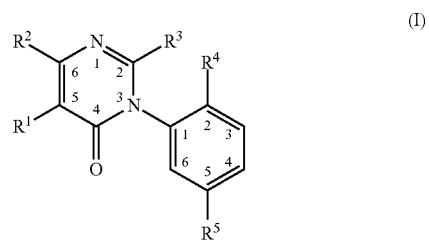

wherein:
  $R^1$ is selected from the group consisting of —H, alkyl and halo;
  $R^2$ is selected from the group consisting of alkyl and alkoxy, wherein the alkyl or alkoxy is optionally substituted with one or more substituents independently selected from the group consisting of $C_{3-6}$cycloalkyl, phenyl and five- or six-membered heterocyclyl; wherein the $C_{3-6}$cycloalkyl, phenyl or five- or six-membered heterocyclyl is substituted with one or more substituents independently selected from the group consisting of alkyl, alkoxy, alkyl-O-alkyl, hydroxyl, hydroxyalkyl, amido, carboxy, acyl, carbamido, cyano, aminoalkyl, thiolalkyl, halo and haloalkyl; or $R^2$ is hydroxyl;
  $R^3$ and $R^4$ are independently selected from the group consisting of —H, alkyl and halo; and
  $R^5$ is selected from the group consisting of carbonyl, $C_{3-6}$cycloalkyl, phenyl and five- or six-membered heterocyclyl; wherein the carbonyl is substituted with

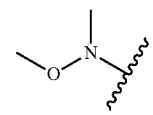 [SMILES: *N(C)OC]

or alkynyl; and the $C_{3-6}$cycloalkyl, phenyl or five- or six-membered heterocyclyl is substituted with one or more substituents independently selected from the group consisting of alkyl, alkoxy, alkyl-O-alkyl, hydroxyl, hydroxyalkyl, amido, carboxy, acyl, carbamido, cyano, aminoalkyl, thiolalkyl, halo and haloalkyl.

2. Compound of claim 1, wherein:
  $R^1$ is selected from the group consisting of —H, $C_{1-5}$alkyl, bromo, chloro and fluoro;
  $R^2$ is $C_{1-5}$alkoxy optionally substituted with one or more substituents independently selected from the group consisting of $C_{3-6}$cycloalkyl, phenyl and five- or six-membered heterocyclyl; wherein the $C_{3-6}$cycloalkyl, phenyl or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl;
  $R^3$ is selected from the group consisting of —H and $C_{1-5}$alkyl;

$R^4$ is selected from the group consisting of —H, $C_{1-5}$alkyl, chloro, bromo and fluoro; and $R^5$ is five- or six-membered heterocyclyl substituted with one or more substituents selected from the group consisting of $C_{1-5}$alkyl, $C_{1-5}$alkoxy, $C_{1-5}$alkyl-O—$C_{1-5}$alkyl, hydroxyl, hydroxy$C_{1-5}$alkyl, amido, carboxy, acyl, carbamido, cyano, amino$C_{1-5}$alkyl, thiol$C_{1-5}$alkyl, halo and halo$C_{1-5}$alkyl.

3. Compound of claim 2, wherein:

$R^1$ is selected from the group consisting of methyl, ethyl, bromo and chloro;

$R^2$ is $C_{1-3}$alkoxy optionally substituted with one or more substituents selected from the group consisting of five- or six-membered cycloalkyl, phenyl and five- or six-membered heterocyclyl; wherein the five- or six-membered cycloalkyl, phenyl or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl;

$R^3$ is selected from the group consisting of —H and $C_{1-3}$alkyl;

$R^4$ is selected from the group consisting of —H, methyl and chloro; and $R^5$ is five- or six-membered heteroaryl substituted with one or more substituents independently selected from the group consisting of $C_{1-5}$alkyl, $C_{1-5}$alkoxy, $C_{1-5}$alkyl-O—$C_{1-5}$alkyl, hydroxyl, hydroxy$C_{1-5}$alkyl, amido, carboxy, acyl, carbamido, cyano, amino$C_{1-5}$alkyl, thiol$C_{1-5}$alkyl, halo and halo$C_{1-5}$alkyl.

4. Compound of claim 3, wherein:

$R^1$ is selected from the group consisting of methyl, ethyl, bromo and chloro;

$R^2$ is methoxy optionally substituted with five- or six-membered cycloalkyl, phenyl, or five- or six-membered heterocyclyl; wherein the five- or six-membered cycloalkyl, phenyl, or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl;

or $R^2$ is hydroxyl;

$R^3$ is selected from the group consisting of —H and $C_{1-3}$alkyl;

$R^4$ is selected from the group consisting of —H, methyl and chloro; and $R^5$ is six-membered heteroaryl substituted with one or more substituents selected from the group consisting of $C_{1-5}$alkyl, $C_{1-5}$alkoxy, $C_{1-5}$alkyl-O—$C_{1-5}$alkyl, hydroxyl, hydroxy$C_{1-5}$alkyl, amido, carboxy, acyl, carbamido, cyano, amino$C_{1-5}$alkyl, thiol$C_{1-5}$alkyl, halo and halo$C_{1-5}$alkyl.

5. Compound of claim 4, wherein:

$R^1$ is selected from the group consisting of methyl, ethyl, chloro and bromo;

$R^2$ is methoxy optionally substituted with phenyl, or five- or six-membered heterocyclyl;

wherein the phenyl, or five- or six-membered heterocyclyl is substituted with one or more substituents independently selected from the group consisting of $C_{1-5}$alkyl, $C_{1-5}$alkoxy, amido, carboxy, acyl, carbamido, cyano, amino$C_{1-5}$alkyl, thiol$C_{1-5}$alkyl, halo and halo$C_{1-5}$alkyl; or $R^2$ is hydroxyl;

$R^3$ is selected from the group consisting of —H and $C_{1-3}$alkyl;

$R^4$ is selected from the group consisting of —H, methyl and chloro; and $R^5$ is selected from the group consisting of pyridinyl, pyrazinyl, pyridazinyl and pyrimidinyl;

wherein the pyridinyl, pyrazinyl, pyridazinyl or pyrimidinyl is substituted with one or more substituents independently selected from the group consisting of $C_{1-5}$alkyl, $C_{1-5}$alkoxy, $C_{1-5}$alkyl-O—$C_{1-5}$alkyl, hydroxyl, hydroxyalkyl, amido, carboxy, acyl, carbamido, cyano, amino$C_{1-5}$alkyl, thiol$C_{1-5}$alkyl, halo and halo$C_{1-5}$alkyl.

6. Compound of claim 5, wherein the compound has the structure of Formula (II):

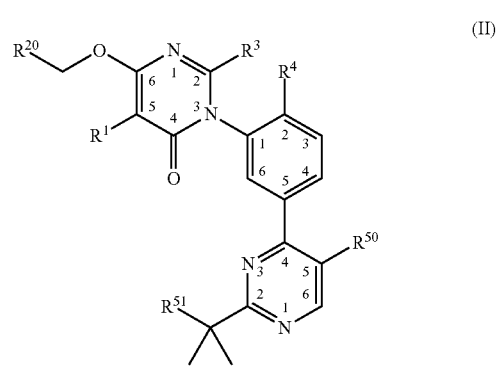

(II)

wherein:

$R^1$ is selected from the group consisting of methyl, ethyl, chloro and bromo;

$R^3$ is selected from the group consisting of —H and methyl;

$R^4$ is selected from the group consisting of —H, methyl and chloro;

$R^{20}$ is phenyl substituted with one or more substituents selected from the group consisting of $C_{1-3}$alkyl, $C_{1-3}$alkoxy, amido, carboxy, formyl, carbamido, cyano, halo and halo$C_{1-3}$alkyl; or $R^{20}$ is five- or six-membered heteroaryl substituted with one or more substituents selected from the group consisting of $C_{1-3}$alkyl, $C_{1-3}$alkoxy, $C_{1-5}$alkyl-O—$C_{1-5}$alkyl, amido, carboxy, formyl, carbamido, cyano, halo and halo$C_{1-3}$alkyl;

$R^{50}$ is selected from the group consisting of —H, $C_{1-3}$alkyl and halo; and $R^{51}$ is selected from the group consisting of —H, $C_{1-3}$alkyl, hydroxyl, amino and thiol.

7. Compound of claim 6, wherein:

$R^1$ is selected from the group consisting of methyl, chloro and bromo;

$R^3$ is methyl;

$R^4$ is selected from the group consisting —H, methyl and chloro;

$R^{20}$ is phenyl substituted with one or more substituents selected from the group consisting of methyl, methoxy, amido, carboxy, formyl, carbamido, cyano and fluoro; or $R^{20}$ is selected from the group consisting thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl and triazinyl, wherein the thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl or triazinyl is substituted with one or more substituents selected from the group consisting of methyl, methoxy, amido, carboxy, formyl, carbamido, cyano, fluoro and trifluoromethyl;
$R^{50}$ is selected from the group consisting —H, methyl and fluoro; and
$R^{51}$ is selected from the group consisting of —H, methyl and hydroxyl.

8. Compound of claim 7, wherein:
$R^1$ is selected from the group consisting of methyl, chloro and bromo;
$R^3$ is methyl;
$R^4$ is selected from the group consisting —H, methyl and chloro;
$R^{20}$ is phenyl substituted with one or more substituents selected from the group consisting of methyl, methoxy, amido, carboxy, formyl carbamido, cyano and fluoro; or $R^{20}$ is selected from the group consisting thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl and triazinyl, wherein the thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl or triazinyl is substituted with one or more substituents selected from the group consisting of methyl, methoxy, amido, carboxy, formyl, carbamido, cyano, fluoro and trifluoromethyl;
$R^{50}$ is methyl; and
$R^{51}$ is selected from the group consisting of methyl and hydroxyl.

9. Compound of claim 8, wherein:
$R^1$ is selected from the group consisting of chloro and bromo;
$R^3$ is methyl;
$R^4$ is methyl;
$R^{20}$ is phenyl substituted with one or more substituents selected from the group consisting of methyl, methoxy and fluoro; or $R^{20}$ is selected from the group consisting pyridinyl, oxazolyl and thiazolyl, wherein the pyridinyl, oxazolyl or thiazolyl is substituted with one or more substituents selected from the group consisting of methyl, methoxy, fluoro and trifluoromethyl;
$R^{50}$ is methyl; and
$R^{51}$ is selected from the group consisting of methyl and hydroxyl.

10. Compound of claim 9, wherein:
$R^1$ is selected from the group consisting of chloro and bromo;
$R^3$ is methyl;
$R^4$ is methyl;
$R^{20}$ is selected from the group consisting of methoxyphenyl, methylphenyl, fluorophenyl, difluorophenyl and methyldifluorophenyl; or $R^{20}$ is selected from the group consisting methylpyridinyl, fluoropyridinyl, difluoropyridinyl, trifluoromethylpyridinyl, methyloxazolyl and methylthiazolyl;
$R^{50}$ is methyl; and
$R^{51}$ is selected from the group consisting of methyl and hydroxyl.

11. Compound of claim 10, wherein:
$R^1$ is selected from the group consisting of chloro and bromo;
$R^3$ is methyl;
$R^4$ is methyl;
$R^{20}$ is selected from the group consisting of 3-methoxyphenyl; 3-methylphenyl; 2,4-difluorophenyl; 4-fluorophenyl; 2,4-difluoro-3-methylphenyl; 2,4-difluoro-5-methylphenyl; 6-fluoropyridin-2-yl; 6-methylpyridin-2-yl; 6-(trifluoromethyl)pyridin-2-yl; 3,5-difluoropyridin-2-yl; 2-methyloxazol-4-yl and 2-methylthiazol-4-yl;
$R^{50}$ is methyl; and
$R^{51}$ is selected from the group consisting of methyl and hydroxyl.

12. Compound of claim 11, selected from the group consisting of:
5-bromo-6-((2,4-difluorobenzyl)oxy)-3-(5-(2-(2-hydroxypropan-2-yl)pyrimidin-4-yl)-2-methylphenyl)-2-methylpyrimidin-4(3H)-one;
5-chloro-6-((2,4-difluorobenzyl)oxy)-3-(5-(2-(2-hydroxypropan-2-yl)pyrimidin-4-yl)-2-methylphenyl)-2-methylpyrimidin-4(3H)-one;
5-chloro-6-((4-fluorobenzyl)oxy)-3-(5-(2-(2-hydroxypropan-2-yl)pyrimidin-4-yl)-2-methylphenyl)-2-methylpyrimidin-4(3H)-one;
3-(5-(2-(tert-butyl)pyrimidin-4-yl)-2-methylphenyl)-5-chloro-2-methyl-6-((3-methylbenzyl)oxy)pyrimidin-4(3H)-one;
5-chloro-3-(5-(2-(2-hydroxypropan-2-yl)pyrimidin-4-yl)-2-methylphenyl)-2-methyl-6-((3-methylbenzyl)oxy)pyrimidin-4(3H)-one;
3-(5-(2-(tert-butyl)pyrimidin-4-yl)-2-methylphenyl)-5-chloro-6-((3-methoxybenzyl)oxy)-2-methylpyrimidin-4(3H)-one;
5-chloro-3-(5-(2-(2-hydroxypropan-2-yl)pyrimidin-4-yl)-2-methylphenyl)-6-((3-methoxybenzyl)oxy)-2-methylpyrimidin-4(3H)-one;
5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one;
(−)-5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one;
(+)-5-chloro-3-(5-(2-(2-hydroxypropan-2-yl)pyrimidin-4-yl)-2-methylphenyl)-2-methyl-6-((2-methyloxazol-4-yl)methoxy)pyrimidin-4(3H)-one;
5-bromo-3-(5-(2-(2-hydroxypropan-2-yl)pyrimidin-4-yl)-2-methylphenyl)-2-methyl-6-((2-methylthiazol-4-yl)methoxy)pyrimidin-4(3H)-one;
5-chloro-3-(5-(2-(2-hydroxypropan-2-yl)pyrimidin-4-yl)-2-methylphenyl)-2-methyl-6-((2-methylthiazol-4-yl)methoxy)pyrimidin-4(3H)-one;
5-bromo-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one;
5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one;
(−)-5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one;
(+)-5-chloro-3-(5-(2-(2-hydroxypropan-2-yl)pyrimidin-4-yl)-2-methylphenyl)-2-methyl-6-((6-methylpyridin-2-yl)methoxy)pyrimidin-4(3H)-one;
5-chloro-3-(5-(2-(2-hydroxypropan-2-yl)pyrimidin-4-yl)-2-methylphenyl)-2-methyl-6-((6-(trifluoromethyl)pyridin-2-yl)methoxy)pyrimidin-4(3H)-one;
5-chloro-6-((6-fluoropyridin-2-yl)methoxy)-3-(5-(2-(2-hydroxypropan-2-yl)pyrimidin-4-yl)-2-methylphenyl)-2-methylpyrimidin-4(3H)-one;
5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one;
(+)-5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one;
(−)-5-chloro-6-((3,5-difluoropyridin-2-yl)methoxy)-3-(5-(2-(2-hydroxypropan-2-yl)pyrimidin-4-yl)-2-methylphenyl)-2-methylpyrimidin-4(3H)-one;

5-chloro-6-((2,4-difluoro-3-methylbenzyl)oxy)-3-(5-(2-(2-hydroxypropan-2-yl)pyrimidin-4-yl)-2-methylphenyl)-2-methylpyrimidin-4(3H)-one; and 5-chloro-6-((2,4-difluoro-5-methylbenzyl)oxy)-3-(5-(2-(2-hydroxypropan-2-yl)pyrimidin-4-yl)-2-methylphenyl)-2-methylpyrimidin-4(3H)-one.

13. Compound of claim 5, wherein the compound has the structure of Formula (III):

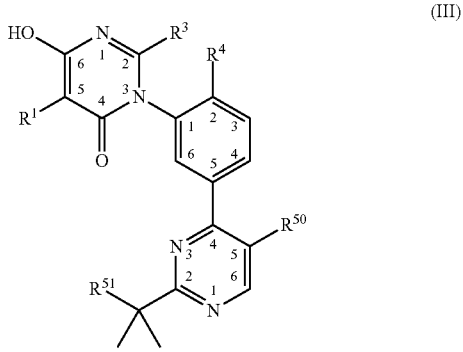

(III)

wherein:
R$^1$ is selected from the group consisting of methyl, ethyl, chloro and bromo;
R$^3$ is selected from the group consisting of —H and methyl;
R$^4$ is selected from the group consisting of —H, methyl and chloro;
R$^{50}$ is selected from the group consisting of —H, C$_{1-3}$alkyl and halo; and
R$^{51}$ is selected from the group consisting of —H, C$_{1-3}$alkyl, hydroxyl, amino and thiol.

14. Compound of claim 13, wherein:
R$^1$ is selected from the group consisting of methyl, chloro and bromo;
R$^3$ is methyl;
R$^4$ is selected from the group consisting —H, methyl and chloro;
R$^{50}$ is selected from the group consisting —H, methyl and fluoro; and
R$^{51}$ is selected from the group consisting of —H, methyl and hydroxyl.

15. Compound of claim 14, which is 5-chloro-6-hydroxy-3-{5-[2-(1-hydroxy-1-methyl-ethyl)-pyrimidin-4-yl]-2-methyl-phenyl}-2-methyl-3H-pyrimidin-4-one.

16. Compound of claim 1, wherein the compound has the structure of Formula (IV):

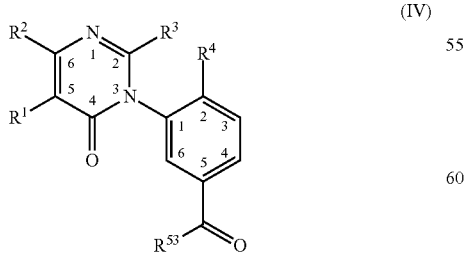

(IV)

wherein:
R$^1$ is selected from the group consisting of —H, C$_{1-5}$alkyl, bromo, chloro and fluoro;

R$^2$ is C$_{1-5}$alkoxy optionally substituted with one or more substituents independently selected from the group consisting of C$_{3-6}$cycloalkyl, phenyl and five- or six-membered heterocyclyl; wherein the C$_{3-6}$cycloalkyl, phenyl or five- or six-membered heterocyclyl is substituted with one or more substituents independently selected from the group consisting of C$_{1-5}$alkyl, C$_{1-5}$alkoxy, amido, carboxy, acyl, carbamido, cyano, aminoC$_{1-5}$alkyl, thiolC$_{1-5}$alkyl, halo and haloC$_{1-5}$alkyl; or R$^2$ is hydroxyl;
R$^3$ is selected from the group consisting of —H and C$_{1-5}$alkyl;
R$^4$ is selected from the group consisting of —H, C$_{1-5}$alkyl, chloro, bromo and fluoro; and
R$^{53}$ is selected from the group consisting of

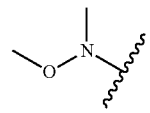

or alkynyl.

17. Compound of claim 16, wherein:
R$^1$ is selected from the group consisting of methyl, ethyl, bromo and chloro;
R$^2$ is C$_{1-3}$alkoxy optionally substituted with one or more substituents selected from the group consisting of five- or six-membered cycloalkyl, phenyl and five- or six-membered heterocyclyl; wherein the five- or six-membered cycloalkyl, phenyl or five- or six-membered heterocyclyl is substituted with one or more substituents independently selected from the group consisting of C$_{1-5}$alkyl, C$_{1-5}$alkoxy, amido, carboxy, acyl, carbamido, cyano, aminoC$_{1-5}$alkyl, thiolC$_{1-5}$alkyl, halo and haloC$_{1-5}$alkyl; or R$^2$ is hydroxyl;
R$^3$ is selected from the group consisting of —H and C$_{1-3}$alkyl;
R$^4$ is selected from the group consisting of —H, methyl and chloro; and
R$^{53}$ is selected from the group consisting of

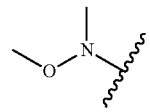

or C$_{2-5}$alkynyl.

18. Compound of claim 16, wherein:
R$^1$ is selected from the group consisting of methyl, ethyl, bromo and chloro;
R$^2$ is methoxy optionally substituted with five- or six-membered cycloalkyl, phenyl, or five- or six-membered heterocyclyl; wherein the five- or six-membered cycloalkyl, phenyl, or five- or six-membered heterocyclyl is substituted with one or more substituents independently selected from the group consisting of C$_{1-5}$alkyl, C$_{1-5}$alkoxy, amido, carboxy, acyl, carbamido, cyano, aminoC$_{1-5}$alkyl, thiolC$_{1-5}$alkyl, halo and haloC$_{1-5}$alkyl; or R$^2$ is hydroxyl;
R$^3$ is selected from the group consisting of —H and C$_{1-3}$alkyl;
R$^4$ is selected from the group consisting of —H, methyl and chloro; and $R^{53}$ is selected from the group consisting of

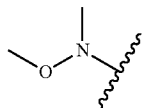

or ethynyl.

19. Compound of claim 18, wherein the compound has the structure of formula (V):

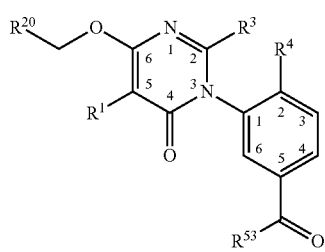

wherein:
$R^1$ is selected from the group consisting of methyl, ethyl, bromo and chloro;
$R^3$ is selected from the group consisting of —H and $C_{1-3}$alkyl;
$R^4$ is selected from the group consisting of —H, methyl and chloro;
$R^{20}$ is phenyl substituted with one or more substituents selected from the group consisting of $C_{1-3}$alkyl, $C_{1-3}$alkoxy, amido, carboxy, formyl, carbamido, cyano, halo and halo$C_{1-3}$alkyl; or $R^{20}$ is five- or six-membered heteroaryl substituted with one or more substituents selected from the group consisting of $C_{1-3}$alkyl, $C_{1-3}$alkoxy, $C_{1-5}$alkyl-O—$C_{1-5}$alkyl, amido, carboxy, formyl, carbamido, cyano, halo and halo$C_{1-3}$alkyl;
$R^{53}$ is selected from the group consisting of

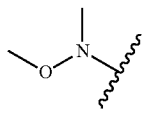

or ethynyl.

20. Compound of claim 19, wherein:
$R^1$ is selected from the group consisting of methyl, chloro and bromo;
$R^3$ is methyl;
$R^4$ is selected from the group consisting —H, methyl and chloro;
$R^{20}$ is phenyl substituted with one or more substituents selected from the group consisting of methyl, methoxy, amido, carboxy, formyl, carbamido, cyano and fluoro; or $R^{20}$ is selected from the group consisting thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl and triazinyl, wherein the thienyl, furyl, pyrrolyl, imidazolyl, pyrazolyl, isothiazolyl, oxadiazolyl, oxatriazolyl, thiazolyl, isoxazolyl, oxazolyl, furazanyl, triazolyl, pyridyl, pyrazinyl, pyrimidinyl, pyridazinyl or triazinyl is substituted with one or more substituents selected from the group consisting of methyl, methoxy, amido, carboxy, formyl, carbamido, cyano, fluoro and trifluoromethyl;
$R^{53}$ is selected from the group consisting of

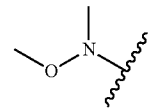 [SMILES: *N(C)OC]

or ethynyl.

21. Compound of claim 20, wherein:
$R^1$ is selected from the group consisting of chloro and bromo;
$R^3$ is methyl;
$R^4$ is methyl;
$R^{20}$ is phenyl substituted with one or more substituents selected from the group consisting of methyl, methoxy and fluoro; or $R^{20}$ is selected from the group consisting pyridinyl, oxazolyl and thiazolyl, wherein the pyridinyl, oxazolyl or thiazolyl is substituted with one or more substituents selected from the group consisting of methyl, methoxy, fluoro and trifluoromethyl;
$R^{53}$ is selected from the group consisting of

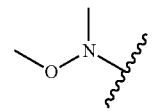 [SMILES: *N(C)OC]

or ethynyl.

22. Compound of claim 21, wherein:
$R^1$ is selected from the group consisting of chloro and bromo;
$R^3$ is methyl;
$R^4$ is methyl;
$R^{20}$ is selected from the group consisting of methoxyphenyl, methylphenyl, fluorophenyl, difluorophenyl and methyldifluorophenyl; or $R^{20}$ is selected from the group consisting methylpyridinyl, fluoropyridinyl, difluoropyridinyl, trifluoromethylpyridinyl, methyloxazolyl and methylthiazolyl;
$R^{53}$ is selected from the group consisting of

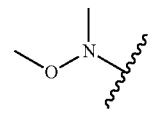

or ethynyl.

23. Compound of claim 22, wherein:
$R^1$ is selected from the group consisting of chloro and bromo;
$R^3$ is methyl;
$R^4$ is methyl;
$R^{20}$ is selected from the group consisting of 3-methoxyphenyl; 4-methoxyphenyl, 3-methylphenyl; 2,4-difluorophenyl; 4-fluorophenyl; 2,4-difluoro-3-methylphenyl; 2,4-difluoro-5-methylphenyl; 6-fluoropyridin-2-yl; 6-methylpyridin-2-yl; 6-(trifluoromethyl)pyridin-2-yl; 3,5-difluoropyridin-2-yl; 2-methyloxazol-4-yl and 2-methylthiazol-4-yl;

$R^{53}$ is selected from the group consisting of

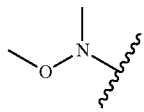

or ethynyl.

24. Compound of claim 21, selected from the group consisting of:
- 3-[5-chloro-4-(4-methoxy-benzyloxy)-2-methyl-6-oxo-6H-pyrimidin-1-yl]-N-methoxy-4,N-dimethyl-benzamide;
- 5-chloro-6-(4-methoxy-benzyloxy)-2-methyl-3-(2-methyl-5-propynoyl-phenyl)-3H-pyrimidin-4-one;
- 3-[5-bromo-4-(2,4-difluoro-benzyloxy)-2-methyl-6-oxo-6H-pyrimidin-1-yl]-N-methoxy-4,N-dimethyl-benzamide;
- 5-bromo-6-(2,4-difluoro-benzyloxy)-2-methyl-3-(2-methyl-5-propynoyl-phenyl)-3H-pyrimidin-4-one;
- 3-[5-chloro-4-(2,4-difluoro-benzyloxy)-2-methyl-6-oxo-6H-pyrimidin-1-yl]-N-methoxy-4,N-dimethyl-benzamide;
- 5-chloro-6-(2,4-difluoro-benzyloxy)-2-methyl-3-(2-methyl-5-propynoyl-phenyl)-3H-pyrimidin-4-one;
- 3-[5-chloro-4-(4-fluoro-benzyloxy)-2-methyl-6-oxo-6H-pyrimidin-1-yl]-N-methoxy-4,N-dimethyl-benzamide;
- 5-chloro-6-(4-fluoro-benzyloxy)-2-methyl-3-(2-methyl-5-propynoyl-phenyl)-3H-pyrimidin-4-one;
- 3-[5-chloro-2-methyl-4-(3-methyl-benzyloxy)-6-oxo-6H-pyrimidin-1-yl]-N-methoxy-4,N-dimethyl-benzamide;
- 5-chloro-2-methyl-6-(3-methyl-benzyloxy)-3-(2-methyl-5-propynoyl-phenyl)-3H-pyrimidin-4-one;
- 3-[5-chloro-4-(3-methoxy-benzyloxy)-2-methyl-6-oxo-6H-pyrimidin-1-yl]-N-methoxy-4,N-dimethyl-benzamide;
- 5-chloro-6-(3-methoxy-benzyloxy)-2-methyl-3-(2-methyl-5-propynoyl-phenyl)-3H-pyrimidin-4-one;
- 3-[5-bromo-2-methyl-4-(2-methyl-thiazol-4-ylmethoxy)-6-oxo-6H-pyrimidin-1-yl]-N-methoxy-4,N-dimethyl-benzamide;
- 5-bromo-2-methyl-3-(2-methyl-5-propynoyl-phenyl)-6-(2-methyl-thiazol-4-ylmethoxy)-3H-pyrimidin-4-one;
- 3-[5-chloro-2-methyl-4-(2-methyl-thiazol-4-ylmethoxy)-6-oxo-6H-pyrimidin-1-yl]-N-methoxy-4,N-dimethyl-benzamide;
- 5-chloro-2-methyl-3-(2-methyl-5-propynoyl-phenyl)-6-(2-methyl-thiazol-4-ylmethoxy)-3H-pyrimidin-4-one;
- 3-[5-bromo-2-methyl-4-(6-methyl-pyridin-2-ylmethoxy)-6-oxo-6H-pyrimidin-1-yl]-N-methoxy-4,N-dimethyl-benzamide;
- 5-bromo-2-methyl-3-(2-methyl-5-propynoyl-phenyl)-6-(6-methyl-pyridin-2-ylmethoxy)-3H-pyrimidin-4-one;
- 3-[5-chloro-2-methyl-4-(6-methyl-pyridin-2-ylmethoxy)-6-oxo-6H-pyrimidin-1-yl]-N-methoxy-4,N-dimethyl-benzamide;
- 5-chloro-2-methyl-3-(2-methyl-5-propynoyl-phenyl)-6-(6-methyl-pyridin-2-ylmethoxy)-3H-pyrimidin-4-one;
- 3-[5-chloro-2-methyl-6-oxo-4-(6-trifluoromethyl-pyridin-2-ylmethoxy)-6H-pyrimidin-1-yl]-N-methoxy-4,N-dimethyl-benzamide;
- 5-chloro-2-methyl-3-(2-methyl-5-propynoyl-phenyl)-6-(6-trifluoromethyl-pyridin-2-ylmethoxy)-3H-pyrimidin-4-one;
- 3-[5-chloro-4-(6-fluoro-pyridin-2-ylmethoxy)-2-methyl-6-oxo-6H-pyrimidin-1-yl]-N-methoxy-4,N-dimethyl-benzamide; and
- 5-chloro-6-(6-fluoro-pyridin-2-ylmethoxy)-2-methyl-3-(2-methyl-5-propynoyl-phenyl)-3H-pyrimidin-4-one.

25. A pharmaceutical composition comprising a therapeutically effective amount of a compound of claim 6 or a pharmaceutically acceptable salt thereof, and a pharmaceutically acceptable carrier.

26. The pharmaceutical composition of claim 25, comprising a therapeutically effective amount of a first active pharmaceutical ingredient in combination with a second active pharmaceutical ingredient, wherein the first active pharmaceutical ingredient is a compound of claim 6, and wherein the second active pharmaceutical ingredient is selected from the group consisting of anti-inflammatory drugs, anti-neoplastic drugs, anti-atherosclerotic drugs, and drugs for treating airway tissue hypersensitivity.

27. The pharmaceutical composition of claim 26, wherein the second active pharmaceutical ingredient is one or more anti-inflammatory drugs, selected from the group consisting of NSAIDs, immunomodulatory drugs and tumor necrosis factor α (TNFα) blockers.

28. The pharmaceutical composition of claim 27, wherein the second active pharmaceutical ingredient is one or more NSAIDs, selected from the group consisting of ibuprofen, naproxen, acetominophen, aspirin, fenoprofen, flurbiprofen, ketoprofen, oxaprozin, diclofenac sodium, diclofenac potassium, etodolac, indomethacin, ketorolac, sulindac, tolmetin, meclofenamate, mefenamic acid, nabumetone, piroxicam and celecoxib.

29. The pharmaceutical composition of claim 27, wherein the second active pharmaceutical ingredient is one or more immunomodulatory drugs, selected from the group consisting of methotrexate, leflunomide, azathioprine, cyclosporine, tacrolimus and cyclophosphamide and rituximab.

30. The pharmaceutical composition of claim 27, wherein the second active pharmaceutical ingredient is one or more TNFα blockers, selected from the group consisting of etanercept, infliximab and adalimumab.

31. The pharmaceutical composition of claim 26, wherein the second active pharmaceutical ingredient is one or more anti-neoplastic drugs, selected from the group consisting of cytostatic drugs, angiogenesis inhibitors, steroids, kinase inhibitors, cytokine blockers and inhibitors of cell adhesion molecules.

32. The pharmaceutical composition of claim 31, wherein the second active pharmaceutical ingredient is one or more cytostatic drugs, selected from the group consisting of cyclophosphamide, doxorubicin, vincristine and prednisone.

33. The pharmaceutical composition of claim 31, wherein the second active pharmaceutical ingredient is one or more angiogenesis inhibitors, selected from the group consisting of etaracizumab and cilengitide.

34. The pharmaceutical composition of claim 31, wherein the second active pharmaceutical ingredient is one or more steroids, selected from the group consisting of corticosteroids, prednisone, prednisolone, methylprednisolone, dexamethasone, hydrocortisone, cortisone, betamethasone and triamcinolone.

35. The pharmaceutical composition of claim 31, wherein the second active pharmaceutical ingredient is one or more kinase inhibitors, selected from the group consisting of afatanib, axitinib, bosutinib, crizotinib, dabrafanib, dasatinib, erlotinib, fostamatinib, gefitinib, imatinib, lapatinib, nilotinib, pazopanib, ruxolitinib, selumetinib, sorafanib, sunitinib, tofasitinib, trametinib, vandetinib, vemurafenib, AV-292 and PCI-32756.

36. The pharmaceutical composition of claim 31, wherein the second active pharmaceutical ingredient is one or more cytokine blockers, selected from the group consisting of anakinra, canakinumab, rilonacept, tocilizumab, AIN457 and ustekinumab.

37. The pharmaceutical composition of claim 31, wherein the second active pharmaceutical ingredient is one or more inhibitors of cell adhesion molecules.

38. The pharmaceutical composition of claim 37, wherein the inhibitor of cell adhesion molecules is catumaxomab.

39. The pharmaceutical composition of claim 26, wherein the second active pharmaceutical ingredient is one or more anti-atherosclerotic drugs, selected from the group consisting of atorvastatin, fluvastatin, lovastatin, pravastatin, rosuvastatin and simvastatin.

40. The pharmaceutical composition of claim 26, wherein the second active pharmaceutical ingredient is one or more drugs for treating airway tissue hypersensitivity, selected from the group consisting of $\beta_2$ agonists, anticholinergic drugs, corticosteroids, phosphodiesterase inhibitors, leukotriene modulators, methyl xanthines and anti-infectives.

41. The pharmaceutical composition of claim 40, wherein the second active pharmaceutical ingredient is one or more $\beta_2$ agonists, selected from the group consisting of salbutamol, terbutaline, salmeterol, isoetharine and formoterol.

42. The pharmaceutical composition of claim 40, wherein the second active pharmaceutical ingredient is one or more anticholinergic drugs, selected from the group consisting of ipratropium and tiotropium.

43. The pharmaceutical composition of claim 40, wherein the second active pharmaceutical ingredient is one or more corticosteroids, selected from the group consisting of budesonide, flunisolide, fluticasone, triamcinalone, beclomethasone, ciclesonide, mometasone and prednisone.

44. The pharmaceutical composition of claim 40, wherein the second active pharmaceutical ingredient is one or more phosphodiesterase inhibitors, selected from the group consisting of theophylline and roflumilast.

45. The pharmaceutical composition of claim 40, wherein the second active pharmaceutical ingredient is one or more leukotriene modulators, selected from the group consisting of montelukast and zafirlukast.

46. The pharmaceutical composition of claim 40, wherein the second active pharmaceutical ingredient is one or more methyl xanthines, selected from the group consisting of theophylline and dyphylline.

47. The pharmaceutical composition of claim 40, wherein the second active pharmaceutical ingredient is one or more anti-infectives, selected from the group consisting of metronidazole, vancomycin, rifamixin and fidaxomicin.

* * * * *